US009541773B2

(12) United States Patent
Bakaraju et al.

(10) Patent No.: US 9,541,773 B2
(45) Date of Patent: *Jan. 10, 2017

(54) LENSES, DEVICES, METHODS AND SYSTEMS FOR REFRACTIVE ERROR

(71) Applicant: BRIEN HOLDEN VISION INSTITUTE, Sydney (AU)

(72) Inventors: Ravi Chandra Bakaraju, Kingsford (AU); Klaus Ehrmann, Queenscliffe (AU); Arthur Ho, Randwick (AU); Brien Anthony Holden, Kensington (AU)

(73) Assignee: Brien Holden Vision Institute, Sydney, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/434,346

(22) PCT Filed: Oct. 4, 2013

(86) PCT No.: PCT/AU2013/001137
§ 371 (c)(1),
(2) Date: Apr. 8, 2015

(87) PCT Pub. No.: WO2014/059465
PCT Pub. Date: Apr. 24, 2014

(65) Prior Publication Data
US 2015/0277145 A1    Oct. 1, 2015

Related U.S. Application Data

(63) Continuation of application No. 13/857,613, filed on Apr. 5, 2013, now Pat. No. 9,195,074.

(30) Foreign Application Priority Data

Oct. 17, 2012    (AU) ................................ 2012904541
Apr. 5, 2013    (AU) ................................ 2013202694
Apr. 5, 2013    (WO) ................ PCT/AU2013/000354

(51) Int. Cl.
G02C 7/04       (2006.01)
G02C 7/06       (2006.01)
(Continued)

(52) U.S. Cl.
CPC ................. *G02C 7/06* (2013.01); *A61B 3/103* (2013.01); *A61F 2/1451* (2015.04); *A61F 2/16* (2013.01);
(Continued)

(58) Field of Classification Search
CPC ............................................ G02C 7/04–7/049
(Continued)

(56) References Cited

U.S. PATENT DOCUMENTS 4,082,432  A    4/1978    Kirschner
5,260,727  A    11/1993   Oksman et al.
(Continued)

FOREIGN PATENT DOCUMENTS

AU    1995039744    2/1998
AU    2004296710    8/2009
(Continued)

OTHER PUBLICATIONS

US 7,780,728, 08/2010, Hong et al. (withdrawn)
(Continued)

*Primary Examiner* — Darryl J Collins
(74) *Attorney, Agent, or Firm* — Jones Day

(57) ABSTRACT

The present disclosure is directed to lenses, devices, methods and/or systems for addressing refractive error. Certain embodiments are directed to changing or controlling the wavefront of the light entering a human eye. The lenses, devices, methods and/or systems can be used for correcting, addressing, mitigating or treating refractive errors and pro-
(Continued)

vide excellent vision at distances encompassing far to near without significant ghosting. The refractive error may for example arise from myopia, hyperopia, or presbyopia with or without astigmatism. Certain disclosed embodiments of lenses, devices and/or methods include embodiments that address foveal and/or peripheral vision. Exemplary of lenses in the fields of certain embodiments include contact lenses, corneal onlays, corneal inlays, and lenses for intraocular devices both anterior and posterior chamber, accommodating intraocular lenses, electro-active spectacle lenses and/or refractive surgery.

17 Claims, 138 Drawing Sheets

(51) Int. Cl.
    A61F 2/16    (2006.01)
    A61B 3/103   (2006.01)
    A61F 2/14    (2006.01)
    G02C 7/02    (2006.01)
(52) U.S. Cl.
    CPC ............. A61F 2/1618 (2013.01); G02C 7/022 (2013.01); G02C 7/04 (2013.01); G02C 7/041 (2013.01); G02C 7/061 (2013.01); G02C 2202/22 (2013.01); G02C 2202/24 (2013.01)
(58) Field of Classification Search
    USPC ............ 351/159.02–159.38, 159.73, 159.78, 351/159.79
    See application file for complete search history.

(56)  References Cited

U.S. PATENT DOCUMENTS

| | | |
|---|---|---|
| 5,422,687 A | 6/1995 | Tanaka et al. |
| 5,530,491 A | 6/1996 | Baude et al. |
| 5,662,706 A | 9/1997 | Legerton et al. |
| 5,682,223 A | 10/1997 | Menezes et al. |
| 5,684,560 A | 11/1997 | Roffman et al. |
| 5,699,141 A | 12/1997 | Monteil et al. |
| 5,715,031 A | 2/1998 | Roffman et al. |
| 5,742,439 A | 4/1998 | Schuster |
| 5,748,371 A | 5/1998 | Cathey et al. |
| 5,757,458 A | 5/1998 | Miller et al. |
| 5,771,088 A | 6/1998 | Perrott |
| 5,777,719 A | 7/1998 | Williams et al. |
| 5,796,462 A | 8/1998 | Roffman et al. |
| 5,805,260 A | 9/1998 | Roffman et al. |
| 5,815,239 A | 9/1998 | Chapman et al. |
| 5,822,091 A | 10/1998 | Baker et al. |
| 5,835,192 A | 11/1998 | Roffman et al. |
| 5,847,802 A | 12/1998 | Menezes et al. |
| 5,864,378 A | 1/1999 | Portney et al. |
| 5,888,122 A | 3/1999 | Gupta et al. |
| 5,912,719 A | 6/1999 | Baude et al. |
| 5,929,969 A | 7/1999 | Roffman et al. |
| RE36,352 E | 10/1999 | Swanson et al. |
| 5,965,330 A | 10/1999 | Evans et al. |
| 5,971,542 A | 10/1999 | Volker et al. |
| 5,980,040 A | 11/1999 | Xu et al. |
| 5,982,543 A | 11/1999 | Fiala et al. |
| 6,045,578 A | 4/2000 | Collins et al. |
| 6,046,867 A | 4/2000 | Rana et al. |
| 6,082,856 A | 7/2000 | Dunn et al. |
| 6,086,203 A | 7/2000 | Blum et al. |
| 6,089,711 A | 7/2000 | Blankenbecler et al. |
| 6,102,946 A | 8/2000 | Nigam |
| 6,116,735 A | 9/2000 | Wada et al. |
| 6,120,148 A | 9/2000 | Fiala et al. |
| 6,123,422 A | 9/2000 | Menezes et al. |
| 6,142,625 A | 11/2000 | Sawano et al. |
| 6,145,987 A | 11/2000 | Baude et al. |
| 6,149,271 A | 11/2000 | Menezes et al. |
| 6,179,420 B1 | 1/2001 | Roffman et al. |
| 6,199,982 B1 | 3/2001 | Oyama et al. |
| 6,199,984 B1 | 3/2001 | Menezes |
| 6,199,986 B1 | 3/2001 | Williams et al. |
| 6,221,105 B1 | 4/2001 | Portney |
| 6,244,708 B1 | 6/2001 | Chapman et al. |
| 6,244,709 B1 | 6/2001 | Vayntraub et al. |
| 6,246,516 B1 | 6/2001 | Ulrich |
| 6,299,311 B1 | 10/2001 | Williams et al. |
| 6,318,859 B1 | 11/2001 | Baudart et al. |
| 6,329,989 B1 | 12/2001 | Qi et al. |
| 6,338,559 B1 | 1/2002 | Williams et al. |
| 6,359,692 B1 | 3/2002 | Groot |
| 6,412,947 B2 | 7/2002 | Yanari |
| 6,428,574 B1 | 8/2002 | Valunin et al. |
| 6,457,826 B1 | 10/2002 | Lett |
| 6,474,814 B1 | 11/2002 | Griffin |
| 6,511,180 B2 | 1/2003 | Guirao et al. |
| 6,520,638 B1 | 2/2003 | Roffman et al. |
| 6,533,416 B1 | 3/2003 | Fermigier et al. |
| 6,536,898 B1 | 3/2003 | Cathey, Jr. |
| 6,537,317 B1 | 3/2003 | Steinert et al. |
| 6,547,391 B2 | 4/2003 | Ross et al. |
| 6,547,822 B1 | 4/2003 | Lang |
| 6,554,425 B1 | 4/2003 | Roffman et al. |
| 6,554,859 B1 | 4/2003 | Lang et al. |
| 6,575,574 B2 | 6/2003 | Dellavecchia et al. |
| 6,576,012 B2 | 6/2003 | Lang |
| 6,582,076 B1 | 6/2003 | Roffman et al. |
| 6,596,025 B2 | 7/2003 | Portney |
| 6,607,274 B2 | 8/2003 | Stantz et al. |
| 6,609,793 B2 | 8/2003 | Norrby et al. |
| 6,634,751 B2 | 10/2003 | Turner et al. |
| 6,648,473 B2 | 11/2003 | Dellavecchia et al. |
| 6,660,035 B1 | 12/2003 | Lang et al. |
| 6,663,619 B2 | 12/2003 | Odrich et al. |
| 6,673,112 B2 | 1/2004 | Nigam |
| 6,705,729 B2 | 3/2004 | Piers et al. |
| 6,709,103 B1 | 3/2004 | Roffman et al. |
| 6,709,105 B2 | 3/2004 | Menezes |
| 6,709,107 B2 | 3/2004 | Jiang et al. |
| 6,719,792 B2 | 4/2004 | Baikoff |
| 6,733,124 B2 | 5/2004 | Miyamura et al. |
| 6,752,499 B2 | 6/2004 | Aller |
| 6,755,524 B2 | 6/2004 | Rubinstein et al. |
| 6,764,179 B2 | 7/2004 | Sakai et al. |
| 6,773,107 B2 | 8/2004 | Ye et al. |
| 6,786,602 B2 | 9/2004 | Abitbol |
| 6,790,232 B1 | 9/2004 | Lang |
| 6,802,605 B2 | 10/2004 | Cox et al. |
| 6,802,606 B2 | 10/2004 | Roffman et al. |
| 6,808,262 B2 | 10/2004 | Chapoy et al. |
| 6,808,265 B2 | 10/2004 | Cox |
| 6,817,714 B2 | 11/2004 | Altmann |
| 6,819,413 B2 | 11/2004 | Neal et al. |
| 6,824,563 B2 | 11/2004 | Lang |
| 6,827,444 B2 | 12/2004 | Williams et al. |
| 6,830,332 B2 | 12/2004 | Piers et al. |
| 6,840,619 B2 | 1/2005 | Dreher |
| 6,851,805 B2 | 2/2005 | Blum et al. |
| 6,874,886 B2 | 4/2005 | Miller et al. |
| 6,874,887 B2 | 4/2005 | Tyson |
| 6,880,933 B2 | 4/2005 | Davis et al. |
| 6,882,473 B2 | 4/2005 | Geier et al. |
| 6,899,425 B2 | 5/2005 | Roffman et al. |
| 6,899,707 B2 | 5/2005 | Scholler et al. |
| 6,902,273 B2 | 6/2005 | Suzaki et al. |
| 6,903,875 B2 | 6/2005 | Achtner |
| 6,923,540 B2 | 8/2005 | Ye et al. |
| 6,924,898 B2 | 8/2005 | Deck |
| 6,926,710 B2 | 8/2005 | Cox et al. |
| 6,929,366 B2 | 8/2005 | Perel et al. |
| 6,955,433 B1 | 10/2005 | Wooley et al. |
| 6,976,997 B2 | 12/2005 | Noolandi et al. |
| 6,986,578 B2 | 1/2006 | Jones |
| 7,004,585 B2 | 2/2006 | Lindacher |
| 7,014,317 B2 | 3/2006 | Gupta et al. |

(56) References Cited

U.S. PATENT DOCUMENTS

| | | |
|---|---|---|
| 7,018,039 B2 | 3/2006 | Legerton et al. |
| 7,018,040 B2 | 3/2006 | Blum et al. |
| 7,025,454 B2 | 4/2006 | Cathey |
| 7,025,455 B2 | 4/2006 | Roffman |
| 7,025,460 B2 | 4/2006 | Smitth et al. |
| 7,036,931 B2 | 5/2006 | Lindacher et al. |
| 7,040,755 B2 | 5/2006 | Legerton et al. |
| 7,040,757 B2 | 5/2006 | Hall et al. |
| 7,048,759 B2 | 5/2006 | Bogaert et al. |
| 7,052,133 B2 | 5/2006 | Lindacher et al. |
| 7,061,693 B2 | 6/2006 | Zalevsky |
| 7,063,422 B2 | 6/2006 | Lindacher |
| 7,066,628 B2 | 6/2006 | Allen |
| 7,073,906 B1 | 7/2006 | Portney |
| 7,077,522 B2 | 7/2006 | Williams |
| 7,080,906 B2 | 7/2006 | Lindacher |
| 7,097,301 B2 | 8/2006 | Legerton et al. |
| 7,101,041 B2 | 9/2006 | Lindacher et al. |
| 7,101,042 B2 | 9/2006 | Perel et al. |
| 7,152,975 B2 | 12/2006 | Ho et al. |
| 7,172,285 B1 | 2/2007 | Altmann et al. |
| 7,178,918 B2 | 2/2007 | Griffin |
| 7,192,138 B2 | 3/2007 | Lindacher et al. |
| 7,204,849 B2 | 4/2007 | Portney |
| 7,207,675 B1 | 4/2007 | Chauveau et al. |
| 7,226,166 B2 | 6/2007 | Della Vecchia et al. |
| 7,237,894 B2 | 7/2007 | Lindacher |
| 7,246,902 B2 | 7/2007 | Meyers |
| 7,246,906 B2 | 7/2007 | Mihashi et al. |
| 7,249,850 B2 | 7/2007 | Donetti et al. |
| 7,261,412 B2 | 8/2007 | Somani et al. |
| 7,264,354 B2 | 9/2007 | Blum et al. |
| 7,270,413 B2 | 9/2007 | Hirohara et al. |
| 7,273,277 B2 | 9/2007 | Sarver |
| 7,287,852 B2 | 10/2007 | Fiala |
| 7,293,873 B2 | 11/2007 | Dai et al. |
| 7,311,400 B2 | 12/2007 | Wakil et al. |
| 7,316,713 B2 | 1/2008 | Zhang |
| 7,318,642 B2 | 1/2008 | Menezes |
| 7,322,695 B2 | 1/2008 | Wooley et al. |
| 7,331,668 B2 | 2/2008 | Azar et al. |
| 7,338,161 B2 | 3/2008 | Chauveau et al. |
| 7,338,165 B2 | 3/2008 | Dai |
| 7,338,173 B2 | 3/2008 | Dick et al. |
| 7,341,345 B2 | 3/2008 | Azar et al. |
| 7,350,916 B2 | 4/2008 | Hong et al. |
| 7,357,509 B2 | 4/2008 | Williams et al. |
| 7,360,894 B2 | 4/2008 | Hirohara |
| 7,364,294 B2 | 4/2008 | Menezes |
| 7,364,299 B2 | 4/2008 | Donnerhacke et al. |
| 7,365,917 B2 | 4/2008 | Zalevsky |
| 7,370,962 B2 | 5/2008 | Roffman et al. |
| 7,374,286 B2 | 5/2008 | Fujieda et al. |
| 7,377,638 B2 | 5/2008 | Gupta et al. |
| 7,377,647 B2 | 5/2008 | Della Vecchia et al. |
| 7,377,648 B2 | 5/2008 | Gross et al. |
| 7,380,937 B2 | 6/2008 | Ye et al. |
| 7,381,221 B2 | 6/2008 | Lang et al. |
| 7,384,143 B2 | 6/2008 | Hall et al. |
| 7,387,387 B2 | 6/2008 | Dai |
| 7,401,922 B2 | 7/2008 | Legerton |
| 7,404,636 B2 | 7/2008 | Blum et al. |
| 7,413,303 B2 | 8/2008 | Guilloux et al. |
| 7,413,566 B2 | 8/2008 | Yee |
| 7,427,134 B2 | 9/2008 | Bourdoncle et al. |
| 7,434,930 B2 | 10/2008 | Lindacher et al. |
| 7,434,936 B2 | 10/2008 | Dai et al. |
| 7,436,595 B2 | 10/2008 | Cathey et al. |
| 7,441,900 B2 | 10/2008 | Mihashi et al. |
| 7,441,901 B2 | 10/2008 | Liang |
| 7,455,407 B2 | 11/2008 | Neal et al. |
| 7,460,288 B2 | 12/2008 | Liang |
| 7,475,985 B2 | 1/2009 | Blum et al. |
| 7,478,907 B2 | 1/2009 | Somani et al. |
| 7,481,533 B2 | 1/2009 | Gupta et al. |
| 7,490,936 B2 | 2/2009 | Blum et al. |
| 7,490,937 B2 | 2/2009 | Ye et al. |
| 7,491,350 B2 | 2/2009 | Silvestrini |
| 7,497,572 B2 | 3/2009 | Ye et al. |
| 7,503,652 B2 | 3/2009 | Menezes |
| 7,503,655 B2 | 3/2009 | Smith et al. |
| 7,506,983 B2 | 3/2009 | To et al. |
| 7,513,620 B2 | 4/2009 | Dai |
| 7,517,083 B2 | 4/2009 | Blum et al. |
| 7,517,084 B2 | 4/2009 | Wooley et al. |
| 7,533,993 B2 | 5/2009 | Blum et al. |
| 7,550,701 B2 | 6/2009 | Cathey et al. |
| 7,562,982 B2 | 7/2009 | Lindacher et al. |
| 7,564,559 B2 | 7/2009 | Choo et al. |
| 7,566,133 B2 | 7/2009 | Yamakaji |
| 7,572,006 B2 | 8/2009 | Begon et al. |
| 7,615,073 B2 | 11/2009 | Deacon et al. |
| 7,625,086 B2 | 12/2009 | Wooley et al. |
| 7,637,612 B2 | 12/2009 | Menezes |
| 7,637,947 B2 | 12/2009 | Smith et al. |
| 7,639,369 B2 | 12/2009 | Owner-Petersen et al. |
| 7,641,337 B2 | 1/2010 | Altmann |
| 7,646,549 B2 | 1/2010 | Zalevsky et al. |
| 7,656,509 B2 | 2/2010 | Haddock et al. |
| 7,656,581 B2 | 2/2010 | Giraudet |
| 7,659,970 B1 | 2/2010 | Simpson et al. |
| 7,665,842 B2 | 2/2010 | Ho et al. |
| 7,673,990 B2 | 3/2010 | Esser et al. |
| 7,677,725 B2 | 3/2010 | Piers et al. |
| 7,690,789 B2 | 4/2010 | Dai et al. |
| 7,695,136 B2 | 4/2010 | Dai |
| 7,701,641 B2 | 4/2010 | Dreher et al. |
| 7,708,410 B2 | 5/2010 | Dai |
| 7,717,558 B2 | 5/2010 | Hong et al. |
| 7,717,562 B2 | 5/2010 | Dai |
| 7,728,949 B2 | 6/2010 | Clarke et al. |
| 7,731,365 B2 | 6/2010 | Catania et al. |
| 7,738,179 B2 | 6/2010 | Nishi |
| 7,748,847 B2 | 7/2010 | Dai |
| 7,753,521 B2 | 7/2010 | Wooley et al. |
| 7,762,668 B2 | 7/2010 | Dai et al. |
| 7,766,482 B2 | 8/2010 | Smith et al. |
| 7,771,048 B2 | 8/2010 | Dai et al. |
| 7,771,053 B2 | 8/2010 | Polland et al. |
| 7,775,665 B2 | 8/2010 | Dellavecchia et al. |
| 7,776,086 B2 | 8/2010 | Miller |
| 7,777,932 B2 | 8/2010 | Zalevsky et al. |
| 7,780,293 B2 | 8/2010 | Andino et al. |
| 7,798,640 B2 | 9/2010 | Chehab et al. |
| 7,803,153 B2 | 9/2010 | Thorn et al. |
| 7,811,320 B2 | 10/2010 | Werblin |
| 7,828,435 B1 | 11/2010 | Rehse |
| 7,828,441 B2 | 11/2010 | Lindacher et al. |
| 7,832,859 B2 | 11/2010 | Phillips |
| 7,837,325 B2 | 11/2010 | Wooley et al. |
| 7,857,451 B2 | 12/2010 | Thibos et al. |
| 7,859,769 B2 | 12/2010 | Zalevsky |
| 7,862,171 B2 | 1/2011 | Varnas et al. |
| 7,876,417 B2 | 1/2011 | Dowski et al. |
| 7,883,206 B2 | 2/2011 | Blum et al. |
| 7,887,187 B2 | 2/2011 | Dai |
| 7,887,531 B2 | 2/2011 | Bartoli |
| 7,891,810 B2 | 2/2011 | Legerton |
| 7,901,076 B2 | 3/2011 | Azar et al. |
| 7,901,077 B2 | 3/2011 | Dai et al. |
| 7,905,595 B2 | 3/2011 | Meyers et al. |
| 7,905,917 B2 | 3/2011 | Altmann |
| 7,918,555 B2 | 4/2011 | Sverdrup et al. |
| 7,922,328 B2 | 4/2011 | Dai et al. |
| 7,924,432 B2 | 4/2011 | Hess et al. |
| 7,926,940 B2 | 4/2011 | Blum et al. |
| 7,931,371 B2 | 4/2011 | Dai |
| 7,931,372 B2 | 4/2011 | Dai et al. |
| 7,936,522 B2 | 5/2011 | Zalevsky |
| 7,944,553 B1 | 5/2011 | Simpson et al. |
| 7,948,637 B2 | 5/2011 | De groot |
| 7,954,950 B2 | 6/2011 | Dreher et al. |
| 7,957,059 B2 | 6/2011 | Unsbo |
| 7,972,000 B2 | 7/2011 | Becker et al. |

(56) References Cited

U.S. PATENT DOCUMENTS

| | | |
|---|---|---|
| 7,976,577 B2 | 7/2011 | Silvestrini |
| 7,977,385 B2 | 7/2011 | Karageozian et al. |
| 7,988,289 B2 | 8/2011 | Chehab et al. |
| 7,992,997 B2 | 8/2011 | Varnas |
| 7,997,725 B2 | 8/2011 | Phillips |
| 7,997,727 B2 | 8/2011 | Ho et al. |
| 7,998,198 B2 | 8/2011 | Angelopoulos et al. |
| 8,002,410 B2 | 8/2011 | Shea |
| 8,016,420 B2 | 9/2011 | Yee et al. |
| 8,025,400 B2 | 9/2011 | Chernyak |
| 8,040,604 B2 | 10/2011 | Zalevsky et al. |
| 8,043,370 B2 | 10/2011 | Bretthauer et al. |
| 8,057,038 B2 | 11/2011 | Dai et al. |
| 8,061,838 B2 | 11/2011 | Giraudet et al. |
| 8,066,767 B2 | 11/2011 | Fiala et al. |
| 8,066,769 B2 | 11/2011 | Werblin |
| 8,079,704 B2 | 12/2011 | Sanger |
| 8,083,759 B2 | 12/2011 | Cox et al. |
| 8,087,778 B2 | 1/2012 | Gupta et al. |
| 8,092,016 B2 | 1/2012 | Blum et al. |
| 8,100,527 B2 | 1/2012 | Hong et al. |
| 8,113,651 B2 | 2/2012 | Blum et al. |
| 8,113,655 B1 | 2/2012 | Tyrin et al. |
| 8,118,427 B2 | 2/2012 | Bonnin et al. |
| 8,128,222 B2 | 3/2012 | Portney |
| 8,142,016 B2 | 3/2012 | Legerton et al. |
| 8,142,017 B2 | 3/2012 | Drobe et al. |
| 8,142,499 B2 | 3/2012 | Somani et al. |
| 8,147,816 B2 | 4/2012 | Till et al. |
| 8,152,300 B2 | 4/2012 | Lindacher |
| 8,167,940 B2 | 5/2012 | Hong et al. |
| 8,171,937 B2 | 5/2012 | Bendett et al. |
| 8,192,020 B2 | 6/2012 | Goto et al. |
| 8,192,022 B2 | 6/2012 | Zalevsky |
| 8,201,941 B2 | 6/2012 | Choo et al. |
| 8,201,943 B2 | 6/2012 | Hammer et al. |
| 8,206,379 B2 | 6/2012 | Homer |
| 8,215,770 B2 | 7/2012 | Blum et al. |
| 8,216,213 B2 | 7/2012 | Gross et al. |
| 8,216,308 B2 | 7/2012 | Blake et al. |
| 8,231,673 B2 | 7/2012 | Sacharoff et al. |
| 8,240,850 B2 | 8/2012 | Apter et al. |
| 8,241,354 B2 | 8/2012 | Hong et al. |
| 8,246,609 B2 | 8/2012 | Zickler et al. |
| 8,251,509 B2 | 8/2012 | Dai et al. |
| 8,256,896 B2 | 9/2012 | Zhao |
| 8,267,515 B2 | 9/2012 | Azar et al. |
| 8,277,047 B2 | 10/2012 | Koschmieder |
| 8,287,592 B2 | 10/2012 | Silvestrini |
| 8,287,593 B2 | 10/2012 | Portney |
| 8,297,751 B2 | 10/2012 | Spratt et al. |
| 8,307,832 B2 | 11/2012 | Schroeder et al. |
| 8,319,937 B2 | 11/2012 | Clarke et al. |
| 8,342,683 B2 | 1/2013 | Payor et al. |
| 8,342,684 B2 | 1/2013 | Ho et al. |
| 8,343,215 B2 | 1/2013 | Miller et al. |
| 8,345,350 B2 | 1/2013 | Epple et al. |
| 8,357,196 B2 | 1/2013 | Jain et al. |
| 8,366,270 B2 | 2/2013 | Pujol et al. |
| 8,372,319 B2 | 2/2013 | Liguori et al. |
| 8,377,124 B2 | 2/2013 | Hong et al. |
| 8,382,281 B2 | 2/2013 | Weeber |
| 8,388,130 B2 | 3/2013 | Legerton |
| 8,388,137 B2 | 3/2013 | Dreher et al. |
| 8,393,733 B2 | 3/2013 | Wooley et al. |
| 8,394,084 B2 | 3/2013 | Palankar et al. |
| 8,403,483 B2 | 3/2013 | Klink et al. |
| 8,409,181 B2 | 4/2013 | Bor |
| 8,410,162 B2 | 4/2013 | Garner et al. |
| 8,419,185 B2 | 4/2013 | Liang |
| 8,426,551 B2 | 4/2013 | Murakami et al. |
| 8,430,508 B2 | 4/2013 | Weeber |
| 8,430,511 B2 | 4/2013 | Legerton |
| 8,434,025 B2 | 4/2013 | Fisher et al. |
| 8,444,267 B2 | 5/2013 | Weeber et al. |
| 8,454,160 B2 | 6/2013 | Dai |
| 8,454,162 B2 | 6/2013 | Zhou et al. |
| 8,454,167 B2 | 6/2013 | Seiler et al. |
| 8,454,862 B2 | 6/2013 | Andino et al. |
| 8,460,376 B2 | 6/2013 | Donitzky et al. |
| 8,474,974 B2 | 7/2013 | Dai |
| 8,480,228 B2 | 7/2013 | Weeber |
| 8,482,858 B2 | 7/2013 | Sprague |
| 8,485,662 B2 | 7/2013 | Collins et al. |
| 8,486,055 B2 | 7/2013 | Knox et al. |
| 8,486,141 B2 | 7/2013 | Lang et al. |
| 8,491,824 B2 | 7/2013 | Goodenough et al. |
| 8,496,701 B2 | 7/2013 | Hermans et al. |
| 8,506,075 B2 | 8/2013 | Bandhauer et al. |
| 8,512,320 B1 | 8/2013 | Knox et al. |
| 8,518,028 B2 | 8/2013 | Brady et al. |
| 8,521,318 B2 | 8/2013 | Zhao |
| 8,529,058 B2 | 9/2013 | Hong et al. |
| 8,529,559 B2 | 9/2013 | Liang |
| 8,531,783 B2 | 9/2013 | Zalevsky et al. |
| 8,535,376 B2 | 9/2013 | Altmann |
| 8,540,370 B2 | 9/2013 | Norrby |
| 8,545,016 B2 | 10/2013 | Dai et al. |
| 8,556,885 B2 | 10/2013 | Hohla et al. |
| 8,573,775 B2 | 11/2013 | Weeber |
| 8,579,436 B2 | 11/2013 | Calixte et al. |
| 8,591,032 B2 | 11/2013 | Thibos et al. |
| 8,602,560 B2 | 12/2013 | Marin et al. |
| 8,608,800 B2 | 12/2013 | Portney |
| 8,619,362 B2 | 12/2013 | Portney |
| 8,623,081 B2 | 1/2014 | Canovas Vidal et al. |
| 8,623,083 B2 | 1/2014 | Piers et al. |
| 8,644,562 B2 | 2/2014 | Tosa et al. |
| 8,646,916 B2 | 2/2014 | Bille |
| 8,647,612 B2 | 2/2014 | Garner et al. |
| 8,652,205 B2 | 2/2014 | Hong et al. |
| 8,662,664 B2 | 3/2014 | Artal et al. |
| 8,668,332 B2 | 3/2014 | Nakajima et al. |
| 8,668,333 B2 | 3/2014 | Portney |
| 8,672,472 B2 | 3/2014 | Holden et al. |
| 8,672,473 B2 | 3/2014 | Martinez et al. |
| 8,672,474 B2 | 3/2014 | Lindacher et al. |
| 8,672,476 B2 | 3/2014 | Roffman et al. |
| 8,684,520 B2 | 4/2014 | Lindacher et al. |
| 8,684,526 B2 | 4/2014 | Neal |
| 8,685,006 B2 | 4/2014 | Wiechmann et al. |
| 8,687,290 B2 | 4/2014 | Jahn et al. |
| 8,690,319 B2 | 4/2014 | Menezes |
| 8,690,942 B2 | 4/2014 | Rombach |
| 8,696,118 B2 | 4/2014 | Back |
| 8,714,741 B2 | 5/2014 | Donoso et al. |
| 8,717,547 B2 | 5/2014 | Gorschboth et al. |
| 8,721,070 B2 | 5/2014 | Loeb et al. |
| 8,740,978 B2 | 6/2014 | Weeber et al. |
| 8,748,818 B2 | 6/2014 | Own et al. |
| 8,757,800 B2 | 6/2014 | Esser et al. |
| 8,764,191 B2 | 7/2014 | Pujol et al. |
| 8,771,348 B2 | 7/2014 | Zhao |
| 8,778,022 B2 | 7/2014 | Blum et al. |
| 8,783,872 B2 | 7/2014 | Giraudet |
| 8,786,520 B2 | 7/2014 | Legerton et al. |
| 8,789,945 B2 | 7/2014 | Suzaki et al. |
| 8,789,947 B2 | 7/2014 | Collins et al. |
| 8,795,706 B2 | 8/2014 | Garner et al. |
| 8,801,176 B2 | 8/2014 | Roffman et al. |
| 8,801,781 B2 | 8/2014 | Tabernero et al. |
| 8,820,927 B2 | 9/2014 | Weeber |
| 8,827,449 B2 | 9/2014 | Dai |
| 8,827,452 B2 | 9/2014 | Zhou et al. |
| 8,830,377 B2 | 9/2014 | Marks et al. |
| 8,833,936 B2 | 9/2014 | Varnas |
| 8,833,940 B2 | 9/2014 | Yee et al. |
| 8,844,823 B2 | 9/2014 | Fritz et al. |
| 8,851,670 B2 | 10/2014 | Dai et al. |
| 8,852,273 B2 | 10/2014 | Hong et al. |
| 8,852,274 B2 | 10/2014 | Doraiswamy et al. |
| 8,858,626 B2 | 10/2014 | Noy |
| 8,862,447 B2 | 10/2014 | Weeber |
| 8,864,306 B2 | 10/2014 | de Juan, Jr. et al. |

(56) References Cited

U.S. PATENT DOCUMENTS

| | | |
|---|---|---|
| 8,864,307 B2 | 10/2014 | Tung |
| 8,864,824 B2 | 10/2014 | Silvestrini et al. |
| 8,882,264 B2 | 11/2014 | Bradley et al. |
| 8,882,268 B2 | 11/2014 | Calixte et al. |
| 8,885,139 B2 | 11/2014 | Peyghambarian et al. |
| 8,888,277 B2 | 11/2014 | Jubin et al. |
| 8,888,279 B2 | 11/2014 | Legerton et al. |
| 8,894,203 B2 | 11/2014 | Bradley et al. |
| 8,894,204 B2 | 11/2014 | Weeber et al. |
| 8,894,208 B2 | 11/2014 | Legerton |
| 8,894,706 B2 | 11/2014 | Portney |
| 8,899,746 B2 | 12/2014 | Back |
| 8,900,296 B2 | 12/2014 | Holliday et al. |
| 8,906,089 B2 | 12/2014 | Piers et al. |
| 8,911,079 B2 | 12/2014 | Roffman et al. |
| 8,911,086 B2 | 12/2014 | Dai |
| 8,911,496 B2 | 12/2014 | Jacobson et al. |
| 8,913,331 B2 | 12/2014 | Zalevsky et al. |
| 8,926,092 B2 | 1/2015 | Weeber |
| 8,931,897 B2 | 1/2015 | Holden et al. |
| 8,950,859 B2 | 2/2015 | Tung |
| 8,950,860 B2 | 2/2015 | Tse et al. |
| 8,955,968 B2 | 2/2015 | Zalevsky |
| 8,974,526 B2 | 3/2015 | Bogaert |
| 8,992,012 B2 | 3/2015 | Wooley et al. |
| 8,998,408 B2 | 4/2015 | Wei et al. |
| 9,016,859 B2 | 4/2015 | Wooley et al. |
| 9,039,172 B2 | 5/2015 | Lindacher et al. |
| 9,195,074 B2 | 11/2015 | Bakaraju et al. |
| 2002/0035358 A1 | 3/2002 | Wang |
| 2002/0058996 A1 | 5/2002 | Silvestrini et al. |
| 2003/0058404 A1 | 3/2003 | Thorn et al. |
| 2003/0065020 A1 | 4/2003 | Gale et al. |
| 2003/0076478 A1 | 4/2003 | Cox |
| 2003/0164440 A1 | 9/2003 | Czarnetzki et al. |
| 2003/0199858 A1 | 10/2003 | Schelonka |
| 2004/0120035 A1 | 6/2004 | Hoffmann |
| 2004/0135968 A1 | 7/2004 | Morgan et al. |
| 2004/0141150 A1 | 7/2004 | Roffman et al. |
| 2004/0156014 A1* | 8/2004 | Piers .................. A61B 3/0025 351/159.41 |
| 2004/0165147 A1 | 8/2004 | Della Vecchia et al. |
| 2004/0201821 A1 | 10/2004 | Tyson |
| 2004/0237971 A1 | 12/2004 | Radhakrishnan et al. |
| 2005/0041203 A1 | 2/2005 | Lindacher et al. |
| 2005/0099600 A1 | 5/2005 | Frey et al. |
| 2005/0124983 A1 | 6/2005 | Frey et al. |
| 2005/0200809 A1 | 9/2005 | Dreher et al. |
| 2005/0203619 A1 | 9/2005 | Altmann |
| 2005/0213031 A1 | 9/2005 | Meyers |
| 2005/0259222 A1 | 11/2005 | Kelch et al. |
| 2005/0261752 A1 | 11/2005 | Chernyak |
| 2006/0020267 A1 | 1/2006 | Marmo |
| 2006/0055071 A1 | 3/2006 | Kendig et al. |
| 2006/0055884 A1 | 3/2006 | Molinari et al. |
| 2006/0066808 A1 | 3/2006 | Blum et al. |
| 2006/0082725 A1 | 4/2006 | Yamaguchi et al. |
| 2006/0116762 A1 | 6/2006 | Hong et al. |
| 2006/0116764 A1 | 6/2006 | Simpson |
| 2006/0116765 A1 | 6/2006 | Blake et al. |
| 2006/0158611 A1 | 7/2006 | Piers et al. |
| 2006/0177430 A1 | 8/2006 | Bhushan et al. |
| 2006/0184243 A1 | 8/2006 | Yilmaz |
| 2006/0192310 A1 | 8/2006 | Lindacher et al. |
| 2006/0197908 A1 | 9/2006 | Legerton et al. |
| 2006/0204861 A1 | 9/2006 | Ben-Eliezer et al. |
| 2006/0227286 A1 | 10/2006 | Hong et al. |
| 2006/0235428 A1 | 10/2006 | Silvestrini |
| 2006/0247765 A1 | 11/2006 | Fedor |
| 2006/0251316 A1 | 11/2006 | Tucker et al. |
| 2006/0256283 A1 | 11/2006 | Legerton et al. |
| 2006/0271184 A1 | 11/2006 | Silvestrini |
| 2006/0279699 A1 | 12/2006 | Liang |
| 2007/0008493 A1 | 1/2007 | Kratzer |
| 2007/0038202 A1 | 2/2007 | Celestino et al. |
| 2007/0159562 A1 | 7/2007 | Haddock et al. |
| 2007/0159593 A1 | 7/2007 | Hibino et al. |
| 2007/0195276 A1 | 8/2007 | Plut |
| 2007/0202612 A1 | 8/2007 | Winter-Jensen et al. |
| 2007/0211214 A1 | 9/2007 | Dai |
| 2007/0255401 A1 | 11/2007 | Lang |
| 2007/0279585 A1 | 12/2007 | Bartoli |
| 2007/0282438 A1 | 12/2007 | Hong et al. |
| 2008/0033301 A1 | 2/2008 | Dellavecchia et al. |
| 2008/0033546 A1 | 2/2008 | Liang |
| 2008/0039937 A1 | 2/2008 | Obrebski |
| 2008/0079895 A1 | 4/2008 | Jubin et al. |
| 2008/0193504 A1 | 8/2008 | Menko |
| 2008/0208335 A1 | 8/2008 | Blum et al. |
| 2008/0212024 A1 | 9/2008 | Lai |
| 2008/0218687 A1 | 9/2008 | Phillips |
| 2008/0221674 A1 | 9/2008 | Blum et al. |
| 2008/0275433 A1 | 11/2008 | Russmann et al. |
| 2008/0297721 A1 | 12/2008 | Gupta et al. |
| 2008/0319428 A1 | 12/2008 | Wiechmann et al. |
| 2009/0015785 A1 | 1/2009 | Blum et al. |
| 2009/0059163 A1 | 3/2009 | Pinto |
| 2009/0062911 A1 | 3/2009 | Bogaert |
| 2009/0103044 A1 | 4/2009 | Duston et al. |
| 2009/0157179 A1 | 6/2009 | Pinto et al. |
| 2009/0160075 A1 | 6/2009 | Simpson et al. |
| 2009/0168015 A1 | 7/2009 | Wooley et al. |
| 2009/0171305 A1 | 7/2009 | El Hage |
| 2009/0210054 A1 | 8/2009 | Weeber et al. |
| 2009/0216218 A1 | 8/2009 | Somani et al. |
| 2009/0227677 A1 | 9/2009 | Garner et al. |
| 2009/0234336 A1 | 9/2009 | Chernyak et al. |
| 2009/0324691 A1 | 12/2009 | Mahadevan et al. |
| 2009/0326650 A1 | 12/2009 | Zickler et al. |
| 2009/0326652 A1 | 12/2009 | Azar |
| 2010/0004741 A1 | 1/2010 | Gupta et al. |
| 2010/0016965 A1 | 1/2010 | Hong et al. |
| 2010/0026958 A1 | 2/2010 | Wooley et al. |
| 2010/0036489 A1 | 2/2010 | Lindacher et al. |
| 2010/0057202 A1 | 3/2010 | Bogaert |
| 2010/0079723 A1 | 4/2010 | Kingston et al. |
| 2010/0087921 A1 | 4/2010 | Simpson |
| 2010/0094413 A1 | 4/2010 | Rombach et al. |
| 2010/0097569 A1 | 4/2010 | Weeber et al. |
| 2010/0131059 A1 | 5/2010 | Callahan et al. |
| 2010/0157240 A1 | 6/2010 | Schmid et al. |
| 2010/0161051 A1 | 6/2010 | Hong |
| 2010/0182566 A1 | 7/2010 | Becker et al. |
| 2010/0195044 A1 | 8/2010 | Collins et al. |
| 2010/0204325 A1 | 8/2010 | Blanda et al. |
| 2010/0204571 A1 | 8/2010 | Dellavecchia et al. |
| 2010/0204788 A1 | 8/2010 | Van noy |
| 2010/0211169 A1 | 8/2010 | Stanley et al. |
| 2010/0281021 A1 | 11/2010 | Weeber et al. |
| 2010/0315589 A1 | 12/2010 | Portney |
| 2010/0318186 A1 | 12/2010 | Bumbalough et al. |
| 2010/0324408 A1 | 12/2010 | Klink et al. |
| 2010/0331830 A1 | 12/2010 | Bischoff et al. |
| 2010/0331831 A1 | 12/2010 | Bischoff et al. |
| 2011/0028948 A1 | 2/2011 | Raksi et al. |
| 2011/0028949 A1 | 2/2011 | Raksi et al. |
| 2011/0029073 A1 | 2/2011 | Liang |
| 2011/0037942 A1 | 2/2011 | Lieberman et al. |
| 2011/0153248 A1 | 6/2011 | Gu et al. |
| 2011/0166651 A1 | 7/2011 | Fiala |
| 2011/0184514 A1 | 7/2011 | Angelopoulos et al. |
| 2011/0228226 A1 | 9/2011 | Pixton et al. |
| 2011/0264081 A1 | 10/2011 | Reich et al. |
| 2011/0270389 A1 | 11/2011 | Glazer et al. |
| 2012/0016352 A1 | 1/2012 | Dick et al. |
| 2012/0033177 A1 | 2/2012 | Sarver et al. |
| 2012/0033182 A1 | 2/2012 | Dai |
| 2012/0035598 A1 | 2/2012 | Stobrawa et al. |
| 2012/0041553 A1 | 2/2012 | Gupta et al. |
| 2012/0062836 A1 | 3/2012 | Tse et al. |
| 2012/0075579 A1 | 3/2012 | Roffman et al. |
| 2012/0075580 A1 | 3/2012 | Roffman et al. |
| 2012/0075581 A1 | 3/2012 | Roffman et al. |
| 2012/0078239 A1 | 3/2012 | Reinstein et al. |

(56) References Cited

U.S. PATENT DOCUMENTS

| | | |
|---|---|---|
| 2012/0095370 A1 | 4/2012 | Wanders et al. |
| 2012/0113386 A1 | 5/2012 | Back |
| 2012/0120365 A1 | 5/2012 | Legerton et al. |
| 2012/0123534 A1 | 5/2012 | Yoon et al. |
| 2012/0130486 A1 | 5/2012 | Yoon |
| 2012/0140165 A1 | 6/2012 | Soriano et al. |
| 2012/0140167 A1 | 6/2012 | Blum |
| 2012/0143325 A1 | 6/2012 | Christie et al. |
| 2012/0148633 A1 | 6/2012 | Sun et al. |
| 2012/0158131 A1 | 6/2012 | Angelopoulos et al. |
| 2012/0194780 A1 | 8/2012 | Back |
| 2012/0206692 A1 | 8/2012 | Yamaguchi et al. |
| 2012/0239144 A1 | 9/2012 | Azar |
| 2012/0245683 A1 | 9/2012 | Christie et al. |
| 2012/0268712 A1 | 10/2012 | Egan et al. |
| 2012/0271287 A1 | 10/2012 | Gross et al. |
| 2012/0271412 A1 | 10/2012 | Feingold et al. |
| 2012/0287512 A1 | 11/2012 | Egan et al. |
| 2012/0310223 A1 | 12/2012 | Knox et al. |
| 2012/0320333 A1 | 12/2012 | Holden et al. |
| 2012/0320334 A1 | 12/2012 | Ho et al. |
| 2012/0327363 A1 | 12/2012 | Wooley et al. |
| 2013/0010260 A1 | 1/2013 | Tumlinson et al. |
| 2013/0040895 A1 | 2/2013 | Robinson et al. |
| 2013/0046381 A1 | 2/2013 | Zalevsky et al. |
| 2013/0050637 A1 | 2/2013 | Roffman et al. |
| 2013/0050651 A1 | 2/2013 | Azar et al. |
| 2013/0072591 A1 | 3/2013 | Sandstedt et al. |
| 2013/0072917 A1 | 3/2013 | Kaschke et al. |
| 2013/0096544 A1 | 4/2013 | Donoso et al. |
| 2013/0100537 A1 | 4/2013 | Matthae et al. |
| 2013/0107201 A1 | 5/2013 | Argal et al. |
| 2013/0107204 A1 | 5/2013 | Spratt et al. |
| 2013/0135579 A1 | 5/2013 | Krug et al. |
| 2013/0138094 A1 | 5/2013 | Fabrikant |
| 2013/0138208 A1 | 5/2013 | Simonov et al. |
| 2013/0165911 A1 | 6/2013 | Raksi et al. |
| 2013/0169925 A1 | 7/2013 | Caldeira et al. |
| 2013/0169928 A1 | 7/2013 | Caldeira et al. |
| 2013/0169930 A1 | 7/2013 | Caldeira et al. |
| 2013/0170017 A1 | 7/2013 | Caldeira et al. |
| 2013/0170022 A1 | 7/2013 | Caldeira et al. |
| 2013/0173029 A1 | 7/2013 | Caldeira et al. |
| 2013/0182215 A1 | 7/2013 | Tung |
| 2013/0182216 A1 | 7/2013 | Ho et al. |
| 2013/0190735 A1 | 7/2013 | Hohla et al. |
| 2013/0201464 A1 | 8/2013 | Epple et al. |
| 2013/0204237 A1 | 8/2013 | Fabrikant |
| 2013/0211515 A1 | 8/2013 | Blum et al. |
| 2013/0222765 A1 | 8/2013 | Thompson et al. |
| 2013/0226162 A1 | 8/2013 | Knox et al. |
| 2013/0226293 A1 | 8/2013 | Venkateswaran |
| 2013/0235338 A1 | 9/2013 | Weeber |
| 2013/0242255 A1 | 9/2013 | Caldarise et al. |
| 2013/0245754 A1 | 9/2013 | Blum et al. |
| 2013/0250235 A1 | 9/2013 | Foulds et al. |
| 2013/0258279 A1 | 10/2013 | Dai |
| 2013/0261744 A1 | 10/2013 | Gupta et al. |
| 2013/0268071 A1 | 10/2013 | Vilupuru et al. |
| 2013/0278888 A1 | 10/2013 | Bakaraju et al. |
| 2013/0278891 A1 | 10/2013 | Zhao |
| 2013/0282116 A1 | 10/2013 | Van Der Mooren et al. |
| 2013/0289450 A1 | 10/2013 | Homer |
| 2013/0297015 A1 | 11/2013 | Johns et al. |
| 2013/0297018 A1 | 11/2013 | Brady et al. |
| 2013/0308094 A1 | 11/2013 | Mohan et al. |
| 2013/0308186 A1 | 11/2013 | Cathey et al. |
| 2013/0308212 A1 | 11/2013 | Kubala et al. |
| 2013/0335701 A1 | 12/2013 | Canovas Vidal et al. |
| 2013/0338767 A1 | 12/2013 | Mazzocchi et al. |
| 2013/0345807 A1 | 12/2013 | Olsen |
| 2014/0009736 A1 | 1/2014 | Zhao |
| 2014/0009742 A1 | 1/2014 | Donoso et al. |
| 2014/0022505 A1 | 1/2014 | Pugh et al. |
| 2014/0022508 A1 | 1/2014 | Ben-Yaish et al. |
| 2014/0028973 A1 | 1/2014 | Scolaro |
| 2014/0029102 A1 | 1/2014 | Zalevsky et al. |
| 2014/0036225 A1 | 2/2014 | Chehab et al. |
| 2014/0039361 A1 | 2/2014 | Yin et al. |
| 2014/0039616 A1 | 2/2014 | Suzaki |
| 2014/0043584 A1 | 2/2014 | Blum |
| 2014/0063445 A1 | 3/2014 | Caldarise et al. |
| 2014/0066909 A1 | 3/2014 | Coleman et al. |
| 2014/0081357 A1 | 3/2014 | Legerton et al. |
| 2014/0081395 A1 | 3/2014 | Weeber |
| 2014/0085726 A1 | 3/2014 | Portney |
| 2014/0095137 A1 | 4/2014 | Dai et al. |
| 2014/0098338 A1 | 4/2014 | Suzaki |
| 2014/0104563 A1 | 4/2014 | Bakaraju et al. |
| 2014/0107631 A1 | 4/2014 | Ferrari |
| 2014/0107777 A1 | 4/2014 | Portney |
| 2014/0111763 A1 | 4/2014 | Griffin |
| 2014/0111764 A1 | 4/2014 | Lai et al. |
| 2014/0113946 A1 | 4/2014 | Abad |
| 2014/0121769 A1 | 5/2014 | Canovas Vidal et al. |
| 2014/0125954 A1 | 5/2014 | Kingston et al. |
| 2014/0132914 A1 | 5/2014 | Holden et al. |
| 2014/0135919 A1 | 5/2014 | Gontijo et al. |
| 2014/0135921 A1 | 5/2014 | Robert et al. |
| 2014/0148737 A1 | 5/2014 | Homer |
| 2014/0155999 A1 | 6/2014 | Vidal Canovas et al. |
| 2014/0156000 A1 | 6/2014 | Campin et al. |
| 2014/0160436 A1 | 6/2014 | Kasthurirangan et al. |
| 2014/0160438 A1 | 6/2014 | Wakil et al. |
| 2014/0168602 A1 | 6/2014 | Weeber |
| 2014/0172092 A1 | 6/2014 | Carson et al. |
| 2014/0179621 A1 | 6/2014 | Patel et al. |
| 2014/0200211 A1 | 7/2014 | Abad |
| 2014/0200665 A1 | 7/2014 | Lang et al. |
| 2014/0204333 A1 | 7/2014 | Blum et al. |
| 2014/0211147 A1 | 7/2014 | Wei et al. |
| 2014/0211149 A1 | 7/2014 | Hansen |
| 2014/0218684 A1 | 8/2014 | Kumar et al. |
| 2014/0236134 A1 | 8/2014 | Wiechmann et al. |
| 2014/0240655 A1 | 8/2014 | Pugh et al. |
| 2014/0240656 A1 | 8/2014 | Pugh et al. |
| 2014/0243385 A1 | 8/2014 | Garner et al. |
| 2014/0243972 A1 | 8/2014 | Wanders |
| 2014/0247423 A1 | 9/2014 | Drobe |
| 2014/0247424 A1 | 9/2014 | Drobe |
| 2014/0257480 A1 | 9/2014 | Van Der Mooren et al. |
| 2014/0268034 A1 | 9/2014 | Wooley et al. |
| 2014/0277430 A1 | 9/2014 | Franssen et al. |
| 2014/0277434 A1 | 9/2014 | Weeber et al. |
| 2014/0277437 A1 | 9/2014 | Currie |
| 2014/0288538 A1 | 9/2014 | Sluyterman van Langeweyde |
| 2014/0293426 A1 | 10/2014 | Dobschal |
| 2014/0303725 A1 | 10/2014 | Barrett et al. |
| 2014/0308771 A1 | 10/2014 | Brigham et al. |
| 2014/0320800 A1 | 10/2014 | Collins et al. |
| 2014/0330376 A1 | 11/2014 | Kleinman |
| 2014/0333894 A1 | 11/2014 | Dai |
| 2014/0340632 A1 | 11/2014 | Pugh et al. |
| 2014/0362338 A1 | 12/2014 | de Juan, Jr. et al. |
| 2015/0022775 A1 | 1/2015 | Ando et al. |
| 2015/0036102 A1 | 2/2015 | Ghosh et al. |
| 2015/0092157 A1 | 4/2015 | Tessieres et al. |
| 2015/0277145 A1 | 10/2015 | Bakaraju et al. |

FOREIGN PATENT DOCUMENTS

| | | |
|---|---|---|
| AU | 2004269429 | 8/2010 |
| AU | 2005260234 | 12/2010 |
| AU | 2007258008 | 5/2011 |
| AU | 2006301940 | 3/2012 |
| AU | 2010289653 | 4/2012 |
| AU | 2007212045 | 5/2012 |
| AU | 2010319453 | 5/2012 |
| AU | 2011223499 | 9/2012 |
| AU | 2011223500 | 10/2012 |
| AU | 2007281018 | 1/2013 |
| AU | 2008316316 | 1/2013 |
| AU | 2008316726 | 2/2013 |
| AU | 2007204641 | 4/2013 |

(56) References Cited

FOREIGN PATENT DOCUMENTS

| | | |
|---|---|---|
| AU | 2013203024 | 5/2013 |
| AU | 2013206684 | 7/2013 |
| AU | 2013213472 | 8/2013 |
| AU | 2008254861 | 10/2013 |
| AU | 2013201501 | 10/2013 |
| AU | 2013231016 | 10/2013 |
| AU | 2010246164 | 1/2014 |
| AU | 2012283742 | 1/2014 |
| AU | 2008293695 | 2/2014 |
| AU | 2010246165 | 2/2014 |
| AU | 2010246171 | 2/2014 |
| AU | 2010308489 | 2/2014 |
| AU | 2012270984 | 2/2014 |
| AU | 2013211446 | 2/2014 |
| AU | 2014200281 | 2/2014 |
| AU | 2012291464 | 3/2014 |
| AU | 2009327455 | 4/2014 |
| AU | 2009330163 | 5/2014 |
| AU | 2014202701 | 6/2014 |
| AU | 2011284783 | 7/2014 |
| AU | 2013202694 | 8/2014 |
| AU | 2014200420 | 8/2014 |
| AU | 2013232736 | 10/2014 |
| AU | 2013243237 | 10/2014 |
| AU | 2014201288 | 10/2014 |
| AU | 2014224341 | 11/2014 |
| AU | 2012244130 | 12/2014 |
| AU | 2014262297 | 12/2014 |
| AU | 2012273287 | 3/2015 |
| AU | 2013332247 | 4/2015 |
| AU | 2015201867 | 4/2015 |
| CA | 2530787 | 12/2004 |
| CA | 2545390 | 6/2005 |
| CN | 101686802 | 3/1920 |
| CN | 101315467 | 12/2008 |
| CN | 101566727 | 12/2010 |
| CN | 102323658 | 1/2012 |
| CN | 104049381 | 9/2014 |
| CN | 104094164 | 10/2014 |
| CN | 104094165 | 10/2014 |
| CN | 101981489 | 11/2014 |
| CN | 103257458 | 2/2015 |
| CN | 104375283 | 2/2015 |
| CN | 102722037 | 3/2015 |
| DE | 102004063091 | 7/2006 |
| DE | 102006045838 | 4/2008 |
| DE | 102006053117 | 5/2008 |
| DE | 102006053118 | 5/2008 |
| DE | 102006053120 | 5/2008 |
| DE | 102008049401 | 4/2010 |
| DE | 102009009382 | 8/2010 |
| EP | 0732608 | 9/1996 |
| EP | 1080387 | 3/2001 |
| EP | 0746272 | 10/2001 |
| EP | 1188076 | 3/2002 |
| EP | 1196807 | 4/2002 |
| EP | 1046075 | 6/2002 |
| EP | 1229876 | 8/2002 |
| EP | 1001720 | 10/2002 |
| EP | 1284685 | 2/2003 |
| EP | 0958513 | 8/2003 |
| EP | 1347328 | 9/2003 |
| EP | 1285305 | 11/2003 |
| EP | 1264204 | 5/2005 |
| EP | 1546791 | 6/2005 |
| EP | 1639399 | 3/2006 |
| EP | 1740346 | 1/2007 |
| EP | 1750633 | 2/2007 |
| EP | 1805552 | 7/2007 |
| EP | 1667612 | 12/2008 |
| EP | 2021914 | 2/2009 |
| EP | 2043556 | 4/2009 |
| EP | 2043558 | 4/2009 |
| EP | 1562467 | 7/2009 |
| EP | 2076810 | 7/2009 |
| EP | 2088978 | 8/2009 |
| EP | 1567907 | 9/2009 |
| EP | 2094193 | 9/2009 |
| EP | 2106566 | 10/2009 |
| EP | 2115519 | 11/2009 |
| EP | 1381908 | 8/2010 |
| EP | 1188091 | 10/2010 |
| EP | 2278387 | 1/2011 |
| EP | 2334260 | 6/2011 |
| EP | 2403429 | 1/2012 |
| EP | 2425294 | 3/2012 |
| EP | 1991151 | 4/2012 |
| EP | 2113226 | 7/2012 |
| EP | 2363097 | 9/2012 |
| EP | 2590594 | 5/2013 |
| EP | 2616876 | 7/2013 |
| EP | 2642332 | 9/2013 |
| EP | 2415425 | 1/2014 |
| EP | 2440962 | 8/2014 |
| EP | 2765952 | 8/2014 |
| EP | 2806827 | 12/2014 |
| EP | 2813882 | 12/2014 |
| EP | 2018594 | 4/2015 |
| ES | 2421464 | 9/2013 |
| ES | 2406381 | 4/2014 |
| FR | 2803922 | 7/2001 |
| GB | 2430047 | 1/2009 |
| JP | 2000089173 | 3/2000 |
| JP | 2003015093 | 1/2003 |
| JP | 04528049 | 8/2010 |
| JP | 04807696 | 11/2011 |
| JP | 2012093522 | 5/2012 |
| JP | 05225641 | 7/2013 |
| JP | 2013130659 | 7/2013 |
| JP | 2013180135 | 9/2013 |
| JP | 05346503 | 11/2013 |
| JP | 2013250351 | 12/2013 |
| JP | 2013250352 | 12/2013 |
| JP | 2014074866 | 4/2014 |
| KR | 101063989 | 9/2011 |
| KR | 20130003645 | 6/2013 |
| KR | 101390215 | 4/2014 |
| KR | 20140138756 | 12/2014 |
| MY | 147361 | 11/2012 |
| MY | 147454 | 12/2012 |
| SG | 169355 | 7/1920 |
| SG | 102810 | 4/2006 |
| SG | 112309 | 4/2007 |
| SG | 112312 | 8/2007 |
| SG | 173191 | 9/2011 |
| SG | 176940 | 7/2014 |
| SG | 178588 | 1/2015 |
| SG | 2014006936 | 2/2015 |
| WO | WO 01/35880 | 5/2001 |
| WO | WO 01/89424 | 10/2001 |
| WO | WO 03/040807 | 5/2003 |
| WO | WO 2004/068214 | 8/2004 |
| WO | WO 2005/001553 | 1/2005 |
| WO | WO 2005/006060 | 1/2005 |
| WO | WO 2005/050291 | 6/2005 |
| WO | WO 2005/124433 | 12/2005 |
| WO | WO 2006/018834 | 2/2006 |
| WO | WO 2006/066816 | 6/2006 |
| WO | WO 2006/088440 | 8/2006 |
| WO | WO 2007/010806 | 1/2007 |
| WO | WO 2007/047427 | 4/2007 |
| WO | WO 2009/029481 | 3/2009 |
| WO | WO 2009/029515 | 3/2009 |
| WO | WO 2009/032626 | 3/2009 |
| WO | WO 2009/076670 | 6/2009 |
| WO | WO 2009/101202 | 8/2009 |
| WO | WO 2009/140080 | 11/2009 |
| WO | WO 2010/009254 | 1/2010 |
| WO | WO 2010/009257 | 1/2010 |
| WO | WO 2010/017129 | 2/2010 |
| WO | WO 2010/051172 | 5/2010 |
| WO | WO 2010/071751 | 6/2010 |
| WO | WO 2010/100523 | 9/2010 |
| WO | WO 2010/123618 | 10/2010 |

(56) References Cited

FOREIGN PATENT DOCUMENTS

| | | |
|---|---|---|
| WO | WO 2011/028659 | 3/2011 |
| WO | WO 2011/035033 | 3/2011 |
| WO | WO-2011/049642 | 4/2011 |
| WO | WO 2011/090591 | 7/2011 |
| WO | WO 01/47449 | 10/2011 |
| WO | WO 2012/054651 | 6/2012 |
| WO | WO 2012/127538 | 9/2012 |
| WO | WO 2012/154597 | 11/2012 |
| WO | WO 2013/015743 | 1/2013 |
| WO | WO 2013/018379 | 2/2013 |
| WO | WO 2013/093916 | 6/2013 |
| WO | WO 2013/098870 | 7/2013 |
| WO | WO-2013/101793 | 7/2013 |
| WO | WO 2013/113798 | 8/2013 |
| WO | WO 2013/118499 | 8/2013 |
| WO | WO 2013/123558 | 8/2013 |
| WO | WO 2013/134825 | 9/2013 |
| WO | WO 2013/136361 | 9/2013 |
| WO | WO 2013/149303 | 10/2013 |
| WO | WO 2013/154768 | 10/2013 |
| WO | WO 2013/184239 | 12/2013 |
| WO | WO 2014/008904 | 1/2014 |
| WO | WO 2014/014521 | 1/2014 |
| WO | WO 2014/027689 | 2/2014 |
| WO | WO 2014/015234 | 3/2014 |
| WO | WO 2012/138426 | 4/2014 |
| WO | WO 2014/050879 | 4/2014 |
| WO | WO 2014/062883 | 4/2014 |
| WO | WO 2014/064163 | 5/2014 |
| WO | WO 2014/064210 | 5/2014 |
| WO | WO 2014/085352 | 6/2014 |
| WO | WO 2014/091529 | 6/2014 |
| WO | WO 2014089612 | 6/2014 |
| WO | WO 2014/111831 | 7/2014 |
| WO | WO 2014/120928 | 8/2014 |
| WO | WO 2014/124493 | 8/2014 |
| WO | WO 2014/128033 | 8/2014 |
| WO | WO 2014/128035 | 8/2014 |
| WO | WO 2014/128744 | 8/2014 |
| WO | WO 2014/135986 | 9/2014 |
| WO | WO 2014/156607 | 10/2014 |
| WO | WO 2014/167425 | 10/2014 |
| WO | WO 2014/174067 | 10/2014 |
| WO | WO 2014/177388 | 11/2014 |
| WO | WO 2014/177389 | 11/2014 |
| WO | WO 2014/184399 | 11/2014 |
| WO | WO 2014/185136 | 11/2014 |
| WO | WO 2014198972 | 12/2014 |

OTHER PUBLICATIONS

International Search Report for PCT/AU2013/001137, ISA/AU, Woden ACT, issued Dec. 23, 2013.
International Search Report dated May 20, 2013 for PCT/AU2013/000354.
Patent Examination Report No. 1 for AU2013202694 dated May 17, 2013.
Legras et al. "Through-Focus Visual Performance Measurements and Predictions with Multifocal Contact Lenses" Vision Research 50, p. 1185-1193 (2010).
Bakaraju, Ravi Chandra, "Optical Performance of Simultaneous Vision Multifocal Contact Lenses Using Schematic and Physical Eye Models" PhD Thesis (Sep. 2010).
Yi, Fang, "Wavefront Aberrations and the Depth of Focus of the Human Eye" PhD Thesis (2010).
Charman, W.N., J.A. Jennings, and H. Whitefoot, The refraction of the eye in the relation to spherical aberration and pupil size. Br J Physiol Opt, 1978. 32: p. 78-93.
Millodot, M. and J. Sivak, Contribution of the cornea and lens to the spherical aberration of the eye. Vision Res, 1979. 19(6): p. 685-7.
Campbell, C.E., The effect of spherical aberration of contact lens to the wearer. Am J Optom Physiol Opt, 1981. 58(3): p. 212-7.
Cox, I. and B.A. Holden, Soft contact lens-induced longitudinal spherical aberration and its effect on contrast sensitivity. Optom Vis Sci, 1990. 67(9): p. 679-83.
Rivolta, C., Depth of focus of optical systems with a small amount of spherical aberration. Appl Opt, 1990. 29(22): p. 3249-54.
Gu, M. and C.J. Sheppard, Effects of defocus and primary spherical aberration on three-dimensional coherent transfer functions in confocal microscopes. Appl Opt, 1992. 31(14): p. 2541-9.
Plakitsi, A. and W.N. Charman, Ocular spherical aberration and theoretical through-focus modulation transfer functions calculated for eyes fitted with two types of varifocal presbyopic contact lens. Cont Lens Anterior Eye, 1997. 20(3): p. 97-106.
Legras, R., N. Chateau, and W.N. Charman, Assessment of just-noticeable differences for refractive errors and spherical aberration using visual simulation. Optom Vis Sci, 2004. 81(9): p. 718-28.
Marsack, J.D., et al., On-eye performance of custom wavefront-guided soft contact lenses in a habitual soft lens-wearing keratoconic patient. Journal of Refractive Surgery, 2007. 23(9): p. 960.
Preussner, P.R., Spherical and chromatic aberration in aspherical IOLs. J Cataract Refract Surg, 2007. 33(10): p. 1676; author reply 1676-7.
Beiko, G., Spherical aberration and depth of focus. Ophthalmology, 2008. 115(9): p. 1641; author reply 1641-2.
Guo, H., D.A. Atchison, and B.J. Birt, Changes in through-focus spatial visual performance with adaptive optics correction of monochromatic aberrations. Vision Res, 2008. 48(17): p. 1804-11.
Gambra, E., et al., Accommodative lag and fluctuations when optical aberrations are manipulated. Journal of Vision, 2009. 9(6): p. 4.
Pieh, S., et al., In vitro strehl ratios with spherical, aberration-free, average, and customized spherical aberration-correcting intraocular lenses. Invest Ophthalmol Vis Sci, 2009. 50(3): p. 1264-70.
Rae, S.M., et al., Increasing negative spherical aberration with soft contact lenses improves high and low contrast visual acuity in young adults. Ophthalmic Physiol Opt, 2009. 29(6): p. 593-601.
Theagarayan, B., et al., The effect of altering spherical aberration on the static accommodative response. Ophthalmic Physiol Opt, 2009. 29(1): p. 65-71.
Wang, J.M., et al., Precipitation of process-derived impurities in non-Protein A purification schemes for antibodies. BioPharm International, Oct. 2009, Supp. Downstream Processing 2010: Embracing Innovation: p. 4.
Artal, P., et al., Visual effect of the combined correction of spherical and longitudinal chromatic aberrations. Optics express, 2010. 18(2): p. 1637-1648.
Bakaraju, R.C., et al., Inherent ocular spherical aberration and multifocal contact lens optical performance. Optom Vis Sci, 2010. 87(12): p. 1009-22.
Benard, Y., N. Lopez-Gil, and R. Legras, Subjective depth of field in presence of 4th-order and 6th-order Zernike spherical aberration using adaptive optics technology. J Cataract Refract Surg, 2010. 36(12): p. 2129-38.
Castignoles, F., M. Flury, and T. Lepine, Comparison of the efficiency, MTF and chromatic properties of four diffractive bifocal intraocular lens designs. Optics express, 2010. 18(5): p. 5245-5256.
Jansonius, N. M., Spherical aberration and other higher-order aberrations in the human eye: from summary wave-front analysis data to optical variables relevant to visual perception. J Opt Soc Am A Opt Image Sci Vis, 2010. 27(5): p. 941-50.
Legras, R., Y. Benard, and H. Rouger, Through-focus visual performance measurements and predictions with multifocal contact lenses. Vision Res, 2010. 50(12): p. 1185-93.
Lopez-Gil, N. and V. Fernandez-Sanchez, The change of spherical aberration during accommodation and its effect on the accommodation response. J Vis, 2010. 10(13): p. 12.
Benard, Y., N. Lopez-Gil, and R. Legras, Optimizing the subjective depth-of-focus with combinations of fourth- and sixth-order spherical aberration. Vision Res, 2011. 51(23-24): p. 2471-7.
Gonzalez-Galicia, M.A., et al., Effects of primary spherical aberration, coma, astigmatism, and field curvature on the focusing of ultrashort pulses: Gaussian illumination and experiment. J Opt Soc Am A Opt Image Sci Vis, 2011. 28(10): p. 1990-4.

(56) References Cited

OTHER PUBLICATIONS

Petelczyc, K., et al., Strehl ratios characterizing optical elements designed for presbyopia compensation. Optics express, 2011. 19(9): p. 8693-8699.

Wu, Y. and B.C. Jiang, The effects of spherical aberration on static accommodative responses in emmetropes and myopes. Ophthalmic Physiol Opt, 2011. 31(6): p. 595-602.

Yi, F., D.R. Iskander, and M. Collins, Depth of focus and visual acuity with primary and secondary spherical aberration. Vision Res, 2011. 51(14): p. 1648-58.

Gallego, A.A., et al., Visual Strehl performance of IOL designs with extended depth of focus. Optom Vis Sci, 2012. 89(12): p. 1702-7.

Gong, X.H., et al., Visual and optical performance of eyes with different corneal spherical aberration implanted with aspheric intraocular lens. Int J Ophthalmol, 2012. 5(3): p. 323-8.

Hickenbotham, A., P. Tiruveedhula, and A. Roorda, Comparison of spherical aberration and small-pupil profiles in improving depth of focus for presbyopic corrections. J Cataract Refract Surg, 2012. 38(12): p. 2071-9.

Legras, R., Y. Benard, and N. Lopez-Gil, Effect of coma and spherical aberration on depth-of-focus measured using adaptive optics and computationally blurred images. J Cataract Refract Surg, 2012. 38(3): p. 458-69.

Fernandez, D., et al., Multifocal intraocular lens providing optimized through-focus performance. Opt Lett, 2013. 38(24): p. 5303-6.

Thibos, L.N., et al., Spherical aberration and the sign of defocus. Optom Vis Sci, 2013. 90(11): p. 1284-91.

Xu, R., A. Bradley, and L.N. Thibos, Impact of primary spherical aberration, spatial frequency and Stiles Crawford apodization on wavefront determined refractive error: a computational study. Ophthalmic Physiol Opt, 2013. 33(4): p. 444-55.

Zheleznyak, L. et al., Modified monovision with spherical aberration to improve presbyopic through-focus visual performance. Invest Ophthalmol Vis Sci, 2013. 54(5): p. 3157-65.

Bradley, A., et al., Influence of spherical aberration, stimulus spatial frequency, and pupil apodisation on subjective refractions. Ophthalmic Physiol Opt, 2014. 34(3): p. 309-20.

Charman, W.N., Developments in the correction of presbyopia I: spectacle and contact lenses. Ophthalmic and Physiological Optics, 2014. 34(1): p. 8-29.

Ramos-Lopez, D., A. Martinez-Finkelshtein, and D.R. Iskander, Computational aspects of the through-focus characteristics of the human eye. J Opt Soc Am A Opt Image Sci Vis, 2014. 31(7): p. 1408-15.

Ruiz-Alcocer, J., et al., Optical performance of two new trifocal intraocular lenses: through-focus modulation transfer function and influence of pupil size. Clin Experiment Ophthalmol, 2014. 42(3): p. 271-6.

Schwarz, C. et al., Binocular visual acuity for the correction of spherical aberration in polychromatic and monochromatic light. J Vis, 2014. 14(2).

Villegas, E.A., et al.. Extended depth of focus with induced spherical aberration in light-adjustable intraocular lenses. Am J Ophthalmol, 2014. 157(1): p. 142-9.

Zheleznyak, L., H. Jung, and G. Yoon, Impact of pupil transmission apodization on presbyopic through-focus visual performance with spherical aberration. Invest Ophthalmol Vis Sci, 2014. 55(1): p. 70-7.

* cited by examiner

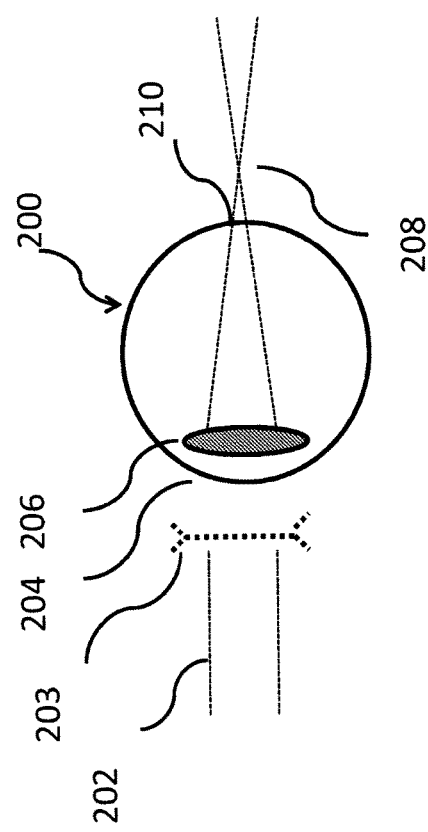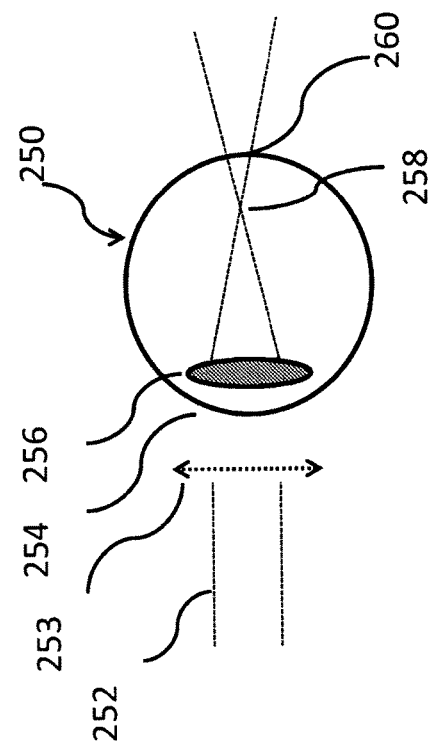
Figure 2

LENSES, DEVICES, METHODS AND SYSTEMS FOR REFRACTIVE ERROR

CROSS REFERENCE TO RELATED MATERIALS

This application is a 371 U.S. National Phase of International Application PCT/AU2013/00137, filed on Oct. 4, 2013 and published in English as WO 2014/059465 A1 on 30 Apr. 24, 2014. This application is related to Australian Provisional Application No. 2012/901,382, entitled, "Devices and Methods for Refractive Error Control" filed on 5 Apr. 2012. This Australian Provisional Application is incorporated herein by reference in its entirety. This application claims priority to PCT/AU2013/000354 entitled Lenses, Devices, Methods and Systems for Refractive Error, filed 5 Apr. 2013; U.S. application Ser. No. 13/857,613 entitled Lenses, Devices and Methods for Ocular Refractive Error filed 5 Apr. 2013; Australian Patent Application No. 2013202694 entitled Lenses, Devices, Methods and Systems for Refractive Error filed 5 Apr. 2013 and Australian Provisional Application No. 2012/904,541 entitled Lenses, Devices and Methods for Ocular Refractive Error", filed 17 Oct. 2012. These Australian Provisional Applications are each both incorporated herein by reference in their entirety. In addition, U.S. Pat. Nos. 7,077,522 and 7,357,509 are each incorporated herein by reference in their entirety.

FIELD

Certain disclosed embodiments include lenses, devices and/or methods for changing or controlling the wavefront of light entering an eye, in particular a human eye.

Certain disclosed embodiments are directed to the configuration of lenses, devices, methods and/or systems for correcting or treating refractive errors.

Certain disclosed embodiments are directed to the configuration of lenses, devices, methods and/or systems for addressing refractive errors while provide excellent vision from far to near without significant ghosting.

Certain disclosed embodiments include lenses, devices and/or methods for correcting, treating, mitigating and/or addressing refractive error, in particular in human eyes. The refractive error may for example arise from myopia or hyperopia, with or without astigmatism. The refractive error may arise from presbyopia, either alone or in combination with myopia or hyperopia and with or without astigmatism.

Certain disclosed embodiments of lenses, devices and/or methods include embodiments that address foveal vision; certain embodiments that address both foveal and peripheral vision; and certain other embodiments address peripheral vision.

Exemplary of lenses in the fields of certain embodiments include contact lenses, corneal onlays, corneal inlays, and lenses for intraocular devices (both anterior and posterior chamber).

Exemplary devices in the fields of certain disclosed embodiments include accommodating intraocular lenses and/or electro-active spectacle lenses.

Exemplary methods in the fields of certain embodiments include methods of changing the refractive state and/or wavefront of light entering an eye and received by a retina of the eye (e.g. refractive surgery, corneal ablation), methods of design and/or manufacture of lenses and optical devices, methods of surgery to alter the refractive state of an eye and methods of controlling stimulus for progression of eye growth.

BACKGROUND

For an image to be perceived clearly, the optics of the eye should result in an image that is focussed on the retina. Myopia, commonly known as short-sightedness, is an optical disorder of the eye wherein on-axis images are focussed in front of the fovea of the retina. Hyperopia, commonly known as long-sightedness, is an optical disorder of the eye wherein on-axis images are focussed behind the fovea of the retina. The focussing of images in front of or behind the fovea of the retina creates a lower order aberration of defocus. Another lower order aberration is astigmatism. An eye may also have higher order optical aberrations, including, for example, spherical aberration, coma and/or trefoil. Many people experiencing natural refractive error are progressing (the refractive error is increasing over time). Progression is particularly widespread in people with myopia.

Schematic representations of eyes exhibiting myopia or hyperopia and astigmatism are shown in FIGS. 1A-C respectively. In a myopic eye 100, the parallel incoming beam of light 102 passes the refractive elements of the eye, namely, the cornea 104 and crystalline lens 106, to a focal point 108 short of the retina 110. The image on the retina 110 is therefore blurred. In a hyperopic eye 120, the parallel incoming beam of light 122 passes the refractive elements of the eye, namely, the cornea 124 and crystalline lens 126, to a focal point 128 beyond the retina 130, again rendering the image on the retina 130 blurred. In an astigmatic eye 140, the parallel incoming beam of light 142 passes the refractive elements of the eye, namely, cornea 144 and crystalline lens 146, and results in two foci, namely tangential 148 and sagittal 158 foci. In the example of astigmatism shown in FIG. 1C, the tangential focus 148 is in front the retina 160 while the sagittal focus 158 is behind the retina 160. The image on the retina in the astigmatic case is referred to as circle of least confusion 160.

At birth human eyes are generally hyperopic, i.e. the axial length of the eyeball is too short for its optical power. With age, from infancy to adulthood, the eyeball continues to grow until its refractive state stabilizes. Elongation of the eye in a growing human may be controlled by a feedback mechanism, known as the emmetropisation process, so that the position of focus relative to the retina plays a role in controlling the extent of eye growth. Deviation from this process would potentially result in refractive disorders like myopia, hyperopia and/or astigmatism. While there is ongoing research into the cause of deviation of emmetropisation from stabilising at emmetropia, one theory is that optical feedback can provide a part in controlling eye growth. For example, FIG. 2 shows cases that would, under a feedback mechanism theory of the emmetropisation process, alter the emmetropisation process. In FIG. 2A, the parallel incoming beam of light 202 passes through a negative refractive element 203 and the refractive elements of the eye (the cornea 204 and crystalline lens 206), to form an image at focus point 208, overshooting the retina 210. The resulting image blur on the retina, called hyperopic defocus, is an example of defocus that may encourage eye growth under this feedback mechanism. In contrast, as seen in FIG. 2B, the parallel incoming beam of light 252 passes through a positive refractive element 253, the refractive elements of the eye (cornea 254 and crystalline lens 256) to form an image at focus point 258 in front of the retina 260. The resulting image blur, called myopic defocus, on this retina is considered to be an example of defocus induced at the retina that would not encourage eye growth. Therefore, it has been proposed that progression of myopic refractive error can be controlled by positioning of the focus in front of the retina. For an astigmatic system, the spherical equivalent, i.e. the mid-point between the tangential and sagittal foci, may be positioned in front of the retina. These proposals have not however provided a full explanation or solution, particularly in the case of progressing myopia.

A number of optical device designs and refractive surgery methods have been proposed to control the growth of the eye during emmetropisation. Many are generally based on refinements to the idea summarised above that foveal imagery provides a stimulus that controls the growth of the eye. In humans, the eye grows longer during emmetropisation and cannot grow shorter. Accordingly, during emmetropisation an eye may grow longer to correct for hyperopia, but it cannot grow shorter to correct for myopia. Proposals have been made for addressing myopia progression.

In addition to proposed optical strategies to counter the development of refractive error and its progression, in particular myopia, there has also been interest in strategies that involve non-optical intervention like pharmacological substances, such as atropine or pirenzipine.

Another condition of the eye is presbyopia, in which the eye's ability to accommodate is reduced or the eye has lost its ability to accommodate. Presbyopia may be experienced in combination with myopia, hyperopia, astigmatism and higher order aberrations. Different methods, devices and lenses to address presbyopia have been proposed, including in the form of bifocal, multifocal or progressive addition lenses/devices, which simultaneously provide two or more foci to the eye. Common types of lenses used for presbyopia include the following: single vision reading glasses, bifocal or multifocal spectacles; centre-near or centre-distance bifocal and multifocal contact lenses, concentric (ring-type) bifocal contact lenses or multifocal intraocular lenses.

In addition, on occasion it is necessary to remove the crystalline lens of an eye, for example if the person is suffering from cataracts. The removed natural crystalline lens may be replaced by an intraocular lens. Accommodating intraocular lenses allow the eye to control the refractive power of the lens, for example through haptics extending from the lens to the ciliary body.

Masking has been proposed as a way to improve the depth of focus of the eye. However, masking results in loss of light to the eye which is an undesirable quality as it at least deteriorates the contrast of the images cast on the retina. In addition, these features are a challenge to implement on lenses for example, contact and/or intra ocular lenses.

Some problems with existing lenses, devices, methods and/or systems are that, for example, they attempt to correct refractive errors but compromise the quality of the vision at different distances and/or introduce ghosting and/or distortion. Accordingly, what is needed are lenses, devices, methods and/or systems for mitigating and/or addressing refractive errors, for example, myopia, hyperopia or presbyopia, with or without astigmatism, without causing at least one or more of the shortcomings discussed herein. Other solutions will become apparent as discussed herein.

SUMMARY

Certain embodiments are directed to various lenses, devices and/or methods for providing an aberration profile for an eye. Characteristics of aberration profiles and/or methodologies for identifying aberration profiles are described for myopic eyes, hyperopic eyes and/or presbyopic eyes.

In addition lenses, devices and methods for an eye with astigmatism are disclosed.

In certain embodiments, a lens for an eye has an optical axis and an aberration profile about its optical axis, the aberration profile having a focal distance and including at least one of a primary spherical aberration component $C(4,0)$ and a secondary spherical aberration component $C(6,0)$. The aberration profile provides a retinal image quality (RIQ) with a through focus slope that degrades in a direction of eye growth; and a RIQ of at least 0.3. The RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive. In other embodiments the RIQ measure may be different, for example, in some embodiments the RIQ measure may be from one of the following: a simple Strehl ratio in spatial domain, a simple Strehl ratio in frequency domain, a visual Strehl ratio with inclusion of cosine of phase transfer function, a visual Strehl ratio with weighted contrast sensitivity function, a multifocal benefit ratio, a metric obtained from a two dimensional correlation analysis in spatial domain, a metric obtained from a two dimensional correlation analysis in frequency domain, or number of phase reversals in frequency domain.

In certain embodiments, a lens includes an optical axis and an aberration profile about the optical axis that provides a focal distance that comprises a $C(2,0)$ Zernike coefficient term; a peak visual Strehl Ratio ('first visual Strehl Ratio') within a through focus range, and a visual Strehl Ratio that remains at or above a second visual Strehl Ratio over the through focus range that includes said focal distance, wherein the visual Strehl Ratio is measured for at least one pupil diameter in the range 3 mm to 5 mm, over a spatial frequency range of 0 to 30 cycles/degree inclusive, at a wavelength selected from within the range 540 nm to 590 nm inclusive, and wherein the first visual Strehl Ratio is at least 0.35, the second visual Strehl Ratio is at least 0.10 and the through focus range is at least 1.8 Dioptres.

In certain embodiments, a lens comprises an optical axis and an aberration profile about the optical axis that provides a focal distance that comprises a $C(2,0)$ Zernike coefficient term; a peak RIQ ('first RIQ') within a through focus range, and a RIQ that remains at or above a second RIQ over the through focus range that comprises said focal distance, wherein the RIQ is visual Strehl Ratio with inclusion of cosine of the phase transfer function measured for at least one pupil diameter in the range 3 mm to 5 mm, over a spatial frequency range of 0 to 30 cycles/degree inclusive, at a wavelength selected from within the range 540 nm to 590 nm inclusive, and wherein the first RIQ is at least 0.3, the second visual Strehl Ratio is at least 0.10 and the through focus range is at least 1.8 Dioptres. In other embodiments the RIQ measure may be different, for example, in some embodiments the RIQ measure may be from one of the following: a simple Strehl ratio in spatial domain, a simple Strehl ratio in frequency domain, a visual Strehl ratio in spatial domain, a visual Strehl ratio in frequency domain, a visual Strehl ratio with weighted contrast sensitivity function, a multifocal benefit ratio, a metric obtained from a two dimensional correlation analysis in spatial domain, a metric obtained from a two dimensional correlation analysis in frequency domain, or number of phase reversals in frequency domain. In certain embodiments, a method for a presbyopic eye includes identifying a wavefront aberration profile for the eye, the wavefront aberration profile including at least two spherical aberration terms greater than C(4,0). The prescription focal distance of the aberration profile is determined taking into account said spherical aberration and wherein the prescription focal distance is at least +0.25 D relative to a focal distance for a C(2,0) Zernike coefficient term of the wavefront aberration profile. The method may include producing a device, lens and/or corneal profile for the eye to affect said wavefront aberration profile.

In certain embodiments, a method for a myopic eye includes identifying a wavefront aberration profile for the eye and applying or prescribing the aberration profile. The wavefront aberration profile includes at least two spherical aberration terms, wherein the prescription focal distance of the aberration profile is determined taking into account said spherical aberration and wherein the prescription focal distance is at least +0.10 D relative to a focal distance for a C(2,0) Zernike coefficient term of the wavefront aberration profile. The wavefront aberration profile also provides a degrading retinal image quality in the direction posterior to the retina.

Certain embodiments are directed to, a method for a hyperopic eye, the method comprising identifying a wavefront aberration profile for the eye and applying or prescribing the aberration profile. The wavefront aberration profile includes at least two spherical aberration terms, wherein the prescription focal distance of the wavefront aberration profile is determined taking into account said spherical aberration. At the prescription focal distance the wavefront aberration profile provides an improving retinal image quality in the direction posterior to the retina.

In certain embodiments a computational device includes an input to receive first combination of aberrations, one or more processors to compute a second combination of aberrations for one or more optical surfaces, and an output to output the second combination of aberrations, wherein the computed second combination of aberrations provides in combination with the first combination of aberrations a total combination of higher order aberrations (HOA) as disclosed herein. In certain embodiments, the computational device may be used to generate power profiles, aberration profiles, wavefront ablation profiles or combinations thereof. These computations may then be used for contact lenses, corneal inlays, corneal onlays, single and dual element intra-ocular lenses anterior and/or posterior chamber, accommodative intra-ocular lenses, wavefront ablation for corneal refractive surgery techniques and other suitable devices and/or applications.

The aberration profiles disclosed herein may be used over the optic zone of the lens, a portion of the optic zone of the lens or a substantial portion of the optic zone of the lens. How much of the optic zones of the lens that involves the aberration profile may depend on a particular application of the embodiments disclosed. In certain applications, the aberration profiles disclosed herein may be used over at least two, three or four portions of the optical zone of the lens. These multiple portions may be discrete portions, overlapping portions or combinations thereof. The multiple portions of the aberration used over one or more portions of the optic zone of the lens may have the same aberration or power profiles, substantially the same aberration or power profiles, different aberration or power profiles or combinations thereof. In certain embodiments, the aberration profiles disclosed herein may be used over at least 10%, 20%, 30%, 40% or 50% of the optical zone of the lens. In certain embodiments, the aberration profiles and or power profiles disclosed herein may be used over between 5% to 10%, 5% to 30%, 5%, to 50%, 5% to 75%, 5% to 95%, 50% to 95% or 60% to 99% of the optical zone of the lens.

A lens for an eye, the lens comprising: an optical axis and an aberration profile associated with the optical axis; and a focal distance; wherein the aberration profile comprises four or more higher order aberrations; wherein the lens is configured to provide visual performance over near, intermediate and far distances that is at least substantially equivalent to the visual performance of a correctly prescribed single-vision lens at the far visual distance and to provide minimal ghosting at far, intermediate and near distances; wherein the lens is also configured to provide a Strehl ratio of at least 0.2 at the focal distance and to provide a through-focus slope of the Strehl ratio that degrades in a negative power end of the through-focus range; and wherein the Strehl Ratio is measured substantially along the optical axis for at least a portion of the optic zone diameter in the range 3 mm to 6 mm, over a spatial frequency range of 0 to 30 cycles/degree inclusive and at a wavelength selected from within the range 540 nm to 590 nm inclusive.

The described and/or claimed specific higher order aberration profiles and the resulting through-focus retinal image quality have inter alias the advantage that they provide minimal ghosting at various distances from far, intermediate and near.

The described and/or claimed specific at least three higher order aberration terms and the resulting through-focus retinal image quality have inter alias the advantage that they provide minimal ghosting at various distances from far, intermediate and near.

The described and/or claimed specific at least four higher order aberration terms and the resulting through-focus retinal image quality have inter alias the advantage that they provide minimal ghosting at various distances from far, intermediate and near.

The described and/or claimed specific higher order aberration profiles and the resulting through-focus retinal image quality have inter alias the advantage that they provide improved vision at various distances from far, intermediate and near.

The described and/or claimed specific higher order aberration profiles and the resulting through-focus retinal image quality have inter alias the advantage that they provide improved vision and minimise ghosting at various distances from far, intermediate and near.

The described and/or claimed specific higher order aberration profiles and the resulting RIQ of at least 0.3 and the through focus RIQ slope that degrades in a direction of eye growth, have inter alias the advantage that they provide minimal ghosting at various distances from far, intermediate and near and have a potential to reduce the progression of myopia.

The described and/or claimed specific higher order aberration profiles and the resulting RIQ of at least 0.3 and the through focus RIQ slope that improves in a direction of eye growth, have inter alias the advantage that they provide minimal ghosting at various distances from far, intermediate and near and have a potential correction for hyperopia.

The described and/or claimed specific higher order aberration profiles including at least four spherical aberration terms selected from the group C(4,0) to C(20,0) have inter alias the advantage that they provide lenses that improve vision and minimise ghosting at various distances from far, intermediate and near and have a potential correction for hyperopia.

The described and/or claimed specific higher order aberration profiles and the resulting in the first visual Strehl Ratio is at least 0.35, the second visual Strehl Ratio is at least 0.1 and the through focus range is at least 1.8 D, have inter alias the advantage that they provide improved vision at distances ranging from far and intermediate, and/or provide minimal ghosting at distances ranging from far and intermediate.

The described and/or claimed specific higher order aberration profiles and the resulting in the first visual Strehl Ratio is at least 0.35, the second visual Strehl Ratio is at least 0.1 and the through focus range is at least 2.25 D, have inter alias the advantage that they provide improved vision at distances ranging from far, intermediate and near, and/or provide minimal ghosting at distances ranging from far, intermediate and near.

The described and/or claimed specific higher order aberration profiles and the resulting retinal image quality in multifocal lenses have inter alias the advantage that they provide a visual performance over intermediate and far distances that is at least substantially equivalent to the visual performance of a correctly prescribed single-vision lens at the far visual distance; and is configured to provide minimal ghosting at far, intermediate and near distances.

The described and/or claimed specific higher order aberration profiles and the resulting through-focus retinal image quality have inter alias the advantage that they provide minimal ghosting at various distances from far, intermediate and near.

The described and/or claimed specific higher order aberration profiles and the resulting through-focus retinal image quality have inter alias the advantage that they provide minimal ghosting at various distances from far and intermediate.

The described and/or claimed specific two or more higher order aberrations having one or more of the following components: a primary spherical aberration C(4,0), a secondary spherical aberration C(6,0), a tertiary spherical aberration C(8,0), a quaternary spherical aberration C(10,0), a pentanary spherical aberration C(12,0), a hexanary spherical aberration C(14,0), a heptanary spherical aberration C(16,0), an octanary spherical aberration C(18,0) and a nanonary spherical aberration C(20,0) and the resulting through focus slope of the visual Strehl ratio so that the slope visual Strehl ratio decreases in a direction of eye growth, have inter alias the advantage that they provide improved vision at far distance, minimal ghosting and have a potential to reduce the progression of myopia.

The described and/or claimed specific aberration profiles that is comprised of at least two spherical aberration terms and a defocus term have inter alias the advantage that they provide in lenses a visual performance at the near visual distance that is within two units of the visual performance of the appropriately prescribed single-vision lens at far distance.

The described and/or claimed specific aberration profiles that is comprised of at least two spherical aberration terms and a defocus term have inter alias the advantage that they provide multifocal lenses with a visual performance on a visual analogue scale at a near visual distance has a score of 9 or above in 25%, 30%, 35%, 40%, 45%, 50% or 55% of a representative sample of presbyopes.

The described and/or claimed specific higher order aberration profiles selected at least in part from a group comprising spherical aberration coefficients from C(4,0) to C(20,0), have inter alias the advantage that they provide correction of astigmatism up to 1 Dioptre without substantial use of rotationally stable toric lens design features.

The described and/or claimed specific higher order aberration profiles selected at least in part from a group comprising spherical aberration coefficients from C(4,0) to C(20,0), have inter alias the advantage that they provide expansion of the depth-of-focus of the eye by altering the retinal image quality over a range of distances.

The described and/or claimed intra-ocular lens systems with a first lens, a second lens and at least three higher order aberration terms have inter alias the advantage that they provide improved vision along a range of substantially continuous visual distances, including near, intermediate and far distances that is substantially equivalent to the visual performance of a correctly prescribed single-vision lens at the far visual distance.

The described and/or claimed power profiles with a transition between a maxima and a minima, and the maxima is within 0.2 mm of the centre of the optic zone and the minima is less than or equal to 0.3, 0.6, 0.9 or 1 mm distance from the maxima and the amplitude of the transition between the maxima and the minima is at least 2.5 D, 4 D, 5 D, or 6 D have inter alias the advantage that they provide a lens that is configured to provide a visual performance over intermediate and far distances that is at least substantially equivalent to the visual performance of a correctly prescribed single-vision lens at the far visual distance and the lens is configured to provide minimal ghosting at far, intermediate and near distances.

Further embodiments and or advantages of one or more embodiments will become apparent from the following description, given by way of example and with reference to the accompanying drawings.

BRIEF DESCRIPTION OF THE DRAWINGS

These and other features, aspects, and advantages of the present disclosure will become better understood with regard to the following description, appended claims, and accompanying figures.

FIGS. 2A and 2B are schematic representations respectively of hyperopic defocus and myopic defocus induced at the retina.

DETAILED DESCRIPTION

Figure 1:
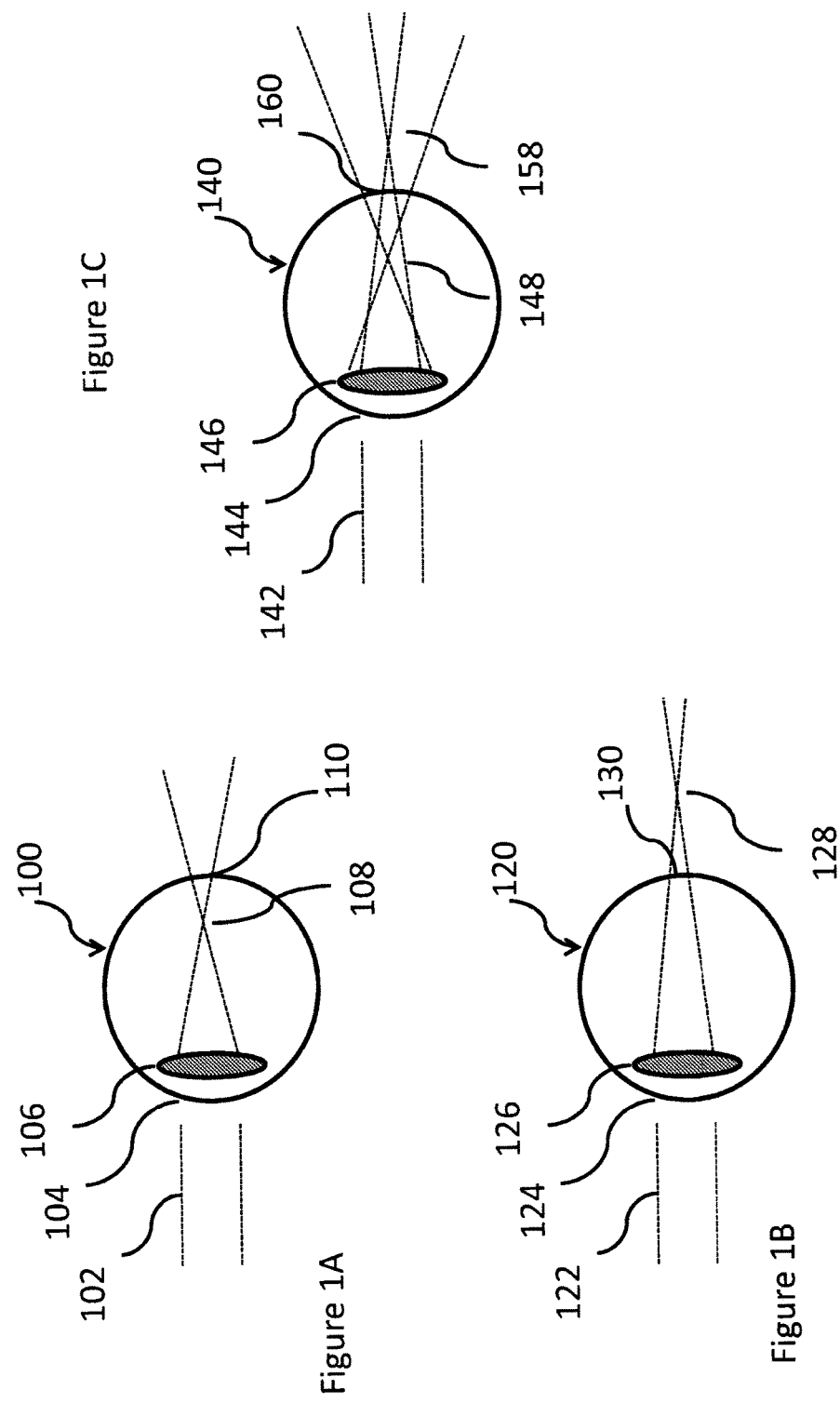
FIGS. 1A-1C are schematic representations of eyes exhibiting myopia, hyperopia and astigmatism respectively.

The present disclosure will now be described in detail with reference to one or more embodiments, some examples of which are illustrated and/or supported in the accompanying figures. The examples and embodiments are provided by way of explanation and are not to be taken as limiting to the scope of the disclosure.

Furthermore, features illustrated or described as part of one embodiment may be used by themselves to provide other embodiments and features illustrated or described as part of one embodiment may be used with one or more other embodiments to provide a further embodiments. It will be understood that the present disclosure will cover these variations and embodiments as well as other variations and/or modifications.

It will be understood that the term "comprise" and any of its derivatives (e.g., comprises, comprising) as used in this specification is to be taken to be inclusive of features to which it refers, and is not meant to exclude the presence of any additional features unless otherwise stated or implied. The features disclosed in this specification (including accompanying claims, abstract, and drawings) may be replaced by alternative features serving the same, equivalent or similar purpose, unless expressly stated otherwise.

The subject headings used in the detailed description are included only for the ease of reference of the reader and should not be used to limit the subject matter found throughout the disclosure or the claims. The subject headings should not be used in construing the scope of the claims or the claim limitations.

As defined herein, the term aberration profile may be an arrangement of one or more aberrations in a one dimensional, a two dimensional or a three dimensional distribution. The arrangement may be continuous or discontinuous. Aberration profiles may be brought about by an arrangement of one or more power profiles, power patterns and power distributions in a one dimensional, a two dimensional or a three dimensional distribution. The arrangement may be continuous or discontinuous. Aberrations may be rotationally symmetric or asymmetric.

As used herein, the terms "across the range of dioptric distances" and "a range of dioptric distances" means a range of distances as corresponding to equivalent units of dioptres. For example, a linear range of distances from 100 cm to 50 cm corresponds to a range of dioptric distances of 1 D to 2 D, respectively.

The optical and/or visual performance of the human eye may be limited by one or more optical and/or visual factors. Some of the factors may include monochromatic and polychromatic optical wavefront aberrations and the retinal sampling which may impose a Nyquist limit on spatial vision. Some other factors may include the Stiles-Crawford effect and/or scattering. These factors or combinations of these factors may be used to determine retinal image quality (RIQ), according to certain embodiments. For example, retinal image quality (RIQ) may be obtained by measuring wavefront aberrations of the eye with or without a correcting lens in place using appropriate adjustments using factors such factors as Stiles Crawford effect if required. As disclosed herein, various ways of determining RIQ may also be used such as, but not limited to, a simple Strehl ratio, point spread function, modulation transfer function, compound modulation transfer function, phase transfer function, optical transfer function, Strehl ratio in spatial domain, Strehl ratio in Fourier domain, or combinations thereof.

Visual acuity, as used herein, may sometimes be used as a measure of an aspect of visual performance. Visual acuity measurement evaluates the limit when a visual target, such as a letter, or a letter "E" ('illiterate' E) or a letter "C" (Landolt C), or some other target, may no longer be resolved, identified or correctly reported by the patient who is undertaking the visual acuity measurement. The limit is related to, among other factors, the spatial frequency or spatial frequencies (how finely spaced the visual target details are) of the visual target and the contrast of the visual target. The limit of visual acuity may be reached when the contrast of the image of the visual target, created by the optics of an eye with or without additional optical devices, is too low to be discerned by the visual system (including the retina, visual pathway and visual cortex).

The model eye used to evaluate the performance of certain exemplary embodiments is Escudero-Navarro model eye with modifications to the lenticular surfaces to make it substantially aberration-free. However, the present disclosure is not limited to particular model eyes. Other model eyes may be used to evaluate the performance of embodiments disclosed herein. Some examples of such model eyes are:

a) A single refractive surface reduced model eye encompassing an anterior corneal surface and a retinal surface, wherein an intra-ocular fluid with a certain refractive index separates the above two surfaces;
b) A reduced model eye with two refractive surfaces, which may be formed by addition of a posterior corneal surface to the model eye described in (a);
c) A reduced model eye with three refractive surfaces, which may be formed by addition of two lenticular surfaces are added to the model eye (a) and the refractive index between the two lenticular surfaces being substantially greater than the refractive index of the intra-ocular fluid;
d) A model eye with four refractive surfaces, for example, Lotmar's model eye, Liou-Brennan's model eye, or Gullstrand's model eye;
e) One of the model eyes discussed from (a) to (d), wherein one of the surfaces disclosed may be substantially spherical;
f) One of the model eyes discussed from (a) to (d), wherein one of the surfaces may be substantially non-spherical;

the posterior surface of the lens is propagated to the retinal space by adapting a two-dimensional Fourier transformation.

Section 1

Retinal Image Quality (RIQ)

With use of a wavefront aberrometer, such as a Hartmann-Shack instrument, the optical characteristics of a candidate eye with or without refractive correction, model eye with or without refractive correction can be measured so as to identify a measure of retinal image quality (RIQ). In some examples, the model eye used may be a physical model that is anatomically, optically equivalent to an average human eye. In certain examples, the RIQ can be calculated via optical calculation methods like ray-tracing and/or Fourier optics. Several measures of RIQ are described herein.

(A) Strehl Ratio

Once the wavefront aberration of the candidate eye is availed, the image quality at the retina of the eye can be determined by computing the simple Strehl ratio, as described in the Equation 1. In certain applications, the image quality at the retina of the eye may be characterised by calculating a simple Strehl ratio as illustrated in Equation 1. The Strehl ratio can be computed in both spatial domain (i.e. using Point spread function as shown below in the equation 1(a))) and in Fourier domain (i.e. using Optical transfer function as shown below in equation 1(b)). The Strehl ratio measure is bound between 0 and 1, where 1 is associated with best achievable image quality. In certain embodiments, the image quality produced by a lens and/or device at its focal distance may be calculated without the use of model eyes. For example, equations 1(a) and 1(b) may also be used without a model eye.

$$\text{Strehl's ratio in spatial domain} = \frac{\int\int_{-\infty}^{+\infty}\left(\left|FT\left\{A(\rho,\theta)*\exp\left[\frac{2\pi i}{\lambda}*W(\rho,\theta)\right]\right\}\right|^2\right)}{\int\int_{-\infty}^{+\infty}\left(\left|FT\left\{A(\rho,\theta)*\exp\left[\frac{2\pi i}{\lambda}*Wdiff(\rho,\theta)\right]\right\}\right|^2\right)} \quad \text{Equation 1(a)}$$

$$\text{Strehl's ratio in spatial domain} = \frac{\int\int_{-\infty}^{+\infty}\left(\left|FT\left(\left|FT\left\{A(\rho,\theta)*\exp\left[\frac{2\pi i}{\lambda}*W(\rho,\theta)\right]\right\}\right|^2\right)\right|\right)}{\int\int_{-\infty}^{+\infty}\left(\left|FT\left(\left|FT\left\{A(\rho,\theta)*\exp\left[\frac{2\pi i}{\lambda}*Wdiff(\rho,\theta)\right]\right\}\right|^2\right)\right|\right)} \quad \text{Equation 1(b)}$$

g) One of the model eyes discussed from (a) to (d), wherein one of the surfaces may be substantially aspherical;
h) One of the model eyes discussed from (a) to (d), wherein one of the surfaces may be substantially decentred or tilted;
(i) A modified model eye (d), wherein the refractive index in between the lenticular surfaces may be considered to have gradient-refractive index; and
(j) Personalised model eyes based upon the characteristic features measured of a particular human eye or a selected group of human eyes.

The performance of some exemplary embodiments may be evaluated without ray-tracing through the combination of optical device, lens and the selected model eye, but instead with use of Fourier optics wherein the wavefront defined at

(B) Monochromatic RIQ

U.S. Pat. No. 7,077,522 B2 describes a vision metric called the sharpness metric. This metric can be computed by convolving a point spread function with a neural quality function. Further, U.S. Pat. No. 7,357,509 describes several other metrics to gauge optical performance of the human eye. One such RIQ measure is the visual Strehl Ratio, which is calculated in the frequency domain. In certain applications, the RIQ measure is characterised by visual Strehl Ratio which is calculated in the frequency domain. The visual Strehl Ratio in the frequency domain is described by Equation 2 and is bound between 0 and 1, where 1 is associated with best achievable image quality at the retina. This metric addresses monochromatic aberrations.

monochromatic $RIQ$ in frequency domain =      Equation 2

$$\frac{\iint_{-\infty}^{+\infty} CSF(f_x, f_y) * \left(\text{real}\left(FT\left(\left|FT\left\{A(\rho,\theta) * \exp\left[\frac{2\pi i}{\lambda} * W(\rho,\theta)\right]\right\}\right|^2\right)\right)\right)}{\iint_{-\infty}^{+\infty} CSF(f_x, f_y) * \left(FT\left(\left|FT\left\{A(\rho,\theta) * \exp\left[\frac{2\pi i}{\lambda} * Wdiff(\rho,\theta)\right]\right\}\right|^2\right)\right)}$$

The RIQ measure of monochromatic visual Strehl Ratio shows high correlation with objective and subjective visual acuity. This measure may be used to describe RIQ in certain disclosed embodiments. However, other measures described herein and alternatives thereto may be used in the design of optical devices, lenses and/or methods.

(C) Polychromatic RIQ

The visual Strehl Ratio defined by Williams, discussed above, addresses monochromatic light. To accommodate for polychromatic light, a metric called the polychromatic retinal image quality (polychromatic RIQ) is defined that includes chromatic aberrations weighed with spectral sensitivities for selected wavelengths. The polychromatic RIQ measure is defined in Equation 3. In certain applications, the polychromatic RIQ measure may be used to describe RIQ which is characterised by Equation 3.

polychromatic $RIQ =$      Equation 3

$$\frac{\iint_{-\infty}^{+\infty} CSF(f_x, f_y) * \sum_{\lambda min}^{\lambda max} \left(S(\lambda) * \left(\text{real}\left(FT\left(\left|FT\left\{A(\rho,\theta) * \exp\left[\frac{2\pi i}{\lambda} * W(\rho,\theta)\right]\right\}\right|^2\right)\right)\right)\right)}{\iint_{-\infty}^{+\infty} CSF(f_x, f_y) * \sum_{\lambda min}^{\lambda max} \left(S(\lambda) * \left(\left(FT\left(\left|FT\left\{A(\rho,\theta) * \exp\left[\frac{2\pi i}{\lambda} * Wdiff(\rho,\theta)\right]\right\}\right|^2\right)\right)\right)\right)}$$

(D) Monochromatic Global RIQ

The visual Strehl Ratio or monochromatic RIQ discussed herein and in sub-section B primarily addresses on-axis vision. As used herein, unless the context clearly requires otherwise, 'on-axis' is a reference to one or more of the optical, visual or papillary axis. To accommodate for wide angle view (i.e. peripheral visual field), a metric called the global retinal image quality (GRIQ) is defined that includes range of visual field eccentricities. A monochromatic GRIQ measure is defined in Equation 4. In certain applications, the monochromatic GRIQ measure is characterised by Equation 4.

monochromatic Global $RIQ$ in frequency domain =      Equation 4

$$\frac{\int_{\alpha min}^{\alpha max}\int_{\varphi min}^{\varphi max}\left\{\iint_{-\infty}^{+\infty} CSF(f_x,f_y) * \text{real}(FT(|FT\{A(\rho,\theta)*\exp[\frac{2\pi i}{\lambda}*W(\rho,\theta)]\}|^2))\right\}d\varphi d\lambda}{\int_{\alpha min}^{\alpha max}\int_{\varphi min}^{\varphi max}\left\{\iint_{-\infty}^{+\infty} CSF(f_x,f_y) * \left(FT\left(\left|FT\{A(\rho,\theta)*\exp[\frac{2\pi i}{\lambda}*Wdiff(\rho,\theta)]\}\right|^2\right)\right)\right\}d\varphi d\lambda}$$

(E) Polychromatic Global RIQ

One other form of RIQ metric that accommodates for polychromatic light and wide angle view (i.e. peripheral visual field), a metric is called the polychromatic global retinal image quality (GRIQ) is defined that includes chromatic aberrations weighed with spectral sensitivities for selected wavelengths and range of visual field eccentricities. A polychromatic GRIQ measure is defined in Equation 5. In certain applications, the polychromatic GRIQ measure is characterised by Equation 5.

polychromatic Global $RIQ =$      Equation 5

$$\frac{\int_{\alpha min}^{\alpha max}\int_{\varphi min}^{\varphi max}\left\{\iint_{-\infty}^{+\infty} CSF(f_x,f_y) * \sum_{\lambda min}^{\lambda max}\left(S(\lambda)*\left(\text{real}\left(FT\left(\left|FT\{A(\rho,\theta)*\exp[\frac{2\pi i}{\lambda}*W(\rho,\theta)]\}\right|^2\right)\right)\right)\right)\right\}d\varphi d\lambda}{\int_{\alpha min}^{\alpha max}\int_{\varphi min}^{\varphi max}\left\{\iint_{-\infty}^{+\infty} CSF(f_x,f_y) * \sum_{\lambda min}^{\lambda max}\left(S(\lambda)*\left(\left(FT\left(\left|FT\{A(\rho,\theta)*\exp[\frac{2\pi i}{\lambda}*Wdiff(\rho,\theta)]\}\right|^2\right)\right)\right)\right)\right\}d\varphi d\lambda}$$

In Equations 1 to 5:
- f specifies the tested spatial frequency, this can be in the range of $F_{min}$ to $F_{max}$ (denoting the boundary limits on the spatial frequency content), for example $F_{min}$=0 cycles/degree; $F_{max}$=30 cycles/degree; $f_x$ and $f_y$ specifies the tested spatial frequency in x and y directions;
- CSF ($f_x$, $f_y$) denotes a contrast sensitivity function, which in a symmetric form can be defined as CSF (F)=2.6 (0.0192+0.114*f)*exp$^{-(0.114*f)^{1.1}}$;
- FT denotes, in one form of the equation, a 2 D Fourier transform, for example, a 2 D fast Fourier transform;
- A($\rho$, $\theta$) and W($\rho$, $\theta$) denotes pupil amplitude function across the pupil diameter and wavefront of the test case, respectively;
- Wdiff($\rho$, $\theta$) denotes wavefront of the diffraction limited case;
- $\rho$ and $\theta$ are normalised polar coordinates, where p represents the radial coordinate and $\theta$ represents the angular coordinate or the azimuth;
- $\lambda$ denotes wavelength;
- $\alpha$ denotes field angle;
- $\phi$ denotes the meridian angle;
- S($\lambda$) denotes spectral sensitivity.

The wavefront, for example, can be written as a function set of standard Zernike polynomials up to a desired order, as described below, $$W(\rho, \theta) = \sum_{i=1}^{k} a_i Z_i(\rho, \theta)$$

Where, $\alpha_i$ denotes the $i^{th}$ coefficient of Zernike polynomial
$Z_i(\rho, \theta)$, denotes the $i^{th}$ Zernike polynomial term
'k', represents the highest term of the expansion These polynomials can be represented in the Optical Society of America format or Malacara format or other available Zernike polynomial expansion formats. Apart from the Zernike method of constructing the wavefront and/or wavefront phase, other non-Zernike methods of wavefront construction may also be adopted, i.e., Fourier expansion, Taylor expansion, Bessel functions, even polynomials, odd polynomials, sum of sine, sum of cosine, super conics, Q-type aspheres, B-splines, wavelets or combinations thereof. Spectral sensitivity functions may be selected for use in equation 5, for example, from population average; specific lighting conditions such as photopic, mesopic or scotopic conditions; sub-population averages such as a specific age group; a specific individual or combinations thereof.

(F) Global RIQ Metric Integrated Myopic Impetus Exposure Time

The factors discussed herein with regard to RIQ variants include one or more of the following: wavefront aberration, chromaticity and spectral sensitivity, Stiles-Crawford effect of the first kind, and optical and/or visual performance in the peripheral retina. Another factor that may be included is the amount of time spent at various accommodative states on an average day (the daily amount of near work), also known as the myopic impetus exposure time, T (A). This provides the following GRIQ variant:

$$\int_{Amin}^{Amax} T(A) * GRIQ(dA) \quad \text{Equation 6}$$

(G) Other Possible RIQ Measures

As discussed herein, other measures of RIQ may also be used in the design of devices, lenses and/or methods. One example of an alternative RIQ measure is simple modulation transfer function (MTF). Referring to Equation 2, a polychromatic MTF is formed by computing the modulus of real part of the optical transfer function and in addition excluding the step of convolution with the CSF function. A monochromatic MTF is formed if S ($\lambda$) is also removed from Equation 2.

Other measures of RIQ used in the designs of devices, lenses and/or methods may include multifocal benefit ratio. Referring to Equation 2, a multifocal benefit ratio metric may be computed by dividing the RIQ metric for the design with the RIQ metric obtained for a single vision lens. This multifocal benefit ratio may further be computed at various dioptric vergences, thereby providing through-focus multifocal benefit ratio.

No of phase reversals may be included as one other measure of RIQ used in the designs of devices, lenses and/or methods. The number of phase reversals metric may be obtained from the phase transfer function. The phase transfer function is obtained as the inverse tangent angle of imaginary part of the optical transfer function divided by the real part of the optical transfer function. Non-linear optimisation routines may be deployed to find designs solutions that reduce the number of phase reversals across a range of dioptric vergence.

Another measure of RIQ that may be used in the designs of devices, lenses and/or methods is to include a Phase transfer function information in the monochromatic RIQ or the visual Strehl ratio calculations. For example, one method of including phase transfer information in the visual Strehl ratio calculations is to convolve the real part of the optical transfer function in the Equation 2 with cosine of the phase transfer function as described in the equation 7.

monochromatic $RIQ$ in frequency domain with $PTF =$ Equation 7

$$\frac{\int\int_{-\infty}^{+\infty} CSF(f_x, f_y) * \cos(PTF(f_x, f_y)) * \text{real}\left(FT\left(\left|FT\left\{A(\rho, \theta) * \exp\left[\frac{2\pi i}{\lambda} * W(\rho, \theta)\right]\right\}\right|^2\right)\right)}{\int\int_{-\infty}^{+\infty} CSF(f_x, f_y) * \cos(PTF(f_x, f_y)) * \left(FT\left(\left|FT\left\{A(\rho, \theta) * \exp\left[\frac{2\pi i}{\lambda} * Wdiff(\rho, \theta)\right]\right\}\right|^2\right)\right)}$$

Another measure of RIQ that may be used in the designs of devices, lenses and/or methods is to include a weighted contrast sensitivity function and weighted phase transfer function information in the monochromatic RIQ calculations.

monochromatic $RIQ$ in frequency domain with weighted $PTF$ and $CSF =$ Equation 8

$$\frac{\int\int_{-\infty}^{+\infty} (a * CSF(f_x, f_y)) * (b * \cos(PTF(f_x, f_y))) * \text{real}\left(FT\left(\left|FT\left\{A(\rho, \theta) * \exp\left[\frac{2\pi i}{\lambda} * W(\rho, \theta)\right]\right\}\right|^2\right)\right)}{\int\int_{-\infty}^{+\infty} (a * CSF(f_x, f_y)) * (b * \cos(PTF(f_x, f_y))) * \left(FT\left(\left|FT\left\{A(\rho, \theta) * \exp\left[\frac{2\pi i}{\lambda} * Wdiff(\rho, \theta)\right]\right\}\right|^2\right)\right)}$$

where a and b are weights applied to CSF ($f_x$, fy) and PTF ($f_x$, fy) respectively.

Another measure of RIQ that may be used in the designs of devices, lenses and/or methods is to include individualised contrast sensitivity function for a particular human eye.

monochromatic *RIQ* in frequency domain for a particular human eye =  Equation 9

$$\frac{\int\int_{-\infty}^{+\infty}(\text{Indv\_CSF}(f_x, f_y)) * \cos(PTF(f_x, f_y)) * \text{real}\left(FT\left(\left|FT\left\{A(\rho, \theta) * \exp\left[\frac{2\pi i}{\lambda} * W(\rho, \theta)\right]\right\}\right|^2\right)\right)}{\int\int_{-\infty}^{+\infty}(\text{Indv\_CSF}(f_x, f_y)) * \cos(PTF(f_x, f_y)) * \left(FT\left(\left|FT\left\{A(\rho, \theta) * \exp\left[\frac{2\pi i}{\lambda} * Wdiff(\rho, \theta)\right]\right\}\right|^2\right)\right)}$$

Where Indv_CSF is contrast sensitivity function of a particular human eye for which the optical device, lens and/or method is being applied.

Other measures of RIQ that may be used in the designs of devices, lenses and/or methods may include two dimensional correlation analysis in spatial domain. Two dimensional correlation analysis in spatial domain is performed by obtaining the correlation coefficient when the point spread function of the optimised design is correlated with the point spread function of the diffraction limited system. Such correlation coefficients may be obtained for numerous configurations spanning various pupil diameters and/or distance ranges. The correlation coefficient obtained may range from −1 to 1, where values close to −1 indicates high negative correlation, values close to 0 indicate poor correlation and values close to 1 indicate high positive correlation. For the purpose of the correlation analysis, simulated images may be used for correlation analysis that are obtained by convolving point spread function with the objects in image space.

Other measures of RIQ that may be used in the designs of devices, lenses and/or methods may include two dimensional correlation analysis in frequency domain. Two dimensional correlation analysis in frequency domain is performed by obtaining the correlation coefficient when the optical transfer function of the optimised design is correlated with the optical transfer function of the diffraction limited system. Such correlation coefficients may be obtained for numerous configurations spanning various pupil diameters and/or distance ranges. The correlation coefficient obtained may range from −1 to 1, where values close to −1 indicates high negative correlation, values close to 0 indicate poor correlation and values close to 1 indicate high positive correlation. For the purpose of the correlation analysis, one of the following input variables may be selected: real part of optical transfer function, imaginary part of optical transfer function, modulation transfer function and phase transfer function.

Section 2

Through Focus RIQ

RIQ may also be considered anterior and/or posterior to the retina. The RIQ anterior and/or posterior to the retina is called 'through focus RIQ' herein and abbreviated as TFRIQ herein. Similarly, RIQ at and/or around the retina may also be considered over a range of focal lengths (i.e., when the eye accommodates, which causes changes in refractive characteristics of the eye in addition to the focal length to change). Certain embodiments may consider not only RIQ at the retina, but also the change in through focus RIQ. This is in contrast to an approach that may, for example, consider only the RIQ at the retina and/or an integral or summation of RIQ measures at or around the retina. For example, certain embodiments of the lenses, devices and/or methods disclosed herein effect, or are designed to effect for an eye with particular refractive characteristics, a change in or control over the extent or rate of change in RIQ in the directions anterior to the retina (i.e., the direction from the retina towards the cornea) and/or posterior to the retina. Certain embodiments may also effect, or are designed to effect, a change in or control over the variation in RIQ with focal distance. For example several candidate lens designs may be identified through effecting a change in the RIQ in the direction posterior to the retina and then a single design or subset of designs may be identified taking account of variation in RIQ with change in focal length. In certain embodiments, the process described above is reversed. In particular, a set of designs is selected based on changes in RIQ at the retina with focal distance. Selection within the set is then made with reference to the TFRIQ. In certain embodiments, a single evaluation process is conducted that combines consideration of TFRIQ and changes of RIQ at the retina with the focal distance. For example, an average measure of RIQ with changes in focal distance may be used to identify a design. The average measure may give more weight to particular focal distances (e.g. distance vision, intermediate vision and near vision and therefore may be weighted differently).

For example, an average measure of RIQ with changes in focal distance may be used to identify a design that may be used with certain devices, lenses and/or methods disclosed herein. For example, a measure of RIQ averaged over a range of focal distances. The average measure may be a weighted average measure that may give more weight or emphasis to particular focal distances (e.g. distance vision, intermediate vision and near vision and therefore may be weighted differently).

RIQ may also be considered anterior and/or posterior to the retina. The RIQ anterior and/or posterior to the retina is called 'through focus RIQ' herein and abbreviated as TFRIQ. Similarly, RIQ at and/or around the retina may also be considered over a range of focal lengths. For example, when the eye accommodates, which causes changes in refractive characteristics of the eye its focal length also changes. Certain embodiments may consider not only RIQ at the retina, but also the change in through focus RIQ. This is in contrast to an approach that may, for example, consider only the RIQ at the retina and/or an integral or summation of RIQ measures at or around the retina. For example, certain embodiments of the lenses, devices and/or methods disclosed herein effect, or are designed to effect for, an eye with particular refractive characteristics, a change in or control over the extent or rate of change in RIQ in the directions anterior to the retina (i.e., the direction from the retina towards the cornea) and/or posterior to the retina. Certain embodiments may also effect, or are designed to effect, a change in or control over the variation in RIQ with focal distance. For example, several candidate lens designs may be identified through effecting a change in the RIQ in the direction posterior to the retina and then a single design or subset of designs may be identified taking account of variation in RIQ with change in focal distance. In some embodiments, the process described above is reversed. In particular, a set of designs is selected based on changes in RIQ at the retina with focal distance. Selection within the set is then made with reference to the TFRIQ. In some embodiments, a single evaluation process is conducted that combines consideration of TFRIQ and changes of RIQ at the retina with the focal distance. For example, an average measure of RIQ with changes in focal distance may be used to identify a design that may be used with certain devices, lenses and/or methods disclosed herein. The average measure may give more weight to particular focal distances (e.g., distance vision, intermediate vision and near vision and therefore may be weighted differently). In certain embodiments, through focus and/or changes of RIQ at the retina with focal distance are considered for one or more of the following: i) on-axis, ii) integrated around on-axis, for example in an area corresponding to or approximating a pupil size, with or without consideration of the Stiles-Crawford effect, iii) off-axis (where off-axis means a location, set of locations and/or integral of locations on the retina outside the fovea, which may be where light at field angles more than about 10 degrees is focussed), and iv) one or more combinations of i) to iii). In certain applications, the field angles are about 15 or more, 20 or more, 25 or more or 30 or more degrees.

While the description herein refers to quantitative measures of RIQ, qualitative measures may also be used to assist the design process of an aberration profile in addition to the quantitative measures. For example, the visual Strehl Ratio at a particular through focus location is computed or determined based on the point spread function. As can be seen from the example images referred to in the following section, the point spread function can be visually evaluated. This provides for a method of qualitatively evaluating through focus.

In some embodiments, an image quality produced by a lens and/or device at its focal distance is computed without the use of a model eye. The image quality produced by a lens and/or device may be calculated anterior and/or posterior to the focal distance of the lens and/or device. The image quality anterior and/or posterior to the focal distance may be referred to as through focus image quality. The through-focus range has a negative and a positive power end relative to the focal distance.

Section 3

Aberrations Affecting Image Quality at the Retina and TFRIQ

The influence of lower order aberrations on RIQ and TFRIQ is known in the art. The use of corrective lower order aberrations represents a traditional method of refractive error correction for an eye. Accordingly, the identification of an aberration profile consisting of lower order aberrations to correct for defocus and astigmatism will not be described herein in detail.

Figure 3:
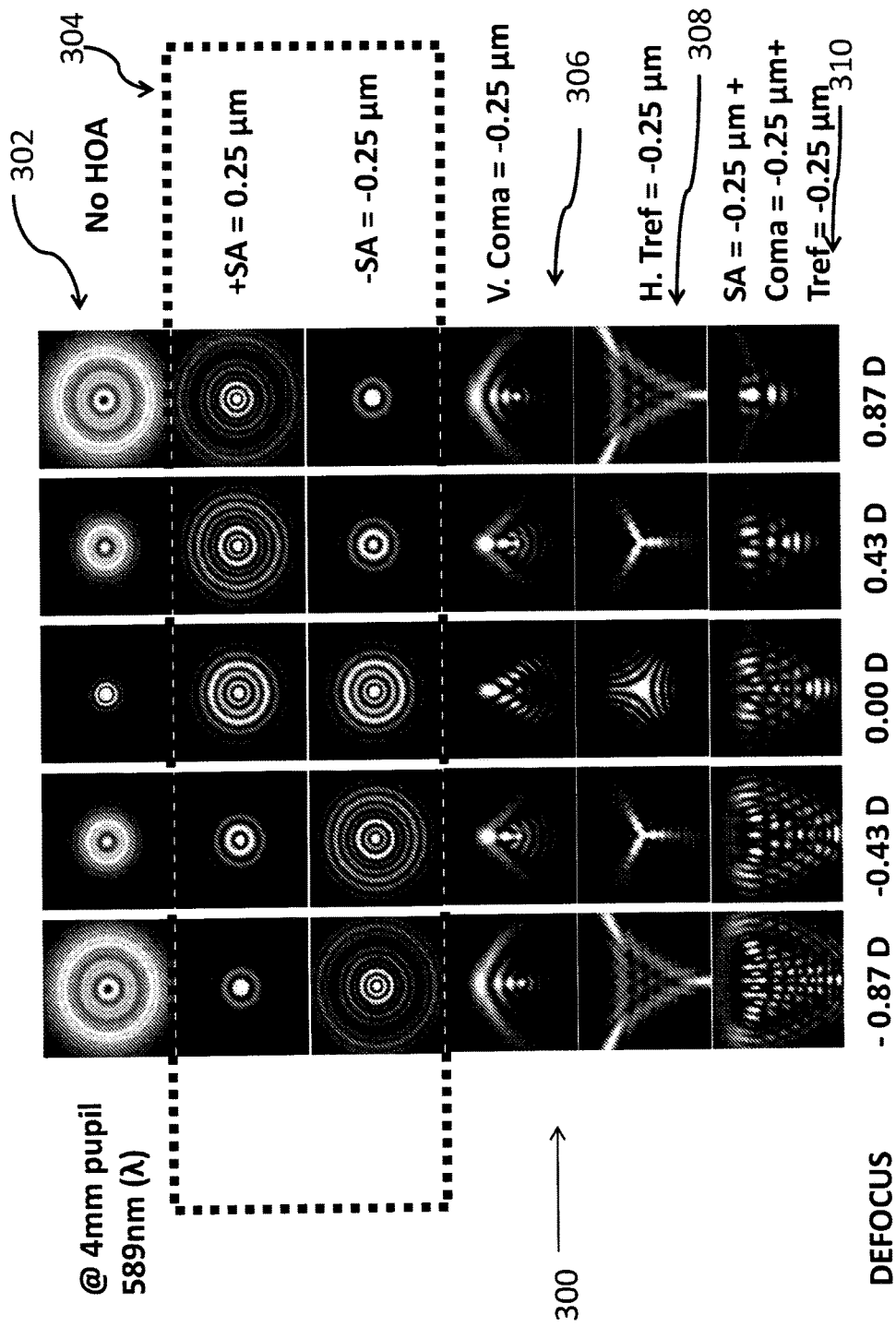
FIG. 3 shows a two-dimensional through-focus point spread function computed at the retinal plane without higher order aberrations (HOA) and in the presence of HOA of spherical aberration, vertical coma and horizontal trefoil, according to certain embodiments.

The influence of higher order aberrations (HOA) on image quality is demonstrated in FIG. 3 from the through-focus two-dimensional point spread functions (300). In FIG. 3 the rows show the point spread functions for a selection of aberrations and the horizontal axis shows the extent of defocus for the relevant aberration, in Dioptres.

Exemplary HOA on image quality are illustrated in FIG. 3, according to certain embodiments. This is illustrated by the through-focus two-dimensional point spread functions 300 illustrated in FIG. 3. In FIG. 3, the rows show the point spread functions for a selection of aberrations and the horizontal axis shows the extent of defocus for the certain relevant aberration, in Dioptres.

The point spread functions without higher order aberrations 302 (in the illustrated example images at the retina in an eye with myopia or hyperopia alone), with vertical coma 306 alone, and with horizontal trefoil 308 alone, remain symmetrical with positive and negative defocus. With positive and negative primary spherical aberrations, either alone 304 or in combination 310 with coma and/or trefoil, the through-focus in the point spread function is asymmetrical for positive and negative defocus. With certain HOA positive and negative defocus has unequal effects on the image quality. It can be seen that these unequal effects are more pronounced for spherical aberrations. The HOA that exhibit asymmetrical effects on RIQ, visual acuity and/or contrast sensitivity have application certain of the lenses, devices and/or methods disclosed herein.

The interactions occurring between HOA and defocus influence the TFRIQ. Some HOA interact favourably with defocus to improve RIQ, while others interact unfavourably to cause RIQ degradation. The most commonly measured higher order ocular aberrations include spherical aberration, coma and trefoil. Apart from these, the HOA profiles obtained with some multifocal optical designs precipitate considerable magnitudes of wavefront aberrations, often expressed up to the 10th order in Zernike polynomial representation.

In general terms, in the Zernike pyramid, the terms closer to the centre are often more influential, or useful, when gauged in terms of the resultant optical effects than those at the edge/corner. This may be because the terms farther away from the centre have a relatively large planar area on the wavefront compared to those whose angular frequency is closer to zero. In certain applications, Zernike terms that have the highest potential, or substantially greater potential, to interact with defocus are, for example, the terms with even radial order having zero angular frequency component, i.e., the fourth, sixth, eighth, and tenth order Zernike coefficients, representing primary, secondary, tertiary and quaternary, spherical aberrations. Other Zernike coefficients representing other order of spherical aberration may also be used.

The foregoing description of aberrations identifies some of the aberrations that affect retinal RIQ and through focus RIQ. The description is not, nor is it intended to be, an exhaustive description of the various aberrations that affect retinal RIQ and through focus RIQ. In various embodiments, additional aberrations that affect the retinal RIQ and/or through focus RIQ may be considered, the relevant aberrations being identified having regard to the current refractive state of the ocular system (meaning the eye together with lenses or optical devices that affect the wavefront received by the retina) and a target retinal RIQ/through focus RIQ.

Section 4

Optimising RIQ

When designing and/or selecting a required change in refractive state of an eye, a measure of RIQ and through focus RIQ is typically performed for certain disclosed embodiments. In particular, finding a magnitude and sign of defocus that interacts with one or more of the relevant aberrations and produce an acceptable RIQ and through focus RIQ is typically performed. The search is performed for the best or at least an acceptable combination of RIQ and through focus RIQ. In certain embodiments, the selected combination is determined by evaluating the RIQ and the through focus RIQ and selecting the combination that is suitable, substantially optimised, or optimised for the application. In certain embodiments described herein, a merit function $S=1/RIQ$ is used for this purpose. In certain embodiments, the approximation of a merit function S=1/RIQ may be used for this purpose.

Identifying aberration coefficients that optimise, or substantially optimise, RIQ at the retina may be achieved, in certain embodiments; by finding a minimum, or substantially minimum, value of the function S. Considering the RIQ optimisation routine over a range of dioptric distances (through-focus) adds complexity to the optimisation process. Various methods can be used to address this complexity.

One example is to use a non-linear, unconstrained optimization routine, over the chosen group of Zernike SA coefficients as variables, according to certain embodiments. A random element, either automatic and/or through human intervention may be incorporated to shift to different locations so as to find alternative local minima of the function S. The criteria by which the optimisation routine evaluates performance may be a combination of retinal RIQ and keeping the through focus RIQ within predefined bounds of the retinal RIQ. The bounds may be defined in various ways, for example as a range about the value for retinal RIQ. The range may be fixed (e.g. plus or minus 0.15 for visual Strehl ratio or similar measure), or may vary (e.g. be within a defined rate of change with increasing distance from the retina). In certain embodiments, the range may be fixed to one or more of the following ranges: plus or minus 0.05, or plus or minus 0.1 or plus or minus 0.15. These ranges may be used with one or more of the following: a simple Strehl ratio, point spread function, modulation transfer function, phase transfer function, optical transfer function, Strehl ratio in Fourier domain, or combinations thereof.

As explained in more detail herein, the goal function for TFRIQ may change depending on whether the objective of the merit function is to provide a TFRIQ with a slope that provides stimulus either to inhibit or to encourage eye growth of the candidate eye, under an optical feedback explanation of emmetropisation, at least in certain embodiments. In certain other applications, for example correction to ameliorate presbyopia, the objective of the merit function is to provide a TFRIQ with an acceptable low slope in magnitude or a slope that substantially equal to zero. In certain other presbyopic embodiments, a slope with acceptably low in magnitude for TFRIQ may be considered from one or more of the following: a) slope of TFRIQ about zero, b) slope of TFRIQ equal to zero, c) slope of TFRIQ greater than zero and less than 0.25 per dioptre, d) slope of TFRIQ greater than −0.25 and less than zero per dioptre, e) slope of TFRIQ greater than zero and less than 0.5 per dioptre or f) slope of TFRIQ greater than −0.5 and less than zero per dioptre.

Another approach is to limit the number of possible combinations of aberration profiles. One way of limiting the possible aberration values is to specify that the Zernike coefficients can only have values corresponding to increments of 0.05 μm focus, or another increment interval. In certain embodiments, the Zernike coefficients may have values corresponding to increments of about 0.01 μm, about 0.02 μm, about 0.03 μm, about 0.04 μm or about 0.05 μm. In certain embodiments, the Zernike coefficients may have values corresponding to increments of 0.01 μm, 0.02 μm, 0.03 μm, 0.04 μm or 0.05 μm. In certain embodiments, the Zernike coefficients may have values corresponding to from increments selected within one or more following ranges: 0.005 μm to 0.01 μm, 0.01 μm to 0.02 μm, 0.02 μm to 0.03 μm, 0.03 μm to 0.04 μm, 0.04 μm to 0.05 μm, or 0.00 μm to 0.05 μm. The interval can be selected having regard to the available computational resources. By limiting the number of allowable coefficient values it is possible to simulate the performance of a substantial portion of the aberration profiles formed by the combinations of Zernike coefficients, following which those with the best or acceptable on-axis RIQ and through focus RIQ can be identified. The results of this process may be used to constrain more fine-tuned analysis, for example by returning to an optimisation routine with coefficient values within a small range around an identified candidate combination of higher order aberrations.

Section 5

Controlling Stimulus for Emmetropisation by Optical Feedback

A person may be identified as being at risk of developing myopia based on, for example, one or more of the following indicators, including whether their parents experienced myopia and/or myopia, their ethnicity, lifestyle factors, environmental factors, amount of near work, etc. Other indications or combinations of indicators may also be used, according to certain embodiments. For example, a person may be identified as being at risk of developing myopia if their eye and/or eyes have a RIQ at the retina that improves in the direction of eye growth. The RIQ can be obtained either with or without refractive correction that is currently in use (for example: with or without a current prescription of spectacle or contact lens). In certain embodiments, the use of improving RIQ in the direction of eye growth may be used alone or in conjunction with one or more other indicators, for example the other indicators listed herein.

From one perspective, the emmetropisation process can be explained under an optical feedback mechanism that is based on RIQ at the retina and/or the slope of TFRIQ in the anterior-posterior direction to the retina. According to this perspective on emmetropisation, the candidate eye is stimulated to grow to the position where the merit function S of the optimisation routine is minimised or substantially minimised. Under this explanation of emmetropisation process, at least for human eyes, if the location of a local, or the global minimum of the merit function S, then the eye may be stimulated to grow longer, in certain embodiments. In yet another application, the substantial minimum of the merit function optimisation routine may be a local minimum or global minimum. In other applications, if the location of a local or the global minimum of the merit function S is posterior to the retina or if through focus RIQ improves posterior to the retina, then the eye may be stimulated to grow longer. For example, if the location of a local or the global minimum of the merit function S is located on the retina or anterior to the retina, then the eye may remain at the same length.

The following description herein describes how combinations of selected HOA can affect a change in through focus RIQ. These aberrations can readily be incorporated into a lens, optical device and/or used in a method of changing the aberration profile of the wavefront of the incoming light received by the retina.

In certain embodiments, characterizations of these aberrations can readily be incorporated into a lens, optical device and/or used in a method of changing the aberration profile of the wavefront of the incoming light received by the retina. This provides a mechanism by which certain embodiments may change the refractive state of a candidate eye. In certain embodiments, the lens, optical device and/or method will at least include the aberration characteristics of the embodiments to alter the refractive state of a candidate eye.

As described in more detail herein, achieving a target TFRIQ is considered together with achieving or obtaining substantially closer to a target on-axis RIQ at the retina for a particular focal length, which is typically distance vision, in certain embodiments, In certain applications, one or more of the following are referred as distance vision is objects greater than 6 meters. In other applications, a target TFRIQ may be considered for another focal length alternative to distance vision, for example intermediate vision or near vision. In some applications, intermediate vision may be defined as the range from about 0.5 to 6 meters. In some applications, near vision may be defined as the range from 0.3 to 0.5 meters.

As described in more detail herein, achieving a target TFRIQ is considered together with achieving or obtaining substantially closer to a target on-axis RIQ at the retina for a particular focal distance, which is typically distance vision, One or more of the following may be referred to as distance vision objects greater than 6 meters. In some embodiments, a target TFRIQ may be considered for another focal distance alternative to distance vision, for example intermediate vision or near vision. In some embodiments, intermediate vision may be defined as the range from about 0.5 to 6 meters. In some applications, near vision may be defined as the range from 0.3 to 0.5 meters.

For the examples described herein the RIQ was evaluated, or characterised by, using the visual Strehl Ratio shown in Equation 2.

(A) Primary Spherical Aberration, Coma and Trefoil

The interactions between primary spherical aberration, coma and trefoil and their affect on eye growth can be described, or characterised by, using a wavefront phase function defined using defocus, primary spherical aberration (PSA), coma and trefoil terms of a standard Zernike expansion. Other ways are also possible.

The pupil size was fixed at 4 mm and the calculations were performed at 589 nm wavelength. For the purposes of evaluating affects of aberration profiles on ocular growth, it was assumed that a location of a minimum of the above described function S posterior to the retina provides a stimulus to grow to that location and that there will not be stimulus for eye growth if the minimum of the function S is on or in front of the retina. In other words, it is assumed that the image formed on the retina provides a stimulus to grow to minimise the function S. The range of values of PSA, horizontal and vertical coma, and horizontal and vertical trefoil that were used in the simulations are:

PSA=(−0.30, −0.15, 0.00, 0.15, 0.30) μm
Horizontal Coma=(−0.30, −0.15, 0.00, 0.15, 0.30) μm
Vertical Coma=(−0.30, −0.15, 0.00, 0.15, 0.30) μm
Horizontal Trefoil=(−0.30, −0.15, 0.00, 0.15, 0.30) μm and
Vertical Trefoil=(−0.30, −0.15, 0.00, 0.15, 0.30) μm.

With a total of 3125 combinations tested, overall it was observed that spherical aberration primarily governed the direction of improving RIQ.

FIGS. 4 to 7 illustrate the stimulus for eye growth resulting from TFRIQ for a selection of the combinations, in particular the combined effects of PSA together with horizontal and vertical coma, and together with horizontal and vertical trefoil, in accordance with certain embodiments. FIGS. 4 to 7 are on a continuous scale and white (0) indicates no progression and grey-to-black transition indicates the amount of progression in Dioptres.

Figure 4:
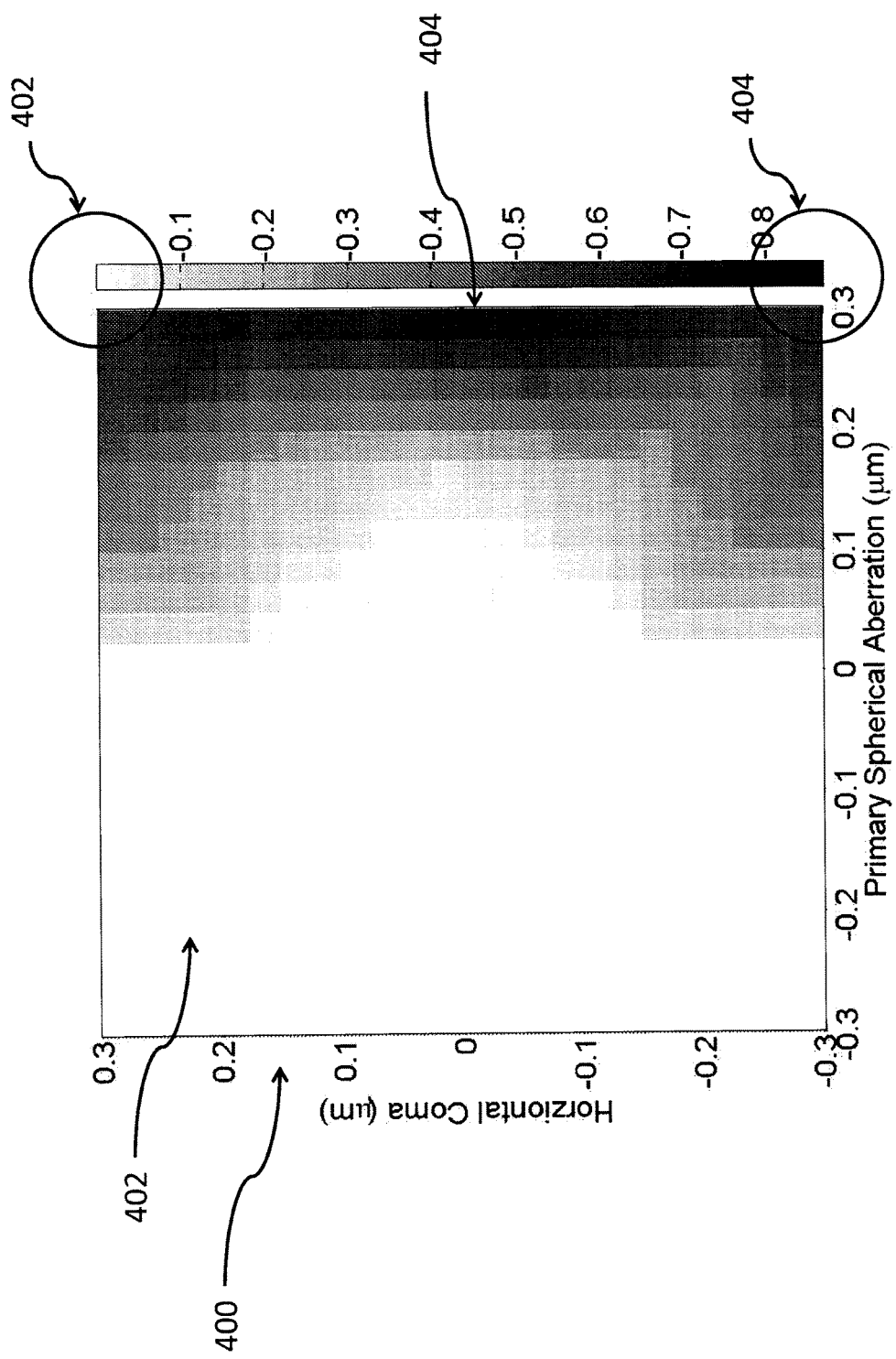
FIGS. 4 to 7 show graphs of the interaction of primary spherical aberration with horizontal coma, vertical coma, horizontal trefoil and vertical trefoil respectively, according to certain embodiments.
Figure 5:
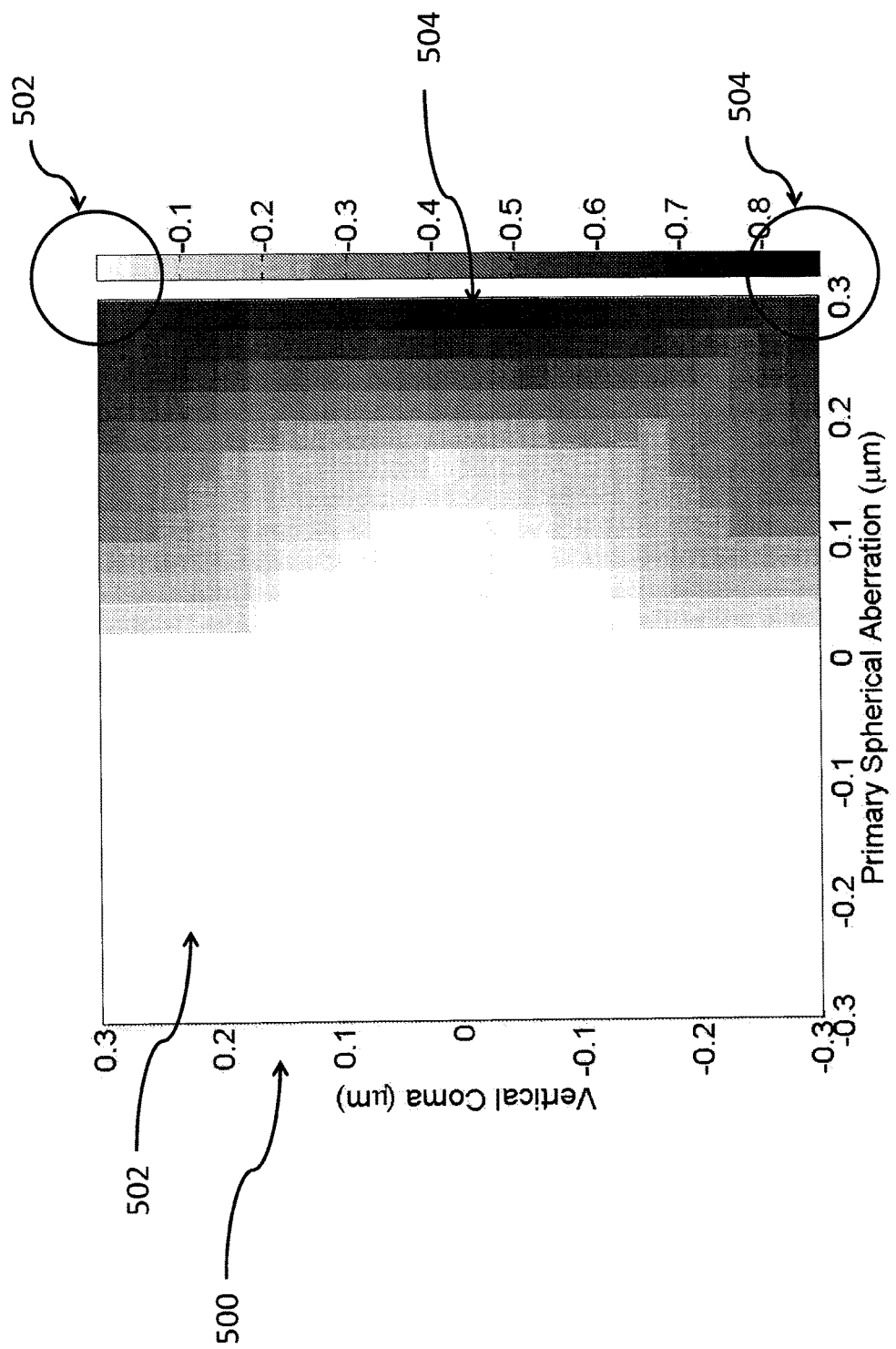
Figure 6:
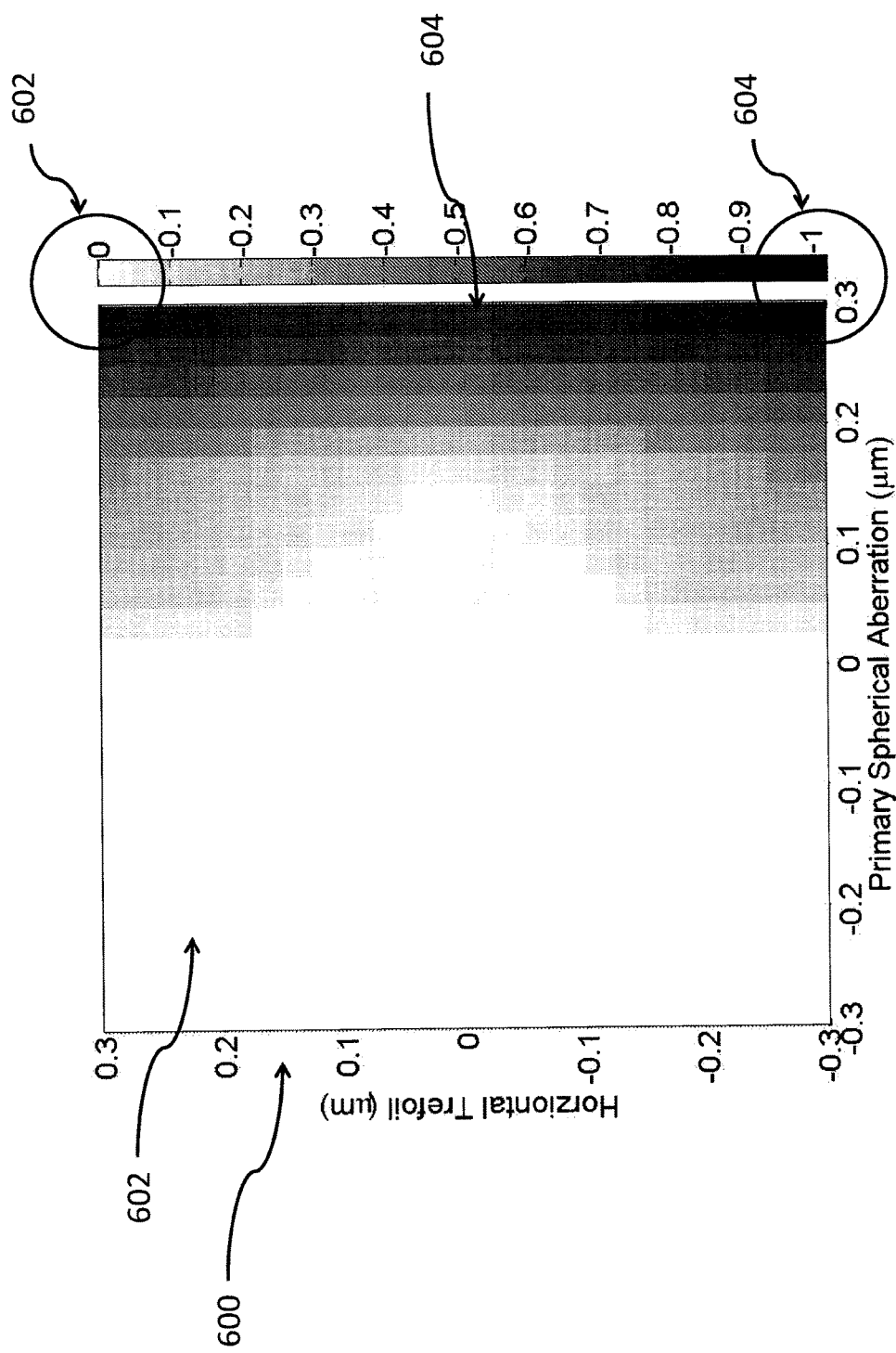
Figure 7:
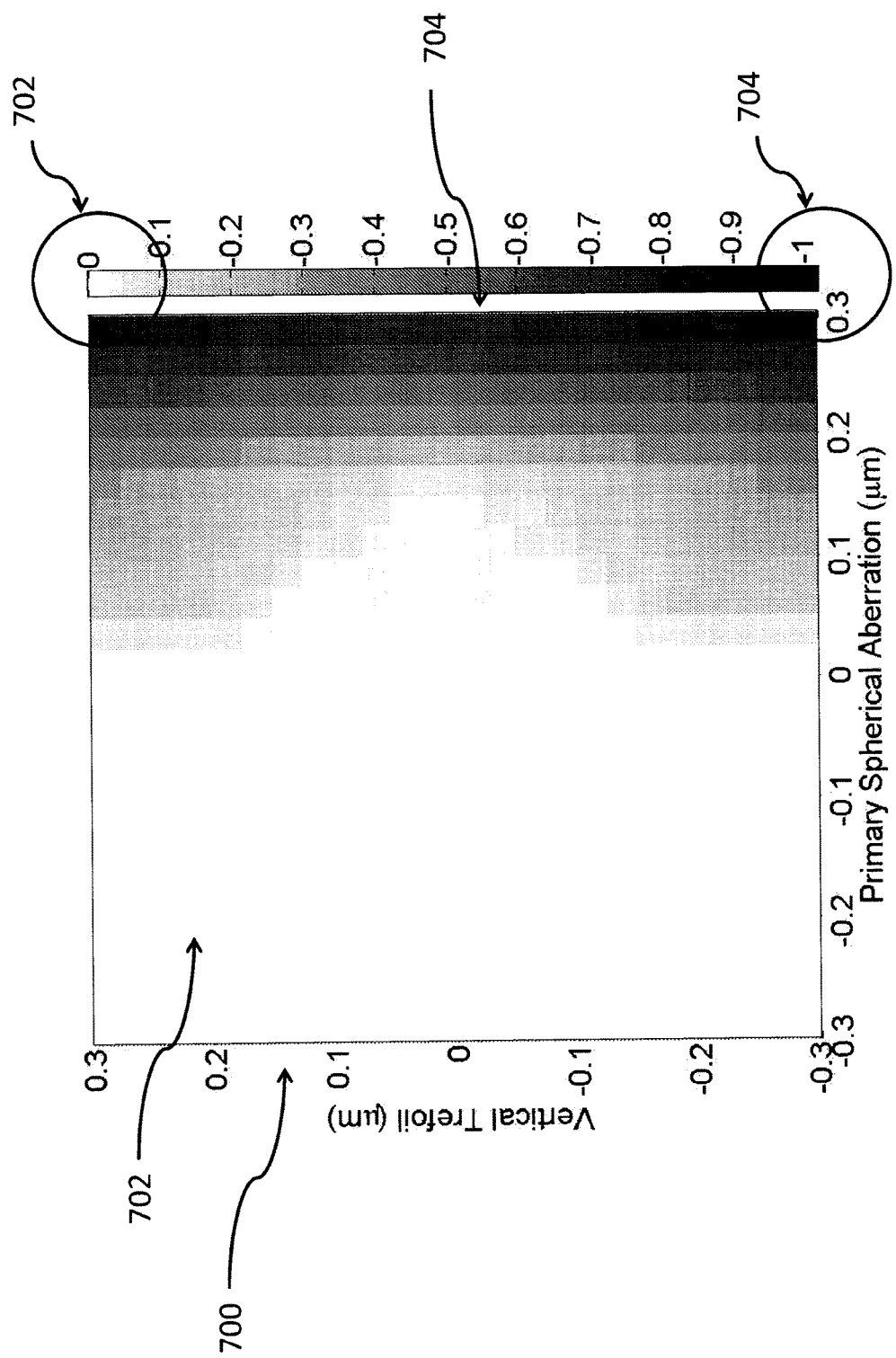

FIG. 4 shows a graph 400 of the interaction of primary spherical aberration and horizontal coma. The grey plot indicates the amount of progression of myopia that is stimulated by the combination of these two aberrations, where white 402 indicates no stimulus for progression and shades towards black 404 indicate stimulus for progression of myopia (in this case up to −0.8 D) as a result of PSA combined with horizontal coma. FIG. 5 shows a graph 500 of myopia progression as a function of the interaction of primary spherical aberration and vertical coma. Like in FIG. 4, white areas 502 indicate no stimulus for progression and dark areas 504 indicate stimulus for progression. FIG. 6 shows a graph 600 of the interaction of primary spherical aberration and horizontal trefoil. FIG. 7 shows a graph 700 of myopia progression as a function of the interaction of primary spherical aberration and vertical trefoil. For the combinations shown in FIGS. 4 to 7, about 52% of the combinations provide stimulus to encourage eye growth.

Stimulus for eye growth may accordingly be removed by controlling the refractive state of an eye to be within one or more of the white areas in FIGS. 4 to 7. This may be achieved, for example, by designing a lens or optical device that when applied modifies the refractive characteristics of the eye, to result in the retina of the eye experiencing a through focus RIQ that does not substantially improve, or does not improve, in the direction of eye growth (posterior to the retina) or which decreases in the direction of eye growth.

Although trefoil and coma in the range of −0.30 to 0.30 μm over a 4 mm pupil do not appear to have a significant impact on the direction of growth (the maximum progression effect is only −0.1 D), positive PSA seems to accelerate growth while negative PSA seems to inhibit growth. The PSA therefore appears to have the dominant effect. Accordingly, at least for an eye with positive PSA and optionally one of coma and trefoil, adding negative PSA may inhibit eye growth under the optical feedback explanation of emmetropisation. It follows that providing negative PSA to an eye, or at least removing positive PSA may remove the stimulus for eye growth. The coma and trefoil in the eye may be left unchanged or optionally partially or fully corrected (preferably within the range of −0.30 to 0.30 μm).

(B) Spherical Aberration and Astigmatism Interaction

To illustrate the interactions between primary spherical aberration and astigmatism, a wavefront phase function was defined using these aberrations (including both horizontal/vertical and oblique components) and defocus. FIGS. 8 to 13 (unlike FIGS. 4 to 7) are on a binary scale—where white (1) indicates test cases that cause stimulus for progression (i.e. increase in ocular growth) and black (0) indicates candidate combinations that result in no progression or very little progression (i.e., no ocular growth stimulus or a stop signal). The scale has no units. FIGS. 8 to 13 illustrate certain disclosed embodiments.

Figure 8:
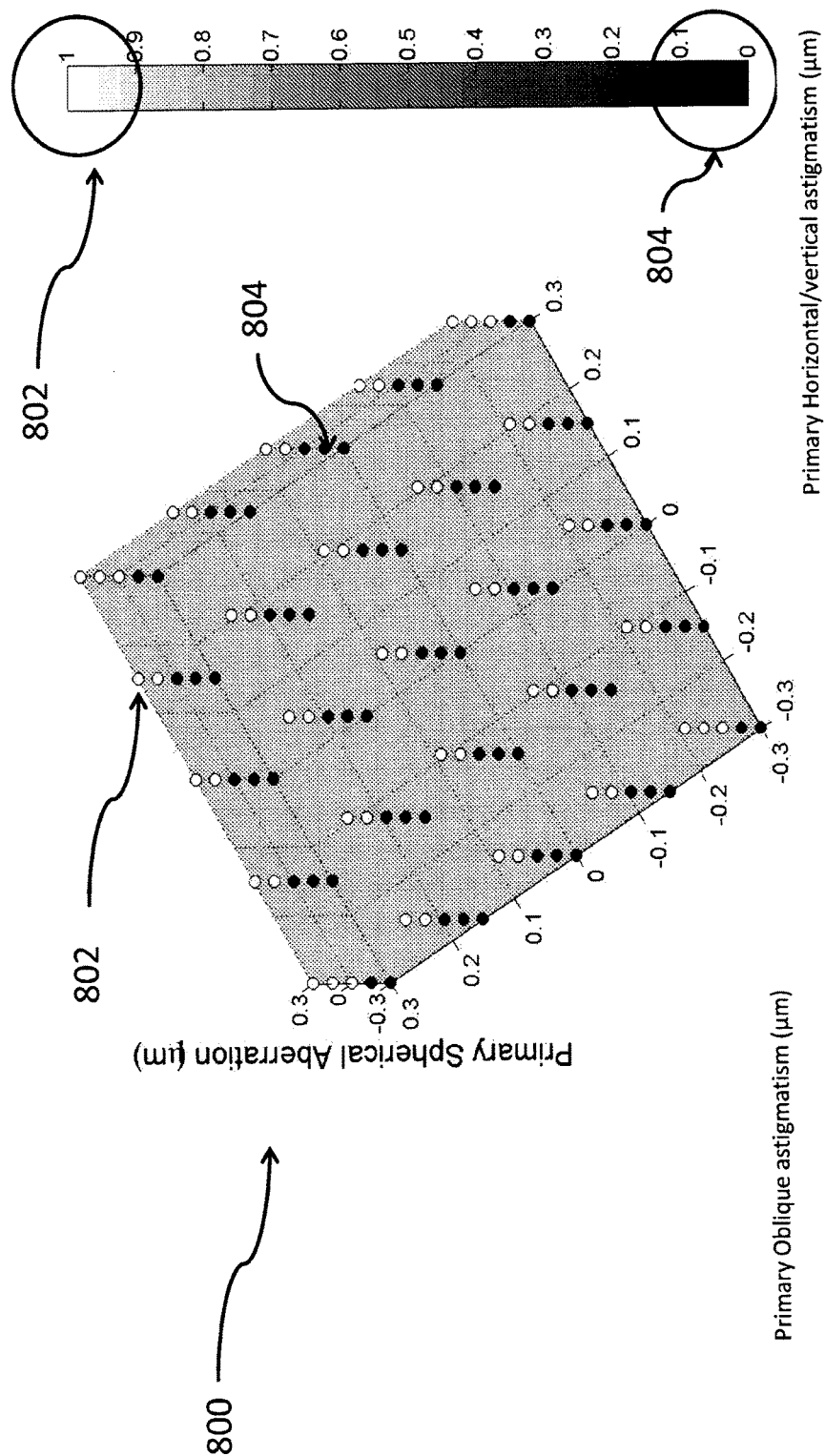
FIG. 8 shows a graph indicating the magnitude of myopia progression under an optical feedback mechanism for eye growth, for primary spherical aberration vs. primary vertical astigmatism vs. primary horizontal astigmatism, according to certain embodiments.

FIG. 8 is an exemplary that shows a graph 800 indicating the magnitude of myopia progression for PSA vs. a primary oblique astigmatic component (POA) vs. a primary horizontal/vertical astigmatic (PHV) component. In this example, the graph 800 indicates those combinations of PSA and astigmatism that may result in stimulus for myopia progression (white) and those combinations that will not result in stimulus for myopia progression (black). Neither POA nor PHV appear to have a significant impact on the effects of PSA.

Figure 9:
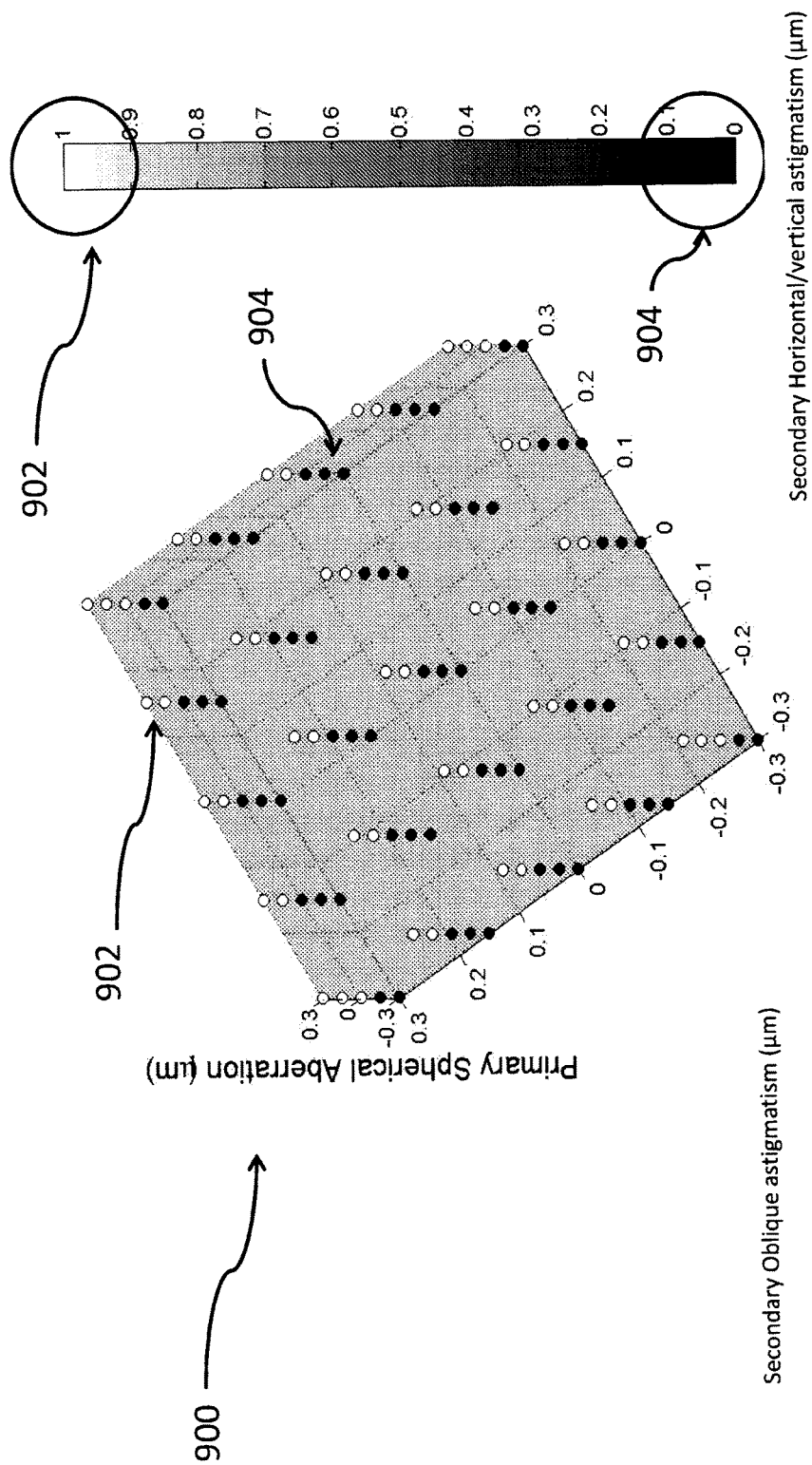
FIG. 9 shows a graph indicating the magnitude of myopia progression for primary spherical aberration vs. secondary vertical astigmatism vs. secondary horizontal astigmatism, according to certain embodiments.

FIG. 9 is an exemplary shows a graph 900 indicating the magnitude of myopia progression for PSA vs. a secondary oblique astigmatic (SOA) component vs. a secondary horizontal/vertical astigmatic (SHV) component, according to certain embodiments. In this example, neither SOA nor SHV appear to have a significant impact on the effects of PSA.

A stimulus for eye growth may accordingly be removed by controlling the refractive state of an eye to be within one or more of the white areas in FIGS. 8 and 9.

From FIGS. 8 and 9, is an exemplary, the primary and secondary astigmatic components seem to have, or have, a small influence on enhancing or inhibiting eye growth, when combined with PSA. Accordingly, considering these aberrations, this indicates priority may be provided to PSA. In addition, it may be determined whether the eye has high levels of POA, PHV, SOA and/or SHV. If this is the case, in this example, then correcting these aberrations (by reducing or substantially eliminating them) may also assist in removing stimulus for eye growth.

(C) Higher Order Spherical Aberrations

For unaided or single-vision spectacle corrected eyes a fourth order Zernike expansion may be used to describe, or characterise, the wavefront at the exit pupil. However, this may not necessarily the case when, for example, contact lenses are used for correction, especially with multifocal contact lenses (both aspheric and concentric), substantial amounts of fifth order and higher HOA may be used. Multifocal contact lenses may, for example, be described using up to about the tenth or twentieth order of Zernike polynomials. In such cases the magnitudes and signs of the higher order spherical aberrations start to play a significant role (in addition to PSA).

To illustrate the interactions between primary, secondary, tertiary and/or quatemrnary spherical aberrations of a standard Zernike expansion, a wavefront phase was defined using these terms and defocus. Several combinations of HOA as predicted from modelled data with such multifocal contact lenses were used. Selective sets of these HOA that demonstrate interactions to produce peak RIQ were obtained via dedicated non-linear optimization routines. The calculations were performed over a 4 mm pupil, and at 589 nm wavelength. It was observed that at least the first three modes of spherical aberration of the inherent eye played a role in governing the direction of stimulus for eye growth and in some cases higher modes of spherical aberration also played a role. In certain applications, these roles were significant.

The results described below relate to secondary spherical aberration (SSA), tertiary spherical aberration (TSA) and quaternary spherical aberration (QSA), but spherical aberrations with higher orders may also be used in embodiments of the lenses, devices and/or methods described herein.

For four types of spherical aberrations, a range from −0.30 to 0.30 μm was used to investigate the effects of the combinations of HOA. These ranges for these types of aberrations do not necessarily accord with normative distributions of aberrations associated with eyes because the occurrence of these higher order aberrations are not necessarily associated with the eyes but with the optical devices (such as multifocal contact lenses) alone or in combination with the eyes.

Furthermore, the range from −0.30 to 0.30 μm is merely used to illustrate the effects, but when determining combinations of HOA to provide an aberration profile in a lens or optical device, or to be effected by surgical procedures, larger or smaller ranges may be used.

Figure 10:
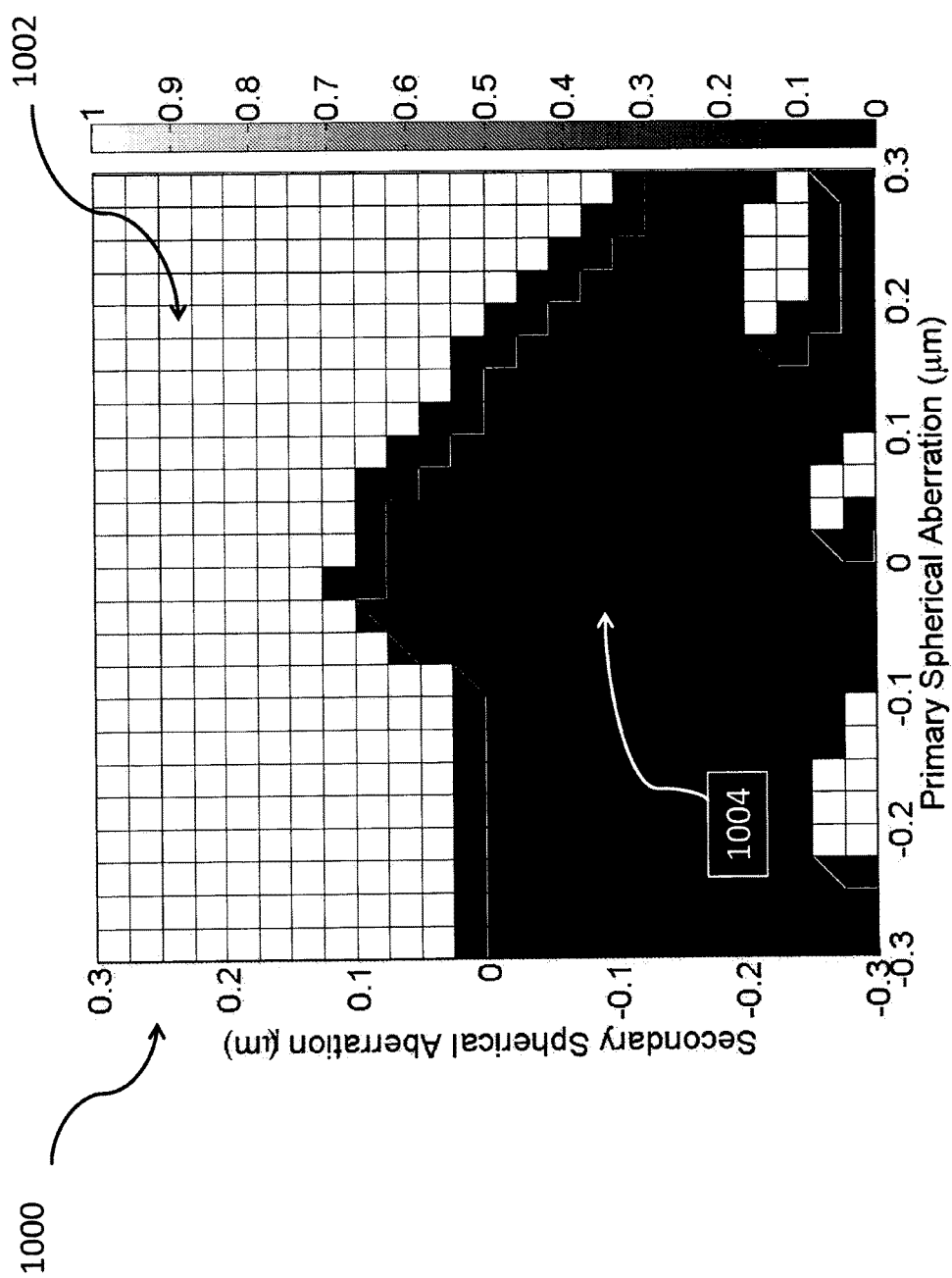
FIG. 10 shows a graph indicating the myopia progression on a binary scale for primary spherical aberration vs. secondary spherical aberration, according to certain embodiments.
Figure 11:
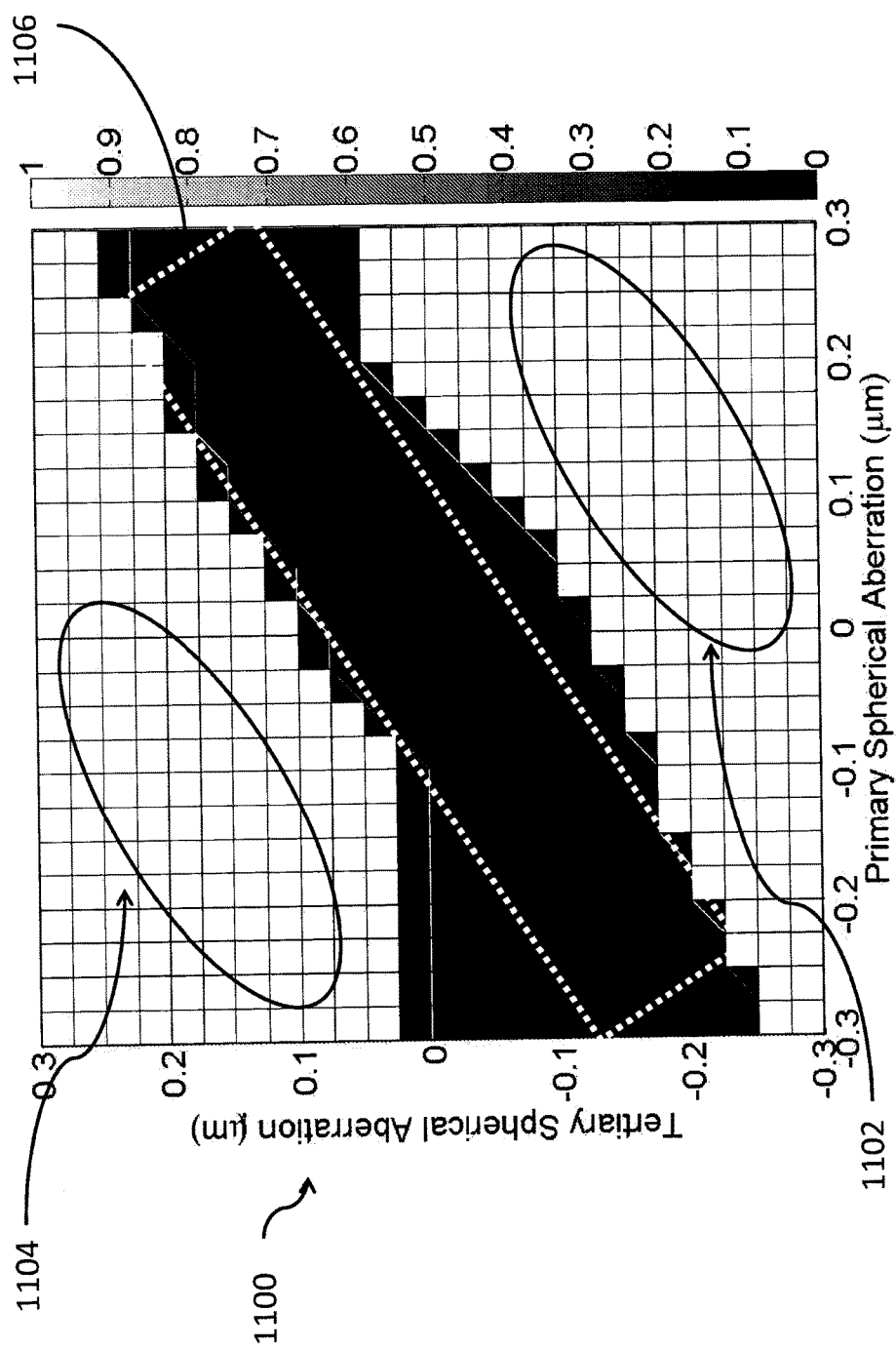
FIG. 11 shows a graph indicating the myopia progression on a binary scale for primary spherical aberration vs. tertiary spherical aberration, according to certain embodiments.
Figure 12:
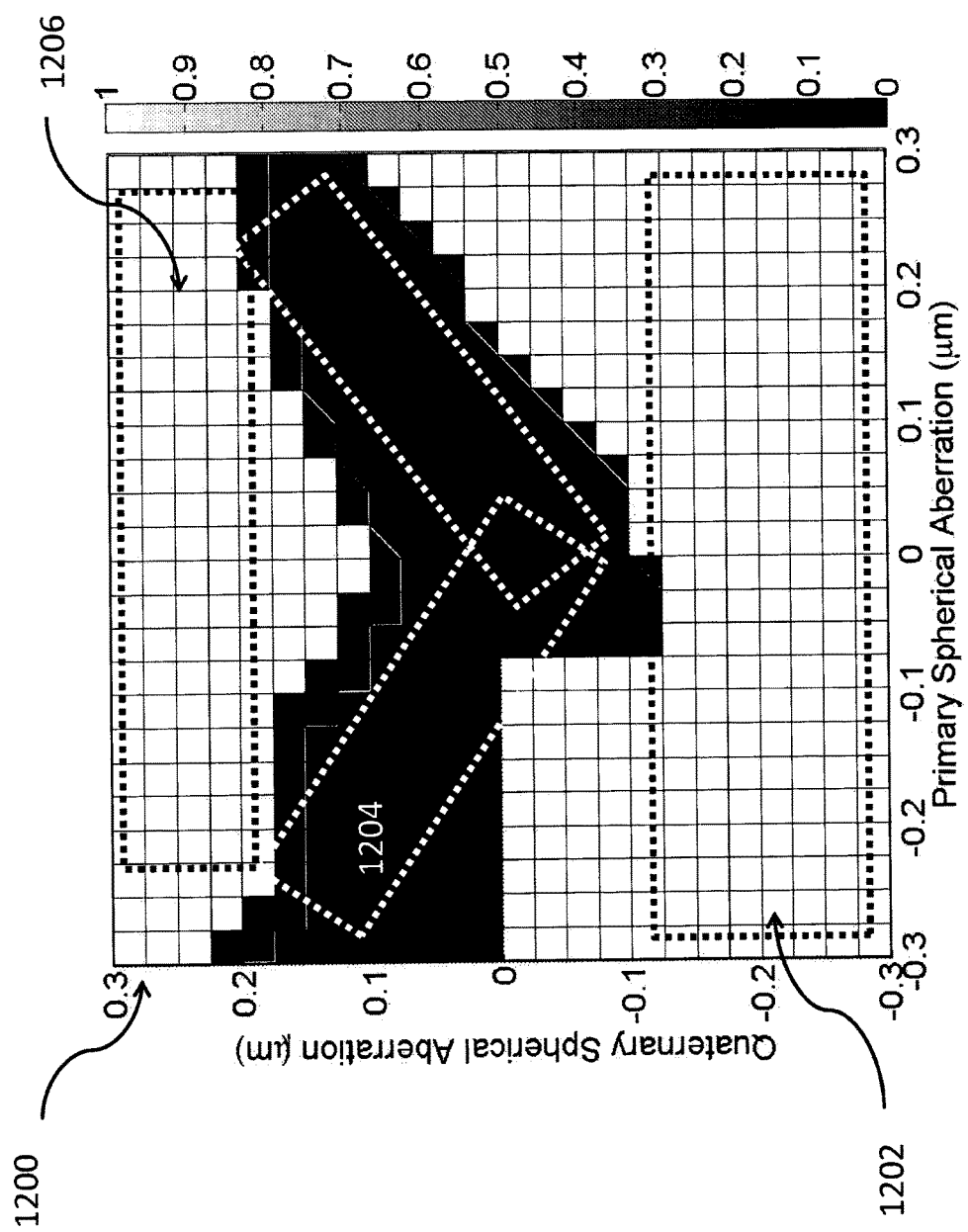
FIG. 12 shows a graph indicating the myopia progression on a binary scale for primary spherical aberration vs. quaternary spherical aberration, according to certain embodiments.

FIGS. 10 to 12 are exemplary that show the stimulus for myopia progression as a function of PSA together with SSA, TSA and QSA respectively, according to certain embodiments. In this example, this schema is a binary colour plot, where white (0) indicates wavefront aberration combinations that provide stimulus for myopia progression under the feedback mechanism described herein and black (1) indicates combinations that discourage myopia progression. From these graphs it is apparent that the higher orders of spherical aberrations have an impact on the stimulus for progression of myopia. In this example, about 82% of the combinations investigated suggest stimulus for eye growth. Interactions of the spherical aberration terms depend on their individual signs and then their individual magnitudes.

FIG. 10 is an exemplary that shows a graph 1000 indicating the presence of stimulus for myopia progression as a function of combinations of PSA and SSA, according to certain embodiments. In FIG. 10, it can be seen that when PSA in the range −0.30 μm to 0.20 μm is combined with negative SSA ranging from 0.00 to −0.30 μm, there is little or no improvement of RIQ in the direction of eye growth, thus no myopia progression is predicted (i.e. in the area indicated 1004). However, when PSA ranging from 0.20 to 0.30 μm is considered with negative SSA of about −0.10 μm, it seems to aggravate the progression, as indicated in the area 1002. Overall, the sign of SSA seems to have a governing effect on the effect of the wavefront aberrations and the resultant retinal image quality. In this example, negative SSA of considerable magnitudes (i.e. greater than −0.20 μm) predicts a protective effect against myopia progression when combined with either positive or negative PSA, when PSA and SSA are the only two HOA involved in the wavefront aberration of the candidate eye.

FIG. 11 is an exemplary that shows a graph 1100 indicating the presence of stimulus for myopia progression as a function of combinations of PSA and TSA, according to certain embodiments. When PSA and TSA have the same sign and TSA is about ⅘th of PSA in magnitude, as indicated by rectangular box 1106, no or little myopia progression is predicted (black area). However, in this example, with other combinations of PSA and TSA, for example as indicated in areas 1102 and 1104, myopia progression can be expected.

FIG. 12 is an exemplary that shows a graph 1200 indicating the presence of stimulus for myopia progression as a function of combinations of PSA and QSA, according to certain embodiments. In this example, when PSA and QSA have opposite signs and QSA is about ⅘th of PSA in magnitude, as indicated by the predominantly black area 1204, no myopia progression is predicted. However, with other combinations of PSA and QSA, (for example as indicated in white areas 1202 and 1206) myopia progression can be expected.

Figure 13:
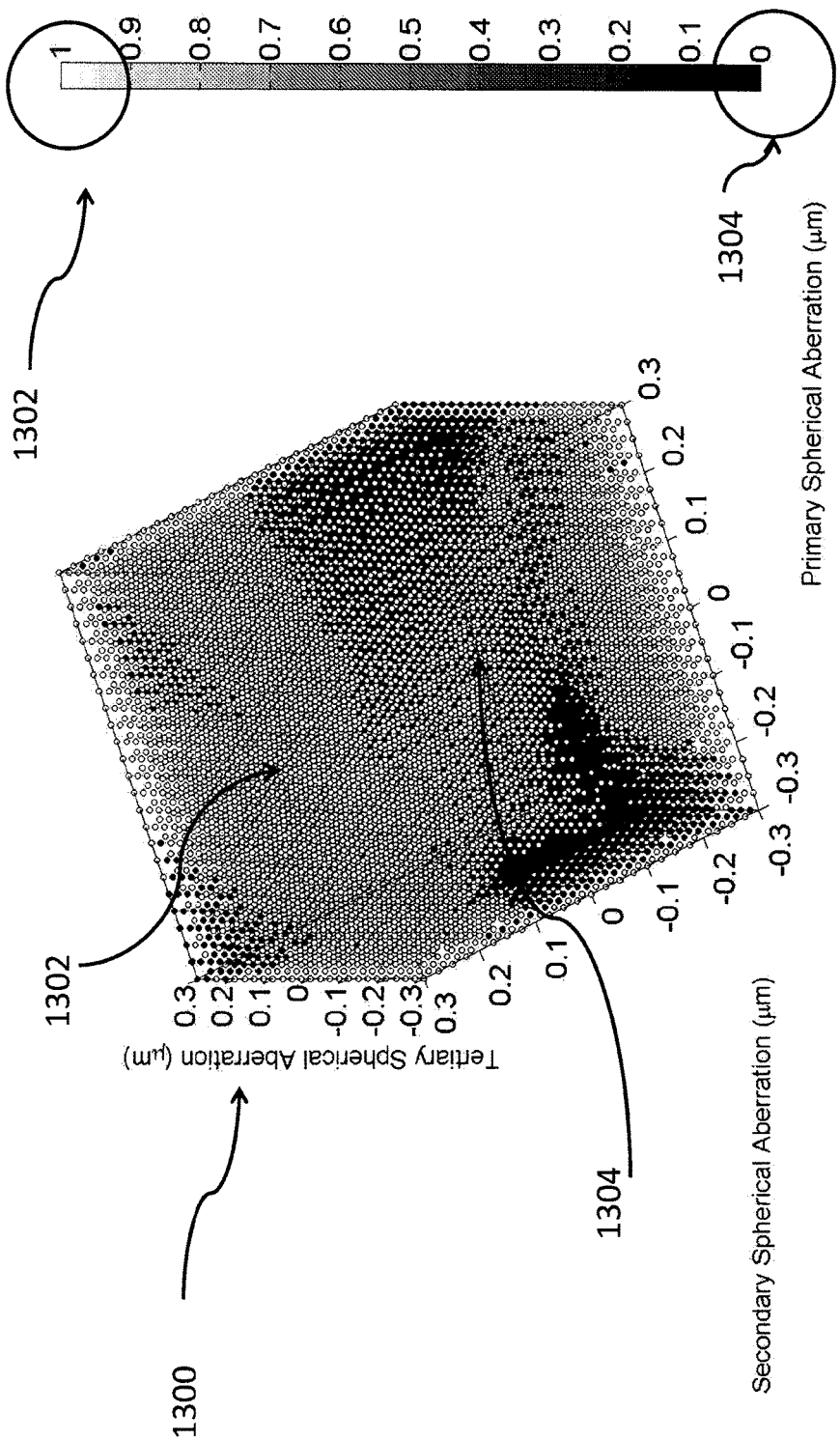
FIG. 13 shows a graph indicating the myopia progression on a binary scale for primary spherical aberration vs. secondary spherical aberration vs. tertiary spherical aberration, according to certain embodiments.

FIG. 13 is an exemplary that is a graph (1300) showing the presence of stimulus for progression of myopia as a function of PSA, SSA and TSA, according to certain embodiments. This schema is a binary colour plot, where 1 (white) indicates wavefront aberration combinations that favour myopia progression; while 0 (black) indicates combinations that discourage myopia progression (i.e. do not provide stimulus for eye growth).

TABLE 1

Combination sets of higher order aberrations which discourage the eye growth (i.e. potential treatment for myopia), according to certain embodiments.

| SNo | Specific higher order aberration in addition to defocus | Magnitude and sign of the higher order aberration |
|---|---|---|
| 1 | PSA only | $-0.30$ μm $<=$ PSA $< 0.125$ μm |
| 2 | SSA only | $-0.30$ μm $<=$ SSA $<= 0.075$ μm |
| 3 | TSA only | $-0.30$ μm $<=$ TSA $<= 0.075$ μm |
| 4 | QSA only | $-0.10$ μm $<=$ QSA $<= 0.075$ μm |
| 5 | PSA & SSA | $-0.30$ μm $<=$ PSA $<= 0.20$ μm and $-0.25$ μm $<=$ SSA $<= 0.025$ μm |
| 6 | PSA & TSA | $-0.30$ μm $<=$ PSA $<= 0.30$ μm and TSA $=$ (PSA/2) μm $+/- 0.075$ μm |
| 7 | PSA & QSA | $-0.30$ μm $<=$ PSA $<= 0.30$ μm and QSA $=$ (|PSA|/3) μm $+/- 0.075$ μm |
| 8 | PSA, SSA, TSA | $-0.30$ μm $<=$ PSA $< -0.05$ μm & $0.05$ μm $<$ PSA $< 0.30$ μm; $-0.30$ μm $<=$ SSA $< 0.05$ μm; $-0.20$ μm $<=$ TSA $< -0.025$ μm & $0.025$ μm $<$ TSA $< 0.20$ μm; |
| 9 | PSA, SSA, TSA and QSA | $-0.30$ μm $<=$ PSA $< -0.05$ μm & $0.05$ μm $<$ PSA $< 0.30$ μm; $-0.30$ μm $<=$ SSA $< 0.05$ μm; $-0.20$ μm $<=$ TSA $< -0.025$ μm & $0.025$ μm $<$ TSA $< 0.20$ μm; $-0.20$ μm $<=$ QSA $< -0.025$ μm & $0.025$ μm $<$ QSA $< 0.20$ μm; |

The majority of the black filled circles 1304 are in the region governed by negative SSA, with a few exceptions. Further, combinations in which PSA and TSA have the same sign coupled with negative SSA seem to provide a protective effect against myopia progression. The combinations of PSA, SSA, TSA and QSA that have a protective effect against myopia progression under the optical feedback explanation of emmetropisation (which include the black areas shown in FIG. 13) can be summarised as shown in the Table 1.

The majority of the white circles 1302 are in the region governed by positive SSA, with a few exceptions. Further, combinations in which the PSA and TSA have the same sign coupled with positive SSA may provide a treatment effect for hyperopia. The combinations of PSA, SSA, TSA and QSA that have a treatment effect against hyperopia under the optical feedback explanation of emmetropisation (including the white areas shown in FIG. 13) can be summarised as shown in the Table 2.

TABLE 2

Combination sets of higher order aberrations which encourage eye growth (i.e. potential treatment for hyperopia), according to certain embodiments.

| SNo | Higher order aberration in addition to defocus | Magnitude and sign of the higher order aberration |
|---|---|---|
| 1 | PSA only | $0.30$ μm $=>$ PSA $>= 0.125$ μm |
| 2 | SSA only | $0.30$ μm $=>$ SSA $> 0.075$ μm |
| 3 | TSA only | $0.30$ μm $=>$ TSA $> 0.075$ μm |
| 4 | QSA only | $-0.30$ μm $<=$ QSA $<= -0.125$ μm or $0.30$ μm $=>$ QSA $> 0.075$ μm |
| 5 | PSA & SSA | $-0.30$ μm $<=$ PSA $<= 0.30$ μm and $0.30$ μm $>=$ SSA $> 0.075$ μm |
| 6 | PSA & TSA | $-0.30$ μm $<=$ PSA $<= 0.30$ μm and (PSA/2) μm $+ 0.075$ μm $<=$ TSA $< 0.30$ μm or $-0.30$ μm $<=$ TSA $<$ (PSA/2) μm $- 0.075$ μm |
| 7 | PSA & QSA | $-0.30$ μm $<=$ PSA $<= 0.30$ μm and QSA in the range $-0.20$ to $0.20$ μm but excluding values where QSA $=$ (|PSA|/3) μm $+/- 0.075$ μm |
| 8 | PSA, SSA, TSA | $-0.30$ μm $<=$ PSA $< -0.05$ μm & $0.05$ μm $<$ PSA $< 0.30$ μm; $6.075$ μm $<=$ SSA $< 0.30$ μm; $-0.20$ μm $<=$ TSA $< -0.025$ μm & $0.025$ μm $<$ TSA $< 0.20$ μm; |
| 9 | PSA, SSA, TSA and QSA | $-0.30$ μm $<=$ PSA $< -0.05$ μm & $0.05$ μm $<$ PSA $< 0.30$ μm; $0.075$ μm $<=$ SSA $< 0.30$ μm; $-0.20$ μm $<=$ TSA $< -0.025$ μm & $0.025$ μm $<$ TSA $< 0.20$ μm; $-0.20$ μm $<=$ QSA $< -0.025$ μm & $0.025$ μm $<$ QSA $< 0.20$ μm; |

Accordingly, when designing a lens, optical device or method of altering the eye, the aberrations may be selected to provide a combination of the aforementioned aberrations that provide for either a protective effect against eye growth for example for myopia, or which encourage eye growth for example for hyperopia. The combination of aberrations may be applied in combination with the required correction of any myopic defocus or hyperopic defocus.

From the foregoing description, it is apparent that the spherical aberration terms, including the primary, secondary, tertiary and quaternary SA terms influence RIQ and through focus RIQ. In addition, it has been found that much higher orders of spherical aberration may also influence RIQ and through focus RIQ. In various embodiments different combinations of spherical aberration are used, including embodiments using combinations of two or more spherical aberration terms that provide a required or acceptable through focus RIQ profile, together with a required or acceptable RIQ at a particular focal length (e.g. distance vision). In certain embodiments, characterizations of one or more of the spherical aberrations may also be used.

Section 6

The Instantaneous Gradient of the Image Quality

The foregoing description of stimulus for eye growth can be explained under an optical feedback mechanism that is based on the location of a peak on-axis RIQ. In certain examples, another alternative approach considered to describe the stimulus for eye growth is via the slope of TFRIQ at the retina. In some embodiments, lenses, methods and/or devices utilise the gradient or slope of the RIQ to control myopia progression, with or without astigmatism. In other embodiments, lenses, methods and/or devices utilise the gradient or slope of the RIQ to treat hyperopia, with or without astigmatism. The gradient or slope of RIQ may be considered for one or more of the following variants of RIQ: a) monochromatic RIQ with or without considering effect of accommodation, b) polychromatic RIQ with or without considering effect of accommodation, c) global RIQ, d) RIQ considered with myopic impetus time signal, e) global RIQ with myopic impetus time signal, each of which is described herein.

In certain embodiments, the lenses, devices and/or methods disclosed herein may be applied to provide stimulus under this optical feedback mechanism explanation of emmetropisation. Embodiments for addressing eye growth under the optical feedback explanation of emmetropisation (e.g. to address myopia progression or to seek to stimulate eye growth to correct hyperopia) may use aberrations to affect one, two or more of the location of the minima, or substantial minima, of the function S relative to the retina and the gradient of the function S through the retina.

Figure 14:
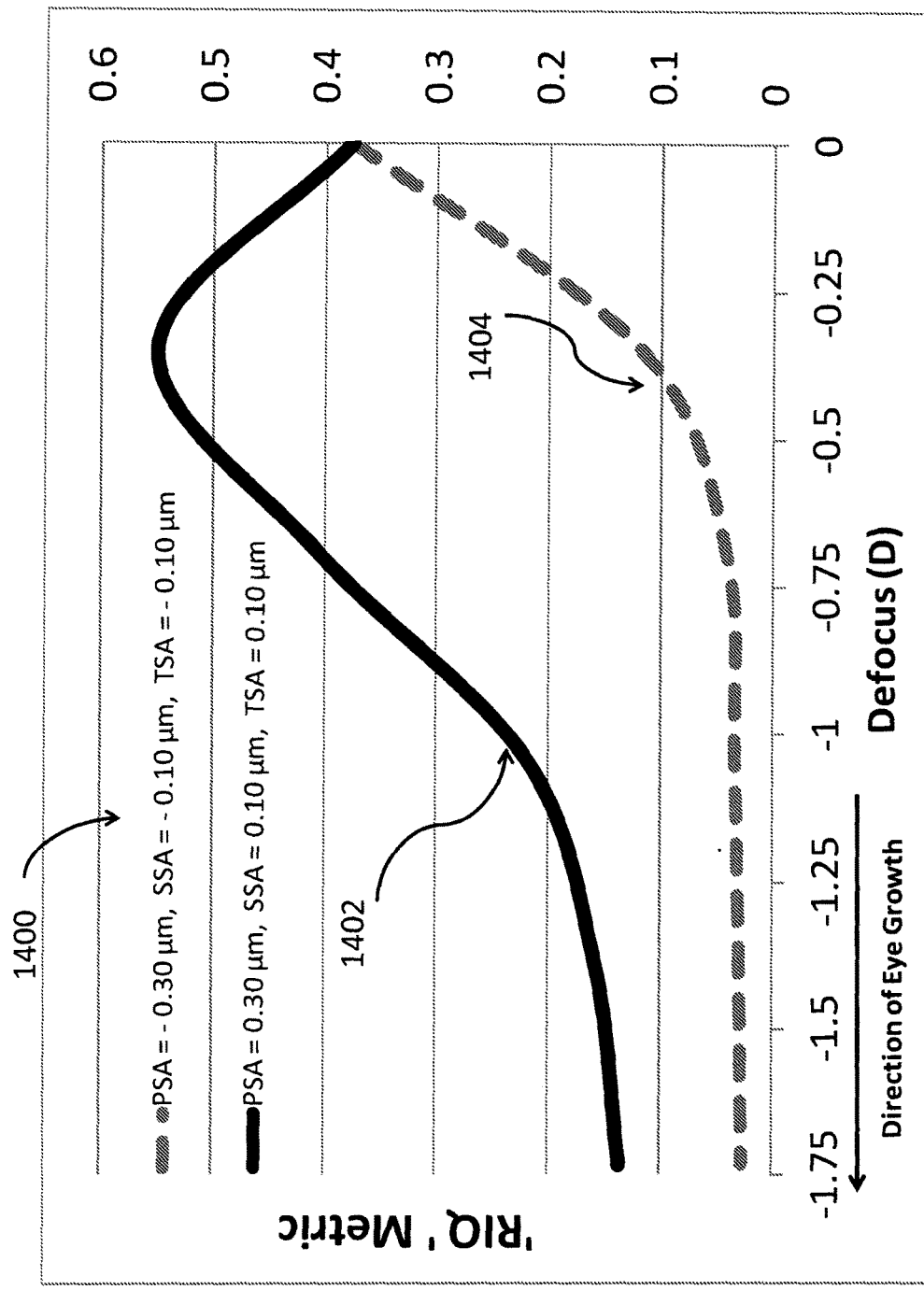
FIG. 14 shows example designs of aberration profiles that provide negative and positive gradient RIQ in a direction of eye growth, according to certain embodiments.

In the following description it is assumed that a positive measure of the gradient of the TFRIQ (increasing RIQ posterior to the retina) provides a stimulus for the development and progression of myopia, while a negative measure of the same retards or halts myopia progression. FIG. 14 is an exemplary that shows a plot of RIQ for two different cases, 1402 and 1404, as a function of through focus in the direction posterior to the retina, according to certain embodiments. The cases are two different combinations of PSA, SSA and TSA that produce identical, or substantially identical, retinal RIQ. As can be seen from the figure, although both sets of selected aberrations produce similar image quality at the retina (defocus=0), with the introduction of defocus (in the direction of eye growth) the retinal image quality of test case 1402 ramps up indicating stimulus for eye growth, while test case 1404 indicates that there would be no stimulus for growth, as the retinal image quality degrades further in the direction of eye growth.

From the results described herein that indicate the effects of HOA on image quality and the resulting progression of myopia, it is possible to determine the relevant HOA combinations that may be used in lenses, optical devices, and/or effected using optical surgery, which, where relevant in combination with the eye's aberrations, may result in the HOA combinations that inhibit or retard eye growth for the treatment of myopia progression. In order to slow down eye growth in myopia, compensating optical devices and/or surgical procedures may be used that, in combination with the optics of the eye, may result in a combination of HOA that results in a negative gradient of TFRIQ, as shown in example 1404 (FIG. 14). For treating hyperopia in certain applications, compensating optical devices and/or surgical procedures may be used that, in combination with the optics of the eye, may result in a combination of HOA that results in a positive gradient of TFRIQ, as shown in example 1402 (FIG. 14).

If an aberration profile has a varying RIQ across a through focus range, then the slope of through focus RIQ at a particular focal length may be changed by selecting a suitable defocus term C(2,0) with the considered RIQ profile. For example, if the slope is positive at a first level of through focus and negative at a second level of through focus, the slope at the retina of a recipient eye may be selected by selectively introducing defocus at either the first or second level. Examples of aberration profiles that have varying RIQ slopes at different levels of defocus are provided herein in relation to embodiments of aberration profiles for application to presbyopia. Many of the embodiments described for presbyopia may be applied to provide a stimulus to retard and/or encourage eye growth under the optical feedback explanation of emmetropisation described herein. Typically, younger people have progressing myopia and as such they may not be experiencing presbyopia. Accordingly, the aberration profile selected may place less weight on achieving high RIQ over a large through focus range and more weight on achieving the highest RIQ at the retina for distance vision in combination with providing a negative slope RIQ profile through the retina (i.e. decreasing RIQ in the direction of eye growth). For the young hypermetropes, again, the selected aberration profile may place less weight on achieving high RIQ over a large through focus range and more weight on achieving the highest RIQ at the retina for distance in combination with provision of a positive slope of RIQ profile behind the retina (in the direction of eye growth).

In certain embodiments, a lens, device and/or method may incorporate an aberration profile that provides, i) an acceptable on-axis RIQ; and ii) a through-focus RIQ with a slope that degrades in the direction of eye growth; to an eye with progressing myopia or an eye that is identified as at risk of developing myopia. In certain embodiments, the measure of acceptable on-axis RIQ can be considered from one or more of the following: on-axis RIQ of 0.3, on-axis RIQ of 0.35, on-axis RIQ of 0.4, on-axis RIQ of 0.45, on-axis RIQ of 0.5, on-axis RIQ of 0.55, on-axis RIQ of 0.6, on-axis RIQ of 0.65, or on-axis RIQ of 0.7. In certain embodiments, the candidate myopia eye may be considered with or without astigmatism.

In certain embodiments, a lens, device and/or method may incorporate an aberration profile that provides, i) an acceptable on-axis RIQ; and ii) a through-focus RIQ with a slope that improves in the direction of eye growth; to an eye with hyperopia. In certain embodiments, the measure of acceptable on-axis RIQ can be considered from one or more of the following: on-axis RIQ of 0.3, on-axis RIQ of 0.35, on-axis RIQ of 0.4, on-axis RIQ of 0.45, on-axis RIQ of 0.5, on-axis RIQ of 0.55, on-axis RIQ of 0.6, on-axis RIQ of 0.65, or on-axis RIQ of 0.7. In certain embodiments, the candidate hyperopic eye may be considered with or without astigmatism. In certain embodiments, the gradient or slope of RIQ may be considered for one or more of the following variants of RIQ: a) monochromatic RIQ with or without considering effect of accommodation, b) polychromatic RIQ with or without considering effect of accommodation, c) global RIQ, d) RIQ considered with myopic impetus time signal, e) global RIQ with myopic impetus time signal, each of which is described herein.

In certain embodiments, the slope across a range of field angles may be considered and/or variations in the RIQ for a range of pupil sizes. For example, an aberration profile may be selected that provides an average mode, or substantially uniform slope, across a range of field angles, such as 10, 20, 30 or 40 degrees that either inhibits or encourages eye growth (and/or cancel existing aberrations in the eye that encourage or inhibit eye growth respectively). The average slope across the range of pupil sizes or at the mode pupil size may also be considered. Alternatively, the design may be selected that has either a positive or negative slope of through focus RIQ for field angles within a range and/or for pupil sizes with a range.

In some embodiments, an image quality produced by a lens and/or device at its focal distance is computed without the use of a model eye. The image quality produced by a lens and/or device may be calculated anterior and/or posterior to the focal distance of the lens and/or device The image quality anterior and/or posterior to the focal distance may be referred to as through focus image quality. The through-focus range has a negative and a positive power end relative to the focal distance. For example, in a through-focus range of −1.5 D to +1.5 D, −1.5 D to 0 D is considered as negative power end, while 0 D to +1.5 D is considered as the positive power end. In some embodiments, the through-focus slope along the negative power end may be considered while in other embodiments, the through-focus slope along positive power end may be considered.

Section 7

Aberration Design or Selection Process

In some embodiments, determining the aberration profile required in a lens, optical device and/or resulting from a procedure includes first identifying the HOA present in the eye. In some embodiments, determining the characterization of the aberration profile required in a lens, optical device and/or resulting from a procedure includes first identifying the HOA present in the eye. Measurements may be taken, for example, using wavefront eye exams that use aberrometry such as with a Shack-Hartmann aberrometer. The eye's existing HOA may then be taken into account. In addition, one or more HOA effects inherent in the lenses or optical devices may also be taken into account.

Figure 15:
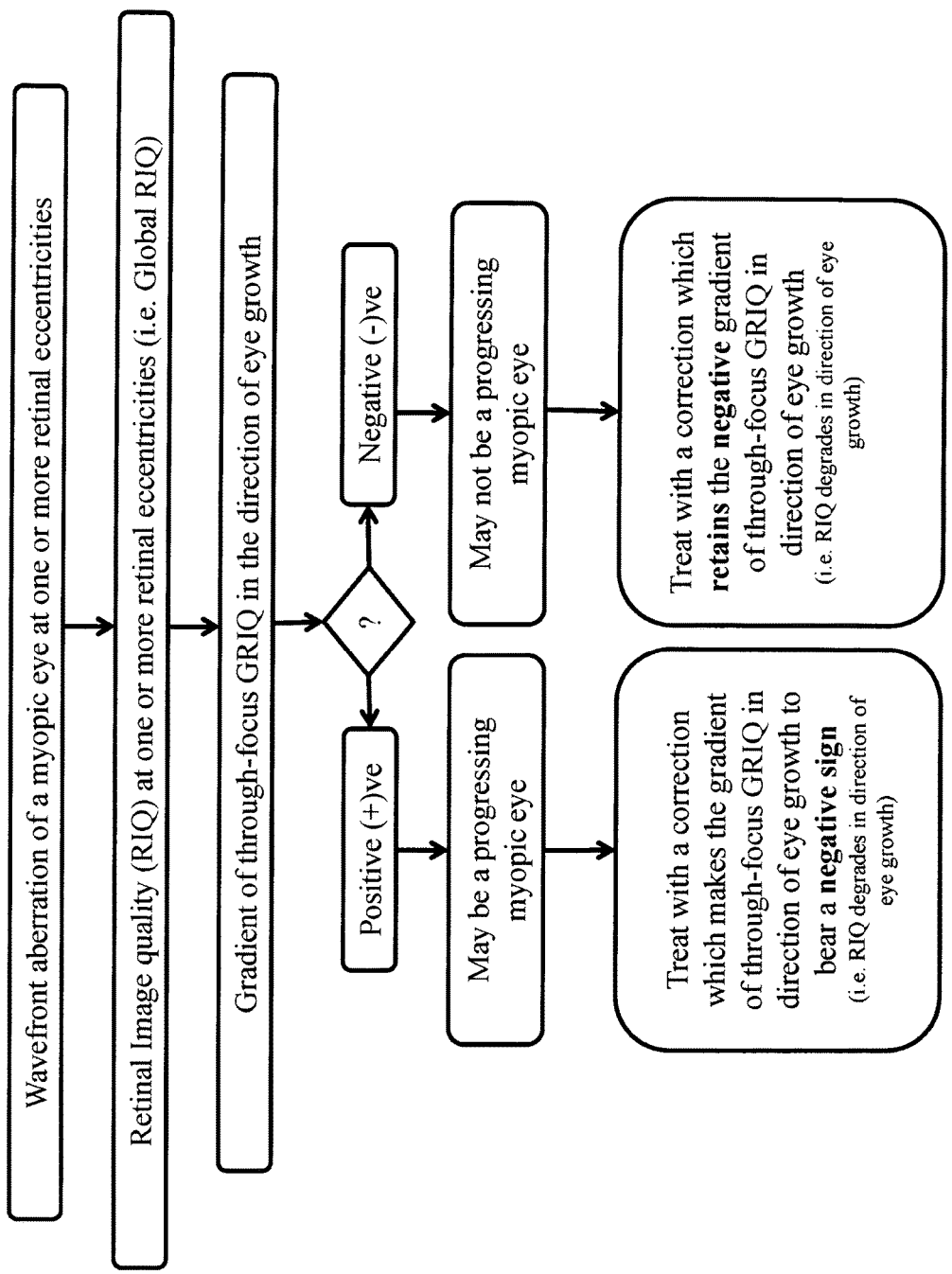
FIG. 15 shows a work flow chart for myopic eyes, progressing or non-progressing according to certain embodiments.
Figure 16:
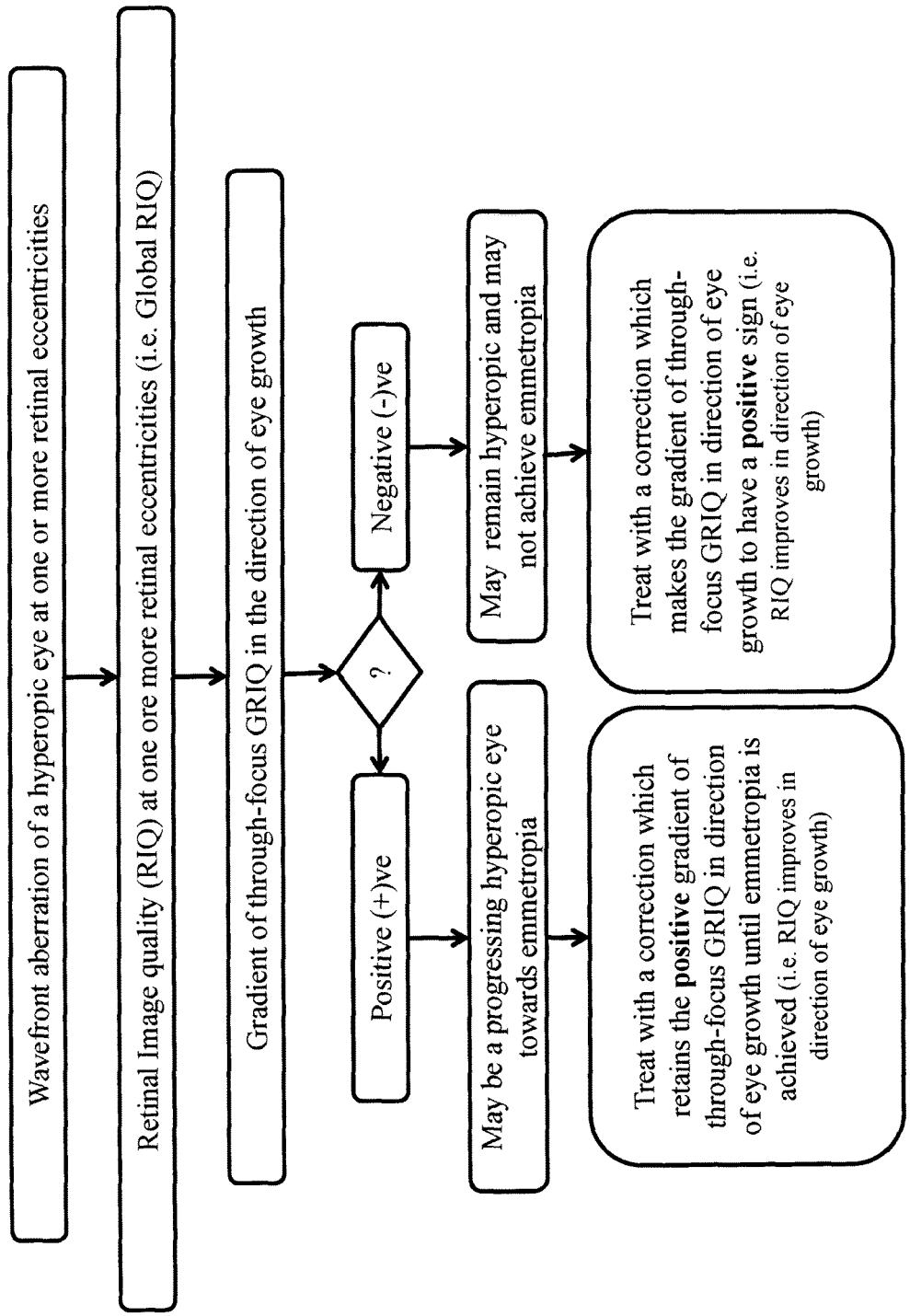
FIG. 16 shows a work flow chart for hyperopic eyes, progressing or non-progressing towards emmetropia, according to certain embodiments.
Figure 17:
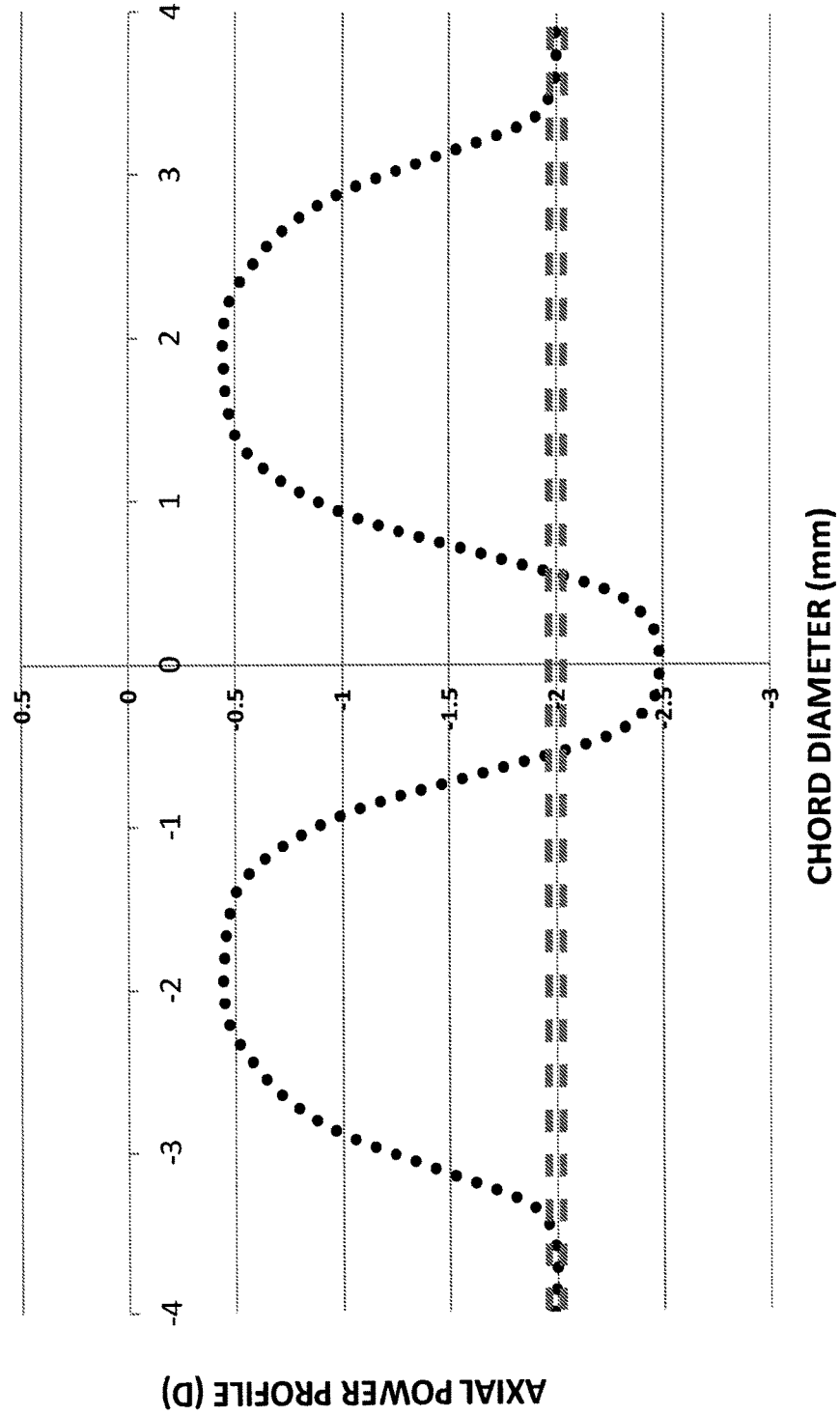
FIGS. 17 to 25 show example designs of power profiles of correcting lens across the optic zone diameter, for affecting optical feedback mechanisms for myopia, according to certain embodiments.
Figure 18:
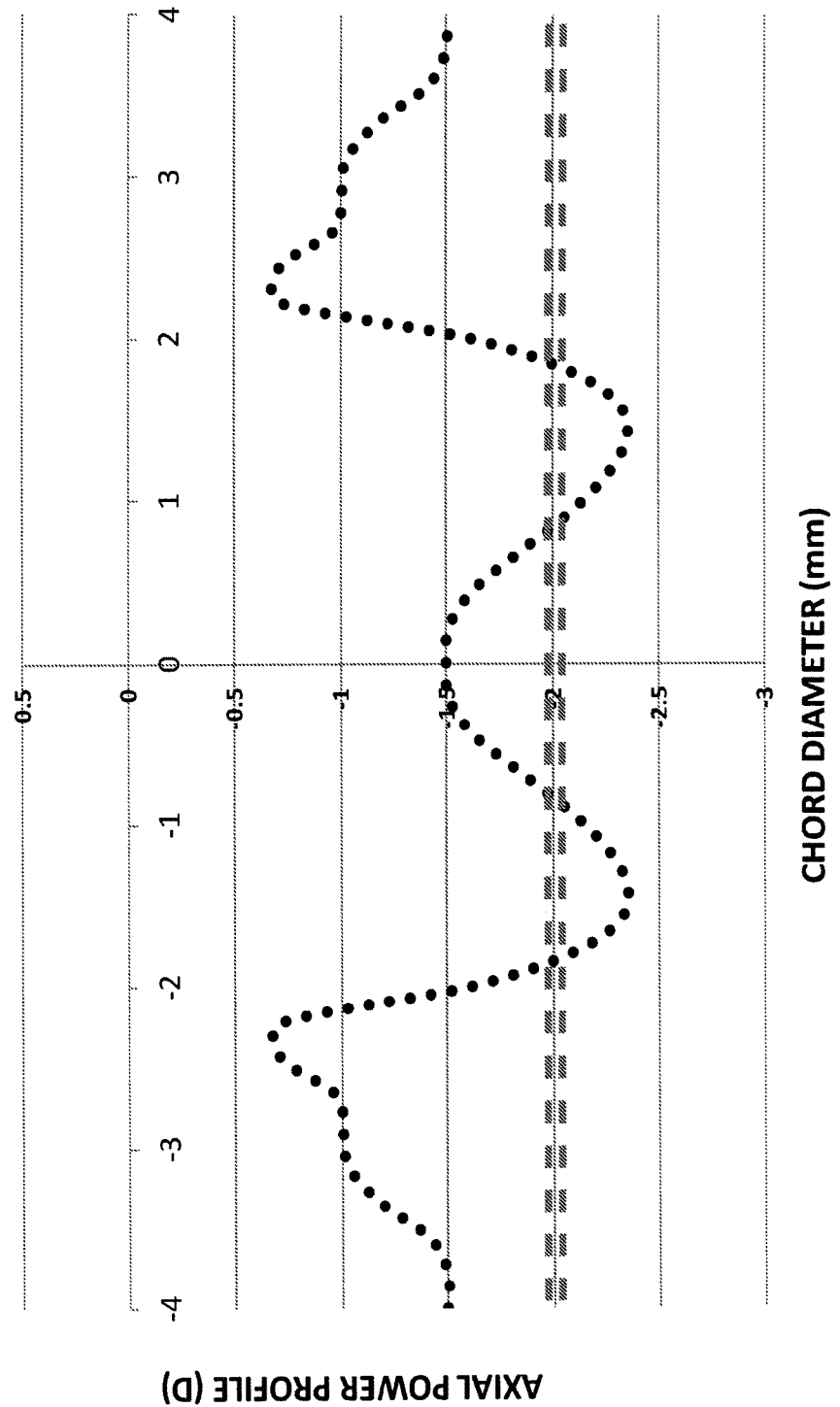
Figure 19:
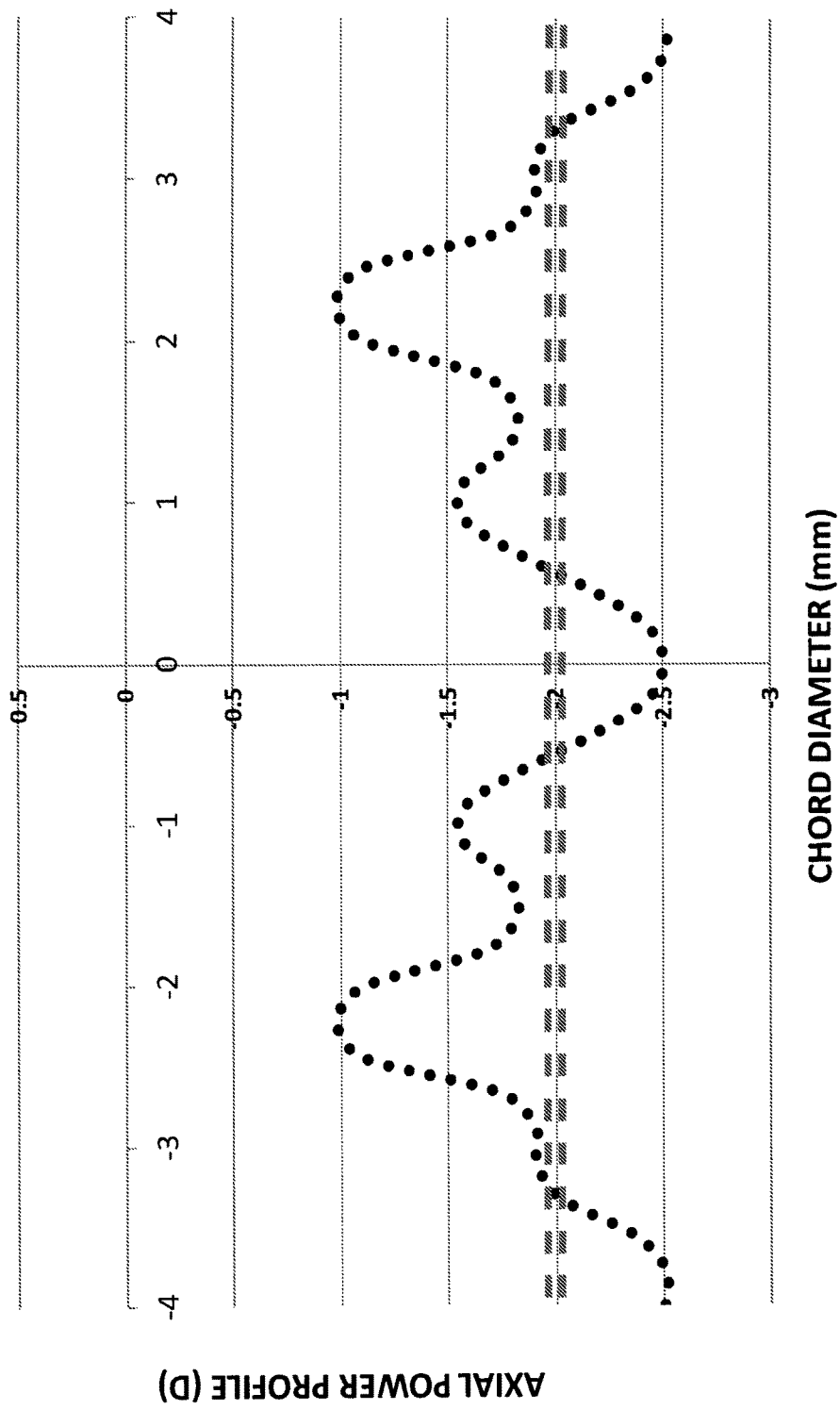
Figure 20:
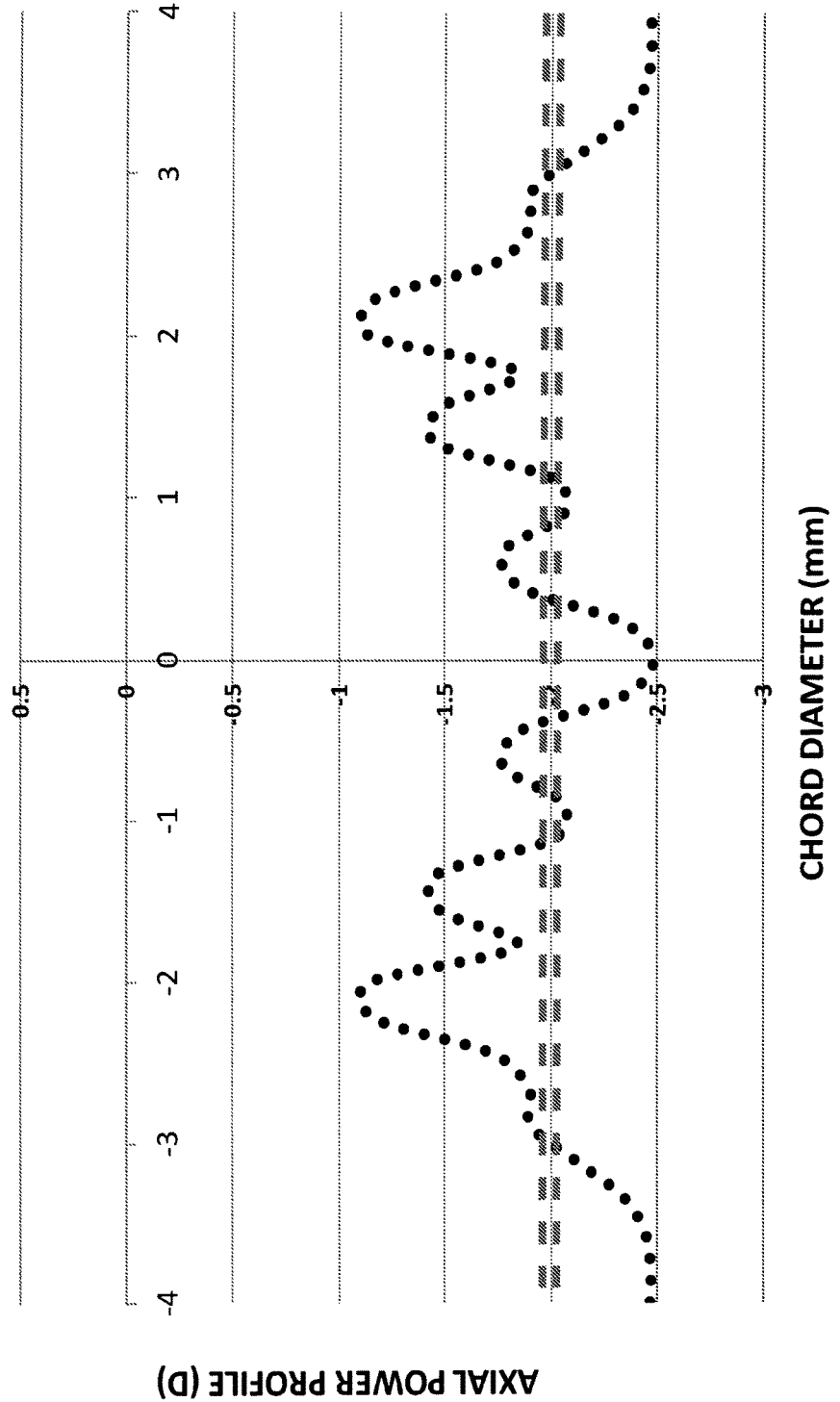
Figure 21:
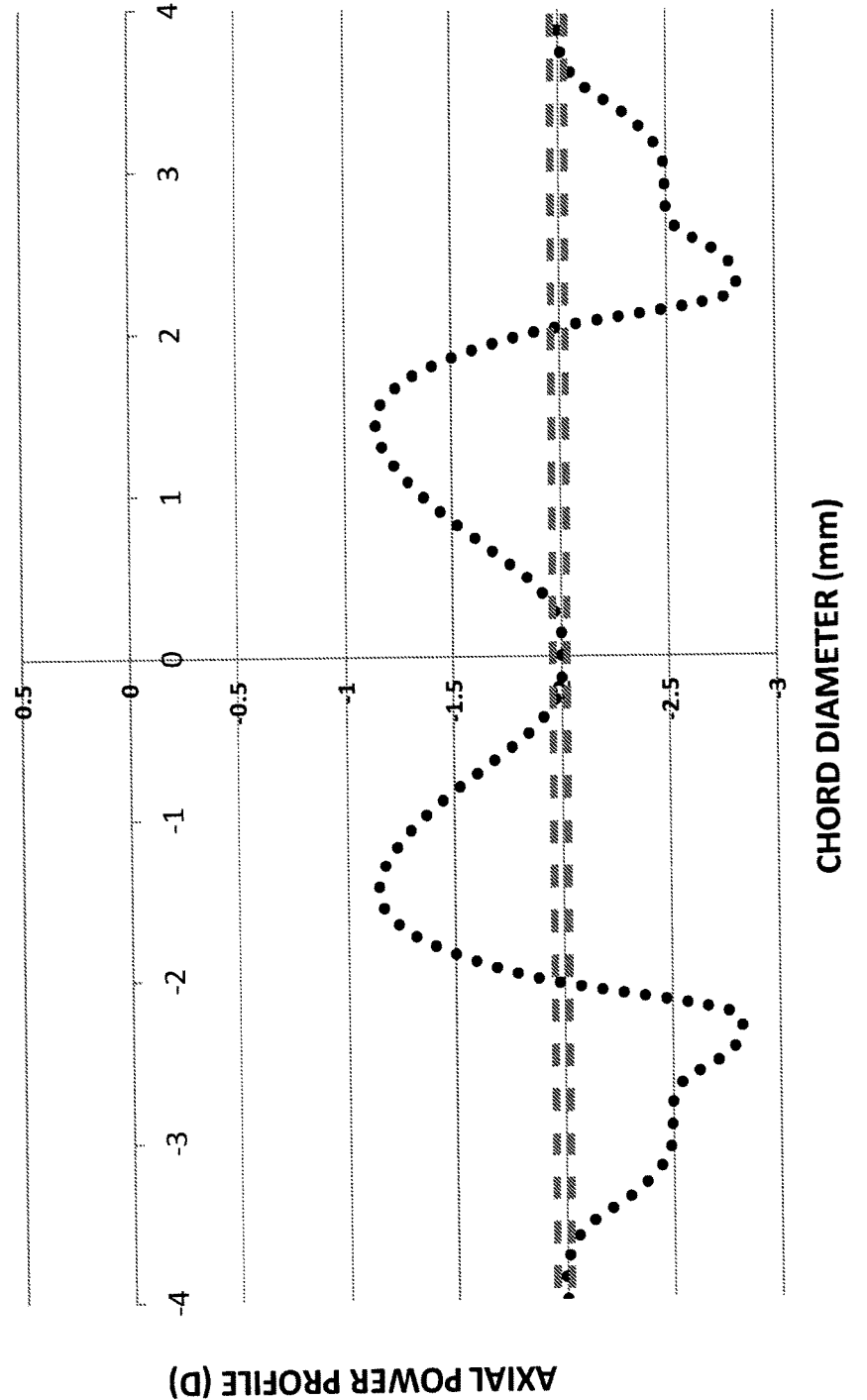
Figure 22:
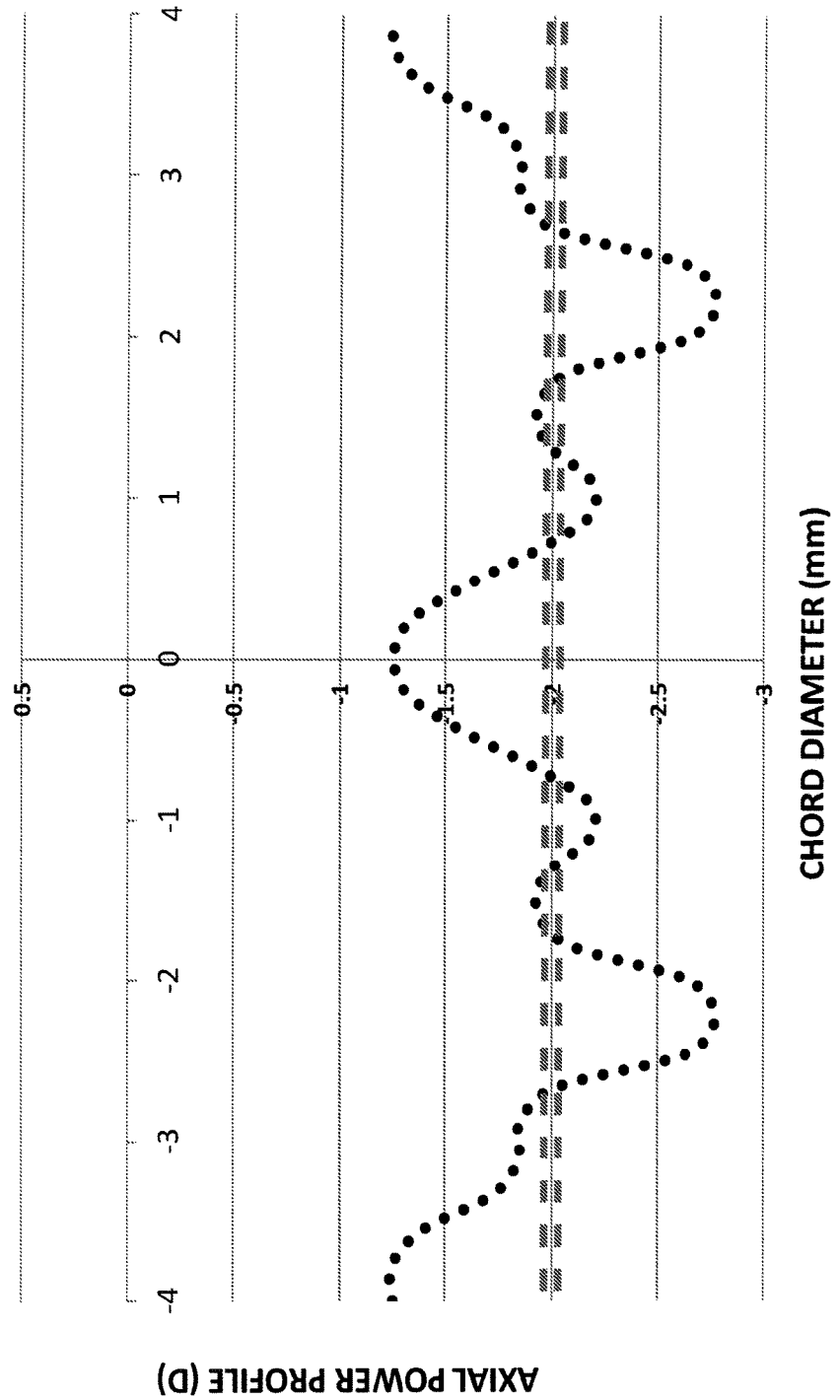
Figure 23:
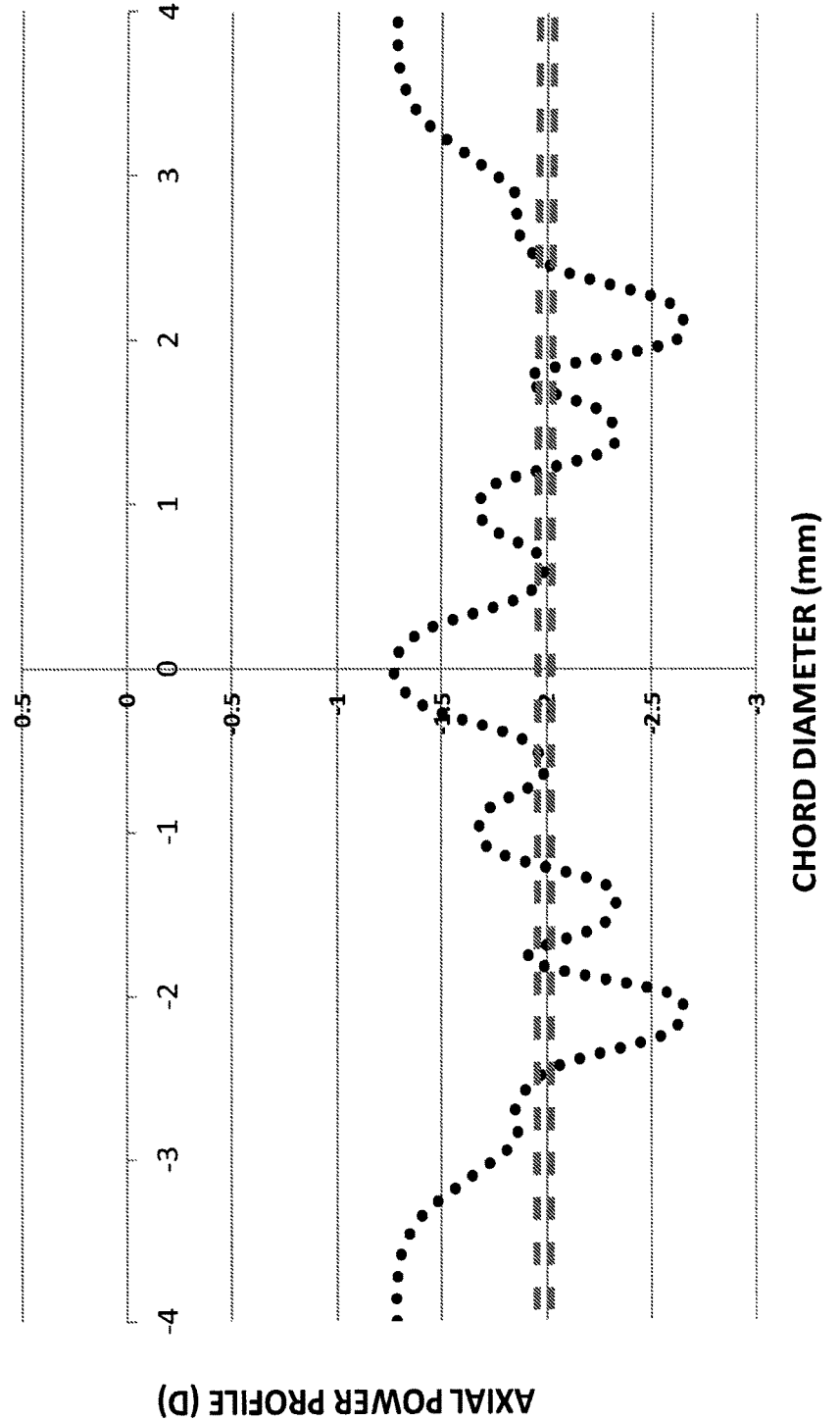
Figure 24:
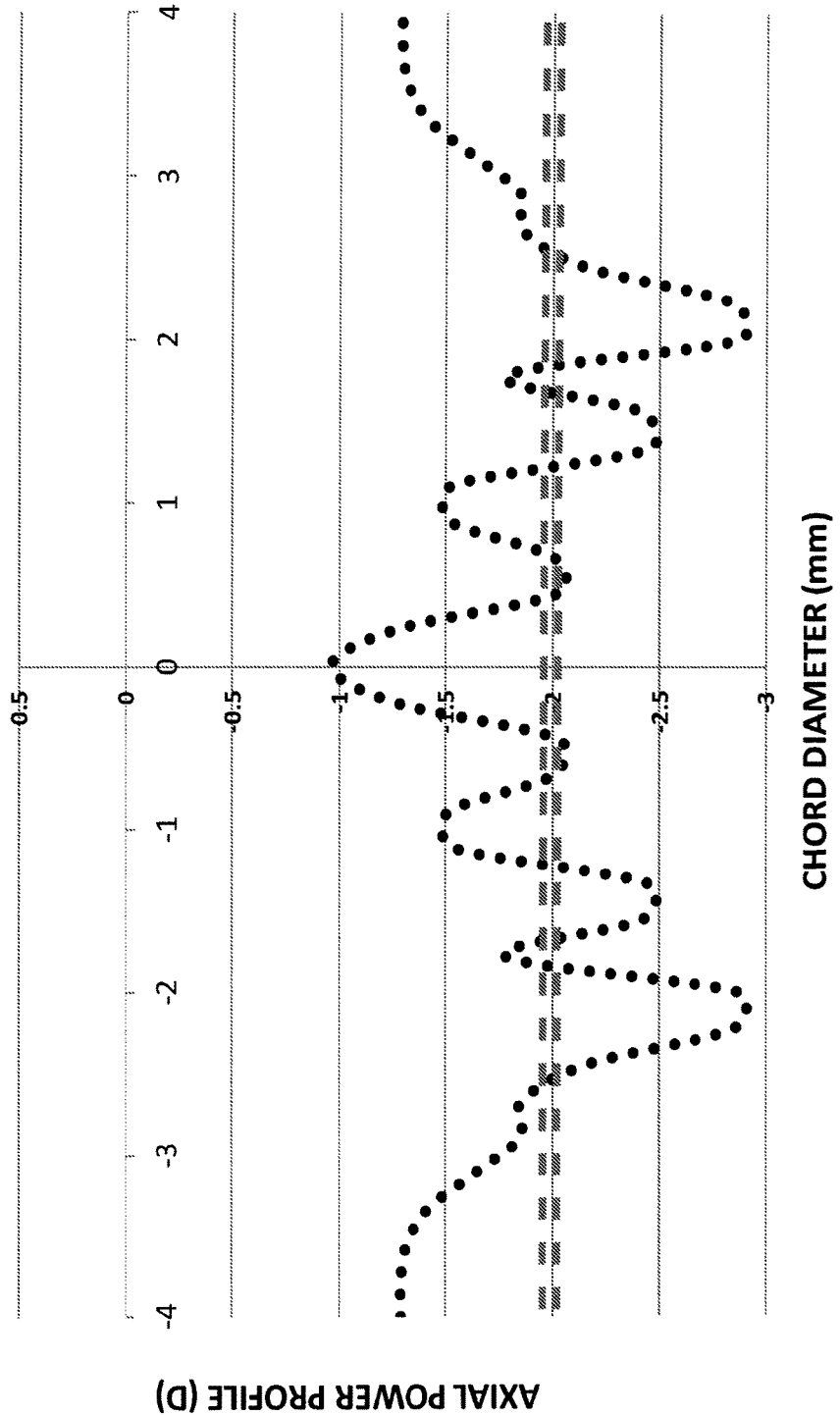
Figure 25:
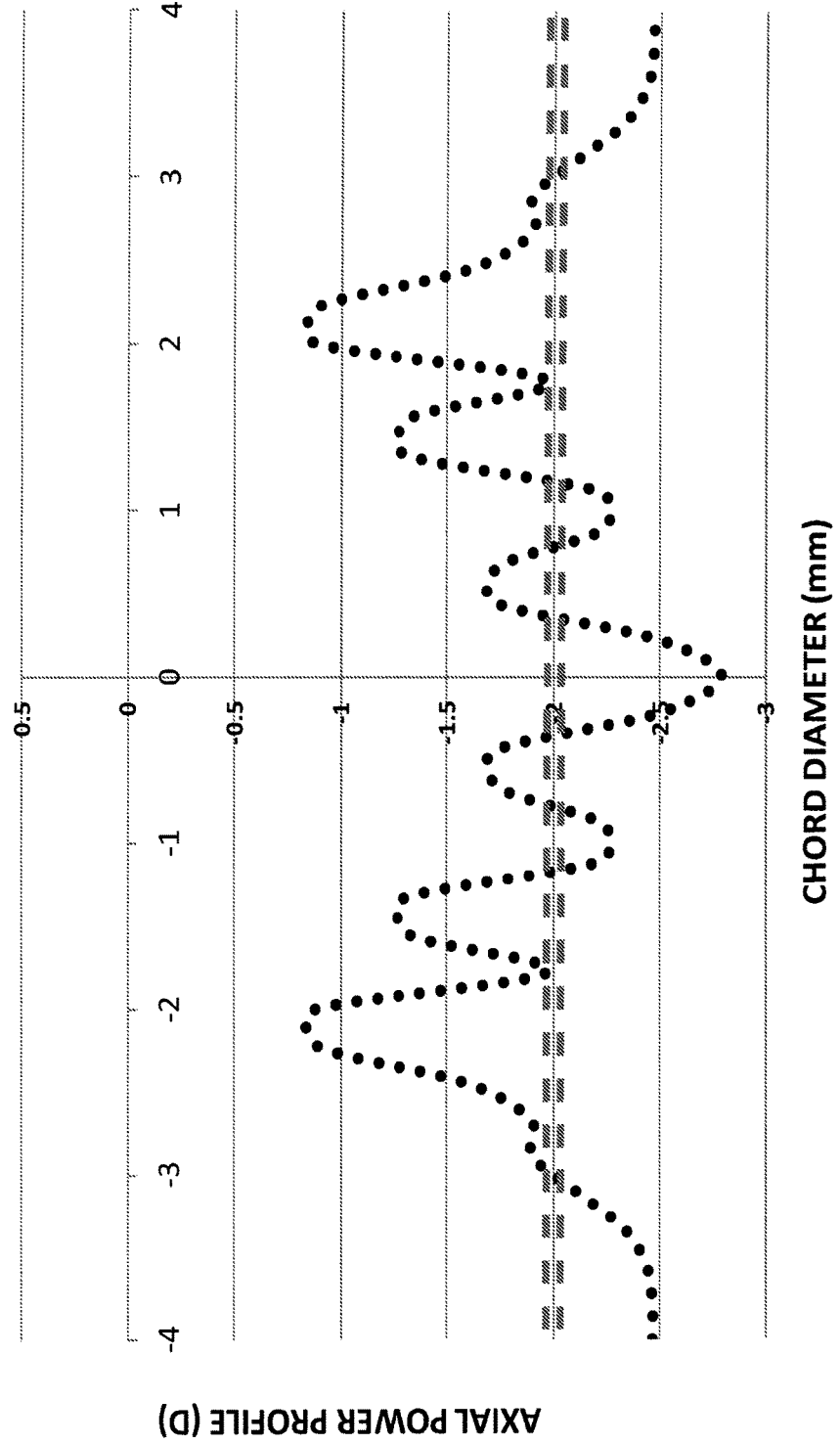

When the requirement is for a lens that provides stimulus for eye growth or to retard eye growth, these existing HOA are then compared to HOA combinations that inhibit or retard myopia progression (for example as discussed above with reference to FIGS. 5 to 14) to determine one or more additional HOA that may be required to reduce or retard or encourage eye growth under the optical feedback mechanism of emmetropisation. These additional combinations are then implemented in the design of lenses or optical devices or implemented using optical surgery. Flowcharts in FIGS. 15 and 16 provide a summary of suitable methods, according to certain embodiments.

Alternatively, in certain applications, the eye's existing aberrations may be disregarded and an aberration profile that provides the required through focus RIQ slope may be provided for the eye by a lens, In certain applications a removable lens so that different aberration profiles may be trialled if required. The aberration profile resulting from the combination of the aberration profile of the lens and the eye may then be measured to determine if the RIQ characteristics are acceptable (for example, provide a particular through focus RIQ slope and acceptable RIQ for distance vision). Alternatively, different lenses may be placed on the eye with measures of objective and/or subjective vision determining which lens to select. Where the lens is selected to provide stimulus inhibiting or encouraging eye growth without regard to the eye's existing aberrations, the selected aberration profile may be one with generally higher values of spherical aberration, so that the sign of the slope is not changed by lower level of HOA in the eye. In certain applications, the goal of the optimisation routine of the merit function in search of combination of HOA may be different. For example, when considering presbyopia the goal may be a combination of aberrations that provide high RIQ over a large through focus range. Where peripheral vision is useful, then the objective may include high RIQ over a large range of field angles. Accordingly, in various embodiments the HOAs are utilised to optimise for the goals of a combination of high RIQ at the retina and one or more of a low slope through focus RIQ, a low change in RIQ with pupil diameter and a high RIQ in the peripheral field.

In certain applications, an acceptable high RIQ is considered to be an RIQ above 0.7, above 0.65, above 0.6, above 0.55, above 0.5, above 0.45, above 0.4, above 0.35, or above 0.3. In certain applications, an acceptable low change in RIQ with pupil diameter may be considered the change in one or more of the following ranges: RIQ change between 0 and 0.05, between 0.05 and 0.1, or between 0.1 and 0.15. In certain other applications, an acceptable low slope of through focus RIQ may be considered from one or more of the following: slope of less than zero, slope of equal to zero, slope of greater than zero, slope of about zero, slope ranging from −0.5 to zero, slope ranging from 0 to 0.5, slope ranging −1 to zero, slope ranging 0 to 1, slope ranging −1 to −0.5, or slope ranging 0.5 to 1. The high RIQ, low change in RIQ and low slope of TFRIQ provided may be combined in or more combinations. For example, the combination of a high RIQ of 0.40 or above, a low change in RIQ with pupil diameter between 0 and 0.05 and low slope of TFRIQ of about zero may be applied to certain embodiments. In other applications, the combination of a high RIQ of 0.3 or above, a low change in RIQ with pupil diameter between 0 and 0.075 and the low slope of TFRIQ ranging from −0.25 to 0.25 or −0.5 to 0.5 may be applied.

The examples that follow have been selected using the RIQ measure in Equation 2. The initial set of designs for analysis was found by computing this RIQ for all, or for a substantially number of, combinations of SA Zernike coefficients up to the 10th order. The coefficients used were constrained to the range −0.3 µm to 0.3 µm and constrained to be a value that is a multiple of 0.025 µm. In certain embodiments, the RIQ used may be based on an approximation or characterization of Equation 2.

An analysis of the initial set of designs included: 1) identifying optimised combinations of Zernike coefficients that provide a high RIQ and a negative slope through focus RIQ about the retina; 2) consideration of the RIQ and through focus RIQ and change in RIQ and through focus RIQ at different pupil sizes; and 3) consideration of the RIQ across the horizontal visual field. The relative weight given to these stages of evaluation may vary for the particular recipient. For the purposes of identifying the following examples, most weight was given to the first criteria.

Section 8

Examples of Optical Designs Addressing the Slope of Through Focus RIQ

Examples of designs for affecting stimulus for eye growth under an optical feedback mechanism are provided herein. The examples below are rotationally symmetric. However, astigmatic designs and other non-rotationally symmetric designs may be produced. When a deliberate decentration of the symmetric designs is imposed so that the optical axes of the correcting contact lens coincides with a reference axis of the eye say pupillary axis or visual axis, some residual amounts of asymmetric aberrations like coma and trefoil can be induced, these may be compensated by the choice of additional higher order asymmetric terms. FIGS. 17 to 25 are exemplary that show the power profile graphs of sample designs that provide a RIQ that degrades in the direction of eye growth for on-axis vision (i.e. at zero field angle), thus providing a stimulus to inhibit eye growth under the optical feedback mechanism explanation of the emmetropisation process, according to certain embodiments. The aberration profile graphs are described as the axial power variation in Dioptres across the optic zone diameter. The examples provided may have application to a progressing myope whose spherical refractive error is −2 D and this information is indicated by a dual grey line on the power profiles.

Figure 26:
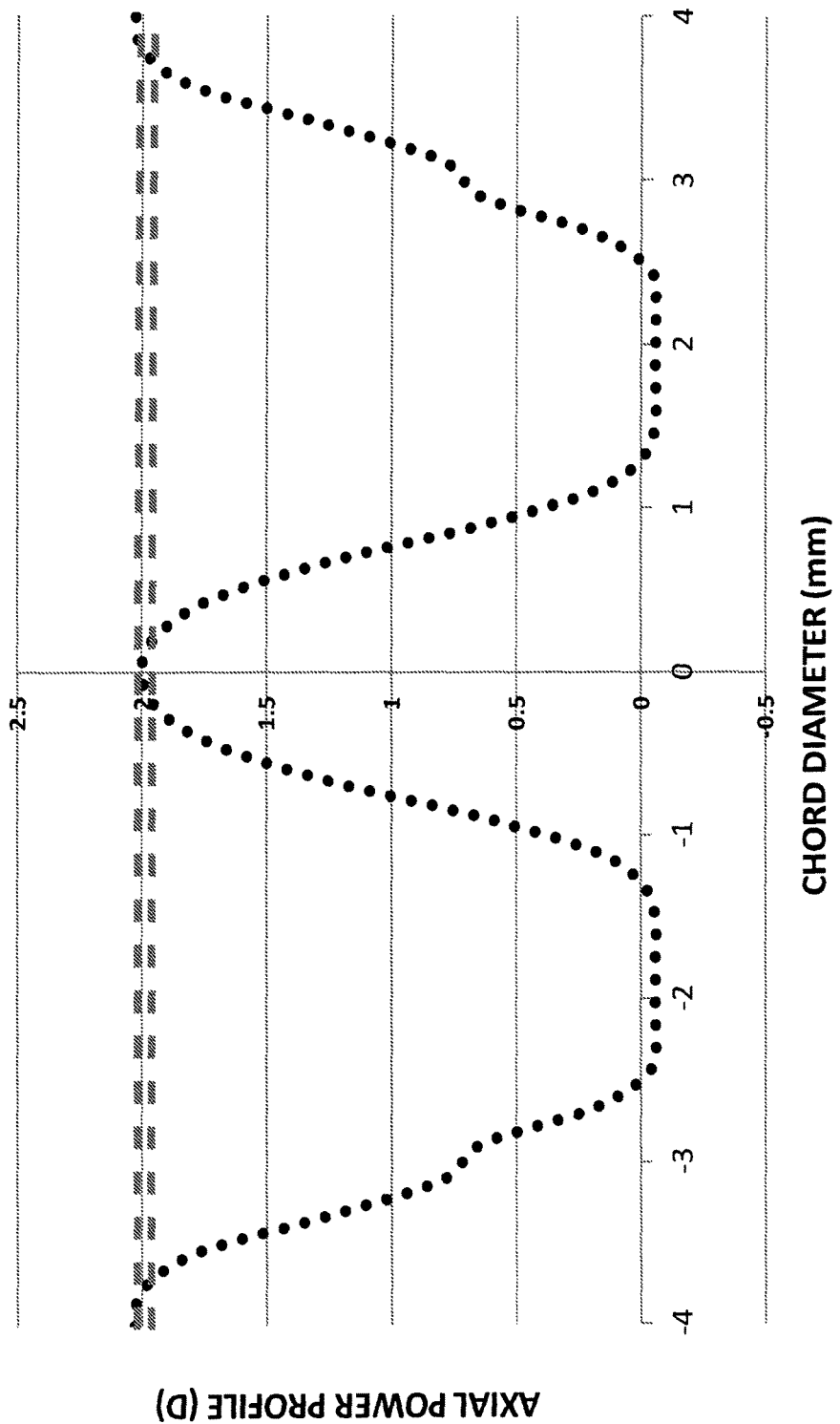
FIG. 26 shows an example design of a power profile of correcting lens across the optic zone diameter, for affecting optical feedback mechanisms for hyperopia, according to certain embodiments.

FIG. 26 is an exemplary that shows the details of a sample design that may be used for hyperopia treatment, according to certain embodiments. This designs was produced by taking a specific aberration profile as an input parameter that would produce a positive gradient of TFRIQ in the direction of eye growth, as indicated in Table 2 and optimising the power profile (front surface of correcting contact lens) to achieve a required positive gradient. The lens design is described as the axial power variation in Dioptres across the optic zone diameter. The example provided may have application to a non-progressing hyperope whose spherical refractive error is +2 D and this information is indicated by a dual grey line on the power profile.

As explained herein, the example power profiles shown in FIGS. 17 to 26 were selected based on the slope of RIQ around the retina, according to certain embodiments. Across these examples, substantial variations in the value of RIQ may occur. These variations occur on-axis, across the pupil diameter, and at different field angles. Additional selection criteria are the value of RIQ and the change in RIQ with field angle. In particular, the selection may be made to maximise one or more of RIQ on-axis, across the pupil diameter (with or without reduction in light of the Stiles-Crawford effect) and at different field angles. In addition, the size of the pupil of the recipient may also be used as a selection criterion—e.g., a first aberration profile may better suit a first recipient with a normal pupil size of 4 mm and a second aberration profile may better suit a second recipient with a normal pupil size of 5 mm. The 'normal' pupil size may optionally be selected having regard to lifestyle factors, such as the amount of time a person spends indoors versus outdoors. Additional examples referred to below incorporate these selection criteria. First however, to provide a point of comparison, the RIQ performance of a single vision lens is described and shown in FIG. 27.

Figure 27:
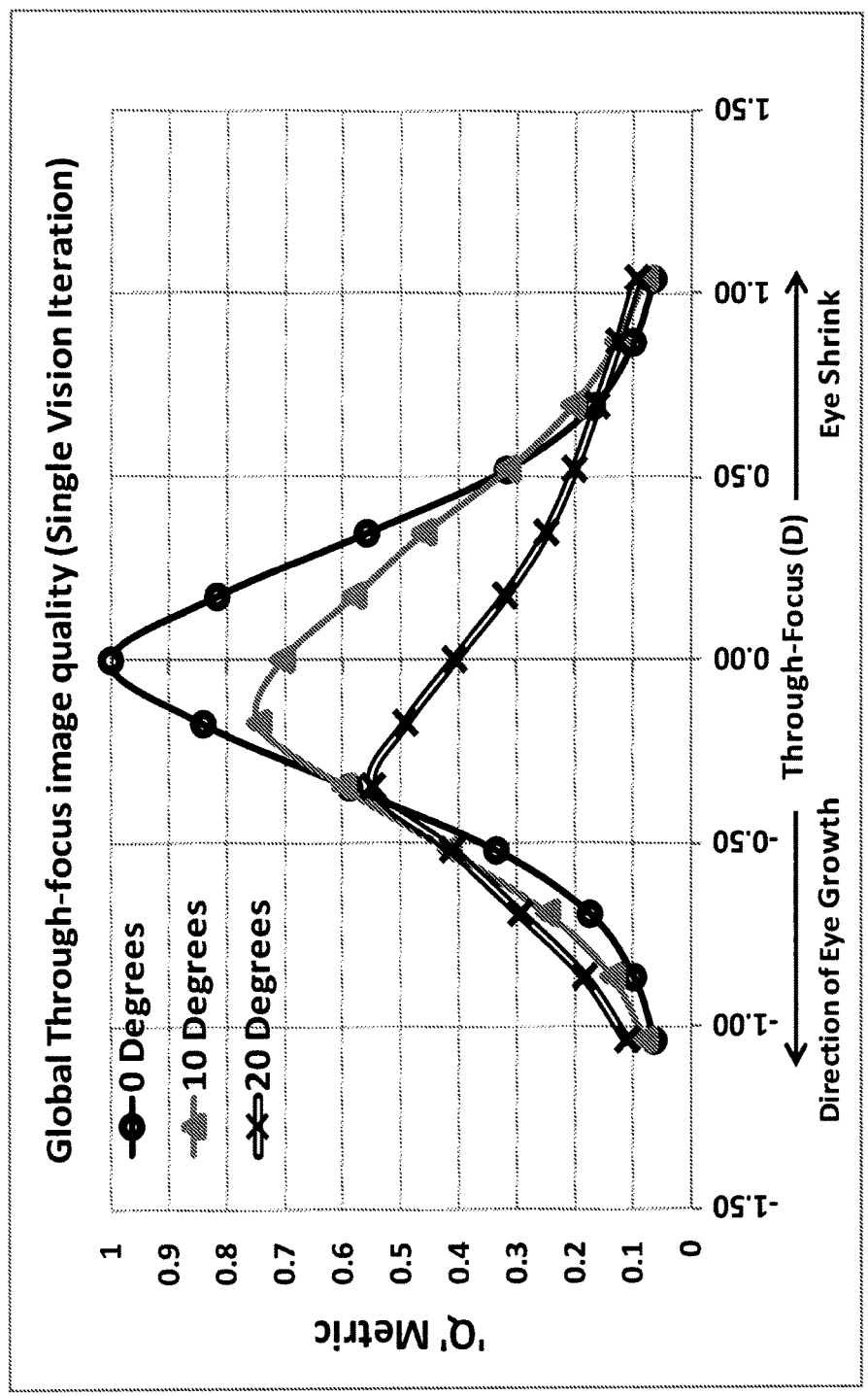
FIG. 27 shows a global through-focus retinal image quality (TFRIQ) for an aberration profile corresponding to a single vision lens.

FIG. 27 is an exemplary that shows a graph of a measure of a through focus RIQ metric, according to certain embodiments, which in this case, and in the following examples, is visual Strehl Ratio (monochromatic). The RIQ may result, for example, from a single vision contact lens with a power of −2 D used to correct a recipient model myopic eye with −2 D only. The horizontal (independent) axis shows the through focus, in Dioptres. The zero (0) value on the horizontal axis represents the location of the focal point of the single vision lens and the vertical (dependent) axis shows the RIQ. Three plots are provided, one for on-axis (circles), one for a field angle of 10 degrees (triangles) and one for a field angle of 20 degrees (crosses).

As used in this example described herein, the term global is used to refer to consideration across a range of field angles, including zero. Thus, the graph shows Global through focus RIQ, as it includes plots across a range of field angles. While a single vision lens has symmetrical RIQ on-axis at zero field angle, it has asymmetrical through focus RIQ at non-zero field angles, including both at 10 and 20 degrees. In particular, the graph shows that RIQ improves in the direction of eye growth at non-zero field angles, according to certain embodiments. Under the optical feedback mechanism explanation of emmetropisation, peripheral as well as on-axis vision provides a stimulus for eye growth. In certain embodiments, the slope of the TFRIQ at the retina to control eye growth (negative slope, or decreasing RIQ for myopia and positive slope, or increasing RIQ for hyperopia) may be across a range of field angles that may or may not include the zero or on-axis field angle. An average measure of the slope of the TFRIQ (also referred to as the average through focus slope of the RIQ) may be used across a selection of, or a range of, field angles. For example, slope of the TFRIQ averaged between at least −20° and +20° field angles. Another example may average the slope of the TFRIQ at at least −20°, 0° and +20° field angles. Broader field angles may also be used for example, between at least −30° and +30° field angles or between at least −40° and +40° field angles.

In certain embodiments, the average slope of the TFRIQ across a selection of or a range of field angles may be a weighted average slope of the TFRIQ that gives more, less or the same weight to different field angles to emphasise or weight the contributions of the different field angles according to the application.

Figure 28:
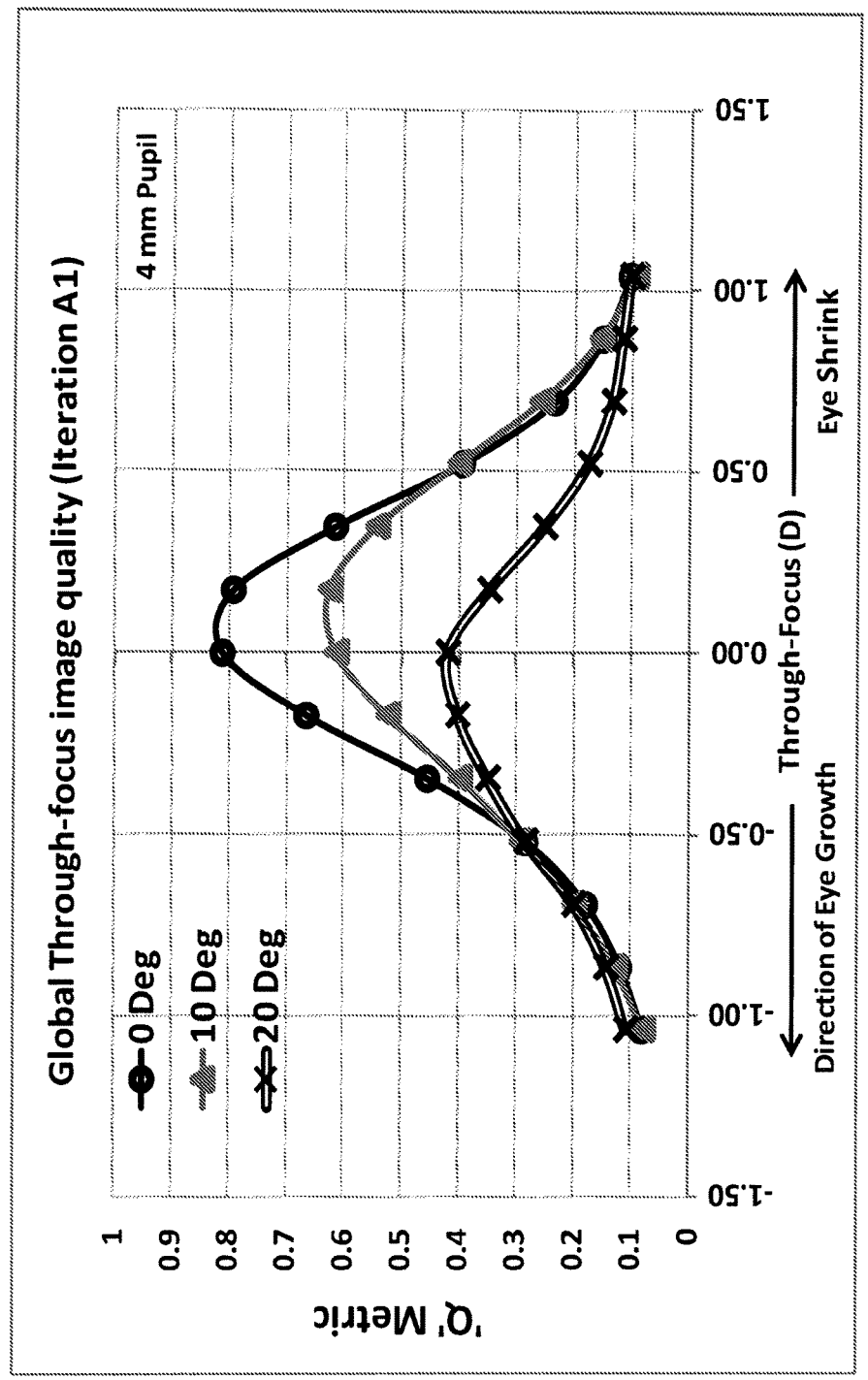
FIG. 28 shows a global TFRIQ for a first aberration profile (Iteration A1), which may have application to a progressing myopic eye.
Figure 29:
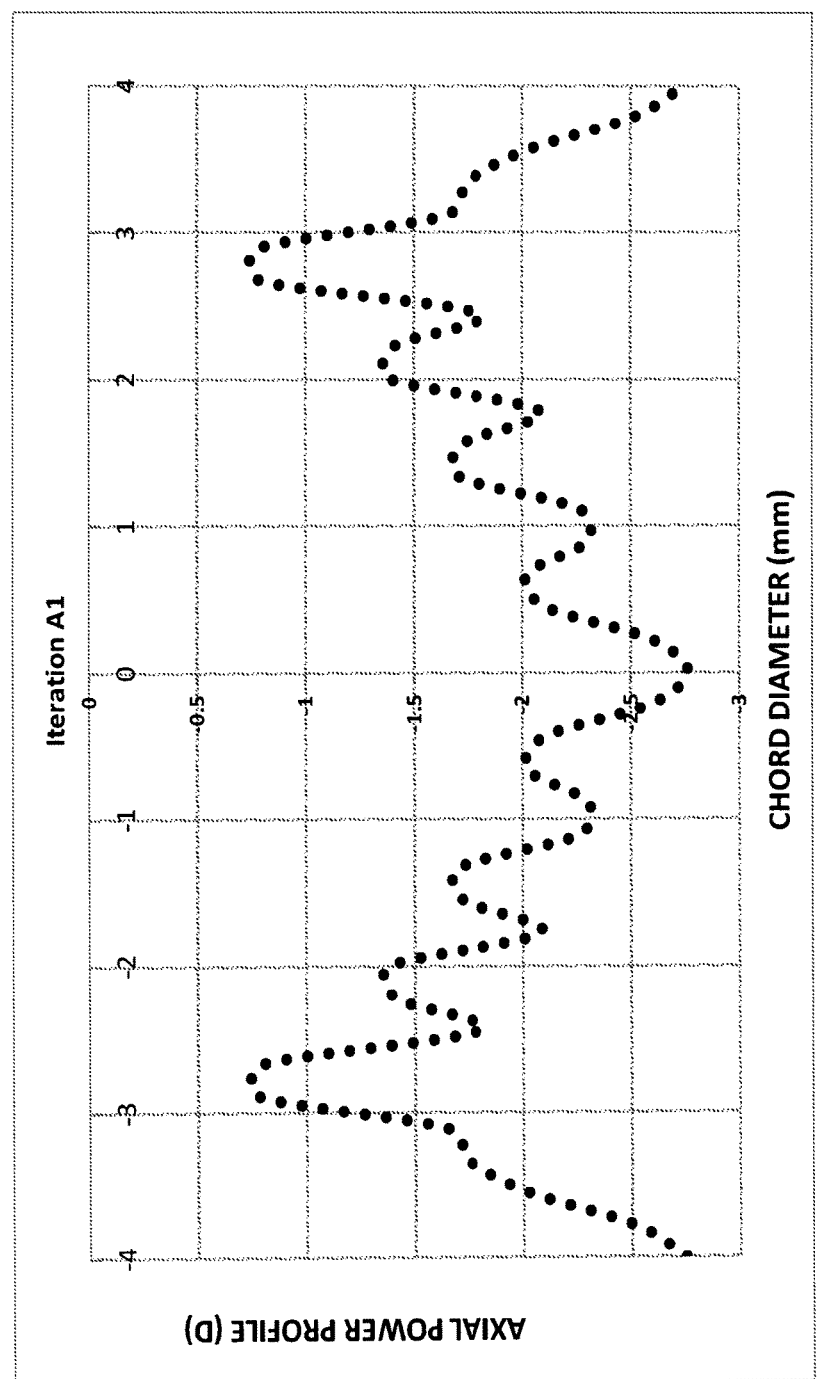
FIG. 29 shows the power profile for a lens for providing the first aberration profile (Iteration A1), according to certain embodiments.

FIG. 28 is an exemplary that shows a graph of RIQ for an embodiment of a lens (named 'Iteration A1') selected to address the optical feedback mechanism explanation of emmetropisation where eye growth is to be discouraged (e.g. to address progressing myopia or to address a risk of developing myopia), according to certain embodiments. The data for FIG. 28 was prepared for a pupil size of 4 mm and to address the same, or substantially the same, level of myopia as for the Single Vision Iteration. Comparing FIG. 28 with FIG. 27, the RIQ no longer improves in a direction of eye growth for non-zero field angles. In particular, the RIQ has a strong trend towards degrading in the direction of eye growth for 10 degrees off-axis. While there may be a slight improvement or no substantially no change in RIQ about the retina at 20 degrees off-axis, the overall effect is strongly biased towards degrading RIQ in the direction of eye growth. FIG. 29 shows a power profile that result in the RIQ graph of FIG. 28.

Figure 30:
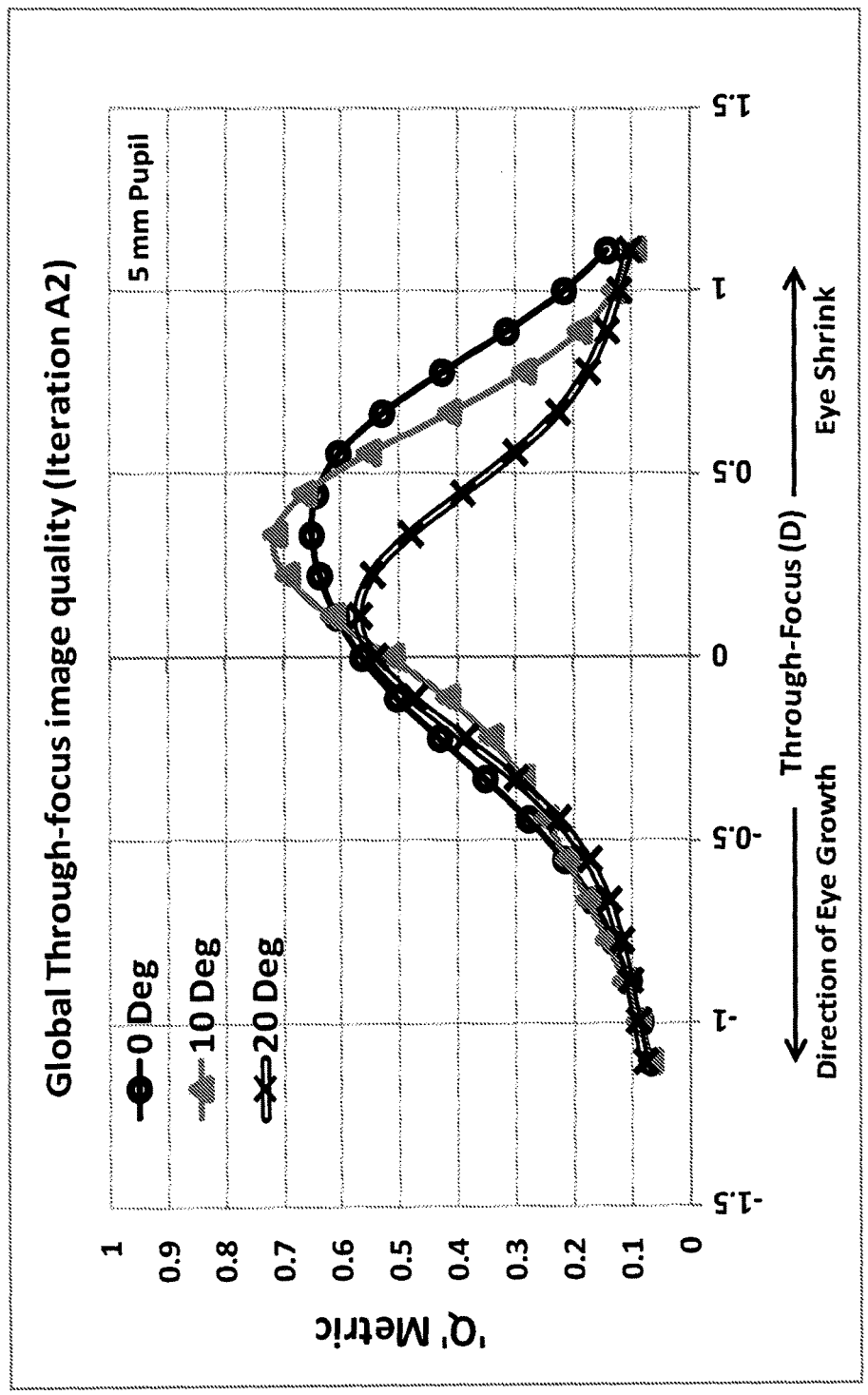
FIG. 30 shows a global TFRIQ for a second aberration profile (Iteration A2), which may also have application to a progressing myopic eye, according to certain embodiments.

FIG. 30 is an exemplary that shows a graph of RIQ for certain embodiments of a lens (Iteration A2) selected to address the optical feedback mechanism explanation of emmetropisation. The data for FIG. 30 was prepared for a pupil size of 5 mm.

Figure 31:
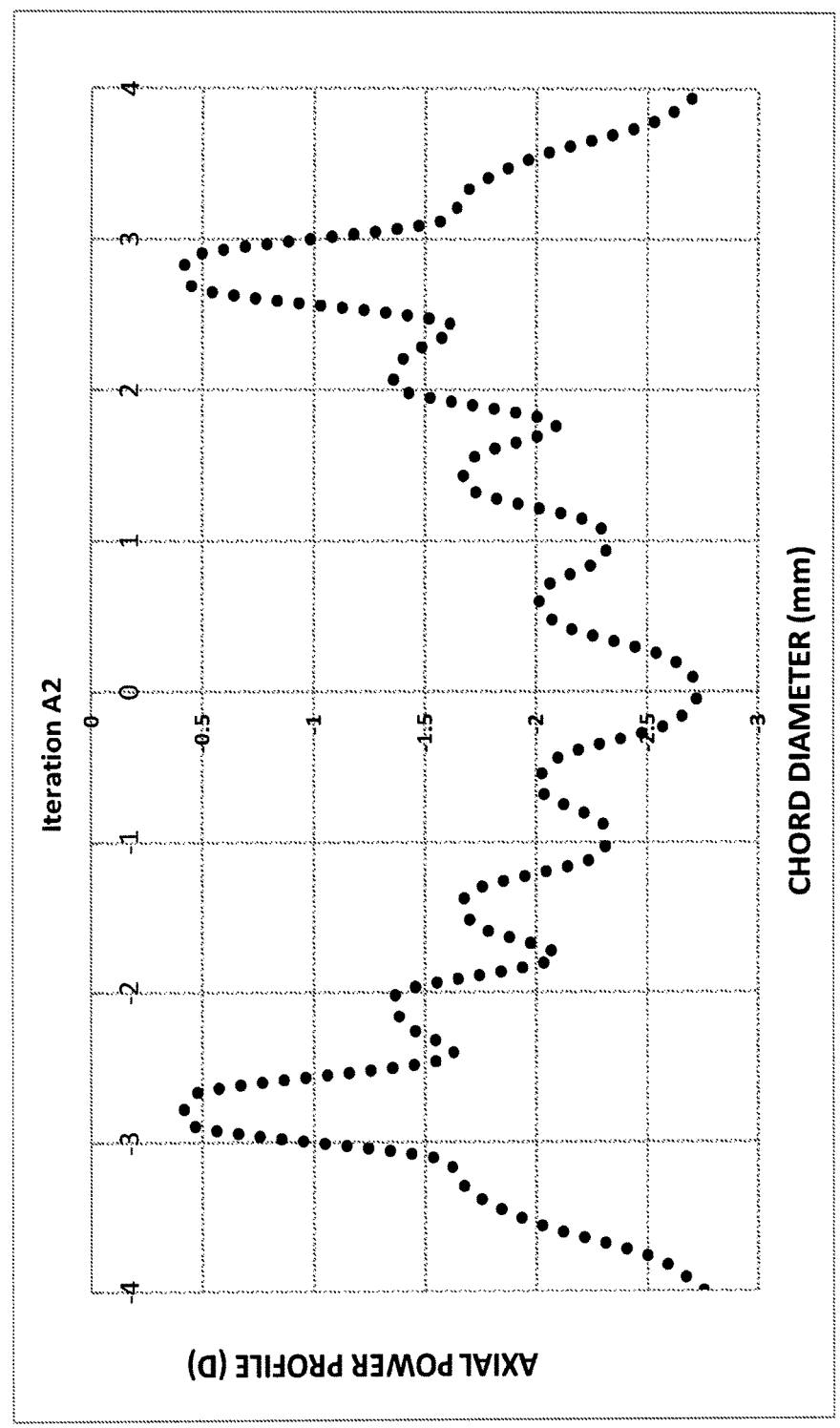
FIG. 31 shows the power profile across full chord diameter for a second aberration profile (Iteration A2), according to certain embodiments.
Figure 32:
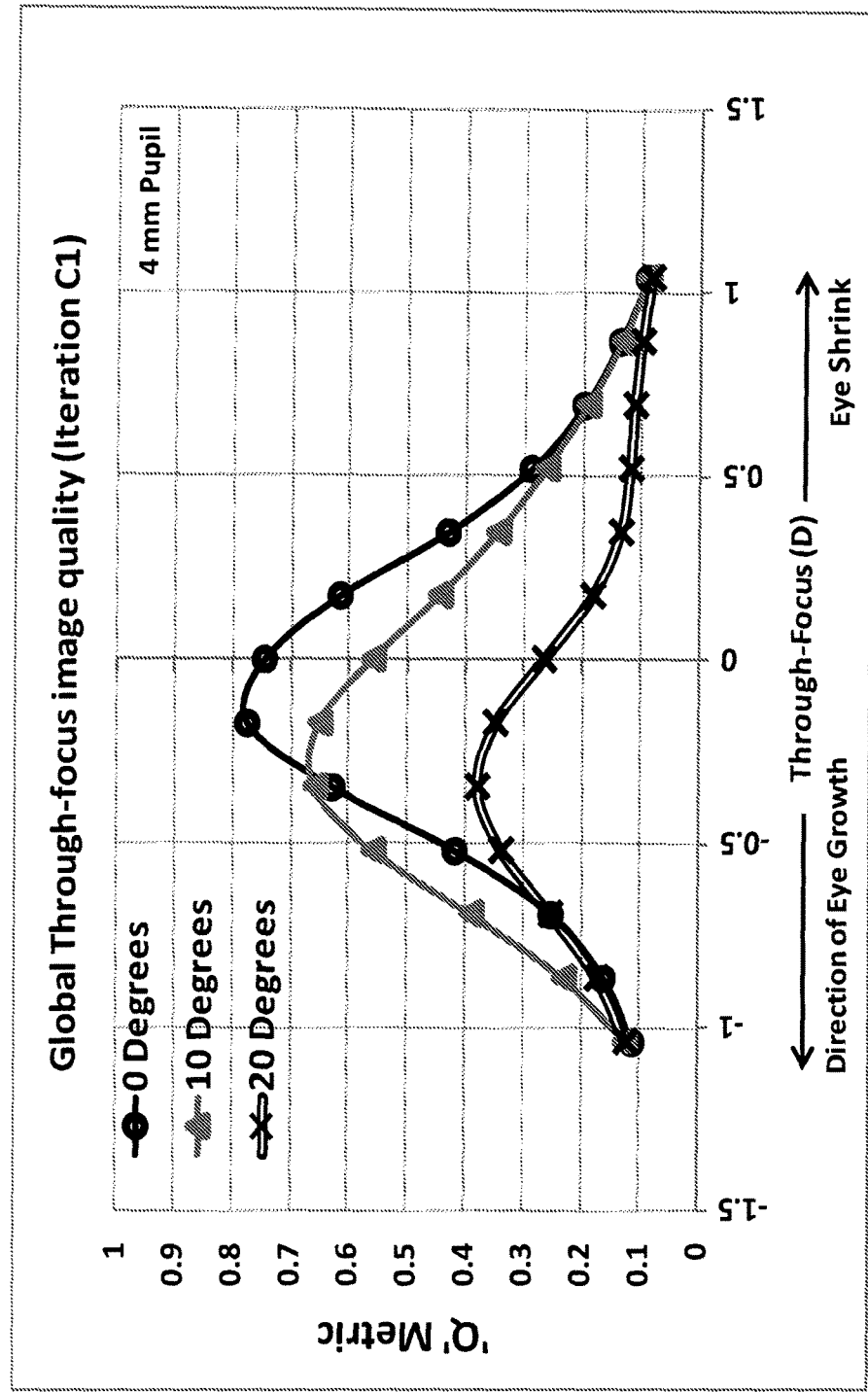
FIGS. 32 and 33 show a global TFRIQ for a third and fourth aberration profile (Iteration C1 and Iteration C2 represented as power profiles across optic chord diameter in FIGS. 34 and 35), which may have application to a hyperopic eye, according to certain embodiments.
Figure 33:
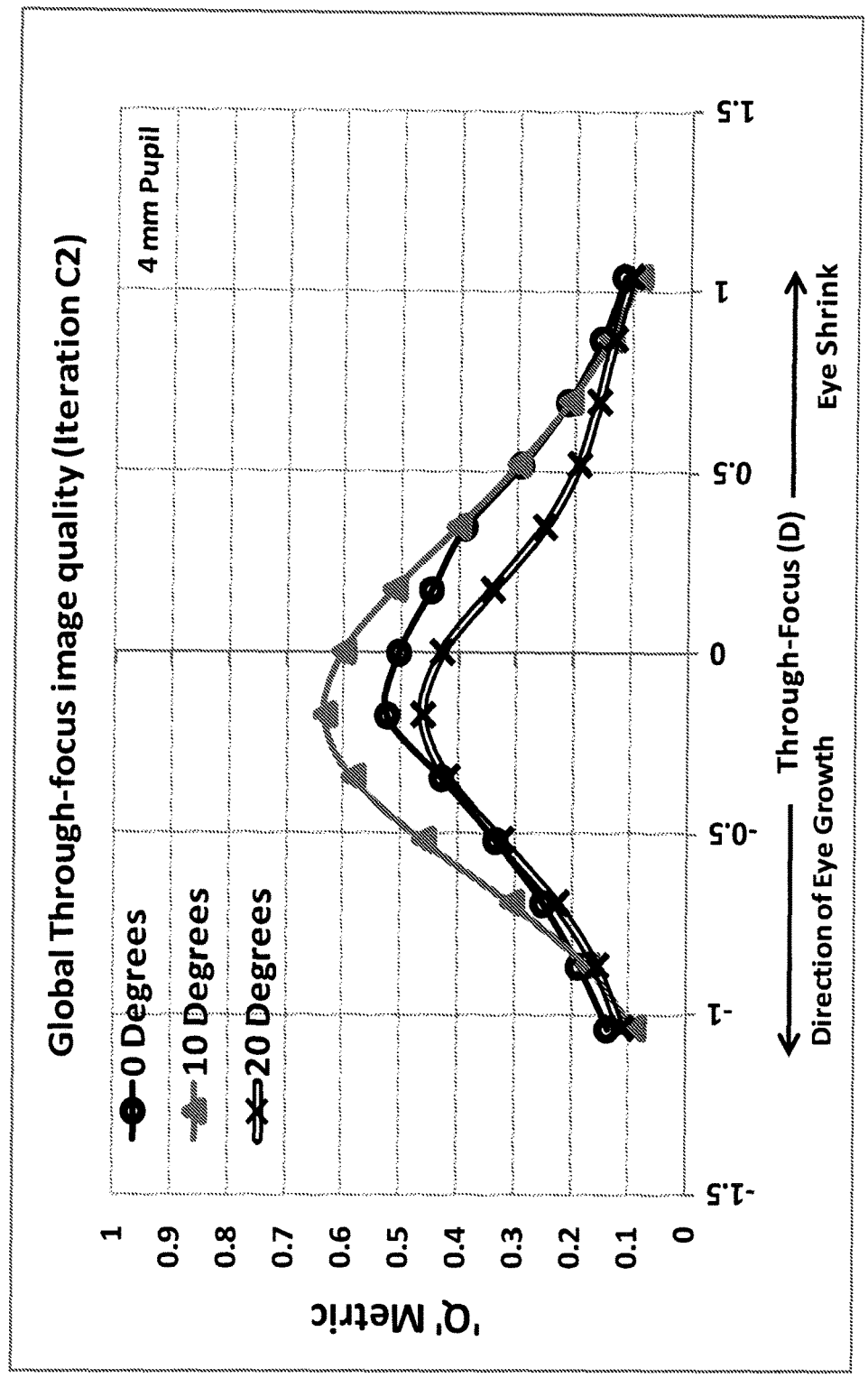
Figure 34:
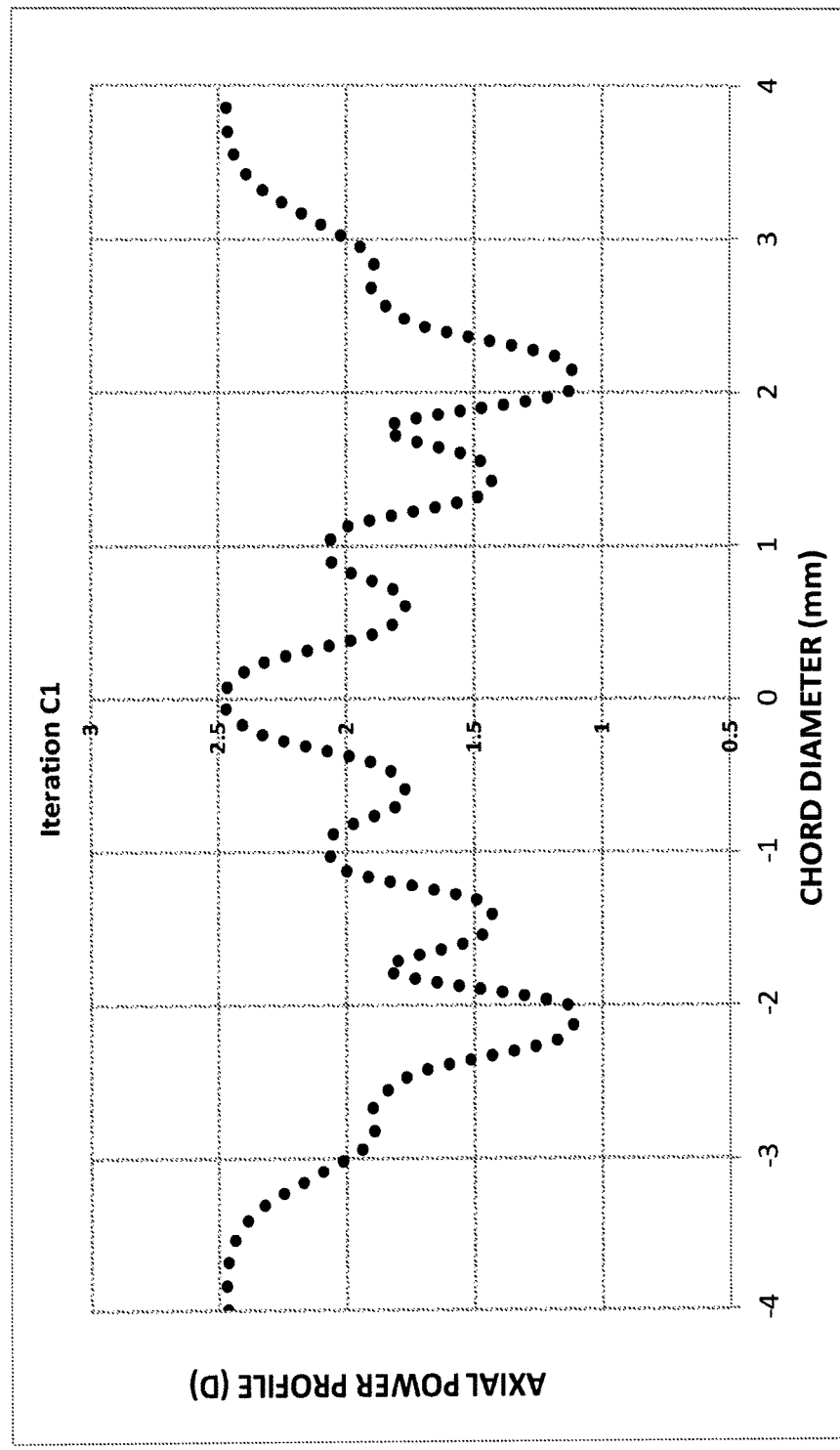
Figure 35:
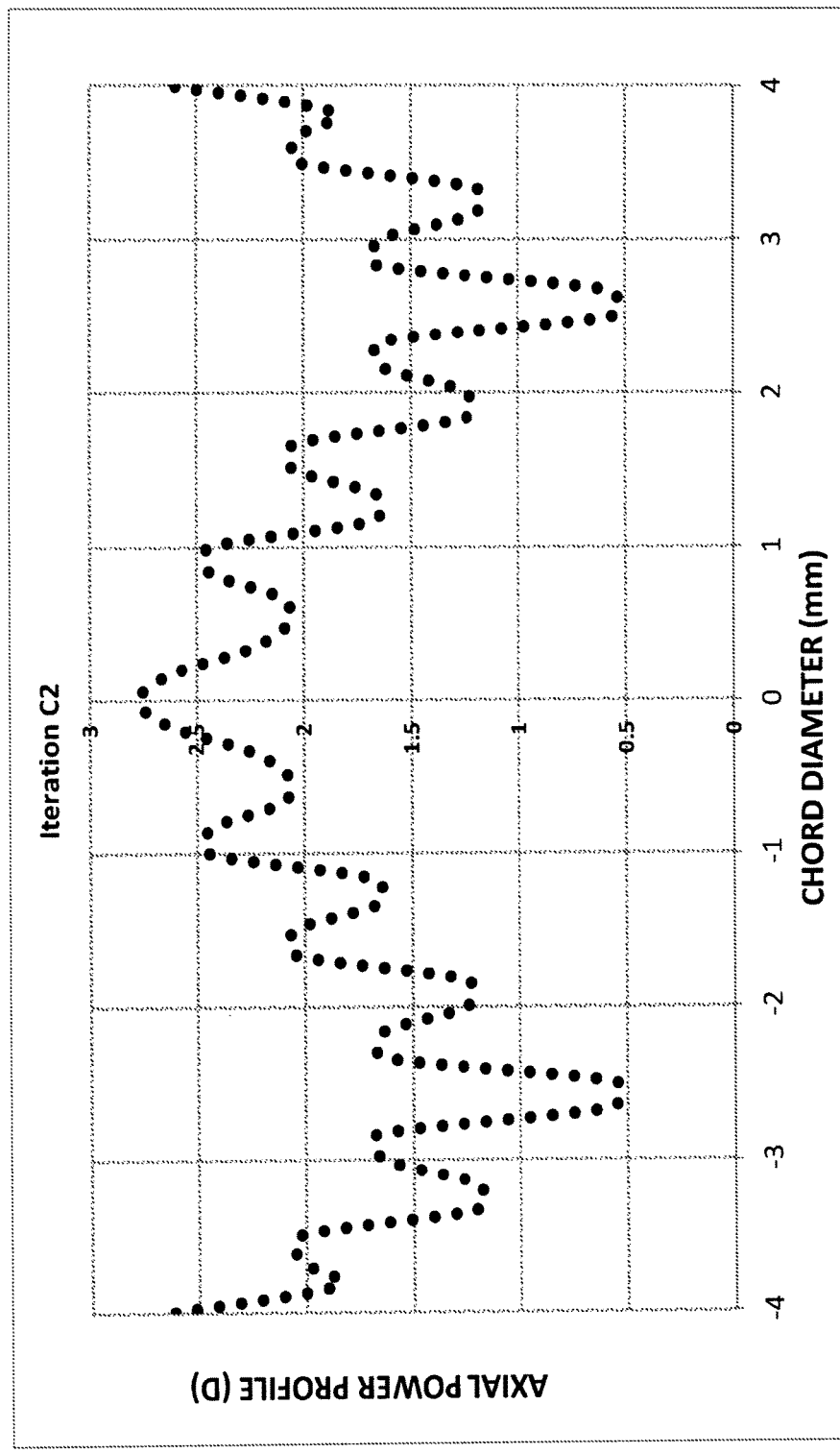

FIGS. 31 and 32 are exemplary that show graphs of the RIQ for two other embodiments of a lens (Iteration C1 and Iteration C2 respectively) selected to address the optical feedback mechanism explanation of emmetropisation, but in this case to provide improving RIQ in the direction of eye growth (e.g. to provide a stimulus to an eye to grow to correct hyperopia). FIGS. 31 and 32 show exemplary embodiments selected with different weights to the selection criteria. In the power profile that gives FIG. 31, achieving a high on-axis RIQ was given more weight than achieving a high RIQ across a large range of field angles.

In the power profile that gives FIG. 32, more weight was given to providing a high RIQ across a large range of field angles than to achieving a high RIQ on-axis. In certain applications, an acceptable high RIQ across a large field angles is considered to be an RIQ above 0.6, above 0.55, above 0.5, above 0.45, above 0.4, above 0.35, or above 0.3. Table 3 lists the defocus and higher order aberrations coefficients up to 20th order, in microns, over a 5 mm pupil diameter for the above described power profiles.

TABLE 3

Defocus and higher order Spherical aberration coefficients over a 5 mm pupil for a single vision lens and four exemplary embodiments with a required slope for through focus RIQ.

| Iteration | C(2,0) | C(4,0) | C(6,0) | C(8,0) | C(10,0) | C(12,0) | C(14,0) | C(16,0) | C(18,0) | C(20,0) |
|---|---|---|---|---|---|---|---|---|---|---|
| Single Vision Lens | −1.800 | 0.000 | 0.000 | 0.000 | 0.000 | 0.000 | 0.000 | 0.000 | 0.000 | 0.000 |
| Iteration A1 | −1.568 | 0.107 | −0.017 | −0.016 | −0.022 | −0.008 | 0.026 | 0.005 | −0.016 | 0.003 |
| Iteration A2 | −1.562 | 0.115 | −0.011 | −0.011 | −0.019 | −0.007 | 0.025 | 0.004 | −0.017 | 0.005 |
| Iteration C1 | 1.468 | −0.135 | 0.020 | 0.029 | 0.036 | 0.011 | −0.036 | −0.008 | 0.022 | −0.003 |
| Iteration C2 | 1.468 | −0.116 | 0.035 | 0.010 | −0.013 | −0.030 | −0.014 | 0.025 | 0.004 | −0.016 |

Section 9

Application to Presbyopia

Presbyopia is a condition where with age an eye exhibits a progressively diminished ability to focus on near objects. The ability to focus on near objects may be referred to as accommodative ability. Pre-presbyopia is an early stage at which patients begin to describe symptoms of diminished ability to focus on near objects. The ability to focus on near objects without use of lenses and/or devices disclosed herein is considered as a non-presbyopic condition. Certain embodiments are directed to providing lenses, devices and/or methods that are configured such that the embodiments provide visual performance that is substantially comparable to the visual performance of a pre-presbyope or non-presbyope over a range of distances with minimal ghosting.

For example, where the near distance is the range of 33 cm to 50 cm or 40 cm to 50 cm; intermediate distance is the range of 50 cm to 100 cm, 50 cm to 80 cm or 50 cm to 70 cm; and far distance is the range of 100 cm or greater, 80 cm or greater or 70 cm or greater. Other distances or range of distances may also be used.

In certain applications, extending the through focus RIQ may provide one or more benefits in the context of presbyopia. The reduced ability of the eye to see at near due to the reduced accommodation may be partially compensated and/or mitigated by using the extended through focus of certain approaches described herein. The benefits may include visual performance at near close to or approaching the visual performance of a properly prescribed single-vision lens for near.

Other benefits may include (i) visual performance at far and intermediate distances substantially equivalent to the visual performance of a properly prescribed single-vision lens for far visual distance; (ii) visual performance over intermediate and far distances that is at least substantially equivalent to the visual performance of a correctly prescribed single-vision lens at the far visual distance; (iii) visual performance, along a range of substantially continuous visual distances, including intermediate and far distances, wherein the visual performance of the multifocal lens is at least substantially equivalent to the visual performance of a correctly prescribed single-vision lens at the far visual distance; and/or (iv) providing visual performance at far and intermediate distances substantially equivalent to the visual performance of a properly prescribed single-vision lens at the far visual distance with minimal, or substantially minimum, ghosting. In certain embodiments, the visual distance over one or more of the following ranges i.e. near intermediate and far distances may be continuous, substantially continuous or continuous over a portion of the near distance or distances, the intermediate distance or distances, or far distance or distances. This may also be true for optical infinity. In certain embodiments, continuous may be defined as near distance range from 33 cm to 50 cm, 40 cm to 50 cm or 33 to 60 cm; intermediate distance range from 50 cm to 100 cm, 50 cm to 80 cm or 50 cm to 70 cm; and far distance range from 100 cm or greater, 80 cm or greater or 70 cm or greater. According to certain disclosed lenses, the lens is configured to provide the visual performance, along continuous visual distances, including near distances, intermediate distances, and far distances.

In some embodiments the through focus RIQ is extended further by taking a monocular optimisation approach, or using one or more of the monocular methods disclosed herein. The monocular optimisation approach in certain embodiments is achieved by extending the through focus RIQ to optimise one eye for distance vision and the other eye for near. In certain embodiments, this optimisation is by selecting different base powers (i.e. effective refractive prescriptions) for the lenses. The extended through focus (for example RIQ) for each lens allows the base powers to be separated, or used without sacrificing, or substantially reducing, far, intermediate, or near vision between the two base powers.

In certain embodiments, one or more of the monocular methods disclosed herein may be used to extend the binocular through-focus RIQ, or the through-focus RIQ, by using an aberration profile for one eye and a different aberration profile for the other eye. The extended through-focus RIQ of each lens optimises one eye for distance vision and the other eye for near without substantially reducing, far, intermediate, and/or near vision, and minimal, or substantially minimal, ghosting with the two aberration profiles.

In certain embodiments, one or more of the monocular methods disclosed herein may be used to extend the binocular through-focus RIQ, or the through-focus RIQ, by using an aberration profile and a base power for one eye and a different aberration profile and a different base power for the other eye. The extended through-focus RIQ of each lens optimises one eye for distance vision and the other eye for near without substantially reducing, far, intermediate, and/or near vision, and minimal, or substantially minimal, ghosting with the two aberration and base power profiles.

Under the monocular approach, in some embodiments, selection of an aberration profile may give a higher priority to the consideration of the RIQ and through focus RIQ, and change in RIQ and through focus RIQ at different pupil sizes (which reflect the change in the eye with different accommodation levels and illumination levels).

Similarly, a lens or optical device may be designed as a bifocal or multifocal or omnifocal lens, with one or both of the parts incorporating aberration profiles as described herein to extend TFRIQ. A combination of bifocal, multifocal, omnifocal lenses, devices, methods and procedures can be used either in one eye or synergistically in both eyes by appropriate selection for each eye that will enhance the binocular performance. For example, one eye may be biased for optimal vision for far and the other eye for optimal vision at near.

A combination of bifocal, multifocal, omnifocal lenses, devices and/or the monocular method that may increase visual performance over a range of dioptric distances by about 1, 1.25, 1.5, 1.75, 2, or 2.25 D. For example, with reference to such method of prescribing bifocal lenses: one eye may have far distance vision in the upper quadrants of performance (RIQ about 0.35, 0.4, 0.45, 0.5 or another selected) and near vision in the lower quadrants of performance (RIQ about 0.1, 0.12, 0.15, 0.17, 0.2 or another selected) and the other eye may have intermediate vision in the upper quadrants of performance (RIQ about 0.35, 0.4, 0.45, 0.5 or another selected) and near vision in the lower quadrants of performance (RIQ about 0.1, 0.12, 0.15, 0.17, 0.2 or another selected).

When different base powers, power profiles or aberration profiles are used in two different eyes; the different base powers, power profiles, aberration profiles may be selected so that the through focus RIQ overlaps to increase the binocular through-focus RIQ. For example, in certain embodiments, the base powers may be selected so that in combination the visual Strehl Ratio does not drop below 0.1, 0.15, 0.2, 0.25, 0.3, 0.35, 0.40 or another selected value, between the combined RIQ profiles.

(A) Examples for Presbyopia

Figure 36:
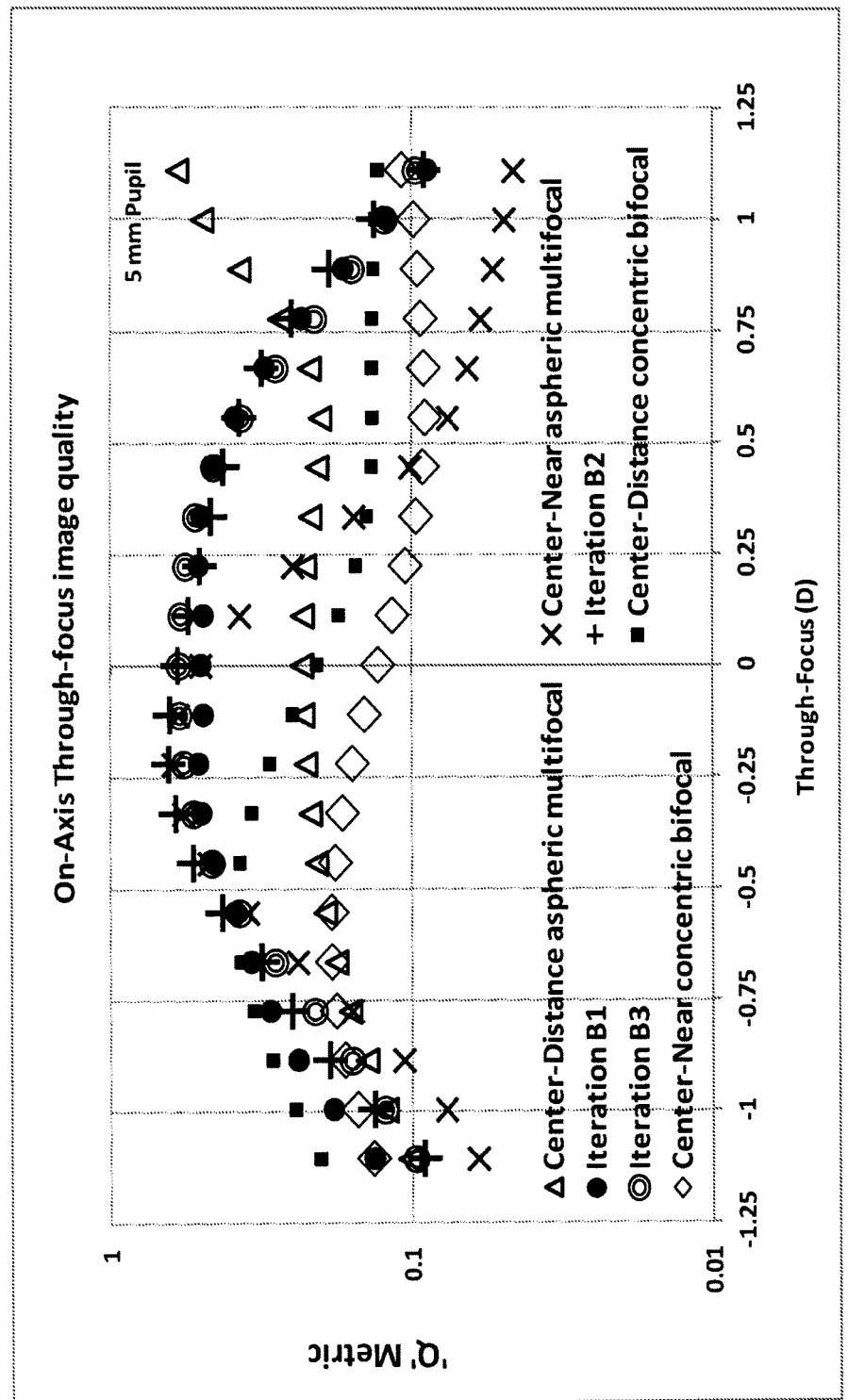
FIG. 36 shows a retinal image quality (RIQ) for seven aberration profiles over a through focus range of 2.5 D. The seven aberration profiles correspond to example centre-distance and centre-near aspheric multifocals and concentric ring/annulus type bifocals and three exemplary aberration profiles (Iteration B1, Iteration B2, Iteration B3) obtained after optimising through focus performance, according to certain embodiments.
Figure 37:
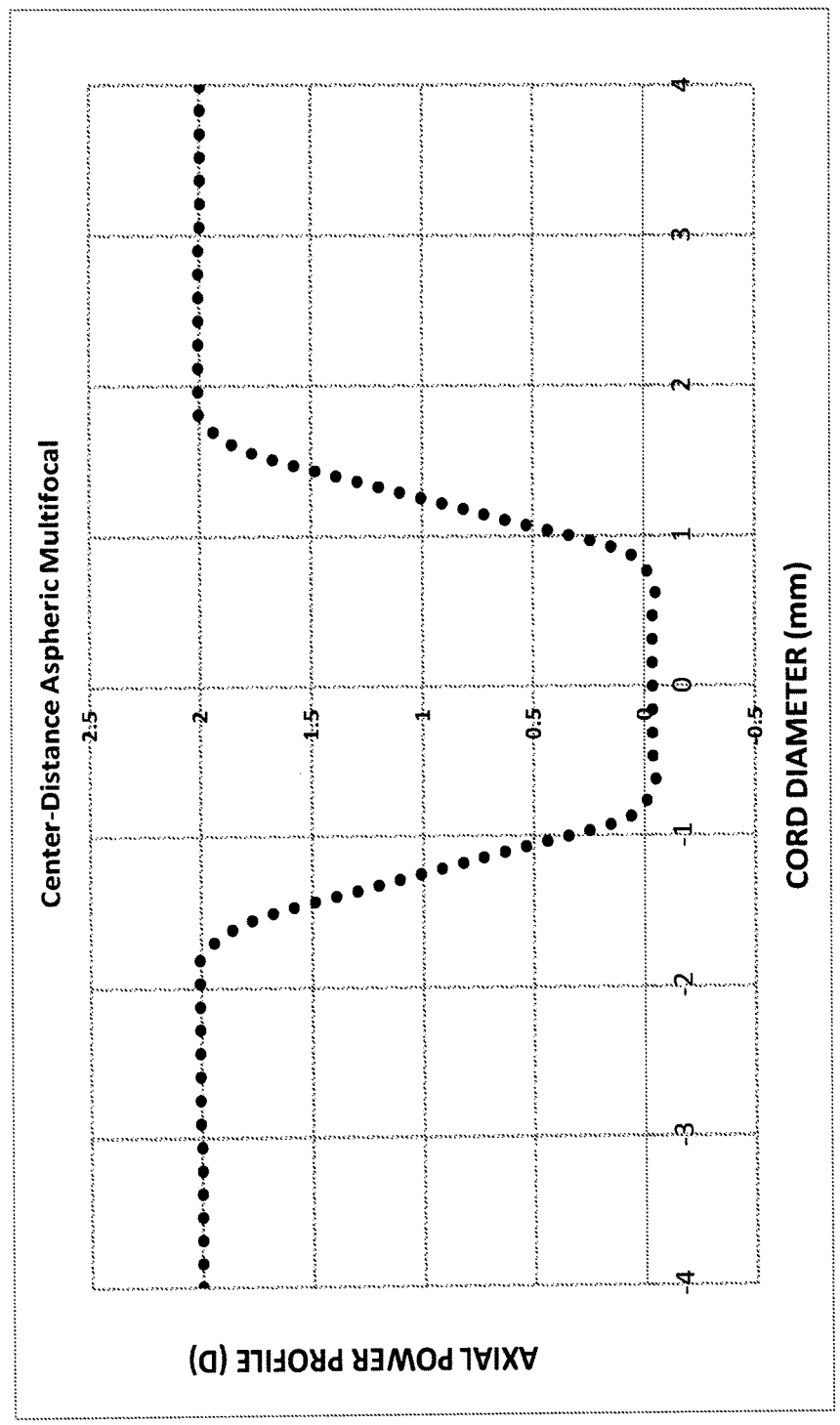
FIGS. 37 to 43 show the power profiles of contact lenses across the optic zone diameter, for providing the TFRIQ described in FIG. 36, according to certain embodiments.

FIG. 36 shows a graph of through focus RIQ (in this case visual Strehl Ratio) for seven power profiles, according to certain embodiments. In this figure the vertical axis (RIQ) is defined on a logarithmic scale. FIG. 36 was obtained for a 5 mm pupil size and an eye with no myopia or hyperopia and no other higher order aberrations. One or more power profiles may be adapted to a myopic or hyperopic eye by incorporating an appropriate correcting defocus term, which does not affect the higher order aberrations defining the power profiles used for form FIG. 36.

The seven power profiles are: a power profile that may appear in a conventional centre-distance aspheric multifocal lens (indicated by triangles in FIG. 36); a power profile that may appear in a conventional centre-near multifocal lens (indicated by 'x' in FIG. 36); a power profile that may appear in a centre-distance concentric bifocal lens (indicated by filled '□' in FIG. 36); a power profile that may appear in a centre-near concentric bifocal lens (indicated by empty '◇' in FIG. 36) and three iterations (Iteration B1, Iteration B2, Iteration B3) including a favourable combination of spherical aberration (indicated by filled circles, bold '+' signs and a concentric circle pairs, respectively, in FIG. 36).

The power profiles for each of these are shown in FIGS. 37 to 43. The centre-distance and centre-near aspheric multifocals had the centre component extend to about 2 mm and the outer zone power commence at a radius of about 1.8 mm. A linear transition was provided between the near and distance power zones. The concentric bifocals both had a ring structure, alternating between an additional power of 2 Dioptres and no addition power (also referred to as base distance power).

Table 4 lists the defocus and higher order spherical aberration coefficients up to $20^{th}$ order, in microns, over a 5 mm pupil diameter, for the three exemplary embodiment power profiles, namely: Iteration B1 (FIG. 41), Iteration B2 (FIG. 42) and Iteration B3 (FIG. 43), respectively.

TABLE 4

Defocus and Spherical aberration coefficients of three exemplary embodiments for presbyopia.

| Iteration | Iteration B1 | Iteration B2 | Iteration B3 |
|---|---|---|---|
| C(2, 0) | −0.096 | −0.092 | 0.033 |
| C(4, 0) | −0.135 | 0.032 | 0.003 |
| C(6, 0) | 0.02 | 0.074 | 0.077 |
| C(8, 0) | 0.029 | −0.015 | −0.045 |
| C(10, 0) | 0.036 | −0.006 | −0.023 |
| C(12, 0) | 0.012 | −0.018 | 0.01 |
| C(14, 0) | −0.036 | −0.009 | 0.014 |
| C(16, 0) | −0.01 | 0.007 | 0.007 |
| C(18, 0) | 0.022 | 0.011 | 0.003 |
| C(20, 0) | 0 | 0.002 | −0.014 |

Figure 38:
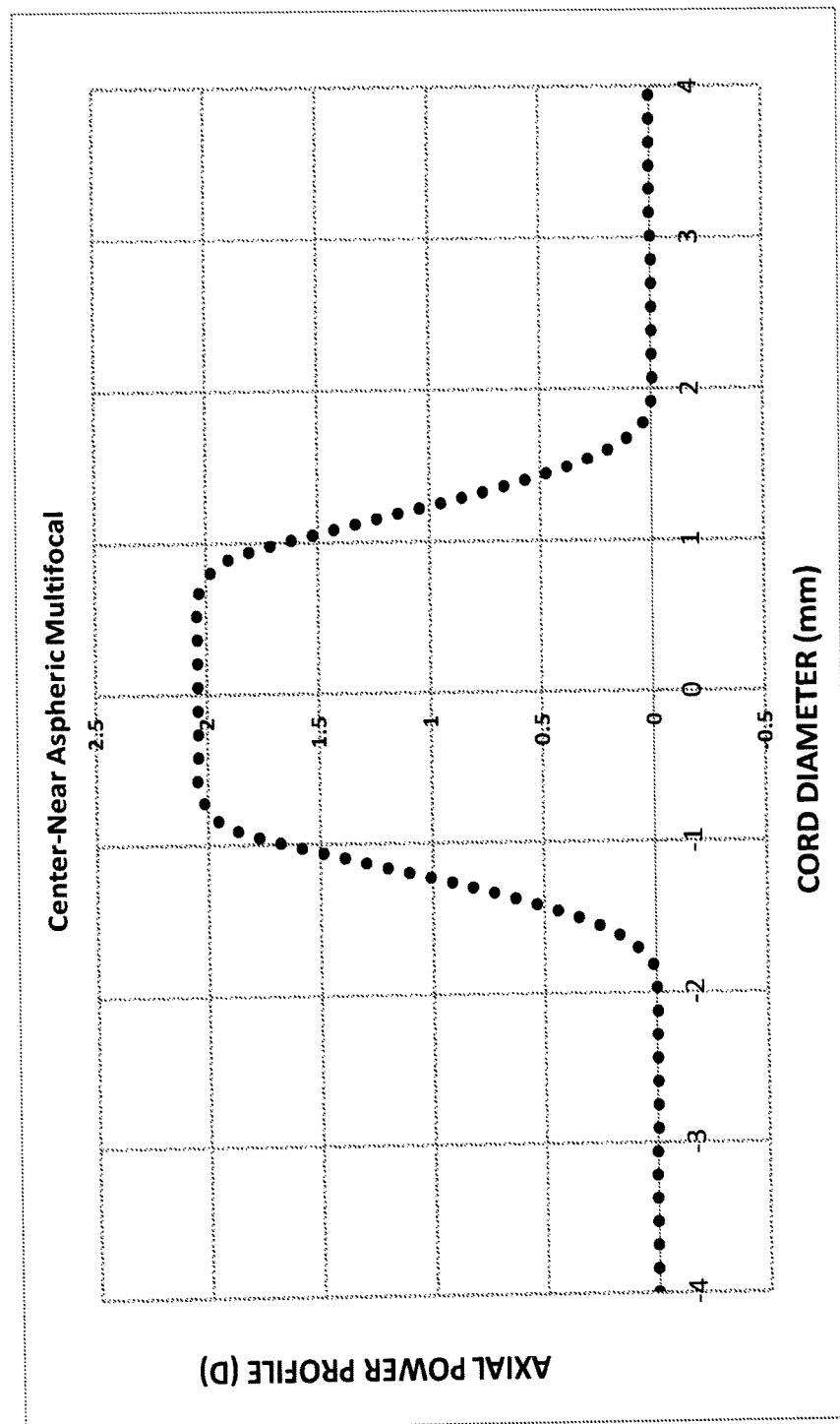
Figure 39:
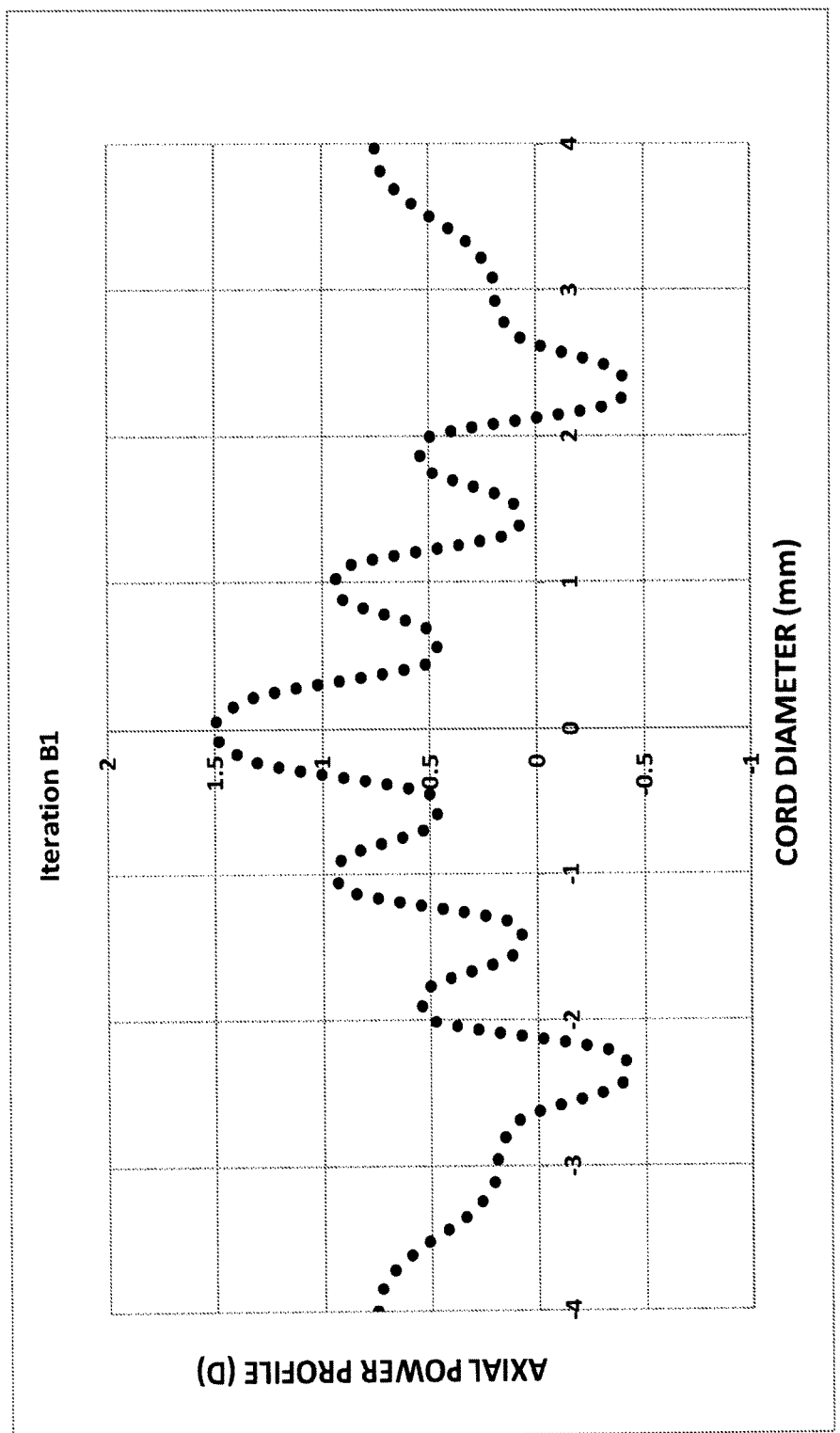
Figure 40:
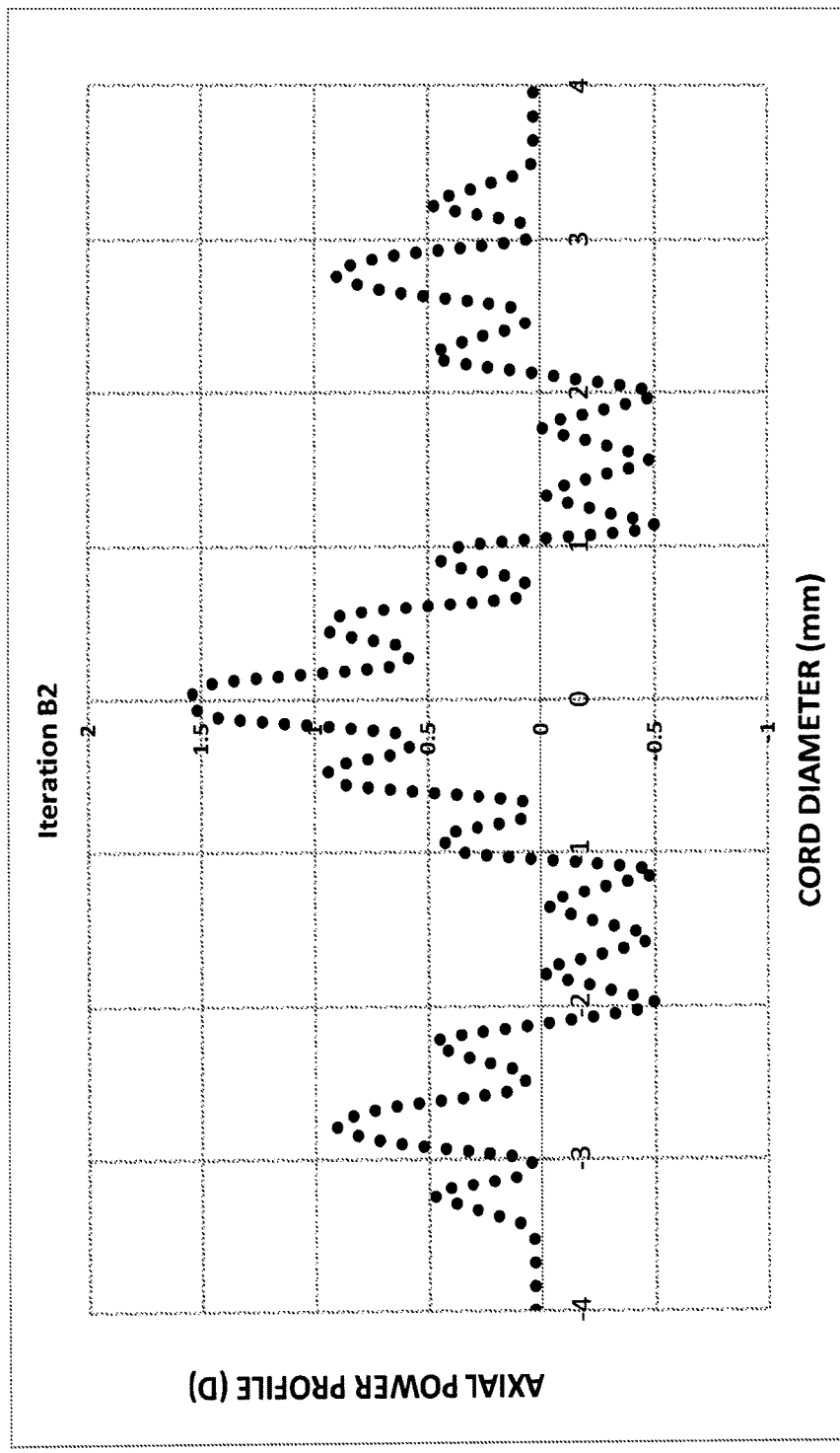

Table 5 lists out the defocus and higher order spherical aberration coefficients up to 20° order, in microns, over a 5 mm pupil diameter, for the described power profiles, namely, centre-distance aspheric multifocal (FIG. 37), and centre-near aspheric multifocal (FIG. 38, respectively.

TABLE 5

Defocus and Higher order spherical aberration coefficients of both centre-distance and centre-near type aspheric multifocal lenses.

| Iteration | Centre-Distance aspheric multifocal | Centre-Near aspheric multifocal |
|---|---|---|
| C(2, 0) | 1.15 | 0.324 |
| C(4, 0) | 0.181 | −0.244 |
| C(6, 0) | −0.09 | 0.114 |
| C(8, 0) | 0.02 | −0.021 |
| C(10, 0) | 0 | −0.013 |
| C(12, 0) | 0 | 0.011 |
| C(14, 0) | 0 | 0 |
| C(16, 0) | 0 | 0 |
| C(18, 0) | 0 | 0 |
| C(20, 0) | 0 | 0 |

In the aspheric multifocal lenses the spherical aberration coefficients progressively decrease in absolute magnitude with an increase in order. This is in contrast to the power profiles of Iteration B1, Iteration B2 and Iteration B3, which include at least one higher order spherical aberration term with an absolute value coefficient greater than the absolute value of the coefficient for a lower order term. This characteristic is present in one or more of the embodiments of power profile described herein. From FIG. 36, it can be noted that the centre-distance aspheric multifocal has a RIQ of 0.23 at 0 D, which substantially inferior than the other power profiles, according to certain embodiments. However, performance of this lens as gauged by the RIQ metric is maintained relatively constant over a large through focus range. For example, at −0.4 Dioptres the RIQ is about 0.2, at 0.67 the RIQ is about 0.18 and at −1 Dioptres, the RIQ is about 0.12.

The centre-near aspheric multifocal has a RIQ at 0 D is about 0.5. With this exemplary design, the RIQ falls to about 0.24 at −0.67 Dioptres (still better than the centre-distance aspheric multifocal). However, beyond that the centre-near aspheric multifocal has a rapidly decreasing RIQ, as can be seen at −1 Dioptre the value of RIQ is about 0.08. Both of the concentric bifocals (centre-distance and -near) have a low RIQ of 0.13 and 0.21 at 0 D. Both of the concentric bifocals maintain their level of RIQ or better over a range of approximately 1.1 Dioptres.

for distance vision to the value for +0.55 D in FIG. 36. Considering Iteration B2 again, the through focus performance (RIQ) would be modified as follows: an RIQ of about 0.4 at distance vision, an RIQ of about 0.53 at −0.4 Dioptres, about 0.64 at −0.67 Dioptres, about 0.52 at −1 Dioptres, about 0.40 at −1.1 Dioptres, and about 0.15 at −1.5 Dioptres.

By shifting the distance vision point in a lens with combinations of HOA that extend through focus RIQ performance, then the lenses, devices and/or methods that provide the combination of HOA can have a substantially improved through focus performance. This is achieved while maintaining at least as good RIQ as a centre near aspheric multifocal and substantially improved RIQ in comparison to a centre distance aspheric multifocal. The amount of defocus plus power added to shift the RIQ curves is a matter of choice, representing a trade-off between distance vision RIQ and near vision RIQ. Table 6 shows the defocus (leftmost column) and RIQ values for the power profiles described above. It also shows the defocus values shifted by +0.55 D, applicable when to Iteration B1, Iteration B2 and/or Iteration B3 is modified by this amount.

TABLE 6

RIQ values for two bifocal lenses, two concentric bifocal lenses and three aberration profiles for extended through focus RIQ.

| Defocus (D) | Centre-Distance aspheric multifocal | Centre-Near aspheric multifocal | Iteration B1 | Iteration B2 | Iteration B3 | Centre-Distance concentric bifocal | Centre-Near concentric bifocal | Defocus shifted by +0.50 |
|---|---|---|---|---|---|---|---|---|
| −1.1085 | 0.1021 | 0.0601 | 0.1342 | 0.0918 | 0.0971 | 0.2025 | 0.1349 | −0.6085 |
| −0.9977 | 0.1212 | 0.0768 | 0.1831 | 0.1338 | 0.1228 | 0.2447 | 0.1524 | −0.4977 |
| −0.8868 | 0.1407 | 0.1062 | 0.2394 | 0.1882 | 0.1577 | 0.2913 | 0.1675 | −0.3868 |
| −0.7760 | 0.1598 | 0.1574 | 0.2957 | 0.2511 | 0.2095 | 0.3362 | 0.1789 | −0.2760 |
| −0.6651 | 0.1776 | 0.2383 | 0.3423 | 0.3160 | 0.2830 | 0.3700 | 0.1851 | −0.1651 |
| −0.5543 | 0.1931 | 0.3481 | 0.3867 | 0.4262 | 0.3723 | 0.3839 | 0.1855 | −0.0543 |
| −0.4434 | 0.2060 | 0.4699 | 0.4550 | 0.5318 | 0.4583 | 0.3735 | 0.1805 | 0.0566 |
| −0.3326 | 0.2162 | 0.5715 | 0.4992 | 0.6099 | 0.5266 | 0.3417 | 0.1709 | 0.1674 |
| −0.2217 | 0.2237 | 0.6185 | 0.5110 | 0.6451 | 0.5691 | 0.2969 | 0.1584 | 0.2783 |
| −0.1109 | 0.2284 | 0.5913 | 0.4924 | 0.6369 | 0.5879 | 0.2495 | 0.1444 | 0.3891 |
| 0.0000 | 0.2304 | 0.4980 | 0.5014 | 0.5993 | 0.5906 | 0.2076 | 0.1300 | 0.5000 |
| 0.1109 | 0.2294 | 0.3702 | 0.4924 | 0.5511 | 0.5825 | 0.1754 | 0.1167 | 0.6109 |
| 0.2217 | 0.2249 | 0.2468 | 0.5110 | 0.5055 | 0.5609 | 0.1539 | 0.1055 | 0.7217 |
| 0.3326 | 0.2160 | 0.1549 | 0.4992 | 0.4648 | 0.5182 | 0.1418 | 0.0973 | 0.8326 |
| 0.4434 | 0.2048 | 0.1010 | 0.4550 | 0.4232 | 0.4513 | 0.1367 | 0.0924 | 0.9434 |
| 0.5543 | 0.2000 | 0.0758 | 0.3867 | 0.3741 | 0.3672 | 0.1358 | 0.0908 | 1.0543 |
| 0.6651 | 0.2173 | 0.0650 | 0.3082 | 0.3154 | 0.2815 | 0.1363 | 0.0917 | 1.1651 |
| 0.7760 | 0.2727 | 0.0588 | 0.2327 | 0.2511 | 0.2095 | 0.1362 | 0.0940 | 1.2760 |
| 0.8868 | 0.3701 | 0.0535 | 0.1694 | 0.1882 | 0.1577 | 0.1347 | 0.0962 | 1.3868 |
| 0.9977 | 0.4907 | 0.0491 | 0.1219 | 0.1338 | 0.1228 | 0.1325 | 0.0992 | 1.4977 |
| 1.1085 | 0.5962 | 0.0458 | 0.0896 | 0.0918 | 0.0971 | 0.1305 | 0.1087 | 1.6085 |

Iteration B1, Iteration B2 and Iteration B3 have at least as good RIQ at 0 D, as the centre near bifocal and also better RIQ across the through-focus range between −0.65 D and 0.75 D as the eye accommodates. For example Iteration B2 has an RIQ of about 0.53 at −0.4 Dioptres, about 0.32 at −0.67 Dioptres and about 0.13 at −1 Dioptres. Through focus performance (RIQ) of Iteration B1, Iteration B2 and Iteration B3 can be further extended. This extension is achieved by shifting the curves to the left in FIG. 36. However, the performance of the centre-near aspheric multifocal lens, in this exemplary, cannot be shifted in this manner without substantially affecting performance, due to the asymmetric RIQ that decreases substantially more rapidly for plus powers (right hand side of FIG. 36).

Figure 115:
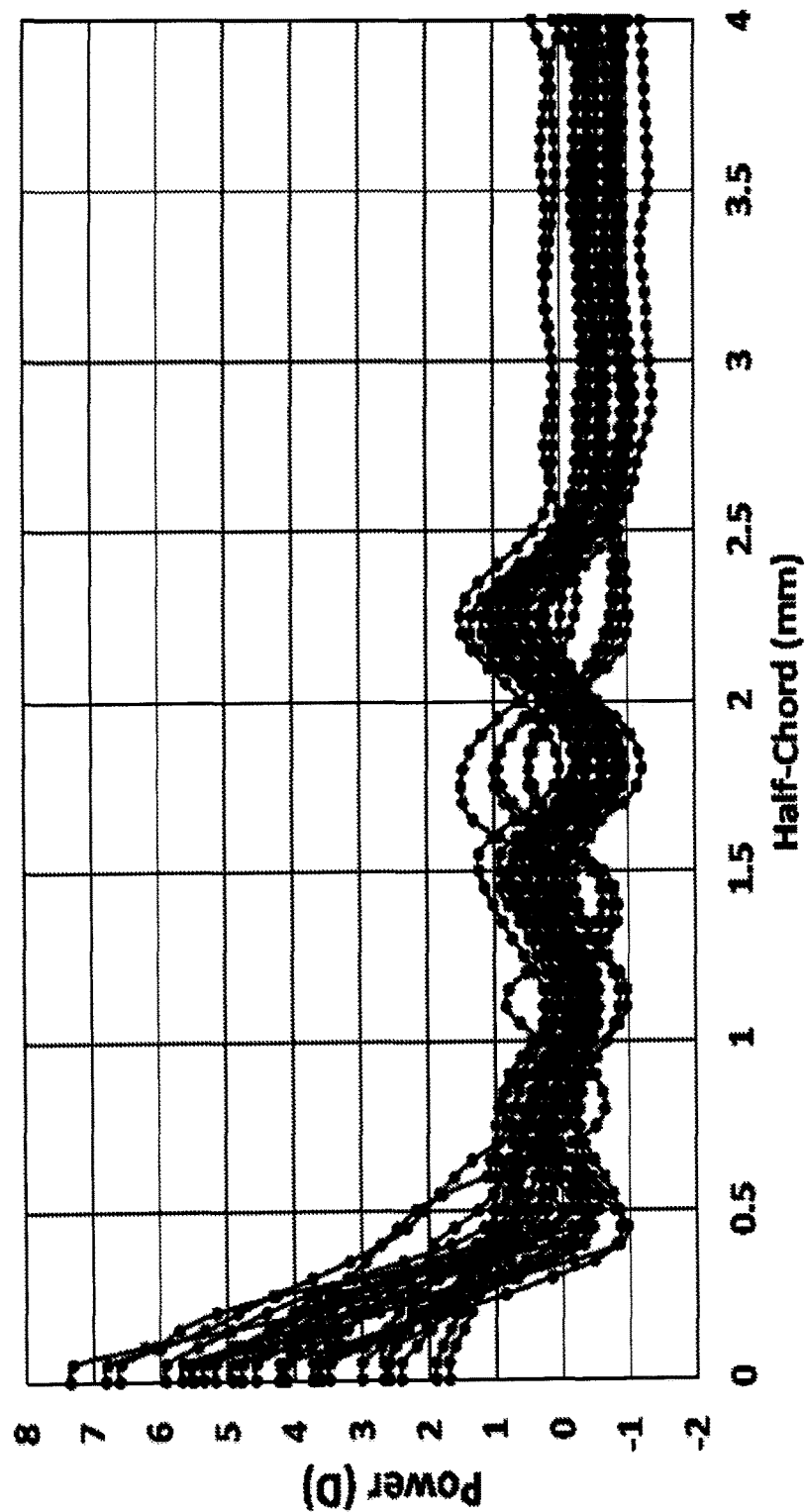
FIG. 115 shows the power profiles of several exemplary embodiments across the half-chord diameter that have varying degrees of plus ranging from +3D to +7 D in various zone widths ranging from 0.25 mm to 1 mm of the half-chord of the lens.
Figure 116:
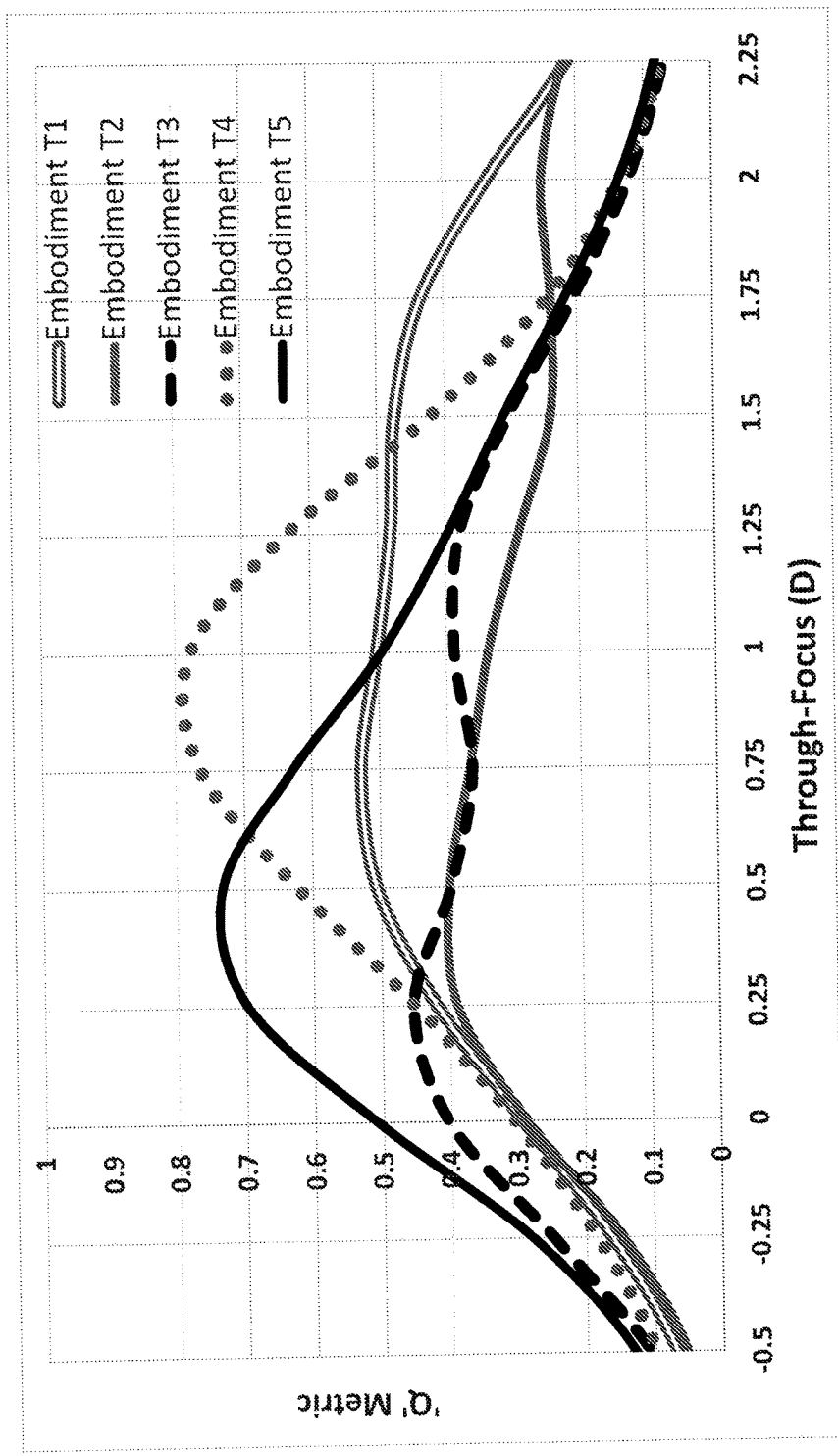
FIG. 116 plots the through-focus image quality ('Q' metric) for five exemplary combinations with higher order aberrations (T1 to T5) that include symmetric higher order aberrations.

For example, the three exemplary iterations have an RIQ of about 0.40 at +0.55 D. Combining the spherical aberration terms with a +0.55 D defocus term will shift the RIQ value FIG. 115 plots the through-focus retinal image quality for five exemplary combinations with higher order aberrations (T1 to T5 shown in the table 6.1) that include only symmetric higher order aberrations. The through-focus retinal image quality computed for the five exemplary higher order aberrations combinations using the monochromatic RIQ (visual Strehl ratio) described in the equation 2. The combinations T1, T4 and T5 used a 3 mm pupil diameter to obtain the through-focus retinal image quality while the combinations T2 and T3 used a 4 mm pupil diameter. These computations for a specific pupil diameter and/or with specific retinal image quality result in exemplary combinations. Other exemplary combinations are also contemplated using one or more of the following: image quality metrics, pupils, spatial frequency ranges to calculate the through focus retinal image quality.

| | Q-metric | | | | |
|---|---|---|---|---|---|
| | Visual Strehl ratio | Visual Strehl ratio | Visual Strehl ratio Pupil | Visual Strehl ratio | Visual Strehl ratio |
| | 3 mm | 4 mm | 4 mm SF | 3 mm | 3 mm |
| | 0 to 30 c/d | 0 to 30 c/d | 0 to 30 c/d Coefficients | 0 to 30 c/d | 0 to 30 c/d |
| | Aberration coefficients of embodiment T1 | Aberration coefficients of embodiment T2 | Aberration coefficients of embodiment T3 | Aberration coefficients of embodiment T4 | Aberration coefficients of embodiment T5 |
| C(2, 0) | 0.426 | 0.907 | 0.56 | 0.357 | 0.181 |
| C(4, 0) | −0.116 | −0.112 | −0.096 | −0.092 | −0.096 |
| C(6, 0) | −0.012 | 0.049 | 0.038 | −0.061 | −0.005 |
| C(8, 0) | −0.040 | 0.058 | 0.019 | 0.028 | −0.021 |
| C(10, 0) | −0.016 | −0.111 | −0.084 | 0.04 | 0.014 |
| C(12, 0) | 0.042 | −0.049 | −0.024 | −0.012 | 0.028 |
| C(14, 0) | 0.012 | 0.063 | 0.055 | −0.017 | −0.013 |
| C(16, 0) | −0.027 | −0.005 | −0.007 | 0.007 | −0.011 |
| C(18, 0) | 0.012 | −0.02 | −0.02 | 0.003 | 0.012 |
| C(20, 0) | 0 | 0.017 | 0.016 | −0.001 | −0.005 |

(B) Effect of Pupil Size

Figure 41:
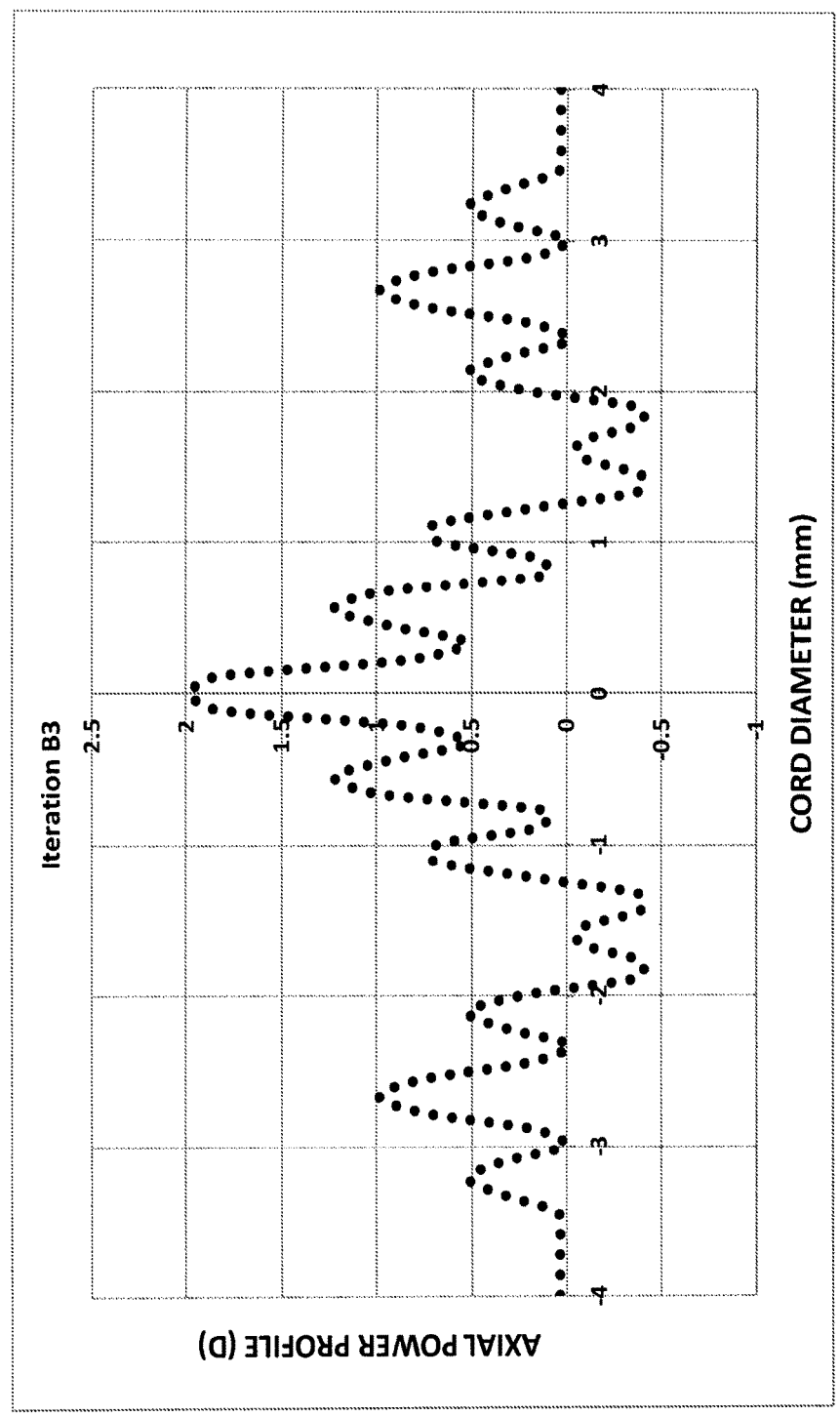
Figure 42:
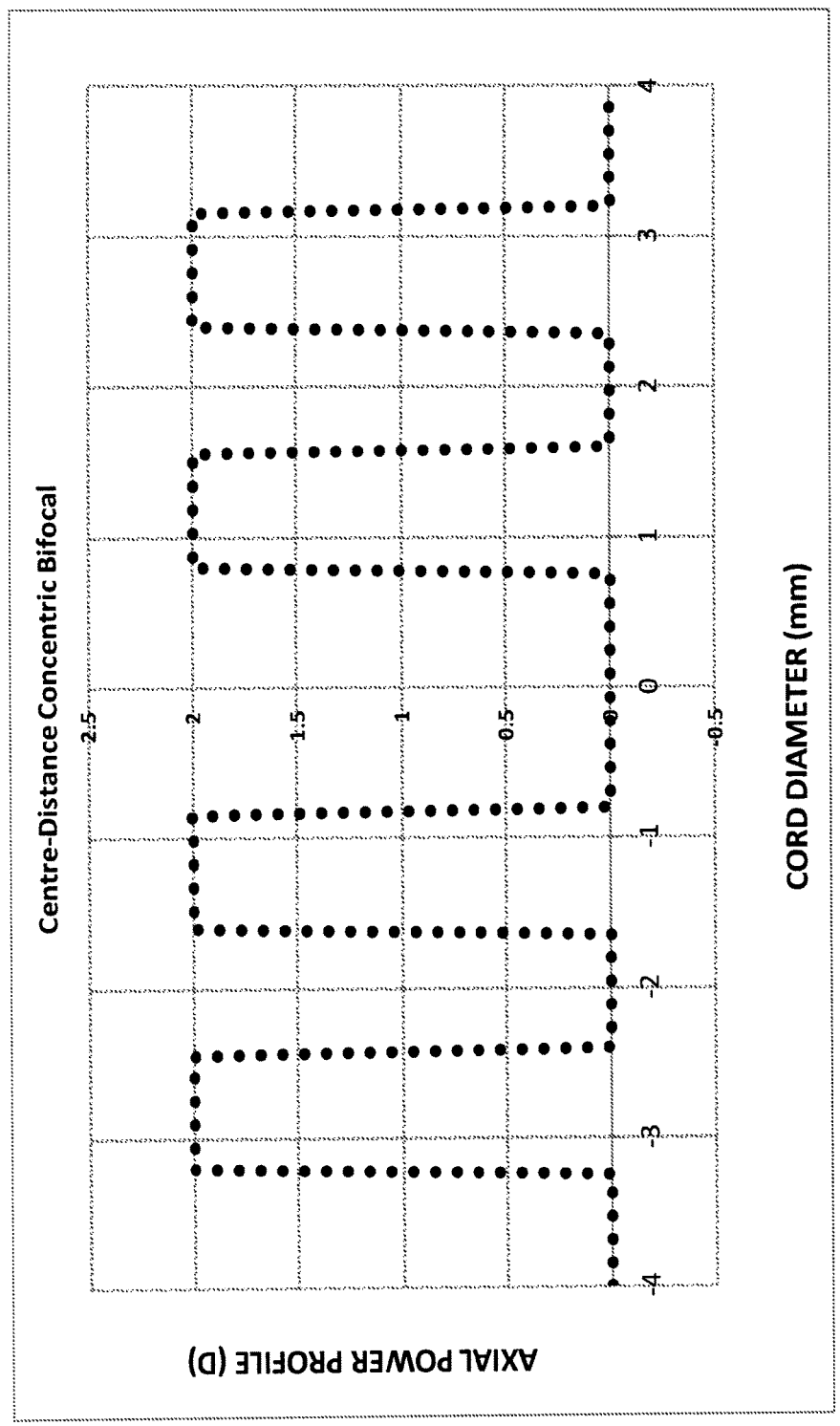
Figure 43:
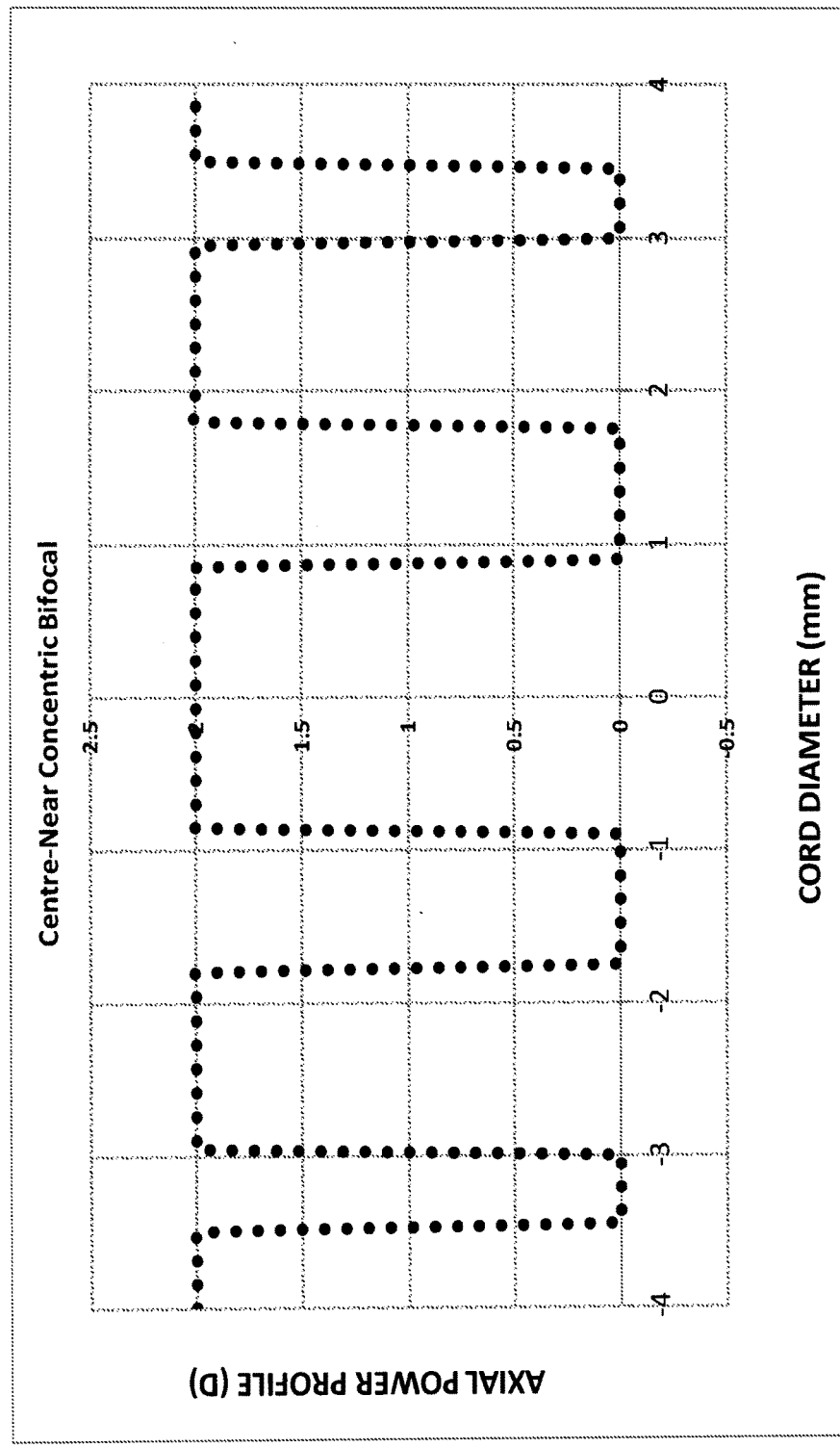
Figure 44:
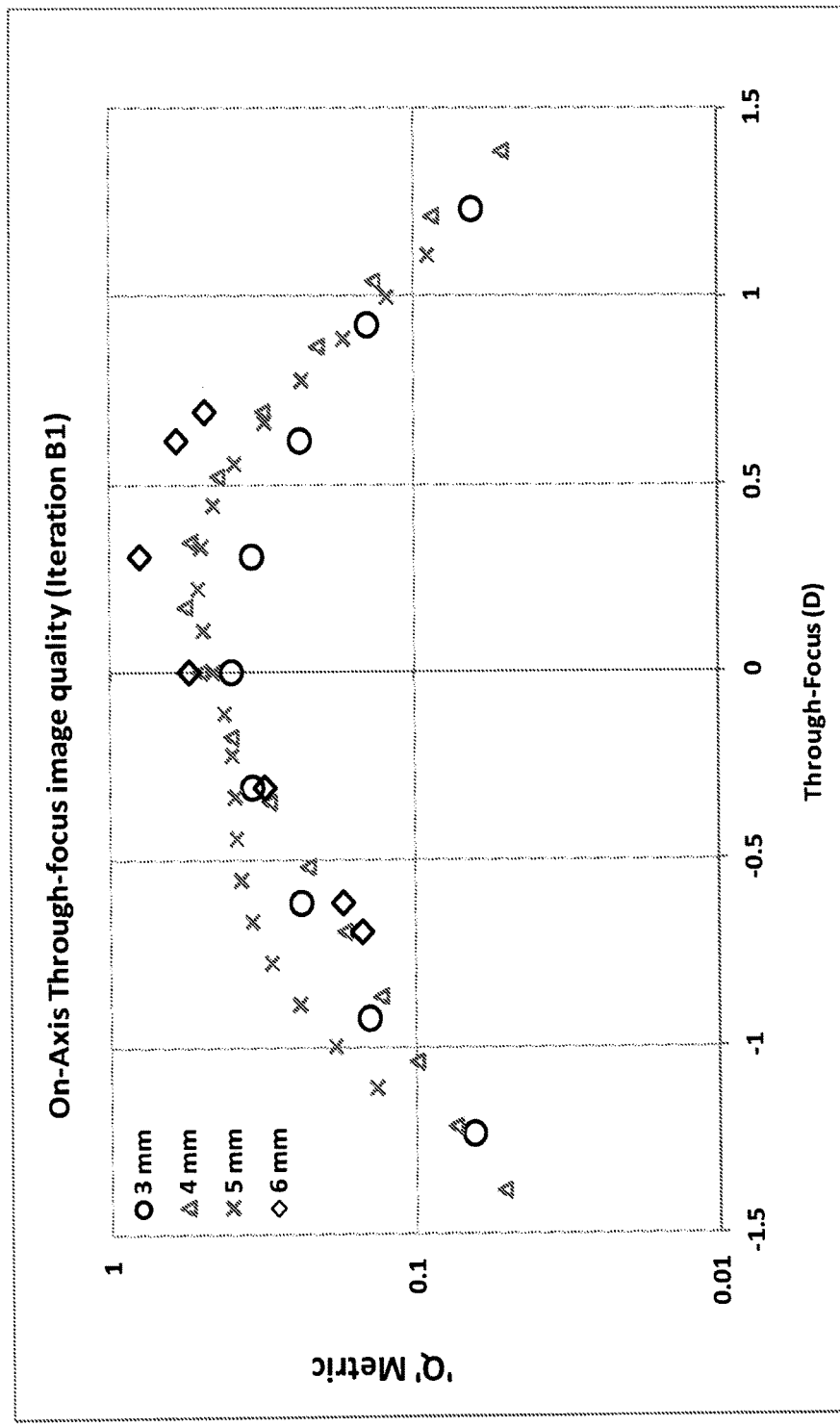
FIGS. 44 to 46 show the on-axis TFRIQ for the three exemplary embodiments for presbyopia (Iteration B1, B2 and B3) across four pupil diameters (3 mm to 6 mm)
Figure 45:
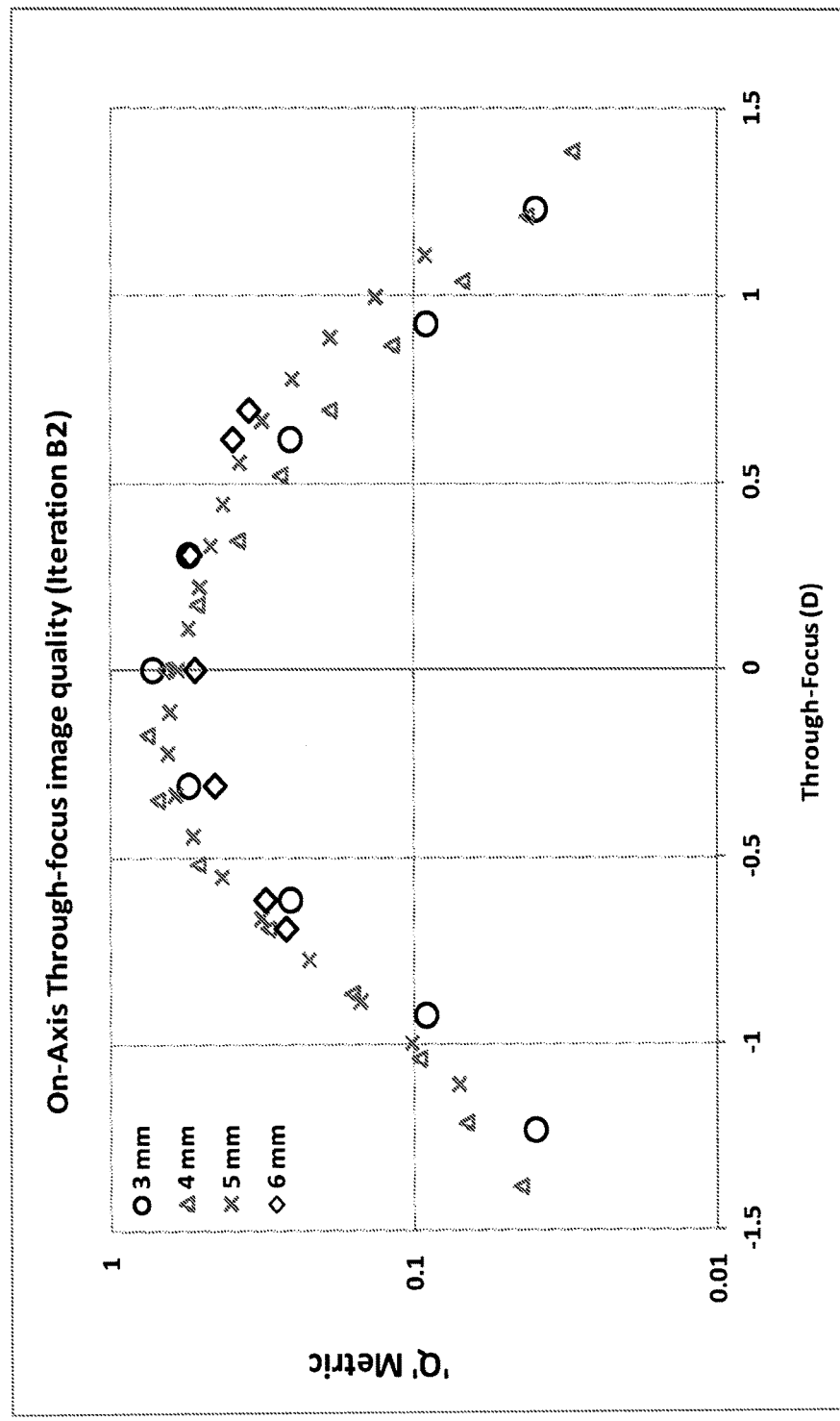
Figure 46:
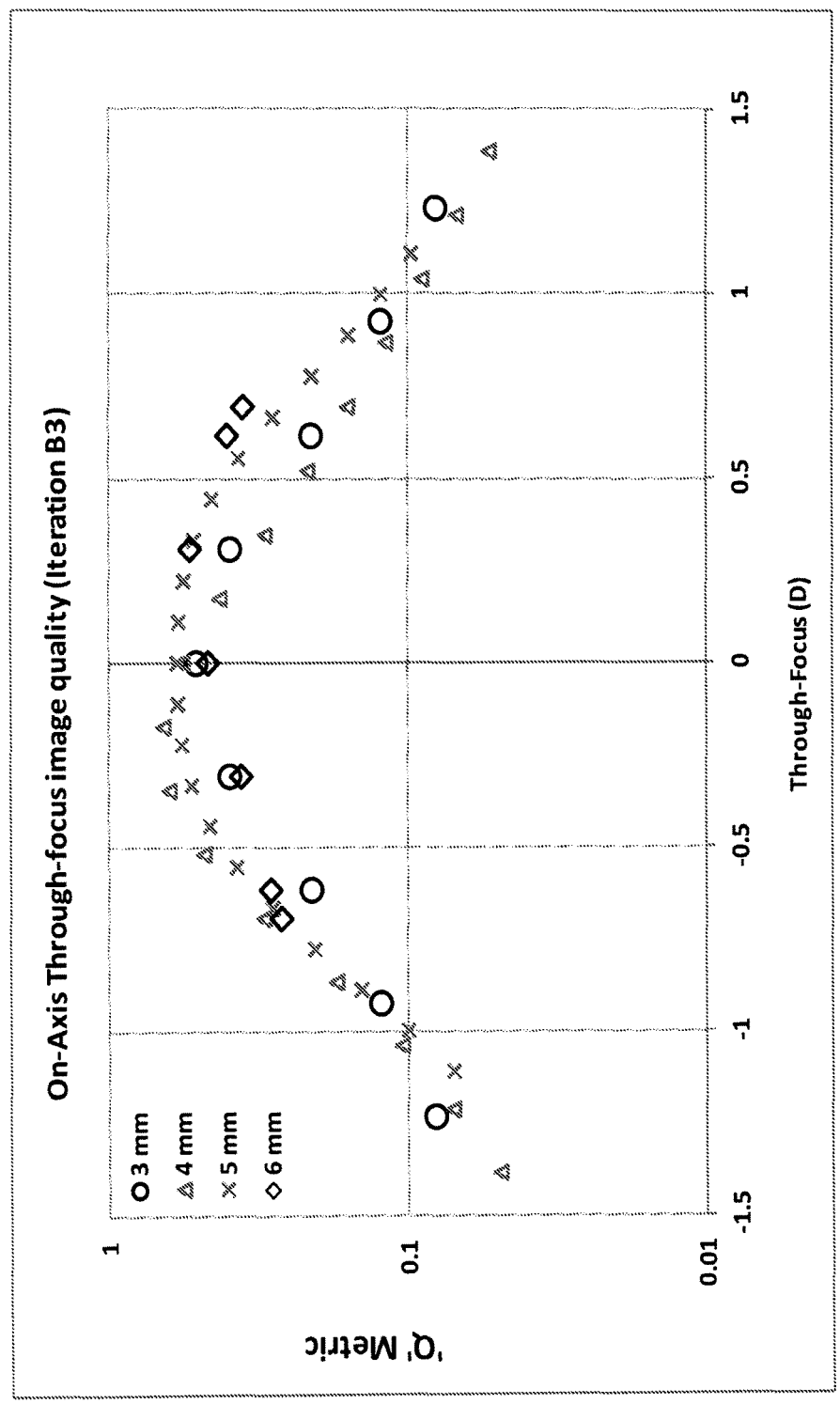
Figure 47:
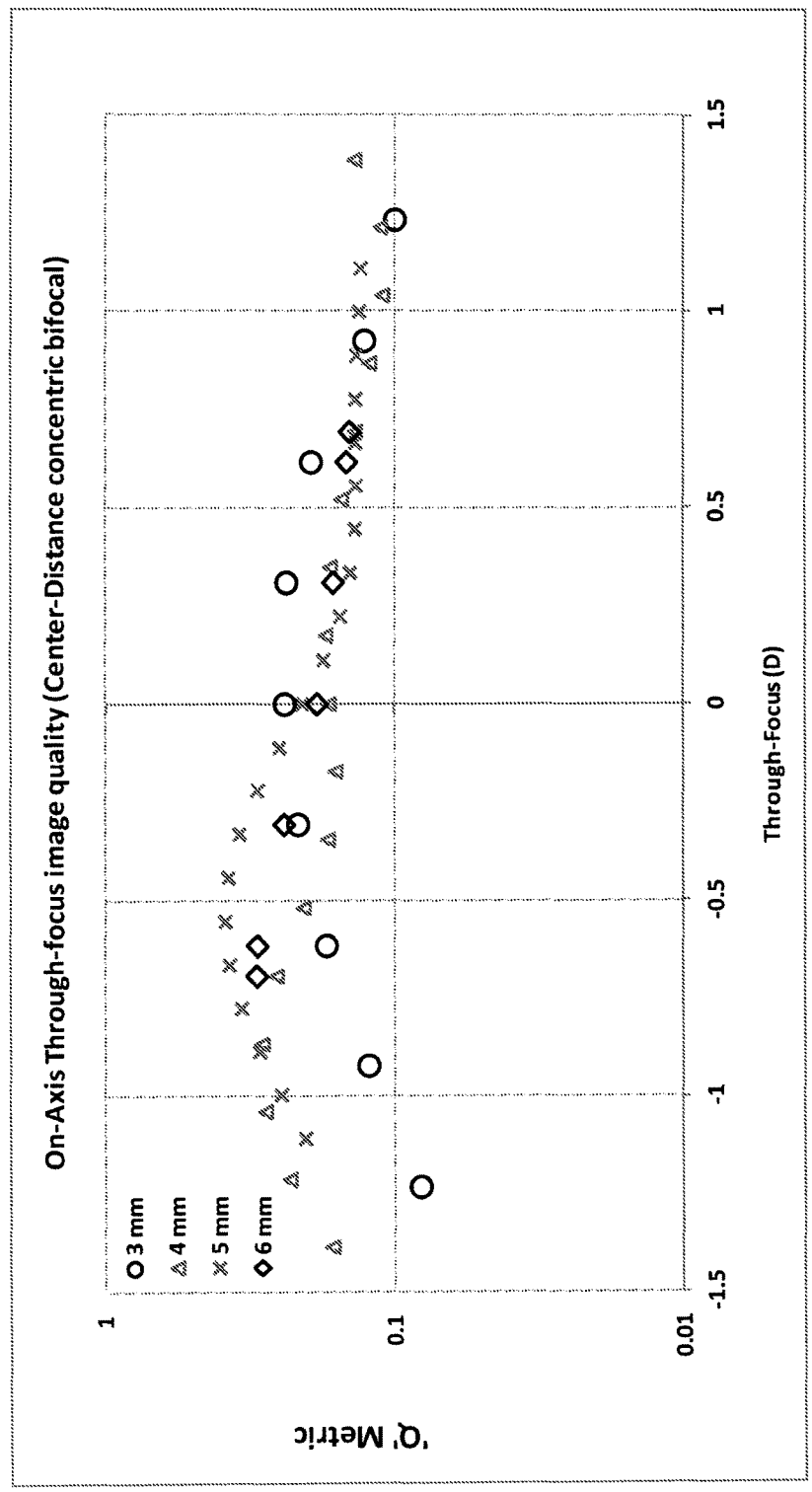
FIGS. 47 and 48 show the on-axis TFRIQ for the centre-distance and centre-near concentric designs across four pupil diameters (3 mm to 6 mm), according to certain embodiments.
Figure 48:
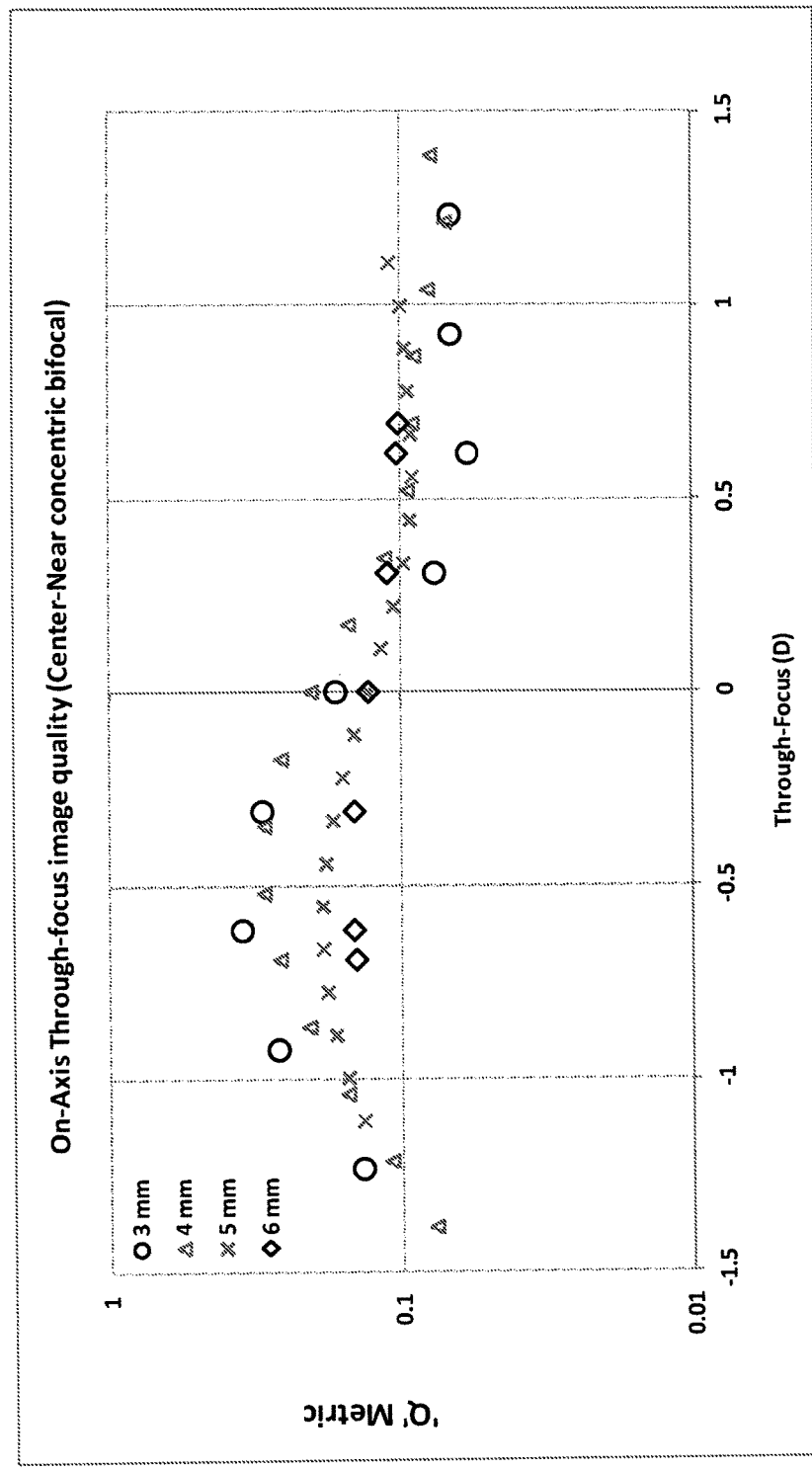
Figure 49:
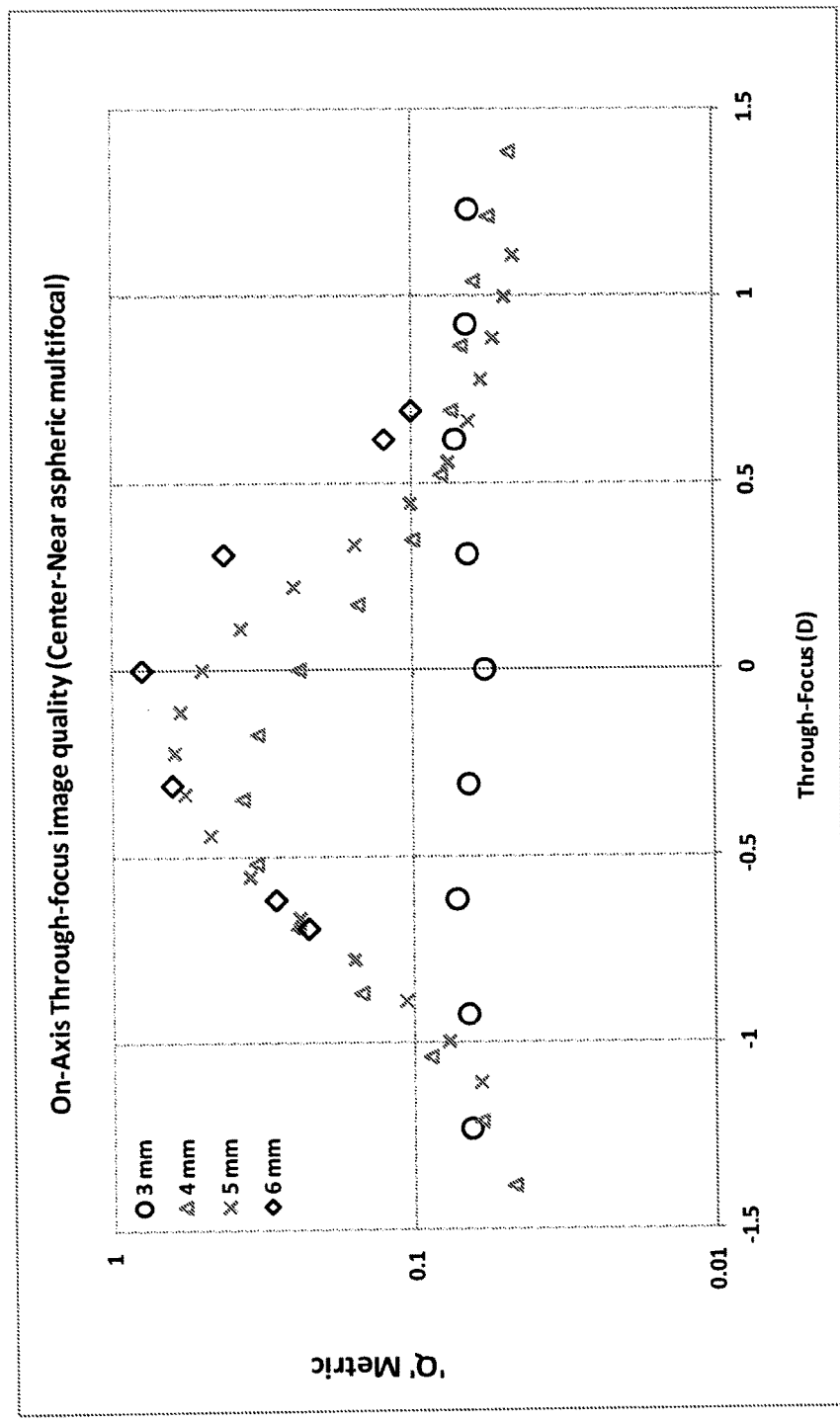
FIGS. 49 and 50 show the on-axis TFRIQ for the centre-distance and centre-near aspheric multifocal designs across four pupil diameters (3 mm to 6 mm), according to certain embodiments.
Figure 50:
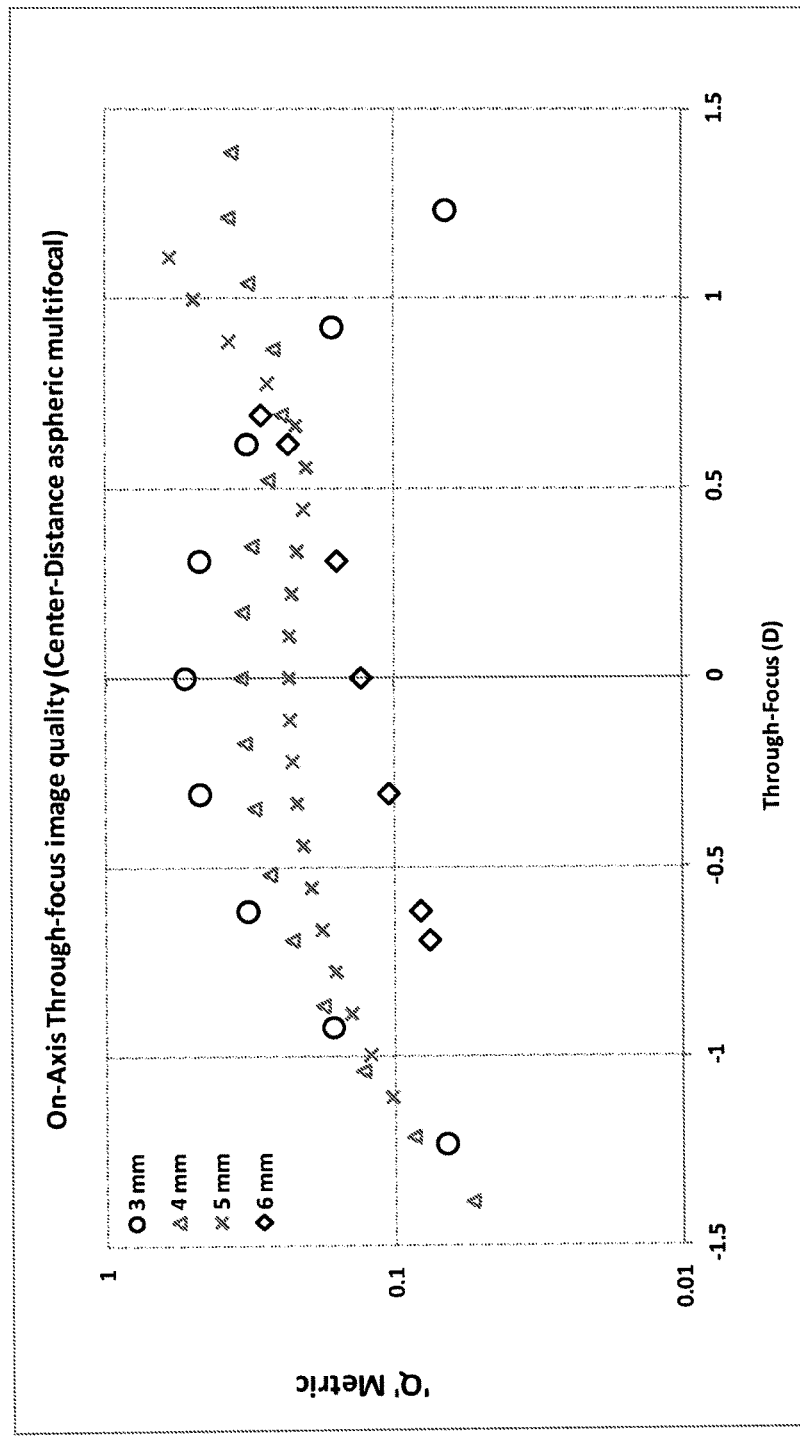

FIGS. 44 to 46 show the variation in through focus RIQ with pupil size for Iteration B1, Iteration B2 and Iteration B3 respectively, according to certain embodiments. The exemplary RIQ profiles are relatively stable, in that the RIQ retains the combination of a relatively high RIQ (in comparison to, for example, a centre distance aspheric multifocal) in combination with a relatively long through focus range (in comparison to, for example, a centre near aspheric multifocal). Figure sets 47, 48 and 49, 50 show the variation in through focus RIQ with pupil size for the two concentric bifocals and two aspheric multifocals, respectively. From these figures it can be seen that, comparatively, the change in RIQ and through focus RIQ performance is less stable for these lenses than Iteration B1 (FIG. 39), Iteration B2 (FIG. 40) and Iteration B3 (FIG. 41). FIGS. 39 to 50 are examples, according to certain embodiments.

(C) Monocular and/or Binocular Design

As described herein, Iteration B2 (FIG. 40) may provide an RIQ of 0.4 or above from distance vision to about an intermediate vergence of about 1.1 Dioptres. When appropriate level of defocus is added to the same iteration while correcting the other eye, TFRIQ can be extended from 1.1 Dioptres to up close, say 2.2 D target vergence, i.e. binocularly combined the candidate eye may maintain an RIQ of 0.4 or above from distance test distance to all the way up to, or substantially up to 2.2 Dioptres. Using this monocular design approach and assuming the recipient accepts the monocular design, the combined through focus performance is substantially extended, according to certain embodiments.

Figure 51:
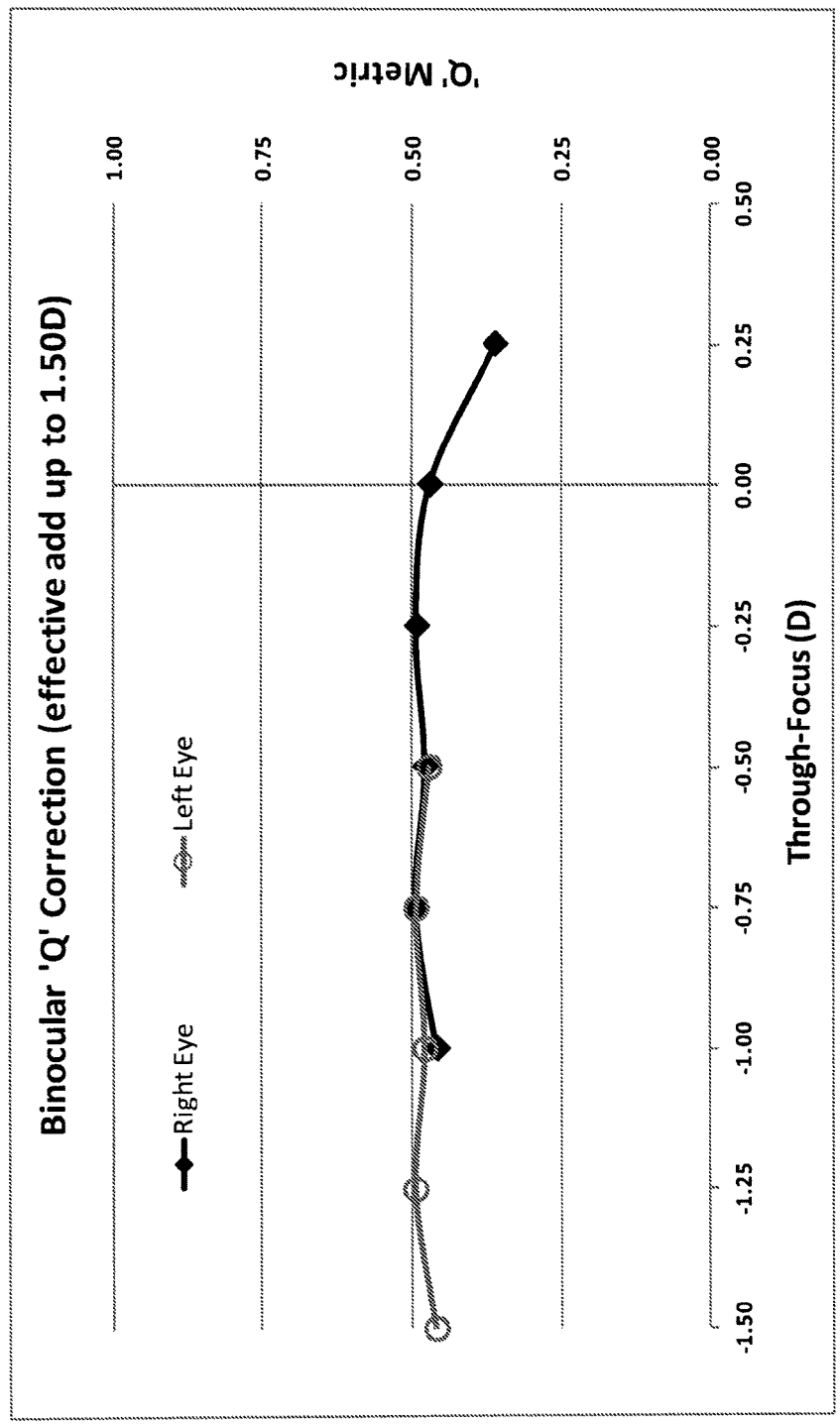
FIGS. 51 and 52 show a monocular correction approach for presbyopia, where different higher order aberration profiles provided for the right and left eyes, by which the through-focus optical and/or visual performance is different in the right and left eye (desired vergences) to provide a combined add power range of 1.5 D and 2.5 D, on the negative side of through-focus curve, respectively, according to certain embodiments.
Figure 52:
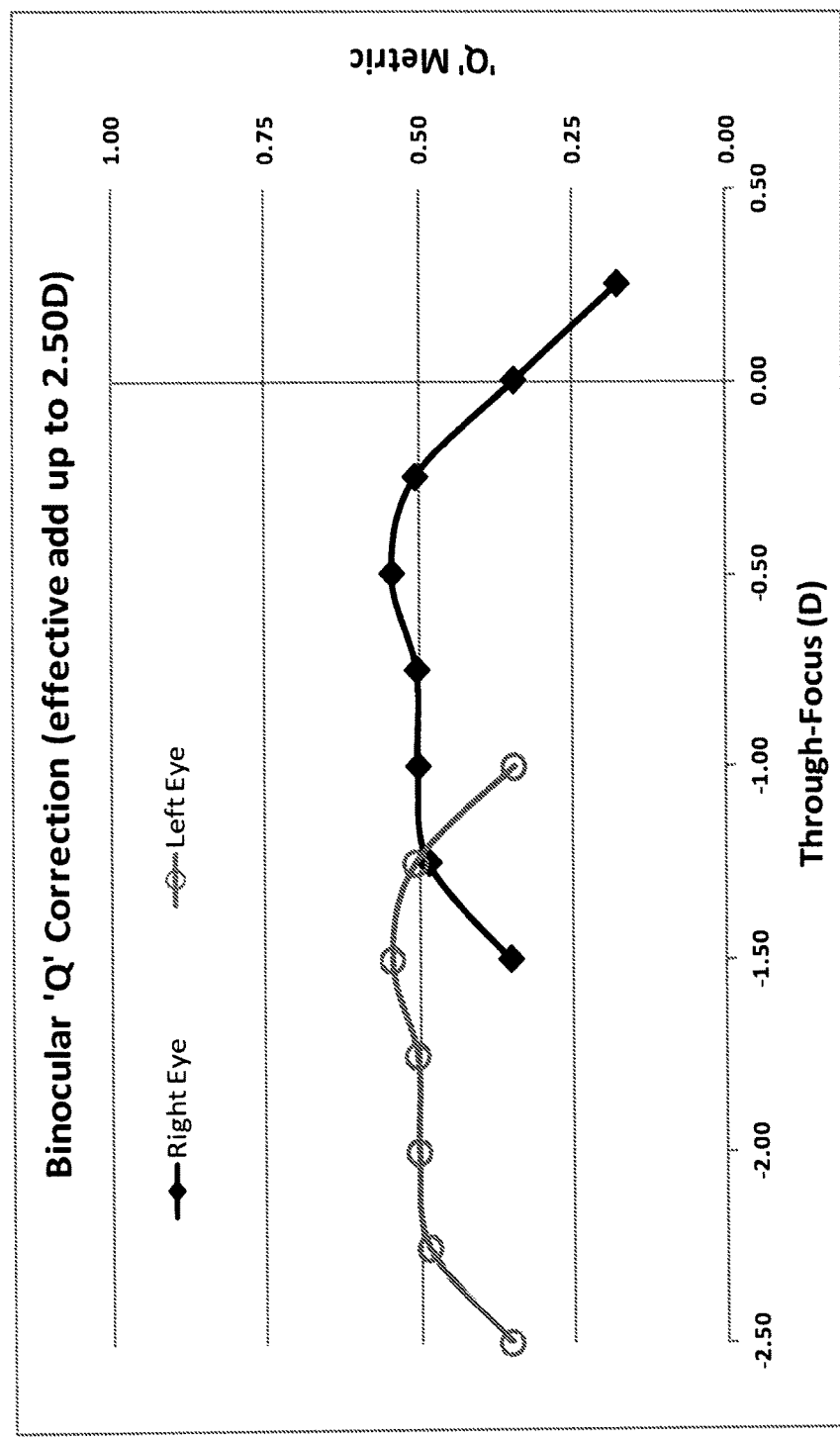

Referring to the through focus profiles shown in FIGS. 51 and 52, which are described herein, under the monocular design approach, one lens will be selected to have a base power (distance refractive prescription) that shifts the through focus curve to the extreme, or subs left (starting at −2.5 D mark) and the other lens selected to have a base power that shifts the through focus curve slightly to the left (starting at −1.5 D mark), according to certain embodiments.

FIGS. 51 and 52 show the TFRIQ of the design of two pairs of power profiles (Binocular 'Q' correction), according to certain embodiments. Each lens in the pair has been designed to extend RIQ in combination with the other lens in the pair. The defocus and higher order spherical aberration coefficients for these combinations are specified in Tables 7 and 8 respectively.

TABLE 7

Defocus and higher order spherical aberration coefficients of first exemplary embodiment for monocular design of lenses for presbyopia (Effective add of 1.5 D in the negative direction of through-focus curve.

| Combination | Right Eye | Left Eye |
|---|---|---|
| C(2, 0) | 0.28 | 0.57 |
| C(4, 0) | −0.1 | 0.125 |
| C(6, 0) | 0.025 | −0.075 |
| C(8, 0) | 0.075 | −0.075 |
| C(10, 0) | 0.025 | −0.025 |
| C(12, 0) | 0.025 | 0 |
| C(14, 0) | 0.025 | 0.025 |
| C(16, 0) | 0.025 | 0.025 |
| C(18, 0) | 0.025 | −0.025 |
| C(20, 0) | 0 | −0.025 |

TABLE 8

Defocus and higher order spherical aberration coefficients of second exemplary embodiment for monocular design of lenses for presbyopia (Effective add of 2.5 D in the negative direction of through-focus curve.

| Combination | Right Eye | Left Eye |
|---|---|---|
| C (2, 0) | 0.433 | 0.866 |
| C(4, 0) | −0.1 | −0.1 |
| C(6, 0) | −0.05 | −0.05 |
| C(8, 0) | 0.025 | 0.025 |
| C(10, 0) | 0.025 | 0.025 |
| C(12, 0) | −0.025 | −0.025 |
| C(14, 0) | −0.025 | −0.025 |
| C(16, 0) | 0 | 0 |
| C(18, 0) | 0 | 0 |
| C(20, 0) | 0 | 0 |

Figure 53:
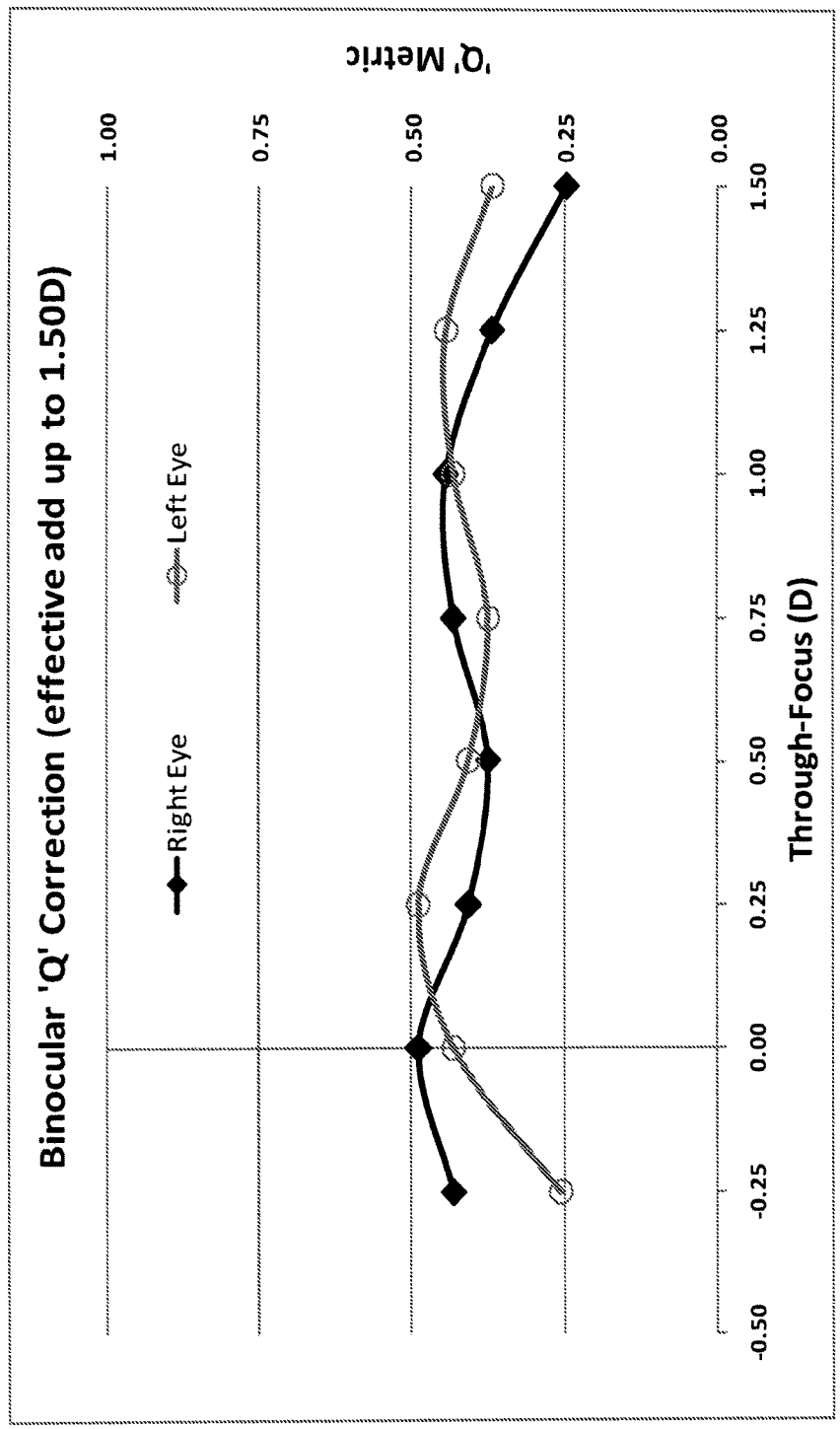
FIGS. 53 and 54 show a monocular correction approach for presbyopia, where different higher order aberration profiles provided for the right and left eyes, by which the through-focus optical and/or visual performance is different in the right and left eye (desired vergences) to provide a combined add power range of 1.5 D and 2.5 D, on the positive side of through-focus curve, respectively, according to certain embodiments.
Figure 54:
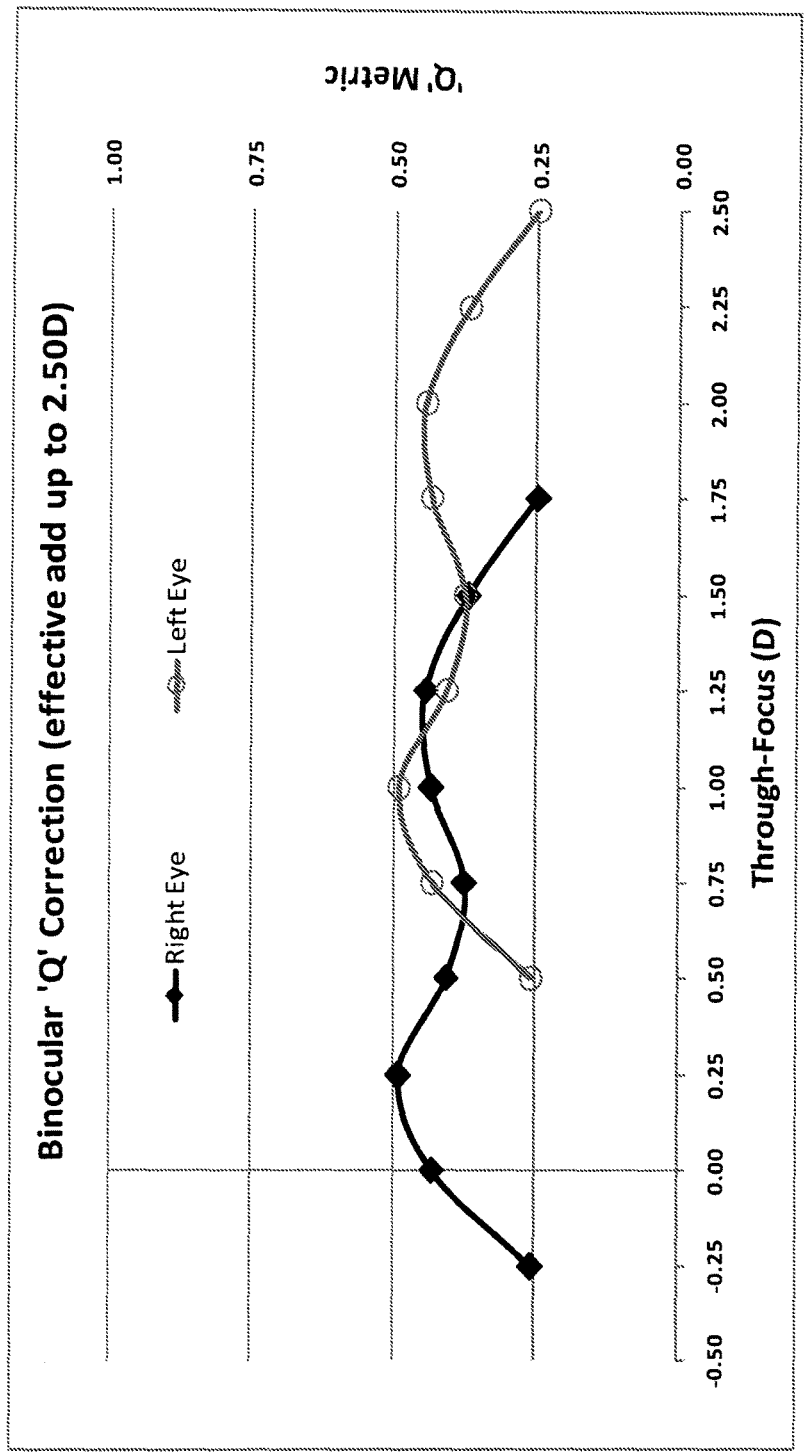

The power profiles described in relation to Table 7 and Table 8 are examples of combinations of higher order aberrations that provide enhanced through-focus performance on the negative side of the through-focus function. Similarly, using this monocular design approach, the combined through-focus performance can also be substantially extended on the right side of the through-focus function, provided an appropriate level of defocus is added to a selected combination of higher order aberrations. FIGS. 53 and 54 show examples with a relatively constant RIQ (>0.35) over a range of defocus, in the positive direction of the through-focus function, according to certain embodiments. The defocus and higher order spherical aberration coefficients for these combinations are specified in Tables 9 and 10, respectively.

TABLE 9

Defocus and higher order spherical aberration coefficients of third exemplary embodiment for monocular design of lenses for presbyopia (Effective add of 1.5 D in the positive direction of through-focus curve).

| Combination | Right Eye | Left Eye |
|---|---|---|
| C (2, 0) | −0.28 | −0.43 |
| C(4, 0) | −0.125 | −0.125 |
| C(6, 0) | −0.05 | −0.05 |
| C(8, 0) | 0.075 | 0.075 |
| C(10, 0) | 0.025 | 0.025 |
| C(12, 0) | −0.025 | −0.025 |
| C(14, 0) | 0 | 0 |
| C(16, 0) | 0 | 0 |
| C(18, 0) | 0 | 0 |
| C(20, 0) | 0 | 0 |

TABLE 10

Defocus and higher order spherical aberration coefficients of fourth exemplary embodiment for monocular design of lenses for presbyopia (Effective add of 2.5D in the positive direction of through-focus curve).

| Combination | Right Eye | Left Eye |
|---|---|---|
| C (2,0) | −0.43 | −0.86 |
| C(4,0) | −0.125 | −0.125 |
| C(6,0) | −0.05 | −0.05 |
| C(8,0) | 0.075 | 0.075 |
| C(10,0) | 0.025 | 0.025 |
| C(12,0) | −0.025 | −0.025 |
| C(14,0) | 0 | 0 |
| C(16,0) | 0 | 0 |
| C(18,0) | 0 | 0 |
| C(20,0) | 0 | 0 |

Figure 117:
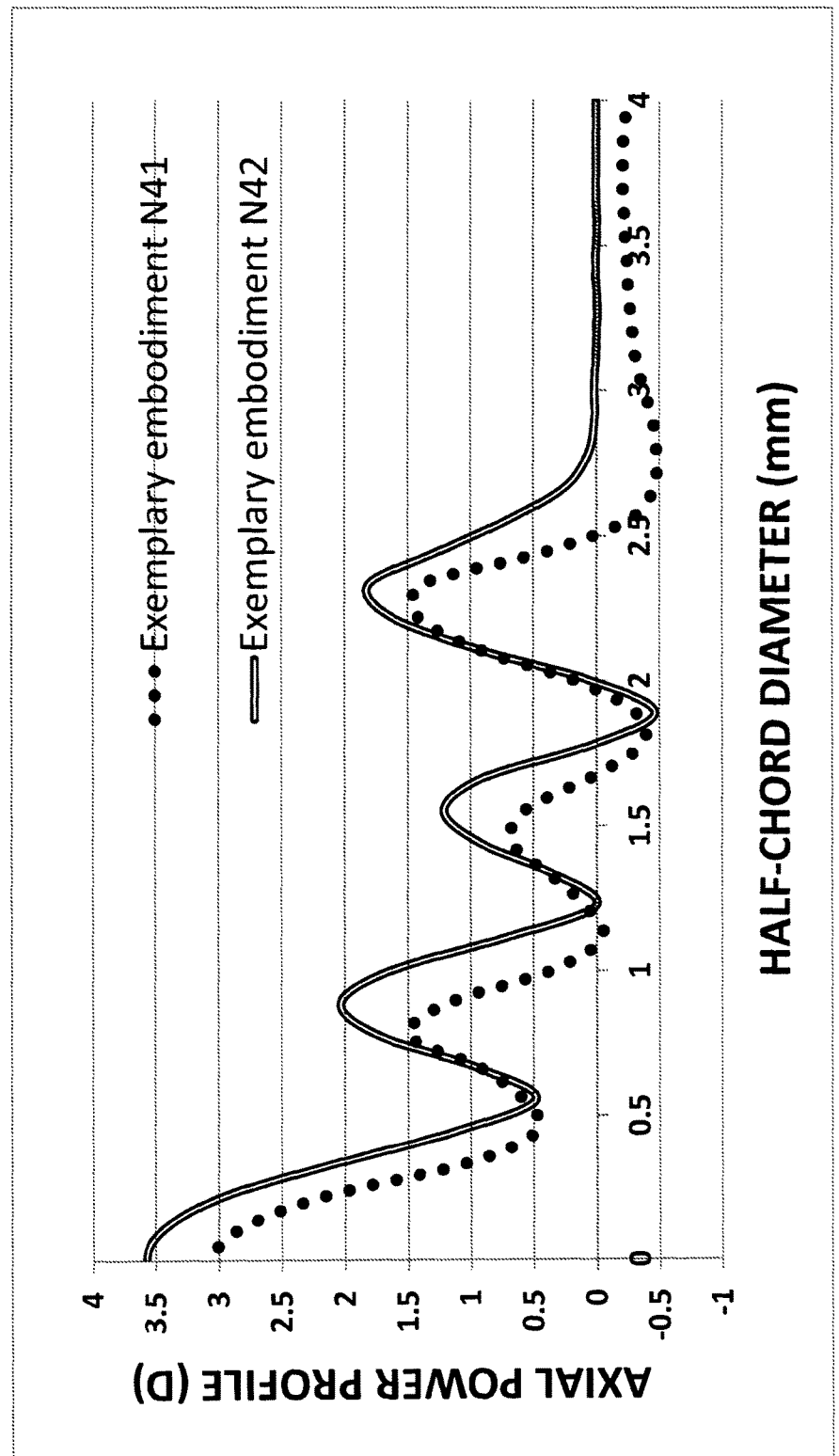
FIG. 117 show the power profiles of two exemplary embodiments of contact lens designs (N41 and N42) across the half-chord diameter.
Figure 118:
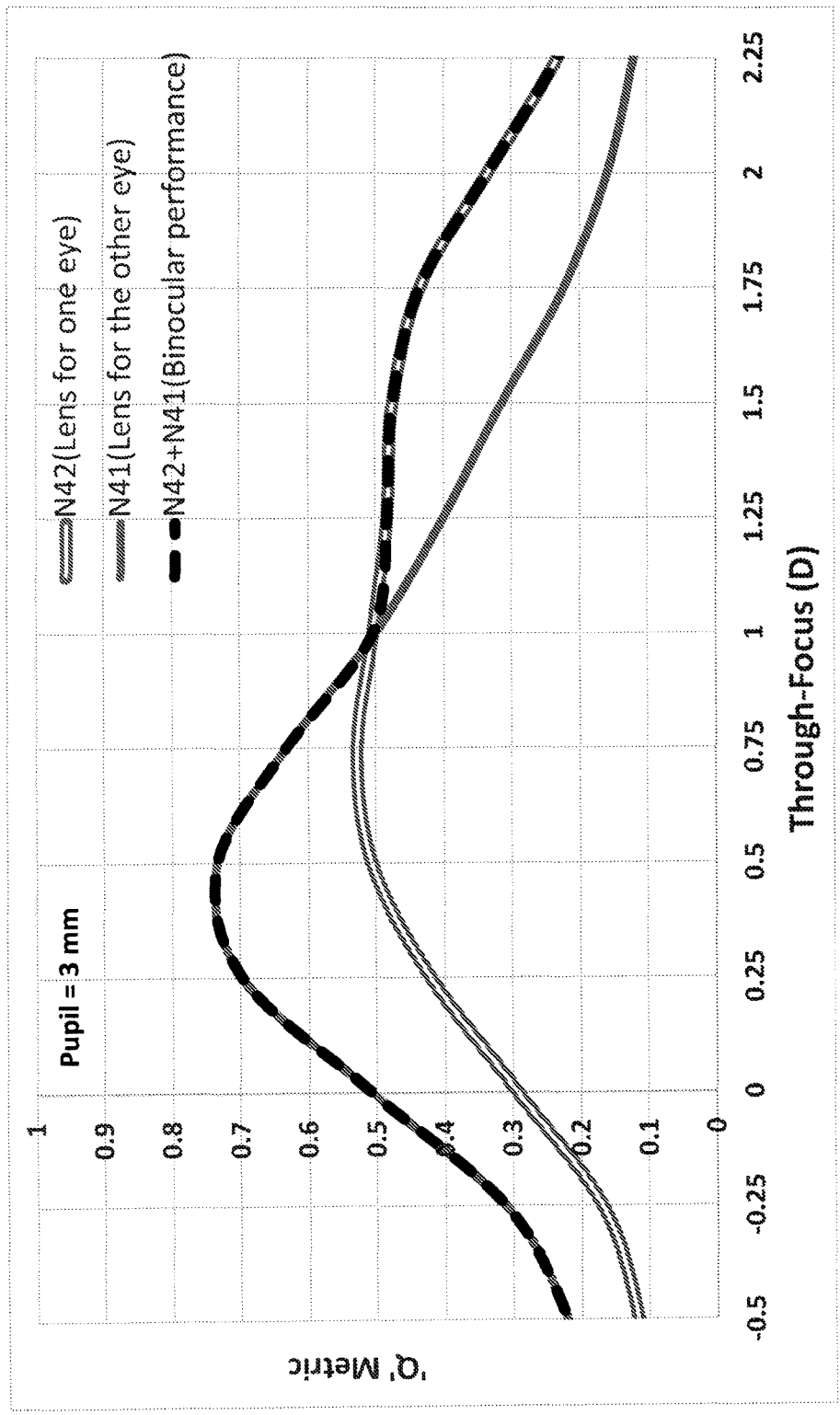
FIG. 118 plots the through-focus image quality ('Q' metric) for two exemplary contact lenses (N41 and N42) calculated at 3 mm pupil diameter. The solid line and dual line represents the through-focus image quality for two exemplary designs N41 and N42, one design is used on one eye and the other design on the fellow eye. The dashed line represents the binocular performance.

FIG. 118 shows the through-focus retinal image quality for two exemplary designs, N41 and N42, which were computed at 3 mm pupil diameter using visual Strehl ratio as the retinal image quality metric, described in section 1. The power profiles of the exemplary embodiment pair, N41 and N42, as a function of half-chord diameter of the optic zone are described in the FIG. 117. This pair of lenses may be prescribed for a pair of eyes, where one design is prescribed for a selected eye and the other design is prescribed for the fellow eye. In this example, as seen in FIG. 118, the solid and the dual lines represents the through-focus retinal image quality for each of the two exemplary designs, N41 and N42, respectively. A pair of exemplary designs with different performance characteristics may be used in a method of correcting a pair of eyes. Using such exemplary methods may result in a coupling and/or summation of the individual performances of each lens that may occur at the visual cortex level in the brain. For example, a summated response for the embodiment pair, N41 and N42, is represented by the dashed line in FIG. 118.

Figure 137:
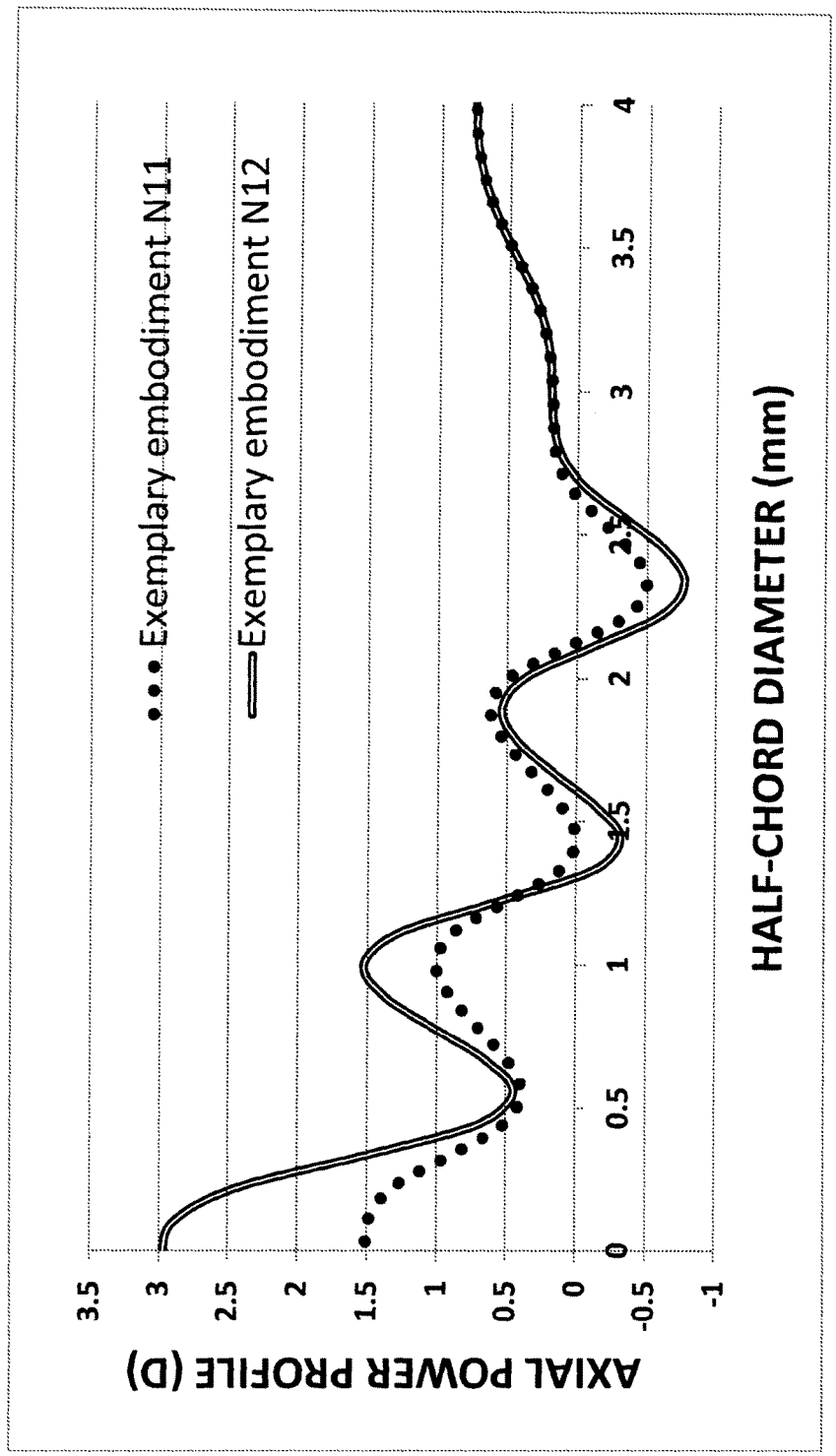
FIG. 137 show the power profiles of two exemplary embodiments of contact lens designs (N11 and N12) across the half-chord diameter.
Figure 138:
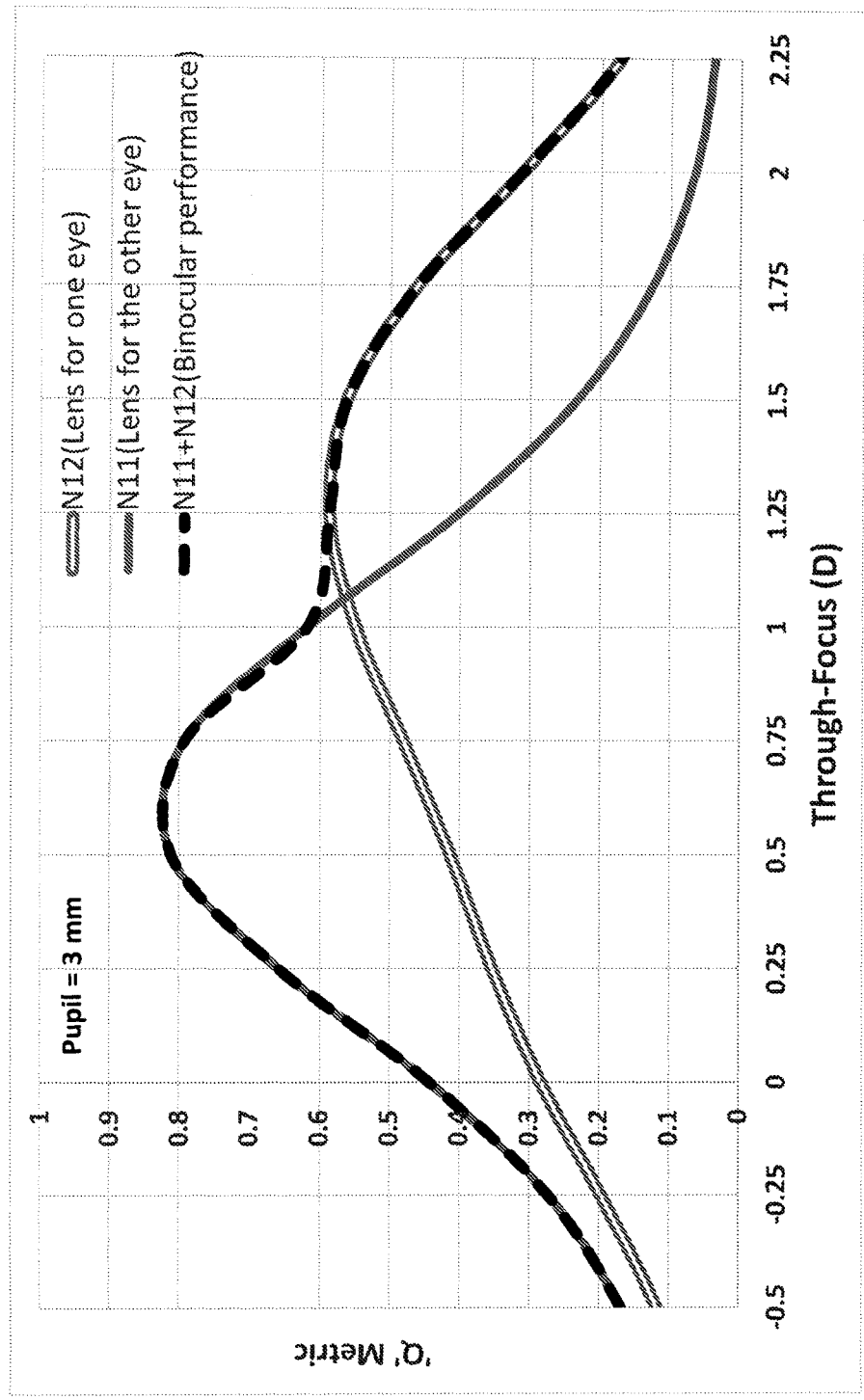
FIG. 138 plots the through-focus image quality ('Q' metric) for two exemplary contact lens (N11 and N12) calculated at 3 mm pupil diameter. The solid line and dual line represents the through-focus image quality for two designs N11 and N12, when each design is used to correct a pair of eyes. The dashed line represents the binocular performance when both the eyes work together in combination.

FIG. 138 shows the through-focus retinal image quality for two exemplary designs, N11 and N12, which were computed at 3 mm pupil diameter using visual Strehl ratio with the inclusion of the cosine of the phase transfer function as the retinal image quality metric, described in section 1. The power profiles of the exemplary embodiment pair, N11 and N12, as a function of half-chord diameter of the optic zone are described in the FIG. 137. This pair of lenses may be prescribed for a pair of eyes, where one design is prescribed for a selected eye and the other design is prescribed for the fellow eye. In this example, as seen in FIG. 138, the solid and the dual lines represents the through-focus retinal image quality for each of the two exemplary designs, N11 and N12, respectively. A pair of exemplary designs with different performance characteristics may be used in a method of correcting a pair of eyes. Using such exemplary methods may result in a coupling and/or summation of the individual performances of each lens is expected at the visual cortex level in the brain. For example, a summated response for the embodiment pair, N11 and N12, is represented by the dashed line in FIG. 138.

Section 10

Design for Enhancing Central Vision

Some embodiments may be used to selectively optimise visual performance under one or more defined viewing conditions. Such viewing conditions may include but are not limited to specific viewing distances, specific lighting conditions, specific vision tasks or combinations thereof. The optical performance may include the retinal image quality metrics described herein. With respect to the designs for enhancing central vision, the visual performance may include visual acuity and/or contrast sensitivity. For example, utilising some of the disclosed embodiments, devices, lenses and/or methods may be produced that are selectively optimised for one or more of the following: high contrast visual acuity, low contrast visual acuity, contrast sensitivity, high illumination, low illumination, photopic (day time viewing), mesopic, scotopic (night-time viewing), distance viewing, computer viewing, reading at near or combinations thereof.

Section 10.A

Design for Peripheral Field

In some embodiments, when selecting a combination of HOA to form a power profile, the weight given to peripheral vision may be increased. This may, for example, be applicable when the recipient plays certain sports in which peripheral vision is important.

Figure 55:
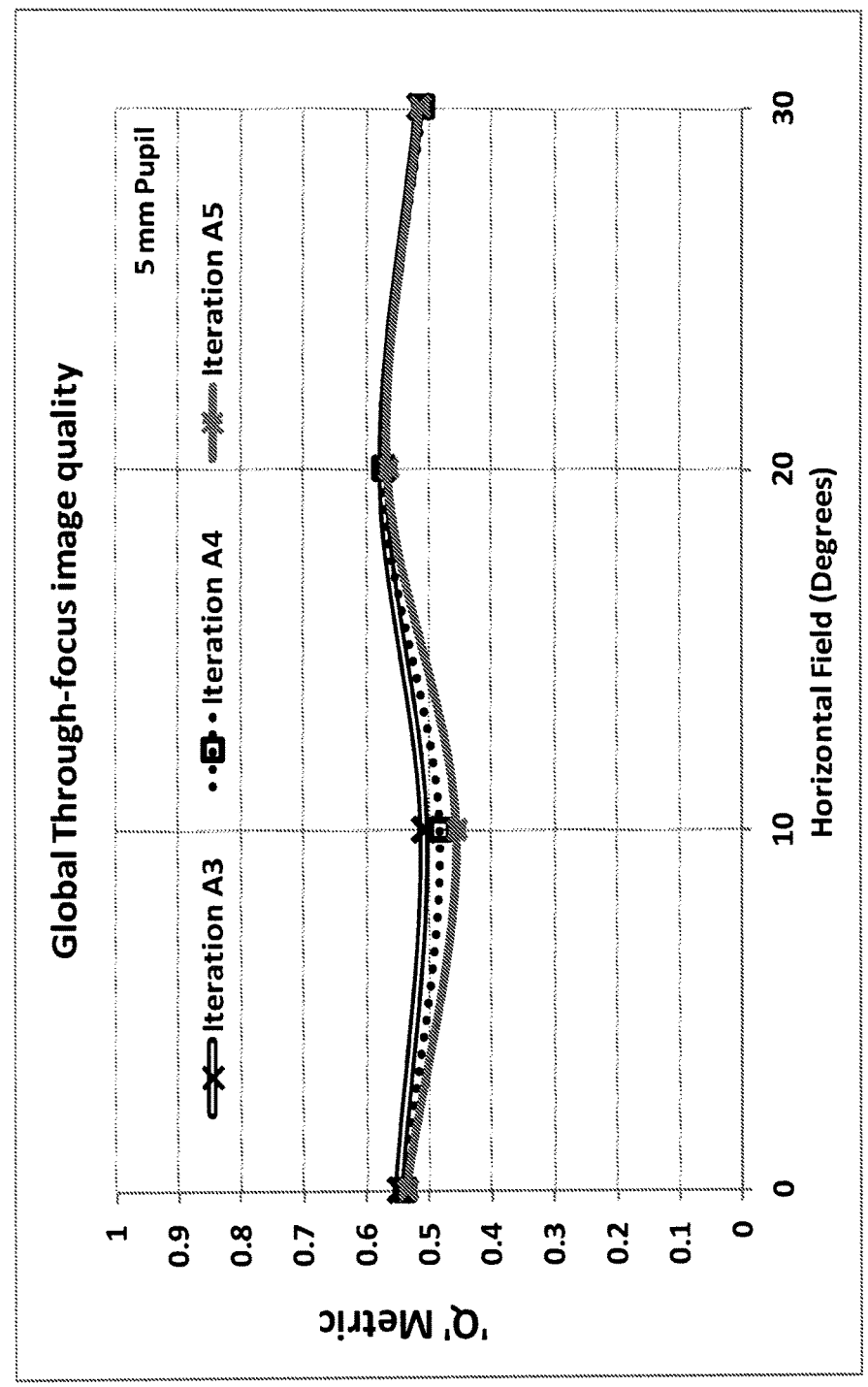
FIG. 55 shows a global TFRIQ for three further iterations of aberration profile (Iterations A3, A4 and A5 represented in FIGS. 56, 57 and 58, respectively), for providing a substantially constant retinal image quality across a horizontal visual field from 0 to 30 degrees, according to certain embodiments.

FIG. 55 shows a graph of RIQ (again visual Strehl Ratio), for three different power profiles that substantially equalise RIQ across the horizontal visual field, according to certain embodiments. The RIQ measures were obtained for a 5 mm pupil. The defocus and higher order spherical aberration coefficients for each power profile are shown in Table 11.

TABLE 11

Defocus and higher order spherical aberration coefficients of three exemplary embodiments for substantially constant RIQ over extended horizontal field angles

| Iteration | Iteration A3 | Iteration A4 | Iteration A5 |
|---|---|---|---|
| C(2,0) | −1.506 | −1.504 | −1.501 |
| C(4,0) | 0.111 | 0.114 | 0.117 |
| C(6,0) | −0.04 | −0.037 | −0.034 |
| C(8,0) | −0.015 | −0.013 | −0.01 |
| C(10,0) | 0.007 | 0.009 | 0.012 |
| C(12,0) | 0.025 | 0.027 | 0.029 |
| C(14,0) | 0.011 | 0.013 | 0.014 |
| C(16,0) | −0.025 | −0.024 | −0.023 |
| C(18,0) | −0.003 | −0.002 | −0.002 |
| C(20,0) | 0.017 | 0.016 | 0.015 |

Figure 56:
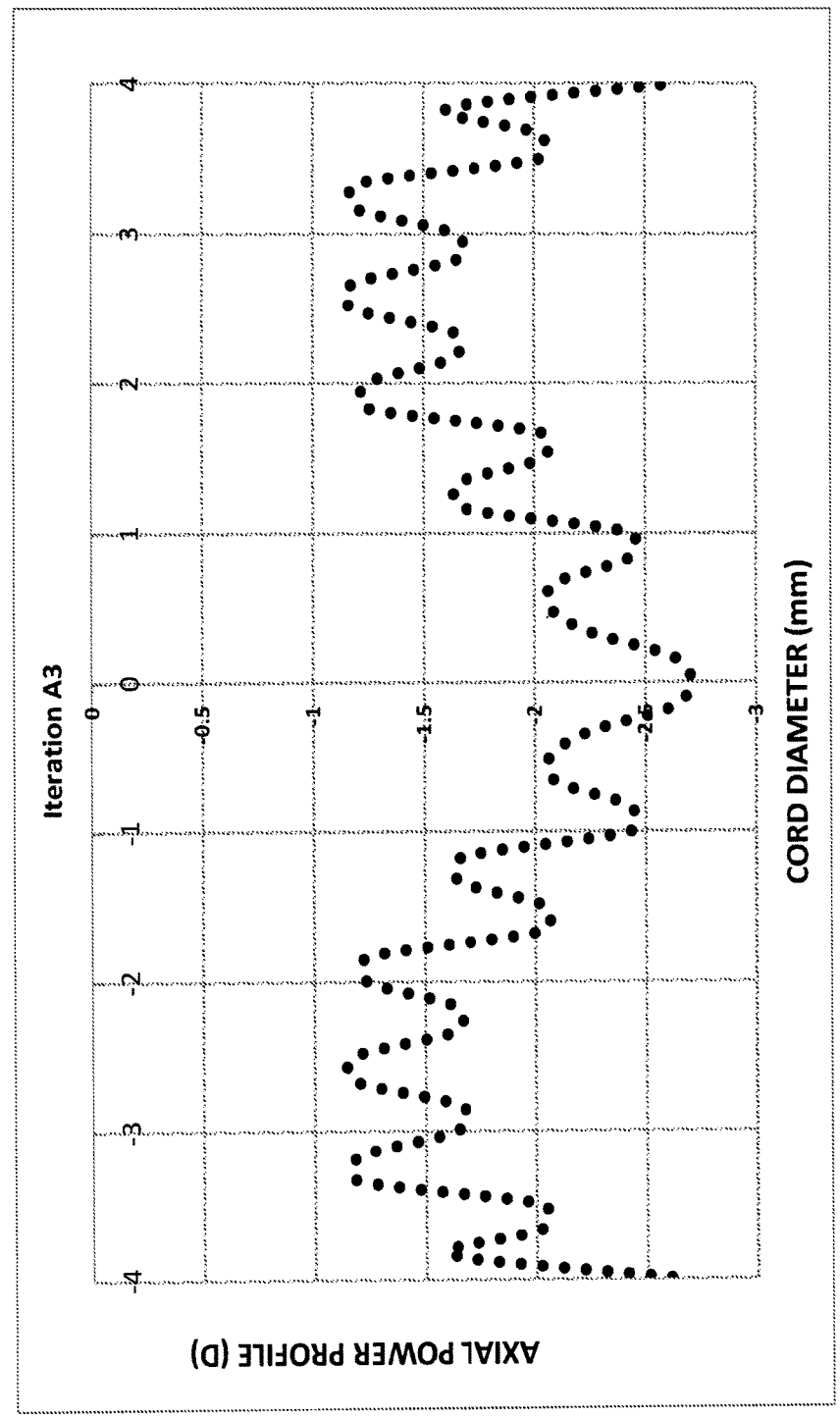
Figure 57:
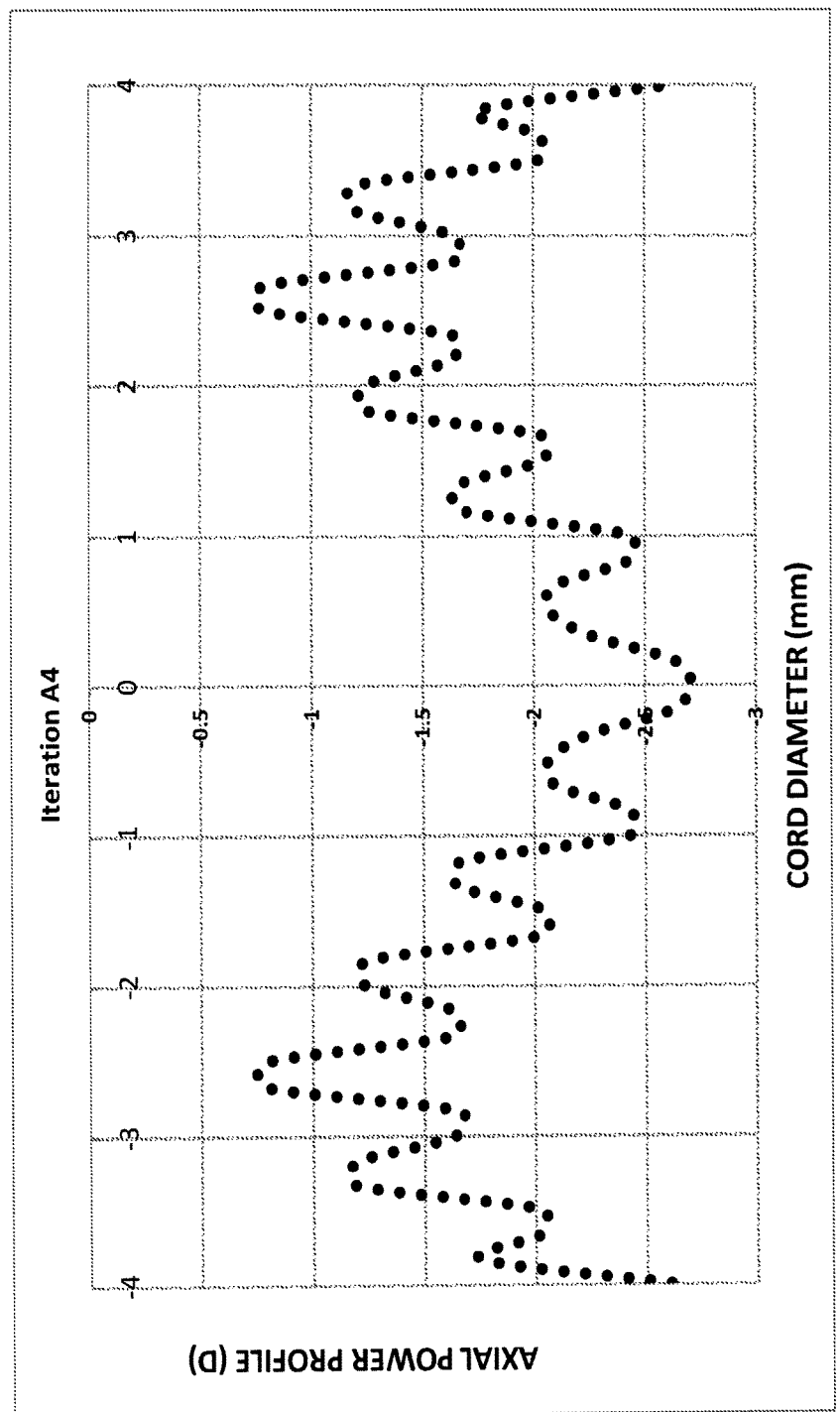
Figure 58:
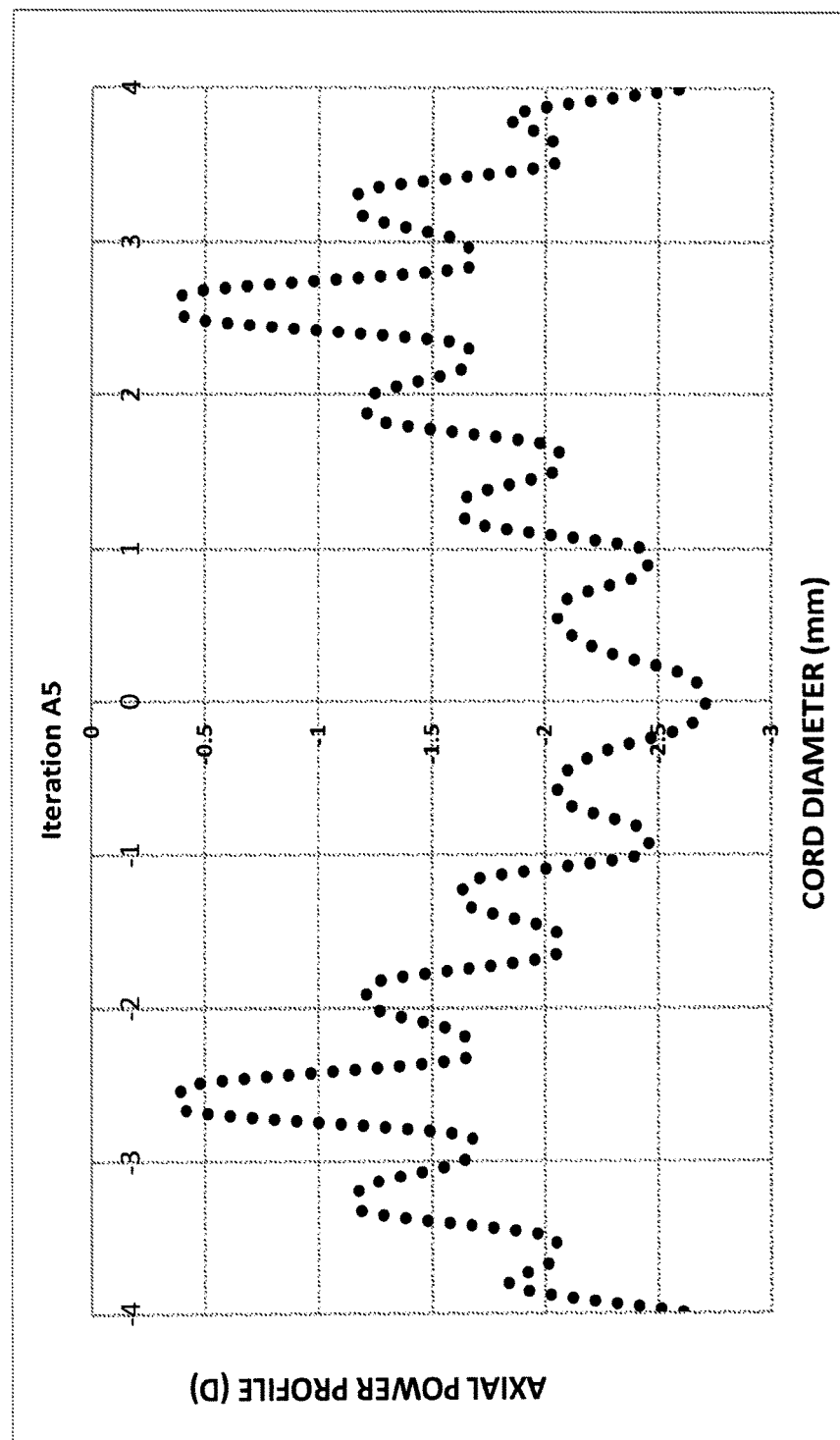

The Iterations A3 (FIG. 56), A4 (FIG. 57) and A5 (FIG. 58) produced an on-axis RIQ of about 0.5 across zero to 30 degrees field angle (if horizontal symmetry is assumed, that is 60 degrees in total across both nasal and temporal fields), according to certain embodiments. The RIQ on-axis is also about 0.5, which is lower than some other embodiments where degradation in RIQ below 0.5 with increasing field angle is permitted.

Accordingly, in certain embodiments, the RIQ on-axis may be traded-off against RIQ at high field angles. For example, RIQ may be permitted to drop to 0.2 at 30 degrees field angle (but remain at 0.5 or above for 20 degrees field angle and less), to allow a selection of HOA that increases on-axis RIQ above those shown in FIG. 55. Power profile designs for peripheral vision may be selected for a lens designed to provide a slope of RIQ (providing stimulus to retard or encourage eye growth under the optical feedback mechanism explanation for emmetropisation), or correction/lenses for presbyopia (emmetropia, myopia or hyperopia) or for other eyes. In certain embodiments, high field angles are one or more of the following: 10 degrees, 20 degrees, 30 degrees or 40 degrees of the visual field. Other suitable high field-angles may also be used in certain applications.

Section 11

Selection of Positive and Negative Phase

Figure 59:
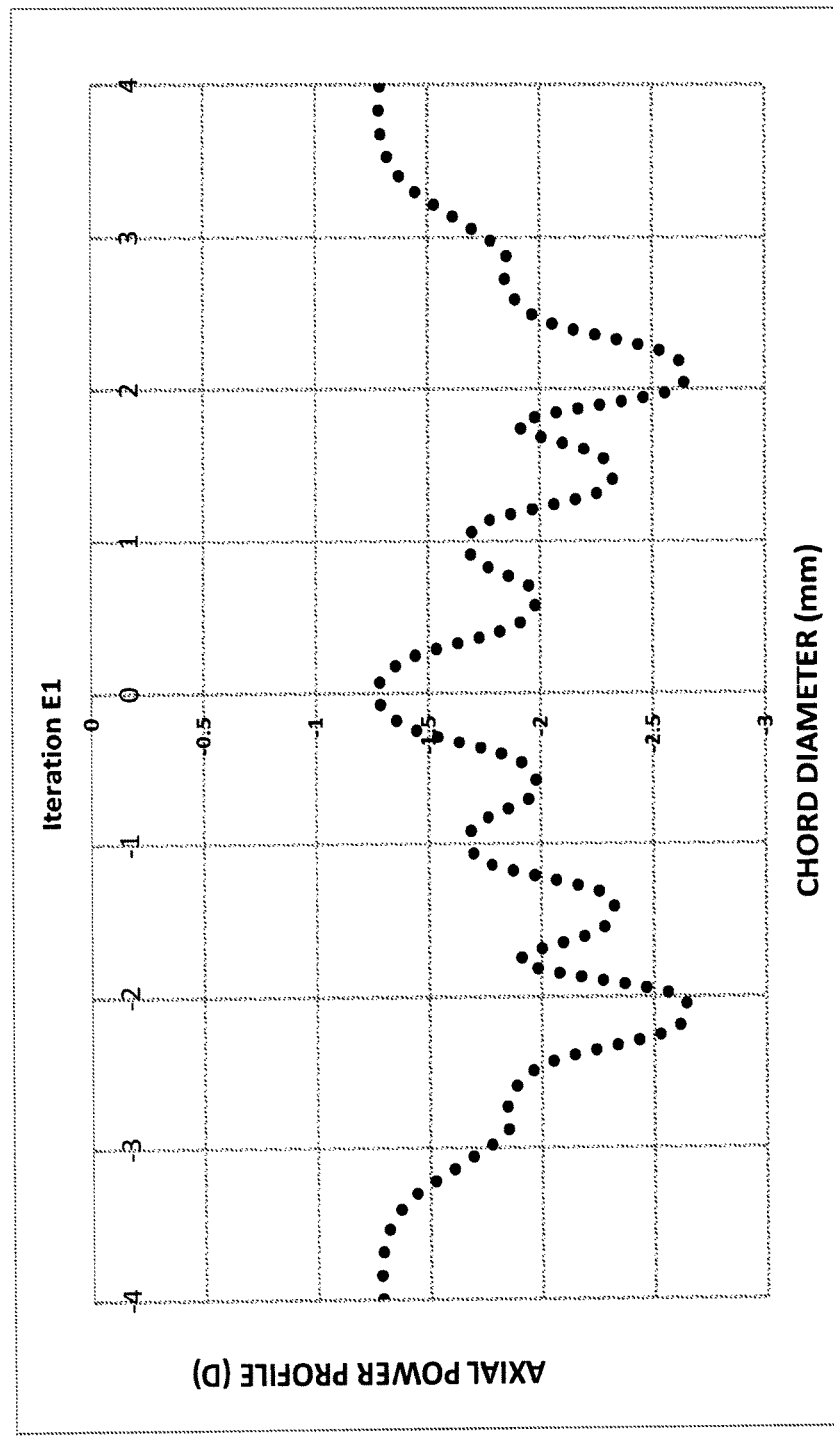
FIGS. 59 and 60 show example designs of the power profile of correcting contact lenses with opposite phase profiles (Iteration E1 and Iteration E2) and FIGS. 61 to 63 show the on-axis TFRIQ for Iterations E1 and E2 with three different levels of inherent primary spherical aberration of the candidate eye, according to certain embodiments.
Figure 60:
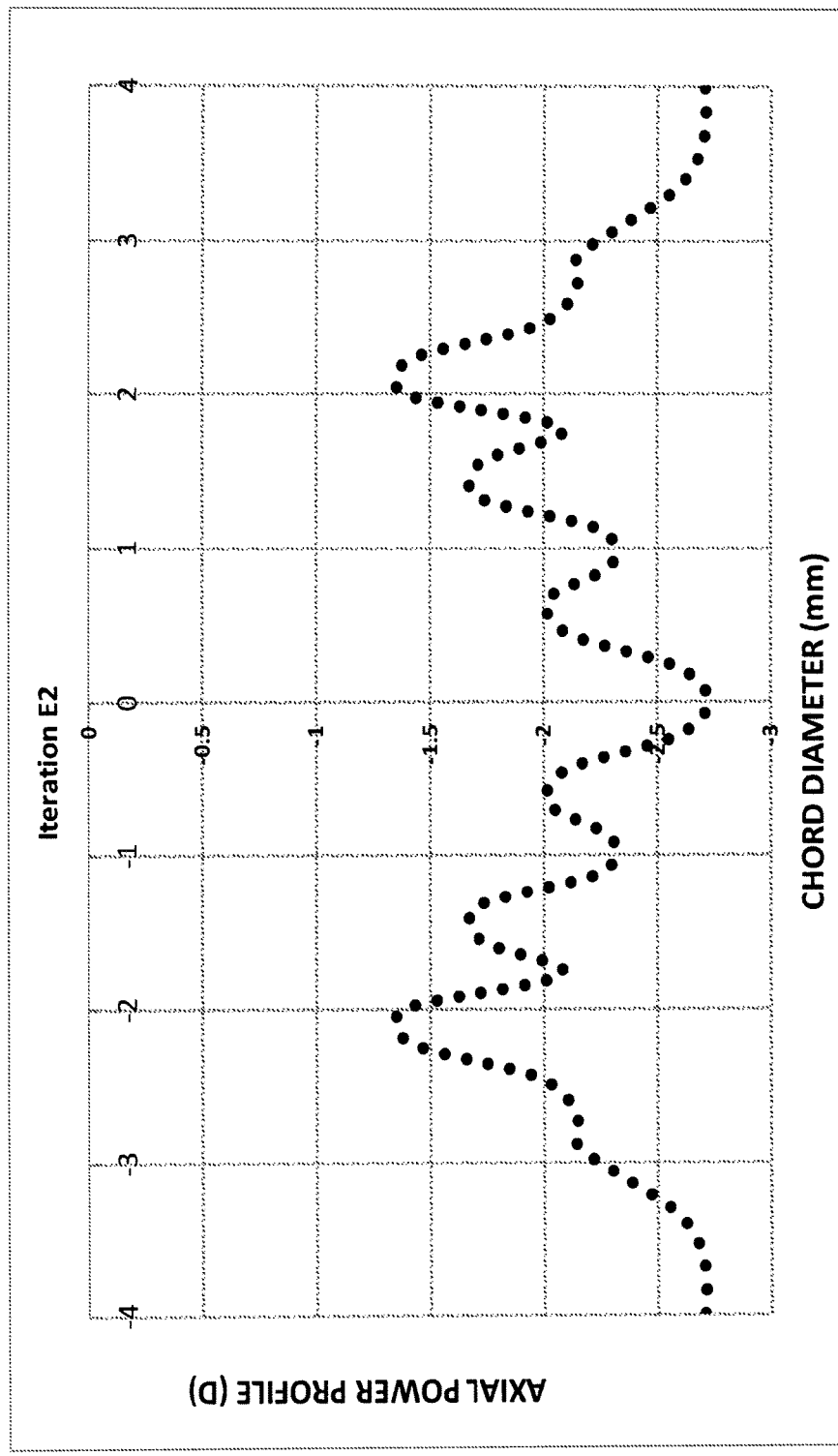
Figure 61:
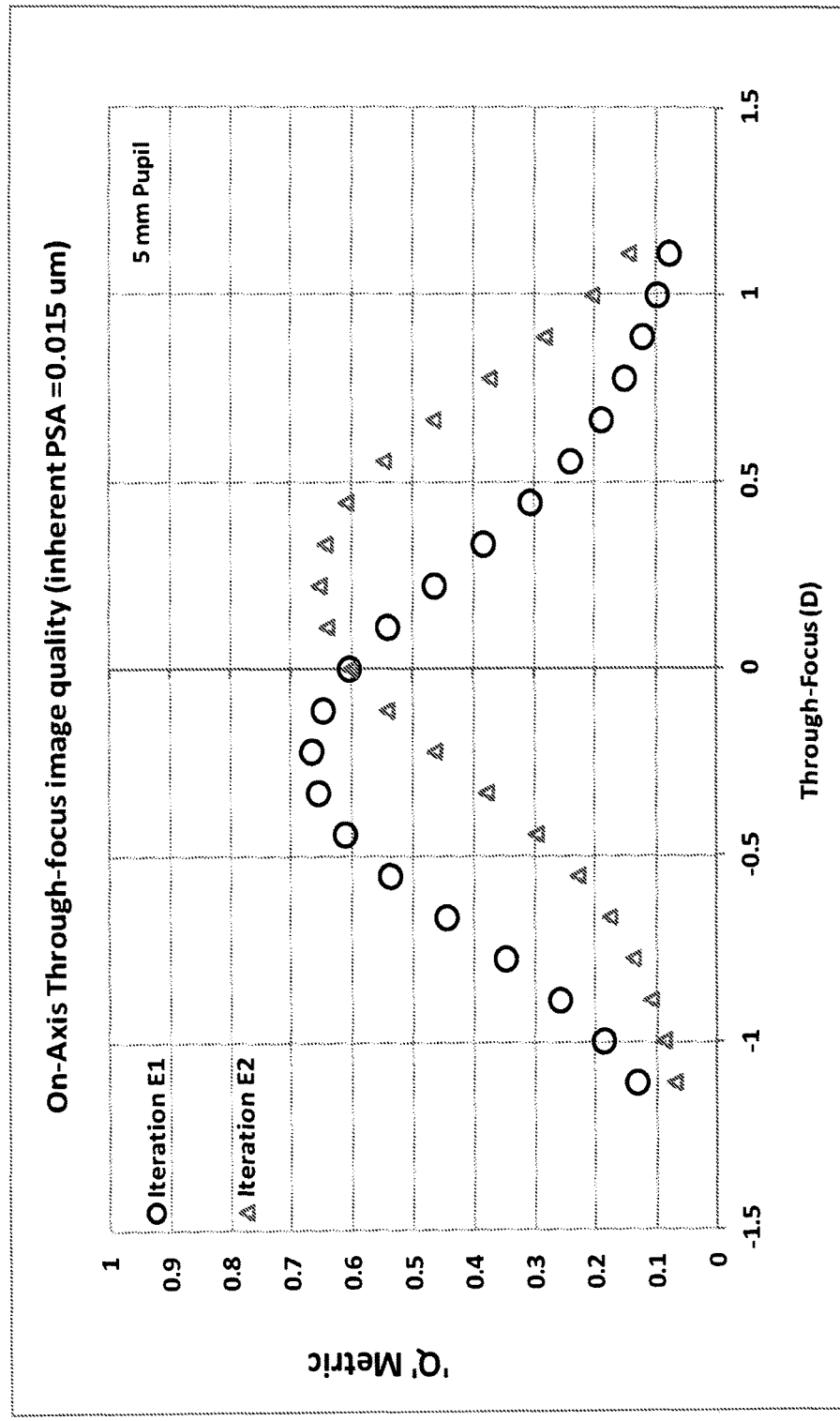

For a particular recipient of a lens, device and/or a method disclosed herein, a selection may be made between two power profiles of opposite phases. In this context, the term 'opposite phase' identifies power profiles that have identical, or substantially identical, magnitudes of specific combination sets of higher order aberrations over a desired pupil, while their signs are opposite to each other. FIGS. 59 and 60 show power profile iterations E1 and E2, which are examples of power profiles with opposite phases, according to certain embodiments. Table 12 reflects the magnitudes and signs of the higher order spherical aberration terms for iterations E1 and E2. The lenses of opposite phase described herein may result in the same, or substantially the same, on-axis peak RIQ. The through focus RIQ performance of such phase profile pairs may be mirror images, or substantially mirror images, of each other across the Y-axis (i.e. shifted apart by defocus), as shown in FIG. 61. However, this would result if the inherent higher order aberration profile is negligibly small (say for example primary spherical aberration in the range of −0.02 μm to 0.02 μm over a 5 mm pupil).

TABLE 12

Defocus and higher order spherical aberration coefficients of two exemplary embodiments with opposite phases (i.e. mirror imaged power profiles across the X-axis).

| Iteration | Iteration E1 | Iteration E2 |
|---|---|---|
| C(2,0) | −2.015 | −1.573 |
| C(4,0) | −0.102 | 0.102 |
| C(6,0) | 0.021 | −0.021 |
| C(8,0) | 0.019 | −0.019 |
| C(10,0) | 0.025 | −0.025 |
| C(12,0) | 0.01 | −0.01 |
| C(14,0) | −0.025 | 0.025 |
| C(16,0) | −0.006 | 0.006 |
| C(18,0) | 0.016 | −0.016 |
| C(20,0) | −0.003 | 0.003 |

The interactions between the inherent aberration profiles of the candidate eyes and a selected phase profile may either have a) an improved or b) degraded effect on the objective and/or subjective optical and/or visual performance. As the TFRIQ is dependent on the inherent aberration profile, a phase profiles selected for instance may be useful to change the slope of TFRIQ in the direction that would favour the emmetropisation process for myopic or hyperopic eyes; or alternatively the same, or similar, phase profile may be used to mitigate the presbyopic symptoms in alternative candidate eyes.

Figure 62:
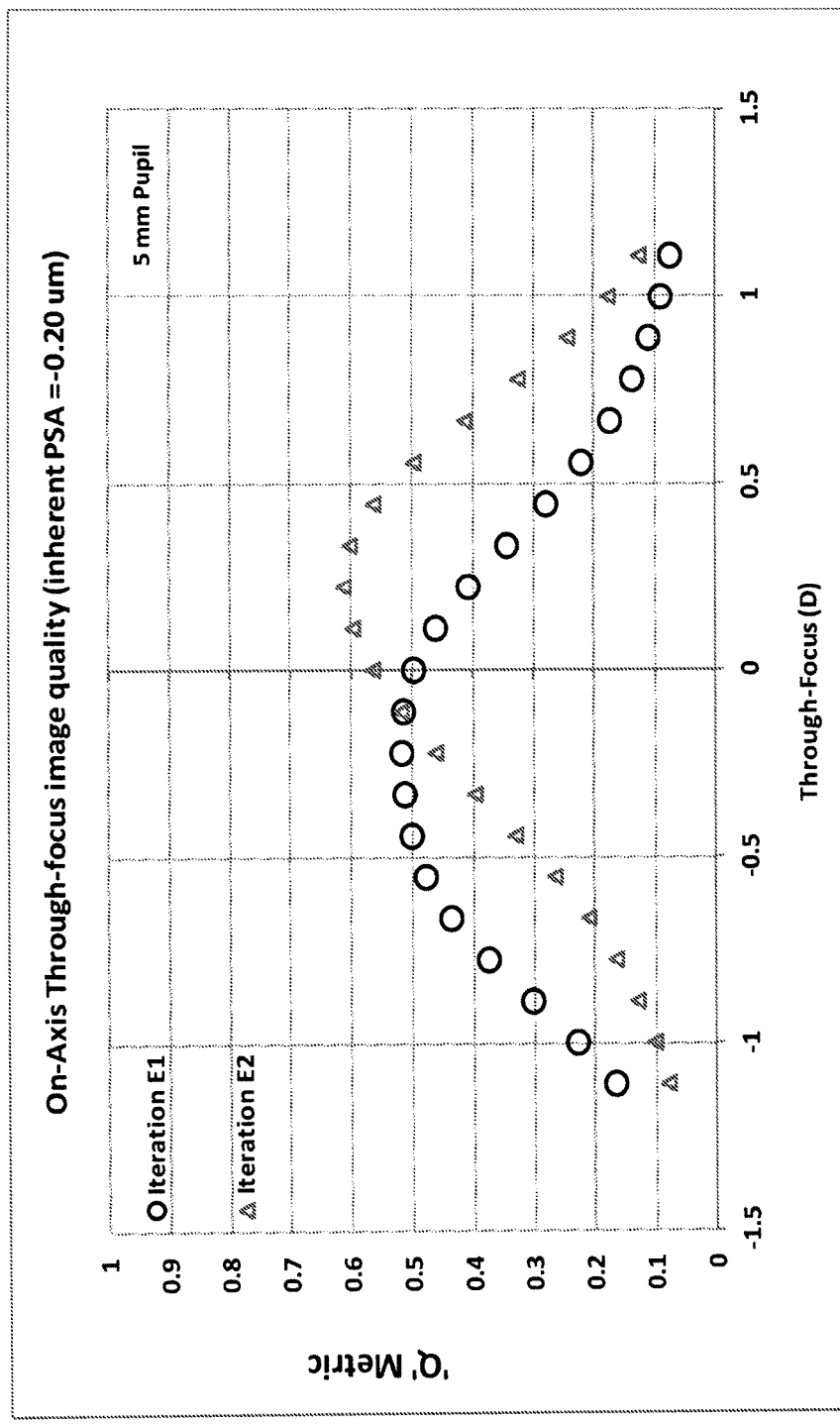
Figure 63:
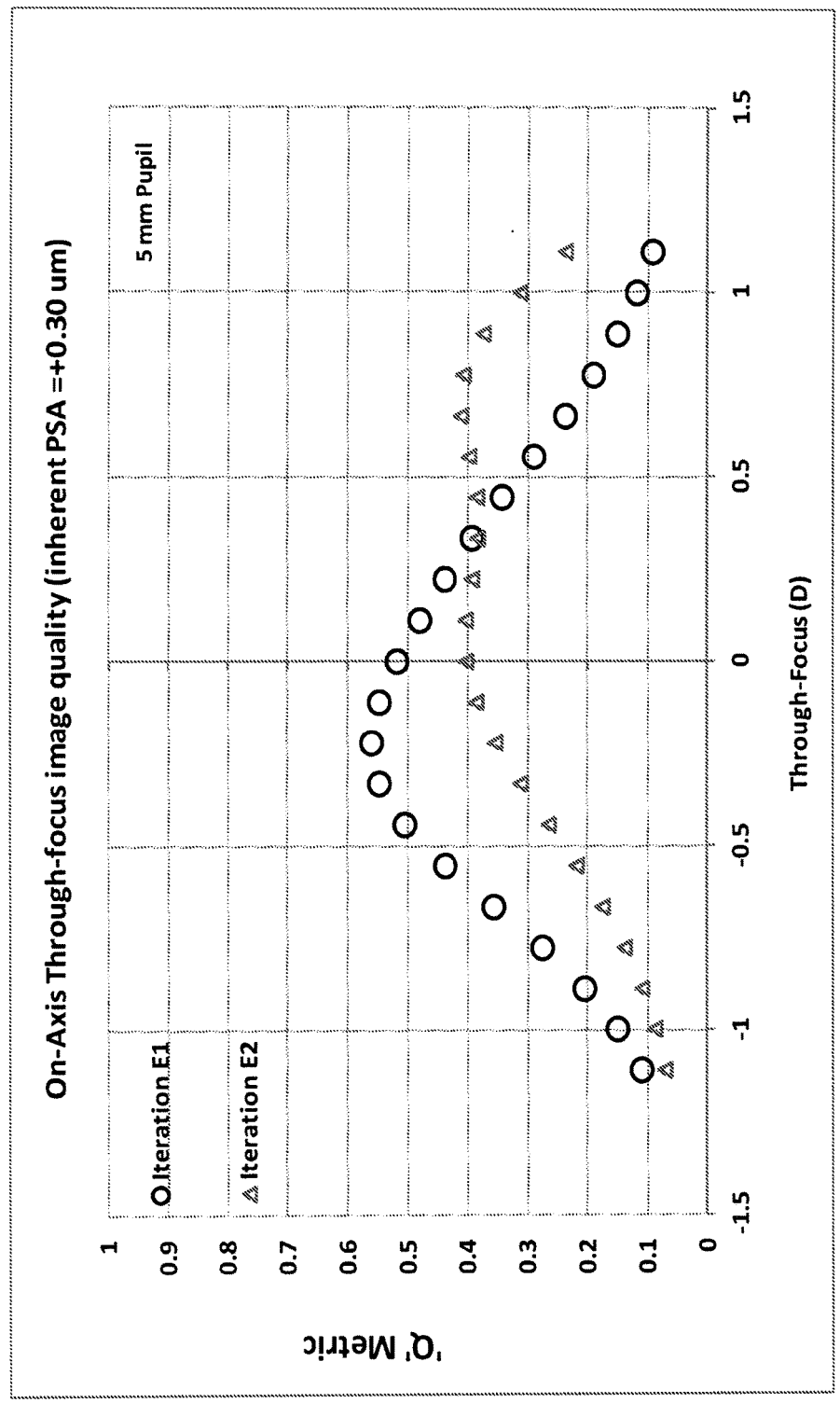

FIGS. 62 and 63 show how the TFRIQ of opposite phase profiles are dependent on the inherent ocular aberration of the candidate eye (in this example positive spherical aberration), according to certain embodiments. Certain embodiments disclosed herein involve providing lenses of the same, or substantially same, design, but opposite phase and allowing the recipient to select the preferred phase. The process of selection can be via an objective assessment of TFRIQ performance metric and/or could be purely a subjective preference via visually guided tests.

Section 12

Combination Identification and Selection

As described herein for certain embodiments, it is possible to provide a desirable on-axis RIQ for distance and appropriate through focus RIQ that would enable better visual performance for distance, intermediate and near vergences by choosing an appropriate combination of HOA. This combination of higher order aberrations may contain a correction for the inherent aberration profile of the test candidate. The Appendix A to this specification lists 78 combinations of higher order spherical aberration coefficients that provide both a usefully high RIQ and an option to provide an extended through focus RIQ in the negative direction (left hand side). Also shown in the Appendix A, as a point of comparison, is a combination which does not have spherical aberration, of any order. The Appendix B shows the TFRIQ values for the combinations listed in the Appendix A. The calculations were performed for a pupil size of 4 mm, however the approach, or method, may be extended to other appropriate and/or desired pupil sizes if required or desired. For example, the method may be used with a pupil size within one or more of following ranges: 1.5 to 8 mm, 2 to 8 mm, 2.5 to 8 mm, 3 to 7 mm, 3 to 8 mm and 3.5 to 7 mm. For example, the method may be used with pupil sizes of about 1.5, 2, 2.5, 3, 3.5, 4, 4.5, 5, 5.5, 6, 6.5, 7, 7.5 or 8 mm.

Figure 64:
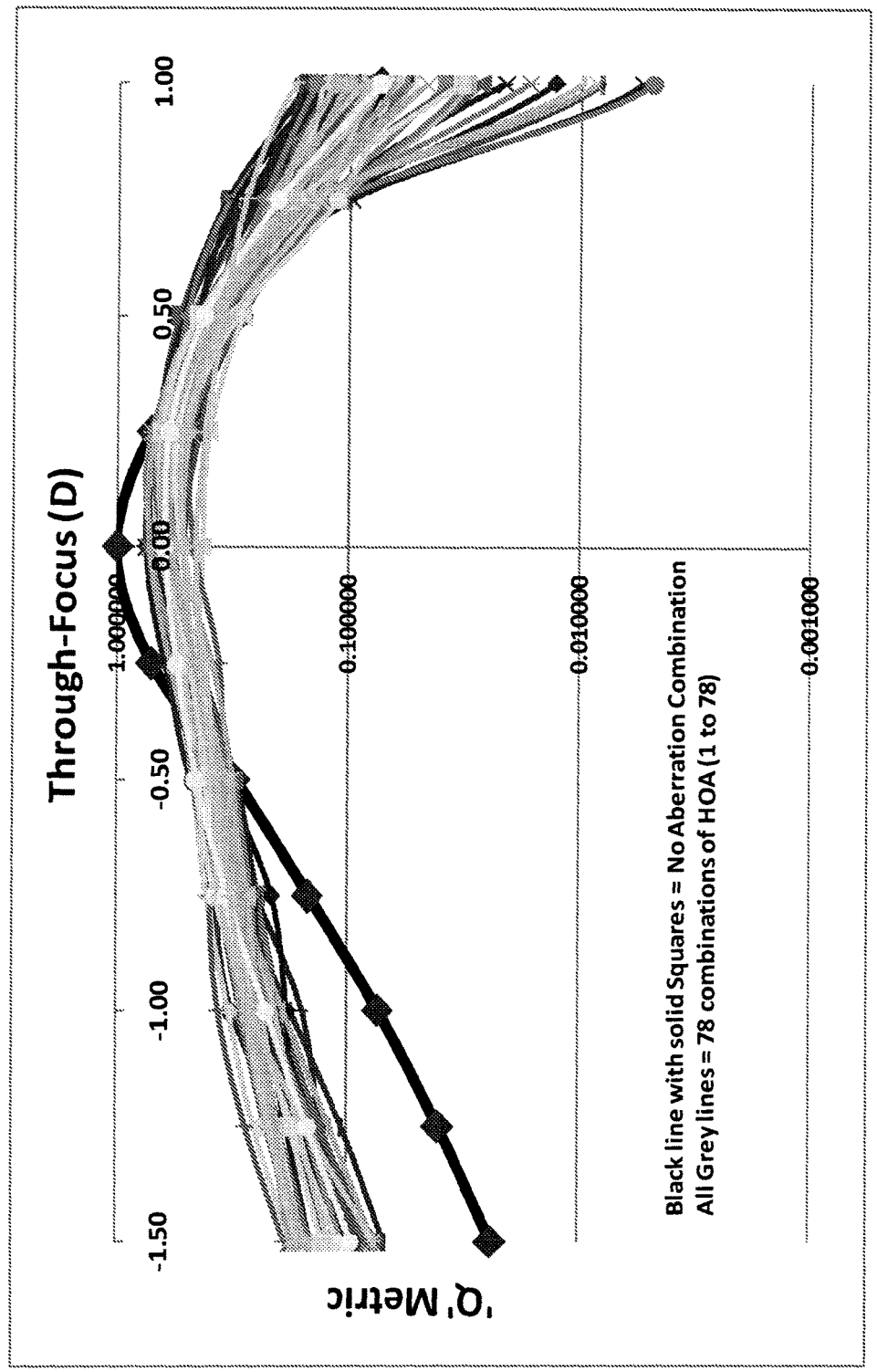
FIG. 64 shows the TFRIQ performance measures (depth of focus) of 78 exemplary aberration profiles (Appendix A) that involve a combination of spherical aberration terms. The Y-axis in the graph denotes 'Q' performance metric and X-axis denotes the through-focus range from −1.5 to +1 D. In this exemplary, the calculations were performed at 4 mm pupil. The solid black line indicates the through-focus performance of a combination that does not have a mode of spherical aberration while the grey lines indicate the 78 combinations which include at least one higher order spherical aberration term. The 78 combinations were selected with regard to performance on the negative side of the through-focus curve, according to certain embodiments.

The TFRIQ measures of the 78 aberration combinations are shown in FIG. 64, the black line showing the symmetrical RIQ that has resulted from a combination that has no higher order aberrations, the lighter lines (i.e. grey lines) showing the enhanced performance in the negative direction of the TFRIQ function for the 78 combinations that involve higher order spherical aberration terms.

From FIG. 64, a number of observations can be made. The 78 profiles with higher order spherical aberration terms provide an extended through focus performance in the negative direction, particularly when an appropriate selection of a negative power is made to shift the plotted through-focus profile towards negative defocus (left). The 78 profiles include a range over which RIQ is 0.1 or higher of at least 2 Dioptres. Several of the 78 profiles include a range over which RIQ is 0.1 or higher of at least 2.25 Dioptres. The 78 profiles include an RIQ (visual Strehl Ratio—monochromatic) that peaks above 0.35. Many of the profiles include an RIQ that peaks above the thresholds of 0.4, 0.5, 0.6 and 0.7 and some combinations result in a peak that lies above 0.8 mark.

The spherical aberration terms vary in the combinations, from one (example: combination 77) through to the nine. In other embodiments even higher orders of spherical aberration terms may be added, to create additional combinations.

Figure 65:
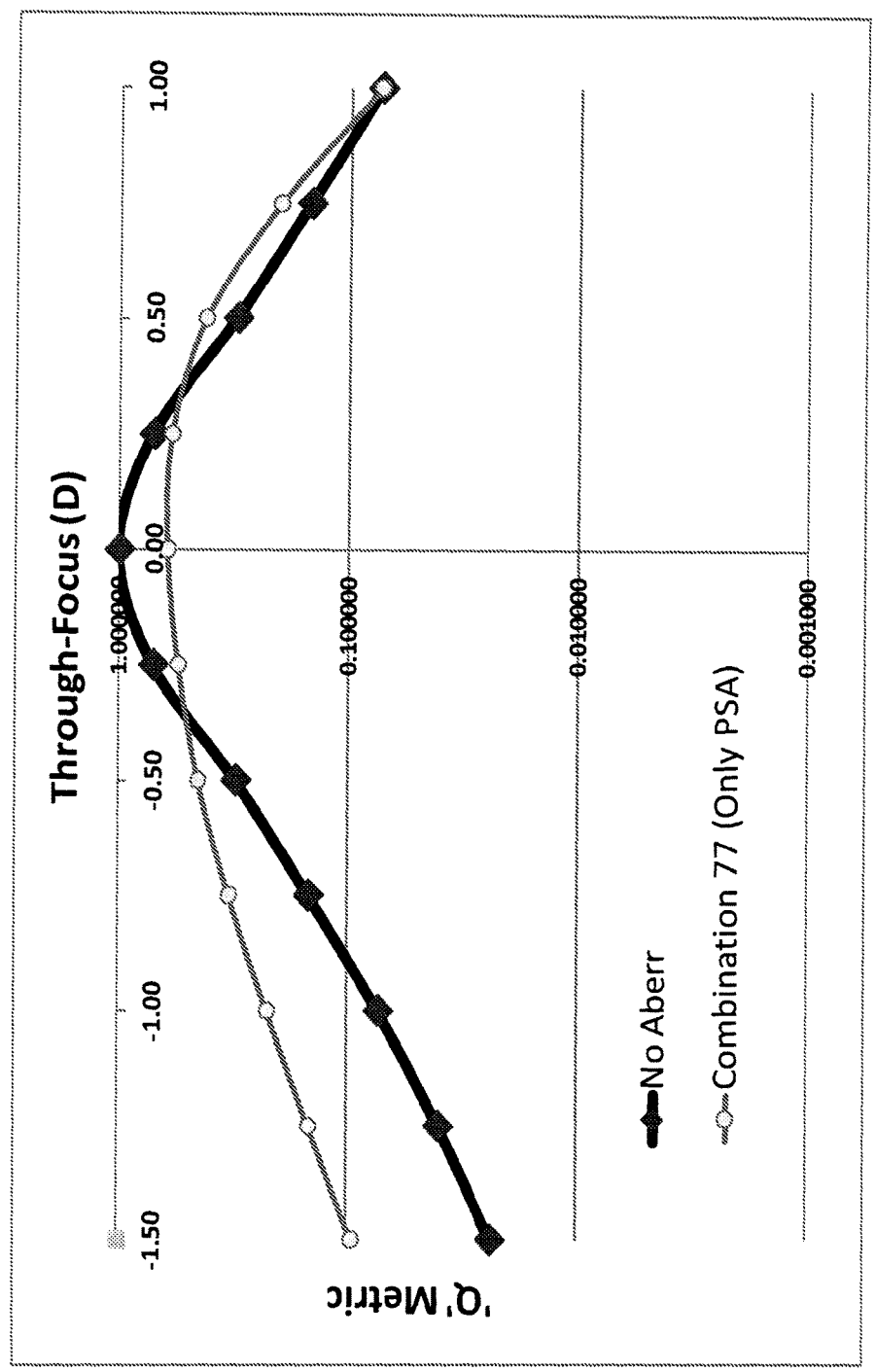
FIG. 65 shows the TFRIQ performance of one exemplary combination from FIG. 56 that involves only positive spherical aberration in comparison with a combination that has no spherical aberration, according to certain embodiments.

The combination 77 in the Appendix A shows that by selecting a particular level of primary spherical aberration, the aberration profile may be beneficially used for a presbyopic eye. See U.S. Pat. No. 6,045,568 for myopia. In contrast, according to certain embodiments, a stimulus to retard eye growth on-axis under the optical feedback explanation of emmetropisation is achieved if the retina is located on the negative side of the graph shown in FIG. 65 (i.e. the focal length of the lens is longer than the eye). In other words, the aberration profile typically includes a C(2,0) term with further negative power over the amount required to correct myopia.

Figure 66:
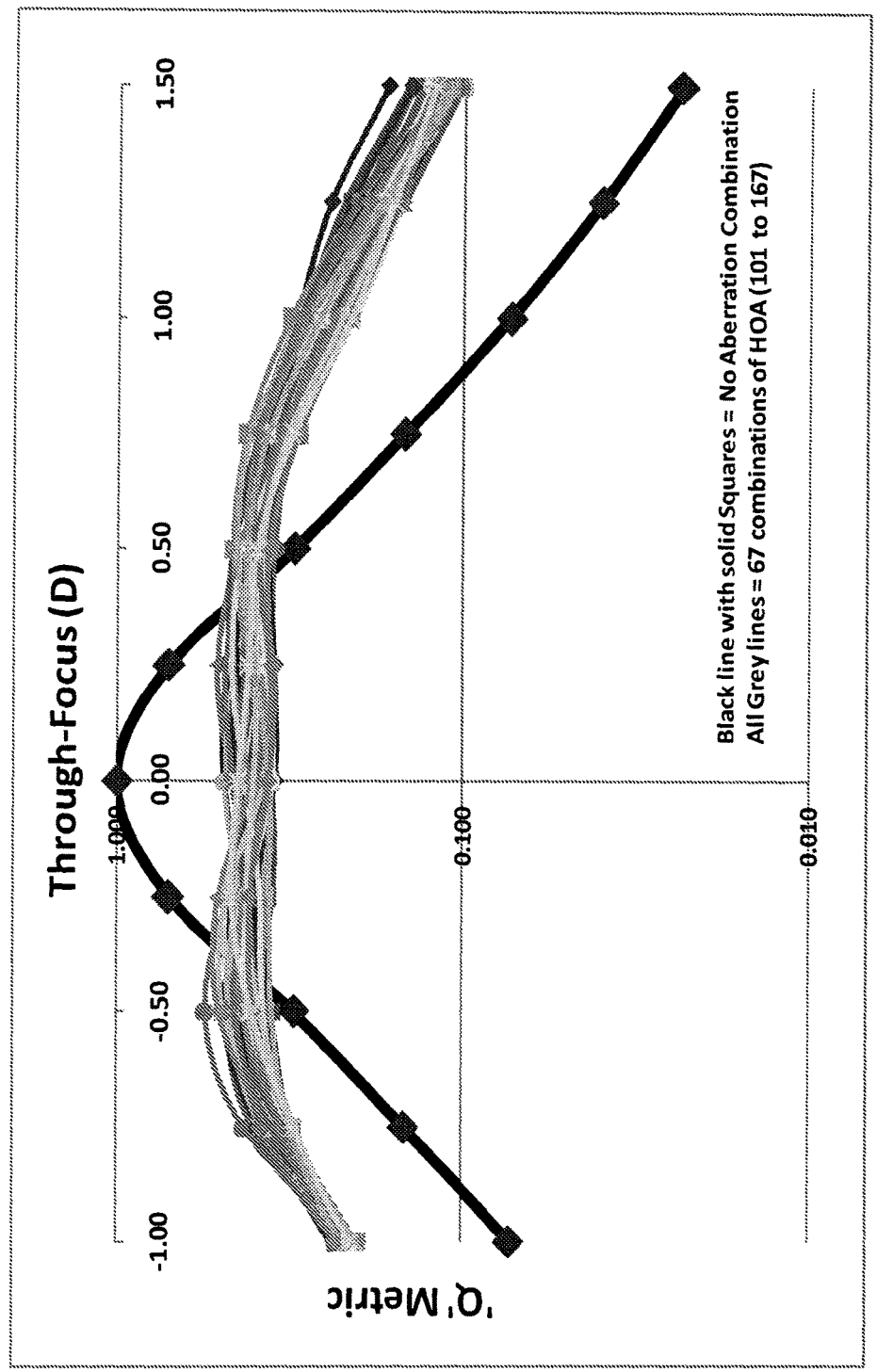
FIG. 66 shows the TFRIQ performance measures (depth of focus) of 67 exemplary aberration profiles that involve a combination of spherical aberration terms (Appendix C). The Y-axis in the graph denotes 'Q' performance metric and X-axis denotes the through-focus range from −1.5 to +1 D. In this exemplary, the calculations were performed at 4 mm pupil. The solid black line indicates the through-focus performance of a combination that does not have a mode of spherical aberration while the grey lines indicate the 67 combinations which include at least one higher order spherical aberration term. These 67 combinations improve performance on the positive side of the through-focus curve, according to certain embodiments.

Appendix C lists another 67 combinations of higher order coefficients that provide both a usefully high RIQ and an option to provide an extended TFRIQ in the positive direction (right hand side of FIG. 66). Also shown in Appendix C, as a point of comparison, is a combination which does not have spherical aberration of any order. The Appendix D shows the TFRIQ values for the combinations listed in Appendix C. Again, calculations were performed for a pupil size of 4 mm, however the approach, or methods, may be extended to other appropriate or desired pupil sizes, if required or desired.

The TFRIQ measures of the 67 aberration combinations are shown in FIG. 66, the black line showing the symmetrical RIQ that has resulted from a combination that has no higher order aberrations, the lighter (i.e. grey) lines showing the enhanced performance in the positive direction of the TFRIQ function, for the 67 combinations that involved higher order spherical aberration terms.

Figure 67:
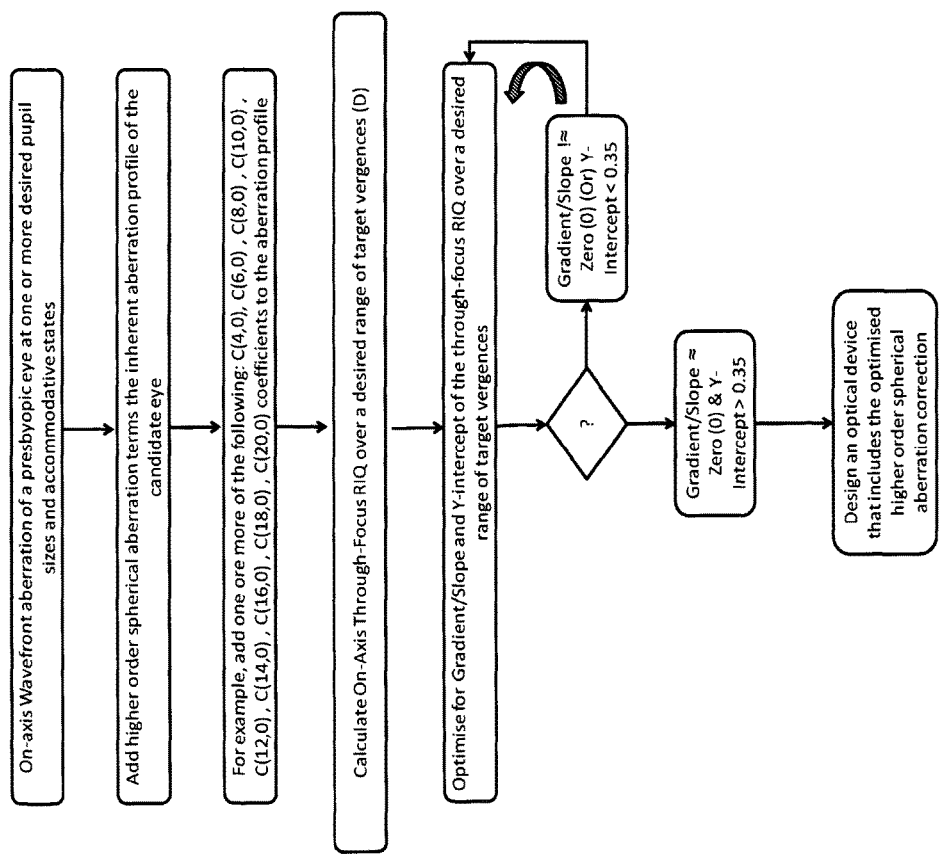
FIG. 67 shows a work flow chart for presbyopic eyes, according to certain embodiments.

From the FIG. 66, a number of observations can be made. The 67 profiles with higher order spherical aberration terms provide an extended through-focus performance in the positive direction particularly when appropriate selection of a negative power is made to shift the plotted through-focus profile towards negative defocus (left). The 67 profiles include a range over which the RIQ is 0.1 or higher or greater than 2.5 D. FIG. 67 shows an example workflow diagram for identifying a power profile for application to a presbyopic eye, according to certain embodiments.

Section 13

Spherical Aberration and Astigmatism

Iterations B1, B2 and B3 have been described herein for emmetropic presbyopia. When considering the astigmatic presbyopia, at least two different methods can be adopted. A first method of correction is completed by considering astigmatic refractive error as an equivalent sphere. In this method, the spherical equivalent prescription is deduced by dividing the cylindrical/astigmatic power divided two (S=−C/2). This is a very common approach often considered to address low to moderate amounts of astigmatism, say up to −1.5 D. Once the equivalent sphere is availed, the same, or substantially the same, iterations described herein, say for example B1, B2 or B3 can be used as an effective prescription, once the defocus term is adjusted to suit the spherical equivalent.

Figure 68:
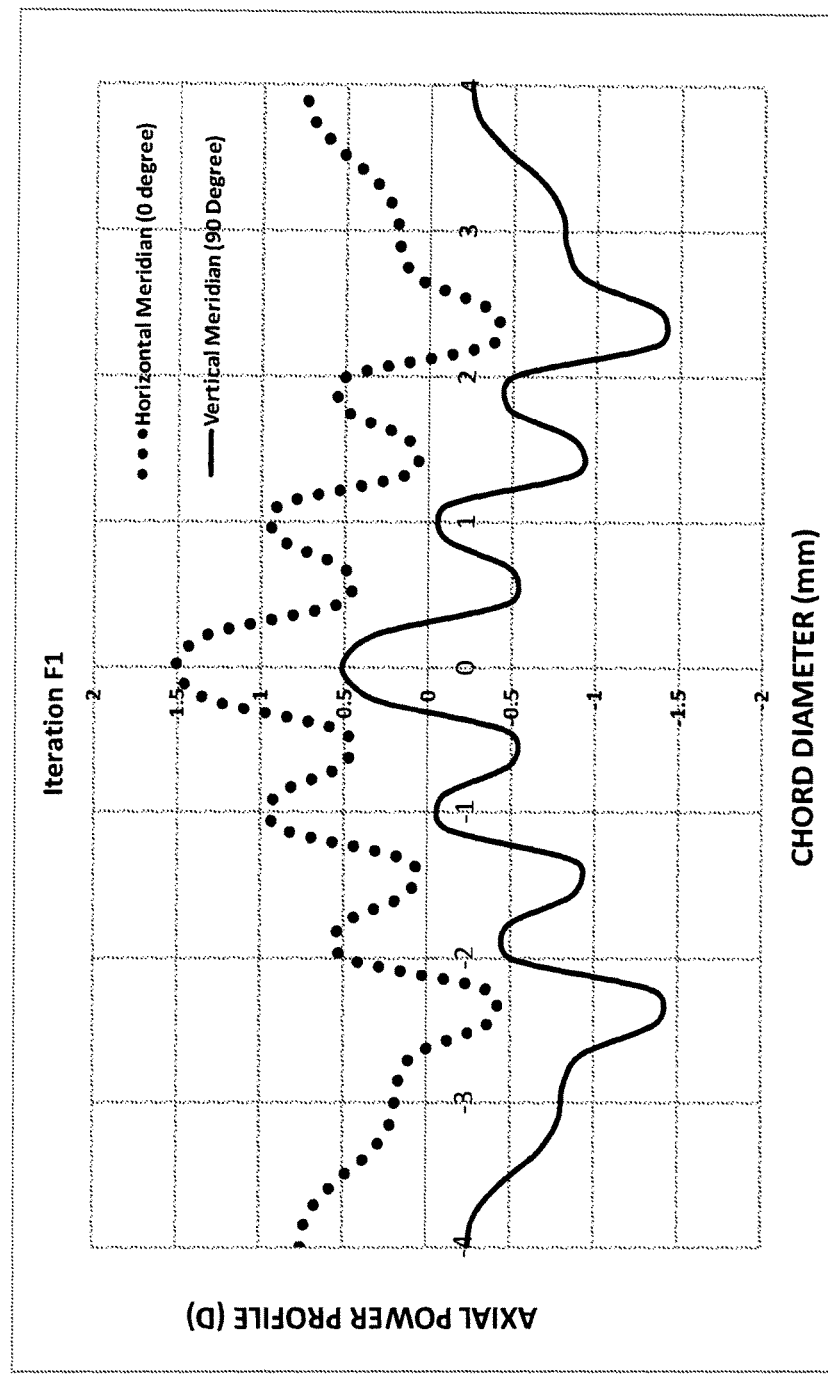
FIG. 68 shows a power profile for a toric prescription of a contact lens for both astigmatism and presbyopia, according to certain embodiments.

A second method considers preparation of a toric prescription for both astigmatism and presbyopia. FIG. 68 shows an exemplary embodiment that includes a toric power profile to treat both astigmatism and presbyopia. In this case, the prescription is made to correct an individual who has an astigmatic correction of −1 D @ 90 and requires an additional power to enable near viewing. As can be noted from the figure, the difference between the horizontal and vertical meridian is −1 D, this magnitude is set to correct the astigmatism in the above case; while the higher order spherical aberration combination is aimed to mitigate the presbyopic symptoms. Other suitable methods may also be used or incorporated into some of the disclosed embodiments.

The aberration profiles of some exemplary embodiments with substantially rotationally symmetric terms may be selected to mask and/or correct astigmatism up to at least −0.5 DC, −0.75 DC, −1 DC and −1.25 DC. In some embodiments, the correction of astigmatism may not be dependent on the axis of the astigmatism corrected. In some embodiments, the choice of rotationally symmetric aberrations to mask and/or correct astigmatism may be limited to at least $10^{th}$, $14^{th}$, $18^{th}$ or $20^{th}$ order Zernike polynomial expansion. In the current example, shown in Table 12.1, the calculations were performed using 5 mm pupil, 0 to 25 cycles/degree spatial frequency range and visual Strehl ratio as the through focus retinal image quality metric. However, other combinations of pupil sizes, retinal image quality metrics and/or spatial frequencies may also be used for such computations.

TABLE 12.1

Defocus and higher order spherical aberration coefficients of an exemplary embodiments which masks astigmatism of about −1.25DC at any axis. The computations were performed using visual Strehl ratio as the RIQ metric at 5 mm pupil diameter and a spatial frequency range of 0 to 25 cycles/degree.

| | |
|---|---|
| Astigmatism introduced | −1.25DC × 90 |
| Pupil size | 5 |
| Spatial Frequency | 0 to 25 c/d |
| Retinal image quality metric | VSOTF |
| Zernike coefficients for the selected combination | |
| C(2,0) | 0 |
| C(4,0) | −0.069 |
| C(6,0) | −0.002 |
| C(8,0) | −0.001 |
| C(10,0) | −0.063 |
| C(12,0) | −0.004 |
| C(14,0) | 0.075 |

TABLE 12.1-continued

Defocus and higher order spherical aberration coefficients of an exemplary embodiments which masks astigmatism of about −1.25DC at any axis. The computations were performed using visual Strehl ratio as the RIQ metric at 5 mm pupil diameter and a spatial frequency range of 0 to 25 cycles/degree.

| | |
|---|---|
| C(16,0) | 0.027 |
| C(18,0) | −0.036 |
| C(20,0) | −0.023 |

Section 13.A

Applications to Vision Improvement

Some embodiments are directed to lenses, optical devices and/or methods comprising the aberration profiles that are beneficial because they improve vision for seeing at certain levels of visual details; for example, for visual details at a desired spatial frequency or a desired range of spatial frequencies. Improvement of vision may be in the form of improvement of retinal image quality, visual acuity, contrast sensitivity at a desired spatial frequency or a range of spatial frequencies and/or combinations thereof.

Visual acuity may sometimes be used as a measure of an aspect of visual performance. Visual acuity measurement evaluates the limit when a visual target, such as a letter, or a letter "E" ('illiterate' E) or a letter "C" (Landolt C), or some other target, may no longer be resolved, identified or correctly reported by the patient who is undertaking the visual acuity measurement. The limit is related to, among other factors, the spatial frequency or spatial frequencies (how finely spaced the visual target details are) of the visual target and the contrast of the visual target. The limit of visual acuity may be reached when the contrast of the image of the visual target, created by the optics of an eye with or without additional optical devices, is too low to be discerned by the visual system (including the retina, visual pathway and visual cortex). Since the retinal image contrast required for discerning a retinal image increases with increasing spatial frequency (i.e. contrast has to be greater for finer detailed targets), for targets of a range of fineness of details (or spatial frequencies), an eye, or eye with optical devices typically is able to discern the highest spatial frequency, or the finest details for which the contrast of the retinal image is equal to or greater than the minimum contrast required for detecting the details.

In some embodiments, one way by which visual acuity may be improved is to increase the contrast of the retinal image at the level of fineness of details (or spatial frequencies) near to and/or slightly greater than (i.e. finer details or higher spatial frequency) the visual acuity of the natural eye or eye with optical devices.

Certain embodiments are directed to aberration profiles that increase contrast from slightly lower than or near to the visual acuity of a natural eye or a natural eye with conventional optical devices, to near to or slightly higher than the visual acuity of the natural eye or the natural eye with conventional optical devices.

Figure 134:
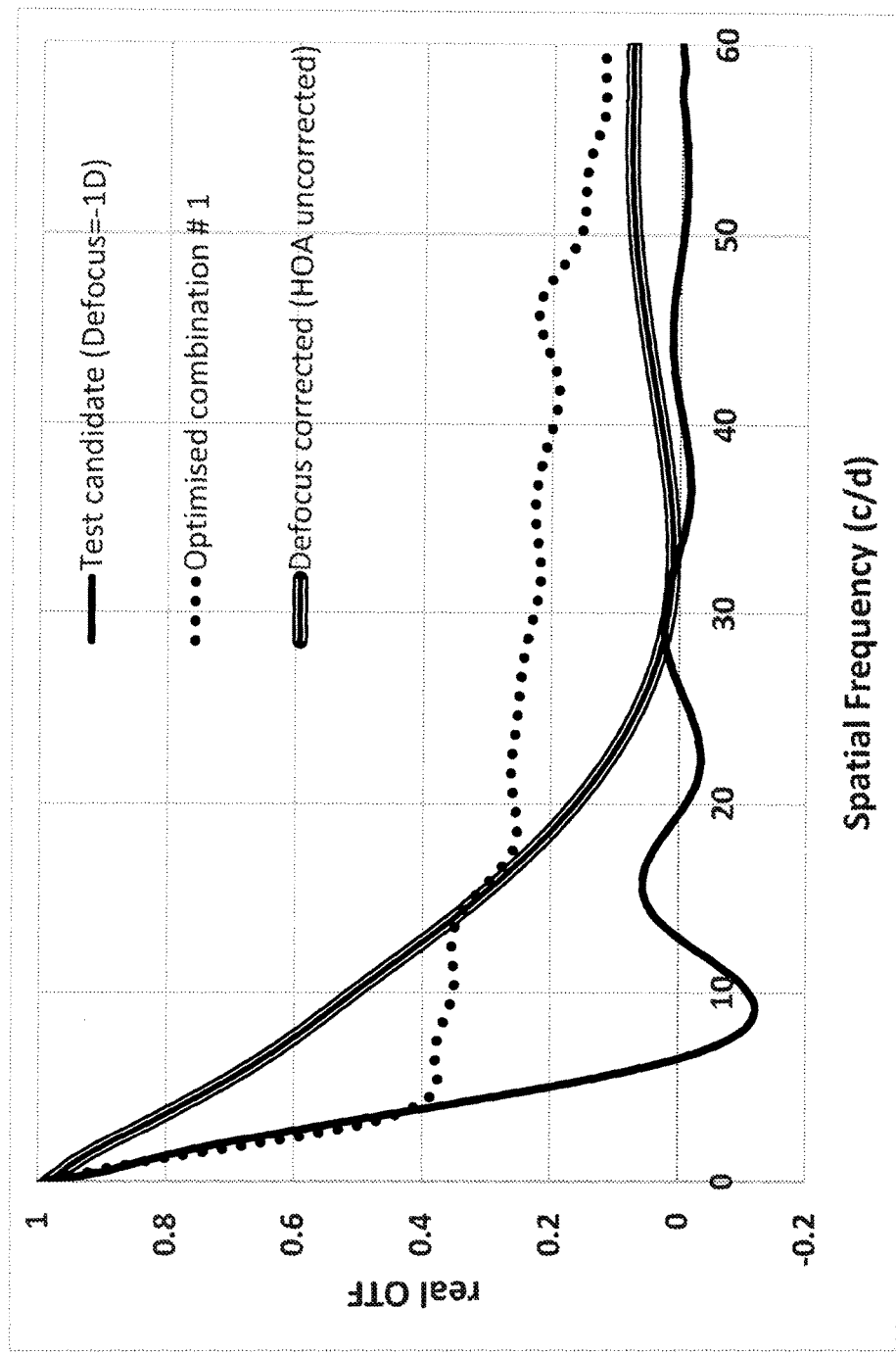
FIGS. 134 to 136 plots the real part of optical transfer function as a function of spatial frequencies for three sets of exemplary aberration combinations. In these figures, the solid line represents the candidate eye with −1 D of defocus with no other higher order aberrations, the double line represents the candidate eye when defocus is corrected and higher order aberrations are left uncorrected. The triple line represents one set of higher order aberration combinations #1, #2 and #3 described in tables 12.2.

In one exemplary embodiment, an eye may have a best-corrected visual acuity (i.e. the best visual acuity achievable using the best correction using conventional optical devices for its refractive error, which may be myopia or hyperopia or astigmatism or some combinations thereof) of 6/6 (or 20/20) acuity. This visual acuity level may be equated to a spatial frequency of 30 cycles per degree. That is, targets with finer details, and higher spatial frequencies, may be producing retinal image contrasts that are too low to be discerned by the retina and visual system. In this exemplary embodiment, shown in the FIG. 134, the optimised aberration combination provides an enhanced (higher) contrast retinal image at the spatial frequency range of 20 cycles per degree to 60 cycles per degree; that is, from slightly lower than the best-corrected visual acuity of the exemplary eye (with the corrected defocus terms and uncorrected higher order aberrations) to slightly higher than the best-corrected visual acuity of the exemplary eye. The increased contrast translates to an increase in RIQ for the exemplary eye. With the increased contrast at this range of spatial frequencies provided by the higher order aberration of this exemplary embodiment, the exemplary eye may achieve better vision performance and/or improved visual acuity.

In yet another application, the eye may be amblyopic; i.e. suffering from amblyopia. Amblyopia is a vision condition in which even with the best optical correction, the eye is not able to attain visual acuity that is usually attainable by normal eyes. An amblyopic eye may have very low visual acuity such as 6/9 (i.e. 20/30), 6/12 (i.e. 20/40) or worse. For such eyes, there may be benefits by improving vision, including improving contrast at or near the limits of visual acuity of the amblyopic eye. Hence, exemplary aberration profiles may provide enhanced contrast, and/or enhanced RIQ (which may be either monochromatic RIQ, or polychromatic RIQ) at a range of spatial frequencies according to the level of amblyopia of the eye. In some embodiments, the range of spatial frequencies for enhancement of RIQ may be selected according to the application, such as the individual patient's or eye's visual needs. For example, the range of spatial frequencies may be 5 to 15 cycles/degree, 10 to 15 cycles/degree, 10 to 20 cycles/degree, 15 to 20 cycles/degree, 15 to 25 cycles/degree, 20 to 25 cycles/degree, 20 to 30 cycles/degree, or 25 to 30 cycles/degree, 25 to 35 cycles/degree, 30 to 35 cycles/degree or 30 to 40 cycles/degree.

The fovea is the point on the retina that supports the most acute vision. In most normally-sighted eyes, the image of an object being 'looked at' is located onto the fovea by rotation of the eye. This alignment of the visual object with the fovea is called "fixation". The ability of the retina to resolve fine details decreases away from the fovea (central vision). Further out to the peripheral retina (peripheral vision), the visual acuity is progressively poorer. There are certain eyes that engage eccentric fixation. Eccentric fixation is the vision phenomenon when the eye does not use foveal vision. Such eyes, when attempting to 'look' at an object, may place the image on some point in the peripheral retina. The field angle range relative to the central retina or fovea (which may be regarded as an optical axis of an eye, or of a model eye) that the image may be placed by the eccentric fixating eye varies from eye to eye, but is typically consistent for the same eye. This field angle range may be over a field angle of from on-axis (i.e. 0°) to the optical axis of the eye to 5° from the optical axis of the eye, or from on-axis to 100 from the optical axis of the eye. In eyes with greater amounts of eccentric fixation, this field angle range may be over a field angle of from 5° from the optical axis of the eye to 15° from the optical axis of the eye; or the field angle range may be over a field angle of from 10° from the optical axis of the eye to 20° from the optical axis of the eye Certain embodiments are directed to aberration profiles that provide a global RIQ (GRIQ) in which the range of field angles over which the GRIQ is effected need not include the central, on-axis or foveal visual point. Certain embodiments are directed to aberration profiles that increase contrast from slightly lower than or near to the peripheral visual acuity of an eye or an eye with conventional optical devices within a region of peripheral or eccentric viewing, to near to or slightly higher than the peripheral visual acuity of an eye or an eye with conventional optical devices within a region of peripheral or eccentric viewing. For example, the peripheral visual acuity of an eye with some embodiments may be 20/80 (i.e. 6/24) or better at 20 degree field angle.

|  | Candidate eye with Defocus = −1 D | Candidate eye when defocus is corrected and HOA is left uncorrected |
|---|---|---|
| Pupil | 6 | 6 |
| SF-min | 0 | 0 |
| SF-max | 60 | 60 |
| C(2,−2) | 0 | 0 |
| C(2,0) | 1.29E+00 | 0 |
| C(2,2) | 0 | 0 |
| C(3,−1) | 0 | −0.075 |
| C(3,−1) | 0 | 0.075 |
| C(4,−2) | 0 | 0.05 |
| C(4,0) | 0 | 0.3 |
| C(4,2) | 0 | −0.05 |
| C(5,−1) | 0 | 0 |
| C(5,1) | 0 | 0 |
| C(6,−2) | 0 | −0.025 |
| C(6,0) | 0 | 0 |
| C(6,2) | 0 | 0.025 |
| C(8,0) | 0 | 0 |
| C(10,0) | 0 | 0 |
| C(12,0) | 0 | 0 |
| C(14,0) | 0 | 0 |
| C(16,0) | 0 | 0 |
| C(18,0) | 0 | 0 |
| C(20,0) | 0 | 0 |

Figure 135:
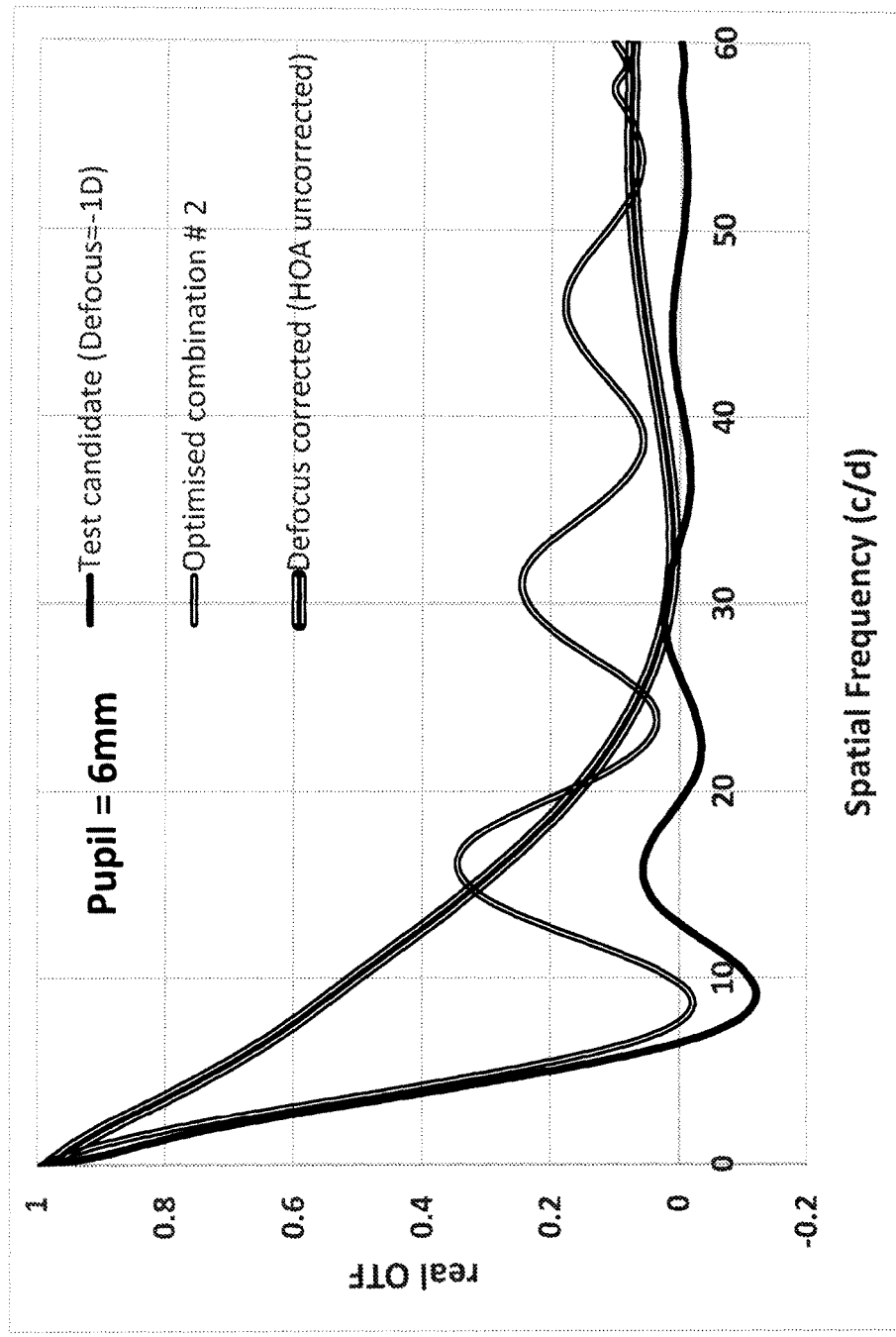
Figure 136:
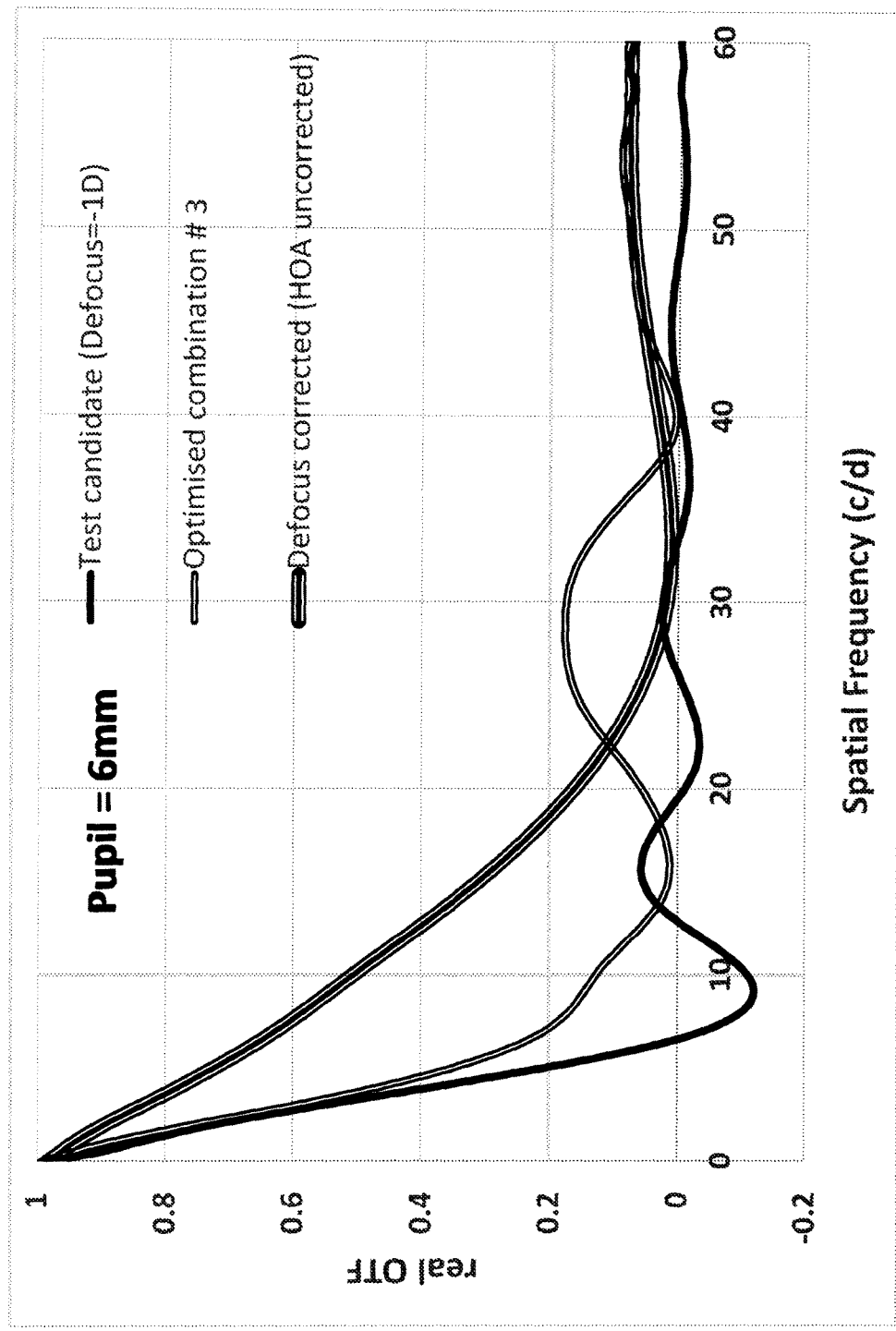

Table 12.1 shows the aberration profiles for a) the candidate eye with −1 D; and b) when the defocus term of the candidate eye is corrected and higher order aberrations are left uncorrected. The optical performance of these two combinations in terms of the real part of the optical transfer function as a function of spatial frequencies are provided in FIGS. 134, 135 and 136.

In one other application, an eccentrically fixating eye may have a best-corrected peripheral visual acuity (i.e. the best visual acuity achievable using the best correction using conventional optical devices for its refractive error, which may be myopia or hyperopia or astigmatism or some combinations thereof, and for which visual acuity is measured at the eye's eccentric fixation visual point) of 6/18 (or 20/60) acuity. This eccentric fixating, peripheral visual acuity level may be equated to a spatial frequency of 10 cycles per degree. In some exemplary embodiments, the combination of the higher aberration profiles provides an enhanced (higher) contrast retinal image at the spatial frequency range of 10 cycles per degree to 20 cycles per degree, as seen in combination #2 in FIG. 135; that is, from slightly lower than or near to the peripheral visual acuity of the measured best-corrected (peripheral) visual acuity of the exemplary eccentric fixating eye, to near to or slightly higher than the measured best-corrected visual acuity of the measured best-corrected visual acuity of the exemplary eccentric fixating eye.

In other applications, the range of angles of eccentric fixation may vary between 5° from the optical axis of the eye to 15° from the optical axis of the eye. In another embodiment, the combination of the higher aberration profiles provides an enhanced (higher) contrast retinal image at the spatial frequency range of 20 cycles per degree to 30 cycles per degree, as seen in combination #3 in FIG. 136. The aberration profiles of the exemplary higher order aberration combination improved contrast that may translates to an increase in GRIQ for the exemplary eye within a field angle range selected to match the range of angle of eccentric fixation. When the optimised higher order aberration combinations are configured to the exemplary eye such that they increase the contrast at certain ranges of spatial frequencies and field angles that have been selected to substantially match the range of angles of eccentric fixation, the exemplary eye may achieve better vision performance and improved contrast for a range of eccentric fixation.

|  | Combination # 1 | Combination # 2 | Combination # 3 |
|---|---|---|---|
| Pupil | 6 | 6 | 6 |
| SF-min | 5 | 10 | 25 |
| SF-max | 60 | 20 | 35 |
| C(2,−2) | 1.18E−10 | −1.30E−08 | 2.29E−09 |
| C(2,0) | 0 | 0 | 0 |
| C(2,2) | 2.42E−04 | −2.25E−03 | −1.14E−03 |
| C(3,−1) | −2.11E−09 | −3.54E−09 | 4.46E−09 |
| C(3,−1) | −1.95E−09 | −2.25E−08 | 4.43E−09 |
| C(4,−2) | −8.62E−10 | 1.15E−10 | 8.58E−10 |
| C(4,0) | 4.42E−02 | −7.83E−03 | −1.24E−02 |
| C(4,2) | −8.78E−04 | −2.56E−03 | 1.02E−04 |
| C(5,−1) | −1.97E−09 | 4.03E−09 | −4.44E−08 |
| C(5,1) | −2.04E−09 | 1.43E−08 | −4.46E−08 |
| C(6,−2) | −4.17E−10 | −7.37E−09 | 2.06E−08 |
| C(6,0) | −7.70E−02 | −1.41E−01 | −5.85E−02 |
| C(6,2) | 4.46E−04 | 3.71E−03 | −1.57E−04 |
| C(8,0) | −2.61E−03 | 7.00E−02 | 2.50E−02 |
| C(10,0) | −7.61E−02 | −3.09E−02 | −3.50E−02 |
| C(12,0) | 1.13E−01 | −4.01E−02 | −4.08E−02 |
| C(14,0) | 1.25E−01 | 2.28E−02 | −4.27E−02 |
| C(16,0) | −1.05E−01 | −1.47E−02 | 5.21E−02 |
| C(18,0) | −9.37E−02 | −3.06E−03 | 5.53E−02 |
| C(20,0) | 1.84E−02 | 2.69E−02 | −1.60E−02 |

Table 12.2 shows the optimised aberration profiles that provides improvement in the real part of the optical transfer function at selected spatial frequencies (observed in FIGS. 134, 135 and 136), when compared with optical performance obtained with the two aberration combinations provided in Table 12.1.

Section 14

Implementation

There are several methods that may be used for designing or modelling the lenses and/or devices disclosed herein. One exemplary method for designing one or more optical devices comprises: (a) setting a group of target requirements and a group of performance requirements for the one or more optical devices that comprises two or more of the following: a focal distance, an optic zone, an image quality at the focal distance, a through-focus image quality about the focal distance; wherein the image quality is one of the following: monochromatic, polychromatic or global image quality; wherein the image quality is calculated in a spatial domain or a Fourier domain, the image quality is calculated for at least a portion of the optic zone diameter between 3 mm to 8 mm and for one of the following spatial frequency ranges: 0 to 15 c/d, 0 to 20 c/d, 0 to 25 c/d, 0 to 30 c/d, 0 to 45 c/d, 0 to 60 c/d, 5 to 30 c/d or 0 to 60 c/d wherein the image quality is calculated by using one of the following: tray-tracing, Fourier optics or direct wavefront propagation; (b) defining a wavefront representation of the one or more optical devices; wherein the wavefront representation optionally comprises one of the following: apodisation, no apodisation, inverse apodisation or Stiles-Crawford effect as apodisation; wherein the wavefront representation is described using one or more of the following mathematical descriptions: Zernike polynomials, Fourier series, extended even or odd polynomials, extended aspheres, super conics and Bessel series; (c) optimising the represented wavefront in order to substantially achieve the target requirements of the performance of the one or more optical devices by using non-linear optimisation computation routines. In some other exemplary methods, the optimisation of the represented wavefront may be performed to achieve the performance requirement at least one particular distance. In yet another exemplary method, the optimisation of the represented wavefront may be performed achieve the performance requirement at least two particular distances.

In yet another exemplary method, the optimisation of the represented wavefront may be performed achieve the performance requirement at least three particular distances. In yet another exemplary method, the optimisation of the represented wavefront may be performed achieve the performance requirement at least four particular distances. In yet another exemplary method, the particular distances optimised for may be spaced apart by at least 0.5 D. In yet another exemplary method, the particular distances optimised for may be spaced apart by at least 1 D.

In yet another exemplary method, the optimisation of the represented wavefront may be performed to have a negative or positive slope of through-focus image quality in the negative or positive end of the through-focus range. Other suitable methods for designing and/or modelling the lenses and/or devices disclosed herein may also be used.

Aberration profiles of the types described herein may be implemented in a number of lenses, ocular devices and/or methods. For example, contact lenses (hard or soft), corneal onlays, corneal inlays, and lenses for intraocular devices (both anterior and posterior chamber) may include the combination aberration profiles discussed. Techniques to design lenses and to achieve a power profile are known and will are not described herein in any detail. The aberration profiles can be applied to spectacle lenses. However, because the aberration profiles require alignment of the eye with the centre of the optics providing the aberration profile, then benefit may only be apparent for one particular direction of gaze. Recently electro-active lenses have been proposed that can track the direction of gaze and change the refractive properties of the lenses in response. Using electro-active lenses the aberration profile can move with the eye, which may increase the utility of the disclosed aberration profiles for spectacle lenses.

The aberration profile may be provided on a lens which is an intraocular lens. In some embodiments, the intraocular lens may include haptics that provide for accommodation. In other embodiments, the lens may have a fixed focal length. The aberration profile may be provided on a supplementary endo-capsular lens.

Figure 69:
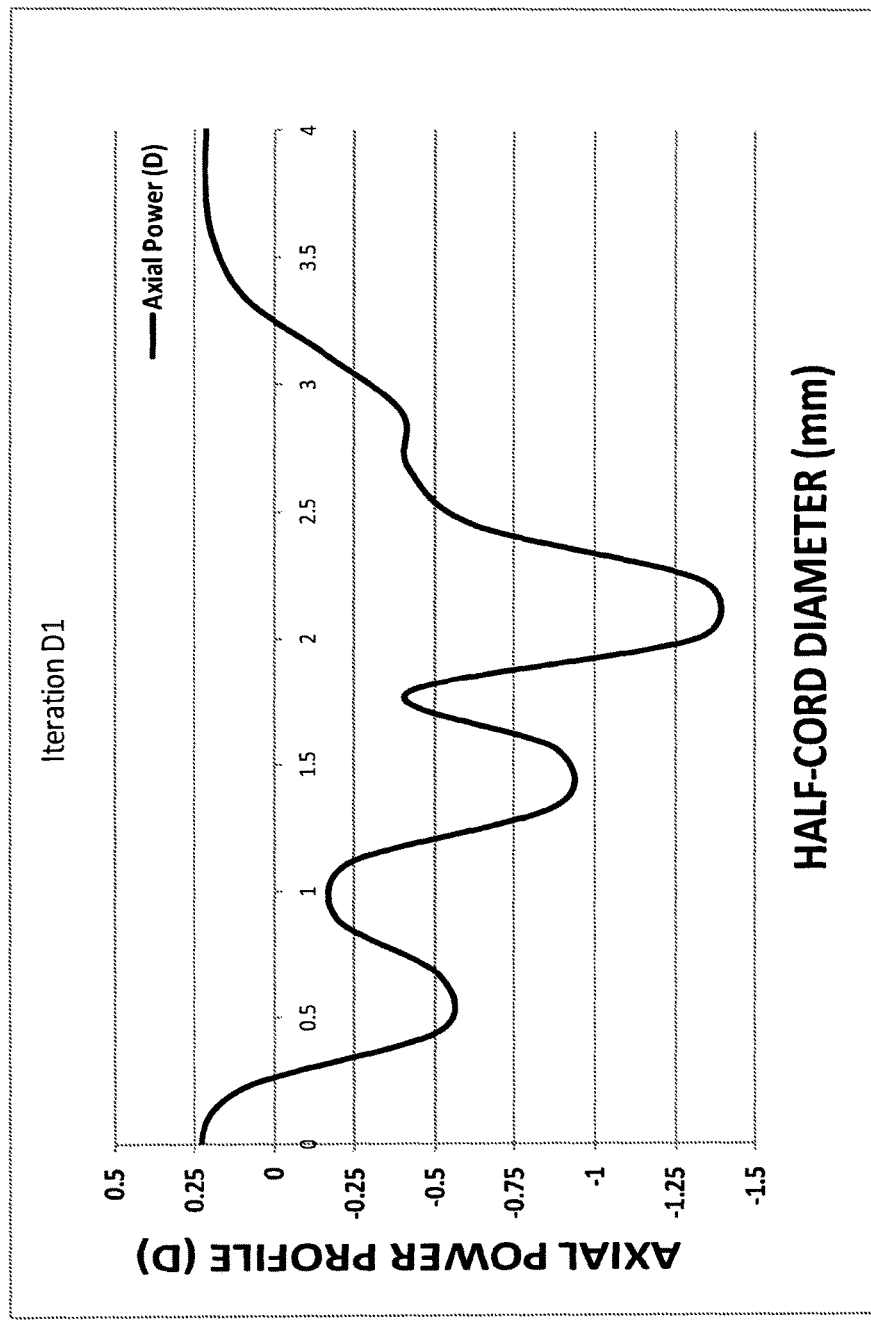
FIG. 69 shows an example lens power profile, which is availed from an exemplary combination of spherical aberration terms
Figure 70:
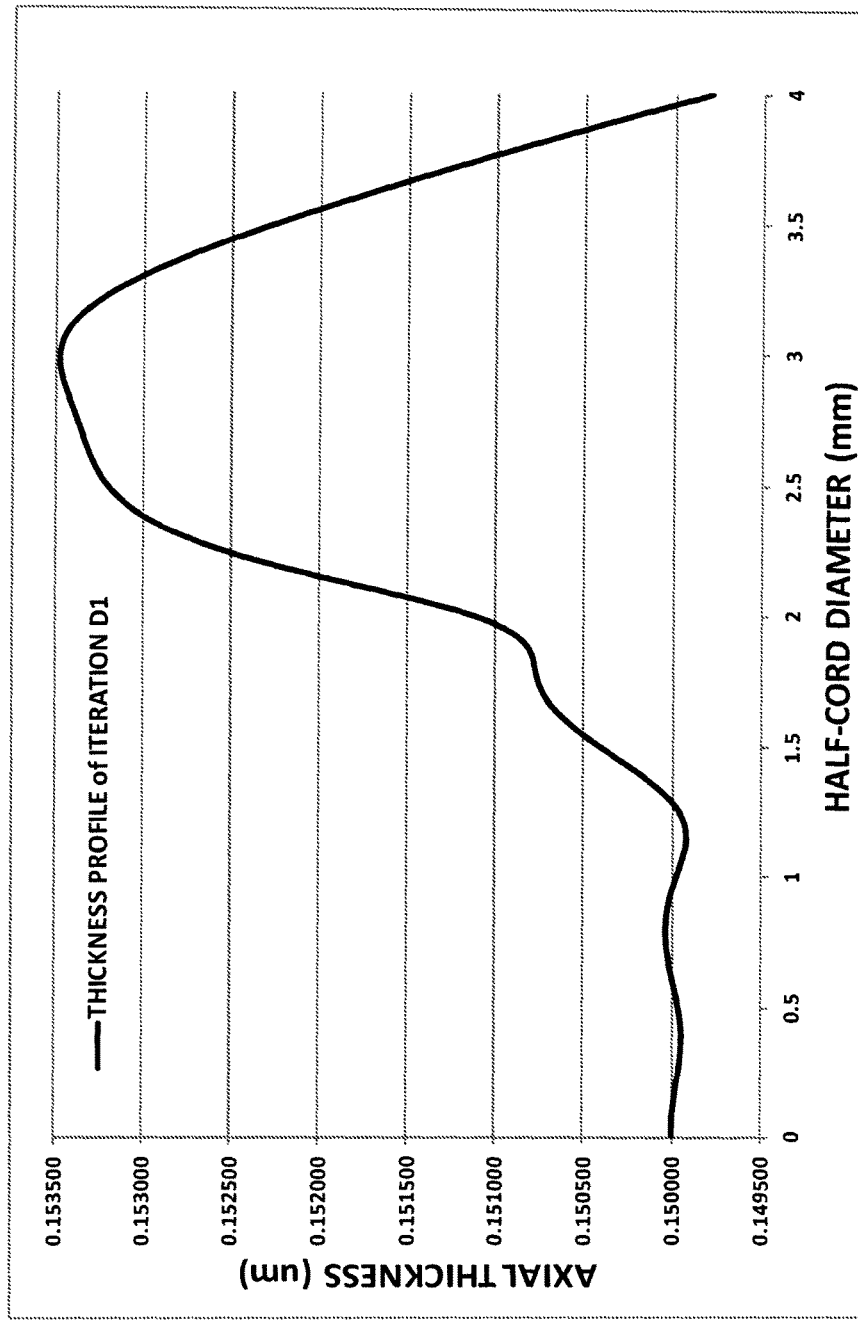
FIG. 70 shows the lens power profile converted to an axial thickness profile for a contact lens, according to certain embodiments.

In certain applications, one or more of the disclosed aberration profiles may be provided to an eye through computer-assisted surgery and/or methods of altering the power and/or aberration profile of the eye. For example implant, laser sculpting, laser ablation, thermokeratoplasty, lens sculpting are used for such a purpose. Examples of such methods include radial keratotomy (RK), photorefractive keratotomy (PRK), thermokeratoplasty, conductive keratoplasty, laser assisted in-situ keratomileusis (LASIK), laser assisted in-situ epi-keratomileusis (LASEK) and/or clear lens extraction. For example refractive surgery or corneal ablation may be used to form a selected aberration profile. The desired power profile or the desired change in corneal shape and/or power is substantially determined, or determined, and input to the laser system for application to the eye of the patient. Procedures may also be used to input a desired profile and/or aberration profile to the crystalline lens itself either by implant, laser ablation and/or laser sculpting to achieve a desired outcome. This includes, but not limited to, systems that currently exist, including wavefront guided femto-second lasers.

Where the aberration profiles are to be included in a lens, then the aberration profile may first be translated into a lens thickness profile for input to computer assisted manufacturing. Taking for example, the lens power profile D1 shown in FIG. 69, which is a combination of Zernike higher order spherical aberration terms, is converted to an axial thickness, or a surface, profile for a contact lens, taking account of the refractive index of the contact lens material (in this case, contact lens material refractive index of 1.42). An example thickness profile is shown in FIG. 70. In certain embodiments, features of the power or thickness profiles can either be put on the front or the back surface or a combination of both, under consideration of the refractive indices of lens and cornea. Once one or more of the following parameters, i.e., the thickness profile, power profile, back surface shape, diameter and refractive index of the material have been determined, one or more of the parameters are input to a computer assisted lathe, or other manufacturing systems to produce the contact lens. Similar approaches can be adopted for other lenses and optical systems such as intra-ocular lenses, anterior and/or posterior chamber lenses, corneal implants, refractive surgery or combinations thereof. The aberration profile may be selected and identified as a custom lens for an individual. The process for design of the aberration profile may include measuring the wavefront aberration of the eye and designing an aberration profile to achieve a through focus RIQ profile described herein. The design process includes identifying the spherical aberration in the natural eye and designing an aberration profile for the lens, device and/or method that, in combination with the spherical aberration of the eye provides a required, or desired, RIQ profile. As described herein, the required, or desired, RIQ profile may differ depending on the application of the lens—as different requirements may apply between, for example, a person with progressing myopia and a person with presbyopia. In some embodiments, other aberrations in the eye, for example astigmatism, coma or trefoil are ignored.

In other embodiments, these are taken into account. For example, as described herein, the presence of astigmatism affects the combinations of aberrations that provide a through focus RIQ that inhibits eye growth under the optical feedback explanation of emmetropisation. In other embodiments, these aberrations are incorporated into the design. For example, when producing a lens design, a base lens may be produced that corrects for defocus and corrects one or more of astigmatism, coma and trefoil. On top of this base profile is provided a spherical aberration profile designed to achieve (in the sense of using as an objective design) the profiles described herein. The spherical aberration profile may be selected using a trial and error, or iterative-convergence approach, for example by identifying a candidate profile, computing the through focus RIQ and evaluating whether the through focus RIQ has an acceptable profile. In another approach aberration profiles may be designed for population average, mean, median or other statistical representations or metrics. One approach for designing population average, mean, median or other statistical representations or metrics, lenses is to normalise, or customise, or tailor, or optimise, the design for a pupil size.

In certain embodiments, the description of the aberration profiles, first derivatives of the power profiles, second derivatives of the power profiles, Fourier transformation of the power profiles, power profiles and image profiles of the power profiles and/or other suitable or appropriate measures of one or more optical characteristics or one or more performance metrics for lenses, devices and/or methods has been provided to some extent by way of mathematical explanation or derivation. This allows to some extent for precision in deriving and/or describing the aberration profiles, first derivatives of the power profiles, second derivatives of the power profiles, Fourier transformation of the power profiles, power profiles and image profiles of the power profiles for lenses.

However, in certain applications, lenses, devices and/or methods may or may not have precision that is comparable to, or commensurate with or derived from the mathematical calculations. For example tolerances and inaccuracies arising during manufacture may or may not result in variations of the lens profile. In certain embodiments, the power profile and/or aberration profile of a lens may be approximately measured using, for example, a wavefront aberrometer. From this an approximate measure of through focus RIQ may be determined; for example, using visual Strehl Ratio. In certain embodiments, the power profile and/or aberration profile of a lens may be characterised by using, for example, suitable instruments and/or techniques such as Hartman-Shack aberrometry, ray-tracing, lens power mapping, focimetry, interferometry, phase contrast, ptchyography, Foucault knife-edge systems, or combinations thereof. From these characterisations one or more of the following: aberration profiles, first derivatives of the power profiles, second derivatives of the power profiles, Fourier transformation of the power profiles, power profiles and image profiles of the power profiles and/or other suitable or appropriate measures of one or more optical characteristics or one or more performance metrics, may be measured, derived or otherwise determined.

Aberration profiles may be implemented in a number of lenses, devices and/or methods, according to certain embodiments. For example, the lens may be characterised by testing the lens on a ray tracing or physical model eye with a focal length equal to, or substantially equal to, the focal distance of the lens. The aberration profile of the lens, including higher order aberration profiles, that would result in an image on the retina which may be quantified using one or more of the RIQ metrics disclosed. In certain embodiments, the model eye may have no, or substantially no, aberrations. In certain embodiments, the RIQ metric may be visual Strehl ratio. In other embodiments, the pupil size may be selected from one or more of the following ranges: 2 to 8 mm, 2 to 7 mm, 2 to 6 mm, 3 to 6 mm, 3 to 5 mm, 4 to 6 mm or 5 to 7 mm. In some other embodiments, the spatial frequency ranges can be selected from one of the following: 0 to 30 cycles/degree, 0 to 60 cycles/degree or 0 to 45 cycles/degree. In other embodiments, the selected wavelength for calculations of one or more RIQ metrics may be selected from one or more of the following: 540 nm to 590 nm inclusive, 420 nm to 760 nm inclusive, 500 nm to 720 nm inclusive or 420 nm to 590 nm inclusive. In certain embodiments, the RIQ may be measured on an on-axis model eye. In other applications an off-axis model eye may be used to obtain other RIQ variants like the global RIQ. The through-focus RIQ may be calculated on the model eye by using spherical lenses in front the model eye.

Certain embodiments disclosed herein are directed to methods of correcting vision whereby a lens of one or more of the disclosed embodiments is prescribed according to one or more target refractive powers, an appropriate power profile, and the lens is fitted to an eye to provide a visual performance for the eye, along a range of substantially continuous visual distances, including intermediate and far distances, wherein the visual performance of the lens is at least substantially equivalent to the visual performance of a correctly prescribed single-vision lens at the far visual distance.

Certain embodiments disclosed herein are directed to methods of correcting vision whereby a lens of one or more of the disclosed embodiments is prescribed according to one or more target refractive powers, an appropriate power profile, and the lens is fitted to an eye to improve the visual performance for the eye. In certain applications, one or more methods disclosed herein may be used for correcting vision of the eye according to certain embodiments, whereby the eye is affected by one or more of the following: myopia, hyperopia, emmetropia, astigmatism, presbyopia and optically aberrated.

Certain embodiments, may be used in methods for correcting the vision of a pair of eyes, whereby one or both of the eyes is optically aberrated possesses at least one higher-order aberration. Certain embodiments, may be used in methods of correcting binocular vision, whereby two lenses of one or more embodiments disclosed herein are prescribed according to a first and a second target refractive power, a first and a second power profile are selected, and the two lenses fitted to a pair of eyes improve the visual performance of the two eyes combined compared to individual eyes separately. In certain methods disclosed herein, the first target refractive power is different from the second target refractive power.

Certain embodiments are directed to methods of correcting binocular vision, whereby the first target refractive power is selected to improve visual performance at a visual distance that is at least one of the following: far, intermediate, near; and the second target refractive power is selected to improve visual performance at a visual distance that is at least one of the following: far, intermediate, near, wherein the visual distance at which the visual performance for which the first target refractive power is selected is different from the visual distance at which the visual performance for which the second target refractive power is selected. In certain applications, one or more methods disclosed herein may be used for correcting vision of the eye according to certain embodiments, whereby the refractive state of the eye may be classified as one or more of the following: myopia, hyperopia, emmetropia, regular astigmatism, irregular astigmatism, optically aberrated, presbyopia, non-presbyopia.

Certain embodiments are directed to methods of manufacturing lenses where the lenses are configured or designed according to a reference eye, whereby the lens features that are configured are selected from one or more of the following: focal length, refractive power, power profile, number of spherical aberration terms, magnitude of spherical aberration terms; whereby the reference eye is selected from one or more of the following: an individual eye, both eyes of an individual person, statistical representation of eyes a sample of an affected population, computational model of an eye and/or computational model of eyes of an affected population.

In certain embodiments, aperture size may be used to characterise an entrance pupil of the eye and/or a portion of the optic zone of a lens and/or device. In certain applications, the effective aperture size may be defined as an opening that is greater than or equal to 1.5 mm, 2 mm, 3 mm, 4 mm, 5 mm, 6 mm or 7 mm, this is in contrast to pin-hole apertures which typically have a diameter, for example, less than 1.5 mm. For example, certain embodiments are directed to a lens comprising: an optical axis; at least two optical surfaces; wherein the lens is configured to provide a visual performance on a presbyopic eye substantially equivalent to the visual performance of a single-vision lens on the pre-presbyopic eye; and wherein the lens has an aperture size greater than 1.5 mm.

Certain embodiments are directed to one or more methods of surgical correction of vision to improve visual performance. For example, a method for surgical correction may comprise the steps of: (1) computing one or more targeted modifications to the optical properties, power and/or physical structure of an eye; wherein the targeted modifications comprise: at least one desired refractive power and at least one appropriate power profile; at least one aberration profile, wherein the aberration profile is comprised of at least two spherical aberration term and a defocus term; and a visual performance along substantially continuous visual distances including near, intermediate and far, wherein the visual performance of the eye along the substantially continuous visual distance is substantially equivalent to the visual performance of an eye wearing an correctly prescribed single-vision lens for the far visual distance; (2) inputting the desired modifications to an ophthalmic surgical system; and (3) applying the desired modifications to the eye with the ophthalmic surgical system. In certain applications, the visual performance of the eye is further characterised by minimal, or no, ghosting at near, intermediate and far visual distances.

In certain applications, the vision performance of the correctly prescribed single vision lens provides a visual acuity for the eye that is the best-corrected visual acuity. In certain applications, the best-corrected visual acuity is a visual acuity that cannot be substantially improved by further manipulating the power of the correctly prescribed single vision lens. In certain applications, the aberration profile comprises three or more spherical aberration terms and a defocus term.

Certain embodiments are directed to lenses that provide substantially equivalent, or equivalent or better optical and/or visual performance than a correctly prescribed single vision lens at far visual distance. As used in certain embodiments, correctly prescribed may mean a prescribed single vision lens at the far visual distance that provides a visual acuity for an eye that is the best-corrected visual acuity and cannot be substantially improved by further manipulating or adjusting the power of the lens. As used in certain embodiments, appropriately, properly, effectively, prescribed may mean a prescribed single vision lens at the far visual distance that provides a visual acuity for an eye that approximates the best-corrected visual acuity and cannot be substantially improved by further manipulating or adjusting the power of the lens.

Certain embodiments are directed to one or more methods of surgical correction of vision to improve visual performance. For example, a method of correcting vision comprising the steps of: (1) computing one or more targeted modifications to an eye; wherein the modifications provides to the eye: at least one optical characteristic; wherein the at least one optical characteristic comprises at least one aberration profile; the aberration profile comprises at least two spherical aberration term and a defocus term; and a visual performance at intermediate and far visual distances that is at least substantially equivalent to the eye fitted with an correctly prescribed single-vision lens for far visual distance; wherein when tested with a defined visual rating scale of 1 to 10 units, the visual performance of the eye at the near visual distance is within two units of the visual performance of the eye fitted with an correctly prescribed single-vision lens at far distance; (2) inputting the desired modifications to an ophthalmic surgical system; and (3) applying the targeted modifications to the eye with the ophthalmic surgical system. In certain applications, the visual performance additionally provides substantially minimal ghosting to the vision of the eye at near, intermediate and far visual distances. In certain applications, the substantially equivalent to or better visual performance is determined at least in part by a visual rating scale of 1 to 10 units.

Certain embodiments are directed to one or more methods of surgical correction of vision to improve visual performance. For example, methods of vision correction may comprise the steps of: (1) computing one or more targeted modifications to an eye; wherein the modifications provide to the eye: at least one optical characteristic; wherein the at least one optical characteristic comprises at least one aberration profile; the aberration profile comprises at least two spherical aberration term and a defocus term; and a visual performance at intermediate and far visual distances, that is substantially equivalent to, or better than, the eye fitted with a correctly prescribed single-vision lens for far visual distance; and wherein the visual performance is further characterised by minimal ghosting to the vision of the eye at least at far distance; (2) inputting the desired modifications to an ophthalmic surgical system; and (3) applying the desired modifications to the eye with the ophthalmic surgical system. In certain applications, the minimal ghosting is attaining a score of less than or equal to 2.4, 2.2, 2, 1.8, 1.6 or 1.4 on the vision rating ghosting scale of 1 to 10 units.

Certain embodiments are directed to one or more devices and/or systems for the surgical correction of vision to improve visual performance. For example, a device and/or system for correcting vision of an eye may comprise: (1) an input module; (2) a computation module; and (3) a delivery module; wherein the input module is configured to receive input relevant to the vision correction of the eye; the computation module is configured to compute one or more targeted modifications to the eye; wherein the modifications provides to the eye: at least one targeted refractive power and at least one appropriate power profile; at least one aberration profile, wherein the aberration profile being comprised of at least two spherical aberration term and a defocus term; and a visual performance, along substantially continuous visual distances, including intermediate and far, wherein the visual performance of the eye along the substantially continuous visual distance is substantially equivalent to the visual performance of an eye wearing an correctly prescribed single-vision lens for the far visual distance; and the delivery module uses the computed targeted modifications to the eye computed by the computation module to deliver the targeted modifications to the eye. In certain applications, the visual performance of the eye is further characterised by minimal, or no, ghosting at near, intermediate and far visual distances.

In certain applications, the correctly prescribed single vision lens provides a visual acuity for the eye that is the best-corrected visual acuity. In certain applications, the best-corrected visual acuity is a visual acuity that cannot be substantially improved by further manipulating the power of the correctly prescribed single vision lens. In certain applications, the aberration profile comprises three or more spherical aberration term and a defocus term. In certain applications, the delivery module may be an ophthalmic refractive surgical system such as a femto-second laser.

Certain embodiments are directed to one or more devices and/or systems for the surgical correction of vision to improve visual performance. For example, a device and/or system for correcting vision of an eye may comprise: (1) an input module; (2) a computation module; and (3) a delivery module; wherein the input module is configured to receive input relevant to the vision correction of the eye; the computation module is configured to compute one or more desired modifications to the eye; wherein the modifications provides to the eye: at least one optical characteristic; wherein the at least one optical characteristic comprises at least one aberration profile; the aberration profile comprises at least two spherical aberration term and a defocus term; and a visual performance at intermediate and far visual distances that is substantially equivalent to or better than the eye fitted with an correctly prescribed single-vision lens for far visual distance; and when tested with a defined visual rating scale of 1 to 10 units, the visual performance of the eye at the near visual distance is within two units of the visual performance of the eye fitted with an correctly prescribed single-vision lens at far distance; the delivery module utilising desired modifications to the eye computed by the computation module to deliver the desired modifications to the eye.

In certain applications, the visual performance in addition, provides minimal ghosting to the vision of the eye at near, intermediate and far visual distances. In certain applications, the substantially equivalent to or better visual performance is substantially determined at least in part by a visual rating scale of 1 to 10 units. In certain applications, the delivery module is an ophthalmic refractive surgical system such as a femto-second laser.

Certain embodiments are directed to one or more devices and/or systems for the surgical correction of vision to improve visual performance. For example, a device and/or system for correcting vision of an eye may comprise: (1) an input module; (2) a computation module; and (3) a delivery module; wherein the input module is configured to receive input relevant to the vision correction of the eye; wherein the computation module is configured to compute one or more targeted modifications to the eye; wherein the modifications provides to the eye: at least one optical characteristic; wherein the at least one optical characteristic comprises at least one aberration profile; wherein the aberration profile comprises at least two spherical aberration terms and a defocus term; and a visual performance at intermediate and far visual distances, that is substantially equivalent to, or better than, the eye fitted with a correctly prescribed single-vision lens for far visual distance; and wherein the visual performance is characterised by minimal ghosting to the vision of the eye at least at far distance; and the delivery module utilising the computed targeted modifications to the eye computed by the computation module to deliver the desired modifications to the eye.

In certain applications, the minimal ghosting has a score of less than or equal to 2.4, 2.2, 2, 1.8, 1.6 or 1.4 on the vision rating ghosting scale of 1 to 10 units. In certain applications, the delivery module is an ophthalmic refractive surgical system such as a femto-second laser.

In certain embodiments, the lens is configured to provide vision substantially equivalent, or better, to distance vision corrected with a correctly prescribed lens for the refractive error for distance across a dioptric range of 0 D to 2.5 D or from infinity to 40 cm with minimal ghosting for emmetropes, myopes, hyperopes and astigmats.

In certain applications, the lenses substantially correct the distance refractive error; wherein the lens is configured to enable myopia to be slowed without the loss of vision as is usually associated with multifocal contact lenses and provides excellent vision across the visual field for example, 30 degrees nasal to 30 degrees temporal and also allows the provision of lenses that give retinal image quality of 0.4 or above for either a chosen focal distance or averaged across focal distances from infinity to 40 cm with an average of 0.3 retinal image quality. Such lenses when optimising retinal image quality provide exceptionally clear high contrast images at the chosen distances; wherein the lens provides exceptional image quality and visual performance with minimal ghosting across the range of dioptric distances from infinity to near for the correction of refractive errors and treatment of presbyopia and myopia control; when tested with a defined overall visual rating scale of 1 to 10 units, the multifocal lens is configured such that the overall visual performance of the multifocal lens is substantially equivalent to or better than an correctly prescribed single-vision lens for far visual distance.

In certain embodiments, the visual performance of a candidate eye, along a range of substantially continuous visual distances, including near, intermediate and far distances, wherein the visual performance of the multifocal lens is at least substantially equivalent to the visual performance of a correctly prescribed single-vision lens at the far visual distance.

In certain embodiments, the term minimal ghosting may mean a lack of an undesired secondary image appearing at the image plane of the optical system. In certain embodiments, the term minimal ghosting may be used to represent an undesired secondary image appearing on the retina of the eye. Conversely, the term lack of ghosting may represent an undesired double image appearing on the retina of the eye. In certain embodiments, minimal ghosting may represent a lack of an undesired double image perceived by the candidate eye. In other applications, minimal ghosting represents a lack of false out-of-focus image appearing along side of the primary image in an optical system.

Section 14.A

Asymmetric HOA and Image Quality

In certain embodiments, the choice of higher order aberrations being optimised for a desired through-focus image quality may include asymmetric higher order aberrations from one or more of the following: primary horizontal astigmatism, primary vertical astigmatism, secondary horizontal astigmatism, primary horizontal coma, primary vertical coma, secondary primary horizontal coma, secondary vertical coma, etc in addition to the rotationally symmetric higher order aberrations disclosed herein. In some other embodiments, the choice of asymmetric higher order aberrations may also include tertiary, quaternary, pentanary, hexanary, octanary, nanonary asymmetric higher order aberrations. For example, the Zernike coefficients represented by C(3,−1), C(3,1), C(5,−1), C(5,1), C(7,−1), C(7,1), C(9,−1), C(9,1), C(11,−1), C(11,1), (8,−2), (8,2), (10,−2), (10,2), (12,−2), (12,2), (14,−2), (14,2), etc.

|  |  | Design combination | | | |
| --- | --- | --- | --- | --- | --- |
|  |  | IC-1 | IC-2 | IC-3 | IC-4 |
| Image Quality metric |  | Simple Strehl (Frequency Domain) | Visual Strehl with PTF (Frequency Domain) | Simple Strehl (Frequency Domain) | Visual Strehl with PTF (Frequency Domain) |
| Spatial Frequency |  | 0 to 20 cyc/deg | 0 to 25 cyc/deg | 0 to 25 cyc/deg | 0 to 25 cyc/deg |
|  | Pupil | 4 | 3 | 3 | 4 |
| Zernike coefficients | C(2,−2) | 0.122 | 0.150 | 0.000 | 0.000 |
|  | C(2,0) | 0 | 0 | 0 | 0 |
|  | C(2,2) | −0.002 | 0.150 | 0.000 | −0.168 |
|  | C(3,−1) | 0 | 0 | 0 | 0 |
|  | C(3,−1) | 0 | 0 | 0 | 0 |
|  | C(4,−2) | 0.113 | −0.054 | 0.000 | 0.000 |
|  | C(4,0) | −0.200 | −0.150 | −0.076 | −0.200 |
|  | C(4,2) | 0.002 | 0.051 | 0.000 | −0.089 |
|  | C(5,−1) | 0 | 0 | 0 | 0 |
|  | C(5,1) | 0 | 0 | 0 | 0 |
|  | C(6,−2) | 0.050 | 0.010 | 0.000 | 0.000 |
|  | C(6,0) | −0.133 | −0.140 | −0.150 | −0.079 |
|  | C(6,2) | 0.000 | −0.006 | 0.000 | 0.049 |
|  | C(8,0) | −0.148 | −0.091 | 0.018 | 0.040 |
|  | C(10,0) | −0.053 | −0.055 | −0.099 | 0.075 |
|  | C(12,0) | 0.010 | −0.009 | −0.069 | 0.054 |
|  | C(14,0) | −0.051 | 0.014 | −0.052 | 0.000 |
|  | C(16,0) | −0.086 | 0.032 | −0.044 | −0.034 |
|  | C(18,0) | −0.050 | 0.027 | −0.004 | −0.037 |
|  | C(20,0) | −0.014 | 0.020 | −0.040 | −0.018 |

Figure 132:
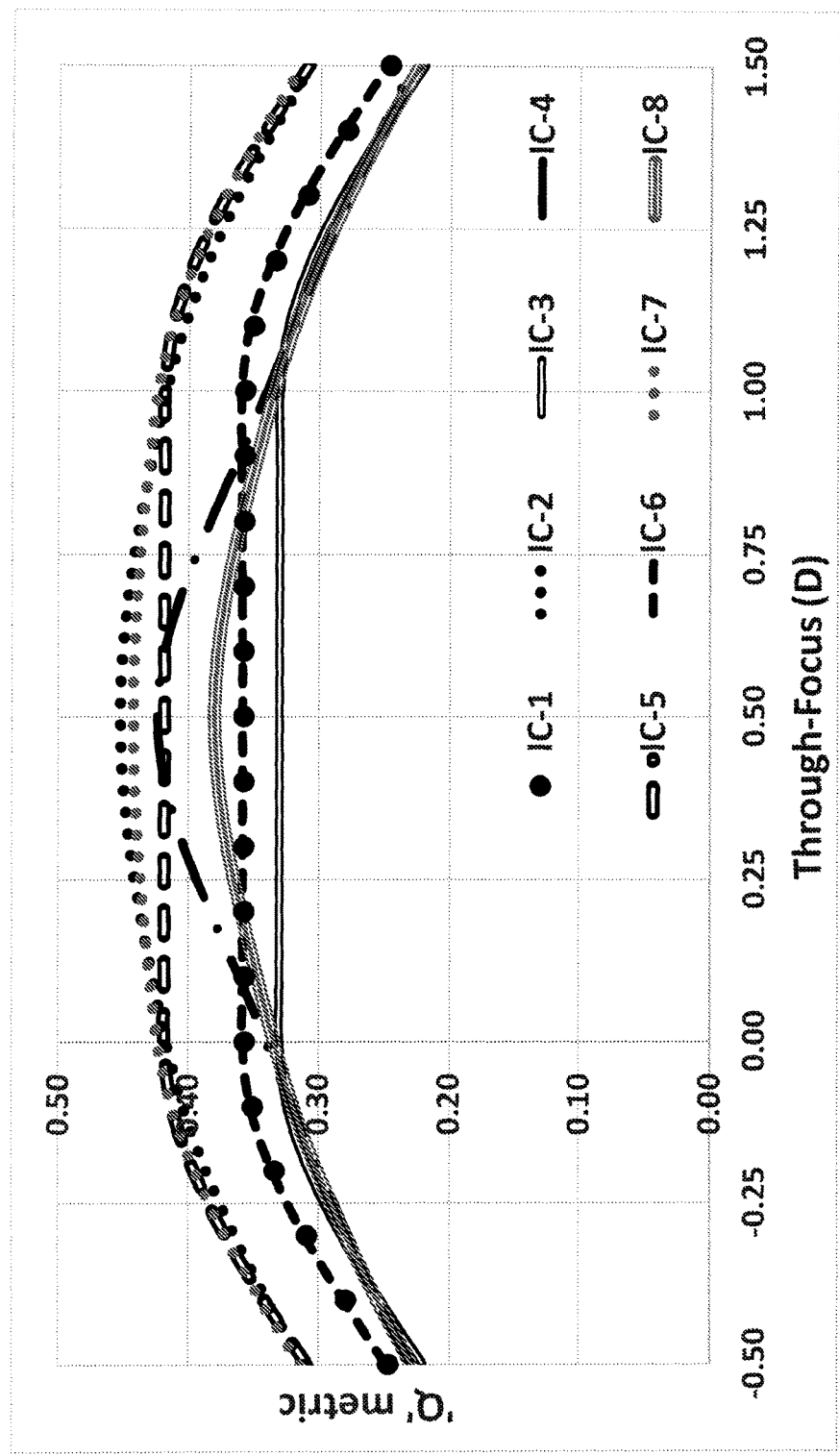
FIG. 132 plots the through-focus image quality ('Q' metric) for eight exemplary example combinations of with higher order aberrations, including both symmetric and asymmetric higher order aberrations.
Figure 133:
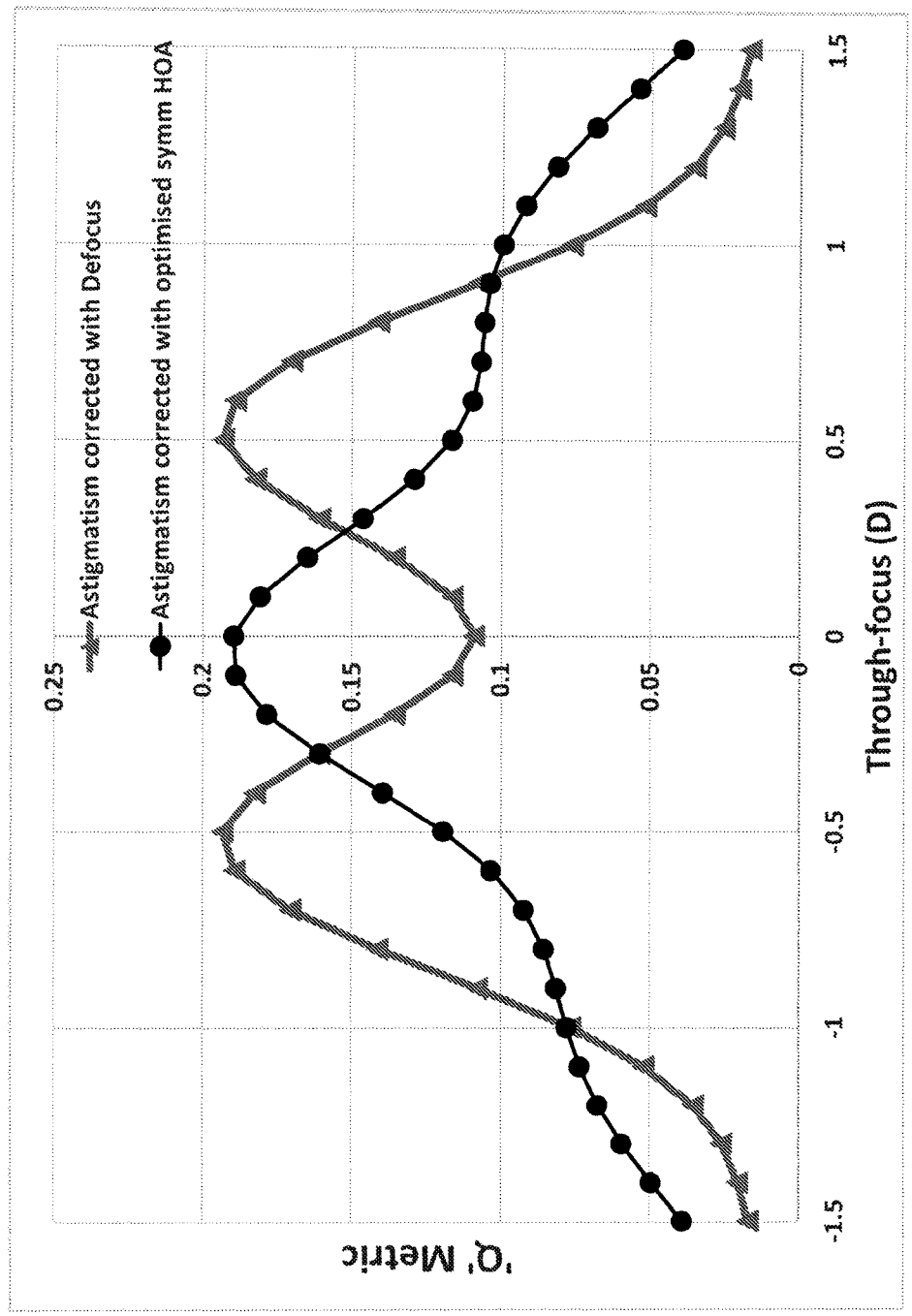
FIG. 133 plots the through-focus image quality ('Q' metric) for two exemplary example combinations. The solid line with triangle symbols represents the through-focus image quality obtained when −1.25 DC at 90 degrees of astigmatism is combined with various levels of defocus. The solid line with circle symbols represents the through-focus image quality when −1.25 DC at 90 degrees of astigmatism is combined with the higher order aberration combination described in table 12.1 at various levels of defocus.

Table 12.4 shows the optimised higher order aberration combinations including both symmetric and asymmetric higher order aberrations (IC-1 to IC-4 that provides a through focus image quality described in the FIG. 132.

For example, the optimised higher order aberration combinations IC-1 to IC-8 shown in the table 12.4 are configured to provide the through focus image quality shown in the FIG. 132. The computations discussed in this section are performed for pupil diameter of 3 mm and 4 mm and using the simple Strehl ratio and visual Strehl ratio in frequency domain as image quality metrics. In other embodiments, computations with other pupil diameters ranging from 3 to 8 mm and utilising other image quality metrics described in the section 1 may also be used.

|  |  | Design combination | | | |
| --- | --- | --- | --- | --- | --- |
|  |  | IC-5 | IC-6 | IC-7 | IC-8 |
| Image Quality metric |  | Visual Strehl with PTF (Frequency Domain) | Simple Strehl (Frequency Domain) | Simple Strehl (Frequency Domain) | Visual Strehl with PTF (Frequency Domain) |
| Spatial Frequency |  | 0 to 30 cyc/deg | 0 to 30 cyc/deg | 0 to 20 cyc/deg | 0 to 30 cyc/deg |
|  | Pupil | 3 | 3 | 3 | 4 |
| Zernike coefficients | C(2,−2) | 0.000 | 0.000 | 0.000 | −0.200 |
|  | C(2,0) | 0 | 0 | 0 | 0 |
|  | C(2,2) | 0.000 | 0.000 | 0.063 | −0.181 |
|  | C(3,−1) | 0 | 0 | 0 | 0 |
|  | C(3,−1) | 0 | 0 | 0 | 0 |
|  | C(4,−2) | 0.000 | 0.000 | 0.000 | 0.053 |
|  | C(4,0) | −0.103 | −0.012 | −0.051 | −0.200 |
|  | C(4,2) | 0.000 | 0.000 | −0.060 | −0.056 |
|  | C(5,−1) | 0 | 0 | 0 | 0 |
|  | C(5,1) | 0 | 0 | 0 | 0 |
|  | C(6,−2) | 0 | 0 | 0 | −0.038 |
|  | C(6,0) | 0 | 0.083 | −0.010 | −0.162 |
|  | C(6,2) | 0 | 0 | −0.026 | 0.037 |
|  | C(8,0) | −0.002 | −0.001 | −0.064 | −0.037 |
|  | C(10,0) | −0.014 | −0.023 | −0.020 | 0.027 |
|  | C(12,0) | 0.020 | 0.017 | 0.061 | 0.092 |
|  | C(14,0) | 0.042 | 0.001 | 0.062 | 0.087 |
|  | C(16,0) | 0.016 | −0.020 | 0.038 | 0.073 |
|  | C(18,0) | −0.018 | 0.007 | 0.043 | 0.035 |
|  | C(20,0) | −0.019 | 0.020 | 0.033 | 0.014 |

Table 12.5 shows the optimised higher order aberration combinations including both symmetric and asymmetric higher order aberrations (IC-5 to IC-8 that provide a through focus image quality described in the FIG. 132.

Section 14.B

Decentred and/or Non Co-Axial

The eye comprises various components and surfaces that combine to produce the optical characteristics of the eye. In lens design, it is sometimes useful to assume the eye, its components and associated surfaces are co-axial. There are, however, other cases when the components and associated surfaces of the eye may not be assumed to be co-axial. For example, the axis of the cornea may not be aligned with the centre of the pupil. Non-alignment of axes may be a translation and/or a tilt. Combinations of translation and tilt misalignment may also occur. When two or more landmarks (e.g. axes, centre, etc) are mutually or relatively misaligned (i.e. not co-axial or "spaced-apart"), the eye, or eye and lens combination, is not symmetrical. The direction of misalignment may be superiorly (or upwards), or inferiorly (or downwards), or nasally (in the direction across the eye towards the nose of the patient), or temporally (in the direction across the eye towards the nearer ear of the patient), or one or more combinations of those directions.

In certain embodiments, a lens may comprise an optic zone that may be circular, elliptical, non-circular, non-elliptical or combinations thereof. For example, a contact lens. The optic zone may also be rotationally asymmetrical and/or laterally (mirror-image) asymmetrical. With respect to optical performance and/or visual performance, an optic zone may have an optical axis, the optical axis being associated with the optical performance and/or visual performance provided by the aberration profile of the types described herein.

In some embodiments, the centre, geometrical centre or centroid (defined, for example, as a standard mathematical, geometry definition for the centroid of a shape) of the optic zone may be spaced-apart (i.e. not co-located) from its optical axis. Such embodiments may be beneficial for the delivery of desired optical performance and/or visual performance to eyes that exhibit, at least in part, non-co-axial alignment of its components and/or associated surfaces. For example, the pupil area may be, at least in part, non-circular and at least in part, decentered/misaligned relative to the cornea of an eye. A contact lens for such an exemplary embodiment may be beneficial to the optical performance and/or visual performance, if the optic zone is decentered while the optic axis of the contact lens remains substantially aligned with the optical axis of the eye. The amount that the centroid of the optic zone and the optical axis of the contact lens may be space-apart may be selected according to an individual eye, a population average, a representative value for a sub-population or combinations thereof, and may be at least 0.1 mm, 0.2 mm, 0.3 mm, 0.4 mm, 0.5 mm, 0.7 mm or 1 mm. In some embodiments, the amount of spacing-apart may be between 0.1 mm to 0.5 mm, 0.5 mm to 1 mm, 1 mm to 1.5 mm, 1.5 mm to 2 mm or 2 mm to 3 mm.

With respect to decentered and non-coaxial lenses, a lens may comprise an optic zone and a carrier. The optic zone is a region, or regions, of a lens that provides the desired optical performance including, for example, aberration profiles of the types described herein. The carrier of a lens is a region, or regions, of a lens that is not intended to provide the optical performance but may be configured to control the interaction of the lens with the eye. For example, a contact lens.

In some embodiments, a carrier may have surface blending, thickness and thickness profiles, edge profiles, etc, to deliver a level of comfort to the contact lens wearer. In other embodiments, a carrier may be configured to control the lateral position or/and rotational orientation of the lens. Such carrier configurations may locate a lens in a particular orientation, or a particular range of orientation, and may be beneficial in lenses which possess an amount of asymmetry by ensuring substantial alignment of the lens when applied to the eye. Configurations may include prism ballast, lens edge truncation, dynamic thin-zones, slab-off, double slab-off, horizontal iso-thickness, corridor of thin-zones, etc. In such embodiments, a lens may comprise an optic zone and a carrier in which the centroid of the optic zone is spaced-apart from the optical axis while the carrier may be configured to control the orientation of the lens. The amount that the centroid of the optic zone and the optical axis of the lens may be space-apart may be selected according to an individual eye, or a population average, or a representative value for a sub-population, and may be at least 0.1 mm, 0.2 mm, 0.3 mm, 0.4 mm, 0.5 mm, 0.7 mm or 1 mm. In some embodiments, the amount of spacing-apart may be between 0.1 mm to 0.5 mm, 0.5 mm to 1 mm, 1 mm to 1.5 mm, 1.5 mm to 2 mm or 2 mm to 3 mm.

In certain embodiments, a lens may comprise an optic zone and a carrier, wherein the internal (nearer an optic zone), external (nearer the outside edge of a lens), or both boundaries of the carrier may be circular, elliptical, non-circular, non-elliptical or combinations thereof. In some embodiments, the carrier and/or the optic zone may have multiple boundaries. The carrier may be rotationally asymmetrical and/or laterally (e.g. mirror-image) asymmetrical. In such embodiments, the centre, geometrical centre or centroid (defined, for example, as a standard mathematical, geometry definition for the centroid of a shape) of the carrier may be spaced-apart (i.e. not co-located) from the optical axis associated with the optic zone of the contact lens, while the carrier may be configured to control the orientation of the contact lens. Such embodiments may be beneficial because they provide desired optical performance and/or visual performance to eyes that exhibit, at least in part, non-co-axial alignment of its components and/or associated surfaces. For example, for a contact lens applied to an eye by placement over the comes, the cornea may be, at least in part, asymmetrical and at least in part, misaligned/non-co-axial with the optical axis of the eye. A contact lens for such exemplary cases may be configured such that the centroid of the carrier is decentered with respect to the optical axis associated with the optic zone of the contact lens. The amount that the optical axis and the centroid of the carrier of the contact lens may be spaced-apart may be selected according to an individual eye, a population average or a representative value for a sub-population, and may be at least 0.1 mm, 0.2 mm, 0.3 mm, 0.4 mm, 0.5 mm, 0.7 mm or 1 mm. In some embodiments, the amount of spacing-apart may be between 0.1 mm to 0.5 mm, 0.5 mm to 1 mm, 1 mm to 1.5 mm, 1.5 mm to 2 mm, 2 mm to 3 mm or 3 mm to 4 mm.

In certain embodiments, a lens may be a contact lens that may comprise an optic zone and a carrier. The optic zone being a region, or regions that provides an optical performance including, for example, aberration profiles of the types described in this application. The carrier may be rotationally asymmetrical and/or laterally (e.g. mirror-image) asymmetrical. In some embodiments, a carrier may have surface blending, thickness and thickness profiles, edge profiles, etc, to deliver a level of comfort to the contact lens wearer. In other embodiments, a carrier may be configured to control the lateral position or/and rotational orientation of a contact lens. Such carrier configurations may locate a contact lens in a particular orientation, or a particular range of orientations. Configurations may include prism ballast, lens edge truncation, dynamic thin-zones, slab-off, double slab-off, horizontal iso-thickness, corridor of thin-zones, etc. For such embodiments, a lens may be a contact lens that may comprise an optic zone and a carrier in which the centre, or geometrical centre, or centroid of the optic zone may be spaced-apart (i.e. not co-located) from the centre, geometrical centre or centroid of the carrier, while the carrier may be configured to control the orientation of the contact lens. Such an arrangement may be beneficial for the delivery of desired optical performance and/or visual performance to eyes that exhibit non-co-axial alignment of its components and/or associated surfaces. The amount that the centroid of the optic zone and the centroid of the carrier of the contact lens may be spaced-apart may be selected according to an individual eye, a population average or a representative value for a sub-population, and may be at least 0.1 mm, 0.2 mm, 0.3 mm, 0.4 mm, 0.5 mm, 0.7 mm or 1 mm. In some embodiments, the amount of spacing-apart may be between 0.1 mm to 0.5 mm, 0.5 mm to 1 mm, 1 mm to 1.5 mm, 1.5 mm to 2 mm or 2 mm to 3 mm.

In certain embodiments, a lens may comprise an optic zone and a carrier in which the centroid of the optic zone, the optical axis and the centre, the geometrical centre or the centroid of the carrier are mutually spaced-apart (i.e. not co-located) from each other, while the carrier may be configured to control the orientation of the contact lens. Such an arrangement may be beneficial for the delivery of desired optical performance and/or visual performance to eyes that exhibit non-co-axial alignment of its components and/or associated surfaces. The amount that the optical axis associated with the optic zone, the centroid of the optic zone, and the centroid of the carrier of the contact lens may be mutually spaced-apart may be selected according to an individual eye, a population average or a representative value for a sub-population, and may be at least 0.1 mm, 0.2 mm, 0.3 mm, 0.4 mm, 0.5 mm, 0.7 mm or 1 mm, and may be pair-wise different (i.e. the amount that the optical axis is spaced-apart from the centroid of the optic zone may differ from the amount that the optical axis is spaced-apart from the centroid of the carrier, and either of the amounts may differ from the amount that the centroid of the optic zone is spaced-apart from the centroid of the carrier. In some embodiments, the amount of spacing-apart may be between 0.1 mm to 0.5 mm, 0.5 mm to 1 mm, 1 mm to 1.5 mm, 1.5 mm to 2 mm or 2 mm to 3 mm.

Section 14.C

Effect of Prism

In some embodiments, the optical device may possess a limited amount of optical tilt or prismatic term in addition to the designed aberration profile. Typically it may be desirable to limit the amount of optical tilt or prism terms such that it does not substantially interfere with vision. In some embodiments, tilt may be introduced intentionally, for example, to help with the rotational stabilisation of toric contact lenses. In certain embodiments, tilt may be introduced unintentionally, for example, due to manufacturing limitations. Typically, the optical performance may be unaffected by tilt. For certain eye conditions, however, optical prism may have a beneficial and/or therapeutic effect by tilting the optical axis differently in one eye compared against its fellow eye. In this case, a rotational stabilisation feature may be included into the design.

Section 14.D

Tear Film/Surface Treatment

Subjective vision ratings may be affected by the on-eye comfort of a contact lens and vice versa. Therefore, visual satisfaction may be enhanced by adding one or more features to a contact lens that provides an increase in perceived comfort. In order for contact lenses to provide an acceptable fit and comfort on an eye, it may be desirable for the lens to be covered by a thin layer of tears on the anterior and posterior surface of the lens. Some embodiments may have one or more surfaces that are treated in a way to manipulate the tear layer such that it contributes to the aberration profile. Certain materials and/or manufacturing processes may be used to manipulate a tear layer. Such materials or manufacturing process may be used with some of the disclosed embodiments. One or more surface treatments may be used to manipulate the tear layer of some embodiments. For example, surface treatment may include one or more of the following: plasma treatment, layer by layer surface coating, adding wetting agents to the packaging solution or contact lenses, applying eye drops or combinations thereof. A contact lens with no pre-lens tear film may also provide consistent optical performance, according to some embodiments.

Section 15

Exemplary Sets of Lens Designs which are Substantially Independent of Inherent Spherical Aberration of the Eye The interactions between the inherent aberration profiles of the candidate eyes and those of a selected combination of a design set may have a) an improved effect; b) degraded effect; or c) no substantial effect on the objective and/or subjective optical and/or visual performance.

The present disclosure provides embodiments directed to choosing between a positive and/or negative phase of a particular combination of aberration profile to be able to attain a specific goal for the candidate eye. The specific goal for instance may be to change the slope of through-focus RIQ in the direction that would favour the emmetropisation process for myopic or hyperopic eyes; or alternatively similar approach, or methods, may be used to mitigate the presbyopic symptoms in alternative candidate eyes.

Certain embodiments are directed to a lens, device and/or method that enables the designing of lenses which when applied to a candidate eye may produce a visual performance that is substantially independent of the aberration profile of that candidate eye. Substantially independent, in certain applications, means that lenses may be designed that provide acceptable and/or similar performance on a plurality of candidate eyes that are within the representative sample of the target populations. In certain applications, methods to obtain a target TFRIQ include use of a non-linear, unconstrained optimization routine and one or more other variables. The variables selected for the non-linear, unconstrained, optimisation routine may include a chosen group of Zernike spherical aberration coefficients, from C(2, 0) to C(20, 0) and one or more other variables. The other variables, for example, may be aberration profiles of a representative sample of the target population.

Figure 71:
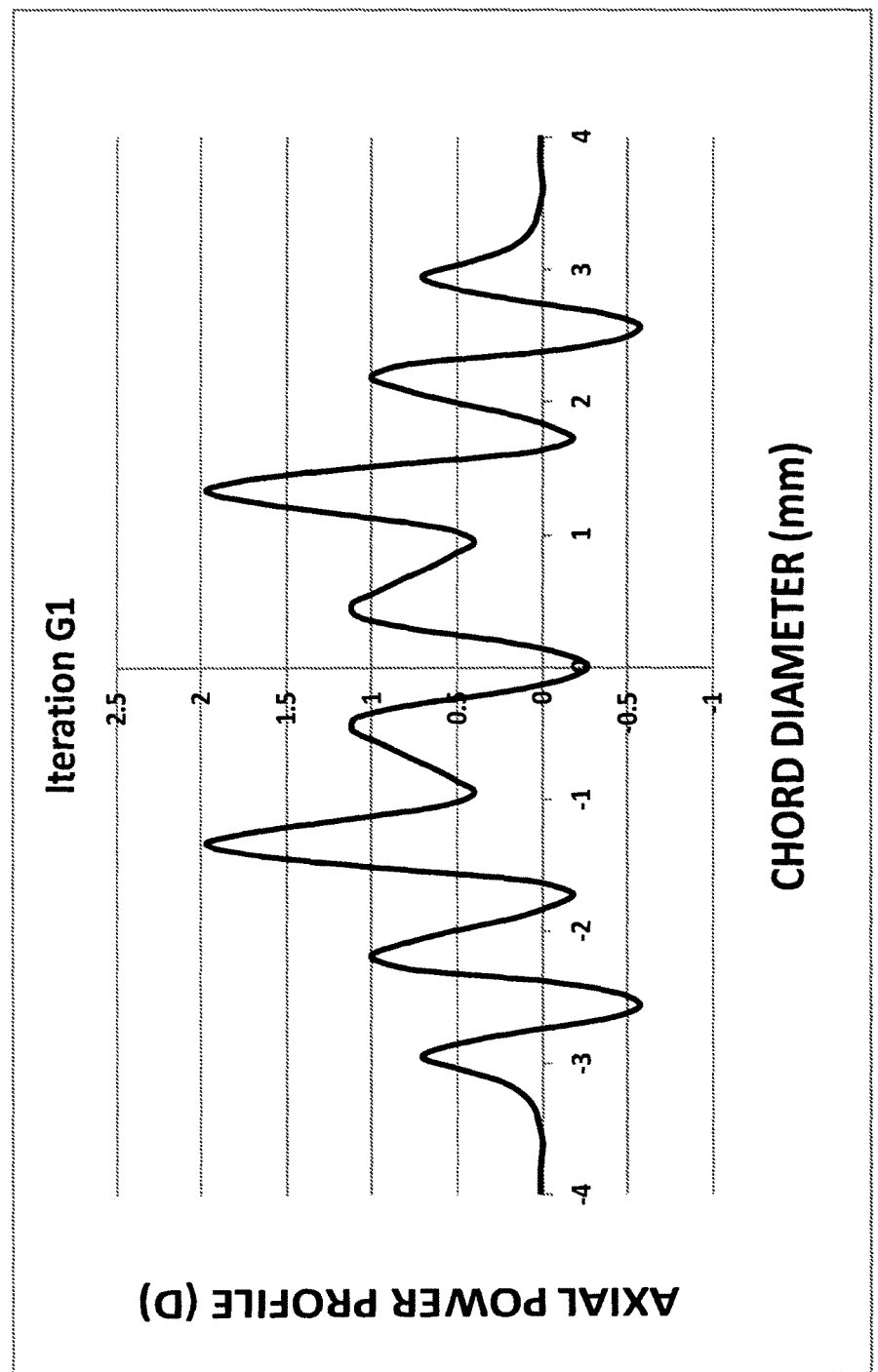
FIG. 71 shows an example of axial power profile of lens across a complete chord diameter (Iteration G1), which is one exemplary of design set whose performance is substantially independent of inherent spherical aberration of the candidate eye, according to certain embodiments.

Lenses may be designed by selecting an optimisation routine to evaluate a through-focus RIQ may include: a) a target TFRIQ; b) a target TFRIQ within predefined bounds; or c) combination of a) and b). Iteration G1 (FIG. 71) is one exemplary of a lens design whose visual performance is independent of the inherent aberration profile of the candidate eye.

Table 13 provides the defocus term and the rest of combinations of spherical aberration terms, denoted in Zernike coefficients C(2,0) to C(20,0), that represents the exemplary design at 4, 5 and 6 mm optic zone or pupil diameter.

TABLE 13

Defocus and higher order spherical aberration coefficients, at 4, 5 and 6 mm optic zone diameter, of an exemplary embodiment whose performance is substantially independent of the inherent spherical aberration of the candidate eye for at least at 4 and 5 mm pupil diameters of the candidate eye.

| Iteration G1 | At 4 mm | At 5 mm | At 6 mm |
| --- | --- | --- | --- |
| C(2,0) | 0.442 | 0.558 | 0.47 |
| C(4,0) | −0.103 | −0.096 | −0.241 |
| C(6,0) | −0.081 | 0.038 | 0.038 |
| C(8,0) | 0.032 | 0.017 | 0.046 |
| C(10,0) | 0.056 | −0.086 | 0.043 |
| C(12,0) | −0.017 | −0.027 | 0.057 |

TABLE 13-continued

Defocus and higher order spherical aberration coefficients, at 4, 5 and 6 mm optic zone diameter, of an exemplary embodiment whose performance is substantially independent of the inherent spherical aberration of the candidate eye for at least at 4 and 5 mm pupil diameters of the candidate eye.

| Iteration G1 | At 4 mm | At 5 mm | At 6 mm |
| --- | --- | --- | --- |
| C(14,0) | −0.023 | 0.053 | −0.056 |
| C(16,0) | 0.01 | −0.005 | −0.053 |
| C(18,0) | 0.004 | −0.017 | 0.051 |
| C(20,0) | −0.002 | 0.017 | 0.006 |

Figure 72:
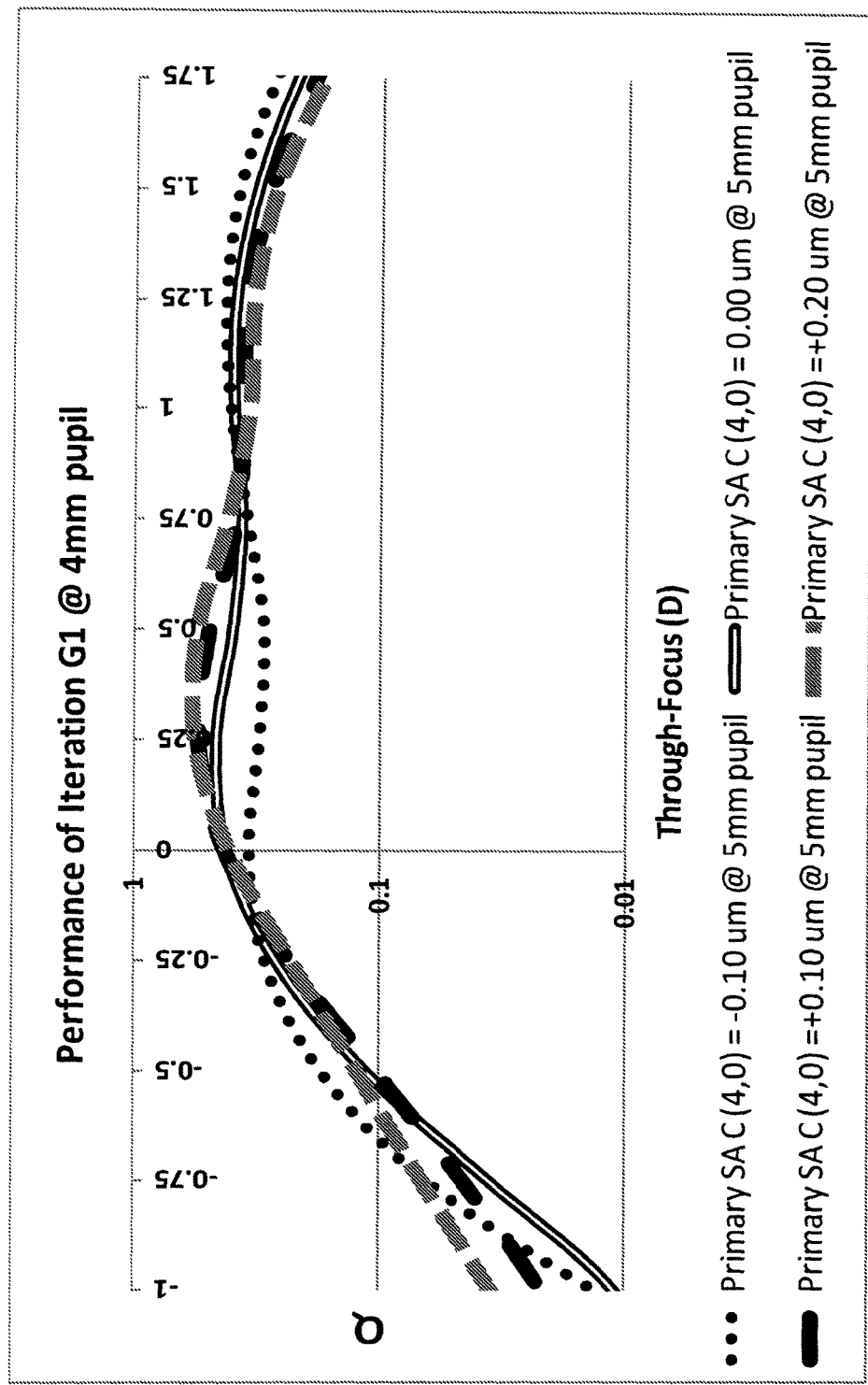
FIG. 72 shows the TFRIQ of an exemplary, described as Iteration G1, at 4 mm pupil diameter. Y-axis denotes RIQ performance metric and X-axis denotes through-focus range from −1 D to +1.75 D. The four different legends, solid black line, solid grey line, dashed black like and, solid double line represent four different levels of spherical aberration in a sample of the affected population at 5 mm pupil diameter, according to certain embodiments.
Figure 73:
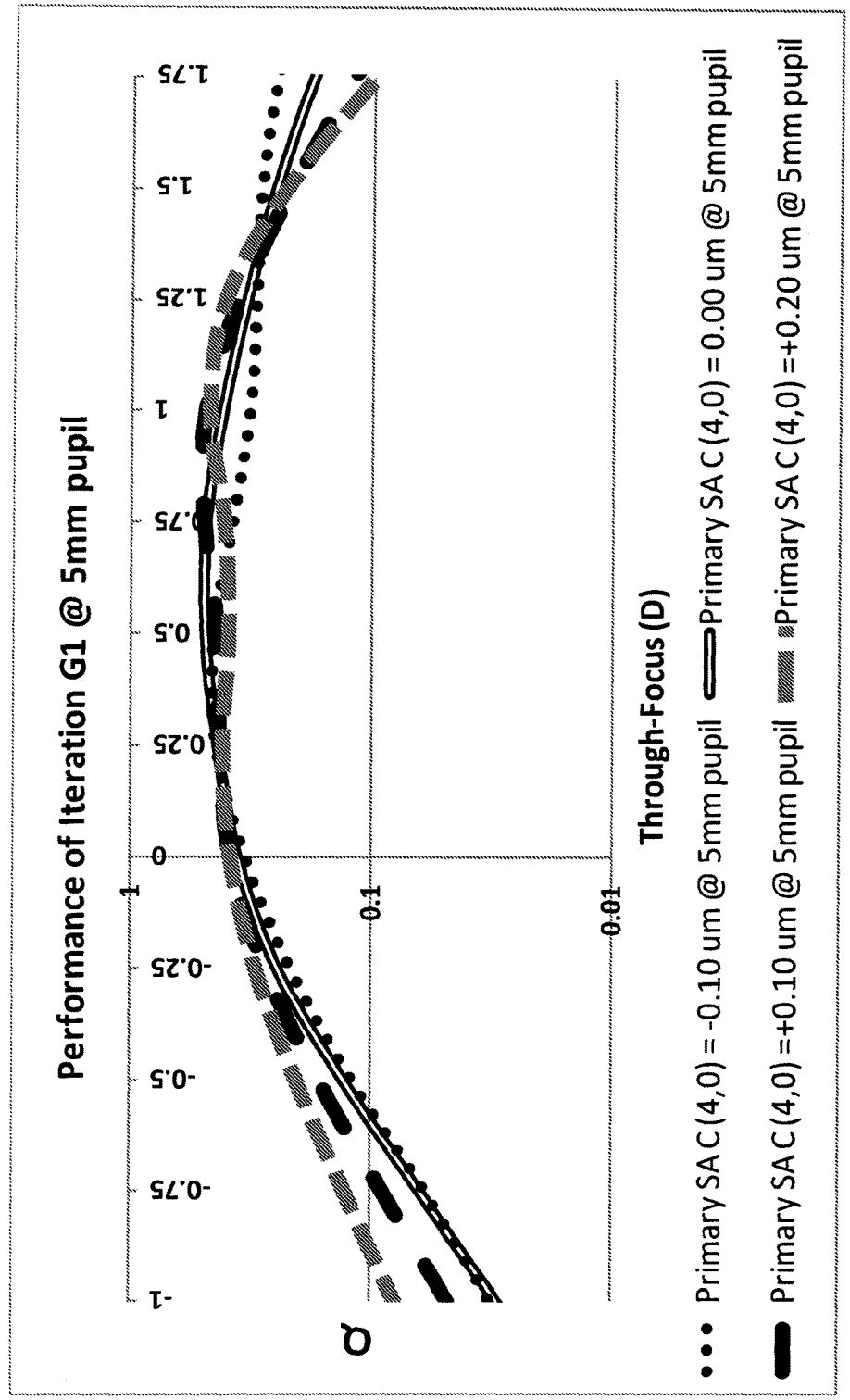
FIG. 73 shows the TFRIQ of an exemplary, described as Iteration G1, at a 5 mm pupil diameter. Y-axis denotes RIQ performance metric and X-axis denotes through-focus range from −1 D to +1.75 D. The four different legends, solid black line, solid grey line, dashed black like and, solid double line represent four different levels of spherical aberration in a sample of the affected population, at 5 mm pupil diameter, according to certain embodiments.

FIG. 72 shows a graph of the through focus performance of Iteration G1 for a 4 mm pupil size, for a range of inherent spherical aberration ranging from −0.1 μm to +0.2 μm (and no other inherent aberrations). FIG. 73 shows the corresponding performance for a 5 mm pupil size. For both the through focus performance is relatively constant despite variations in inherent spherical aberration. Accordingly, lenses of Iteration G1 lenses with aberration profiles of similar characteristics may be prescribed to a relatively large number of recipients in a population. The through focus performance of Iteration G1 for both 5 mm and 4 mm pupil sizes are shown in Tables 14, 15, 16 and 17 for inherent primary spherical aberration of −0.10 μm, 0.00 μm, +0.10 μm and +0.20 μm, respectively, all measured assuming a 5 mm pupil.

TABLE 14

The through focus performance of Iteration G1, for both 5 mm and 4 mm pupil sizes, on candidate eye with an inherent primary spherical aberration C(4,0) of −0.10 μm of the candidate eye measured at 5 mm pupil.

| Defocus | 4 mm | 5 mm |
| --- | --- | --- |
| −2.5 | 0.001 | 0.003 |
| −2.25 | 0.001 | 0.004 |
| −2 | 0.001 | 0.005 |
| −1.75 | 0.002 | 0.007 |
| −1.5 | 0.002 | 0.011 |
| −1.25 | 0.002 | 0.018 |
| −1 | 0.014 | 0.032 |
| −0.75 | 0.065 | 0.060 |
| −0.5 | 0.174 | 0.121 |
| −0.25 | 0.293 | 0.217 |
| 0 | 0.339 | 0.336 |
| 0.25 | 0.309 | 0.443 |
| 0.5 | 0.297 | 0.452 |
| 0.75 | 0.348 | 0.378 |
| 1 | 0.409 | 0.322 |
| 1.25 | 0.428 | 0.305 |
| 1.5 | 0.378 | 0.291 |
| 1.75 | 0.270 | 0.249 |
| 2 | 0.164 | 0.182 |
| 2.25 | 0.096 | 0.115 |
| 2.5 | 0.057 | 0.067 |

TABLE 15

The through focus performance of Iteration G1, for both 5 mm and 4 mm pupil sizes, on candidate eye with an inherent primary spherical aberration C (4,0) of 0.00 μm of the candidate eye measured at 5 mm pupil.

| Defocus | 4 mm | 5 mm |
| --- | --- | --- |
| −2.5 | 0.002 | 0.004 |
| −2.25 | 0.003 | 0.005 |
| −2 | 0.003 | 0.005 |

TABLE 15-continued

The through focus performance of Iteration G1, for both 5 mm and 4 mm pupil sizes, on candidate eye with an inherent primary spherical aberration C (4,0) of 0.00 μm of the candidate eye measured at 5 mm pupil.

| Defocus | 4 mm | 5 mm |
|---|---|---|
| −1.75 | 0.004 | 0.006 |
| −1.5 | 0.005 | 0.008 |
| −1.25 | 0.007 | 0.015 |
| −1 | 0.011 | 0.030 |
| −0.75 | 0.036 | 0.063 |
| −0.5 | 0.115 | 0.131 |
| −0.25 | 0.267 | 0.246 |
| 0 | 0.424 | 0.361 |
| 0.25 | 0.464 | 0.436 |
| 0.5 | 0.398 | 0.492 |
| 0.75 | 0.368 | 0.488 |
| 1 | 0.398 | 0.417 |
| 1.25 | 0.391 | 0.333 |
| 1.5 | 0.320 | 0.252 |
| 1.75 | 0.221 | 0.177 |
| 2 | 0.132 | 0.110 |
| 2.25 | 0.074 | 0.062 |
| 2.5 | 0.040 | 0.035 |

TABLE 16

The through focus performance of Iteration G1, for both 5 mm and 4 mm pupil sizes, on candidate eye with an inherent primary spherical aberration C (4,0) of 0.10 μm of the candidate eye measured at 5 mm pupil.

| Defocus | 4 mm | 5 mm |
|---|---|---|
| −2.5 | 0.003 | 0.006 |
| −2.25 | 0.004 | 0.007 |
| −2 | 0.006 | 0.008 |
| −1.75 | 0.007 | 0.010 |
| −1.5 | 0.008 | 0.015 |
| −1.25 | 0.013 | 0.026 |
| −1 | 0.022 | 0.048 |
| −0.75 | 0.046 | 0.090 |
| −0.5 | 0.105 | 0.166 |
| −0.25 | 0.237 | 0.276 |
| 0 | 0.431 | 0.387 |
| 0.25 | 0.552 | 0.428 |
| 0.5 | 0.496 | 0.439 |
| 0.75 | 0.387 | 0.500 |
| 1 | 0.363 | 0.494 |
| 1.25 | 0.355 | 0.361 |
| 1.5 | 0.282 | 0.218 |
| 1.75 | 0.188 | 0.120 |
| 2 | 0.112 | 0.060 |
| 2.25 | 0.059 | 0.029 |
| 2.5 | 0.028 | 0.015 |

TABLE 17

The through focus performance of Iteration G1, for both 5 mm and 4 mm pupil sizes, on candidate eye with an inherent primary spherical aberration C (4,0) of 0.20 μm of the candidate eye measured at 5 mm pupil.

| Defocus | 4 mm | 5 mm |
|---|---|---|
| −2.5 | 0.005 | 0.008 |
| −2.25 | 0.006 | 0.010 |
| −2 | 0.008 | 0.013 |
| −1.75 | 0.009 | 0.018 |
| −1.5 | 0.012 | 0.029 |
| −1.25 | 0.019 | 0.049 |
| −1 | 0.035 | 0.080 |
| −0.75 | 0.067 | 0.129 |
| −0.5 | 0.123 | 0.205 |
| −0.25 | 0.230 | 0.301 |
| 0 | 0.409 | 0.385 |
| 0.25 | 0.561 | 0.415 |
| 0.5 | 0.546 | 0.393 |
| 0.75 | 0.412 | 0.410 |
| 1 | 0.339 | 0.473 |
| 1.25 | 0.326 | 0.407 |
| 1.5 | 0.264 | 0.227 |
| 1.75 | 0.170 | 0.098 |
| 2 | 0.099 | 0.040 |
| 2.25 | 0.050 | 0.014 |
| 2.5 | 0.021 | 0.004 |

Section 16

Exemplary Sets of Designs as Intra-Ocular Lenses

Figure 74:
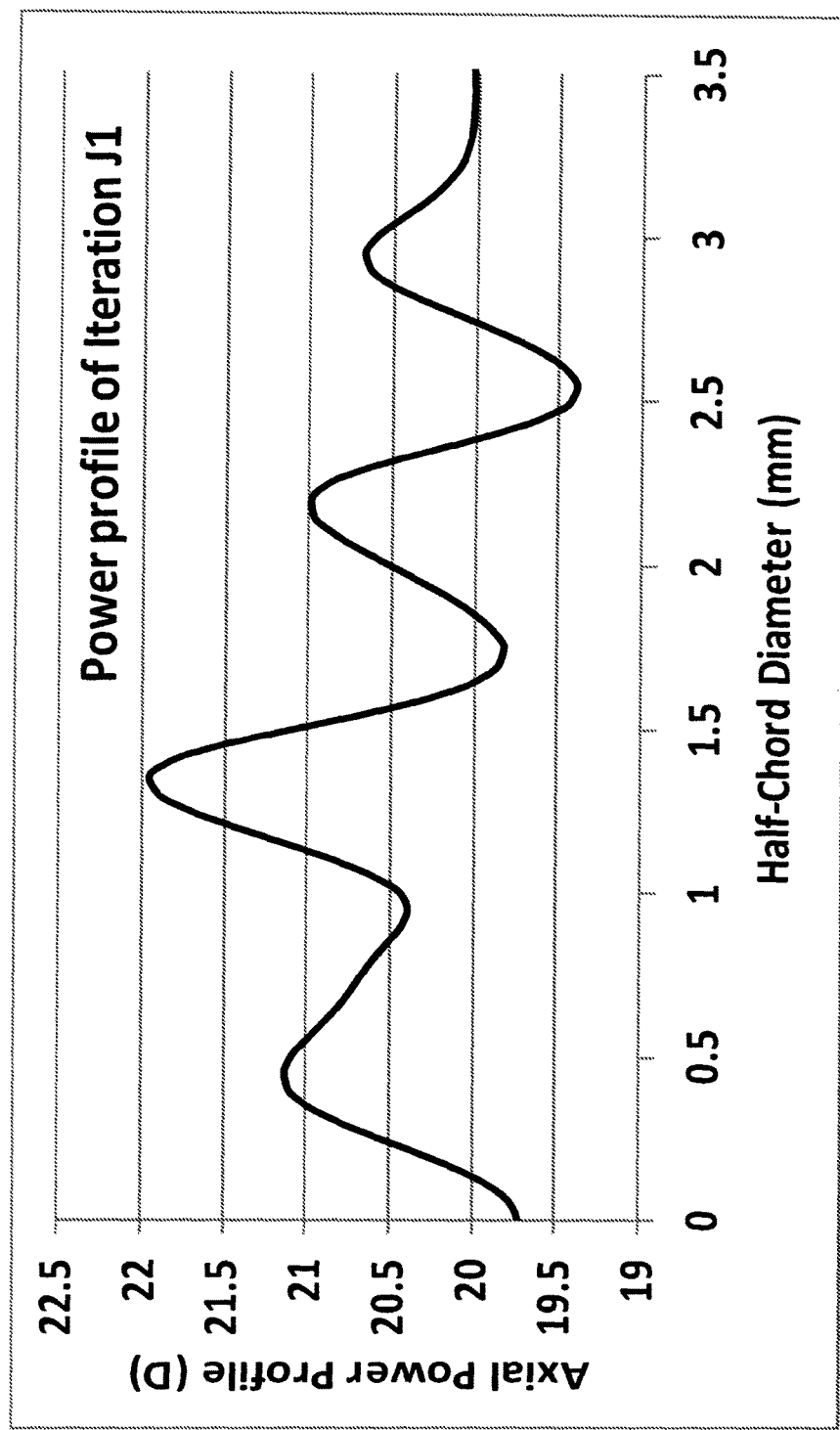
FIG. 74 shows an example of axial power profile of a lens across a half-chord diameter (Iteration J1), which is one exemplary of design set for an intra-ocular lens used to restore vision at distances, encompassing far to near, after removal of the crystalline lens in the eye, according to certain embodiments.
Figure 75:
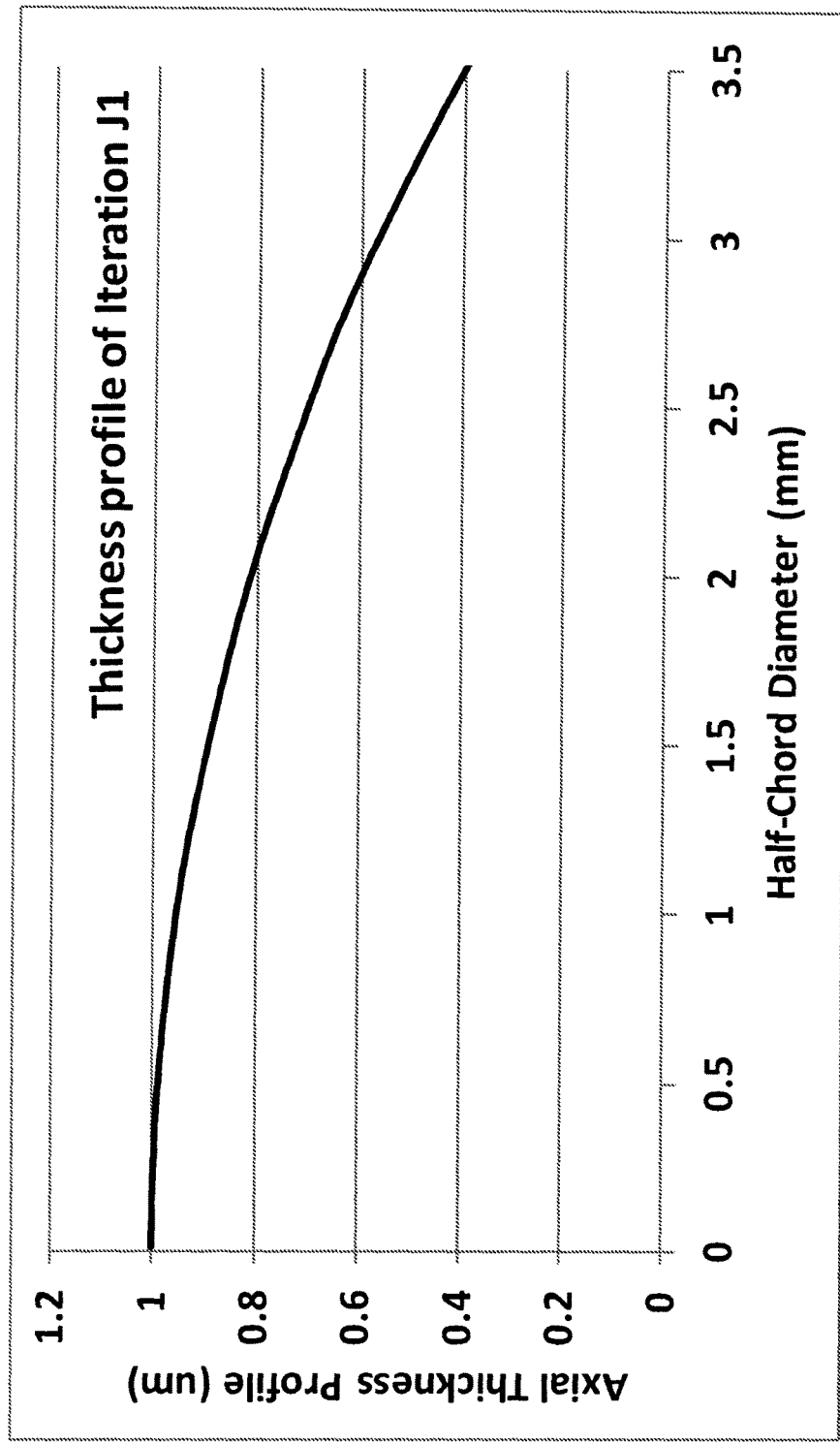
FIG. 75 shows an example of axial thickness profile of a lens (Iteration J1) across a half-chord diameter, which is one exemplary of design set for an intra-ocular lens used to restore vision at distances, encompassing from far to near, after removal of the crystalline lens in the eye, according to certain embodiments.

Aberration profiles may be used in intra-ocular lens applications, according to certain embodiments. For example, the aberration profile, and/or power profile, may be translated into an intra-ocular lens surface profile, using one or more of the following parameters: thickness profile, power profile, aberration profile, front surface, back surface, diameter, and/or refractive index of the material. The surface profile is thereafter provided to a computer assisted or other manufacturing process to produce the intra-ocular lens. The intra-ocular lens produced is configured based at least in part on the surface profile and/or surface profiles generated. In some embodiments, a supplementary intraocular lens may be implanted within an accommodating gel during a post-lens extraction procedure (e.g. lens refilling surgical procedure. The lens power profile (Iteration J1) shown in FIG. 74 is a combination of Zernike higher order spherical aberration terms. The power profile may be converted to an axial thickness profile (FIG. 75) for an intra-ocular lens, taking into account the refractive index of the intra-ocular lens material, according to certain embodiments. Here, the refractive index of intra-ocular lens material is 1.475. Table 18 provides the defocus term and other combinations of spherical aberration terms, denoted in Zernike coefficients C(2,0) to C(20,0), that represent an exemplary design of an intra-ocular lens (FIG. 74) at 4 and 5 mm optic zone diameter.

TABLE 18

Defocus and higher order spherical aberration coefficients, at 4, and 5 mm optic zone diameter or pupil size, for one of the exemplary embodiment of an intra-ocular lens design that provides an improvement in the through-focus optical and/or visual performance of the candidate eye. Iteration J1

| Optic zone or Pupil size | C(2,0) | C(4,0) | C(6,0) | C(8,0) | C(10,0) | C(12,0) | C(14,0) | C(16,0) | C(18,0) | C(20,0) |
|---|---|---|---|---|---|---|---|---|---|---|
| At 4 mm | 12.060 | −0.120 | −0.085 | 0.033 | 0.058 | −0.018 | −0.023 | 0.012 | 0.005 | −0.003 |
| At 5 mm | 18.666 | −0.129 | 0.040 | 0.018 | −0.089 | −0.026 | 0.056 | −0.006 | −0.019 | 0.017 |

Section 16.A

Multi-Element IOLs

The aberration profiles disclosed herein may be used in multi-element intra-ocular lens devices, for example, phakic and pseudophakic intra-ocular lens. The aberration profiles disclosed herein may be used in multi-element intra-ocular lens devices to restore accommodation. For example, the aberration profile may be implemented on one or more elements of the multi-element intra-ocular lens device, by manipulation of one or more of the following parameters of one or more of the elements: thickness profile, power profile, aberration profile, front surface, back surface, spacing between elements and refractive index. The parameters are thereafter provided to a computer assisted or other manufacturing process to produce the multi-element intra-ocular lens device. These processes may include lathing, moulding, etching, ablating and/or other methods. In certain embodiments, the profiles may be created after the lens has been implanted. The intra-ocular lens produced is configured based at least in part on the aberration profile and/or parameters generated.

Due to the multi-dimensional variable space in multi-element intra-ocular lenses, for example, four surfaces in two element designs, the greater number of degrees of freedom provide greater design flexibility and greater number of design solutions. In addition, due to the dynamic configuration of intra-ocular lenses, the distance between the elements changes from distance to near focus, performance may be altered and/or tailored by selection of appropriate aberration profiles on different surfaces of the multi-element intra-ocular lens. One of the benefits of the aberration profiles disclosed herein is that they may be used with multi-element intra-ocular lenses to provide different performances for distance, intermediate and near vision. For example, one may configure the elements for optimum visual performance at distance and extended depth of focus at near range. The visual performance may be visual acuity, contrast sensitivity, minimal ghosting, or combinations thereof.

Section 17

Descriptors for Power Profiles with Use of a Fourier Transform

Figure 76:
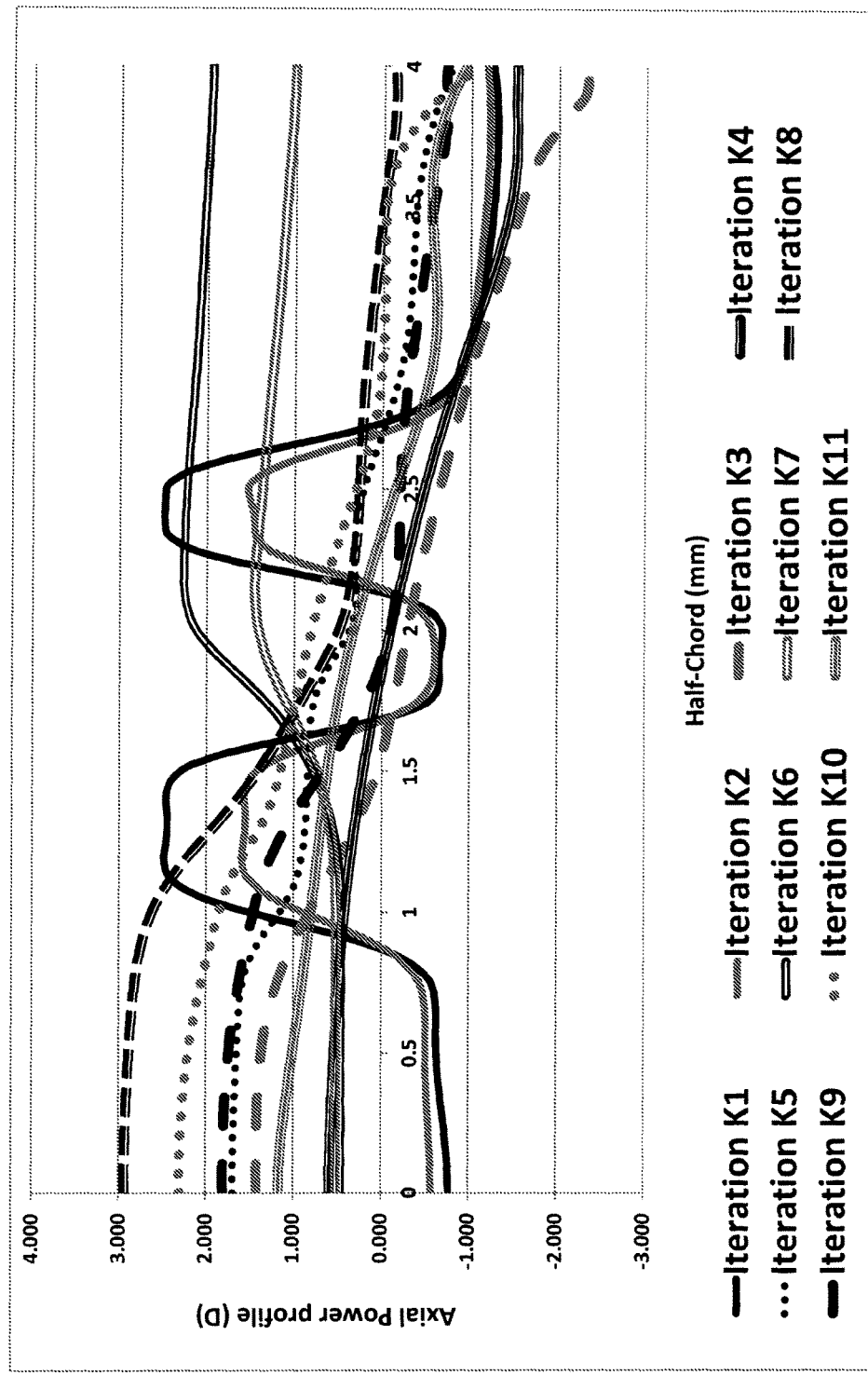
FIG. 76 show power profiles of eleven different contact lenses across a half-chord diameter, these eleven different designs (Iterations K1 to K11). These are some designs of commercial available lenses.
Figure 77:
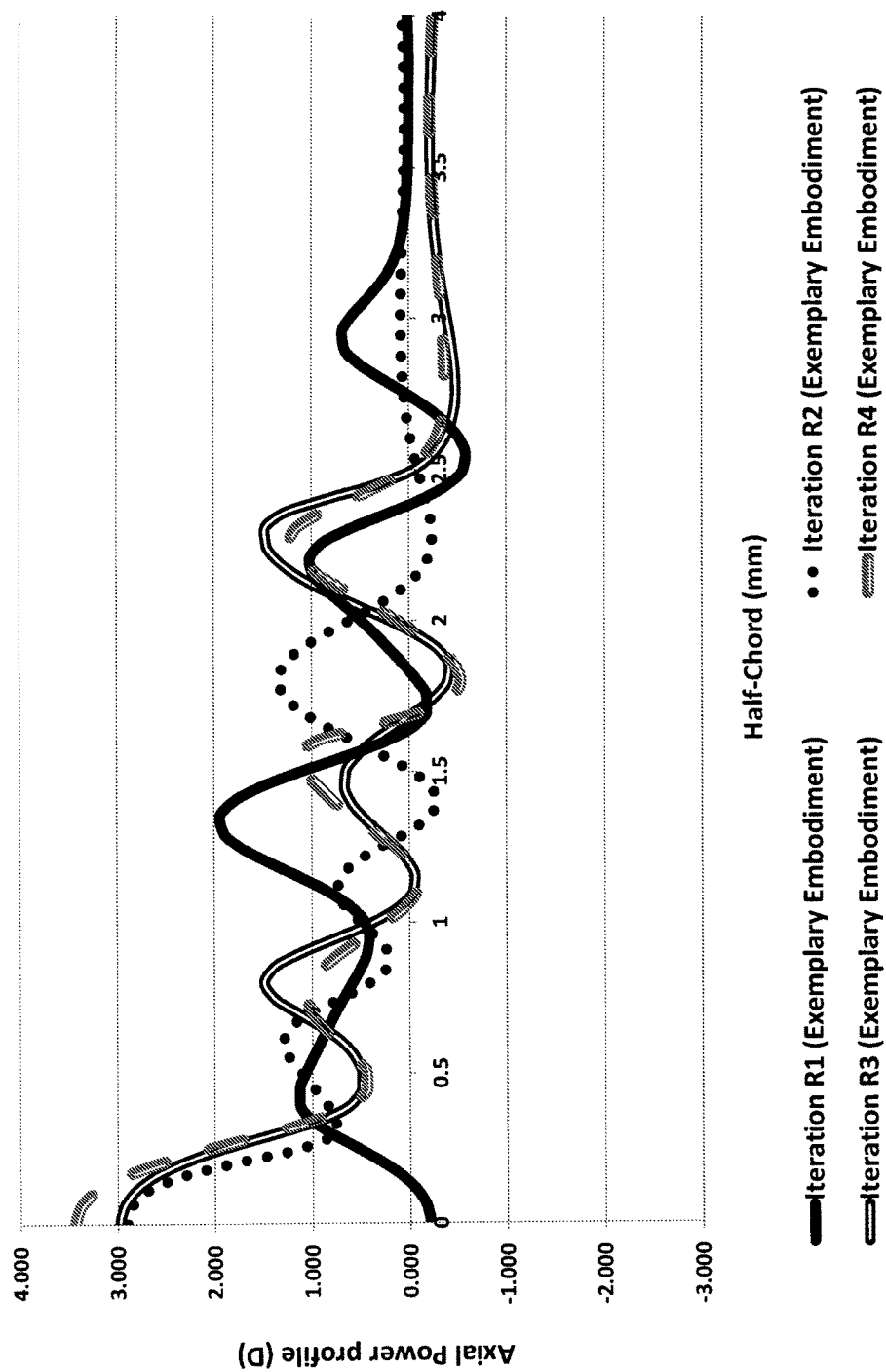
FIG. 77 show power profiles of four different lenses across a half-chord diameter, these four different designs (Iterations R1 to R4) are exemplary of certain embodiments.
Figure 78:
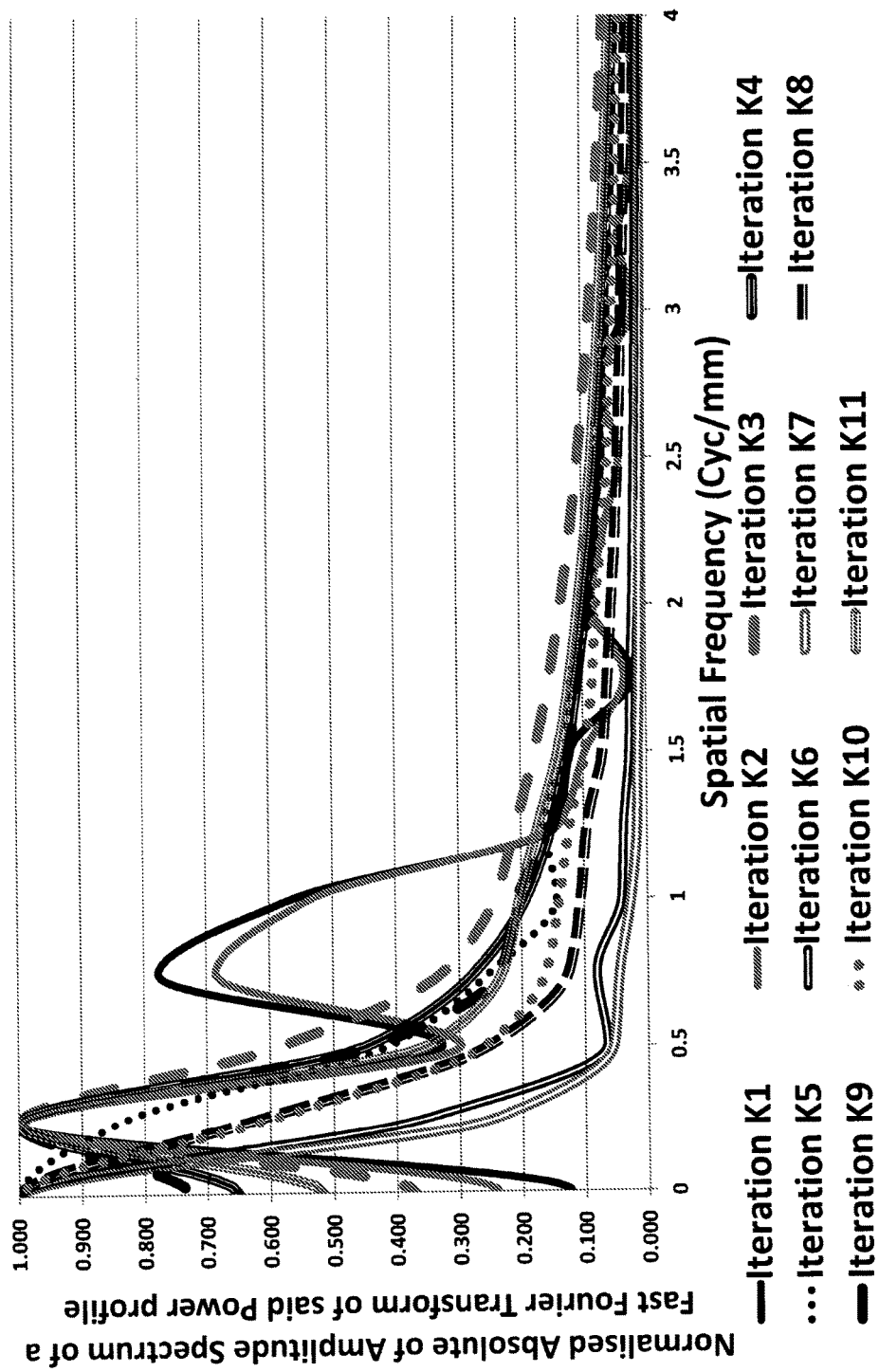
FIG. 78 show the normalised absolute of amplitude spectrum of a Fast Fourier Transform of eleven different contact lenses (Iterations K1 to K11) as a function of spatial frequency in Cycles/mm. These are the eleven lenses presented in FIG. 76.
Figure 79:
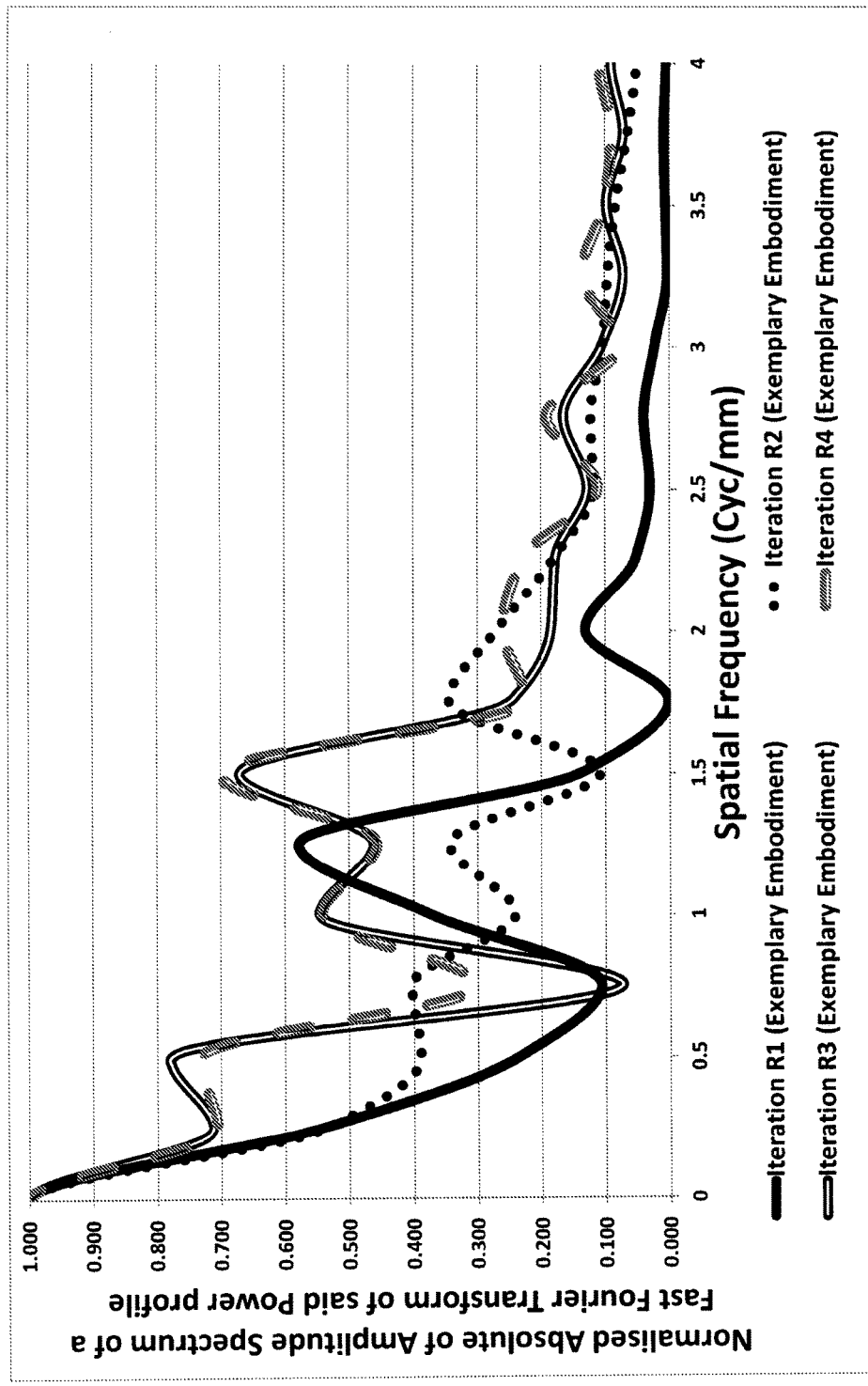
FIG. 79 show the normalised absolute of amplitude spectrum of a Fast Fourier Transform of four different lens designs (Iterations R1 to R4) as a function of spatial frequency in Cycles/mm. These four designs are exemplary of certain embodiments.

Fourier transform methods may be used to characterise the power profiles of certain embodiments and in particular for certain bifocal or multifocal designs. For example, FIG. 76 plots the power profiles for a number of commercially available bifocal and multifocal lenses. FIG. 77 plots the power profiles for a number of bifocal or multifocal lenses according to embodiments. FIG. 78 plots the Fourier transform of the power profiles for the commercially available bifocal and multifocal lenses of FIG. 76. FIG. 79 plots Fourier transforms of power profiles of FIG. 77. For both FIGS. 78 and 79, the horizontal axis represents spatial frequency in cycles per millimeter (cycles/mm) and the vertical axis plots the normalised absolute of the amplitude spectrum from the fast Fourier transform of the power profiles. In these figures, normalised means rescaling of each amplitude spectrum so that the maximum value for the absolute of an amplitude spectrum is rescaled to 1. For example, the normalised absolute of the amplitude spectrum may be obtained by dividing the absolute of amplitude spectrum by the maximum value of the absolute of amplitude spectrum.

A comparison of FIGS. 78 and 79 illustrate differentiation between certain embodiments and the plotted commercially available lenses, as their normalised absolute amplitude of the Fourier transform of their power profiles has normalised absolute amplitude greater than 0.2 at one or more spatial frequencies at or above 1.25 cycles per millimeter. In contrast to the illustrated embodiments FIGS. 77 and 79, none of the currently available commercial lenses have normalised absolute amplitude greater than 0.2 at one or more spatial frequencies at or above 1.25 cycles per millimeter. Certain embodiments such as lenses, bifocal lenses, and/or multifocal lenses may be characterised using Fourier transform. For example, certain embodiments are directed to a lens comprising: an optical axis; at least two surfaces; wherein the lens is characterised by a power profile that has a normalised absolute amplitude of the Fourier transform of the power profile that is greater than 0.2 at one or more spatial frequencies at or above 1.25 cycles per millimeter. In certain applications, the lens is configured with a power profile that has a normalised absolute amplitude of the Fourier transform of the power profile that is greater than 0.2 at one or more spatial frequencies at or above 1.25 cycles per millimeter.

Section 18

Figure 80:
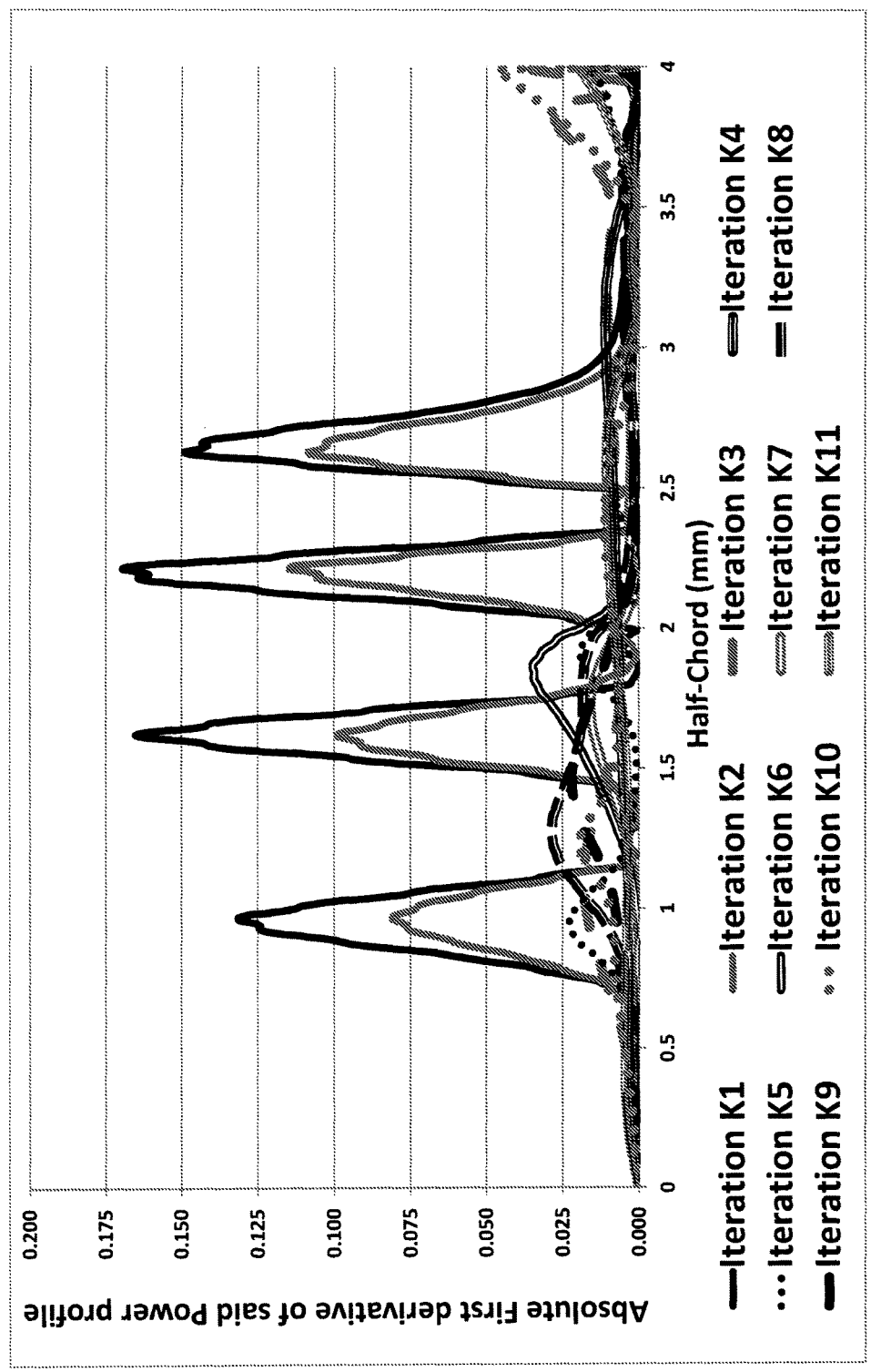
FIG. 80 show the absolute first derivative of eleven different contact lenses (Iteration K1 to K11) as a function of half-chord diameter (mm). These are the eleven lenses presented in FIG. 76.
Figure 81:
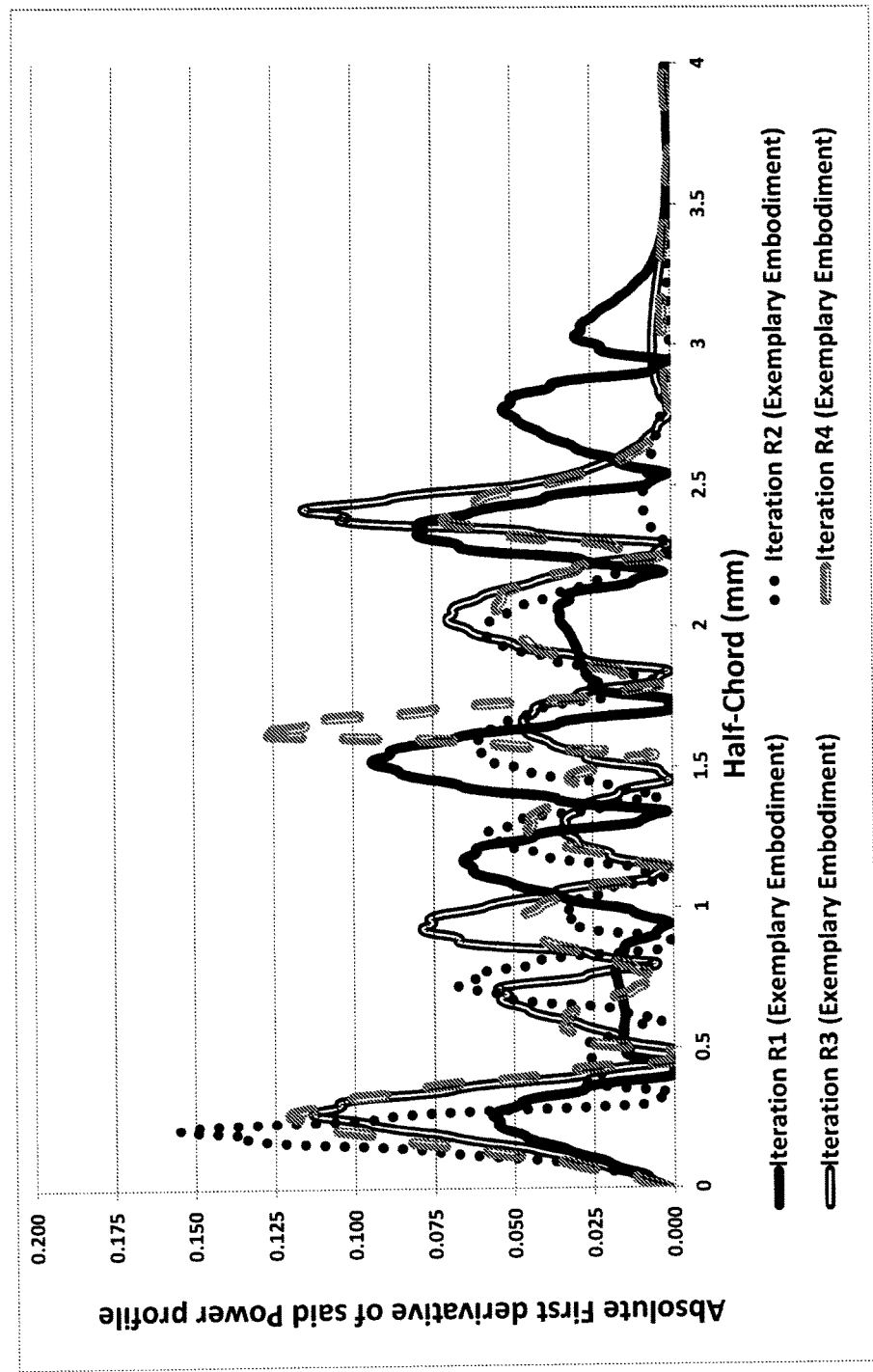
FIG. 81 show the absolute first derivative of four different contact lenses (Iteration R1 to R4) as a function of half-chord diameter (mm). These four designs are exemplary of certain embodiments.
Figure 82:
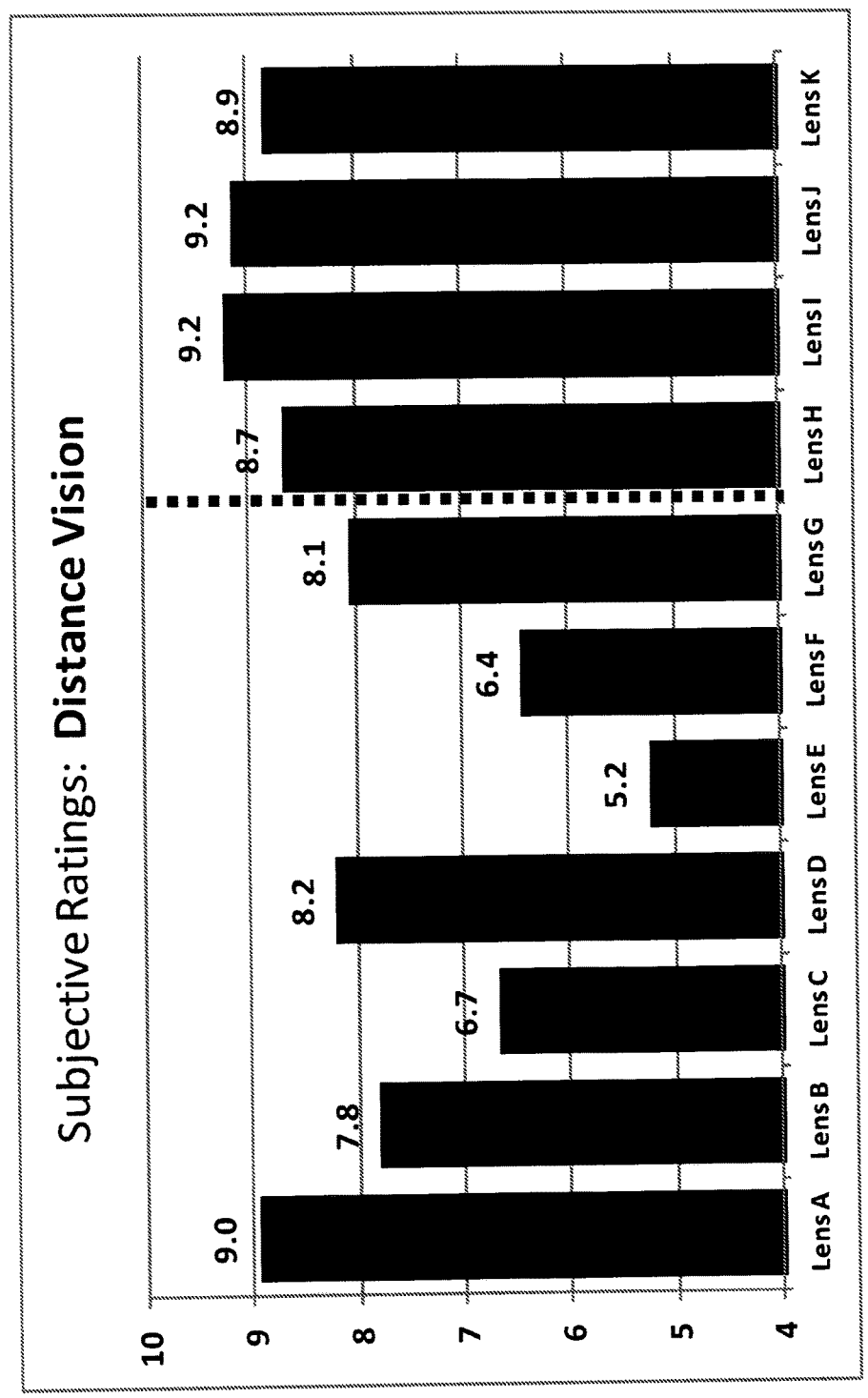
FIG. 82 show the average subjective ratings measured on a visual analogue scale for distance vision for a sample of an affected presbyopic population. Four of the lenses H to K are exemplary of certain embodiments, while lenses A to G are commercial lenses.
Figure 83:
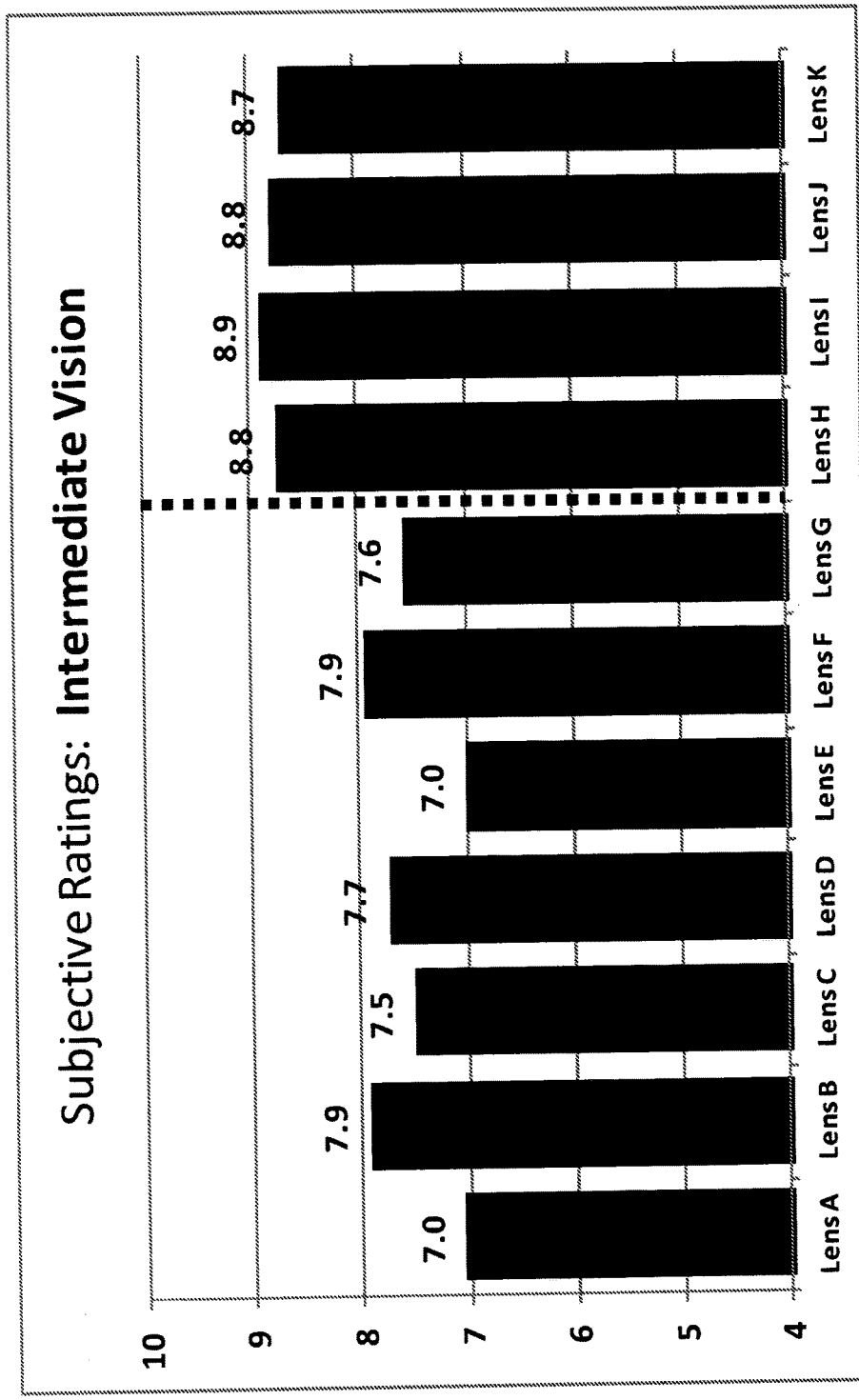
FIG. 83 show the average subjective ratings measured on a visual analogue scale for intermediate vision for a sample of an affected presbyopic population. Four of the lenses H to K are exemplary of certain embodiments, while lenses A to G are commercial lenses.
Figure 84:
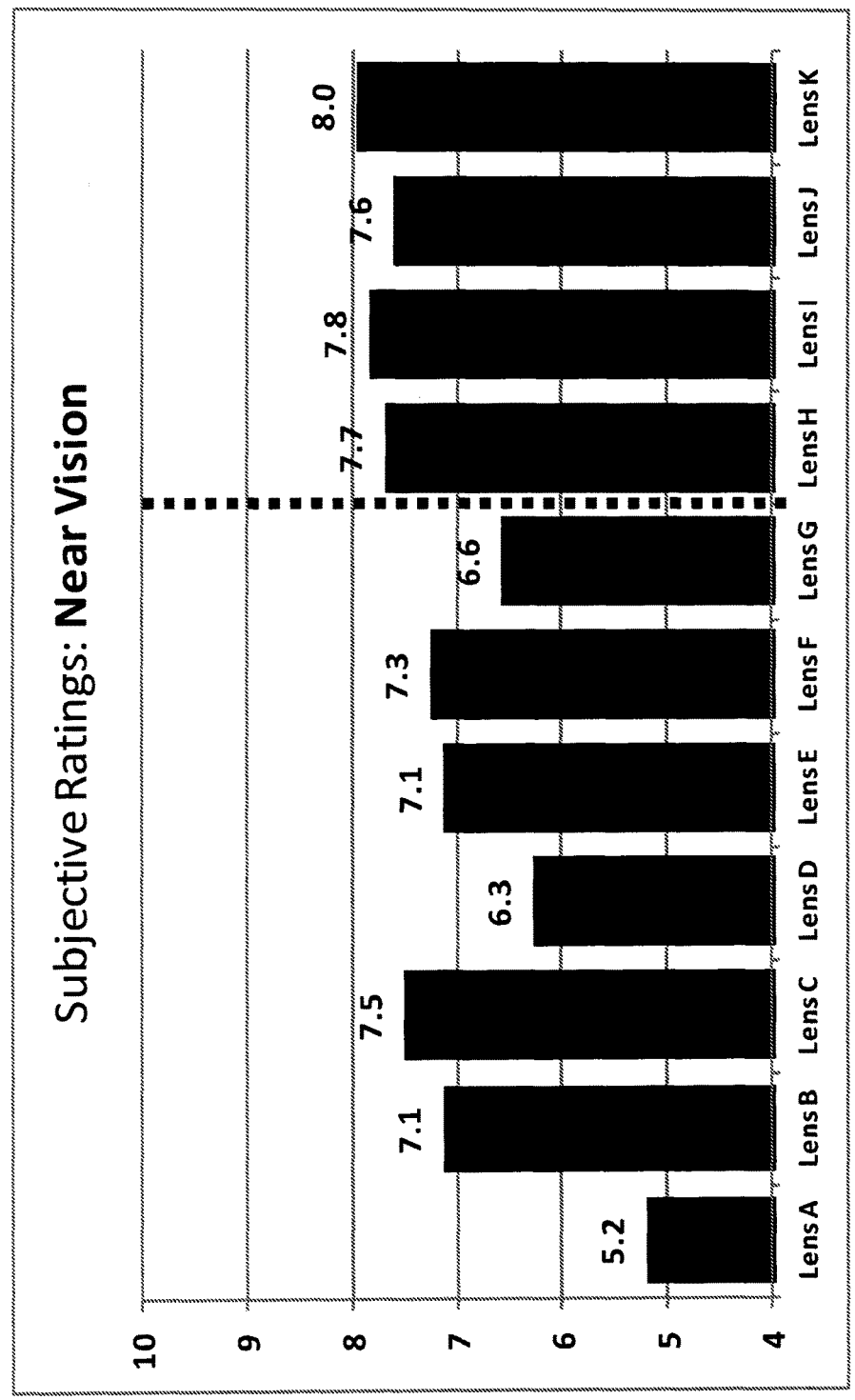
FIG. 84 show the average subjective ratings measured on a visual analogue scale for near vision for a sample of an affected presbyopic population. Four of the lenses H to K are exemplary of certain embodiments, while lenses A to G are commercial lenses FIG. 85 show the average subjective ratings measured on a ghosting analogue scale for distance vision for a sample of an affected presbyopic population. Four of the lenses H to K are exemplary of certain embodiments, while lenses A to G are commercial lenses.
Figure 85:
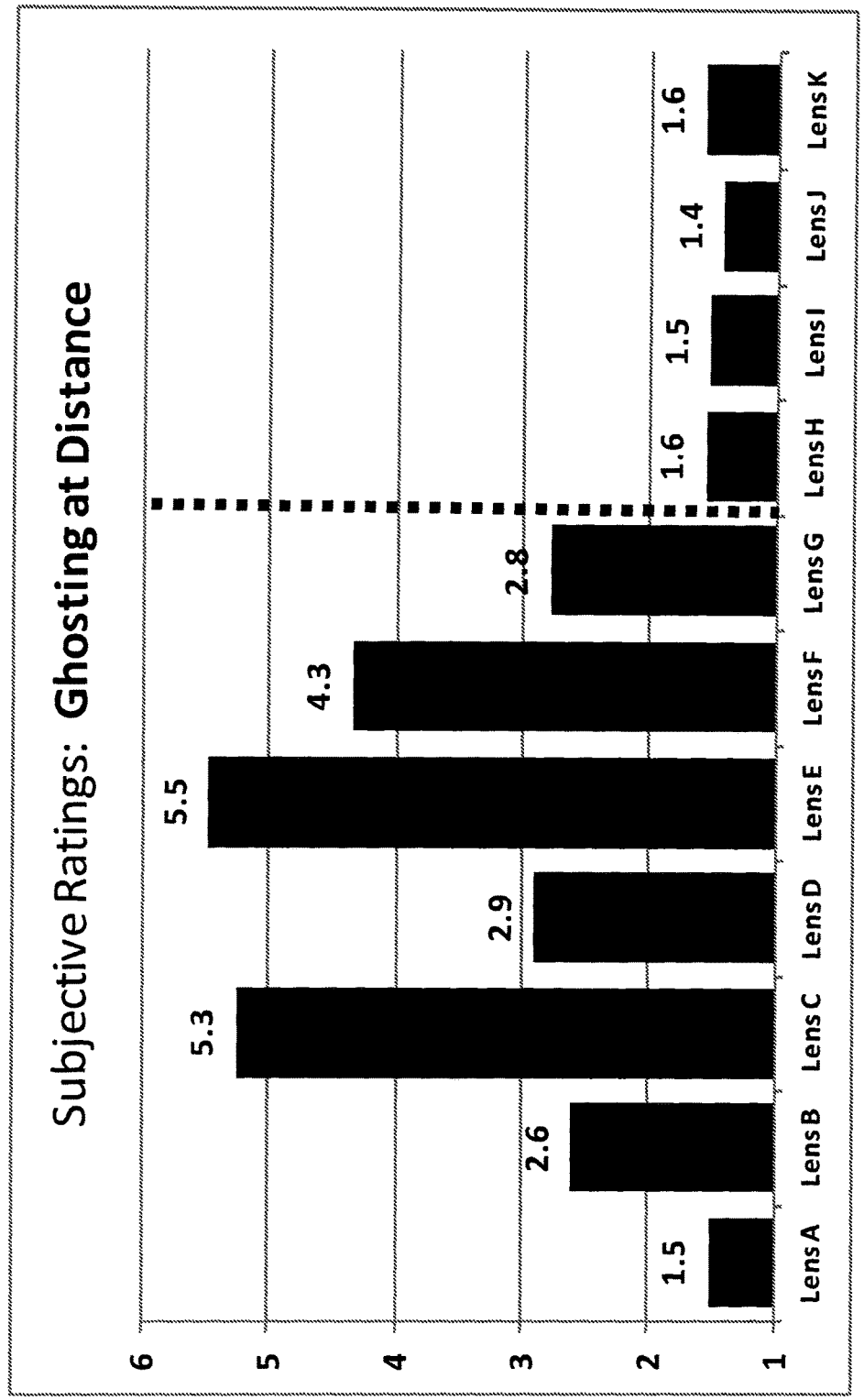
Figure 86:
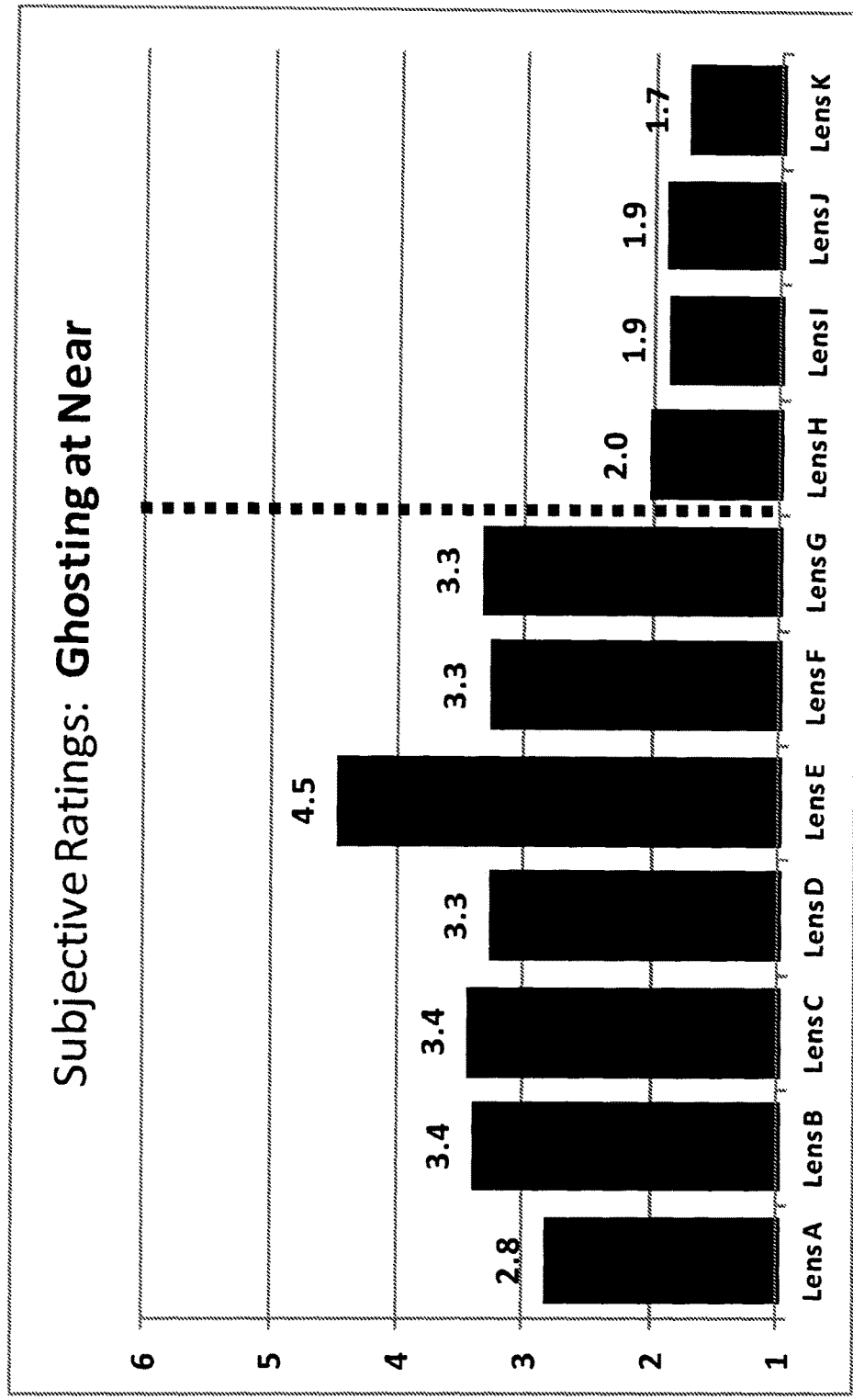
FIG. 86 show the average subjective ratings measured on a ghosting analogue scale for near vision for a sample of an affected presbyopic population. Four of the lenses H to K are exemplary of certain embodiments, while lenses A to G are commercial lenses.
Figure 87:
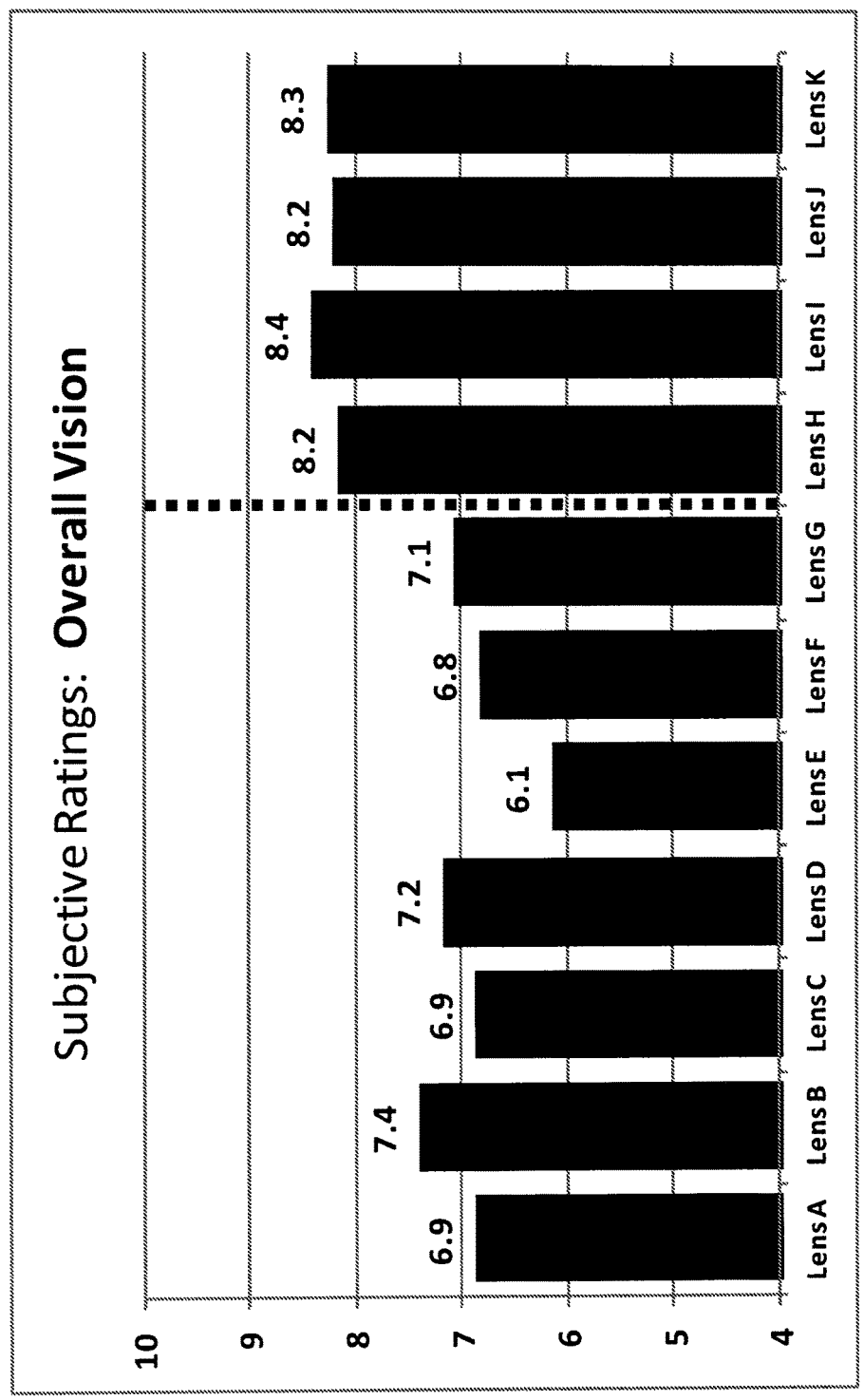
FIG. 87 show the average subjective ratings measured on a visual analogue scale for overall vision for a sample of an affected presbyopic population. Four of the lenses H to K are exemplary of certain embodiments, while lenses A to G are commercial lenses.
Figure 88:
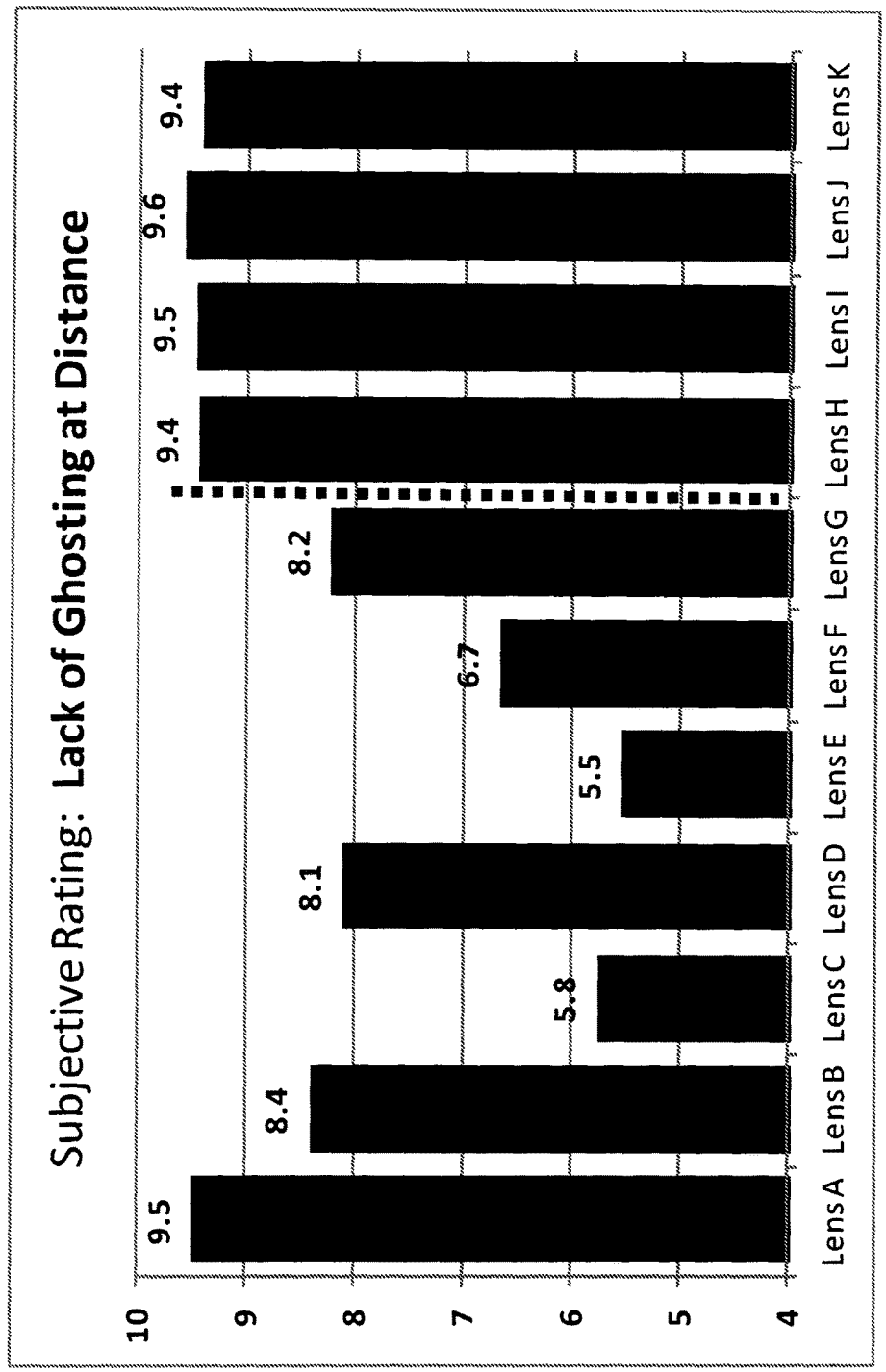
FIG. 88 show the average subjective ratings measured on a lack of ghosting analogue scale for distance vision for a sample of an affected presbyopic population. Four of the lenses H to K are exemplary of certain embodiments, while lenses A to G are commercial lenses.
Figure 89:
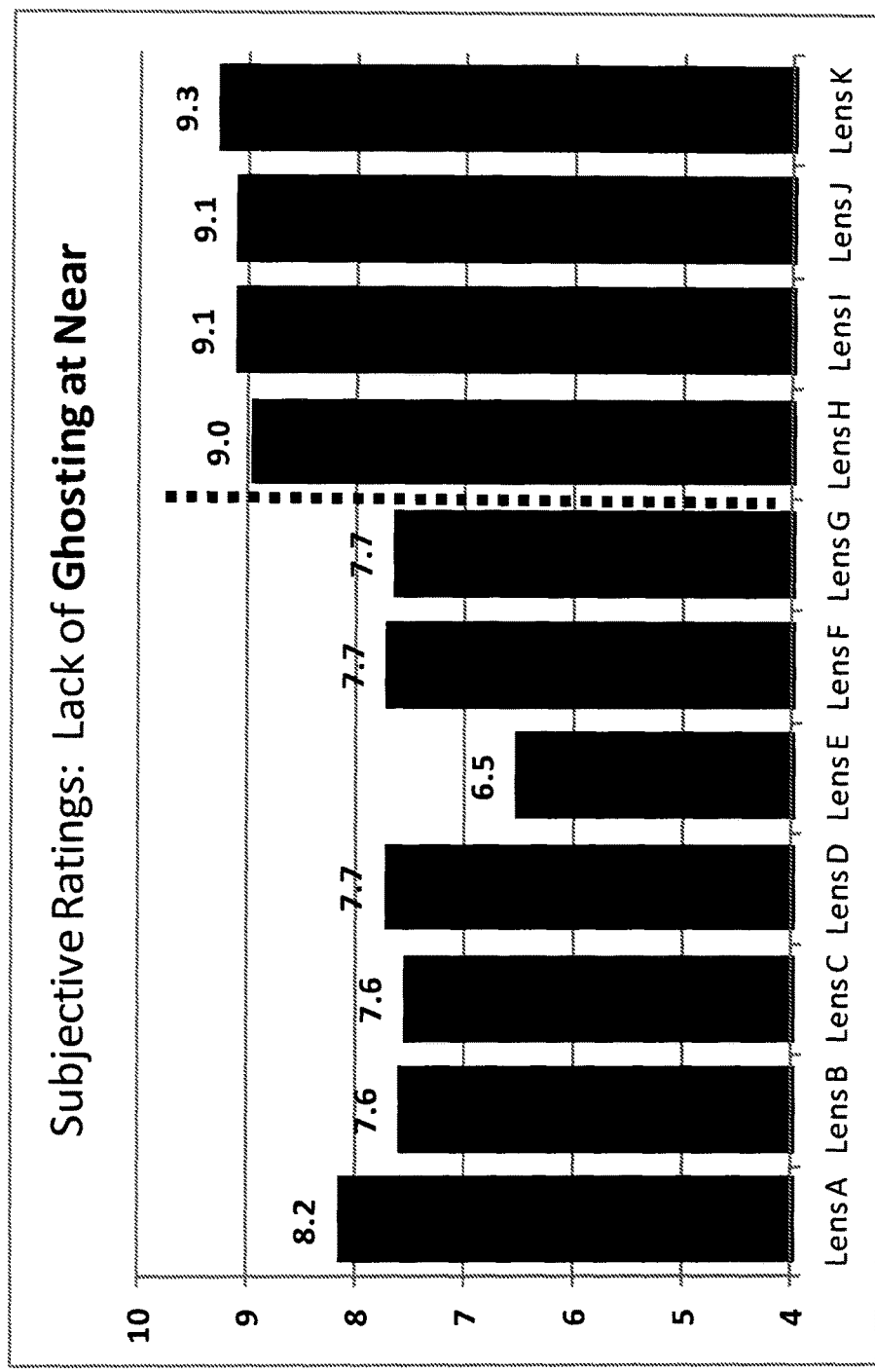
FIG. 89 show the average subjective ratings measured on a lack of ghosting analogue scale for near vision for a sample of an affected presbyopic population. Four of the lenses H to K are exemplary of certain embodiments, while lenses A to G are commercial lenses.
Figure 90:
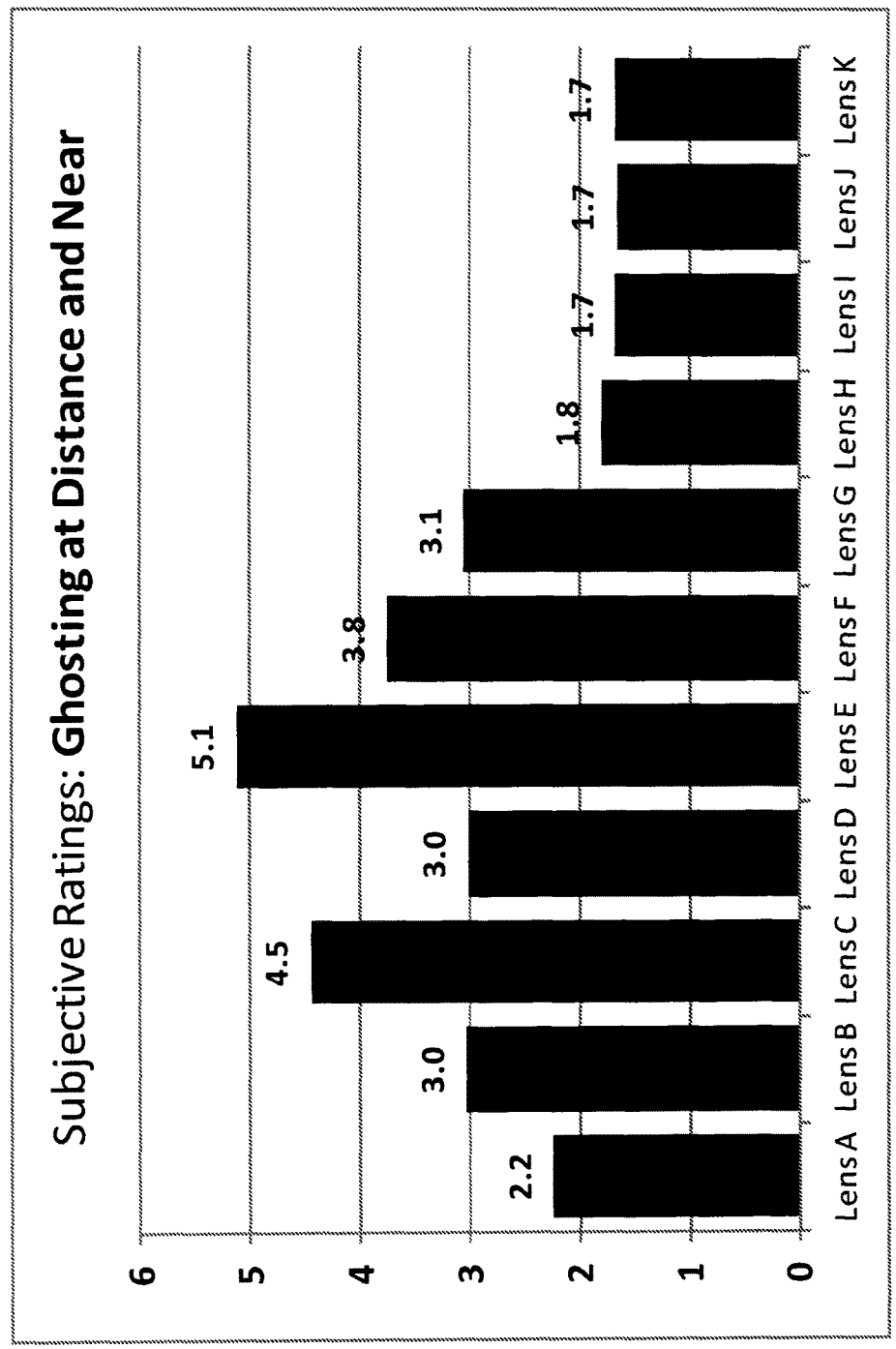
FIG. 90 show the average subjective ratings measured on a ghosting analogue scale for distance and near vision combined for a sample of an affected presbyopic population. Four of the lenses H to K are exemplary of certain embodiments, while lenses A to G are commercial lenses.
Figure 91:
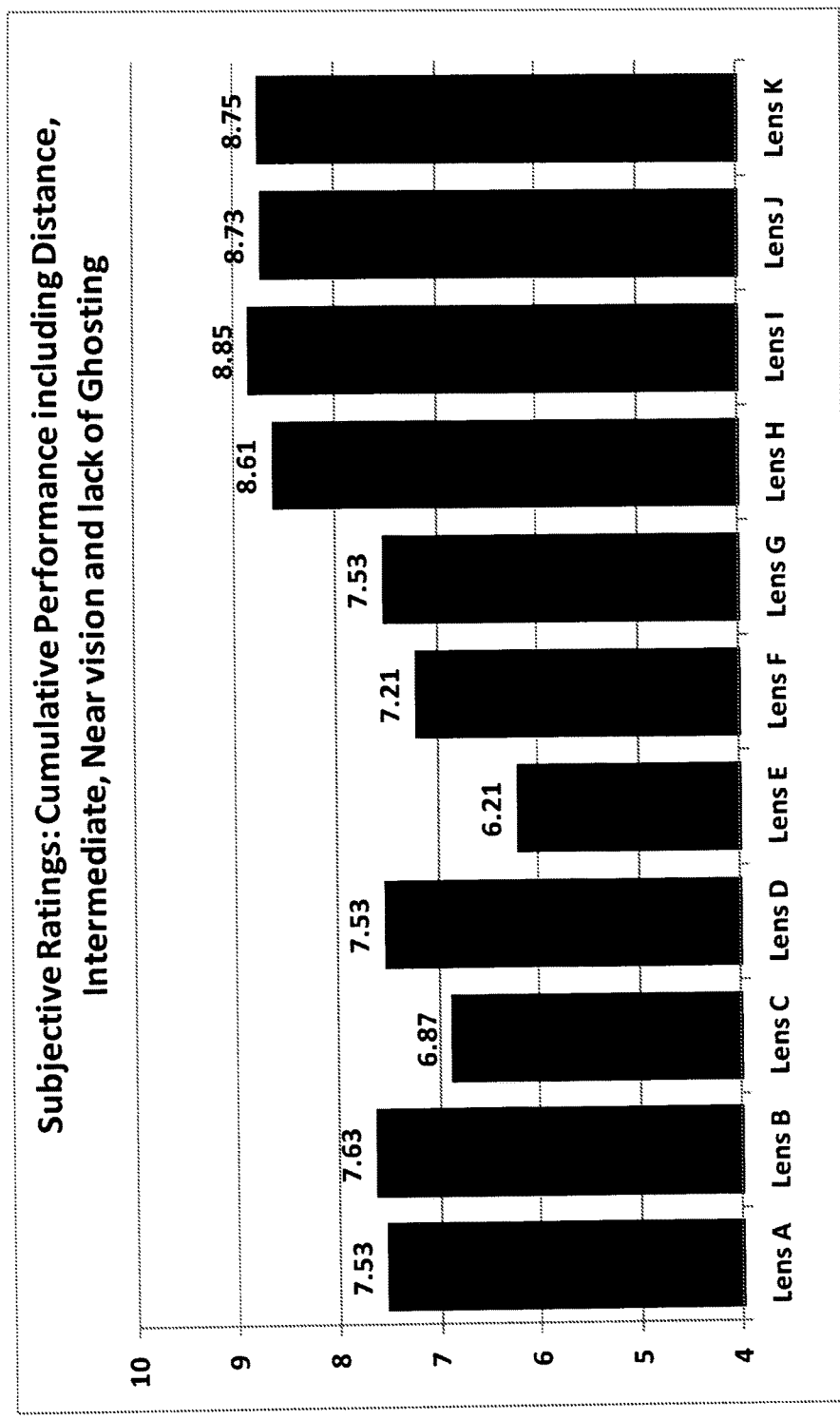
FIG. 91 show the average subjective ratings measured on a visual analogue scale for cumulative performance of vision including distance, intermediate, near vision and lack of ghosting at distance and near for a sample of an affected presbyopic population. Four of the lenses H to K are exemplary of certain embodiments, while lenses A to G are commercial lenses.
Figure 92:
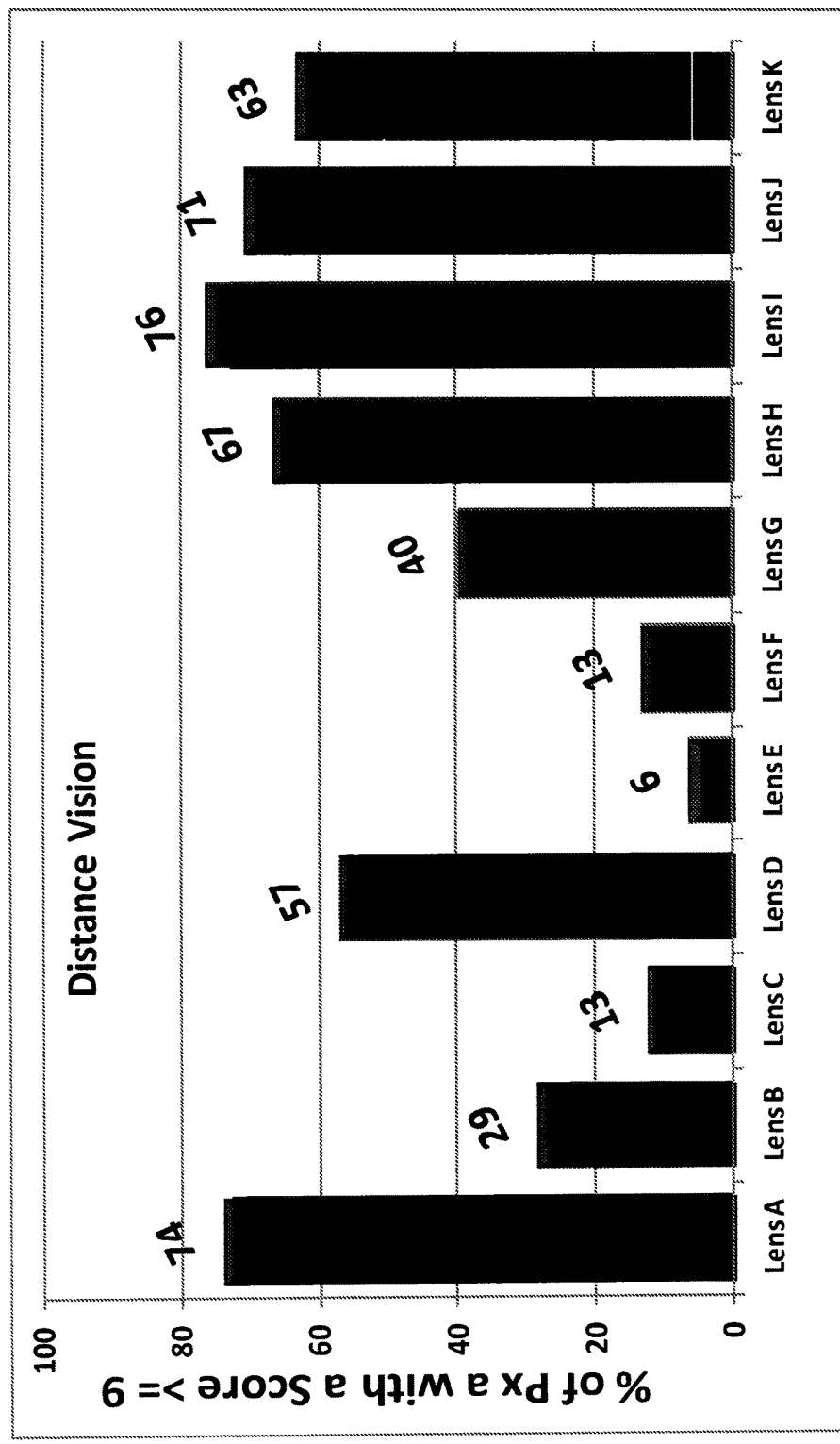
FIG. 92 shows the percentage of people whose subjective rating score on a visual analogue scale was greater than 9, for distance vision. The data were obtained from a sample of an affected presbyopic population. Four of the lenses H to K are exemplary of certain embodiments, while lenses A to G are commercial lenses.
Figure 93:
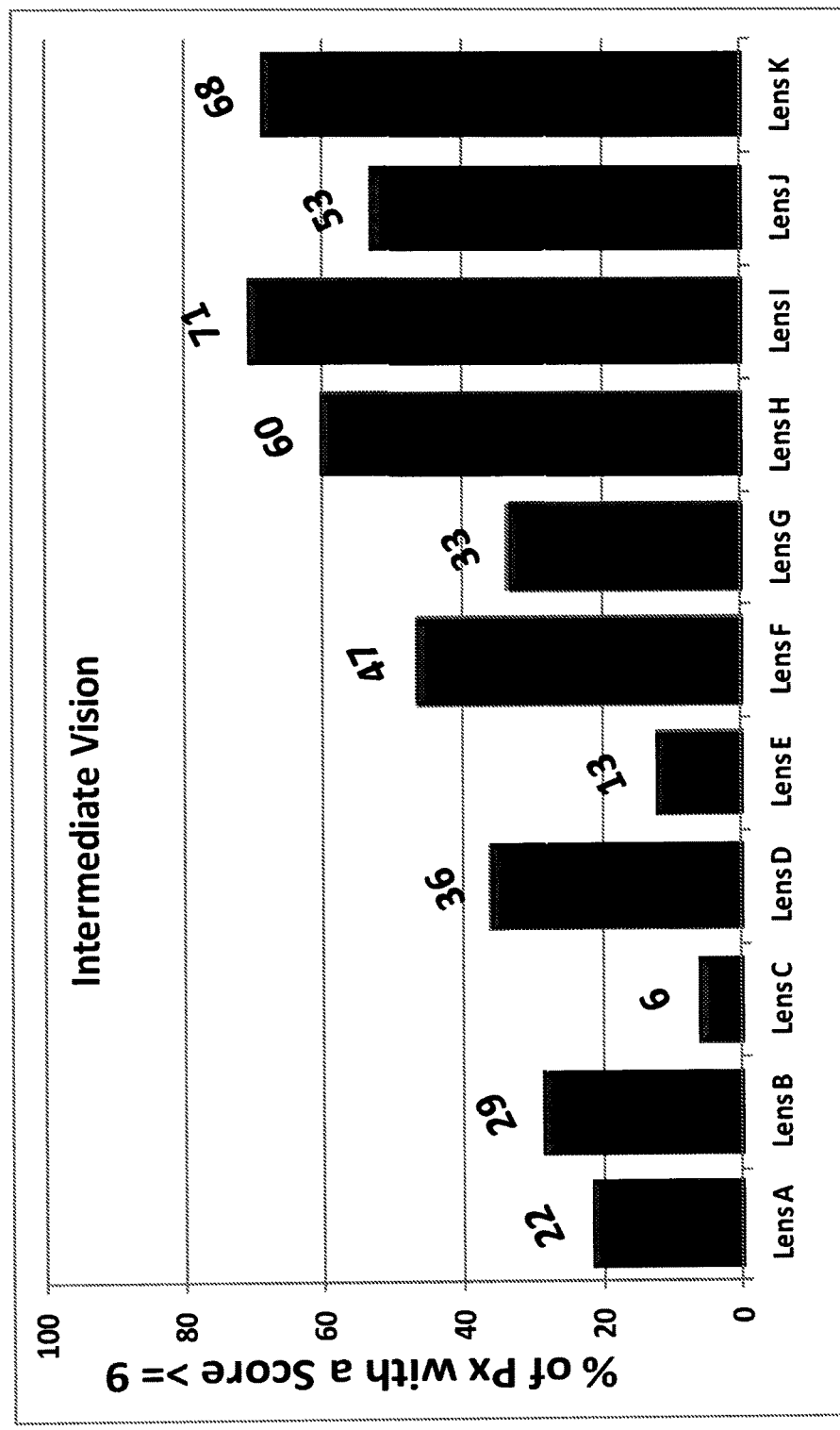
FIG. 93 shows the percentage of people whose subjective rating score on a visual analogue scale was greater than 9, for intermediate vision. The data were obtained from a sample of an affected presbyopic population. Four of the lenses H to K are exemplary of certain embodiments, while lenses A to G are commercial lenses.
Figure 94:
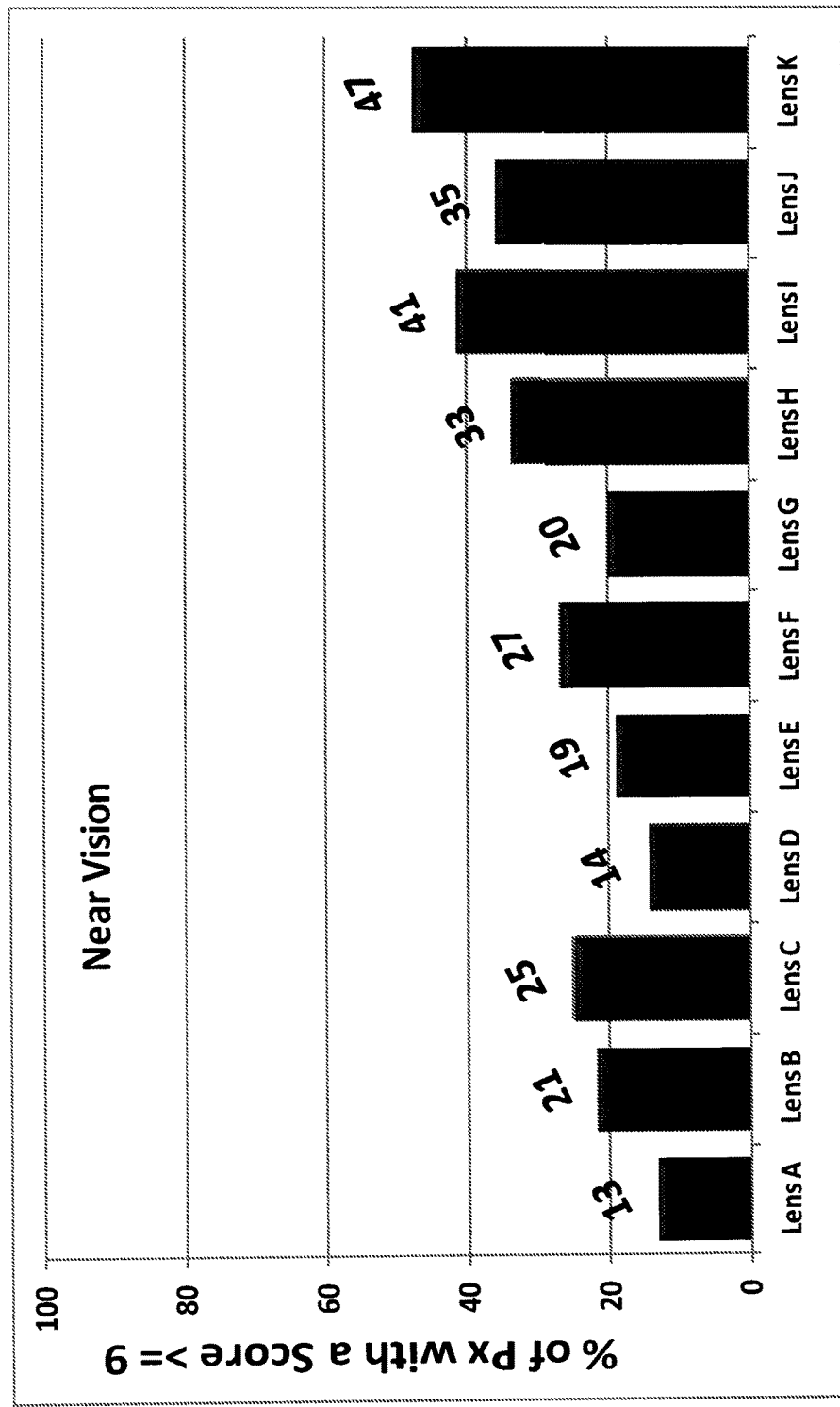
FIG. 94 shows the percentage of people whose subjective rating score on a visual analogue scale was greater than 9, for near vision. The data were obtained from a sample of an affected presbyopic population. Four of the lenses H to K are exemplary of certain embodiments, while lenses A to G are commercial lenses.
Figure 95:
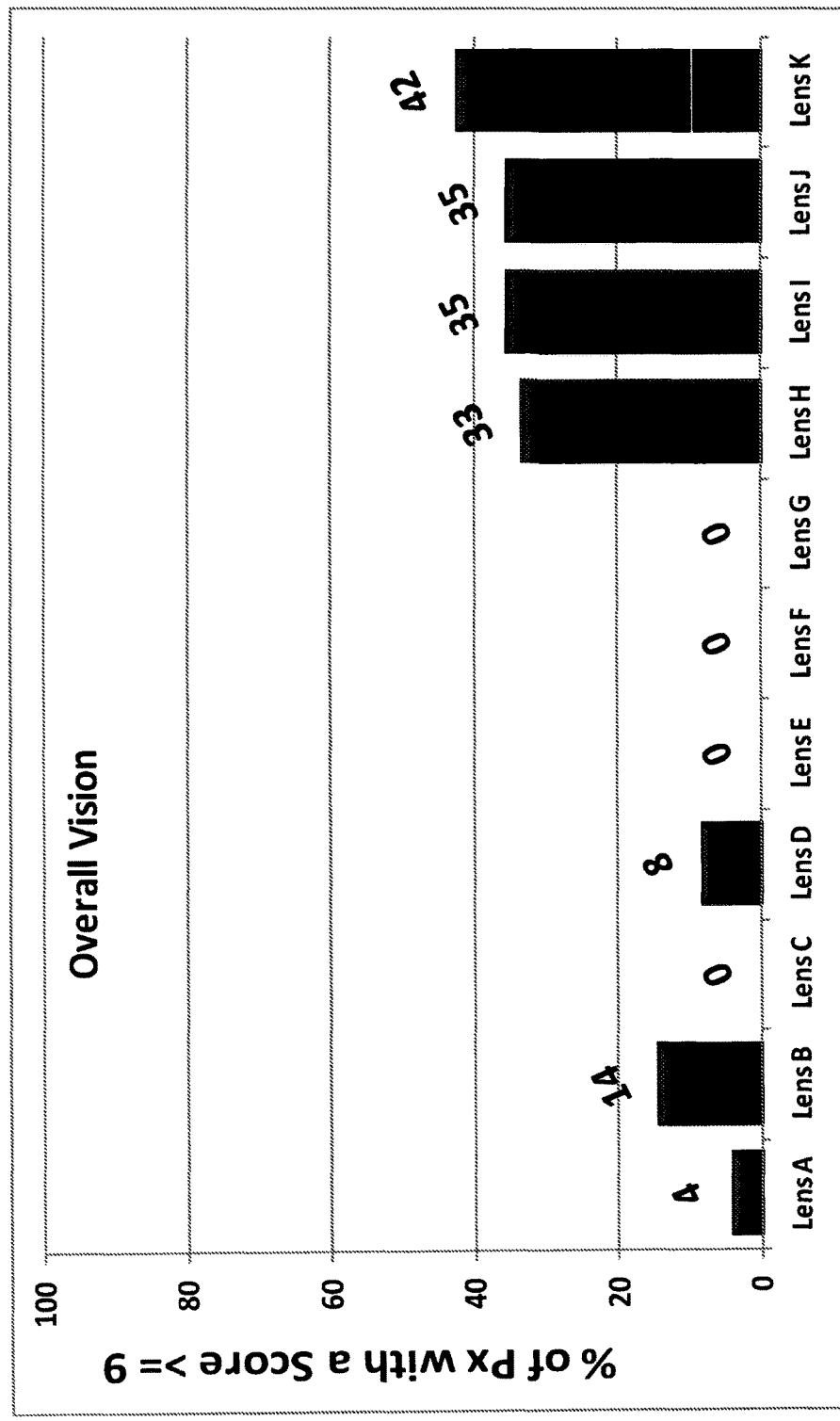
FIG. 95 shows the percentage of people whose subjective rating score on a visual analogue scale was greater than 9, for overall vision. The data were obtained from a sample of an affected presbyopic population. Four of the lenses H to K are exemplary of certain embodiments, while lenses A to G are commercial lenses.
Figure 96:
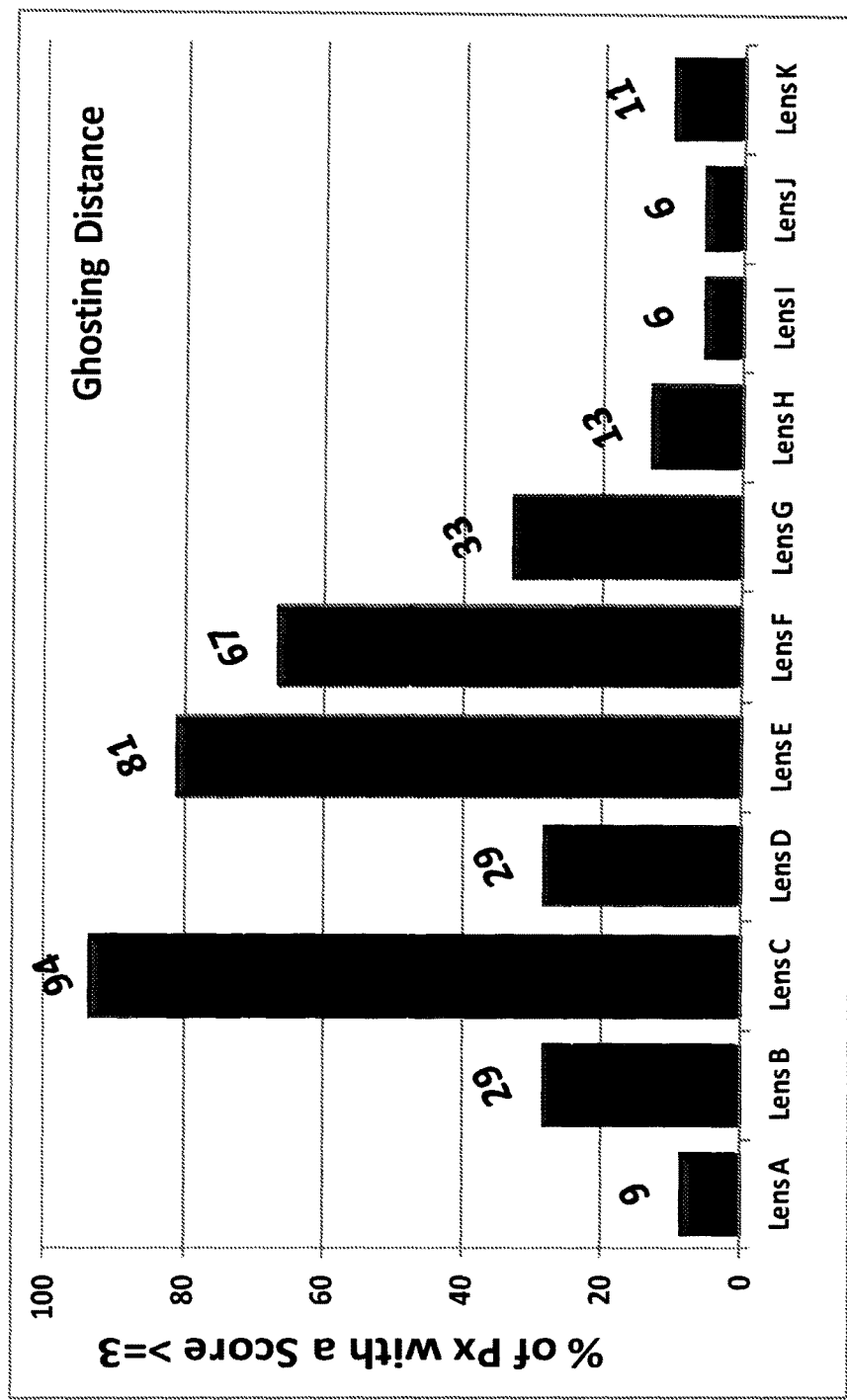
FIG. 96 shows the percentage of people whose subjective rating score on a ghosting analogue scale was greater than 3, for distance vision. The data were obtained from a sample of an affected presbyopic population. Four of the lenses H to K are exemplary of certain embodiments, while lenses A to G are commercial lenses.
Figure 97:
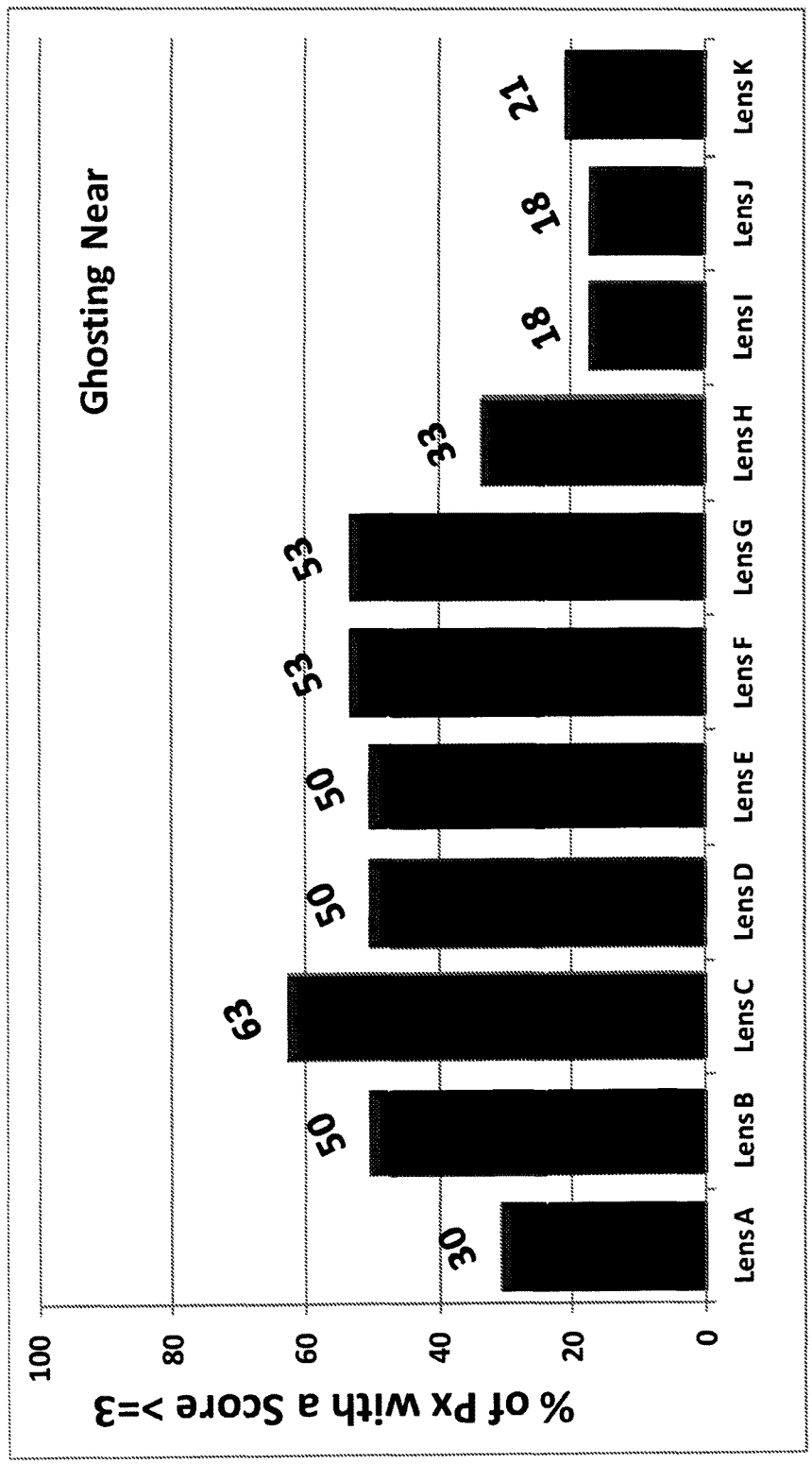
FIG. 97 shows the percentage of people whose subjective rating score on a ghosting analogue scale was greater than 3, for near vision. The data were obtained from a sample of an affected presbyopic population. Four of the lenses H to K are exemplary of certain embodiments, while lenses A to G are commercial lenses.
Figure 98:
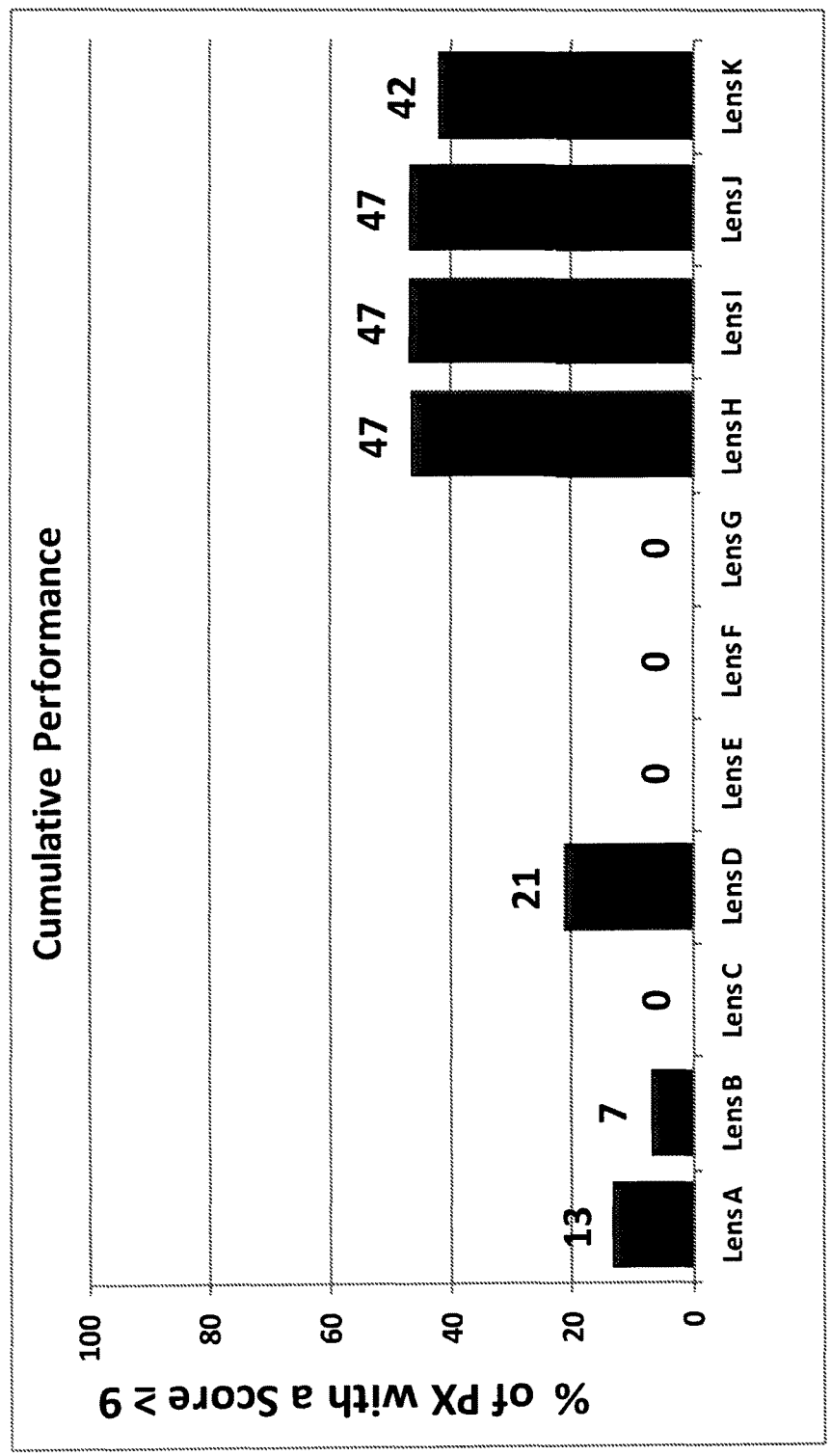
FIG. 98 shows the percentage of people whose subjective rating score on a visual analogue scale was greater than 9, for cumulative vision. The cumulative vision rating was obtained by averaging the distance, intermediate, near, overall vision ratings, also including lack of ghosting for distance and near. The data were obtained from a sample of an affected presbyopic population. Four of the lenses H to K are exemplary of certain embodiments, while lenses A to G are commercial lenses.
Figure 99:
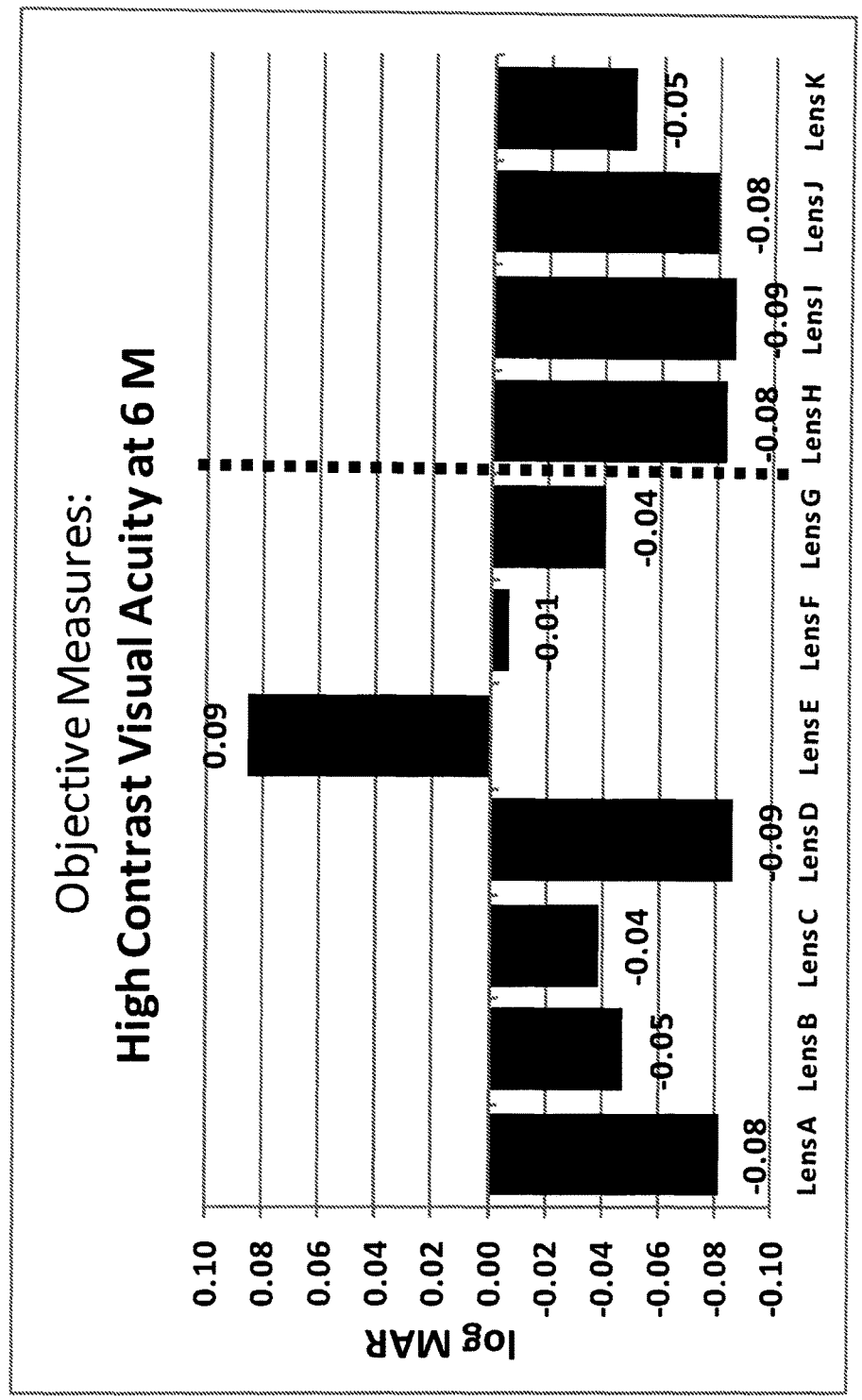
FIG. 99 shows the average objective measures of high-contrast visual acuity on a sample of an affected presbyopic population. The measures were obtained using a test distance of 6 meters and presented in log MAR scale. Four of the lenses H to K are exemplary of certain embodiments, while lenses A to G are commercial lenses.
Figure 100:
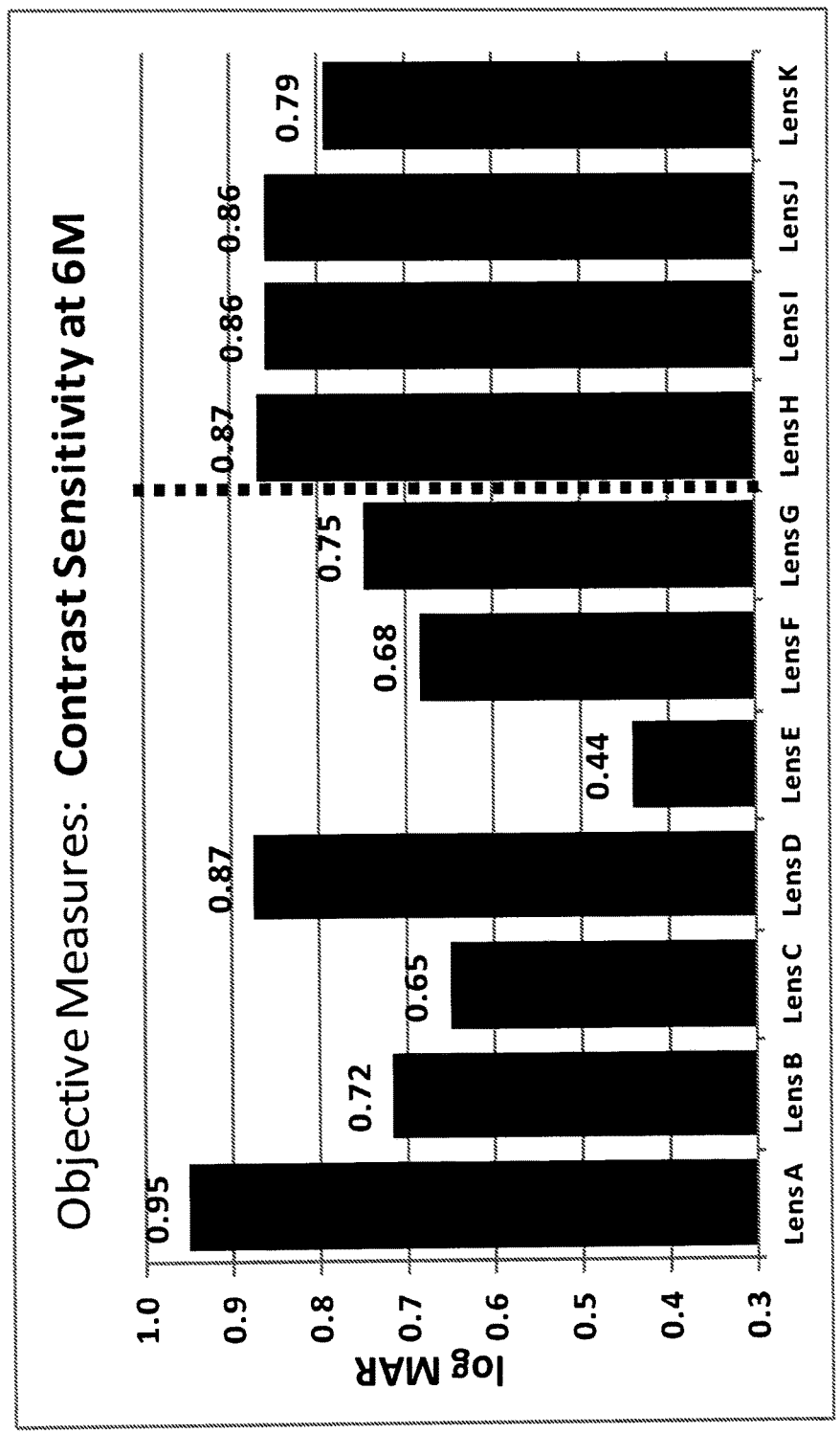
FIG. 100 shows the average objective measures of contrast sensitivity on a sample of an affected presbyopic population. The measures were obtained using a test distance of 6 meters and presented in log scale. Four of the lenses H to K are exemplary of certain embodiments, while lenses A to G are commercial lenses.
Figure 101:
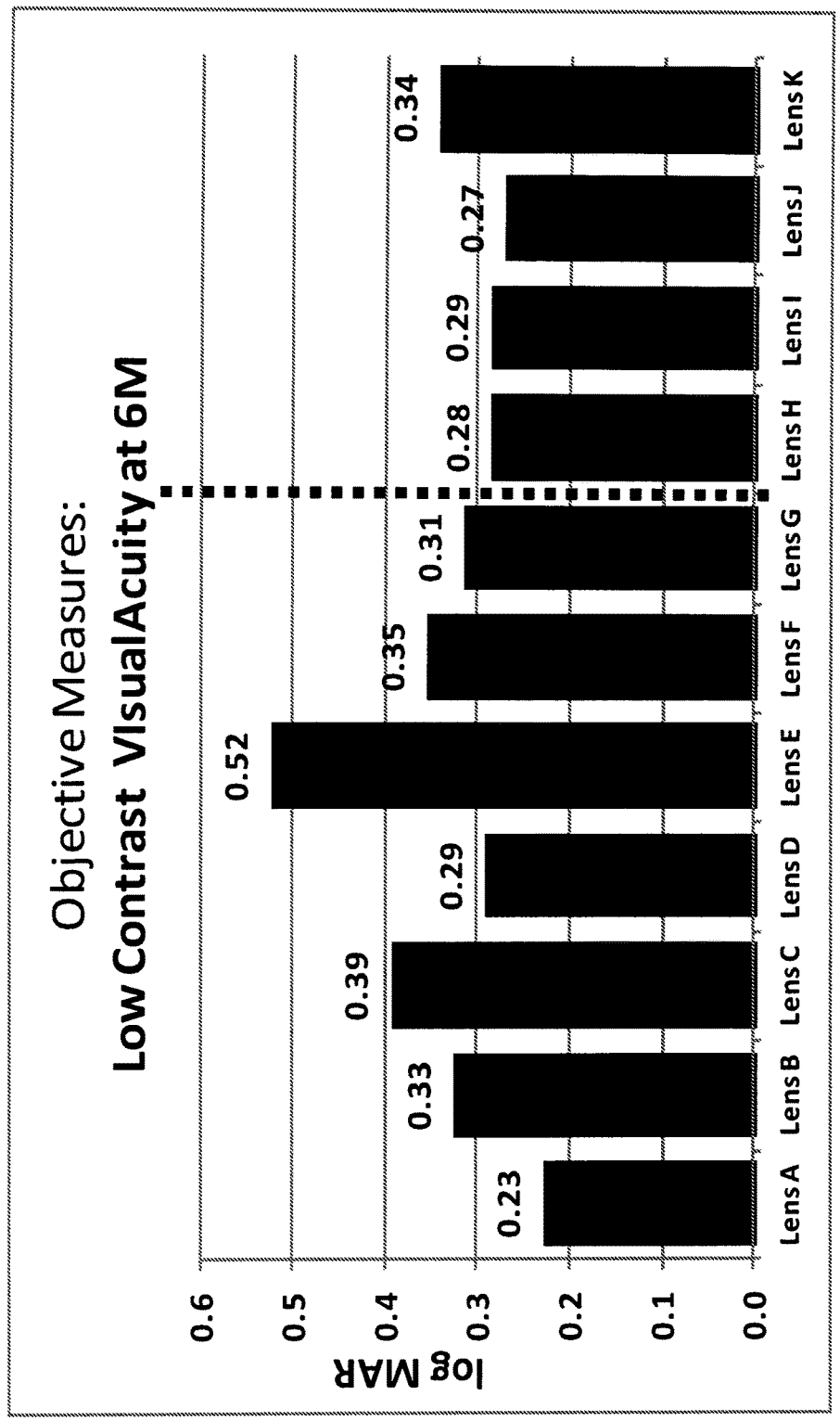
FIG. 101 shows the average objective measures of low-contrast visual acuity on a sample of an affected presbyopic population. The measures were obtained using a test distance of 6 meters and presented in log MAR scale. Four of the lenses H to K are exemplary of certain embodiments, while lenses A to G are commercial lenses.
Figure 102:
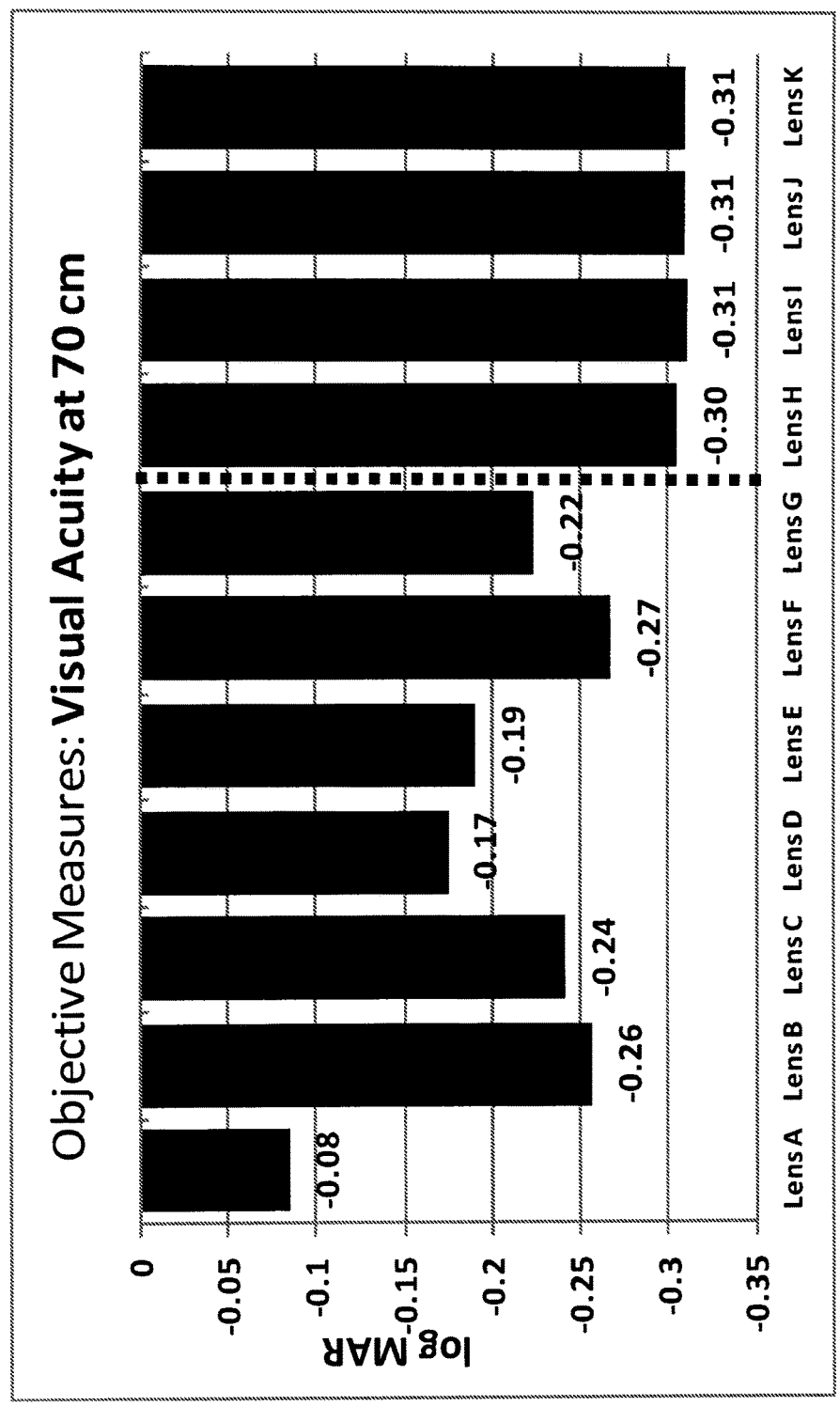
FIG. 102 shows the average objective measures of intermediate visual acuity on a sample of an affected presbyopic population, using a test distance of 70 centimeters. The measures are presented in log MAR scale. Four of the lenses H to K are exemplary of certain embodiments, while lenses A to G are commercial lenses.
Figure 103:
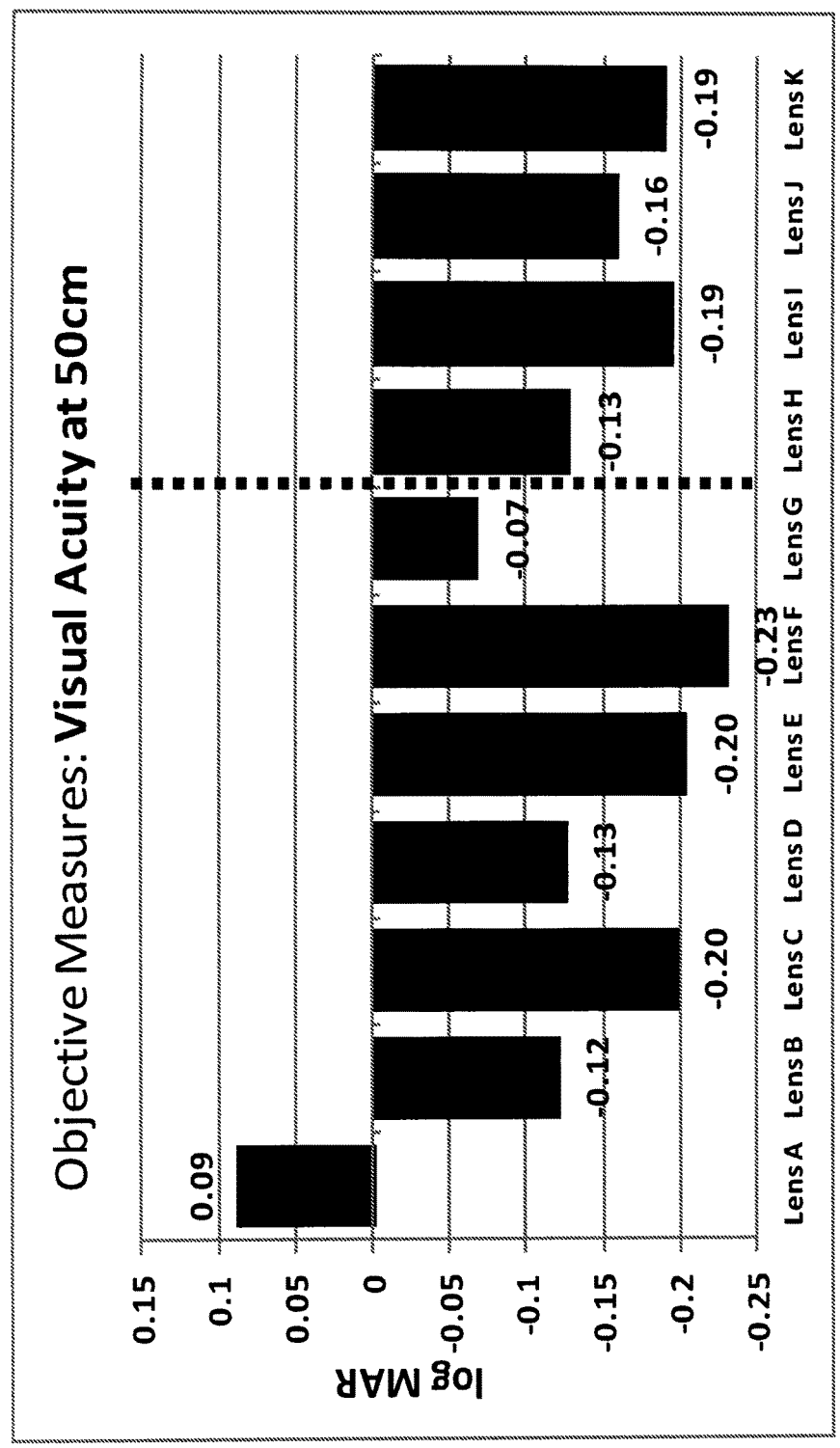
FIG. 103 shows the average objective measures of near visual acuity on a sample of an affected presbyopic population, using a test distance of 50 centimeters. The measures are presented in log MAR scale. Four of the lenses H to K are exemplary of certain embodiments, while lenses A to G are commercial lenses.
Figure 104:
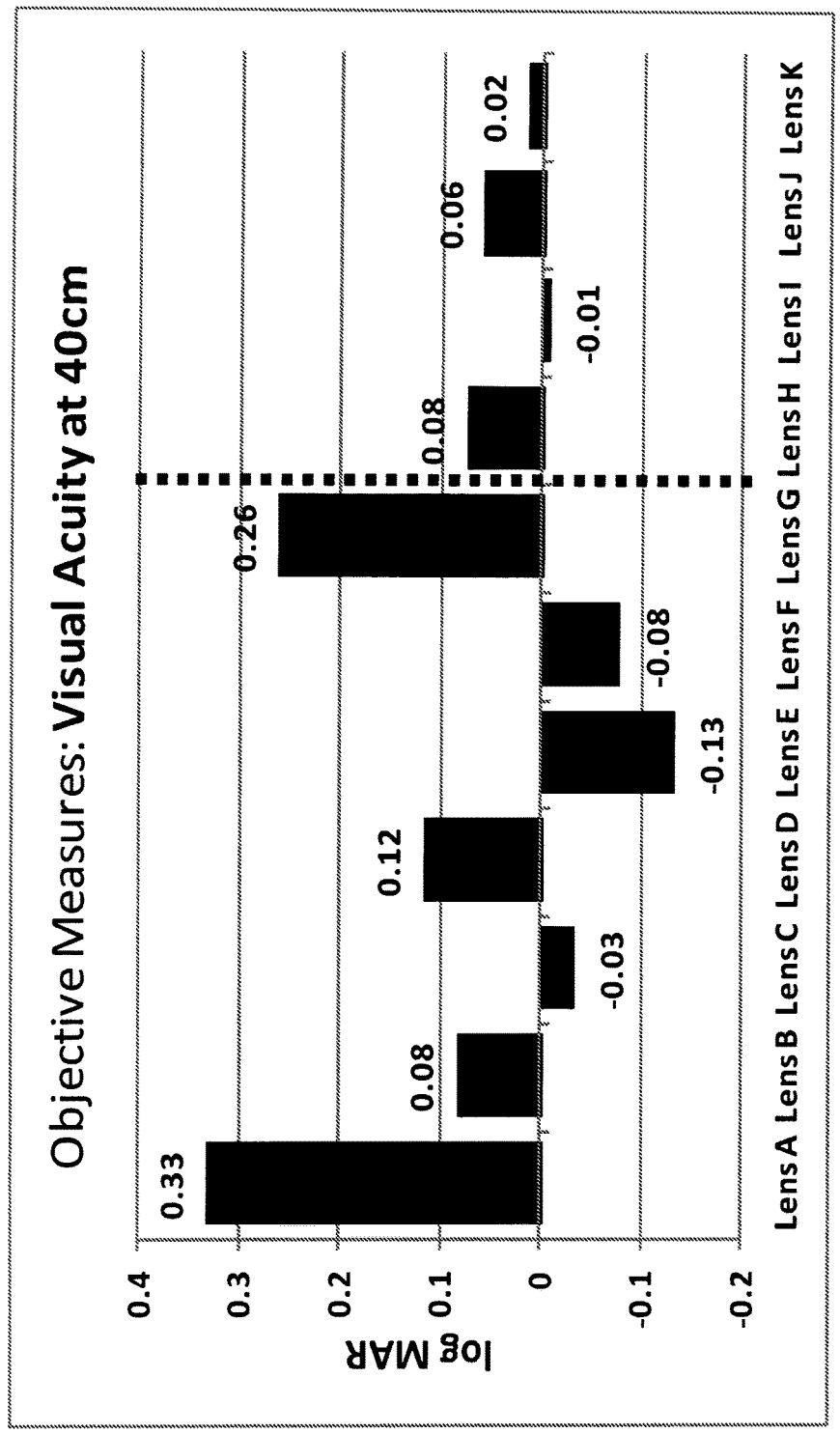
FIG. 104 shows the average objective measures of near visual acuity on a sample of an affected presbyopic population, using a test distance of 40 centimeters. The measures are presented in log MAR scale. Four of the lenses H to K are exemplary of certain embodiments, while lenses A to G are commercial lenses.
Figure 105:
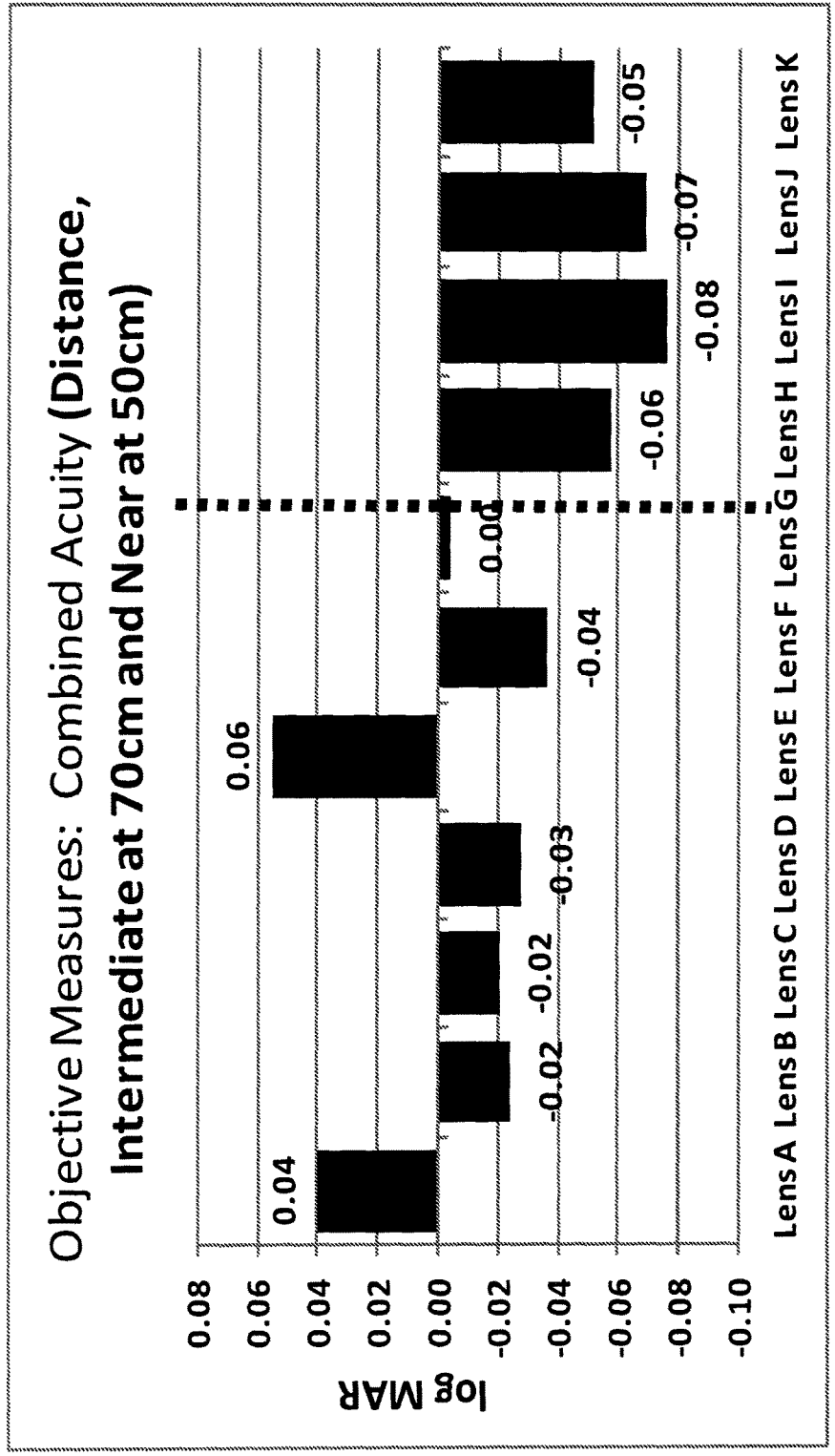
FIG. 105 shows the average objective measures of combined visual acuity on a sample of an affected presbyopic population. The combined visual acuity includes measures at distance, intermediate and near at 50 cm. The measures are presented in log MAR scale. Four of the lenses H to K are exemplary of certain embodiments, while lenses A to G are commercial lenses.
Figure 106:
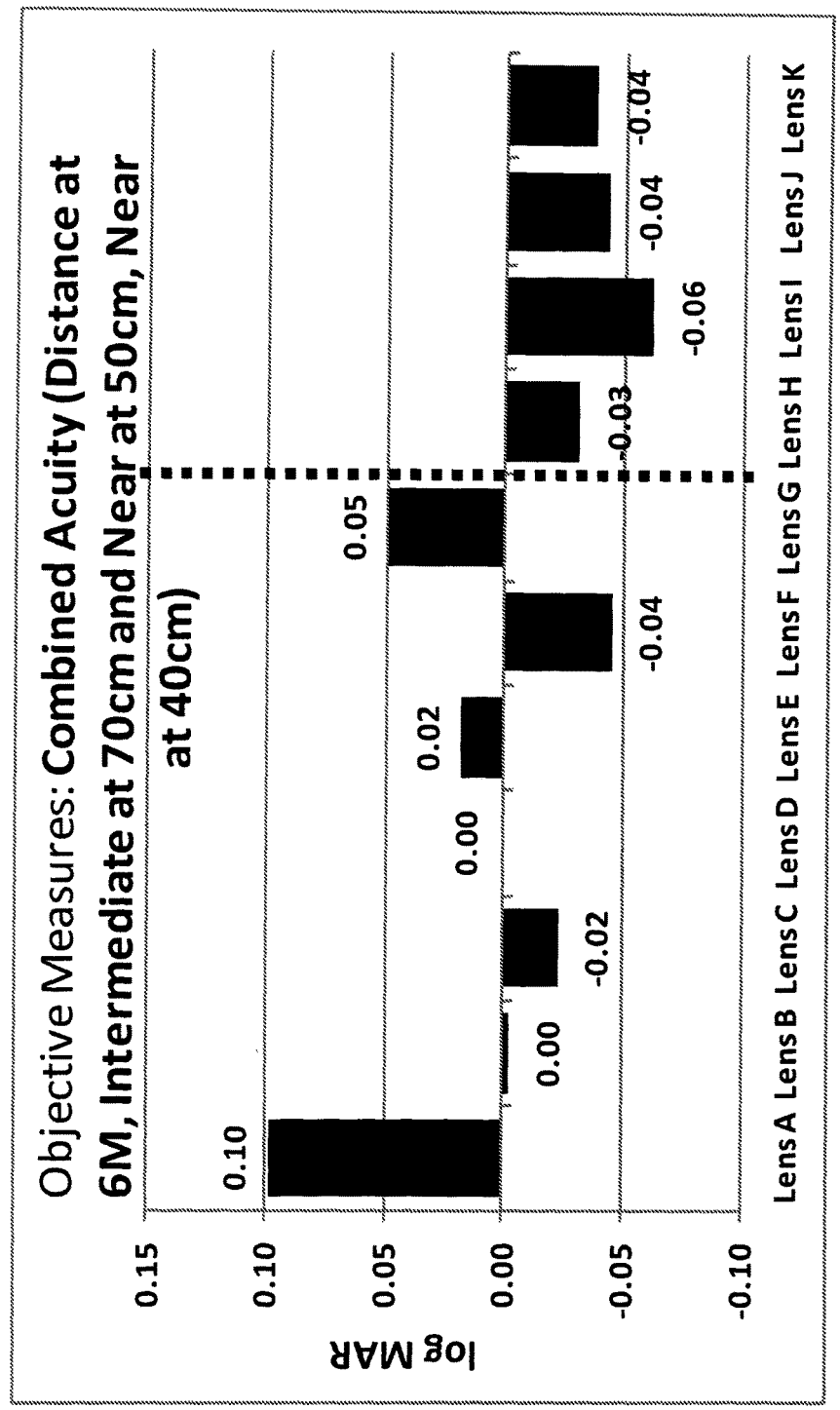
FIG. 106 shows the average objective measures of combined visual acuity on a sample of an affected presbyopic population. The combined visual acuity includes measures at distance, intermediate, near at 50 cm and near at 50 cm. The measures are presented in log MAR scale. Four of the lenses H to K are exemplary of certain embodiments, while lenses A to G are commercial lenses.
Figure 107:
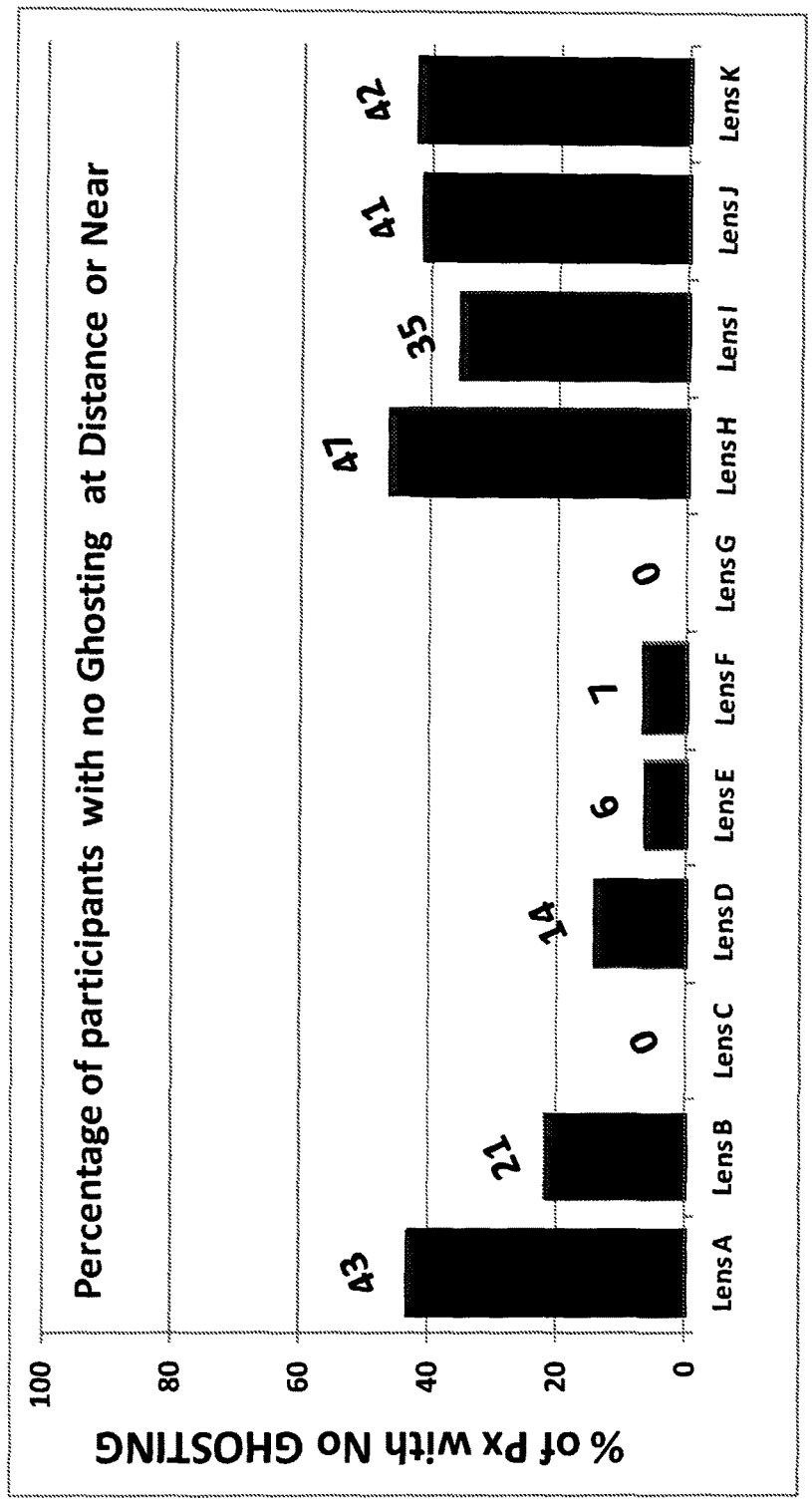
FIG. 107 shows the percentage of people whose subjective rating score on a visual analogue scale was equal to 1, for ghosting at distance or near. The data were obtained from a sample of an affected presbyopic population. Four of the lenses H to K are exemplary of certain embodiments, while lenses A to G are commercial lenses.
Figure 108:
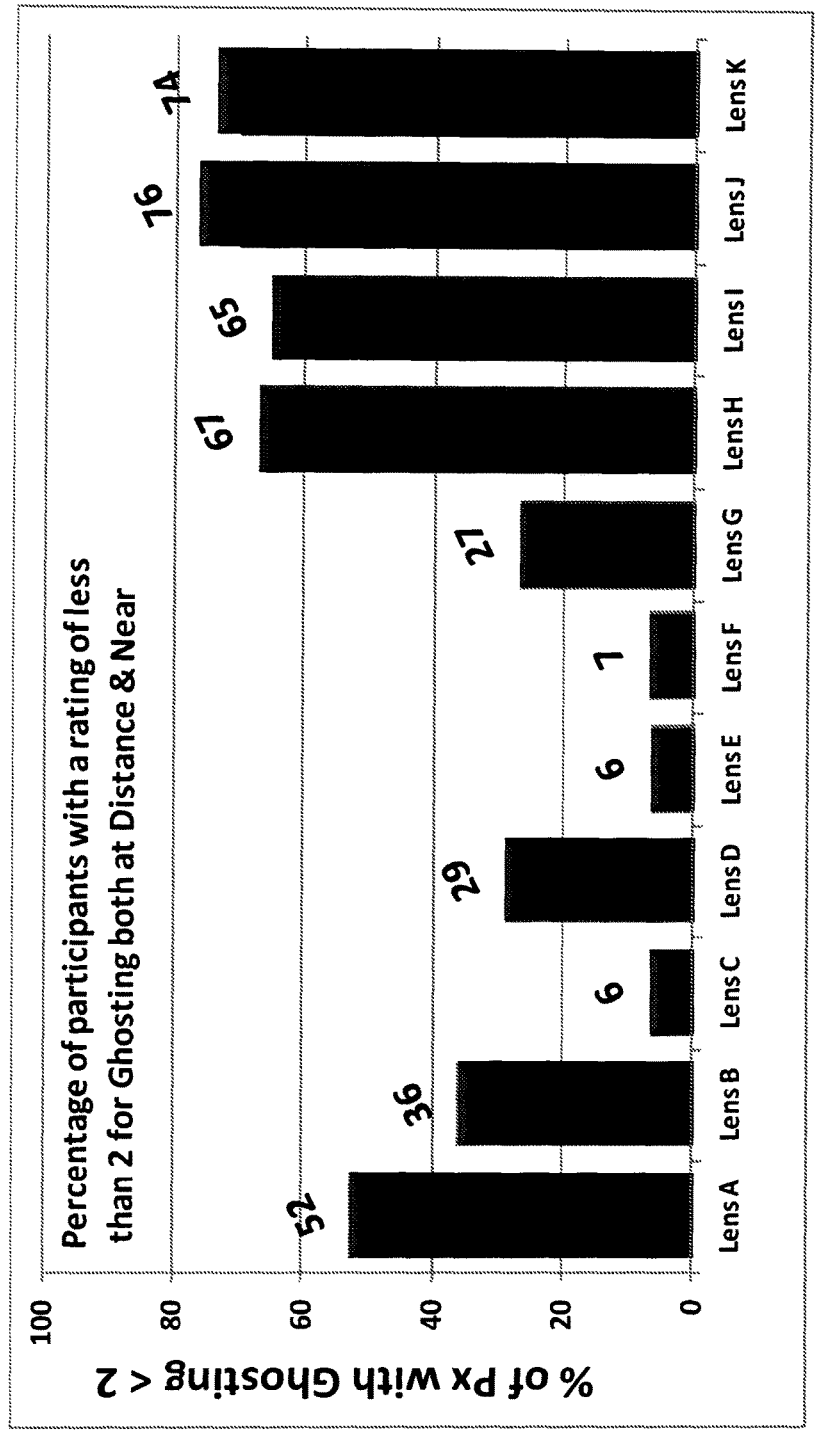
FIG. 108 shows the percentage of people whose subjective rating score on a visual analogue scale was less than 2, for ghosting at distance and near. The data were obtained from a sample of an affected presbyopic population. Four of the lenses H to K are exemplary of certain embodiments, while lenses A to G are commercial lenses.

Descriptors of Power Profiles Using First Derivatives or Rate of Change of Power First derivatives methods may be used to characterise the power profiles of certain embodiments, and in particular, for certain bifocal or multifocal designs. For example, FIG. 76 plots the power profiles for a number of commercially available bifocal and multifocal lenses. FIG. 77 plots the power profiles for a number of multifocal lenses according to embodiments. FIG. 80 plots the first derivative of the power profiles for the commercially available bifocal and multifocal lenses of FIG. 76. FIG. 81 plots the first derivative of power profiles of FIG. 77. For both FIGS. 80 and 81, the horizontal axis represents half-chord of the optic zone diameter and the vertical axis plots the absolute of the first derivative of the power profiles.

A comparison of FIGS. 80 and 81 illustrates differentiation between certain embodiments and the plotted commercially available lenses, as the absolute of the first derivative of the power profiles of the illustrated embodiments have at least 5 peaks whose absolute amplitude is greater than 0.025 with units of 1 D per 0.01 mm. In contrast to the illustrated embodiments FIGS. 80 and 81, none of the currently available commercial lenses have at least 5 peaks with absolute first derivative greater than 0.025 with units of 1 D per 0.01 mm.

Certain embodiments such as lenses, bifocal lenses, and/or multifocal lenses may be characterised using first derivative or rate of change of power. For example, certain embodiments are directed to a lens comprising: an optical axis; at least two surfaces; wherein the lens has a power profile, the power profile is characterised such that the absolute of a first derivative of the power profile has at least 5 peaks whose absolute amplitude is greater than 0.025 with units of 1 D per 0.01 mm along its half-chord. In certain applications, the at least one power profile is characterised such that the absolute of a first derivative of the power profile has at least 5 peaks whose absolute amplitude is greater than 0.025 with units of 1 D per 0.01 mm along its half-chord.

Section 19

Descriptors of Power Profiles with Use of Aperiodic Functions

Certain embodiments of the present disclosure have one or more power profiles that may be characterised by aperiodic functions over a substantial portion of the half-chord optical zone of the lens. Certain embodiments are directed to lenses that are configured such that the at least one power profile is aperiodic over a substantial portion of the half-chord optical zone of the lens. In general terms, an aperiodic function is defined as a function that is not periodic. A periodic function is a function that repeats or duplicates its values in regular intervals, often denoted as periods. For example, trigonometric functions (i.e. sine, cosine, secant, cosecant, tangent and cotangent functions) are periodic as their values are repeated over intervals of $2\pi$ radians. A periodic function can also be defined as a function whose graphical representation exhibits translational symmetry. A function $F(x)$ is said to be periodic with a period P (where P is a non-zero constant), if it satisfies the following condition: $F(x+P)=F(x)$.

Section 20

Descriptors of Power Profiles with Use of Non-Monotonic Functions

Certain embodiments of the present disclosure have one or more power profiles that may be characterised by non-monotonic functions over a substantial portion of the half-chord optical zone of the lens. Certain embodiments are directed to lenses that are configured such that the at least one power profile is non-monotonic over a substantial portion of the half-chord optical zone of the lens. In general terms, a 'monotonic' or 'monotone' function is a function which either is substantially non-increasing or substantially non-decreasing. A function $F(x)$ is said to be non-increasing on an interval I of real numbers if: $F(b)<=F(a)$ for all $b>a$; where a, b are real numbers and are a subset of I; A function $F(x)$ is said to be non-decreasing on an interval I of real numbers if: $F(b)>=F(a)$ for all $b>a$; where a, b are real numbers and are a subset of I.

Section 21

Descriptors of Power Profiles with Use of Non-Monotonic and Aperiodic Functions

Certain embodiments of the present disclosure have one or more power profiles that may be characterised by non-monotonic and aperiodic functions over a substantial portion of the half-chord optical zone of the lens. Certain embodiments are directed to lenses that are configured such that the at least one power profile is non-monotonic and aperiodic over a substantial portion of the half-chord optical zone of the lens. In general, some functions may be both non-monotonic and aperiodic. Such functions possess properties of both non-monotonic and aperiodic function as described herein.

Certain embodiments such as lenses, bifocal lenses, and/or multifocal lenses may be characterised using aperiodic function, non-monotonic function, or combinations thereof. A lens comprising: an optical axis; at least two surfaces; wherein the lens has at least one power profile, the power profile is characterised by a function that is non-monotonic, aperiodic or combinations thereof over a substantial portion of the half-chord optical zone of the lens. In certain applications, the lens is configured with a power profile that is non-monotonic, aperiodic or combinations thereof over a substantial portion of the half-chord optical zone of the lens.

Section 22

Power Profile of Lenses

As is apparent from a visual inspection of at least FIGS. 19, 20, 22-25, 29, 31, 34, 35, 39, 40, 41, 56-60 and 68, certain embodiments have a power profile that has the following combination of characteristics across half-chord diameters:

(i) A power profile that has a moving average that either increases with diameter and then decreases, or decreases with diameter or then increases. For certain contact lens embodiments, the moving average may be calculated over a window of 1 mm from on-axis to about 4 mm. Accordingly, by way of example, the average value may be calculated across the range of on-axis to 1 mm, and recalculated at intervals selected from the group of 0.2 mm, 0.4 mm or 0.6 mm.

(ii) A power profile with transitions between local minima and maxima within a 1 mm change of radius at least 4 times across a 4 mm of the half-chord. For example, referring to FIG. 22, the power profile starts at a local maximum on-axis and transitions to a local minimum at about 1 mm radius; the transitions between local maxima and minima then occur at about 1.6 mm and about 2.3 mm. After that, the power profile may either have the next local minima at about 2.9 mm, a local minimum at about 3.1 mm and a local maximum at about 4 mm, or have the next local maximum at about 4 mm. In some examples, the power profile transitions at least 6 times across a 4 mm of the half-chord. For example, referring to FIG. 24, there are two transitions in the first 1 mm radius, two in the second 1 mm radius, and two transitions in the region from 2 mm to 4 mm. In some examples the power profile transitions at least 8 times across the 4 mm radius range (for example FIG. 29) or at least 12 times across the 4 mm radius range (for example FIG. 35) or at least 15 times (for example FIG. 40).

(iii) The power profile transitions smoothly out to a radius selected from the group of at least 3 mm, at least 3.5 mm and at least 4 mm.

Accordingly, certain embodiments have a power profile with a combination selected from the options within (i) and (ii) and (iii), which provides acceptable vision for at least a subset of a population. These embodiments may have application to myopia, hyperopia, and/or presbyopia, with or without astigmatism. Other embodiments include a combination from the options described above in this section 22, together with one or more of:

(iv) The refractive power on-axis power differs from the prescription power by at least about 0.7 D (e.g. see FIG. 22), or by at least about 1.5 D (e.g. see FIG. 38).

(v) The difference between the global maximum and global minimum power is between approximately 1.5 to 2.5 times the difference between any adjacent local minimum and local maximum within a radius of about 2.5 mm. In other words, the global maximum and global minimum are reached through a stepped change in power profile, that itself transitions between local minima and local maxima.

Section 23

Clinical Performance of Some Exemplary Embodiments Compared with Commercially Available Single Vision, Bifocal and Multifocal Soft Contact Lenses In the following experimental clinical study, performance of four exemplary embodiments described herein (manufactured into the form of soft contact lenses) were compared against seven commercially available lenses including one single vision, one bifocal and five multifocal products whose details are provided in the table herein, Table 19. The study was approved by ethics committee of Bellberry, South Australia.

Experimental Purpose:

The aim of the study was to assess the visual performance of four multifocal soft contact lenses, according to certain embodiments, and six commercially available bifocal and multifocal lens designs.

Study Design:

The study design was a prospective, participant-masked, bilateral wear, cross-over clinical trial with a minimum overnight washout period between the lens assessments. Lens wear duration was up to 2 hours.

Participant Selection:

Participants were included in the study if they met the following criterion:

a) Able to read and comprehend English and give informed consent as demonstrated by signing a record of informed consent.
b) Be at least 18 years old, male or female (the results reported herein are for participants over 45 years).
c) Willing to comply with the wearing and clinical trial visit schedule as directed by the Investigator.
d) Have ocular health findings within normal limits which would not prevent the participant from safely wearing contact lenses.
e) Is correctable to at least 6/6 (20/20) or better in each eye with single vision contact lenses.
f) Have an astigmatism correction of −1.5 D or less.
g) Be experienced or inexperienced at wearing contact lenses.

Participants were excluded from the study if they had one or more of the following conditions:

a) Pre-existing ocular irritation, injury or condition (including infection or disease) of the cornea, conjunctiva or eyelids that would preclude contact lens fitting and safe wearing of contact lenses.
b) Systemic disease that adversely affected ocular health e.g. diabetes, Graves disease, and auto immune diseases such as ankylosing spondylitis, multiple sclerosis, Sjögrens syndrome and systemic lupus erythematosus. Note: Conditions such as systemic hypertension and arthritis would not automatically exclude prospective participants.
c) Use of or a need for concurrent category S3 and above ocular medications at enrolment and/or during the clinical trial.
d) Use of or a need for systemic medication and/or topical medications which may alter normal ocular findings and/or are known to affect a participant's ocular health and/or physiology or contact lens performance either in an adverse or beneficial manner at enrolment and/or during the clinical trial.
e) NB: Systemic antihistamines are allowed on an "as needed basis", provided they are not used prophylactically during the trial and at least 24 hours before the clinical trial product is used.
f) Eye surgery within 12 weeks immediately prior to enrolment for this trial.
g) Previous corneal refractive surgery.
h) Contraindications to contact lens wear.
i) Known allergy or intolerance to the ingredients of the clinical trial products.
j) The investigators excluded anyone who they believe may not be able to fulfil the clinical trial requirements.

TABLE 19

List of the lenses used in the clinical study

| Lens Code | Contact Lenses (Marketed in Australia as) | Manufacturer | Material | Mode of Wear in this Trial | Power (D) | Diameter (mm) | Base Curve (mm) |
|---|---|---|---|---|---|---|---|
| Lens A | AirOptix ® Aqua Single vision | Alcon (USA) | Lotrafilcon B | Daily wear | +4.00D to −10.00 | 14.2 | 8.6 |
| Lens B | Air Optix ® Aqua Multifocal | CIBA VISION (USA) | Lotrafilcon B | Daily Wear | +6.00D to −1.00D Low/Med/High | 14.2 | 8.6 |
| Lens C | ACUVUE ® Bifocal | J&J (USA) | Etafilcon A | Daily Wear | +6.00D to −9.00D +1.50/+2.50D | 14.2 | 8.5 |
| Lens D | Proclear ® Multifocal - Distance design | Cooper Vision (USA) | Omafilcon A | Daily wear | +4.00D to −10.00D Low/High | 14.4 | 8.5 to 8.7 |
| Lens E | Proclear ® Multifocal - Near design | Cooper Vision (USA) | Omafilcon A | Daily wear | +4.00D to −10.00D Low/High | 14.4 | 8.5 to 8.7 |
| Lens F | PureVision ® multifocal | Bausch & Lomb (USA) | Balafilcon A | Daily wear | +6.00D to −10.00D Low/High | 14.0 | 8.6 |
| Lens G | CLARITI ® 1 Day multifocal | Sauflon (UK) | Filcon II multifocal | Daily wear | +5.00D to −6.00 Low/High | 14.1 | 8.6 |
| Lens H | Prototype 1 | Lathe Manufactured | Hioxifilcon A/B/D | Daily wear | +4.00D to −10.00D | 13.5 to 14.5 | 8.1 to 8.7 |

TABLE 19-continued

List of the lenses used in the clinical study

| Lens Code | Contact Lenses (Marketed in Australia as) | Manufacturer | Material | Mode of Wear in this Trial | Power (D) | Diameter (mm) | Base Curve (mm) |
|---|---|---|---|---|---|---|---|
| Lens I | Prototype 2 | Lathe Manufactured | Hioxifilcon A/B/D | Daily wear | +4.00D to −10.00D | 13.5 to 14.5 | 8.1 to 8.7 |
| Lens J | Prototype 3 | Lathe Manufactured | Hioxifilcon A/B/D | Daily wear | +4.00D to −10.00D | 13.5 to 14.5 | 8.1 to 8.7 |
| Lens K | Prototype 4 | Lathe Manufactured | Hioxifilcon A/B/D | Daily wear | +4.00D to −10.00D | 13.5 to 14.5 | 8.1 to 8.7 |

Methods:

For each fitting visit, lenses were fitted bilaterally. After allowing for the lenses to settle, lens performance was assessed including:

1. Visual Acuity a. Log MAR charts were used to obtain measurements for vision at distance under high illumination conditions b. High contrast visual acuity at 6 meters c. Low contrast visual acuity at 6 meters d. Contrast sensitivity using a Pelli-Robson equivalent chart (using Thomson software) equivalent at 6 meters, the text was kept constant at 6/12 letter size while the contrast was reduced as a logarithmic function.

e. Hanks near point chart was used to measure visual acuity at 70 cm (intermediate vision), at 50 cm and 40 cm (near vision) under high illumination conditions. As the Hanks near point chart was designed to be used at 40 cm near, the visual acuity equivalents for 50 cm and 70 cm were calculated. Both intermediate and near visual acuity results were converted to equivalent log MAR Subjective Response Questionnaire:

1. Quality of distance, intermediate and near vision on a visual analogue scale of 1 to 10.

2. Rating of distance and near ghosting on a ghosting analogue scale of 1 to 10.

3. Overall rating of vision performance on a visual analogue scale of 1 to 10.

FIGS. 82 to 108 show the subjective and objective results obtained from the clinical study. The distance, intermediate, near and over all vision ratings were measured on a visual analogue scale ranging from 1 to 10 in steps of 1, where 1 represented blurred and/or hazy vision and 10 represented clear and/or sharp vision. The ghosting vision rating at distance and near were measured on a ghosting visual analogue scale ranging from 1 to 10 in steps of 1, where 1 represented no ghosting and/or doubling and 10 represented extreme ghosting and/or doubling. The lack of ghosting was calculated by subtracting ghosting score from 11 points. Cumulative vision results were obtained by averaging the distance, intermediate and near vision results. Cumulative ghosting results were obtained by averaging the ghosting at distance and near distances.

Section 24

Descriptors of Power Profiles with Use of Zernike Power Polynomials

When a monochromatic wavefront $W(\rho, \theta)$ of an optical system is provided, where $\rho$ is the radial distance and $\theta$ is the angle in polar co-ordinates, an estimate of the refractive power distribution of the wavefront can be defined as:

$$P(\rho, \theta) = \frac{1000}{W(\rho, \theta) + r\left(\frac{\partial W(\rho, \theta)}{\partial r}\right)^{-1}}$$

Where '$\partial W/\partial r$' represents partial derivative of $W(\rho, \theta)$ along the radial distance 'r'. If the monochromatic wavefront $W(\rho, \theta)$ is chosen to be described as a finite series of standard Zernike polynomial expansion, the wavefront-based refractive power may be represented by a set of basic functions and the original set of the wavefront standard Zernike polynomial coefficients, as shown below:

$$P(\rho, \theta) = \frac{1000}{r_{max}} \sum_{j=3}^{p-1} c_j \psi_j\left(\frac{r}{r_{max}}, \theta\right)$$

Where $r_{max}$ corresponds to the pupil radius;

$$\psi_j(\rho, \theta) = \begin{cases} \left(\sqrt{2(n+1)}\right) R_n^m(\rho)\cos(m\theta); \text{ if } m > 0 \\ \left(\sqrt{2(n+1)}\right) R_n^m(\rho)\sin(m\theta); \text{ if } m < 0 \\ \left(\sqrt{(n+1)}\right) R_n^m(\rho); \text{ if } m = 0 \end{cases}$$

Where $$R_n^m(\rho) = \sum_{s=0}^{(\frac{n-|m|}{2})-q} \frac{-1^s((n-s)!)(n-2s)}{s!\left(\left(\frac{n+|m|}{2}-s\right)!\right)\left(\left(\frac{n-|m|}{2}-s\right)!\right)}(\rho^{n-2s-2})$$

Where $$q = \begin{cases} 1, \text{ if } |m| \leq 1 \\ 0, \text{ otherwise} \end{cases}$$

Where n and m are radial and azimuthal components in a double index notation of Zernike polynomial and j is the Zernike coefficient in a single index notation scheme.

For example, list of rotationally symmetric Zernike power polynomial expansions up to $10^{th}$ order i.e. 5 rotationally symmetric terms are listed below:

$P = Z1*4*3\char`^(1/2) + Z2*5\char`^(1/2)*(24*R\char`^2-12) + Z3*7\char`^(1/2)*(120*R\char`^4-120*R\char`^2+24) + Z4*9\char`^(1/2)*(360*R\char`^2-840*R\char`^4+560*R\char`^6-40) + Z5*11\char`^(1/2)*(3360*R\char`^4-840*R\char`^2-5040*R\char`^6+2520*R\char`^8+60)$ Power distribution $= (1/r_{max}^2)*P$ The terms Z1, Z2, Z3, Z4 and Z5 in the above Zernike power polynomial expansion represent C(2,0), C(4,0), C(6,0), C(8,0) and C(10,0) coefficients, respectively.

Zernike power polynomials as described herein may be used to characterise the power profiles of certain embodiments. FIGS. 124 to 127 show the designed power profiles for some exemplary embodiments. FIGS. 119 to 123 show the power profiles for some commercially available multifocal lenses as measured on a commercially available Hartman-Shack based power profiling instrument named Optocraft (Optocraft Gmbh, Germany). Default settings for use of a multifocal lens were used to obtain measured data for commercial lenses. The commercial lenses were symmetric and only a cross section of the power profile was exported for the Zernike power polynomial fit analysis. In this example, the data density, i.e., the number of points used for the fitting analysis was were 400 from 0 to 4 mm in 0.01 mm steps on a half-chord of the optic zone of the lens. The same data density was used when fitting the exemplary embodiments to Zernike power polynomials. A least square approach was used to optimise the best coefficients for the chosen degree/order of the symmetric radial Zernike power polynomial. Once the optimisation routine was completed, the computational routine has resulted in two metrics, coefficient of determination ($R^2$) and root mean square error (RMSE), the smaller the RMSE, the better the fit and the higher the $R^2$ value, the better the fit. As used in this example, best fit means a fit with the lowest order mathematical function that results in a coefficient of determination ($R^2$) greater than 0.975 and/or a root mean square error (RMSE) less than 0.15 D. In cases where the optimisation procedure fails to fit a function that achieves the criteria of $R^2>0.975$ and RMSE<0.15 D, then the order of the function that produces the greatest $R^2$ and/or the lowest RMSE is used to characterise the power profile. However, such power profiles in this example do not meet the criteria of the exemplary embodiments. Certain embodiments may be characterised using radial Zernike power polynomials. Differences between conventional multifocals and exemplary embodiments are shown in tables 20 to 23. As shown in the tables 20 to 23, the number of substantially non-zero, symmetric, Zernike power polynomial coefficients required to best fit the power profiles of the exemplary embodiments is greater than the number of substantially non-zero, symmetric, Zernike power polynomial coefficients required to fit the power profiles of the measured conventional multifocals. As used in this example, best fit means a fit with the lowest order mathematical function that results in a coefficient of determination ($R^2$) greater than 0.975 and/or a root mean square error (RMSE) less than 0.15 D. In cases where the optimisation procedure fails to fit a function that achieves the criteria of $R^2>0.975$ and RMSE<0.15 D, then the order of the function that produces the greatest $R^2$ and/or the lowest RMSE is used to characterise the power profile. However, such power profiles in this example do not meet the criteria of the exemplary embodiments. As shown in tables 20 and 21, the conventional lenses are described by less than 20 coefficients which are non-zero (from C(2,0) to C(40,0)) as compared with the exemplary designs which are described by at least 20 non-zero coefficients. As can be seen from the values of $R^2$ and RMSE in table 21, the commercial designs multifocal 7 and multifocal 8 were reproduced with RMSE>0.25 D using Zernike power polynomials. In contrast, the $R^2$ and RMSE values of the exemplary embodiments 1 to 8 were reproduced with RMSE<0.15 D using Zernike power polynomials (tables 22 and 23) provided a sufficient number of coefficients were used in the calculations.

TABLE 20

Zernike Power Polynomial Coefficients - Commercial multifocals

| Coefficients | Multifocal 1 | Multifocal 2 | Multifocal 3 | Multifocal 4 | Multifocal 5 | Multifocal 6 |
|---|---|---|---|---|---|---|
| C(2,0)  | −2.000E+00 | −1.730E+00 | 7.670E−01  | −5.302E−01 | 6.207E−01  | −5.644E−01 |
| C(4,0)  | −8.010E−01 | −7.475E−01 | −5.321E−01 | −4.660E−01 | −5.859E−01 | −5.275E−01 |
| C(6,0)  | 4.681E−02  | 5.715E−02  | 2.280E−01  | 1.400E−01  | 1.509E−01  | 1.542E−01  |
| C(8,0)  | −4.288E−02 | 3.339E−02  | −1.358E−01 | −1.019E−01 | −6.840E−02 | 6.215E−03  |
| C(10,0) | 2.526E−02  | 1.053E−02  | 5.091E−02  | 5.116E−02  | −2.945E−02 | −4.029E−02 |
| C(12,0) | −1.937E−02 | −1.596E−03 | −4.997E−03 | −3.214E−03 | −1.958E−02 | −1.114E−02 |
| C(14,0) | 3.941E−03  | −3.284E−03 | −5.050E−03 | −1.427E−02 | 1.867E−02  | 7.429E−03  |
| C(16,0) | −7.450E−04 | −5.524E−05 | 1.852E−02  | 1.834E−02  | 2.936E−03  | 3.334E−03  |
| C(18,0) | −1.941E−03 | 1.374E−04  | −7.779E−03 | −1.267E−03 | −9.033E−03 | 7.043E−04  |
| C(20,0) | 3.780E−03  | −3.422E−04 | −3.408E−03 | −5.439E−03 | 8.539E−04  | −2.187E−03 |
| C(22,0) | 0 | 0 | 0 | 0 | 0 | 0 |
| C(24,0) | 0 | 0 | 0 | 0 | 0 | 0 |
| C(26,0) | 0 | 0 | 0 | 0 | 0 | 0 |
| C(28,0) | 0 | 0 | 0 | 0 | 0 | 0 |
| C(30,0) | 0 | 0 | 0 | 0 | 0 | 0 |
| C(32,0) | 0 | 0 | 0 | 0 | 0 | 0 |
| C(34,0) | 0 | 0 | 0 | 0 | 0 | 0 |
| C(36,0) | 0 | 0 | 0 | 0 | 0 | 0 |
| C(38,0) | 0 | 0 | 0 | 0 | 0 | 0 |
| C(40,0) | 0 | 0 | 0 | 0 | 0 | 0 |
| C(42,0) | 0 | 0 | 0 | 0 | 0 | 0 |
| C(44,0) | 0 | 0 | 0 | 0 | 0 | 0 |
| C(46,0) | 0 | 0 | 0 | 0 | 0 | 0 |
| C(48,0) | 0 | 0 | 0 | 0 | 0 | 0 |
| C(50,0) | 0 | 0 | 0 | 0 | 0 | 0 |
| C(52,0) | 0 | 0 | 0 | 0 | 0 | 0 |
| C(54,0) | 0 | 0 | 0 | 0 | 0 | 0 |
| C(56,0) | 0 | 0 | 0 | 0 | 0 | 0 |
| C(58,0) | 0 | 0 | 0 | 0 | 0 | 0 |
| C(60,0) | 0 | 0 | 0 | 0 | 0 | 0 |
| C(62,0) | 0 | 0 | 0 | 0 | 0 | 0 |
| C(64,0) | 0 | 0 | 0 | 0 | 0 | 0 |
| C(66,0) | 0 | 0 | 0 | 0 | 0 | 0 |

TABLE 20-continued

Zernike Power Polynomial Coefficients - Commercial multifocals

| Coefficients | Multifocal 1 | Multifocal 2 | Multifocal 3 | Multifocal 4 | Multifocal 5 | Multifocal 6 |
|---|---|---|---|---|---|---|
| C(68,0) | 0 | 0 | 0 | 0 | 0 | 0 |
| C(70,0) | 0 | 0 | 0 | 0 | 0 | 0 |
| R-Square | 1.00 | 1.00 | 1.00 | 1.00 | 1.00 | 1.00 |
| RMSE | 0.04 | 0.00 | 0.04 | 0.02 | 0.03 | 0.01 |

Figure 119:
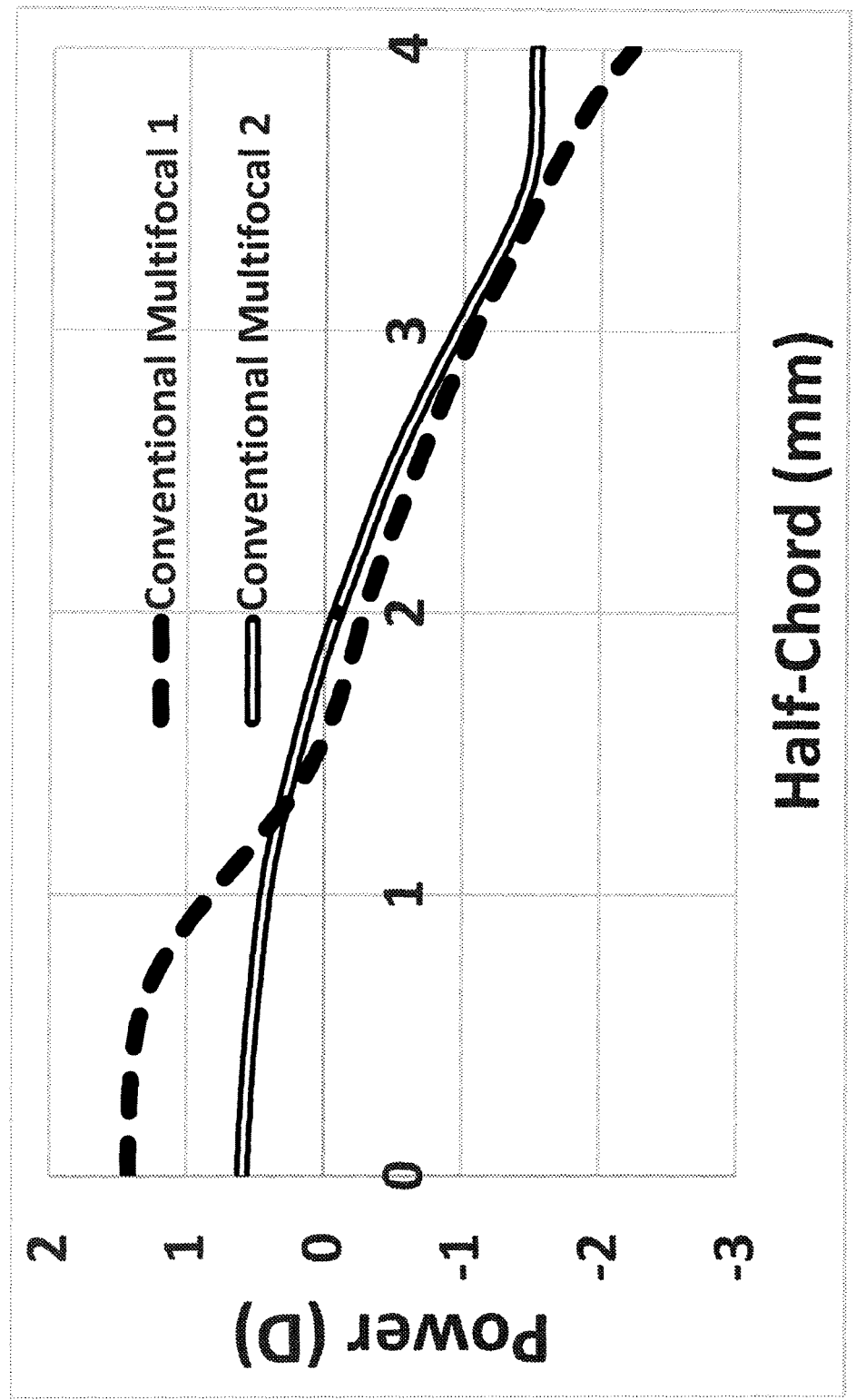
FIGS. 119 to 123 show the measured power profiles of 10 commercial contact lens designs across the half-chord diameter. These power profiles measurements were obtained on a commercial Hartmann-shack based power mapping system Optocraft (Optocraft Gmbh, Germany)
Figure 120:
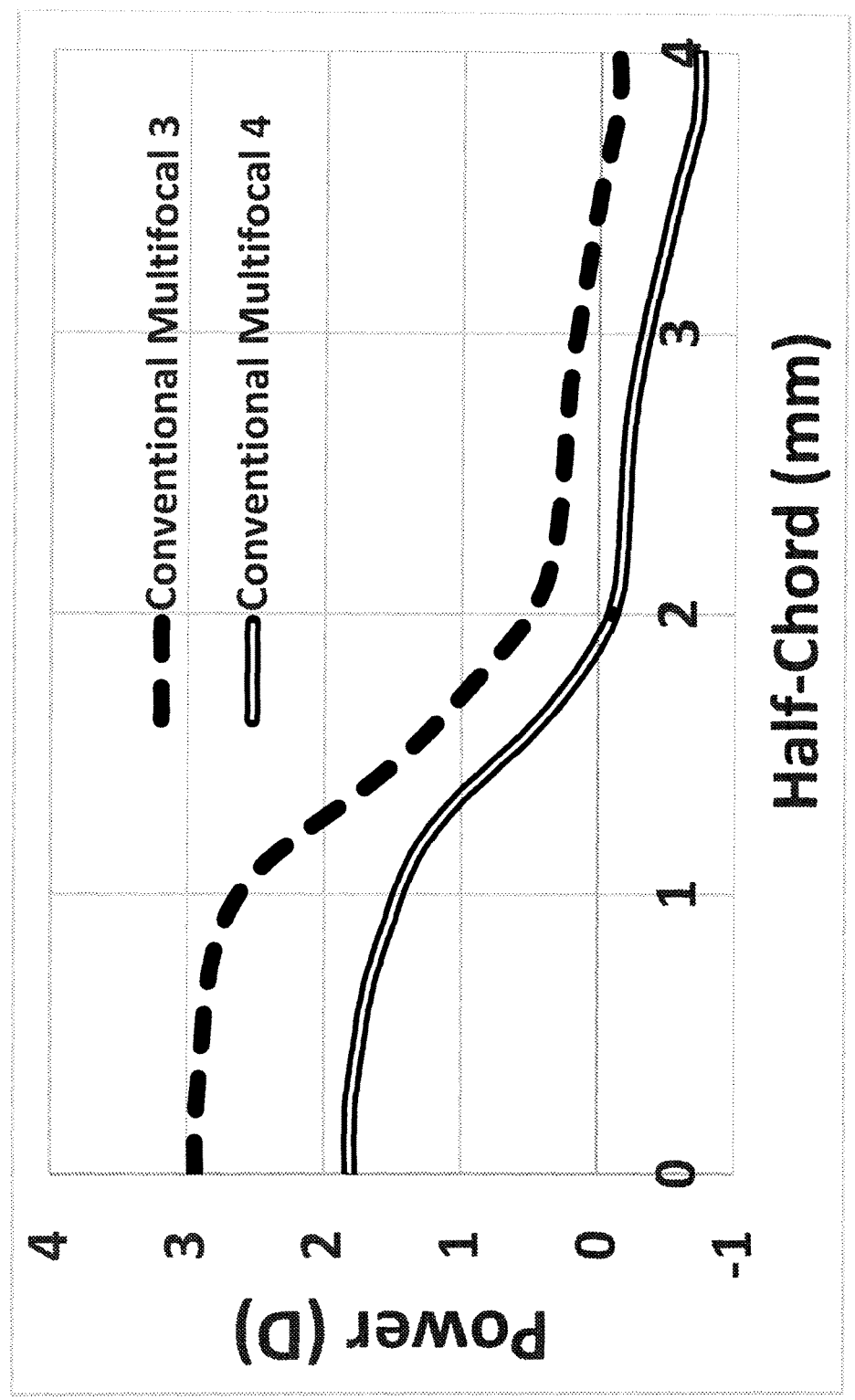
Figure 121:
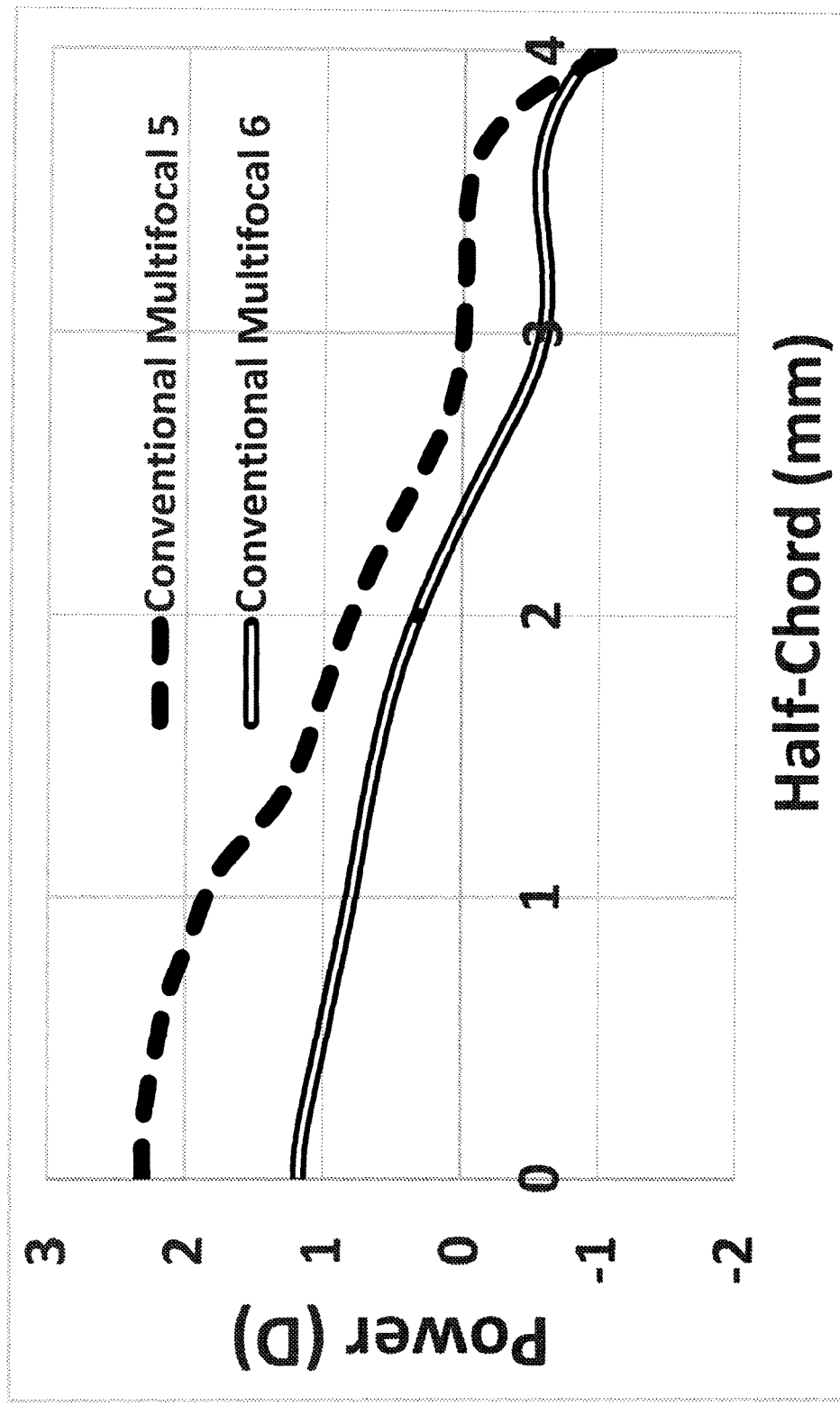
Figure 122:
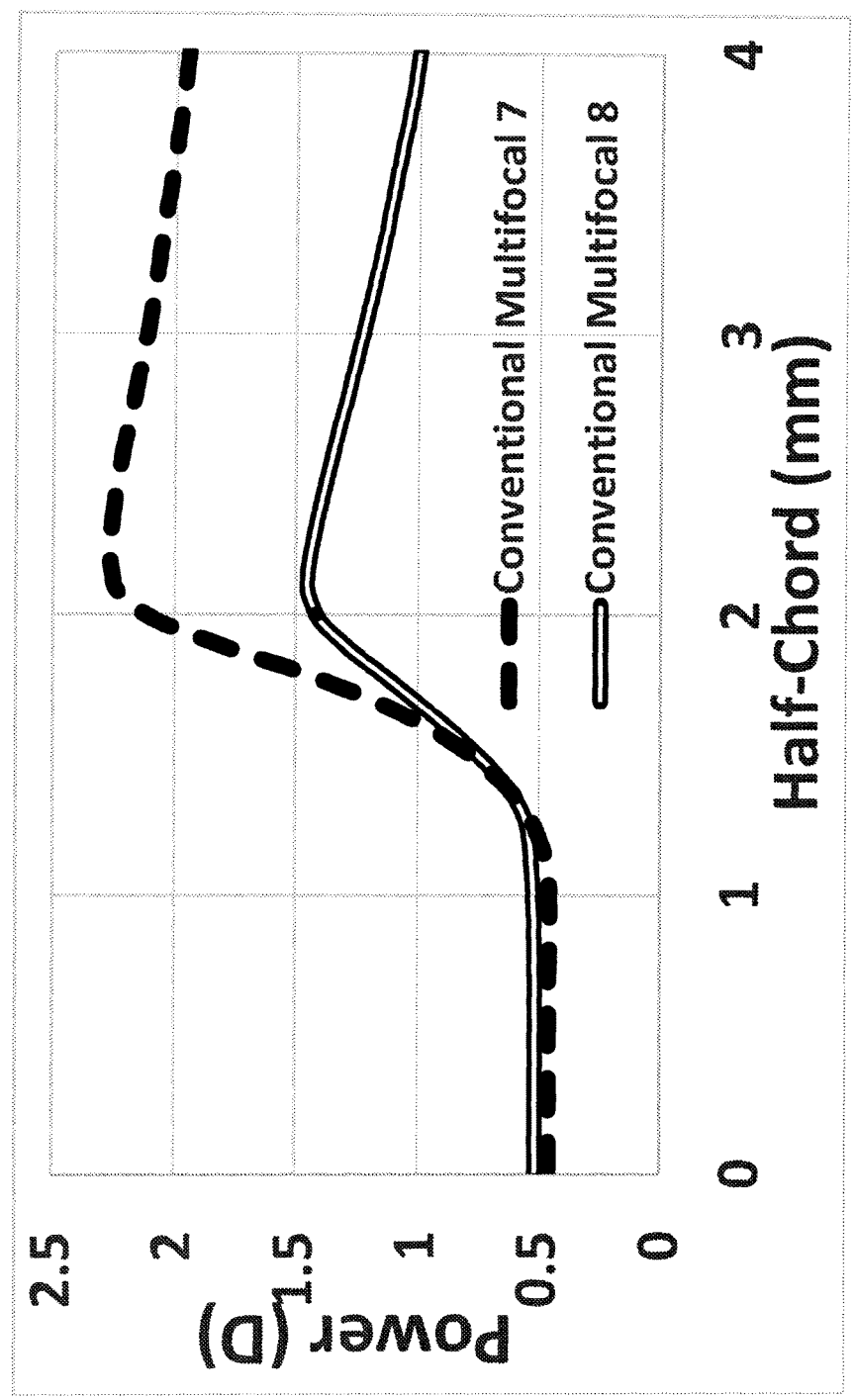
Figure 123:
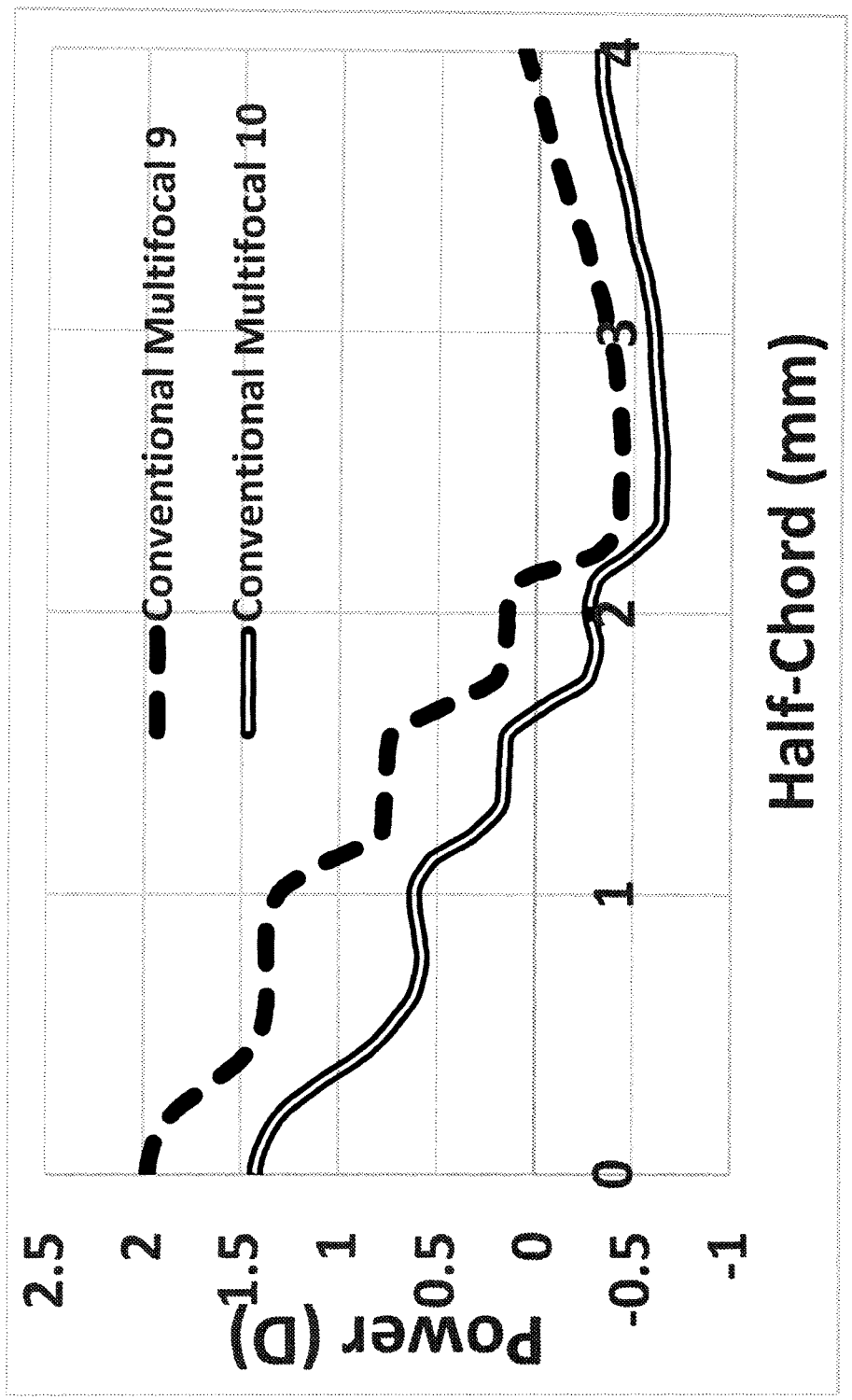
Figure 124:
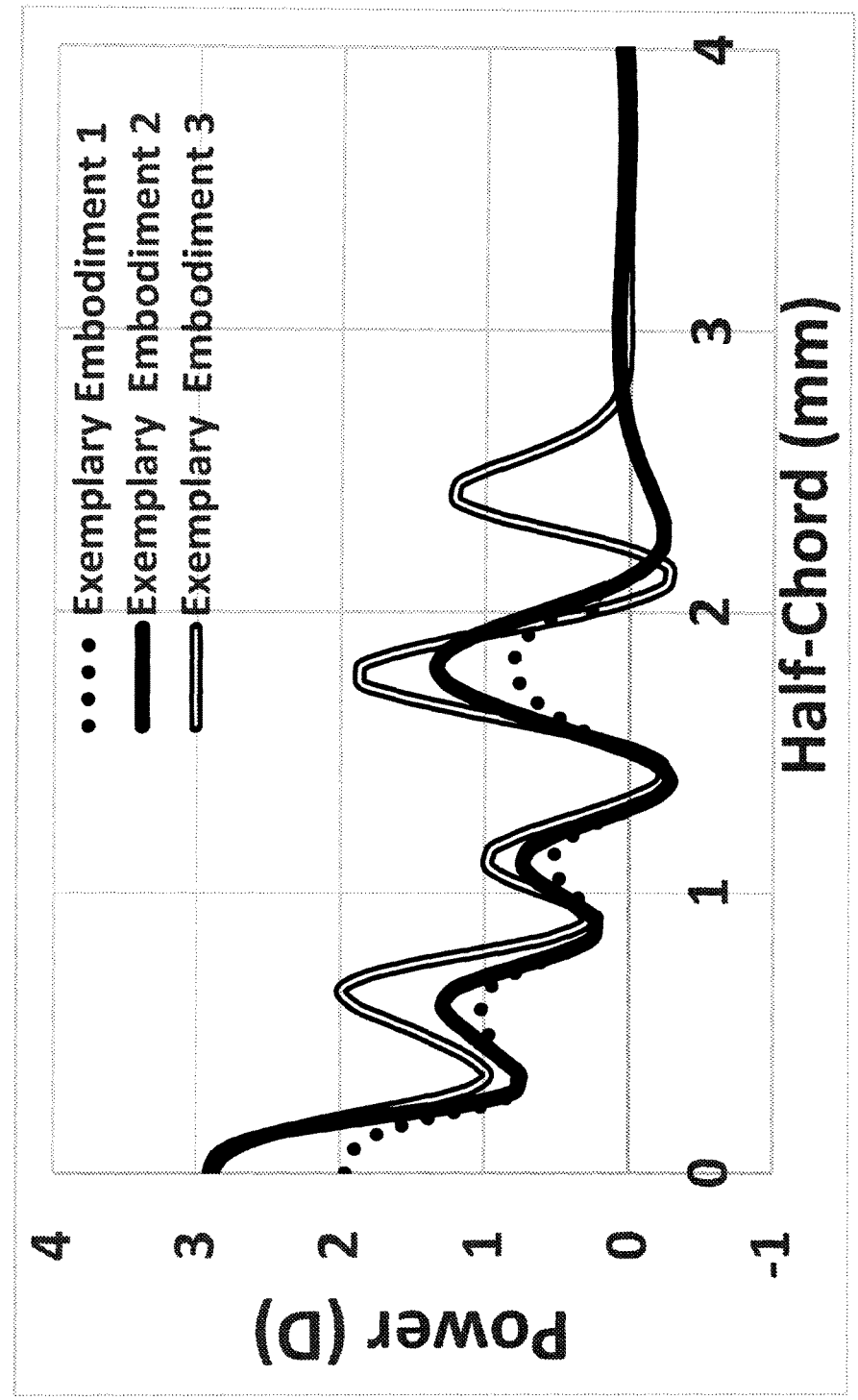
FIGS. 124 to 127 show the power profiles of 12 exemplary embodiments of contact lens designs across the half-chord diameter.
Figure 125:
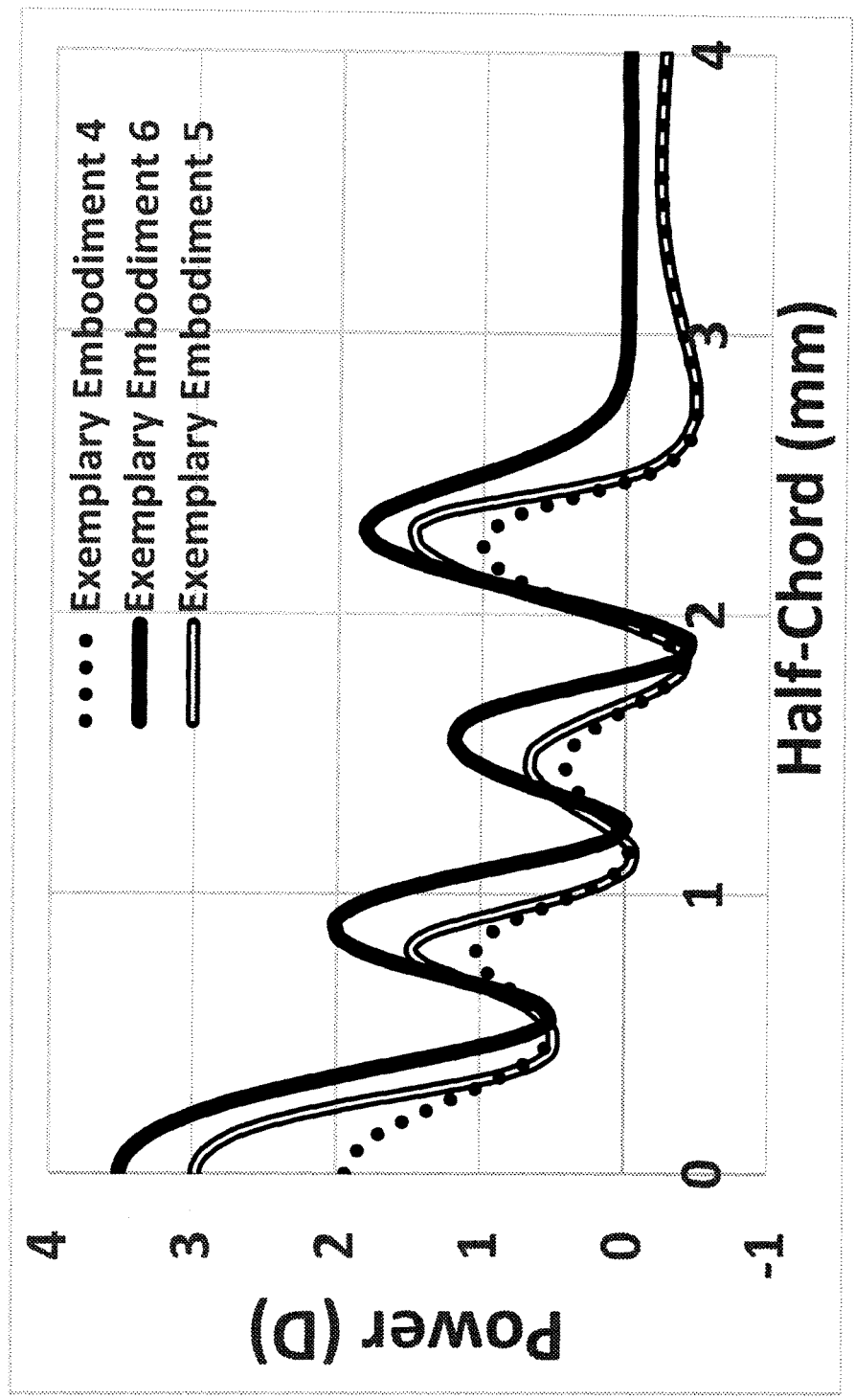
Figure 126:
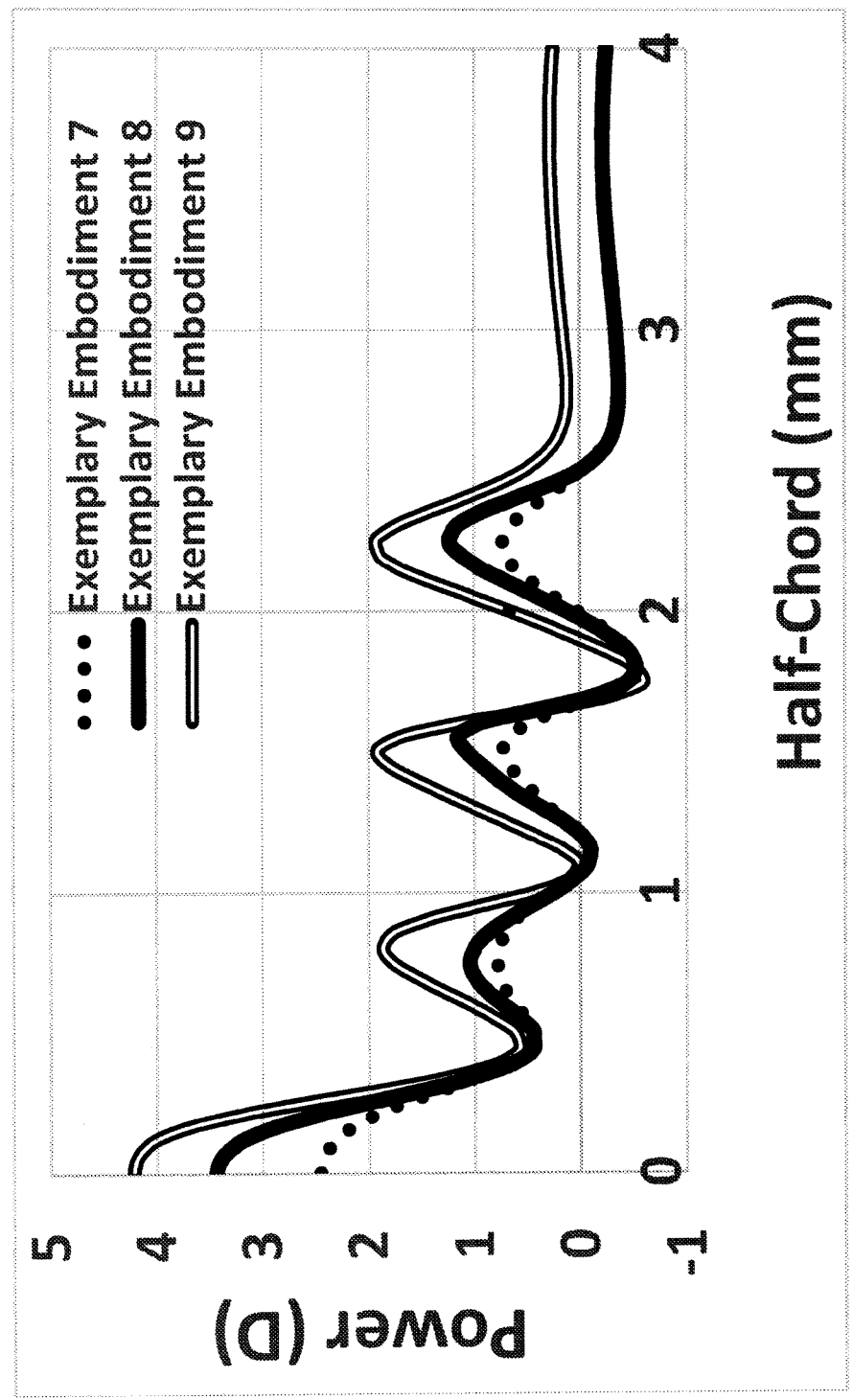
Figure 127:
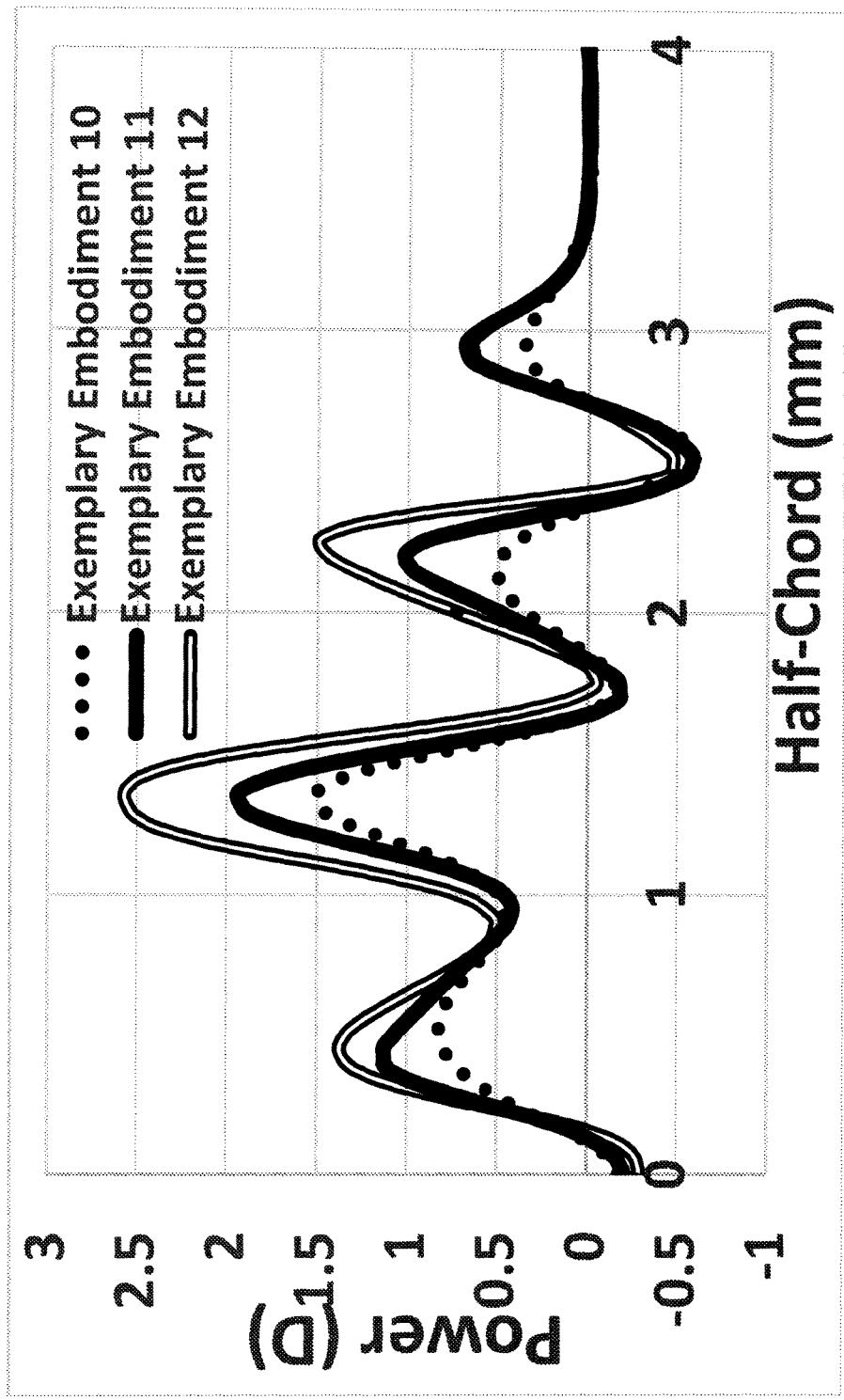
Figure 128:
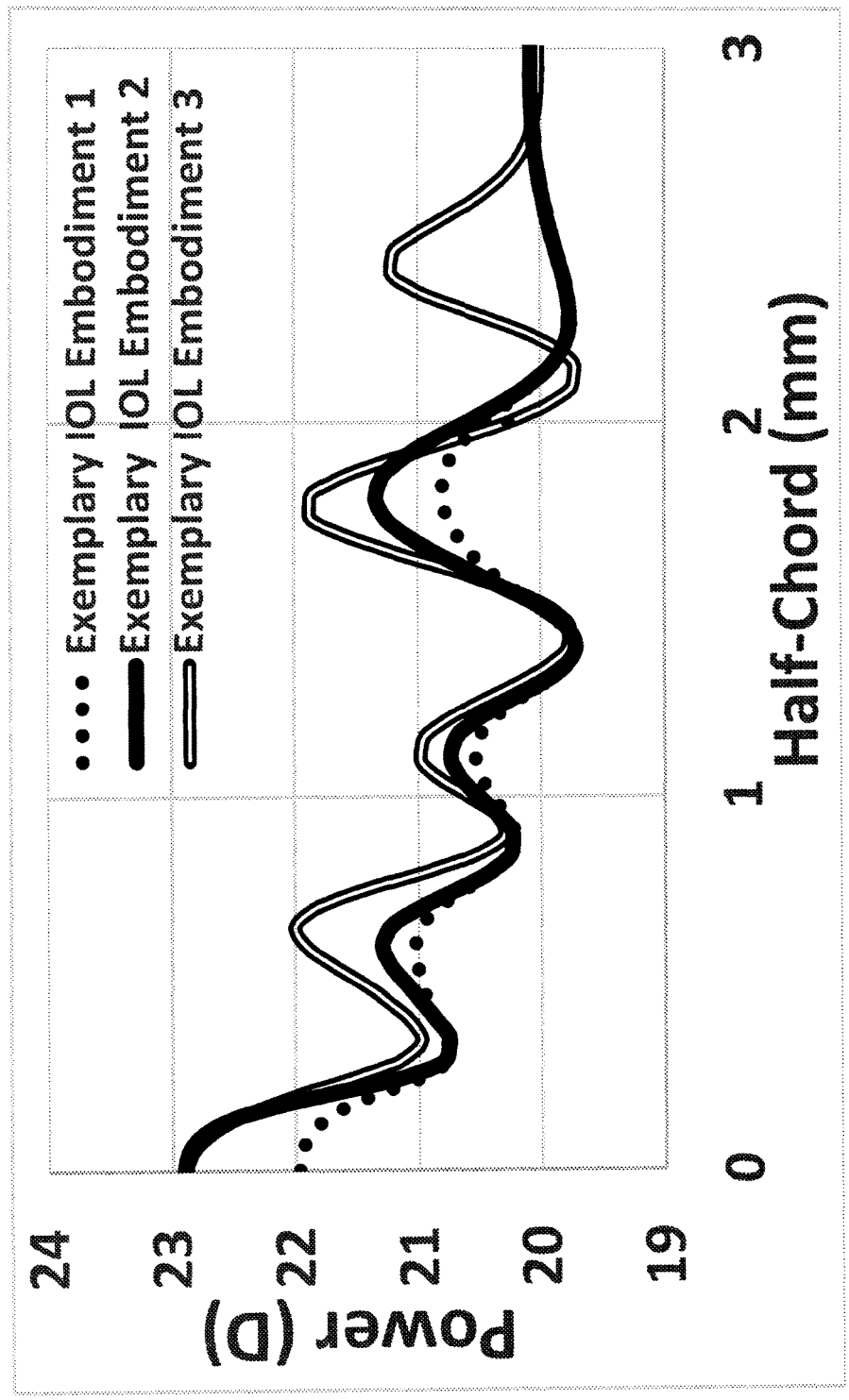
FIGS. 128 to 131 show the power profiles of 12 exemplary embodiments of intra-ocular lens designs across the half-chord diameter.
Figure 129:
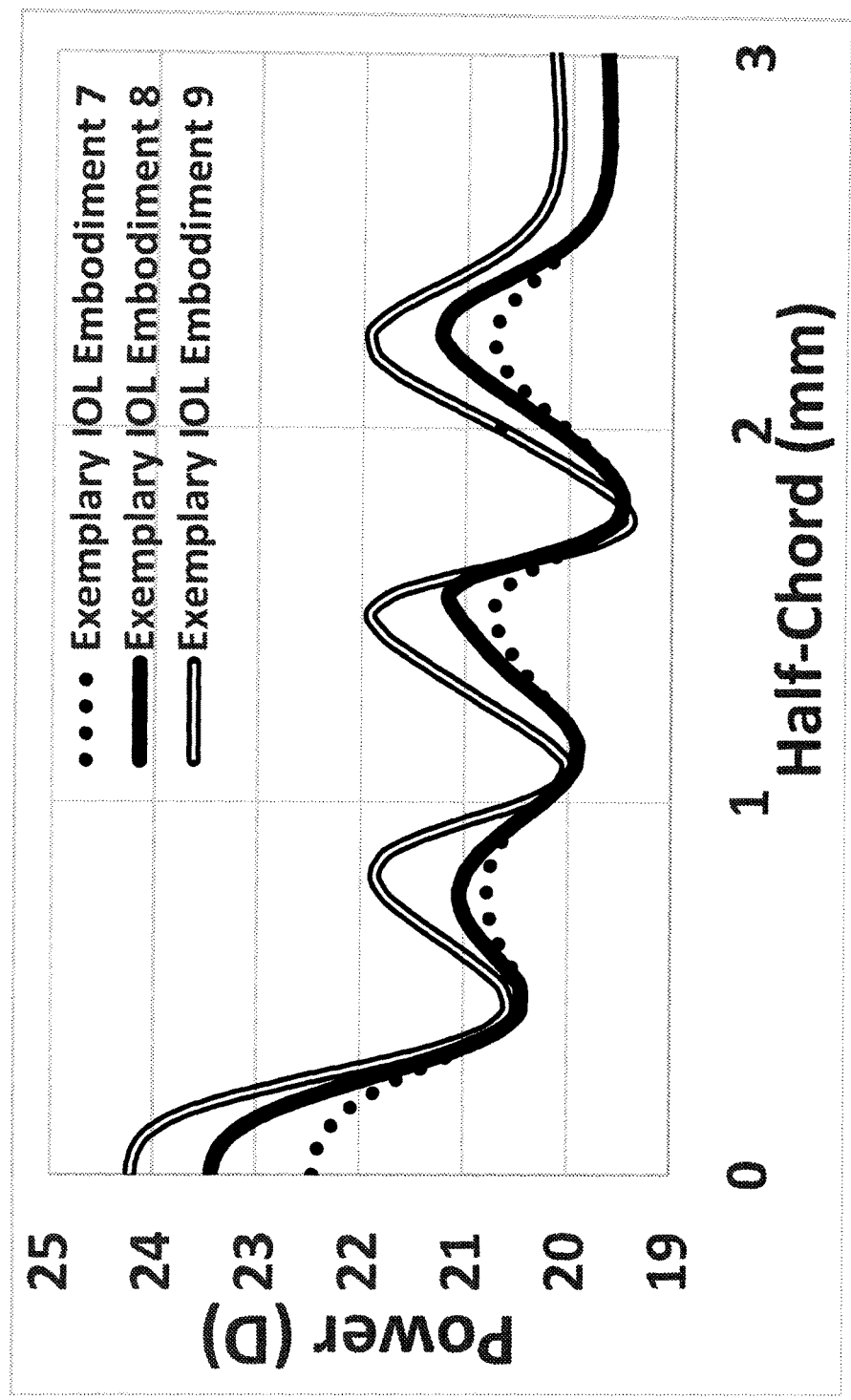
Figure 130:
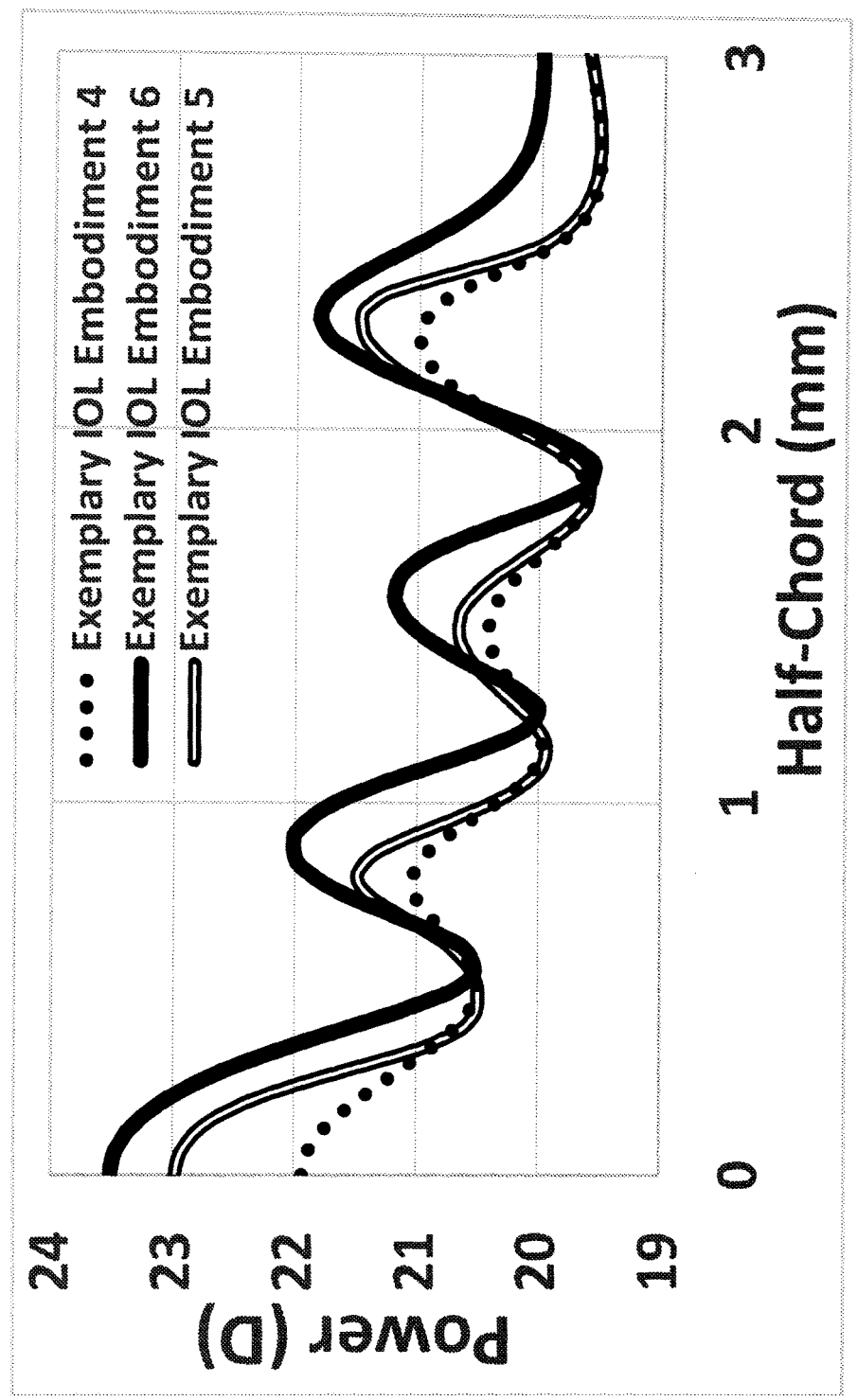
Figure 131:
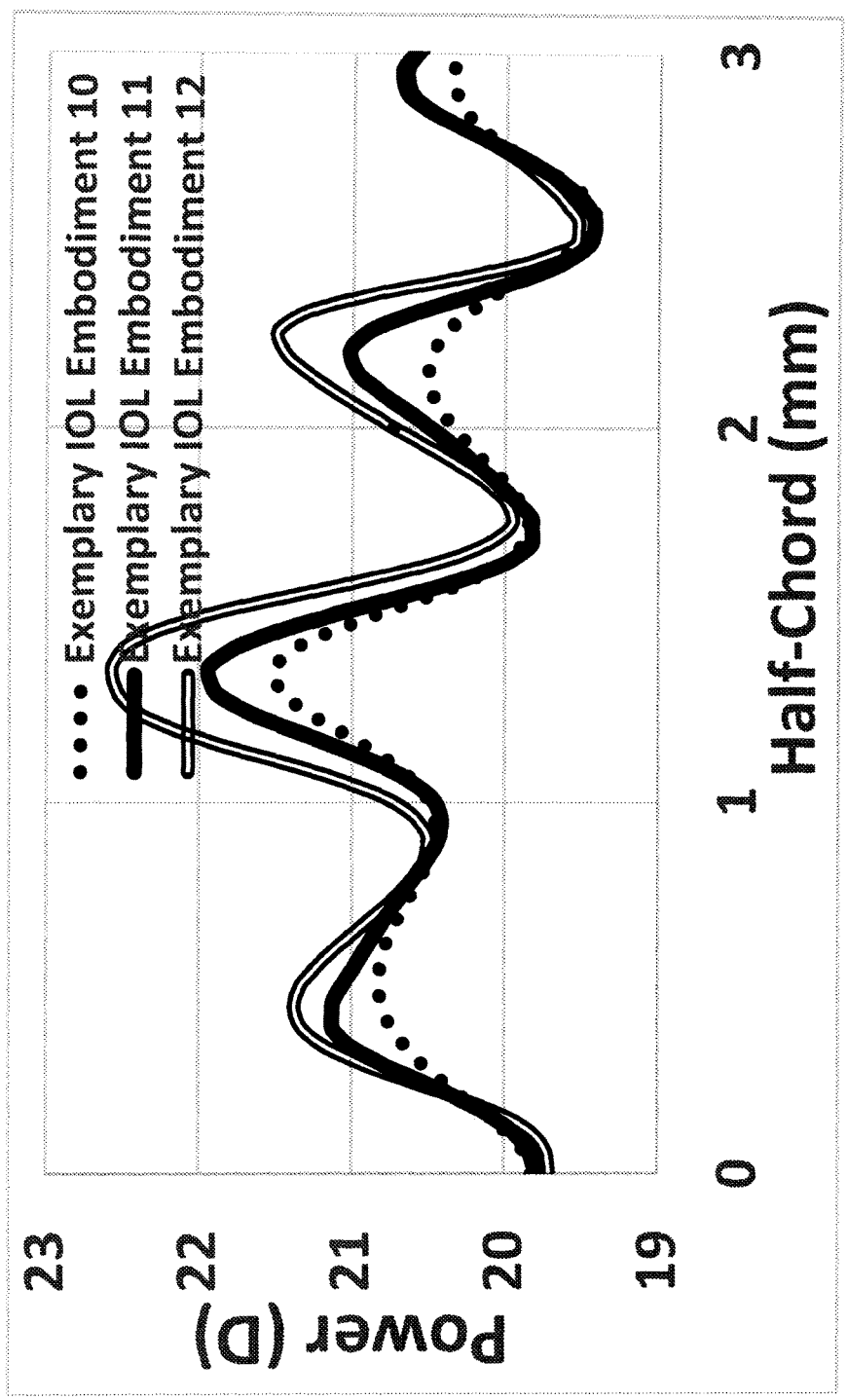

Table 20 shows the values of the rotationally symmetric coefficients when radial Zernike power polynomials are fitted to the power profiles described in FIGS. 119 and 120 via non-linear least square optimisation routine.

TABLE 21

Zernike Power Polynomial Coefficients - Commercial multifocals

| Coefficients | Multifocal 7 | Multifocal 8 | Multifocal 9 | Multifocal10 |
|---|---|---|---|---|
| C(2,0) | 2.000E+00 | 2.000E+00 | −3.513E−01 | −1.031E+00 |
| C(4,0) | 2.373E−01 | −9.382E−03 | −2.129E−01 | −1.436E−01 |
| C(6,0) | −2.674E−01 | −1.370E−01 | 2.835E−01 | 1.933E−01 |
| C(8,0) | 1.339E−01 | 8.387E−02 | −8.365E−02 | −6.085E−02 |
| C(10,0) | −1.370E−02 | −1.971E−02 | −9.280E−03 | 1.546E−03 |
| C(12,0) | −4.285E−02 | −1.437E−02 | 1.689E−02 | 6.472E−03 |
| C(14,0) | 4.462E−02 | 2.032E−02 | −4.245E−03 | −3.095E−03 |
| C(16,0) | −1.898E−02 | −1.025E−02 | −6.685E−03 | −1.626E−03 |
| C(18,0) | −2.518E−03 | 2.929E−05 | 5.956E−03 | −9.733E−05 |
| C(20,0) | 9.978E−03 | 5.319E−03 | 1.080E−03 | 1.764E−03 |
| C(22,0) | −5.685E−03 | −3.982E−03 | −5.456E−03 | −2.246E−03 |
| C(24,0) | −1.051E−03 | 7.688E−04 | 2.668E−03 | −5.335E−04 |
| C(26,0) | 4.671E−03 | 1.396E−03 | 7.324E−04 | 2.846E−03 |
| C(28,0) | −2.796E−03 | −1.348E−03 | −2.197E−03 | −1.714E−03 |
| C(30,0) | −4.901E−04 | 3.974E−04 | 1.157E−03 | −8.392E−04 |
| C(32,0) | 2.376E−03 | 3.274E−04 | 4.228E−03 | 2.467E−03 |
| C(34,0) | −1.938E−03 | −3.972E−04 | −5.684E−03 | −6.234E−04 |
| C(36,0) | 5.063E−04 | −6.133E−05 | −8.093E−03 | −6.723E−03 |
| C(38,0) | 3.930E−04 | 2.413E−04 | 5.137E−03 | 1.647E−03 |
| C(40,0) | −5.948E−04 | −2.563E−04 | 3.633E−03 | 3.610E−03 |
| C(42,0) | 0 | 0 | 0 | 0 |
| C(44,0) | 0 | 0 | 0 | 0 |
| C(46,0) | 0 | 0 | 0 | 0 |
| C(48,0) | 0 | 0 | 0 | 0 |
| C(50,0) | 0 | 0 | 0 | 0 |
| C(52,0) | 0 | 0 | 0 | 0 |
| C(54,0) | 0 | 0 | 0 | 0 |
| C(56,0) | 0 | 0 | 0 | 0 |
| C(58,0) | 0 | 0 | 0 | 0 |
| C(60,0) | 0 | 0 | 0 | 0 |
| C(62,0) | 0 | 0 | 0 | 0 |
| C(64,0) | 0 | 0 | 0 | 0 |
| C(66,0) | 0 | 0 | 0 | 0 |
| C(68,0) | 0 | 0 | 0 | 0 |
| C(70,0) | 0 | 0 | 0 | 0 |
| R-Square | 0.92 | 0.99 | 0.99 | 0.99 |
| RMSE | 1.02 | 0.32 | 0.07 | 0.05 |

Table 21 shows the rotationally symmetric coefficients when radial Zernike power polynomials are fitted to the power profiles described in FIGS. 119 and 120 via non-linear least square optimisation routines.

TABLE 22

Zernike Power Polynomial Coefficients - Exemplary embodiments

| Coefficients | # 1 | # 2 | # 3 | # 4 | # 5 | # 6 |
|---|---|---|---|---|---|---|
| C(2,0) | 2.701E−01 | 1.090E−01 | 4.976E−01 | −2.451E−01 | −7.169E−02 | 7.998E−01 |
| C(4,0) | 9.265E−03 | −1.897E−01 | −4.803E−01 | −2.952E−01 | −3.958E−01 | −4.814E−01 |
| C(6,0) | 1.650E−01 | 1.287E−01 | −2.196E−02 | 6.502E−02 | 6.074E−02 | −3.564E−02 |
| C(8,0) | 4.288E−02 | −2.355E−02 | 4.919E−02 | 4.613E−02 | 7.780E−02 | 7.893E−02 |
| C(10,0) | 3.964E−02 | −4.354E−02 | 1.352E−02 | −5.739E−02 | −6.837E−02 | −6.449E−03 |
| C(12,0) | 8.367E−02 | 5.164E−02 | 1.895E−02 | −6.077E−02 | −8.238E−02 | −1.187E−61 |
| C(14,0) | 4.264E−02 | 2.743E−03 | 6.990E−02 | 6.374E−02 | 8.132E−02 | 4.934E−02 |
| C(16,0) | −5.268E−03 | −4.641E−02 | 4.742E−02 | −4.232E−03 | 9.194E−04 | 3.829E−02 |
| C(18,0) | 5.682E−02 | 4.436E−02 | 4.552E−02 | −4.960E−02 | −6.504E−02 | −6.596E−02 |
| C(20,0) | 1.639E−02 | −7.830E−03 | −2.472E−02 | 2.458E−02 | 2.871E−02 | 5.812E−04 |
| C(22,0) | −8.215E−03 | −2.349E−02 | 1.697E−02 | 1.986E−02 | 3.005E−62 | 4.089E−02 |
| C(24,0) | 2.697E−02 | 3.900E−02 | 3.630E−02 | −3.311E−02 | −4.169E−02 | −2.929E−02 |
| C(26,0) | 1.995E−03 | 3.267E−03 | −4.724E−02 | 3.313E−03 | 2.996E−03 | −2.071E−02 |
| C(28,0) | −5.664E−03 | 2.797E−03 | 3.182E−03 | 2.268E−02 | 3.177E−02 | 3.920E−02 |
| C(30,0) | 1.375E−02 | 3.423E−02 | 3.652E−02 | −2.046E−02 | −2.729E−02 | −2.058E−02 |
| C(32,0) | −1.324E−03 | −1.079E−03 | −2.749E−02 | 2.766E−03 | 2.571E−03 | −1.174E−02 |
| C(34,0) | 3.083E−03 | 2.599E−03 | 9.379E−03 | 1.049E−02 | 1.431E−02 | 2.986E−02 |
| C(36,0) | 7.837E−03 | 1.043E−02 | 3.214E−02 | −1.021E−02 | −1.326E−02 | −2.012E−02 |
| C(38,0) | −4.608E−03 | −1.179E−02 | −1.855E−02 | 2.176E−03 | 2.590E−03 | 1.829E−03 |
| C(40,0) | 1.366E−03 | 2.618E−03 | 6.700E−03 | 2.759E−03 | 2.657E−03 | 4.219E−03 |
| C(42,0) | −2.510E−03 | −1.903E−03 | 3.675E−03 | 3.145E−03 | 7.994E−03 | −9.116E−04 |
| C(44,6) | −2.890E−03 | −5.774E−03 | −8.602E−03 | −2.827E−03 | −4.593E−03 | 3.930E−03 |
| C(46,0) | −4.175E−03 | 2.191E−03 | 5.087E−03 | −1.646E−03 | −5.412E−03 | −1.896E−03 |
| C(48,0) | −9.448E−03 | −4.915E−03 | −1.174E−02 | 1.578E−03 | 2.248E−03 | 5.931E−04 |
| C(50,0) | −1.229E−03 | 1.698E−04 | −7.154E−03 | −2.359E−04 | −9.947E−05 | −7.696E−64 |
| C(52,0) | 6.378E−05 | 2.473E−05 | −3.380E−04 | −1.371E−05 | 0 | 0 |
| C(54,0) | −2.373E−05 | −1.326E−04 | −9.104E−05 | 1.285E−06 | 0 | 0 |

TABLE 22-continued

Zernike Power Polynomial Coefficients - Exemplary embodiments

| Coefficients | # 1 | # 2 | # 3 | # 4 | # 5 | # 6 |
| --- | --- | --- | --- | --- | --- | --- |
| C(56,0) | −5.117E−06 | 9.333E−06 | −7.328E−06 | 2.907E−07 | 0 | 0 |
| C(58,0) | −5.115E−07 | 3.441E−06 | −2.362E−06 | 9.186E−08 | 0 | 0 |
| C(60,0) | −3.461E−07 | 5.216E−07 | −6.425E−07 | −3.161E−09 | 0 | 0 |
| C(62,0) | −6.527E−09 | 7.916E−08 | −1.240E−08 | 0 | 0 | 0 |
| C(64,0) | 1.110E−08 | 2.701E−09 | 1.824E−08 | 0 | 0 | 0 |
| C(66,0) | 2.215E−09 | −1.140E−09 | 4.189E−09 | 0 | 0 | 0 |
| C(68,0) | −3.861E−11 | 7.350E−10 | −1.738E−10 | 0 | 0 | 0 |
| C(70,0) | −9.018E−11 | 2.412E−10 | −1.065E−10 | 0 | 0 | 0 |
| R-Square | 0.989 | 0.987 | 0.978 | 0.996 | 0.993 | 0.997 |
| RMSE | 0.053 | 0.091 | 0.120 | 0.037 | 0.071 | 0.052 |

Table 22 shows the rotationally symmetric coefficients when radial Zernike power polynomials are fitted to the power profiles described in FIGS. 119 and 120 via non-linear least square optimisation routines.

TABLE 23

Zernike Power Polynomial Coefficients - Exemplary embodiments

| Coefficients | # 7 | # 8 | # 9 | # 10 | # 11 | # 12 |
| --- | --- | --- | --- | --- | --- | --- |
| C(2,0) | −2.718E−01 | 3.513E−02 | 9.938E−01 | 2.762E−01 | 4.384E−01 | 6.345E−01 |
| C(4,0) | −3.044E−01 | −2.457E−01 | −4.241E−01 | −1.478E−01 | −3.311E−01 | −6.140E−01 |
| C(6,0) | 2.888E−02 | 1.778E−01 | −9.882E−03 | 1.035E−01 | 9.858E−03 | 4.338E−02 |
| C(8,0) | 9.957E−03 | 1.454E−01 | 4.060E−02 | −9.408E−02 | −1.312E−01 | −8.419E−02 |
| C(10,0) | −4.792E−02 | 6.128E−03 | −5.843E−02 | 4.744E−03 | −1.743E−02 | −3.853E−03 |
| C(12,0) | −5.411E−02 | −1.741E−02 | −7.895E−02 | 5.040E−02 | 4.700E−02 | 6.687E−02 |
| C(14,0) | 3.068E−02 | 7.079E−02 | 4.684E−02 | −1.064E−02 | −6.289E−03 | 1.747E−02 |
| C(16,6) | 4.469E−03 | 2.097E−02 | 1.081E−02 | −1.968E−02 | −2.008E−02 | 2.461E−02 |
| C(18,0) | −3.885E−02 | −4.246E−02 | −6.860E−02 | −1.601E−02 | −1.649E−02 | −2.264E−02 |
| C(20,0) | 6.136E−03 | 1.631E−02 | 2.199E−02 | 3.810E−02 | 5.419E−02 | 5.810E−02 |
| C(22,0) | 2.392E−02 | 4.266E−02 | 3.962E−02 | 5.185E−04 | −6.705E−03 | 9.668E−03 |
| C(24,0) | −3.189E−02 | −3.112E−02 | −5.811E−02 | −4.185E−02 | −7.439E−02 | −9.184E−02 |
| C(26,0) | −2.211E−03 | 1.025E−02 | 9.437E−03 | 2.936E−02 | 2.953E−02 | 3.758E−02 |
| C(28,0) | 1.934E−02 | 4.138E−02 | 3.565E−02 | 6.849E−03 | −1.677E−03 | 1.532E−02 |
| C(30,0) | −1.835E−02 | −2.151E−02 | −3.963E−02 | −2.004E−02 | −4.252E−02 | −4.233E−02 |
| C(32,0) | 9.752E−03 | 1.168E−02 | 1.381E−02 | 9.819E−03 | 5.167E−03 | 1.880E−02 |
| C(34,0) | 5.949E−03 | 1.950E−02 | 7.644E−03 | −5.173E−04 | −3.188E−03 | 1.139E−02 |
| C(36,0) | −1.655E−02 | −1.732E−02 | −1.850E−02 | 6.727E−04 | 1.212E−03 | −1.202E−03 |
| C(38,0) | 8.307E−03 | 2.627E−03 | 1.695E−02 | −1.782E−03 | 2.440E−03 | −1.835E−03 |
| C(40,0) | 2.834E−03 | −3.172E−03 | −1.300E−02 | −1.257E−03 | 1.807E−03 | 2.872E−03 |
| C(42,0) | −3.808E−04 | 1.470E−04 | 4.063E−03 | 6.737E−03 | 5.411E−03 | 3.155E−03 |
| C(44,0) | 1.134E−04 | 5.987E−04 | 1.427E−02 | −2.124E−03 | −9.658E−04 | −5.987E−03 |
| C(46,0) | 9.160E−04 | −7.718E−03 | −2.066E−03 | −4.028E−03 | 4.675E−03 | 1.837E−03 |
| C(48,0) | 9.550E−04 | −3.049E−03 | −3.622E−03 | 1.434E−03 | 4.284E−03 | 3.482E−03 |
| C(50,0) | −9.903E−04 | 1.617E−03 | −1.907E−03 | 3.087E−04 | −2.538E−03 | −3.251E−03 |
| C(52,0) | 0 | 2.347E−04 | 0 | 0 | −3.804E−04 | −7.959E−04 |
| C(54,0) | 0 | −5.306E−05 | 0 | 0 | 5.870E−05 | −6.750E−05 |
| C(56,0) | 0 | 2.745E−06 | 0 | 0 | −8.670E−06 | −3.545E−06 |
| C(58,0) | 0 | 2.304E−06 | 0 | 0 | −3.880E−06 | −1.224E−06 |
| C(60,0) | 0 | 1.550E−07 | 0 | 0 | −4.224E−07 | −1.016E−07 |
| C(62,0) | 0 | 5.520E−08 | 0 | 0 | −7.297E−08 | 4.568E−08 |
| C(64,0) | 0 | 5.160E−09 | 0 | 0 | −2.535E−09 | 8.645E−09 |
| C(66,0) | 0 | −7.325E−10 | 0 | 0 | 1.309E−09 | 1.429E−09 |
| C(68,0) | 0 | 2.637E−10 | 0 | 0 | −5.515E−10 | −4.969E−10 |
| C(70,0) | 0 | 6.793E−11 | 0 | 0 | −1.313E−10 | −2.628E−11 |
| R-Square | 0.991 | 0.990 | 0.976 | 0.995 | 0.994 | 0.985 |
| RMSE | 0.064 | 0.088 | 0.158 | 0.033 | 0.045 | 0.094 |

Table 23 shows the rotationally symmetric coefficients when radial Zernike power polynomials are fitted to the power profiles described in FIGS. 119 and 120 via non-linear least square optimisation routines.

In certain embodiments, a lens comprising: an optical axis; at least two surfaces; wherein the lens has a power profile, the power profile may be reproduced by using at least 30 or 40 non-zero, symmetric, Zernike power polynomial coefficients. In certain embodiments, the power profile may be reproduced by using at least 28, 30, 40, 50, 60, 70 or 80 non-zero, symmetric, Zernike power polynomials. In certain embodiments, the power profile may be reproduced by using between 30 to 40, 30 to 50 or 40 to 80 non-zero, symmetric, Zernike power polynomial coefficients. In certain embodiments, the power profile may be reproduced by using between 30 to 80, 30 to 70 or 30 to 50 non-zero, symmetric, Zernike power polynomial coefficients. In some embodiments, one or more of the Zernike power polynomial coefficients may be zero as long as the highest order Zernike power polynomial coefficients is non-zero or substantially non-zero. For example, a $20^{th}$ order Zernike power polynomial may have a $20^{th}$ order Zernike power polynomial coefficient that is non-zero, or substantially non-zero, while at the same time one or more of the Zernike power polynomial coefficients for orders below the 20$^{th}$ may have zero value.

Section 25

Descriptors of Power Profiles with Use of Fourier Series

Fourier series expansion of the generic form is (rotationally symmetric) given below:

$$P(\rho) = C + \sum_{i=1}^{n} a_i(\cos(\rho)) + b_i(\sin(\rho))$$

where i=1 to n, where i is an integer and n is the order of Fourier series considered; C is the constant; ρ is the radial co-ordinate of power profile; $a_i$ and $b_i$ are the coefficients of the Fourier expansion of the i$^{th}$ order.

Fourier series as described herein may be used to characterise the power profiles of certain embodiments. FIGS. 124 to 127 show the designed power profiles for some exemplary embodiments. FIGS. 119 to 123 show the power profiles for some commercially available multifocal lenses as measured on a commercially available Hartman-Shack based power profiling instrument named Optocraft (Optocraft Gmbh, Germany). Default settings for use of a multifocal lens were used to obtain measured data for commercial lenses. The commercial lenses were symmetric and a cross section of the power profile was exported for the Fourier series fit analysis. In this example, the data density, i.e. the number of points used for the fitting analysis was 400, from 0 to 4 mm in 0.01 mm steps on a half-chord of the optic zone of the lens. The same data density was used when fitting the exemplary embodiments to Fourier series. A least square approach was used to optimise the best coefficients for the chosen degree or order of the Fourier series. Once the optimisation routine was completed, the computational routine has resulted in two metrics, coefficient of determination ($R^2$) and root mean square error (RMSE), the smaller the RMSE, the better the fit and the higher the $R^2$ value, the better the fit. As used in this example, best fit means a fit with the lowest order mathematical function that results in a coefficient of determination ($R^2$) greater than 0.975 and/or a root mean square error (RMSE) less than 0.15 D. In cases where the optimisation procedure fails to fit a function that achieves the criteria of $R^2$>0.975 and RMSE<0.15 D, then the order of the function that produces the greatest $R^2$ and/or the lowest RMSE is used to characterise the power profile. However, such power profiles in this example do not meet the criteria of the exemplary embodiments. Tables 24 to 27 shows the coefficient values of the Fourier series expansion up to 15$^{th}$ order obtained when the power profiles described in FIGS. 119 and 120 are best fitted to the described Fourier series expansion via non-linear least square optimisation routines. In this example, the conventional lenses are described by less than 4 orders of the Fourier series which have non-zero coefficients, in contrast, the exemplary designs need at least 8 orders of the Fourier series which have non-zero coefficients to be reproduced with an RMSE<0.15 D.

In certain embodiments, a lens comprising: an optical axis; at least two surfaces; wherein the lens has a power profile, the power profile may be reproduced by using at least 6, 8, 10, 12, 15$^{th}$ order of the Fourier series expansion which have substantially non-zero coefficients.

TABLE 24

Fourier Series Coefficients - Commercial multifocals

| Coefficients | Multi-focal 1 | Multi-focal 2 | Multi-focal 3 | Multi-focal 4 | Multi-focal 5 | Multi-focal 6 |
|---|---|---|---|---|---|---|
| C | −0.408 | −0.355 | 0.946 | 0.221 | 0.237 | −0.067 |
| a1 | 1.280 | 0.840 | 1.287 | 1.011 | 0.793 | 0.657 |
| b1 | 0.940 | 0.592 | 0.828 | 0.704 | 1.568 | 0.846 |
| a2 | 0.493 | 0.067 | 0.470 | 0.393 | 0.833 | 0.333 |
| b2 | −0.082 | −0.179 | 0.358 | 0.219 | 0.410 | 0.114 |
| a3 | 0 | 0 | 0 | 0 | 0.248 | 0.173 |
| b3 | 0 | 0 | 0 | 0 | −0.217 | −0.164 |
| a4 | 0 | 0 | 0 | 0 | 0 | 0 |
| b4 | 0 | 0 | 0 | 0 | 0 | 0 |
| a5 | 0 | 0 | 0 | 0 | 0 | 0 |
| b5 | 0 | 0 | 0 | 0 | 0 | 0 |
| a6 | 0 | 0 | 0 | 0 | 0 | 0 |
| b6 | 0 | 0 | 0 | 0 | 0 | 0 |
| a7 | 0 | 0 | 0 | 0 | 0 | 0 |
| b7 | 0 | 0 | 0 | 0 | 0 | 0 |
| a8 | 0 | 0 | 0 | 0 | 0 | 0 |
| b8 | 0 | 0 | 0 | 0 | 0 | 0 |
| a9 | 0 | 0 | 0 | 0 | 0 | 0 |
| b9 | 0 | 0 | 0 | 0 | 0 | 0 |
| a10 | 0 | 0 | 0 | 0 | 0 | 0 |
| b10 | 0 | 0 | 0 | 0 | 0 | 0 |
| a11 | 0 | 0 | 0 | 0 | 0 | 0 |
| b11 | 0 | 0 | 0 | 0 | 0 | 0 |
| a12 | 0 | 0 | 0 | 0 | 0 | 0 |
| b12 | 0 | 0 | 0 | 0 | 0 | 0 |
| a13 | 0 | 0 | 0 | 0 | 0 | 0 |
| b13 | 0 | 0 | 0 | 0 | 0 | 0 |
| a14 | 0 | 0 | 0 | 0 | 0 | 0 |
| b14 | 0 | 0 | 0 | 0 | 0 | 0 |
| a15 | 0 | 0 | 0 | 0 | 0 | 0 |
| b15 | 0 | 0 | 0 | 0 | 0 | 0 |
| RSq | 0.999 | 0.999 | 0.996 | 0.993 | 0.995 | 0.998 |
| RMSE | 0.042 | 0.019 | 0.078 | 0.075 | 0.069 | 0.033 |

Table 24 shows the values of the coefficients of the Fourier series expansion (up to 15$^{th}$ order) obtained when the power profiles described in FIGS. 119 to 123 are best fitted to Fourier series expansion via non-linear least square optimisation routines.

TABLE 25

Fourier Series Coefficients - Commercial multifocals

| Coefficients | Multifocal 7 | Multifocal 8 | Multifocal 9 | Multifocal10 |
|---|---|---|---|---|
| C | 2.093 | 1.307 | 1.158 | 0.268 |
| a1 | −0.307 | −0.071 | 1.551 | 1.065 |
| b1 | −1.393 | −0.655 | −0.875 | −0.159 |
| a2 | −0.636 | −0.389 | −0.219 | 0.262 |
| b2 | −1.018 | −0.587 | −0.514 | −0.170 |
| a3 | −0.451 | −0.247 | −0.350 | −0.005 |
| b3 | 0.211 | 0.128 | −0.121 | −0.252 |
| a4 | −0.143 | −0.047 | −0.042 | −0.043 |
| b4 | 0.321 | 0.194 | 0.085 | −0.071 |
| a5 | 0 | 0 | 0 | 0 |
| b5 | 0 | 0 | 0 | 0 |
| a6 | 0 | 0 | 0 | 0 |
| b6 | 0 | 0 | 0 | 0 |
| a7 | 0 | 0 | 0 | 0 |
| b7 | 0 | 0 | 0 | 0 |
| a8 | 0 | 0 | 0 | 0 |
| b8 | 0 | 0 | 0 | 0 |
| a9 | 0 | 0 | 0 | 0 |
| b9 | 0 | 0 | 0 | 0 |
| a10 | 0 | 0 | 0 | 0 |
| b10 | 0 | 0 | 0 | 0 |
| a11 | 0 | 0 | 0 | 0 |
| b11 | 0 | 0 | 0 | 0 |
| a12 | 0 | 0 | 0 | 0 |
| b12 | 0 | 0 | 0 | 0 |
| a13 | 0 | 0 | 0 | 0 |

TABLE 25-continued

Fourier Series Coefficients - Commercial multifocals

| Coefficients | Multifocal 7 | Multifocal 8 | Multifocal 9 | Multifocal 10 |
|---|---|---|---|---|
| b13 | 0 | 0 | 0 | 0 |
| a14 | 0 | 0 | 0 | 0 |
| b14 | 0 | 0 | 0 | 0 |
| a15 | 0 | 0 | 0 | 0 |
| b15 | 0 | 0 | 0 | 0 |
| RSq | 0.996 | 0.996 | 0.990 | 0.991 |
| RMSE | 0.021 | 0.047 | 0.078 | 0.061 |

Table 25 shows the values of the coefficients of the Fourier series expansion (up to $15^{th}$ order) obtained when the power profiles described in FIGS. 119 to 123 are best fitted to Fourier series expansion via non-linear least square optimisation routines.

TABLE 26

Fourier Series Coefficients - Exemplary embodiments

| Coefficients | # 1 | # 2 | # 3 | # 4 | # 5 | # 6 |
|---|---|---|---|---|---|---|
| C | 168.296 | 369.426 | −392.764 | 24.727 | 46.853 | −83.250 |
| a1 | 171.234 | 288.170 | −294.109 | 29.948 | 50.561 | −85.924 |
| b1 | −273.020 | −640.337 | 694.809 | −37.257 | −73.531 | 136.391 |
| a2 | −123.956 | −400.556 | 461.567 | −10.869 | −29.150 | 60.878 |
| b2 | −255.061 | −451.537 | 478.555 | −41.846 | −72.310 | 129.114 |
| a3 | −227.309 | −446.024 | 501.810 | −33.584 | −60.545 | 114.909 |
| b3 | −24.293 | 138.705 | −189.989 | −12.626 | −11.935 | 14.480 |
| a4 | −103.664 | −40.397 | 18.166 | −21.972 | −30.713 | 53.491 |
| b4 | 131.984 | 320.561 | −393.610 | 15.896 | 31.941 | −65.781 |
| a5 | 37.039 | 166.727 | −234.450 | 1.169 | 6.725 | −17.924 |
| b5 | 104.599 | 104.297 | −115.792 | 17.540 | 26.782 | −52.700 |
| a6 | 63.445 | 86.909 | −119.056 | 8.762 | 14.204 | −31.065 |
| b6 | 14.614 | −55.880 | 98.644 | 4.689 | 4.874 | −6.811 |
| a7 | 24.044 | −4.896 | 21.003 | 3.686 | 4.991 | −10.817 |
| b7 | −22.833 | −44.530 | 77.014 | −2.224 | −3.994 | 11.065 |
| a8 | −2.251 | −13.916 | 34.396 | 0.258 | 0.229 | 1.692 |
| b8 | −13.756 | −5.371 | 6.438 | −1.406 | −2.016 | 6.015 |
| a9 | −4.019 | −2.539 | 7.262 | 0 | 0 | 1.527 |
| b9 | −2.198 | 1.745 | −9.661 | 0 | 0 | 0.959 |
| a10 | −0.800 | 0 | −0.785 | 0 | 0 | 0 |
| b10 | 0.214 | 0 | −2.831 | 0 | 0 | 0 |
| a11 | 0 | 0 | 0 | 0 | 0 | 0 |
| b11 | 0 | 0 | 0 | 0 | 0 | 0 |
| a12 | 0 | 0 | 0 | 0 | 0 | 0 |
| b12 | 0 | 0 | 0 | 0 | 0 | 0 |
| a13 | 0 | 0 | 0 | 0 | 0 | 0 |
| b13 | 0 | 0 | 0 | 0 | 0 | 0 |
| a14 | 0 | 0 | 0 | 0 | 0 | 0 |
| b14 | 0 | 0 | 0 | 0 | 0 | 0 |
| a15 | 0 | 0 | 0 | 0 | 0 | 0 |
| b15 | 0 | 0 | 0 | 0 | 0 | 0 |
| RSq | 0.994 | 0.995 | 0.995 | 0.995 | 0.994 | 0.998 |
| RMSE | 0.039 | 0.049 | 0.056 | 0.046 | 0.067 | 0.038 |

Table 26 shows the values of the coefficients of the Fourier series expansion (up to $15^{th}$ order) obtained when the power profiles described in FIGS. 124 to 127 are best fitted to Fourier series expansion via non-linear least square optimisation routines.

TABLE 27

Fourier Series Coefficients - Exemplary embodiments

| Coefficients | # 7 | # 8 | # 9 | # 10 | # 11 | # 12 |
|---|---|---|---|---|---|---|
| C | 58.457 | 39.751 | −122.114 | −251.936 | −459.112 | −497.230 |
| a1 | 56.670 | 43.870 | −99.903 | −233.067 | −420.835 | −434.644 |
| b1 | −95.096 | −62.002 | 212.063 | 422.837 | 771.200 | 845.729 |
| a2 | −45.579 | −23.744 | 128.595 | 225.195 | 413.877 | 480.153 |
| b2 | −82.605 | −62.683 | 157.435 | 357.876 | 645.119 | 673.003 |
| a3 | −71.978 | −52.579 | 154.982 | 336.962 | 606.754 | 645.935 |
| b3 | −1.872 | −11.624 | −37.489 | −19.450 | −42.362 | −93.517 |
| a4 | −26.022 | −27.669 | 23.262 | 105.815 | 183.109 | 152.538 |
| b4 | 41.524 | 27.952 | −109.436 | −220.519 | −396.548 | −439.505 |
| a5 | 13.238 | 6.058 | −55.058 | −92.151 | −166.404 | −203.356 |
| b5 | 25.791 | 24.423 | −42.737 | −129.674 | −226.210 | −215.240 |
| a6 | 14.501 | 13.187 | −33.856 | −90.981 | −157.995 | −159.694 |
| b6 | 1.339 | 4.384 | 17.261 | 10.147 | 20.315 | 45.225 |
| a7 | 3.533 | 4.605 | 0.167 | −17.992 | −29.510 | −17.186 |
| b7 | −4.576 | −3.961 | 17.567 | 42.018 | 72.278 | 78.144 |
| a8 | −0.200 | 0.121 | 6.291 | 11.352 | 19.360 | 24.012 |
| b8 | −1.599 | −1.964 | 2.782 | 14.748 | 24.392 | 20.098 |
| a9 | 0 | 0 | 1.789 | 5.987 | 9.681 | 8.948 |
| b9 | 0 | 0 | −0.716 | −0.718 | −1.304 | −3.406 |
| a10 | 0 | 0 | 0 | 0.482 | 6.687 | 0.151 |
| b10 | 0 | 0 | 0 | −1.023 | −1.632 | −1.711 |
| a11 | 0 | 0 | 0 | 0 | 0 | 0 |
| b11 | 0 | 0 | 0 | 0 | 0 | 0 |
| a12 | 0 | 0 | 0 | 0 | 0 | 0 |
| b12 | 0 | 0 | 0 | 0 | 0 | 0 |
| a13 | 0 | 0 | 0 | 0 | 0 | 0 |
| b13 | 0 | 0 | 0 | 0 | 0 | 0 |
| a14 | 0 | 0 | 0 | 0 | 0 | 0 |
| b14 | 0 | 0 | 0 | 0 | 0 | 0 |
| a15 | 0 | 0 | 0 | 0 | 0 | 0 |
| b15 | 0 | 0 | 0 | 0 | 0 | 0 |
| RSq | 0.994 | 0.991 | 0.990 | 0.993 | 0.993 | 0.991 |
| RMSE | 0.053 | 0.084 | 0.099 | 0.038 | 0.049 | 0.072 |

Table 27 shows the values of the coefficients of the Fourier series expansion (up to $15^{th}$ order) obtained when the power profiles described in FIGS. 124 to 127 are best fitted to Fourier series expansion via non-linear least square optimisation routines.

Section 26

Effect of Plus Power within the Optic Zone on the Optical Transfer Function

Figure 109:
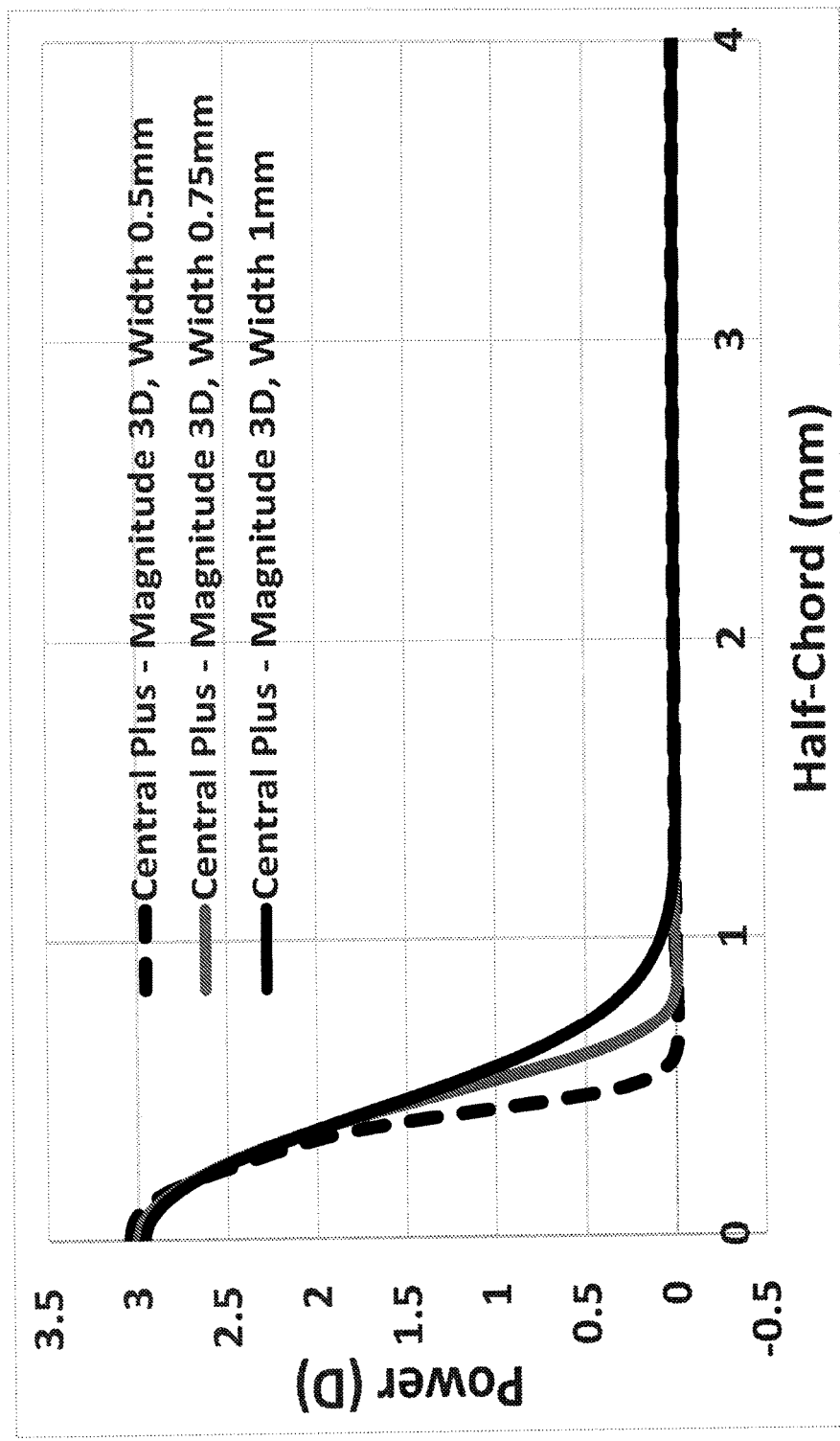
FIG. 109 shows power profiles of three exemplary embodiments across the half-chord diameter. The power profiles of the three designs start at about 3D at the centre and gradually ramp down to 0 D power at 0.5, 0.75 and 1 mm half-chord diameters.
Figure 111:
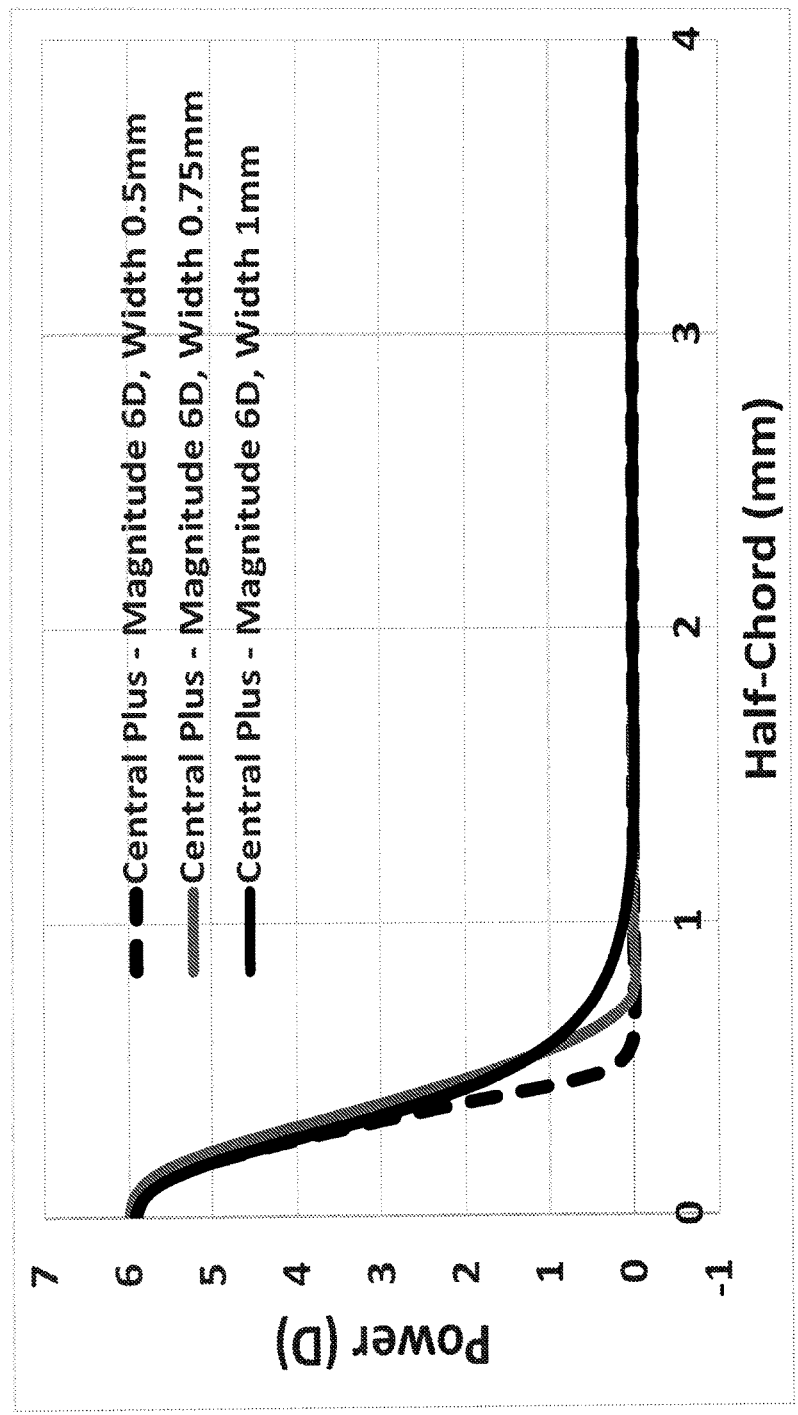
FIG. 111 shows power profiles of three exemplary embodiments across the half-chord diameter. The power profiles of the three designs start at about 6 D at the centre and gradually ramp down to 0 D power at 0.5, 0.75 and 1 mm half-chord diameters.
Figure 113:
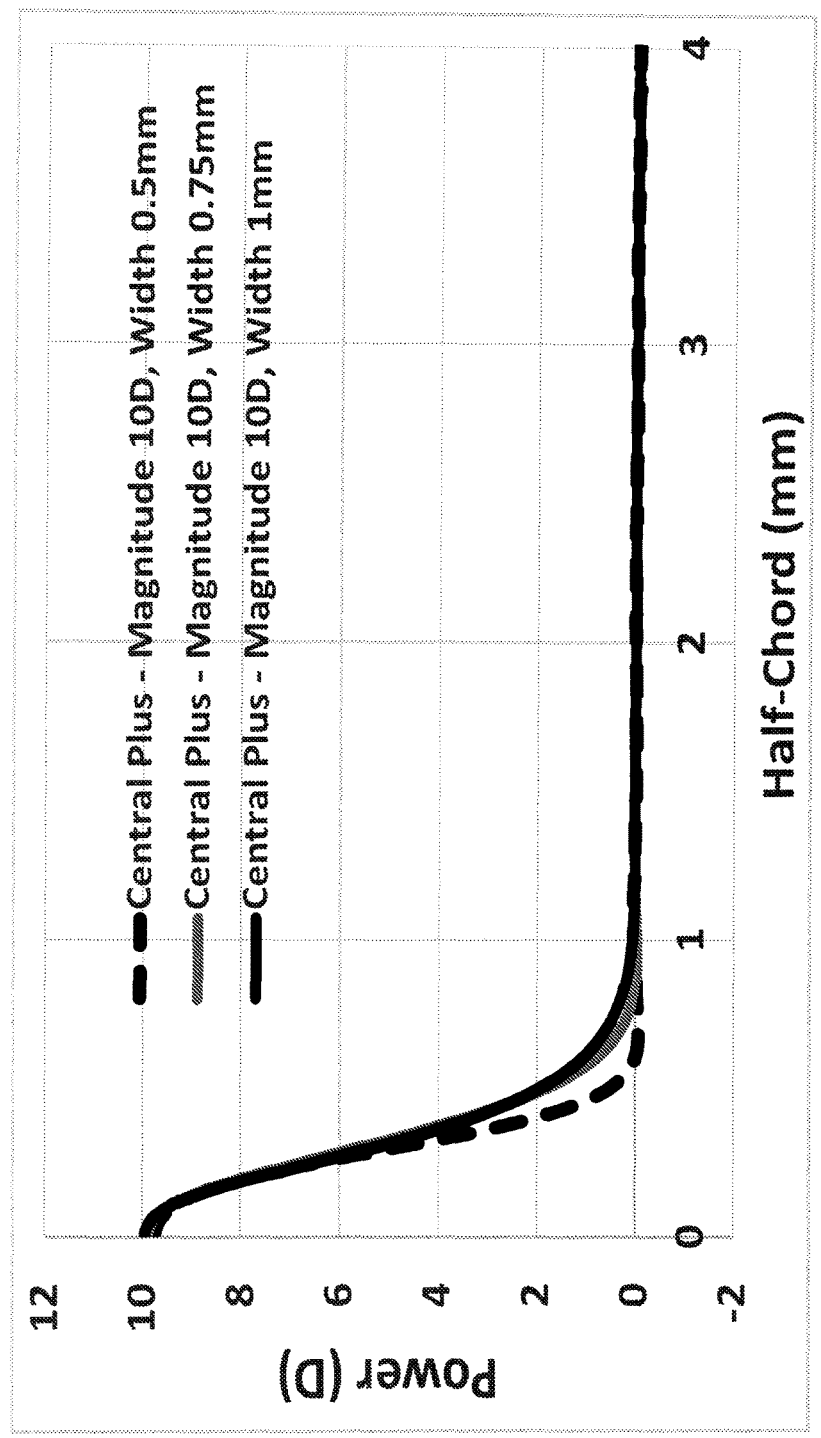
FIG. 113 shows the power profiles of three exemplary embodiments across the half-chord diameter. The power profiles of the three designs start at about 10 D at the centre and gradually ramp down to 0 D power at 0.5, 0.75 and 1 mm half-chord diameters.

FIGS. 109, 111 and 113 show the power profiles as a function of half-chord diameter for some exemplary lens designs. The set of three designs illustrated in each of the FIGS. 109, 111 and 113 have about +3D, +6 D, +10 D power at the centre of half-chord that gradually decreases to 0 D at a certain given point on the half-chord diameter of the lens. In each of the FIGS. 109, 111 and 113, the point of intersection of the power profile and the x-axis occurs at 0.5 mm (dashed black line), 0.75 mm (a solid grey line) and 1 mm (solid black line) on the half-chord for the three different power profiles.

Figure 110:
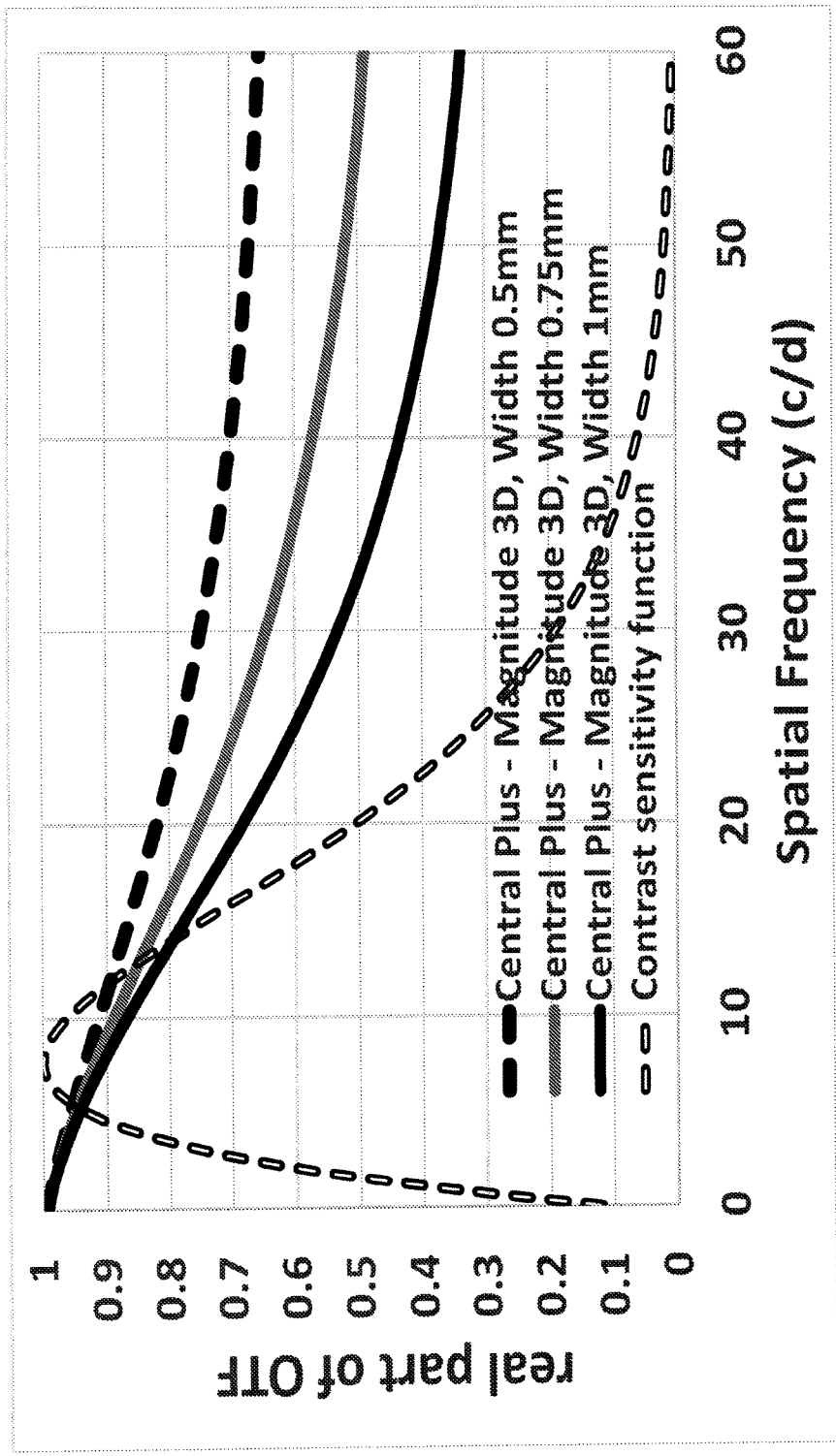
FIG. 110 show the real-part of the optical transfer function (for a 4 mm optic zone diameter) as a function of spatial frequencies for the lenses profiles disclosed in FIG. 109. The neural contrast sensitivity function is also plotted as a function of spatial frequencies to facilitate gauging the impact of the designed plus power in the centre of the lens on the optical transfer function.
Figure 112:
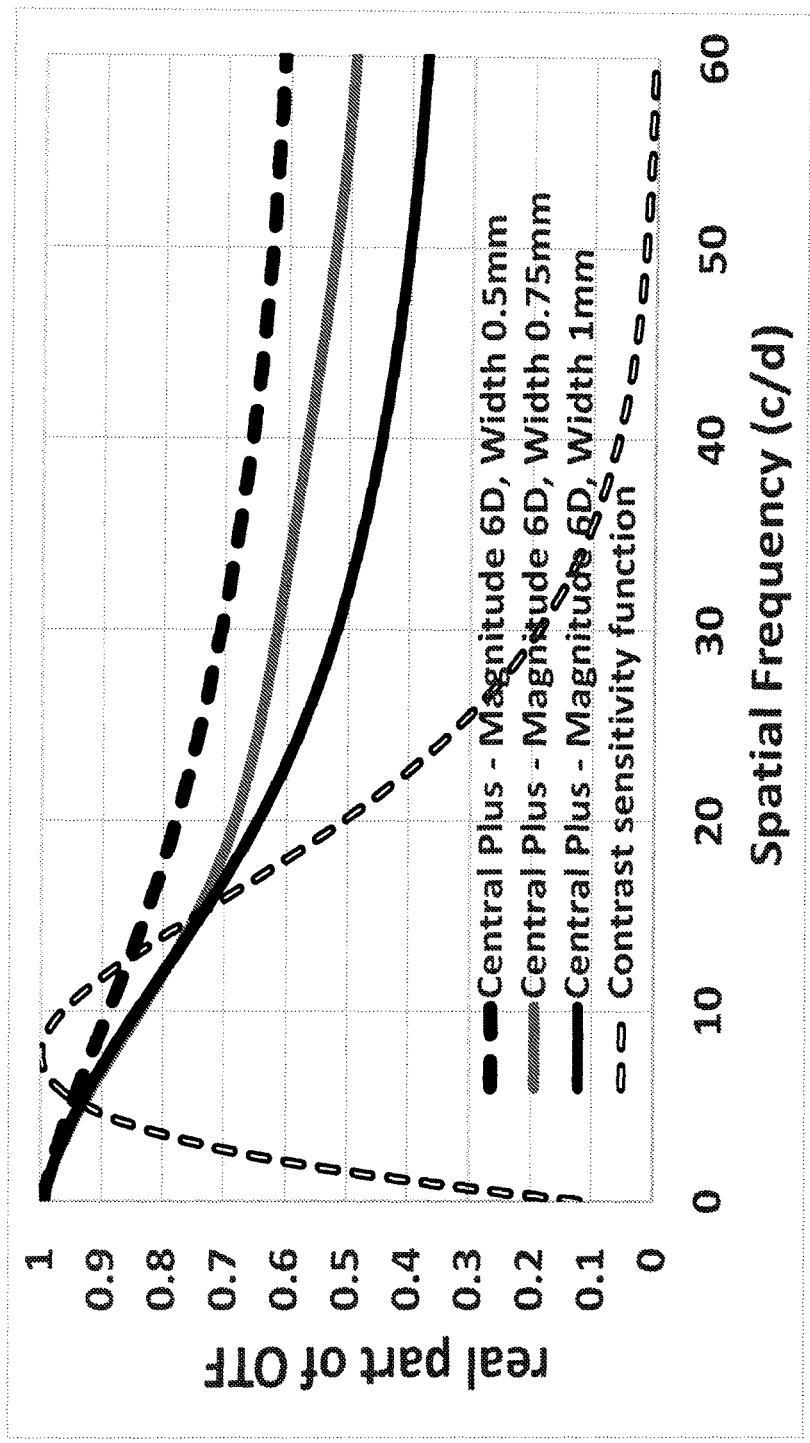
FIG. 112 show the real-part of the optical transfer function (for a 4 mm pupil diameter) as a function of spatial frequencies for the lenses profiles disclosed in FIG. 111. The neural contrast sensitivity function is also plotted as a function of spatial frequencies to facilitate gauging the impact of the designed plus power in the centre of the lens on the optical transfer function.
Figure 114:
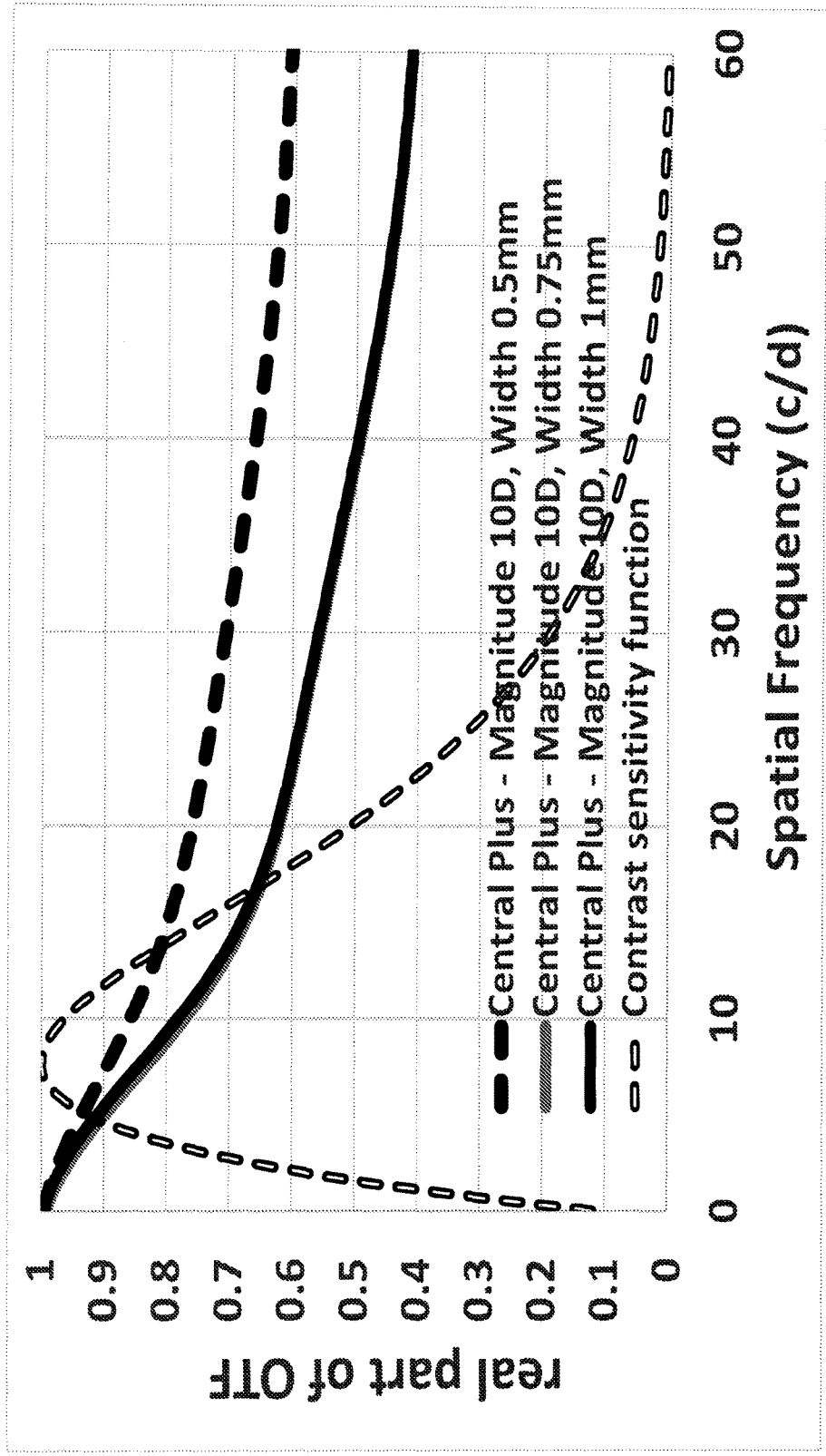
FIG. 114 shows the real-part of the optical transfer function (for a 4 mm pupil diameter) as a function of spatial frequencies for the lenses profiles disclosed in FIG. 114. The neural contrast sensitivity function is also plotted as a function of spatial frequencies to facilitate gauging the impact of the designed plus power in the centre of the lens on the optical transfer function.

FIGS. 110, 112 and 114 show the modelled optical performance of the exemplary power profiles disclosed in FIGS. 109, 111 and 113, respectively. The modelled performance is gauged in terms of the real part of the optical transfer function as a function of various spatial frequencies, obtained. The optical transfer function portion described in the equations disclosed in section 1 was used to gauge the optical performance of the profiles illustrated in these figures. The performance was modelled using a 4 mm pupil diameter. However, other pupil diameters may also be used. The neural contrast sensitivity function is also plotted in the FIGS. 110, 112 and 114 as a function of spatial frequencies to facilitate gauging the impact of the designed plus power in the centre of the lens on the optical transfer function. In the examples illustrated in these figures, the drop in the modulation of the real part of the optical transfer function as a function of spatial frequencies was compared with neural contrast sensitivity function to gauge the impact on vision. As shown in FIGS. 110, 112 and 114, the addition of plus power varying from +3D to +10 D if limited to 0.5 mm of the half-chord diameter of the optic zone of the lens, the drop in the contrast/modulation transfer for mid spatial frequency (i.e. 15 cycles/degree) is 0.8. In contrast, when the addition of plus varying from +3D to +10 D is greater than 0.5 mm or 0.75 mm of the half-chord, then drop in the contrast/modulation transfer for mid spatial frequencies (i.e. cycles/degree) is 0.6. Accordingly, in some embodiments, power profiles may be optimised to have less impact on the optical transfer function by selecting varying degrees of plus power ranging from +3D to +10 D in zone widths ranging from 0.25 mm to 1 mm of the half-chord of the lens. Such embodiments may include other feature discussed in the present disclosure.

Certain embodiments may have power profiles that include appropriate combinations of the power profiles disclosed herein, for example, the power profiles described in sections 22 (i), section 22 (ii) or section 22 (iii). In some combinations, the power profile may also have varying degrees of additional plus power ranging from +3 D to +10 D relative to the prescription power within an appropriate range of the half-chord of the optic zone. For example, in some embodiments, the appropriate range on the half-chord of the optic zone may be one of the following: 0 to 0.25 mm, 0 to 0.5 mm or 0 to 0.75 mm. Such combinations may provide acceptable vision and/or minimal ghosting for at least a subset of a population.

Some embodiments may be directed to lenses, methods and/or devices comprising: an optical axis; a power profile with transitions between maxima and its adjacent minima, wherein the maxima is within 0.2 mm, and the adjacent minima is within at least 0.3, 0.4, 0.5, 0.6, 0.7, 0.8, 0.9 or 1 mm, distance from the centre of an optic zone of the lens, the transition zone between the maxima and its adjacent minima can be continuous, substantially continuous, smooth, substantially smooth, discontinuous or certain combinations thereof; the amplitude of the transition zone between the maxima and its adjacent minima is at least +2 D, +2.25 D, +2.5 D, +2.75 D, +3 D, +3.25 D, +3.5 D, +4 D, +4.5 D, +5 D, +5.5 D, +6 D, +6.5 D, +7 D, +7.5 D, +8 D, +8.5 D, +9 D, +9.5 D or +10 D.

The claimed subject matter according to the explanations given in the specification, especially in the before mentioned embodiments and/or following examples, as well as claimed with the enclosed claims covers all uses of the described lenses, devices and/or and the use of any method covered by the explanation, examples and claims. However, the subject matter of the explanation, examples and claims may also cover uses of the described devices and the use of any method covered with the exception of such uses that comprise or encompass an invasive step representing a substantial physical intervention on the body which requires professional medical expertise to be carried out and which entail a substantial health risk even when carried out with the required professional care and expertise. Such excepted uses and/or steps of uses are for example the implantation and/or modifications of an intraocular lenses, corneal inlays, corneal onlays and corneal refractive surgical procedures, especially within the human or animal body, removal of an intraocular lens, especially of the crystalline lens of an eye, removal of intraocular lenses, corneal inlays, corneal onlays out of the human or animal eye, replacing of the crystalline lens by an intraocular lens and/or replacing of intraocular lenses, corneal inlays and/or corneal onlays in the human and/or animal body.

The claimed subject matter however covers all uses that do not fall under these exceptions, for example, the calculations steps for calculating a correction of a lens and/or device, the calculations steps for calculating, describing and/or characterising a power profile, aberration profile of a lens and/or device, the modification of a lens outside the human and/or animal body, for example, a contact lens, a spectacle lens, a corneal inlay, a corneal onlay or an intraocular lens (anterior or posterior chamber). The application of the claimed methods and/or devices to a model eye formed by a physical model that for example is optically equivalent to an eye, the use of the methods and/or devices in optical calculation methods like ray-tracing and/or Fourier optics.

Other exemplary embodiments are described in the following sets of examples A to X:

Example Set A (A1) A lens for an eye, the lens having an optical axis and an aberration profile about its optical axis, the aberration profile: having a focal distance; and including higher order aberrations having at least one of a primary spherical aberration component C(4,0) and a secondary spherical aberration component C(6,0), wherein the aberration profile provides, for a model eye with no aberrations, or substantially no aberrations, and an on-axis length equal to, or substantial equal to, the focal distance: a retinal image quality (RIQ) with a through focus slope that degrades in a direction of eye growth; and a RIQ of at least 0.3 wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(A2) A lens for an eye, the lens having an optical axis and an aberration profile about its optical axis, the aberration profile: having a focal distance; and including higher order aberrations having at least one of a primary spherical aberration component C(4,0) and a secondary spherical aberration component C(6,0), wherein the aberration profile provides, for a model eye with no aberrations and an on-axis length equal to the focal distance: a retinal image quality (RIQ) with a through focus slope that degrades in a direction of eye growth; and a RIQ of at least 0.3 wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(A3) A lens for an eye, the lens having an optical axis, a focal distance and being characterised by: an aberration profile about the lens's optical axis, the aberration profile: including higher order aberrations having at least one of a primary spherical aberration component C(4,0) and a secondary spherical aberration component C(6,0), wherein the aberration profile provides, for a model eye with no aberrations, or substantially no, aberrations, and an on-axis length equal to, or substantial equal to, the focal distance: a retinal image quality (RIQ) with a through focus slope that degrades in a direction of eye growth; and a RIQ of at least 0.3, wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(A4) A lens for an eye, the lens having at least one optical axis and at least one optical profile substantially about the at least one optical axis, the optical profile: having at least one focal distance; and including one or more higher order aberrations, wherein the profile provides, for a model eye with substantially no aberrations an on-axis length equal to, or substantially equal to, the desired focal distance; a retinal image quality (RIQ) with a through focus slope that improves in a direction of eye growth; and a RIQ of at least 0.3; wherein the RIQ is measured substantially along the optical axis for at least one pupil diameter in the range 3 mm to 6 mm, over a spatial frequency range of 0 to 30 cycles/ degree inclusive and at a wavelength selected from within the range 540 nm to 590 nm inclusive.

(A5) A lens for an eye, the lens having an optical axis and an aberration profile about its optical axis, the aberration profile: having a focal distance; and including higher order aberrations having at least one of a primary spherical aberration component C(4,0) and a secondary spherical aberration component C(6,0), wherein the aberration profile provides, for a model eye with no aberrations, or substantially no, aberrations, and an on-axis length equal to, or substantial equal to, the focal distance: a retinal image quality (RIQ) with a through focus slope that improves in a direction of eye growth; and a RIQ of at least 0.3, wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(A6) A lens for an eye, the lens having an optical axis and an aberration profile about its optical axis, the aberration profile: having a focal distance; and including higher order aberrations having at least one of a primary spherical aberration component C(4,0) and a secondary spherical aberration component C(6,0), wherein the aberration profile provides, for a model eye with no aberrations and an on-axis length equal to the focal distance: a retinal image quality (RIQ) with a through focus slope that improves in a direction of eye growth; and a RIQ of at least 0.3, wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(A7) A lens for an eye, the lens having an optical axis, a focal distance and being characterised by: an aberration profile about the lens's optical axis, the aberration profile: including higher order aberrations having at least one of a primary spherical aberration component C(4,0) and a secondary spherical aberration component C(6,0), wherein the aberration profile provides, for a model eye with no aberrations, or substantially no, aberrations, and an on-axis length equal to, or substantial equal to, the focal distance: a retinal image quality (RIQ) with a through focus slope that improves in a direction of eye growth; and a RIQ of at least 0.3, wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(A8) A lens for an eye, the lens having at least one optical axis and at least one optical profile substantially about the at least one optical axis, the optical profile: having at least one focal distance; and including one or more higher order aberrations, wherein the profile provides, for a model eye with substantially no aberrations an on-axis length equal to, or substantially equal to, the desired focal distance; a retinal image quality (RIQ) with a through focus slope that improves in a direction of eye growth; and a RIQ of at least 0.3; wherein the RIQ is measured substantially along the optical axis for at least one pupil diameter in the range 3 mm to 6 mm, over a spatial frequency range of 0 to 30 cycles/ degree inclusive and at a wavelength selected from within the range 540 nm to 590 nm inclusive.

(A9) The lens of one or more of the above A examples, wherein the focal distance is a prescription focal distance for a myopic eye and wherein the focal distance differs from the focal distance for a C(2,0) Zernike coefficient of the aberration profile.

(A10) The lens of one or more of the above A examples, wherein the focal distance is a prescription focal distance for a hyperopic eye and wherein the focal distance differs from the focal distance for a C(2,0) Zernike coefficient of the aberration profile.

(A11) The lens of one or more of the above A examples, wherein the higher order aberrations include at least two spherical aberration terms selected from the group C(4,0) to C(20,0).

(A12) The lens of one or more of the above A examples, wherein the higher order aberrations include at least three spherical aberration terms selected from the group C(4,0) to C(20,0).

(A13) The lens of one or more of the above A examples, wherein the higher order aberrations include at least four spherical aberration terms selected from the group C(4,0) to C(20,0).

(A14) The lens of one or more of the above A examples, wherein the higher order aberrations include at least five spherical aberration terms selected from the group C(4,0) to C(20,0).

(A15) The lens of one or more of the above A examples, wherein the higher order aberrations include at least six spherical aberration terms selected from the group C(4,0) to C(20,0).

(A16) The lens of one or more of the above A examples, wherein the higher order aberrations include at least seven spherical aberration terms selected from the group C(4,0) to C(20,0).

(A17) The lens of one or more of the above A examples, wherein the magnitude of higher order aberrations included is at least 0.01 μm over a 4 mm, 5 mm or 6 mm pupil diameter.

(A18) The lens of one or more of the above A examples, wherein the magnitude of higher order aberrations included is at least 0.02 μm over a 4 mm, 5 mm or 6 mm pupil diameter.

(A19) The lens of one or more of the above A examples, wherein the magnitude of higher order aberrations included is at least 0.03 μm over a 4 mm, 5 mm or 6 mm pupil diameter.

(A20) The lens of one or more of the above A examples, wherein the magnitude of higher order aberrations included is at least 0.04 μm over a 4 mm, 5 mm or 6 mm pupil diameter.

(A21) The lens of one or more of the above A examples, wherein the magnitude of higher order aberrations included is at least 0.05 μm over a 4 mm, 5 mm or 6 mm pupil diameter.

(A22) The lens of one or more of the above A examples, wherein the magnitude of higher order aberrations included is at least 0.01 μm, 0.02 μm, 0.03 μm or 0.04 μm over a 3 mm pupil diameter.

(A23) The lens of one or more of the above A examples, wherein the average slope over a horizontal field of at least −20° to +20° degrades in a direction of eye growth.

(A24) The lens of one or more of the above A examples, wherein the average slope over a vertical field of at least −20° to +20° degrades in the direction of eye growth.

(A25) The lens of one or more of the above A examples, wherein the slope for a substantial portion of the field angles over a horizontal field of at least −20° to +20° degrades in the direction of eye growth.

(A26) The lens of one or more of the above A examples, wherein the slope for a substantial portion of the field angles over a vertical field of at least −20° to +20° degrades in the direction of eye growth.

(A27) The lens of one or more of the above A examples, wherein the aberration profile provides a RIQ of at least 0.3 at the focal length for a substantial portion of the pupil diameters in the range 3 mm to 6 mm.

(A28) The lens of one or more of the above A examples, wherein the aberration profile provides a RIQ of at least 0.3 at the focal length for a substantial portion of pupil diameters in the range 4 mm to 5 mm.

(A29) The lens of one or more of the above A examples, wherein the through focus slope averaged over the horizontal field of at least −20° to +20° degrades in the direction of eye growth.

(A30) The lens of one or more of the above A examples, wherein the through focus slope averaged over the vertical field of at least −20° to +20° degrades in the direction of eye growth.

(A31) The lens of one or more of the above A examples, wherein the through focus slope for a substantial portion of the field angles over the horizontal field of at least −20° to +20° degrades in the direction of eye growth.

(A32) The lens of one or more of the above A examples, wherein the through focus slope for a substantial portion of the field angles over the vertical field of at least −20° to +20° degrades in the direction of eye growth.

(A33) The lens of one or more of the above A examples, wherein the aberration profile provides a RIQ with a through focus slope that degrades in the direction of eye growth when primary astigmatism is added to the aberration profile.

(A34) The lens of one or more of the above A examples, wherein the aberration profile provides a RIQ with a through focus slope that improves in the direction of eye growth when primary astigmatism is added to the aberration profile.

(A35) The lens of one or more of the above A examples, wherein the aberration profile provides a RIQ with a through focus slope that degrades in the direction of eye growth when secondary astigmatism is added to the aberration profile.

(A36) The lens of one or more of the above A examples, wherein the aberration profile provides a RIQ with a through focus slope that improves in the direction of eye growth when secondary astigmatism is added to the aberration profile.

(A37) The lens of one or more of the above A examples, wherein the RIQ is, or is characterised by:

$$RIQ = \frac{\iint_{-Fmin}^{+Fmax} CSF(x, y) * \left(real\left(\left(\left[FT\left(\left|FT\left\{A(\rho, \theta) * \exp\left[\frac{2\pi i}{\lambda} * W(\rho, \theta)\right]\right\}\right|\right)\right]^2\right)\right)\right)}{\iint_{-Fmin}^{+Fmax} CSF(x, y) * \left(\left(\left[FT\left(\left|FT\left\{A(\rho, \theta) * \exp\left[\frac{2\pi i}{\lambda} * Wdiff(\rho, \theta)\right]\right\}\right|\right)\right]^2\right)\right)}$$

Wherein:

Fmin is 0 cycles/degree and Fmax is 30 cycles/degree;

CSF(x, y) denotes the contrast sensitivity function, $CSF(F)=2.6(0.0192+0.114f)e^{-(0.114f)^{1.1}}$, Where f specifies the tested spatial frequency, in the range of $F_{min}$ to $F_{max}$;

FT denotes a 2 D Fourier transform, for example, a 2 D fast Fourier transform;

$A(\rho,\theta)$ denotes the pupil amplitude function across the pupil diameter;

$W(\rho,\theta)$ denotes wavefront of the test case measured for i=1 to 20;

$$W(\rho, \theta) = \sum_{i=1}^{k} a_i Z_i(\rho, \theta)$$

Wdiff($\rho$, $\theta$) denotes wavefront of the diffraction limited case;

$\rho$ and $\theta$ are normalised polar coordinates, where $\rho$ represents the radial coordinate and $\theta$ represents the angular coordinate or azimuth; and $\lambda$ denotes wavelength.

(A38) The lens of one or more of the above A examples, wherein the RIQ is, or is characterised by:

$$RIQ = \frac{\left(real\left(\left(\left[FT\left(\left|FT\left\{A(\rho,\theta)*\exp\left[\frac{2\pi i}{\lambda}*W(\rho,\theta)\right]\right\}\right|\right)\right]^2\right)\right)\right) \int\int_{-Fmin}^{+Fmax} CSF(x,y)*}{\int\int_{-Fmin}^{+Fmax} CSF(x,y)* \left(\left(\left(\left[FT\left(\left|FT\left\{A(\rho,\theta)*\exp\left[\frac{2\pi i}{\lambda}*Wdiff(\rho,\theta)\right]\right\}\right|\right)\right]^2\right)\right)\right)}$$

Wherein:
Fmin is 0 cycles/degree and Fmax is 30 cycles/degree;
CSF(x, y) denotes the contrast sensitivity function,
$CSF(F)=2.6(0.0192+0.114f)e^{-(0.114f)^{1.1}}$,
Where f specifies the tested spatial frequency, in the range of $F_{min}$ to $F_{max}$;
FT denotes a 2 D Fourier transform, for example, a 2 D fast Fourier transform;
$A(\rho,\theta)$ denotes the pupil amplitude function across the pupil diameter;
$W(\rho,\theta)$ denotes wavefront of the test case measured for i=1 to k;
where k is a positive integer;

$$W(\rho,\theta) = \sum_{i=1}^{k} a_i Z_i(\rho,\theta)$$

Wdiff($\rho$, $\theta$) denotes wavefront of the diffraction limited case;
$\rho$ and $\theta$ are normalised polar coordinates, where $\rho$ represents the radial coordinate and $\theta$ represents the angular coordinate or azimuth; and
$\lambda$ denotes wavelength.

(A39) A lens including an optical axis and an aberration profile about the optical axis that provides: a focal distance for a C(2,0) Zernike coefficient term; a peak visual Strehl Ratio ('first visual Strehl Ratio') within a through focus range, and a visual Strehl Ratio that remains at or above a second visual Strehl Ratio over the through focus range that includes said focal distance, wherein the visual Strehl Ratio is measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive, and wherein the first visual Strehl Ratio is at least 0.35, the second visual Strehl Ratio is at least 0.1 and the through focus range is at least 1.8 Dioptres.

(A40) The lens of one or more of the above A examples, wherein the first visual Strehl Ratio is at least 0.28 or 0.3.

(A41) The lens of one or more of the above A examples, wherein the first visual Strehl Ratio is at least 0.4.

(A42) The lens of one or more of the above A examples, wherein the first visual Strehl Ratio is at least 0.5.

(A43) The lens of one or more of the above A examples, wherein the first visual Strehl Ratio is at least 0.6.

(A44) The lens of one or more of the above A examples, wherein the first visual Strehl Ratio is at least 0.7.

(A45) The lens of one or more of the above A examples, wherein the first visual Strehl Ratio is at least 0.8.

(A46) The lens of one or more of the above A examples, wherein the second visual Strehl Ratio is at least 0.08, 0.1, 0.12, 0.14, 0.16, 0.18 or 0.2.

(A47) The lens of one or more of the above A examples, wherein the through focus range is at least 1.8 Dioptres.

(A48) The lens of one or more of the above A examples, wherein the through focus range is at least 1.9 Dioptres.

(A49) The lens of one or more of the above A examples, wherein the through focus range is at least 2 Dioptres.

(A50) The lens of one or more of the above A examples, wherein the through focus range is at least 2.1 Dioptres.

(A51) The lens of one or more of the above A examples, wherein the through focus range is at least 2.25 Dioptres.

(A52) The lens of one or more of the above A examples, wherein the through focus range is at least 2.5 Dioptres.

(A53) The lens of one or more of the above A examples, wherein the lens has a prescription focal distance located within 0.75 Dioptres of an end of the through focus range.

(A54) The lens of one or more of the above A examples, wherein the lens has a prescription focal distance located within 0.5 Dioptres of an end of the through focus range.

(A55) The lens of one or more of the above A examples, wherein the lens has a prescription focal distance located within 0.3 Dioptres of an end of the through focus range.

(A56) The lens of one or more of the above A examples, wherein the lens has a prescription focal distance located within 0.25 Dioptres of an end of the through focus range.

(A57) The lens of one or more of the above A examples, wherein the end of the through focus range is the negative power end.

(A58) The lens of one or more of the above A examples, wherein the end of the through focus range is the positive power end.

(A59) The lens of one or more of the above A examples, wherein the first visual Strehl Ratio remains at or above the second visual Strehl Ratio over the through focus range and over a range of pupil diameters of at least 1 mm.

(A60) The lens of one or more of the above A examples, wherein the first visual Strehl Ratio remains at or above the second visual Strehl Ratio over the through focus range and over a range of pupil diameters of at least 1.5 mm.

(A61) The lens of one or more of the above A examples, wherein the first visual Strehl Ratio remains at or above the second visual Strehl Ratio over the through focus range and over a range of pupil diameters of at least 2 mm.

(A62) The lens of one or more of the above A examples, wherein the combination of higher order aberrations includes at least one of primary spherical aberration and secondary spherical aberration.

(A63) The lens of one or more of the above A examples, wherein the higher order aberrations include at least two spherical aberration terms selected from the group C(4,0) to C(20,0).

(A64) The lens of one or more of the above A examples, wherein the higher order aberrations include at least three spherical aberration terms selected from the group C(4,0) to C(20,0).

(A65) The lens of one or more of the above A examples, wherein the higher order aberrations include at least five spherical aberration terms selected from the group C(4,0) to C(20,0).

(A66) The lens of one or more of the above A examples, wherein the aberration profile is substantially described using only spherical aberration Zernike coefficients C(4,0) to C(20,0).

(A67) The lens of one or more of the above A examples, wherein the RIQ for every field angle over a horizontal field of at least −10° to +10° is at least 0.2, 0.25, 0.3, 0.35 or 0.4.
(A68) The lens of one or more of the above A examples, wherein the RIQ for every field angle over a horizontal field of at least −20° to +20° is at least 0.2, 0.25, 0.3, 0.35 or 0.4.
(A69) The lens of one or more of the above A examples, wherein the RIQ for every field angle over a horizontal field of at least −30° to +30° is at least 0.2, 0.25, 0.3, 0.35 or 0.4.
(A70) The lens of one or more of the above A examples, wherein the lens does not substantially reduce the amount of light passing through the lens.
(A71) The lens of one or more of the above A examples, wherein the aberration profile is an aberration pattern.
(A72) A method for a presbyopic eye, the method comprising identifying at least one wavefront aberration profile for the eye, the at least one wavefront aberration profile including at least two spherical aberration terms, wherein the prescription focal distance of the lens is determined taking into account said at least one spherical aberration and wherein the prescription focal distance of the lens is at least +0.25 D relative to a focal distance for a C(2,0) Zernike coefficient term of the at least one wavefront aberration and producing one or more of the following: a device, lens and corneal profile for the eye to affect said at least one wavefront aberration profile.
(A73) A method for a myopic or emmetropic eye, the method comprising forming an aberration for the eye and applying or prescribing the aberration profile, the aberration profile: having a focal distance; and including at least one of a primary spherical aberration component C(4,0) and a secondary spherical aberration component C(6,0), wherein the aberration profile provides, for the eye: a retinal image quality (RIQ) with a through focus slope that degrades in a direction of eye growth; and a RIQ of at least 0.3; wherein said RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.
(A74) A method for a hyperopic eye, the method comprising forming an aberration for the eye and applying or prescribing the aberration profile, the aberration profile: having a focal distance; and including at least one of a primary spherical aberration component C(4,0) and a secondary spherical aberration component C(6,0), wherein the aberration profile provides, for the eye: a retinal image quality (RIQ) with a through focus slope that improves in a direction of eye growth; and a RIQ of at least 0.3; wherein said RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.
(A75) The method of one or more of the above A method examples, wherein applying or prescribing the aberration profile comprises providing a lens, the lens having an aberration profile including at least two spherical aberration terms selected from the group C(4,0) to C(20,0).
(A76) The method of one or more of the above A method examples, wherein applying or prescribing the aberration profile comprises providing a lens, the lens having an aberration profile including at least three spherical aberration terms selected from the group C(4,0) to C(20,0).
(A77) The method of one or more of the above A method examples, wherein applying or prescribing the aberration profile comprises providing a lens, the lens having an aberration profile including at least five spherical aberration terms selected from the group C(4,0) to C(20,0).
(A78) A method for a myopic eye, the method comprising identifying a wavefront aberration profile for the eye and applying or prescribing the aberration profile, the wavefront aberration profile including at least two spherical aberration terms, wherein the prescription focal distance of the lens is determined taking into account said spherical aberration and wherein the prescription focal distance is at least +0.1 D relative to a focal distance for a C(2,0) Zernike coefficient term of the wavefront aberration profile and wherein the wavefront aberration profile provides a degrading retinal image quality in the direction posterior to the retina.
(A79) A method for a hyperopic eye, the method comprising identifying a wavefront aberration profile for the eye and applying or prescribing the aberration profile, the wavefront aberration profile including at least two spherical aberration terms, wherein the prescription focal distance of the lens is determined taking into account said spherical aberration and wherein the prescription focal distance is at least +0.1 D relative to a focal distance for a C(2,0) Zernike coefficient term of the wavefront aberration profile and wherein the wavefront aberration profile provides a improving retinal image quality in the direction posterior to the retina.
(A80) The method of one or more of the above A method examples, wherein the prescription focal distance is at least +0.1 D relative to a focal distance for a C(2,0) Zernike coefficient term of the wavefront aberration profile.
(A81) A method for a hyperopic eye, the method comprising identifying a wavefront aberration profile for the eye and applying or prescribing the aberration profile, the wavefront aberration profile including at least two spherical aberration terms, wherein the prescription focal distance of the lens is determined taking into account said spherical aberration and wherein at the prescription focal distance the wavefront aberration profile provides an improving retinal image quality in the direction posterior to the retina.
(A82) The method of one or more of the above A method examples, wherein the lens does not substantially reduce the amount of light passing through the lens.
(A83) The method of one or more of the above A method examples, wherein the aberration profile is an aberration pattern.

Example Set B (B1) A multifocal lens comprising: an optical axis; an effective near additional power of at least 1 D; the optical properties of the multifocal lens are configured with an aberration profile associated with the optical axis; the aberration profile is comprised of a defocus term and at least two spherical aberration terms; and the multifocal lens is configured to provide a visual performance over intermediate and far distances that is at least substantially equivalent to the visual performance of a correctly prescribed single-vision lens at the far visual distance; and is configured to provide minimal ghosting at far, intermediate and near distances.
(B2) The multifocal lens of one or more of the above B examples, wherein the lens is configured to provide near visual acuity of at least 6/6 in individuals that can achieve 6/6 visual acuity.
(B3) The multifocal lens of one or more of the above B examples, wherein the lens is configured to provide at least acceptable visual performance at near distances.
(B4) A multifocal lens comprising: an optical axis; an effective near additional power of at least 0.75 D; the optical properties of the multifocal lens are configured or described based at least in part on an aberration profile associated with the optical axis; the aberration profile is comprised of a defocus term and at least two spherical aberration terms; and the multifocal lens is configured to provide a visual performance, along a range of substantially continuous near visual distances, wherein the visual performance of the multifocal lens is at least substantially equivalent to the visual performance of a correctly prescribed single-vision lens at the far visual distance, the multifocal lens is configured to provide a visual performance, along a range of substantially continuous intermediate and far visual distances, wherein the visual performance of the multifocal lens is at least substantially equivalent to the visual performance of a correctly prescribed single-vision lens at the far visual distance.

(B5) A multifocal lens comprising: an optical axis; the optical properties of the multifocal lens are configured or described based at least in part on an aberration profile associated with the optical axis; wherein the aberration profile is comprised of a defocus term and at least two spherical aberration terms; and wherein the multifocal lens is configured to provide a visual performance, along a range of substantially continuous visual distances, including near, intermediate and far distances, wherein the visual performance of the multifocal lens is at least substantially equivalent to the visual performance of a correctly prescribed single-vision lens at the far visual distance.

(B6) A multifocal lens comprising: an optical axis; the optical properties of the multifocal lens are configured or described based at least in part on an aberration profile associated with the optical axis; the aberration profile is comprised of a defocus term and at least two spherical aberration terms; and the multifocal lens is configured to provide a visual performance, along substantially continuous visual distances, including substantially near distances, substantially intermediate distances, and substantially far distances, wherein the visual performance of the multifocal lens is at least substantially equivalent to the visual performance of an appropriately prescribed single-vision lens at the far visual distance.

(B7) A multifocal lens comprising: an optical axis; the optical properties of the multifocal lens are configured or described based on an aberration profile associated with the optical axis; the aberration profile is comprised of a defocus term and at least two aberration terms; and the multifocal lens is configured to provide a visual performance, along a range of visual distances, including near, intermediate and far distances, wherein the visual performance of the lens is at least equivalent to the visual performance of a single-vision lens at the far visual distance.

(B8) A multifocal lens comprising: an optical axis; the optical properties of the multifocal lens are configured or described based on an aberration profile associated with the optical axis; wherein the aberration profile is comprised of a defocus term and at least two aberration terms; and wherein the multifocal lens is configured to provide a visual performance, along a range of visual distances, including near, intermediate and far distances, wherein the visual performance of the lens is at least equivalent to the visual performance of a single-vision lens at the far visual distance.

(B9) A multifocal lens comprising: an optical axis; the optical properties of the multifocal lens are configured or described based at least in part on an aberration profile associated with the optical axis; the aberration profile is comprised of a defocus term, at least two spherical aberration term and at least one asymmetric term; and the multifocal lens is configured to provide a visual performance, along a range of substantially continuous visual distances, including near, intermediate and far distances, wherein the visual performance of the multifocal lens is at least substantially equivalent to the visual performance of a correctly prescribed single-vision lens at the far visual distance.

(B10) A multifocal lens comprising: an optical axis; the optical properties of the multifocal lens are configured or described based on an aberration profile associated with the optical axis; the aberration profile is comprised of a defocus term and at least two spherical aberration terms; and the multifocal lens is configured to provide a visual performance over intermediate and far distances that is at least substantially equivalent to the visual performance of a correctly prescribed single-vision lens at the far visual distance; and is configured to provide minimal ghosting at far, intermediate and near distances.

(B11) A multifocal lens for correction of presbyopia comprising: an optical axis; the optical properties of the multifocal lens are configured or described based on an aberration profile associated with the optical axis; the aberration profile is comprised of a defocus terms, at least two spherical aberration terms and at least one asymmetric aberration term; and the multifocal lens is configured to provide a visual performance over intermediate and far distances that is at least substantially equivalent to the visual performance of a correctly prescribed single-vision lens at the far visual distance; and is configured to provide minimal ghosting at far, intermediate and near distances.

(B12) A multifocal lens for correction of presbyopia comprising: an optical axis; combinations of one more areas of different focal powers; and the optical properties of the multifocal lens is configured to provide a visual performance for a presbyopic eye over intermediate and far distances that is at least substantially equivalent to the visual performance of a correctly prescribed single-vision lens at the far visual distance; and is configured to provide minimal ghosting at far, intermediate and near distances.

(B13) A multifocal lens comprising: an optical axis; the optical properties of the multifocal lens is characterised at least in part on an aberration profile associated with the optical axis; the aberration profile is comprised of a defocus term and at least two spherical aberration term; and the multifocal lens is configured to provide a visual performance over intermediate and far distances that is at least substantially equivalent to the visual performance of a correctly prescribed single-vision lens at the far visual distance; and is configured to provide minimal ghosting at far, intermediate and near distances.

(B14) A multifocal lens comprising: an optical axis; the optical properties of the multifocal lens are configured or described based at least in part on an aberration profile associated with the optical axis; the aberration profile is comprised of a defocus term and at least two spherical aberration terms; and the multifocal lens is configured to provide a visual performance over intermediate and far distances that is at least substantially equivalent to the visual performance of a prescribed single-vision lens at the far visual distance; and is configured to provide minimal ghosting at far, intermediate and near distances.

(B15) A multifocal lens comprising: an optical axis; the optical properties of the multifocal lens are configured based on an aberration profile associated with the optical axis of the lens; the aberration profile is comprised of a defocus term and at least two spherical aberration terms; and the multifocal lens is configured to provide a visual performance over intermediate and far distances that is at least substantially equivalent to the visual performance of a correctly prescribed single-vision lens at the far visual distance; and is configured to provide minimal ghosting at far, intermediate and near distances.

(B16) A multifocal lens comprising: an optical axis; the optical properties of the multifocal lens being characterised based on an aberration profile associated with the optical axis of the lens; the aberration profile is comprised of a defocus term and at least two spherical aberration terms; and the multifocal lens is configured to provide a visual performance over intermediate and far distances that is at least substantially equivalent to the visual performance of a effectively prescribed single-vision lens at the far visual distance; and is configured to provide minimal ghosting at far, intermediate and near distances.

(B17) The multifocal lens of one or more of the above B examples, wherein the lens does not substantially reduce the amount of light passing through the lens.

(B18) The multifocal lens of one or more of the above B examples, wherein the amount of light passing through the lens is at least 80%, 85%, 90%, 95% or 99%.

(B19) The multifocal lens of one or more of the above B examples, wherein the single-vision lens is one or more of the following: prescribed, appropriately prescribed, correctly prescribed and effectively prescribed.

(B20) The multifocal lens of one or more of the above B examples, wherein the single-vision lens is a lens with a substantially constant power across a substantial portion of an optic zone of the single-vision lens.

(B21) The multifocal lens of one or more of the above B examples, wherein the single-vision lens is a lens with a constant power across a portion of an optic zone of the single-vision lens.

(B22) The multifocal lens of one or more of the above B examples, wherein the single-vision lens is a lens with a substantially constant power across a portion of one or more optic zones of the single-vision lens.

(B23) The multifocal lens of one or more of the above B examples, wherein the multifocal lens is used for a presbyopic eye.

(B24) The multifocal lens of one or more of the above B examples, wherein the lens is configured for a presbyopic eye.

(B25) The multifocal lens of one or more of the above B examples, wherein the lens is configured to optically correct or substantially correct presbyopia.

(B26) The multifocal lens of one or more of the above B examples, wherein the lens is configured to mitigate or substantially mitigate the optical consequences of presbyopia.

(B27) The multifocal lens of one or more of the above B examples, wherein the lens is configured to alter or substantially alter a presbyopic condition to a non-presbyopic condition.

(B28) The multifocal lens of one or more of the above B examples, wherein the multifocal lens is used for at least correcting a presbyopic eye condition and when used provides an appropriate correction to adjust the vision of the user towards substantially normal non-presbyopic vision.

(B29) The multifocal lens of one or more of the above B examples, wherein normal vision is 6/6 or better.

(B30) The multifocal lens of one or more of the above B examples, wherein the multifocal lens is further characterised by minimal, substantially no or no, ghosting at near, intermediate and far distances.

(B31) The multifocal lens of one or more of the above B examples, wherein the multifocal lens is further characterised by minimal, substantially no or no, ghosting at near distances, intermediate distances and far distances.

(B32) The multifocal lens of one or more of the above B examples, wherein the multifocal lens is further configured to provide minimal, substantially no or no, ghosting at near, intermediate and far distances.

(B33) The multifocal lens of one or more of the above B examples, wherein the minimal ghosting is a lack of an undesired secondary image appearing at the image plane of the optical system.

(B34) The multifocal lens of one or more of the above B examples, wherein the minimal ghosting is a lack of an undesired secondary image appearing on the retina of the eye.

(B35) The multifocal lens of one or more of the above B examples, wherein the minimal ghosting is a lack of an undesired double image appearing on the retina of the eye.

(B36) The multifocal lens of one or more of the above B examples, wherein the minimal ghosting is a lack of false out-of-focus image appearing along side of the primary image in an optical system.

(B37) The multifocal lens of one or more of the above B examples, wherein the multifocal lens is further configured to provide a sufficient lack of ghosting in a portion of near, intermediate and far distances.

(B38) The multifocal lens of one or more of the above B examples, wherein the multifocal lens is further configured to provide a sufficient lack of ghosting at near distances, intermediate distances and far distances.

(B39) The multifocal lens of one or more of the above B examples, wherein the multifocal lens is further configured to provide a sufficient lack of ghosting in a portion of two or more of the following: near, intermediate and far distances.

(B40) The multifocal lens of one or more of the above B examples, wherein lack of ghosting is lack of undesired image appearing at the image plane of the optical system.

(B41) The multifocal lens of one or more of the above B examples, wherein lack of ghosting is a lack of false out of focus images appearing along side of the primary image in an optical system.

(B42) The multifocal lens of one or more of the above B examples, wherein the multifocal lens is further configured to provide a sufficient lack of ghosting in a portion of two or more of the following: near distances, intermediate distances and far distances.

(B43) The multifocal lens of one or more of the above B examples, wherein the multifocal lens is further configured to provide the RIQ of at least 0.1, 0.13, 0.17, 0.2, 0.225, or 0.25 in the near distance range, the RIQ of at least 0.27, 0.3, 0.33, 0.35, 0.37 or 0.4 in the intermediate distance range and the RIQ of at least 0.35, 0.37, 0.4, 0.42, 0.45, 0.47, or 0.5 in the far distance range.

(B44) The multifocal lens of one or more of the above B examples, wherein the multifocal lens is further configured to provide the RIQ of at least 0.1 in the near distance range, the RIQ of at least 0.2 in the intermediate distance range and the RIQ of at least 0.3 in the far distance range.

(B45) The multifocal lens of one or more of the above B examples, wherein the multifocal lens is further configured to provide two or more of the following: the RIQ of at least 0.1, 0.13, 0.17, 0.2, 0.225, or 0.25 in the near distance range, the RIQ of at least 0.27, 0.3, 0.33, 0.35, 0.37 or 0.4 in the intermediate distance range and the RIQ of at least 0.35, 0.37, 0.4, 0.42, 0.45, 0.47, or 0.5 in the far distance range.

(B46) The multifocal lens of one or more of the above B examples, wherein the multifocal lens is further configured to provide two or more of the following: the RIQ of at least 0.1 in the near distance range, the RIQ of at least 0.2 in the intermediate distance range and the RIQ of at least 0.3 in the far distance range.

(B47) The multifocal lens of one or more of the above B examples, wherein the RIQs are selected in the near, intermediate and far distance ranges such that the multifocal lens is configured to provide minimal, or no, ghosting in near, intermediate and far distances.

(B48) The multifocal lens of one or more of the above B examples, wherein the multifocal lens is configured to substantially eliminate, or substantially reduce, ghosting at near, intermediate and far distances.

(B49) The multifocal lens of one or more of the above B examples, wherein the multifocal lens is configured to substantially eliminate, or substantially reduce, ghosting at near distances, intermediate distances and far distances.

(B50) The multifocal lens of one or more of the above B examples, wherein near distance is the range of 33 cm to 50 cm or 40 cm to 50 cm; intermediate distance is the range of 50 cm to 100 cm, 50 cm to 80 cm or 50 cm to 70 cm; and far distance is the range of 100 cm or greater, 80 cm or greater or 70 cm or greater.

(B51) The multifocal lens of one or more of the above B examples, wherein near distance is the range of 33 cm to 50 cm or 40 cm to 50 cm; intermediate distance is the range of 50 cm to 100 cm, 50 cm to 80 cm or 50 cm to 70 cm; and far distance is the range of 100 cm or greater, 80 cm or greater or 70 cm or greater and the near, intermediate and far distances are determined by the distance from the object being focused on.

(B52) The multifocal lens of one or more of the above B examples, wherein near distance is the range of 40 cm to 50 cm; intermediate distance is the range of 50 cm to 100 cm; and far distance is the range of 100 cm or greater.

(B53) The multifocal lens of one or more of the above B examples, wherein near distance is the range of 40 cm to 50 cm; intermediate distance is the range of 50 cm to 100 cm; and far distance is the range of 100 cm or greater and the near, intermediate and far distances are determined by the distance from the object being focused on.

(B54) The multifocal lens of one or more of the above B examples, wherein near distance is the range of 40 cm to 50 cm; intermediate distance is the range of 50 cm to 100 cm; and far distance is the range of 100 cm to optical infinity.

(B55) The multifocal lens of one or more of the above B examples, wherein near distance is the range of 40 cm to 50 cm; intermediate distance is the range of 50 cm to 100 cm; and far distance is the range of 100 cm to optical infinity and the near, intermediate and far distances are determined by the distance from the object being focused on.

(B56) The multifocal lens of one or more of the above B examples, wherein the multifocal lens is configured to minimise, or reduce, ghosting at near, intermediate and far distances when used on an eye.

(B57) The multifocal lens of one or more of the above B examples, wherein the multifocal lens is configured to minimise, or reduce, ghosting at near distances, intermediate distances and far distances when used on an eye.

(B58) The multifocal lens of one or more of the above B examples, wherein the range of substantially continuous distances is continuous.

(B59) The multifocal lens of one or more of the above B examples, wherein the range of substantially continuous distances is continuous and goes from 40 cm to optical infinity.

(B60) The multifocal lens of one or more of the above B examples, wherein the range of substantially continuous distances is from 33 cm to optical infinity.

(B61) The multifocal lens of one or more of the above B examples, wherein the lens is configured such that at least 40%, 50%, 60% or 70% of a randomly selected group of 15 affected individuals in the near distances, intermediate distances and far distances perceive minimal, or no, ghosting at near distances, intermediate distances and far distances.

(B62) The multifocal lens of one or more of the above B examples, wherein the lens is configured such that at least 60%, 70%, 80% or 90% of a randomly selected group of 15 affected individuals in the intermediate distances and far distances perceive minimal, or no, ghosting at intermediate distances and far distances.

(B63) The multifocal lens of one or more of the above B examples, wherein the single vision lens provides a visual acuity for the user of one or more of the following: at least 20/20, at least 20/30, at least 20/40, at least about 20/20, at least about 20/30 and at least about 20/40, at far visual distances.

(B64) The multifocal lens of one or more of the above B examples, wherein the aberration profile is comprised of a defocus term and at least two, two or more, three, three or more, four, four or more, five, five or more, six, six or more, seven, seven or more, eight, eight or more, nine, nine or more, ten, or ten or more spherical aberration terms.

(B65) The multifocal lens of one or more of the above B examples, wherein the aberration profile is comprised of a defocus term and at least two, three, four, five, six, seven, eight, nine, or at least ten spherical aberration terms.

(B66) The multifocal lens of one or more of the above B examples, wherein the aberration profile is comprised of a defocus term and spherical aberration terms between C(4,0) and C(6,0), C(4,0) and C(8,0), C(4,0) and C(10,0), C(4,0) and C(12,0), C(4,0) and C(14,0), C(4,0) and C(16,0), C(4,0) and C(18,0), or C(4,0) and C(20,0).

(B67) The multifocal lens of one or more of the above B examples, wherein the single vision lens provides a visual acuity that is the best-corrected visual acuity.

(B68) The multifocal lens of one or more of the above B examples, wherein the best-corrected visual acuity is a visual acuity that cannot be substantially improved by further manipulating the power of the single vision lens.

(B69) The multifocal lens of one or more of the above B examples, wherein the lens has two optical surfaces.

(B70) The multifocal lens of one or more of the above B examples, wherein the least one aberration profile is along the optical axis of the lens.

(B71) The multifocal lens of one or more of the above B examples, wherein the lens has a focal distance.

(B72) The multifocal lens of one or more of the above B examples, wherein the aberration profile includes higher order aberrations having at least one of a primary spherical aberration component C(4,0) and a secondary spherical aberration component C(6,0).

(B73) The multifocal lens of one or more of the above B examples, wherein the aberration profile provides, for a model eye with no, or substantially no, aberrations and an on-axis length equal to the focal distance: the retinal image quality (RIQ) with a through focus slope that degrades in a direction of eye growth; and the RIQ of at least 0.3; wherein the RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(B74) The multifocal lens of one or more of the above B examples, wherein the aberration profile provides, for a model eye with no, or substantially no, aberrations and an on-axis length equal to the focal distance: the retinal image quality (RIQ) with a through focus slope that improves in a direction of eye growth; and the RIQ of at least 0.3; wherein the RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(B75) The multifocal lens of one or more of the above B examples, wherein the lens has an optical axis and an aberration profile about its optical axis, the aberration profile: having a focal distance; and including higher order aberrations having at least one of a primary spherical aberration component C(4,0) and a secondary spherical aberration component C(6,0), wherein the aberration profile provides, for a model eye with no, or substantially no, aberrations and an on-axis length equal, or substantially equal, to the focal distance: the RIQ with a through focus slope that degrades in a direction of eye growth; and the RIQ of at least 0.3; wherein the RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(B76) The multifocal lens of one or more of the above B examples, wherein the lens has an optical axis and an aberration profile about its optical axis, the aberration profile: having a focal distance; and including higher order aberrations having at least one of a primary spherical aberration component C(4,0) and a secondary spherical aberration component C(6,0), wherein the aberration profile provides, for a model eye with no, or substantially no, aberrations and an on-axis length equal, or substantially equal, to the focal distance: the RIQ with a through focus slope that improves in a direction of eye growth; and the RIQ of at least 0.3; wherein the RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(B77) The multifocal lens of one or more of the above B examples, wherein the focal distance is a prescription focal distance for a myopic, hyperopic, astigmatic, and/or presbyopic eye and wherein the focal distance differs from the focal distance for a C(2,0) Zernike coefficient of the aberration profile.

(B78) The multifocal lens of one or more of the above B examples, wherein the higher order aberrations include at least two spherical aberration terms selected from the group C(4,0) to C(20,0).

(B79) The multifocal lens of one or more of the above B examples, wherein the higher order aberrations include at least three spherical aberration terms selected from the group C(4,0) to C(20,0).

(B80) The multifocal lens of one or more of the above B examples, wherein the higher order aberrations include at least five spherical aberration terms selected from the group C(4,0) to C(20,0).

(B81) The multifocal lens of one or more of the above B examples, wherein the average slope over a horizontal field of at least −20° to +20° degrades in a direction of eye growth.

(B82) The multifocal lens of one or more of the above B examples, wherein the average slope over a horizontal field of at least −20° to +200 improves in a direction of eye growth.

(B83) The multifocal lens of one or more of the above B examples, wherein the average slope over a vertical field of at least −20° to +20° degrades in a direction of eye growth.

(B84) The multifocal lens of one or more of the above B examples, wherein the average slope over a vertical field of at least −20° to +20° improves in a direction of eye growth.

(B85) The multifocal lens of one or more of the above B examples, wherein the slope for a substantial portion of the field angles over a horizontal field of at least −20° to +20° degrades in a direction of eye growth.

(B86) The multifocal lens of one or more of the above B examples, wherein the substantial portion of the field angles over a horizontal field is at least 75%, 85%, 95% or 99% of the field angles.

(B87) The multifocal lens of one or more of the above B examples, wherein the substantial portion of the field angles over a horizontal field is every field angle.

(B88) The multifocal lens of one or more of the above B examples, wherein the slope for a substantial portion of the field angles over a vertical field of at least −20° to +20° degrades in the direction of eye growth.

(B89) The multifocal lens of one or more of the above B examples, wherein the substantial portion of the field angles over a vertical field is every angle.

(B90) The multifocal lens of one or more of the above B examples, wherein the slope for a substantial portion of the field angles over a vertical field of at least −20° to +20° degrades in a direction of eye growth.

(B91) The multifocal lens of one or more of the above B examples, wherein the substantial portion of the field angles over a vertical field is every angle.

(B92) The multifocal lens of one or more of the above B examples, wherein the substantial portion of the field angles over a vertical field is at least 75%, 85%, 95% or 99% of the field angles.

(B93) The multifocal lens of one or more of the above B examples, wherein the aberration profile provides the RIQ of at least 0.3 at the focal length for a substantial portion of pupil diameters in the range 3 mm to 6 mm.

(B94) The multifocal lens of one or more of the above B examples, wherein the aberration profile provides the RIQ of at least 0.3 at the focal length for a substantial portion of pupil diameters in the range 4 mm to 5 mm.

(B95) The multifocal lens of one or more of the above B examples, wherein the aberration profile provides the RIQ with a through focus slope that degrades in a direction of eye growth when primary or secondary astigmatism is added to the aberration profile.

(B96) The multifocal lens of one or more of the above B examples, wherein the aberration profile provides the RIQ with a through focus slope that improves in a direction of eye growth when primary or secondary astigmatism is added to the aberration profile.

(B97) The multifocal lens of one or more of the above B examples, wherein the primary or secondary astigmatism is added to the desired aberration profile by altering one or more of the following terms: C(2,−2), C(2,2), C(4,−2), C(4,2), C(6,−2) and/or C(6,2).

(B98) The multifocal lens of one or more of the above B examples, wherein the aberration profile provides the RIQ with a through focus slope that degrades in a direction of eye growth when secondary astigmatism is added to the aberration profile.

(B99) The multifocal lens of one or more of the above B examples, wherein the secondary astigmatism is added to the desired aberration profile by altering one or more of the following terms: C(2,−2), C(2,2), C(4,−2), C(4,2), C(6,−2) and/or C(6,2).

(B100) The multifocal lens of one or more of the above B examples, wherein the RIQ is characterised by $$RIQ = \frac{\left(real\left(\left(\left[FT\left(\left|FT\left\{A(\rho,\theta)*\exp\left[\frac{2\pi i}{\lambda}*W(\rho,\theta)\right]\right\}\right|^2\right)\right]\right)\right)\right) \int\int_{-Fmin}^{+Fmax} CSF(x,y)*}{\int\int_{-Fmin}^{+Fmax} CSF(x,y)* \left(\left(\left(\left[FT\left(\left|FT\left\{A(\rho,\theta)*\exp\left[\frac{2\pi i}{\lambda}*Wdiff(\rho,\theta)\right]\right\}\right|^2\right)\right]\right)\right)\right)}$$

wherein:
Fmin is 0 cycles/degree and Fmax is 30 cycles/degree;
CSF(x, y) denotes the contrast sensitivity function,
CSF(F)=2.6(0.0192+0.114f)e$^{-(0.114f)^{1.1}}$,
where f specifies the tested spatial frequency, in the range of $F_{min}$ to $F_{max}$;
FT denotes a 2 D Fourier transform, for example a 2 D fast Fourier transform;
A(ρ,θ) denotes the pupil amplitude function across the pupil diameter;
W(ρ,θ) denotes wavefront of the test case measured for i=1 to 20

$$W(\rho,\theta) = \sum_{i=1}^{k} a_i Z_i(\rho,\theta);$$

Wdiff(ρ, θ) denotes wavefront of the diffraction limited case;
ρ and θ are normalised polar coordinates, where ρ represents the radial coordinate and θ represents the angular coordinate or azimuth; and
λ denotes wavelength.

(B101) The multifocal lens of one or more of the above B examples, wherein the RIQ is characterised by $$RIQ = \frac{\left(real\left(\left(\left[FT\left(\left|FT\left\{A(\rho,\theta)*\exp\left[\frac{2\pi i}{\lambda}*W(\rho,\theta)\right]\right\}\right|^2\right)\right]\right)\right)\right) \int\int_{-Fmin}^{+Fmax} CSF(x,y)*}{\int\int_{-Fmin}^{+Fmax} CSF(x,y)* \left(\left(\left(\left[FT\left(\left|FT\left\{A(\rho,\theta)*\exp\left[\frac{2\pi i}{\lambda}*Wdiff(\rho,\theta)\right]\right\}\right|^2\right)\right]\right)\right)\right)}$$

wherein:
Fmin is 0 cycles/degree and Fmax is 30 cycles/degree;
CSF(x, y) denotes the contrast sensitivity function,
CSF(F)=2.6(0.0192+0.114f)e$^{-(0.114f)^{1.1}}$,
where f specifies the tested spatial frequency, in the range of $F_{min}$ to $F_{max}$;
FT denotes a 2 D Fourier transform, for example a 2 D fast Fourier transform;
A(ρ,θ) denotes the pupil amplitude function across the pupil diameter;
W(ρ,θ) denotes wavefront of the test case measured for i=1 to k;
where k is a positive integer, $$W(\rho,\theta) = \sum_{i=1}^{k} a_i Z_i(\rho,\theta);$$

Wdiff(ρ, θ) denotes wavefront of the diffraction limited case;
ρ and θ are normalised polar coordinates, where ρ represents the radial coordinate and θ represents the angular coordinate or azimuth; and
λ denotes wavelength.

(B102) The multifocal lens of one or more of the above B examples, wherein the multifocal lens includes an optical axis and an aberration profile along the optical axis that provides: a focal distance for a C(2,0) Zernike coefficient term; a peak visual Strehl Ratio ('first visual Strehl Ratio') within a through focus range, and a visual Strehl Ratio that remains at or above a second visual Strehl Ratio over the through focus range that includes said focal distance, wherein the visual Strehl Ratio is measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive, and wherein the first visual Strehl Ratio is at least 0.35, the second visual Strehl Ratio is at least 0.1 and the through focus range is at least 1.8 Dioptres.

(B103) The multifocal lens of one or more of the above B examples, wherein the multifocal lens includes an optical axis and an aberration profile along the optical axis that provides: a focal distance for a C(2,0) Zernike coefficient term; a peak visual Strehl Ratio ('first visual Strehl Ratio') within a through focus range, and a visual Strehl Ratio that remains at or above a second visual Strehl Ratio over the through focus range that includes said focal distance, wherein the visual Strehl Ratio is measured for a model eye with no aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive, and wherein the first visual Strehl Ratio is at least 0.35, the second visual Strehl Ratio is at least 0.1 and the through focus range is at least 1.8 Dioptres.

(B104) The multifocal lens of one or more of the above B examples, wherein the first visual Strehl Ratio is at least 0.3, 0.35, 0.4, 0.5, 0.6, 0.7 or 0.8.

(B105) The multifocal lens of one or more of the above B examples, wherein the second visual Strehl Ratio is at least 0.1, 0.12, 0.15, 0.18 or 0.2.

(B106) The multifocal lens of one or more of the above B examples, wherein the through focus range is at least 1.7, 1.8, 1.9, 2, 2.1, 2.25 or 2.5 Dioptres.

(B107) The multifocal lens of one or more of the above B examples, wherein the lens has a prescription focal distance located within 0.75, 0.5, 0.3, or 0.25 Dioptres, inclusive, of an end of the through focus range.

(B108) The multifocal lens of one or more of the above B examples, wherein the end of the through focus range is the negative power end.

(B109) The multifocal lens of one or more of the above B examples, wherein the end of the through focus range is the positive power end.

(B110) The multifocal lens of one or more of the above B examples, wherein the visual Strehl Ratio remains at or above the second visual Strehl Ratio over the through focus range and over a range of pupil diameters of at least 1 mm, 1.5 mm, 2 mm, 2.5 mm, or 3 mm.
(B111) The multifocal lens of one or more of the above B examples, wherein the combination of higher order aberrations includes at least one of primary spherical aberration and secondary spherical aberration.
(B112) The multifocal lens of one or more of the above B examples, wherein the higher order aberrations include at least two, three, or five spherical aberration terms selected from the group C(4,0) to C(20,0).
(B113) The multifocal lens of one or more of the above B examples, wherein the aberration profile is substantially characterized using only spherical aberration Zernike coefficients C(4,0) to C(20,0).
(B114) The multifocal lens of one or more of the above B examples, wherein the RIQ for a substantial portion of the angles over a horizontal field of at least −10° to +10°, −20° to +20° or −30° to +30° is at least 0.4.
(B115) The multifocal lens of one or more of the above B examples, wherein the RIQ for a substantial portion of the angles over a horizontal field of at least −10° to +10°, −20° to +20° or −30° to +30° is at least 0.35.
(B116) The multifocal lens of one or more of the above B examples, wherein the RIQ for a substantial portion of the angles over a horizontal field of at least −10° to +10°, −20° to +20° or −30° to +30° is at least 0.3.
(B117) The multifocal lens of one or more of the above B examples, wherein the lens is one or more of the following: contact lens, corneal onlays, corneal inlays, anterior chamber intraocular lens or posterior chamber intraocular lens.
(B118) The multifocal lens of one or more of the above B examples, wherein the lens is one of the following: contact lens, corneal onlays, corneal inlays, anterior chamber intraocular lens or posterior chamber intraocular lens.
(B119) The multifocal lens of one or more of the above B examples, wherein a first multifocal lens is provided based on one or more of the above of the B examples and a second multifocal lens is provided based on one or more of the B examples to form a pair of lenses.
(B120) The multifocal lens of one or more of the above B examples, wherein the first multifocal lens is provided based on one or more of the B examples and a second lens is provided to form a pair of lenses.
(B121) The multifocal lens of one or more of the above B examples, wherein a pair of multifocal lenses are provided for use by an individual to substantially correct the individual's vision.
(B122) The multifocal lens of one or more of the above B examples, wherein the aberration profile is an aberration pattern.
(B123) A method for making or using one or more of the multifocal lenses of one or more of the above B examples.

Example Set C (C1) A lens comprising: an optical axis; at least two optical surfaces; wherein the lens is configured to provide a visual performance on a presbyopic eye substantially equivalent to the visual performance of a single-vision lens on the pre-presbyopic eye; and wherein the lens has an aperture size greater than 1.5 mm.
(C2) A lens comprising: an optical axis; at least two optical surfaces; wherein the lens is configured to provide a visual performance on a presbyopic eye substantially equivalent to the visual performance of a correctly prescribed single-vision lens on the pre-presbyopic eye; and wherein the lens has an aperture size greater than 1.5 mm.
(C3) A lens comprising: an optical axis; at least two optical surfaces; wherein the lens is configured to provide a visual performance for a presbyopic condition substantially equivalent to the visual performance of an appropriately prescribed single-vision lens for the pre-presbyopic condition; and wherein the lens has an aperture size greater than 1.5 mm.
(C4) A lens comprising an optical axis; at least two optical surfaces; wherein the lens is configured to provide a visual performance on a presbyopic eye substantially equivalent to the visual performance of a effectively prescribed single-vision lens on the pre-presbyopic eye; and wherein the lens has an aperture size greater than 1.5 mm.
(C5) The lens of one or more of the above of the C examples, wherein the lens is configured based on an aberration profile associated with the optical axis; the aberration profile is comprised of a defocus term and at least two spherical aberration terms; and the lens is configured to provide the visual performance, along a range of substantially continuous visual distances, including near, intermediate and far distances.
(C6) The lens of one or more of the above C examples, wherein the lens does not substantially reduce the amount of light passing through the lens.
(C7) The lens of one or more of the above C examples, wherein the amount of light passing through the lens is at least 80%, 85%, 90%, 95% or 99%.
(C8) The lens of one or more of the above of the C examples, wherein the lens is configured to provide the visual performance, along substantially continuous visual distances, including substantially near distances, substantially intermediate distances, and substantially far distances.
(C9) The lens of one or more of the above of the C examples, wherein the lens is configured to provide the visual performance, along continuous visual distances, including near distances, intermediate distances, and far distances.
(C10) The lens of one or more of the above of the C examples, wherein the lens is configured to provide the visual performance, along a range of visual distances, including near, intermediate and far distances.
(C11) The lens of one or more of the above of the C examples, wherein the aberration profile is comprised of the defocus term, the at least two spherical aberration terms and at least one asymmetric higher order aberration term.
(C12) The lens of one or more of the above of the C examples, wherein the lens is characterised in part by the aberration profile associated with the optical axis of the lens.
(C13) The lens of one or more of the above C examples, wherein the single-vision lens is one of the following: prescribed, correctly prescribed, appropriately prescribed, properly prescribed or effectively prescribed.
(C14) The lens of one or more of the above C examples, wherein the lens is one or more of the following: contact lens, corneal onlays, corneal inlays, intra-ocular contact lens, intraocular lens, anterior chamber intraocular lens and posterior chamber intraocular lens.
(C15) The lens of one or more of the above C examples, wherein the lens is one of the following: contact lens, corneal onlays, corneal inlays, intra-ocular contact lens, intraocular lens, anterior chamber intraocular lens or posterior chamber intraocular lens.

(C16) The lens of one or more of the above C examples, wherein the single-vision lens is a lens with a substantially constant power across a substantial portion of an optic zone of the single-vision lens.
(C17) The lens of one or more of the above C examples, wherein the single-vision lens is a lens with a constant power across a portion of an optic zone of the single-vision lens.
(C18) The lens of one or more of the above C examples, wherein the single-vision lens is a lens with a substantially constant power across one or more portions of the optic zone of the single-vision lens.
(C19) The lens of one or more of the above C examples, wherein the single-vision lens is a lens with a constant power across one or more portions of the optic zone of the single-vision lens.
(C20) The lens of one or more of the above C examples, wherein the lens is configured to optically correct or mitigate presbyopia.
(C21) The lens of one or more of the above C examples, wherein the lens is configured to alter, or substantially alter, a presbyopic condition to a non-presbyopic condition.
(C22) The lens of one or more of the above C examples, wherein the lens is used for at least correcting a presbyopic eye condition and when used provides a best available fit to adjust the vision of the user towards substantial normal vision.
(C23) The lens of one or more of the above C examples, wherein the lens is further characterised by minimal, or no, ghosting at near, intermediate and far distances.
(C24) The lens of one or more of the above C examples, wherein the lens is further configured to provide minimal, or no, ghosting at near, intermediate and far distances.
(C25) The lens of one or more of the above C examples, wherein the lens is further configured to provide a sufficient lack of ghosting in a substantial portion of near, intermediate and far distances.
(C26) The lens of one or more of the above C examples, wherein the lens is further configured to provide a sufficient lack of ghosting in a substantial portion of two or more of the following: near, intermediate and far distances.
(C27) The lens of one or more of the above C examples, wherein the lens is further configured to provide a sufficient lack of ghosting in two or more of the following: near, intermediate and far distances.
(C28) The lens of one or more of the above C examples, wherein the lens is further configured to provide the RIQ of at least 0.1, 0.12, 0.14, 0.16, 0.18 or 0.2 in the near distance range, the RIQ of at least 0.3, 0.32, 0.34, 0.36, 0.38 or 0.4 in the intermediate distance range and the RIQ of at least 0.4, 0.45, 0.5, 0.6 or 0.7 in the far distance range.
(C29) The lens of one or more of the above C examples, wherein the lens is further configured to provide the RIQ of at least 0.15 in the near distance range, the RIQ of at least 0.25 in the intermediate distance range and the RIQ of at least 0.3 in the far distance range.
(C30) The lens of one or more of the above C examples, wherein the lens is further configured to provide the RIQ of at least 0.2 in the near distance range, the RIQ of at least 0.3 in the intermediate distance range and the RIQ of at least 0.4 in the far distance range.
(C31) The lens of one or more of the above C examples, wherein the lens is further configured to provide two or more of the following: the RIQ of at least 0.1, 0.12, 0.14, 0.16, 0.18 or 0.2 in the near distance range, the RIQ of at least 0.3, 0.32, 0.34, 0.36, 0.38 or 0.4 in the intermediate distance range and the RIQ of at least 0.4, 0.45, 0.5, 0.6 or 0.7 in the far distance range.

(C32) The lens of one or more of the above C examples, wherein RIQs are selected in the near, intermediate and far distance ranges such that the lens is configured to provide minimal, or no, ghosting in near, intermediate and far distances.
(C33) The lens of one or more of the above C examples, wherein the lens is configured to substantially eliminate, or substantially reduce, ghosting at near, intermediate and far distances.
(C34) The lens of one or more of the above C examples, wherein near distance is the range of 33 cm to 50 cm or 40 cm to 50 cm; intermediate distance is the range of 50 cm to 100 cm, 50 cm to 80 cm or 50 cm to 70 cm; and far distance is the range of 100 cm or greater, 80 cm or greater or 70 cm or greater.
(C35) The lens of one or more of the above C examples, wherein near distance is the range of 33 cm to 50 cm or 40 cm to 50 cm; intermediate distance is the range of 50 cm to 100 cm, 50 cm to 80 cm or 50 cm to 70 cm; and far distance is the range of 100 cm or greater, 80 cm or greater or 70 cm or greater and the near, intermediate and far distances are determined by the distance from the object being focused on.
(C36) The lens of one or more of the above C examples, wherein near distance is the range of 40 cm to 50 cm; intermediate distance is the range of 50 cm to 100 cm; and far distance is the range of 100 cm or greater.
(C37) The lens of one or more of the above C examples, wherein near distance is the range of 40 cm to 50 cm; intermediate distance is the range of 50 cm to 100 cm; and far distance is the range of 100 cm or greater and the near, intermediate and far distances are determined by the distance from the object being focused on.
(C38) The lens of one or more of the above C examples, wherein near distance is the range of 40 cm to 50 cm; intermediate distance is the range of 50 cm to 100 cm; and far distance is the range of 100 cm to optical infinity.
(C39) The lens of one or more of the above C examples, wherein near distance is the range of 40 cm to 50 cm; intermediate distance is the range of 50 cm to 100 cm; and far distance is the range of 100 cm to optical infinity and the near, intermediate and far distances are determined by the distance from the object being focused on.
(C40) The lens of one or more of the above C examples, wherein the lens is configured to minimize, or reduce, ghosting at near, intermediate and far distances when used on the pre-presbyopic eye.
(C41) The lens of one or more of the above C examples, wherein ghosting is measured when the lens is used on the pre-presbyopic eye.
(C42) The lens of one or more of the above C examples, wherein the range of substantially continuous distances is continuous.
(C43) The lens of one or more of the above C examples, wherein the range of substantially continuous distances is continuous and goes from 40 cm to optical infinity.
(C44) The lens of one or more of the above C examples, wherein the range of substantially continuous distances is from 33 cm to optical infinity.
(C45) The lens of one or more of the above C examples, wherein the lens is configured such that at least 40%, 50%, 60% or 70% of a randomly selected group of 15 affected individuals in the near, intermediate and far distance ranges perceive minimal, or no, ghosting at near, intermediate and far distances.
(C46) The lens of one or more of the above C examples, wherein the lens is configured such that at least 60%, 70%, 80% or 90% of a randomly selected group of 15 affected individuals in the near, intermediate and far distance ranges perceive minimal, or no, ghosting at near, intermediate and far distances.

(C47) The lens of one or more of the above C examples, wherein the single vision lens provides a visual acuity for the user of one or more of the following: at least 20/20, at least 20/30, at least 20/40, at least about 20/20, at least about 20/30 and at least about 20/40, at far visual distance.

(C48) The lens of one or more of the above C examples, wherein the aberration profile is comprised of the defocus term and the at least two, two or more, three, three or more, four, four or more, five, five or more, six, six or more, seven, seven or more, eight, eight or more, ten, or ten or more spherical aberration terms.

(C49) The lens of one or more of the above C examples, wherein the aberration profile is comprised of the defocus term and the at least two, three, four, five, six, seven, eight, or at least ten spherical aberration terms.

(C50) The multifocal lens of one or more of the above C examples, wherein the aberration profile is comprised of a defocus term and spherical aberration terms between C(4,0) and C(6,0), C(4,0) and C(8,0), C(4,0) and C(10,0), C(4,0) and C(12,0), C(4,0) and C(14,0), C(4,0) and C(16,0), C(4,0) and C(18,0) or C(4,0) and C(20,0).

(C51) The lens of one or more of the above C examples, wherein the best-corrected visual acuity is a visual acuity that cannot be substantially improved by further manipulating the power of the single vision lens.

(C52) The lens of one or more of the above C examples, wherein the least one aberration profile is along the optical axis of the lens.

(C53) The lens of one or more of the above C examples, wherein the aberration profile includes higher order aberrations having at least one of a primary spherical aberration component C(4,0) and a secondary spherical aberration component C(6,0).

(C54) The lens of one or more of the above C examples, wherein the aberration profile provides, for a model eye with no aberrations and an on-axis length equal to the focal distance: the RIQ with a through focus slope that degrades in a direction of eye growth; and the RIQ of at least 0.30; wherein the RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(C55) The lens of one or more of the above C examples, wherein the aberration profile provides, for a model eye with no aberrations and an on-axis length equal to the focal distance: the RIQ with a through focus slope that improves in a direction of eye growth; and the RIQ of at least 0.3; wherein the RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(C56) The lens of one or more of the above C examples, wherein the lens has the optical axis and the aberration profile about the lens optical axis, the aberration profile: having the focal distance; and including higher order aberrations having the at least one of a primary spherical aberration component C(4,0) and the secondary spherical aberration component C(6,0), wherein the aberration profile provides, for the model eye with no aberrations and an on-axis length equal to the focal distance: the RIQ with a through focus slope that degrades in a direction of eye growth; and the RIQ of at least 0.3; wherein the RIQ is visual Strehl Ratio measured along the optical axis for the at least one pupil diameter in the range 3 mm to 6 mm, over a spatial frequency range of 0 to 30 cycles/degree inclusive and at a wavelength selected from within the range 540 nm to 590 nm inclusive.

(C57) The lens of one or more of the above C examples, wherein the focal distance is a prescription focal distance for a myopic eye and wherein the focal distance differs from the focal distance for a C(2,0) Zernike coefficient of the aberration profile.

(C58) The lens of one or more of the above C examples, wherein the higher order aberrations include at least two spherical aberration terms selected from the group C(4,0) to C(20,0).

(C59) The lens of one or more of the above C examples, wherein the higher order aberrations include at least three spherical aberration terms selected from the group C(4,0) to C(20,0).

(C60) The lens of one or more of the above C examples, wherein the higher order aberrations include at least five spherical aberration terms selected from the group C(4,0) to C(20,0).

(C61) The lens of one or more of the above C examples, wherein the average slope over a horizontal field of at least −20° to +20° degrades in a direction of eye growth.

(C62) The lens of one or more of the above C examples, wherein the average slope over a vertical field of at least −20° to +20° degrades in a direction of eye growth.

(C63) The lens of one or more of the above C examples, wherein the slope for a substantial portion of the field angles over a horizontal field of at least −20° to +20° degrades in a direction of eye growth.

(C64) The lens of one or more of the above C examples, wherein the slope for a substantial portion of the field angles over a vertical field of at least −20° to +20° degrades in the direction of eye growth.

(C65) The lens of one or more of the above C examples, wherein the substantial portion of the field angles over the vertical field is every angle.

(C66) The lens of one or more of the above C examples, wherein the substantial portion of the field angles over a horizontal field is every field angle.

(C67) The lens of one or more of the above C examples, wherein the slope for a substantial portion of the field angles over a vertical field of at least −20° to +20° degrades in a direction of eye growth.

(C68) The lens of one or more of the above C examples, wherein the substantial portion of the field angles over a vertical field is every angle.

(C69) The lens of one or more of the above C examples, wherein the aberration profile provides the RIQ of at least 0.3 at the focal length for a substantial portion of pupil diameters in the range 3 mm to 6 mm.

(C70) The lens of one or more of the above C examples, wherein the aberration profile provides the RIQ of at least 0.3 at the focal length for a substantial portion of pupil diameters in the range 4 mm to 5 mm.

(C71) The lens of one or more of the above C examples, wherein the aberration profile provides the RIQ with a through focus slope that degrades in a direction of eye growth when primary astigmatism is added to the aberration profile.

(C72) The lens of one or more of the above C examples, wherein the aberration profile provides the RIQ with a through focus slope that degrades in a direction of eye growth when secondary astigmatism is added to the aberration profile.

(C73) The lens of one or more of the above C examples, wherein the RIQ is characterised by $$RIQ = \frac{\int\int_{-Fmin}^{+Fmax} CSF(x, y) * \left(real\left(\left[\left|FT\left(\left|FT\left\{A(\rho, \theta) * \exp\left[\frac{2\pi i}{\lambda} * W(\rho, \theta)\right]\right\}\right|\right)\right|^2\right]\right)\right)}{\int\int_{-Fmin}^{+Fmax} CSF(x, y) * \left(\left(\left[\left|FT\left(\left|FT\left\{A(\rho, \theta) * \exp\left[\frac{2\pi i}{\lambda} * Wdiff(\rho, \theta)\right]\right\}\right|\right)\right|^2\right]\right)\right)}$$

wherein:
Fmin is 0 cycles/degree and Fmax is 30 cycles/degree;
CSF(x, y) denotes the contrast sensitivity function,
CSF(F)=2.6(0.0192+0.114f)e^{-(0.114f)^1.1}
where f specifies the tested spatial frequency, in the range of $F_{min}$ to $F_{max}$;
FT denotes a 2 D fast Fourier transform;
A(ρ,θ) denotes the pupil amplitude function across the pupil diameter;
W(ρ,θ) denotes wavefront of the test case measured for i=1 to 20

$$W(\rho, \theta) = \sum_{i=1}^{k} a_i Z_i(\rho, \theta);$$

Wdiff(ρ, θ) denotes wavefront of the diffraction limited case;
ρ and θ are normalised polar coordinates, where ρ represents the radial coordinate and θ represents the angular coordinate or azimuth; and
λ denotes wavelength.

(C74) The lens of one or more of the above C examples, wherein the RIQ is characterised by $$RIQ = \frac{\int\int_{-Fmin}^{+Fmax} CSF(x, y) * \left(real\left(\left[\left|FT\left(\left|FT\left\{A(\rho, \theta) * \exp\left[\frac{2\pi i}{\lambda} * W(\rho, \theta)\right]\right\}\right|\right)\right|^2\right]\right)\right)}{\int\int_{-Fmin}^{+Fmax} CSF(x, y) * \left(\left(\left[\left|FT\left(\left|FT\left\{A(\rho, \theta) * \exp\left[\frac{2\pi i}{\lambda} * Wdiff(\rho, \theta)\right]\right\}\right|\right)\right|^2\right]\right)\right)}$$

wherein:
Fmin is 0 cycles/degree and Fmax is 30 cycles/degree;
CSF(x, y) denotes the contrast sensitivity function,
CSF(F)=2.6(0.0192+0.114f)e^{-(0.114f)^1.1}
where f specifies the tested spatial frequency, in the range of $F_{min}$ to $F_{max}$;
FT denotes a 2 D Fourier transform, for example a 2 D fast Fourier transform;
A(ρ, θ) denotes the pupil amplitude function across the pupil diameter;
W(ρ, θ) denotes wavefront of the test case measured for i=1 to k;
wherein k is a positive integer;

$$W(\rho, \theta) = \sum_{i=1}^{k} a_i Z_i(\rho, \theta);$$

Wdiff(ρ, θ) denotes wavefront of the diffraction limited case;
ρ and θ are normalised polar coordinates, where ρ represents the radial coordinate and θ represents the angular coordinate or azimuth; and
λ denotes wavelength.

(C75) The lens of one or more of the above C examples, wherein the lens includes the optical axis and the aberration profile about the optical axis that provides: the focal distance for the C(2,0) Zernike coefficient term; a peak visual Strehl Ratio ('first visual Strehl Ratio') within a through focus range, and a visual Strehl Ratio that remains at or above a second visual Strehl Ratio over the through focus range that includes the focal distance, wherein the visual Strehl Ratio is measured for the model eye with no aberration and is measured along the optical axis for at least one pupil diameter in the range 3 mm to 5 mm, over the spatial frequency range of 0 to 30 cycles/degree inclusive, at the wavelength selected from within the range 540 nm to 590 nm inclusive, and wherein the first visual Strehl Ratio is at least 0.35, the second visual Strehl Ratio is at least 0.1 and the through focus range is at least 1.8 Dioptres.

(C76) The lens of one or more of the above C examples, wherein the first visual Strehl Ratio is at least 0.4, 0.5, 0.6, 0.7 or 0.8.

(C77) The lens of one or more of the above C examples, wherein the second visual Strehl Ratio is at least 0.1, 0.12, 0.14, 0.16, 0.18 or 0.2.

(C78) The lens of one or more of the above C examples, wherein the through focus range is at least 1.7, 1.8, 1.9, 2, 2.1, 2.25 or 2.5 Dioptres.

(C79) The lens of one or more of the above C examples, wherein the lens has a prescription focal distance located within 0.75, 0.5, 0.3, or 0.25 Dioptres, inclusive, of an end of the through focus range.

(C80) The lens of one or more of the above C examples, wherein the end of the through focus range is the negative power end.

(C81) The lens of one or more of the above C examples, wherein the end of the through focus range is the positive power end.

(C82) The lens of one or more of the above C examples, wherein the visual Strehl Ratio remains at or above the second visual Strehl Ratio over the through focus range and over a range of pupil diameters of at least 1 mm, 1.5 mm or 2 mm.

(C83) The lens of one or more of the above C examples, wherein the combination of higher order aberrations includes at least one of primary spherical aberration and secondary spherical aberration.

(C84) The lens of one or more of the above C examples, wherein the higher order aberrations include at least two, three, or five spherical aberration terms selected from the group C(4,0) to C(20,0).

(C85) The lens of one or more of the above C examples, wherein the aberration profile is substantially characterized using only spherical aberration Zernike coefficients C(4, 0) to C(20, 0).

(C86) The lens of one or more of the above C examples, wherein the RIQ for a substantial portion of the angles over a horizontal field of at least −10° to +10°, −20° to +20° or −30° to +30° is at least 0.3, 0.35 or 0.4.

(C87) The lens of one or more of the above C examples, wherein the RIQ for every angle over a horizontal field of at least −10° to +10°, −20° to +20° or −30° to +30° is at least 0.3, 0.35 or 0.4.

(C88) The lens of one or more of the above C examples, wherein a first lens is provided based on one or more of the C examples and a second lens is provided based on one or more of the C examples to form a pair of lenses.

(C89) The lens of one or more of the above C examples, wherein a first lens is provided based on one or more of the C examples and a second lens is provided to form a pair of lenses.

(C90) The lens of one or more of the above C examples, wherein the pair of lenses are provide for use by an individual to substantially correct the individuals version.

Example Set D (D1) A lens for an eye, the lens having at least one optical axis and at least one optical profile substantially about at least one optical axis, the optical profile comprising: at least one focal distance; and one or more higher order aberrations, wherein the optical profile provides for: a model eye with substantially no aberrations and an on-axis length equal to, or substantially equal to, the desired focal distance; a retinal image quality (RIQ) with a through focus slope that degrades in a direction of eye growth; and a RIQ of at least 0.3; and wherein the RIQ is measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(D2) A lens for an eye, the lens having at least one optical axis and at least one optical profile substantially about at least one optical axis, the optical profile comprising: at least one focal distance; and one or more higher order aberrations, wherein the optical profile provides for: a model eye with no aberrations and an on-axis length equal to the desired focal distance; a retinal image quality (RIQ) with a through focus slope that degrades in a direction of eye growth; and a RIQ of at least 0.3; and wherein the RIQ is measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(D3) A lens for an eye, the lens having an optical axis and at least one optical profile substantially about the optical axis the optical profile comprising: at least one focal distance; and one or more higher order aberrations, wherein the optical profile provides for a model eye with substantially no aberrations and an on-axis length equal to, or substantially equal to, the desired focal distance; a retinal image quality (RIQ) with a through focus slope that improves in a direction of eye growth; and a RIQ of at least 0.3; and wherein the RIQ is measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(D4) A lens for an eye, the lens having an optical axis and an aberration profile about the optical axis the aberration profile comprising: a focal distance; and higher order aberrations having at least one of a primary spherical aberration component $C(4,0)$ and a secondary spherical aberration component $C(6,0)$, wherein the aberration profile provides for: a model eye with no aberrations, or substantially no aberrations, and an on-axis length equal to the focal distance: a retinal image quality (RIQ) with a through focus slope that degrades in a direction of eye growth; and a RIQ of at least 0.3; wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(D5) A lens for an eye, the lens having an optical axis and an aberration profile about the optical axis the aberration profile comprising: a focal distance; and higher order aberrations having at least one of a primary spherical aberration component $C(4,0)$ and a secondary spherical aberration component $C(6,0)$, wherein the aberration profile provides for a model eye with no aberrations and an on-axis length equal to the focal distance; a retinal image quality (RIQ) with a through focus slope that degrades in a direction of eye growth; and a RIQ of at least 0.3; wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(D6) A lens for an eye, the lens having an optical axis and at least one optical profile substantially about the optical axis the optical profile comprising: at least one focal distance; and one or more higher order aberrations, wherein the optical profile provides for: a model eye with substantially no aberrations an on-axis length equal to, or substantially equal to, the desired focal distance; a retinal image quality (RIQ) with a through focus slope that improves in a direction of eye growth; and a RIQ of at least 0.3; and wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(D7) A lens for an eye, the lens having an optical axis and an aberration profile about the optical axis the aberration profile comprising: a focal distance; and higher order aberrations having at least one of a primary spherical aberration component $C(4,0)$ and a secondary spherical aberration component $C(6,0)$, wherein the aberration profile provides for: a model eye with no aberrations, or substantially no aberrations, and an on-axis length equal to the focal distance: a retinal image quality (RIQ) with a through focus slope that improves in a direction of eye growth; and a RIQ of at least 0.3; wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(D8) A lens for an eye, the lens having an optical axis and a surface structure, wherein the surface structure is configured to generate an aberration profile about the optical axis, the aberration profile comprising: a focal distance; and higher order aberrations having at least one of a primary spherical aberration component $C(4,0)$ and a secondary spherical aberration component $C(6,0)$, wherein the aberration profile provides, for a model eye with no aberrations, or substantially no aberrations, and an on-axis length equal to the focal distance: a retinal image quality (RIQ) with a through focus slope that improves in a direction of eye growth; and a RIQ of at least 0.3; wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(D9) A lens for an eye, the lens having an optical axis and at least one optical profile substantially about the optical axis, the optical profile comprising: at least one focal distance; and one or more higher order aberrations, wherein the optical profile provides, for a model eye with substantially no aberrations an on-axis length equal to, or substantially equal to, the desired focal distance; a retinal image quality (RIQ) with a through focus slope that improves in a direction of eye growth; and a RIQ of at least 0.3; wherein said RIQ is measured substantially along the optical axis for at least one pupil.

(D10) The lens of one or more of the above D examples, wherein the single-vision lens is one or more of the following: prescribed, appropriately prescribed, correctly prescribed and effectively prescribed.

(D11) The lens of one or more of the above D examples, wherein the single-vision lens is a lens with a substantially constant power across a substantial portion of an optic zone of the single-vision lens.

(D12) The lens of one or more of the above D examples, wherein the single-vision lens is a lens with a constant power across a portion of an optic zone of the single-vision lens.

(D13) The lens of one or more of the above D examples, wherein the single-vision lens is a lens with a substantially constant power across a portion of one or more optic zones of the single-vision lens.

(D14) The lens of one or more of the above of the above D examples, wherein the lens is used for a presbyopic eye.

(D15) The lens of one or more of the above D examples, wherein the lens is configured for a presbyopic eye.

(D16) The lens of one or more of the above D examples, wherein the lens is configured to optically correct or substantially correct presbyopia.

(D17) The lens of one or more of the above D examples, wherein the lens is configured to mitigate or substantially mitigate the optical consequences of presbyopia.

(D18) The lens of one or more of the above D examples, wherein the lens is configured to alter or substantially alter a presbyopic condition to a non-presbyopic condition.

(D19) The lens of one or more of the above D examples, wherein the lens is used for at least correcting a presbyopic eye condition and when used provides an appropriate correction to adjust the vision of the user towards substantially normal non-presbyopic vision.

(D20) The lens of one or more of the above D examples, wherein normal vision is 6/6 or better.

(D21) The lens of one or more of the above D examples, wherein the lens is further characterised by minimal, substantially no or no, ghosting at near, intermediate and far distances.

(D22) The lens of one or more of the above D examples, wherein the lens is further characterised by minimal, substantially no or no, ghosting at near distances, intermediate distances and far distances.

(D23) The lens of one or more of the above D examples, wherein the lens is further configured to provide minimal, substantially no or no, ghosting at near, intermediate and far distances.

(D24) The lens of one or more of the above D examples, wherein the minimal ghosting is a lack of an undesired secondary image appearing at the image plane of the optical system.

(D25) The lens of one or more of the above D examples, wherein the minimal ghosting is a lack of an undesired secondary image appearing on the retina of the eye.

(D26) The lens of one or more of the above D examples, wherein the minimal ghosting is a lack of an undesired double image appearing on the retina of the eye.

(D27) The lens of one or more of the above D examples, wherein the minimal ghosting is a lack of false out-of-focus image appearing along side of the primary image in an optical system.

(D28) The lens of one or more of the above D examples, wherein the lens is further configured to provide a sufficient lack of ghosting in a portion of near, intermediate and far distances.

(D29) The lens of one or more of the above D examples, wherein the lens is further configured to provide a sufficient lack of ghosting at near distances, intermediate distances and far distances.

(D30) The lens of one or more of the above D examples, wherein the lens is further configured to provide a sufficient lack of ghosting in a portion of two or more of the following: near, intermediate and far distances.

(D31) The lens of one or more of the above D examples, wherein lack of ghosting is lack of undesired image appearing at the image plane of the optical system.

(D32) The lens of one or more of the above D examples, wherein lack of ghosting is a lack of false out of focus images appearing along side of the primary image in an optical system.

(D33) The lens of one or more of the above D examples, wherein the lens is further configured to provide a sufficient lack of ghosting in a portion of two or more of the following: near distances, intermediate distances and far distances.

(D34) The lens of one or more of the above D examples, wherein the lens is further configured to provide the RIQ of at least 0.1, 0.13, 0.17, 0.2, 0.225, or 0.25 in the near distance range, the RIQ of at least 0.27, 0.3, 0.33, 0.35, 0.37 or 0.4 in the intermediate distance range and the RIQ of at least 0.35, 0.37, 0.4, 0.42, 0.45, 0.47, or 0.5 in the far distance range.

(D35) The lens of one or more of the above D examples, wherein the lens is further configured to provide two or more of the following: the RIQ of at least 0.1, 0.13, 0.17, 0.2, 0.225, or 0.25 in the near distance range, the RIQ of at least 0.27, 0.3, 0.33, 0.35, 0.37 or 0.4 in the intermediate distance range and the RIQ of at least 0.35, 0.37, 0.4, 0.42, 0.45, 0.47, or 0.5 in the far distance range.

(D36) The lens of one or more of the above D examples, wherein the RIQs are selected in the near, intermediate and far distance ranges such that the lens is configured to provide minimal, or no, ghosting in near, intermediate and far distances.

(D37) The lens of one or more of the above D examples, wherein the lens is configured to substantially eliminate, or substantially reduce, ghosting at near, intermediate and far distances.

(D38) The lens of one or more of the above D examples, wherein the lens is configured to substantially eliminate, or substantially reduce, ghosting at near distances, intermediate distances and far distances.

(D39) The lens of one or more of the above D examples, wherein near distance is the range of 33 cm to 50 cm or 40 cm to 50 cm; intermediate distance is the range of 50 cm to 100 cm, 50 cm to 80 cm or 50 cm to 70 cm; and far distance is the range of 100 cm or greater, 80 cm or greater or 70 cm or greater.

(D40) The lens of one or more of the above D examples, wherein near distance is the range of 33 cm to 50 cm or 40 cm to 50 cm; intermediate distance is the range of 50 cm to 100 cm, 50 cm to 80 cm or 50 cm to 70 cm; and far distance is the range of 100 cm or greater, 80 cm or greater or 70 cm or greater and the near, intermediate and far distances are determined by the distance from the object being focused on.

(D41) The lens of one or more of the above D examples, wherein near distance is the range of 40 cm to 50 cm; intermediate distance is the range of 50 cm to 100 cm; and far distance is the range of 100 cm or greater.

(D42) The lens of one or more of the above D examples, wherein near distance is the range of 40 cm to 50 cm; intermediate distance is the range of 50 cm to 100 cm; and far distance is the range of 100 cm or greater and the near, intermediate and far distances are determined by the distance from the object being focused on.

(D43) The lens of one or more of the above D examples, wherein near distance is the range of 40 cm to 50 cm; intermediate distance is the range of 50 cm to 100 cm; and far distance is the range of 100 cm to optical infinity.

(D44) The lens of one or more of the above D examples, wherein near distance is the range of 40 cm to 50 cm; intermediate distance is the range of 50 cm to 100 cm; and far distance is the range of 100 cm to optical infinity and the near, intermediate and far distances are determined by the distance from the object being focused on.

(D45) The lens of one or more of the above D examples, wherein the lens is configured to minimize, or reduce, ghosting at near, intermediate and far distances when used on an eye.

(D46) The lens of one or more of the above D examples, wherein the lens is configured to minimize, or reduce, ghosting at near distances, intermediate distances and far distances when used on an eye.

(D47) The lens of one or more of the above D examples, wherein the range of substantially continuous distances is continuous.

(D48) The lens of one or more of the above D examples, wherein the range of substantially continuous distances is continuous and goes from 40 cm to optical infinity.

(D49) The lens of one or more of the above D examples, wherein the range of substantially continuous distances is from 33 cm to optical infinity.

(D50) The lens of one or more of the above D examples, wherein the lens is configured such that at least 40%, 50%, 60% or 70% of a randomly selected group of 15 affected individuals in the near distances, intermediate distances and far distances perceive minimal, or no, ghosting at near distances, intermediate distances and far distances.

(D51) The lens of one or more of the above D examples, wherein the lens is configured such that at least 60%, 70%, 80% or 90% of a randomly selected group of 15 affected individuals in the intermediate distances and far distances perceive minimal, or no, ghosting at intermediate distances and far distances.

(D52) The lens of one or more of the above D examples, wherein the single vision lens provides a visual acuity for the user of one or more of the following: at least 20/20, at least 20/30, at least 20/40, at least about 20/20, at least about 20/30 and at least about 20/40, at far visual distances.

(D53) The lens of one or more of the above D examples, wherein the aberration profile is comprised of a defocus term and at least two, two or more, three, three or more, four, four or more, five, five or more, six, six or more, seven, seven or more, eight, eight or more, nine, nine or more, ten, or ten or more spherical aberration terms.

(D54) The lens of one or more of the above D examples, wherein the aberration profile is comprised of a defocus term and at least two, three, four, five, six, seven, eight, nine, or at least ten spherical aberration terms.

(D55) The lens of one or more of the above D examples, wherein the aberration profile is comprised of a defocus term and spherical aberration terms between $C(4,0)$ and $C(6,0)$, $C(4,0)$ and $C(8,0)$, $C(4,0)$ and $C(10,0)$, $C(4,0)$ and $C(12,0)$, $C(4,0)$ and $C(14,0)$, $C(4,0)$ and $C(16,0)$, $C(4,0)$ and $C(18,0)$, or $C(4,0)$ and $C(20,0)$.

(D56) The lens of one or more of the above D examples, wherein the single vision lens provides a visual acuity that is the best-corrected visual acuity.

(D57) The lens of one or more of the above D examples, wherein the best-corrected visual acuity is a visual acuity that cannot be substantially improved by further manipulating the power of the single vision lens.

(D58) The lens of one or more of the above D examples, wherein the lens has two optical surfaces.

(D59) The lens of one or more of the above D examples, wherein the least one aberration profile is along the optical axis of the lens.

(D60) The lens of one or more of the above D examples, wherein the lens has a focal distance.

(D61) The lens of one or more of the above D examples, wherein the aberration profile includes higher order aberrations having at least one of a primary spherical aberration component $C(4,0)$ and a secondary spherical aberration component $C(6,0)$.

(D62) The lens of one or more of the above D examples, wherein the focal distance is a prescription focal distance for a myopic, hyperopic, astigmatic, and/or presbyopic eye and wherein the focal distance differs from the focal distance for a $C(2,0)$ Zernike coefficient of the aberration profile.

(D63) The lens of one or more of the above D examples, wherein the higher order aberrations include at least two spherical aberration terms selected from the group $C(4,0)$ to $C(20,0)$.

(D64) The lens of one or more of the above D examples, wherein the higher order aberrations include at least three spherical aberration terms selected from the group $C(4,0)$ to $C(20,0)$.

(D65) The lens of one or more of the above D examples, wherein the higher order aberrations include at least five spherical aberration terms selected from the group $C(4,0)$ to $C(20,0)$.

(D66) The lens of one or more of the above D examples, wherein the average slope over a horizontal field of at least $-20°$ to $+20°$ degrades in a direction of eye growth.

(D67) The lens of one or more of the above D examples, wherein the minimal ghosting is a lack of an undesired secondary image appearing at the image plane of the optical system.

(D68) The lens of one or more of the above D examples, wherein the minimal ghosting is a lack of an undesired secondary image appearing on the retina of the eye.

(D69) The lens of one or more of the above D examples, wherein the minimal ghosting is a lack of an undesired double image appearing on the retina of the eye.

(D70) The lens of one or more of the above D examples, wherein the minimal ghosting is a lack of false out-of-focus image appearing along side of the primary image in an optical system.

(D71) The lens of one or more of the above D examples, wherein the average slope over a horizontal field of at least $-20°$ to $+20°$ improves in a direction of eye growth.

(D72) The lens of one or more of the above D examples, wherein the average slope over a vertical field of at least $-20°$ to $+20°$ degrades in a direction of eye growth.

(D73) The lens of one or more of the above D examples, wherein the average slope over a vertical field of at least −20° to +20° improves in a direction of eye growth.

(D74) The lens of one or more of the above D examples, wherein the slope for a substantial portion of the field angles over a horizontal field of at least −20° to +20° degrades in a direction of eye growth.

(D75) The lens of one or more of the above D examples, wherein the substantial portion of the field angles over a horizontal field is at least 75%, 85%, 95% or 99% of the field angles.

(D76) The lens of one or more of the above D examples, wherein the substantial portion of the field angles over a horizontal field is every field angle.

(D77) The lens of one or more of the above D examples, wherein the slope for a substantial portion of the field angles over a vertical field of at least −20° to +20° degrades in a direction of eye growth.

(D78) The lens of one or more of the above D examples, wherein the substantial portion of the field angles over a vertical field is every angle.

(D79) The lens of one or more of the above D examples, wherein the substantial portion of the field angles over a vertical field is at least 75%, 85%, 95% or 99% of the field angles.

(D80) The lens of one or more of the above D examples, wherein the aberration profile provides the RIQ of at least 0.3 at the focal length for a substantial portion of pupil diameters in the range 3 mm to 6 mm.

(D81) The lens of one or more of the above D examples, wherein the aberration profile provides the RIQ of at least 0.3 at the focal length for a substantial portion of pupil diameters in the range 4 mm to 5 mm.

(D82) The lens of one or more of the above D examples, wherein the aberration profile provides the RIQ with a through focus slope that degrades in a direction of eye growth when primary or secondary astigmatism is added to the aberration profile.

(D83) The lens of one or more of the above D examples, wherein the aberration profile provides the RIQ with a through focus slope that improves in a direction of eye growth when primary or secondary astigmatism is added to the aberration profile.

(D84) The lens of one or more of the above D examples, wherein the primary or secondary astigmatism is added to the desired aberration profile by altering one or more of the following terms: C(2,−2), C(2,2), C(4,−2), C(4,2), C(6,−2), and/or C(6,2).

(D85) The lens of one or more of the above D examples, wherein the aberration profile provides the RIQ with a through focus slope that degrades in a direction of eye growth when secondary astigmatism is added to the aberration profile.

(D86) The lens of one or more of the above D examples, wherein the secondary astigmatism is added to the desired aberration profile by altering one or more of the following terms: C(2,−2), C(2,2), C(4,−2), C(4,2), C(6,−2), and/or C(6,2).

(D87) The lens of one or more of the above D examples, wherein the RIQ is characterised by $$RIQ = \frac{\int\int_{-Fmin}^{+Fmax} CSF(x,y) * \left(\text{real}\left(\left[FT\left(\left|FT\{A(\rho,\theta)*\exp\left[\frac{2\pi i}{\lambda}*W(\rho,\theta)\right]\}\right|^2\right)\right]\right)\right)}{\int\int_{-Fmin}^{+Fmax} CSF(x,y) * \left(\left(\left[FT\left(\left|FT\{A(\rho,\theta)*\exp\left[\frac{2\pi i}{\lambda}*Wdiff(\rho,\theta)\right]\}\right|^2\right)\right]\right)\right)}$$

wherein:
Fmin is 0 cycles/degree and Fmax is 30 cycles/degree;
CSF(x, y) denotes the contrast sensitivity function, CSF(F)=2.6(0.0192+0.114f)e^{−(0.114*f)^1.1},
where f specifies the tested spatial frequency, in the range of $F_{min}$ to $F_{max}$=;
FT denotes a 2 D fast Fourier transform;
A(ρ, θ) denotes the pupil amplitude function across the pupil diameter;
W(ρ, θ) denotes wavefront of the test case measured for i=1 to 20

$$W(\rho,\theta) = \sum_{i=1}^{k} a_i Z_i(\rho,\theta);$$

Wdiff(ρ, θ) denotes wavefront of the diffraction limited case;
ρ and θ are normalised polar coordinates, where ρ represents the radial coordinate and θ represents the angular coordinate or azimuth; and
λ denotes wavelength.

(D88) The lens of one or more of the above D examples, wherein the RIQ is characterised by $$RIQ = \frac{\int\int_{-Fmin}^{+Fmax} CSF(x,y) * \left(\text{real}\left(\left[FT\left(\left|FT\{A(\rho,\theta)*\exp\left[\frac{2\pi i}{\lambda}*W(\rho,\theta)\right]\}\right|^2\right)\right]\right)\right)}{\int\int_{-Fmin}^{+Fmax} CSF(x,y) * \left(\left(\left[FT\left(\left|FT\{A(\rho,\theta)*\exp\left[\frac{2\pi i}{\lambda}*Wdiff(\rho,\theta)\right]\}\right|^2\right)\right]\right)\right)}$$

wherein:
Fmin is 0 cycles/degree and Fmax is 30 cycles/degree;
CSF(x, y) denotes the contrast sensitivity function, CSF(F)=2.6(0.0192+0.114f)e^{−(0.114*f)^1.1},
where f specifies the tested spatial frequency, in the range of $F_{min}$ to $F_{max}$;
FT denotes a 2 D Fourier transform, for example a 2 D fast Fourier transform;
A(ρ, θ) denotes the pupil amplitude function across the pupil diameter;
W(ρ, θ) denotes wavefront of the test case measured for i=1 to k;
where k is a positive integer;

$$W(\rho,\theta) = \sum_{i=1}^{k} a_i Z_i(\rho,\theta);$$

Wdiff(ρ, θ) denotes wavefront of the diffraction limited case;

ρ and θ are normalised polar coordinates, where ρ represents the radial coordinate and θ represents the angular coordinate or azimuth; and λ denotes wavelength.

(D89) The lens of one or more of the above D examples, wherein the lens includes an optical axis and an aberration profile along the optical axis that provides: a focal distance for a C(2,0) Zernike coefficient term; a peak visual Strehl Ratio ('first visual Strehl Ratio') within a through focus range, and a visual Strehl Ratio that remains at or above a second visual Strehl Ratio over the through focus range that includes said focal distance, wherein the visual Strehl Ratio is measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive, and wherein the first visual Strehl Ratio is at least 0.35, the second visual Strehl Ratio is at least 0.1 and the through focus range is at least 1.8 Dioptres.

(D90) The lens of one or more of the above D examples, wherein the lens includes an optical axis and an aberration profile along the optical axis that provides: a focal distance for a C(2,0) Zernike coefficient term; a peak visual Strehl Ratio ('first visual Strehl Ratio') within a through focus range, and a visual Strehl Ratio that remains at or above a second visual Strehl Ratio over the through focus range that includes said focal distance, wherein the visual Strehl Ratio is measured for a model eye with no aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive, and wherein the first visual Strehl Ratio is at least 0.35, the second visual Strehl Ratio is at least 0.1 and the through focus range is at least 1.8 Dioptres.

(D91) The lens of one or more of the above D examples, wherein the first visual Strehl Ratio is at least 0.3, 0.35, 0.4, 0.5, 0.6, 0.7 or 0.8.

(D92) The lens of one or more of the above D examples, wherein the second visual Strehl Ratio is at least 0.1, 0.12, 0.15, 0.18 or 0.2.

(D93) The lens of one or more of the above D examples, wherein the through focus range is at least 1.7, 1.8, 1.9, 2, 2.1, 2.25 or 2.5 Dioptres.

(D94) The lens of one or more of the above D examples, wherein the lens has a prescription focal distance located within 0.75, 0.5, 0.3, or 0.25 Dioptres, inclusive, of an end of the through focus range.

(D95) The lens of one or more of the above D examples, wherein the end of the through focus range is the negative power end.

(D96) The lens of one or more of the above D examples, wherein the end of the through focus range is the positive power end.

(D97) The lens of one or more of the above D examples, wherein the visual Strehl Ratio remains at or above the second visual Strehl Ratio over the through focus range and over a range of pupil diameters of at least 1 mm, 1.5 mm, 2 mm, 2.5 mm, or 3 mm.

(D98) The lens of one or more of the above D examples, wherein the combination of higher order aberrations includes at least one of primary spherical aberration and secondary spherical aberration.

(D99) The lens of one or more of the above D examples, wherein the higher order aberrations include at least two, three, or five spherical aberration terms selected from the group C(4,0) to C(20,0).

(D100) The lens of one or more of the above D examples, wherein the aberration profile is substantially characterized using only spherical aberration Zernike coefficients C(4, 0) to C(20, 0).

(D101) The lens of one or more of the above D examples, wherein the RIQ for a substantial portion of the angles over a horizontal field of at least −10° to +10°, −20° to +20° or −30° to +30° is at least 0.4.

(D102) The lens of one or more of the above D examples, wherein the RIQ for a substantial portion of the angles over a horizontal field of at least −10° to +10°, −20° to +20° or −30° to +30° is at least 0.35.

(D103) The lens of one or more of the above D examples, wherein the RIQ for a substantial portion of the angles over a horizontal field of at least −10° to +10°, −20° to +20° or −30° to +30° is at least 0.3.

(D104) The lens of one or more of the above D examples, wherein the lens is one or more of the following: contact lens, corneal onlays, corneal inlays, anterior chamber intraocular lens or posterior chamber intraocular lens.

(D105) The lens of one or more of the above D examples, wherein the lens is one of the following: contact lens, corneal onlays, corneal inlays, anterior chamber intraocular lens or posterior chamber intraocular lens.

(D106) The lens of one or more of the above D examples, wherein a first lens is provided based on one or more of the D examples and a second lens is provided based on one or more of the D examples to form a pair of lenses.

(D107) The lens of one or more of the above D examples, wherein the first lens is provided based on one or more of the D examples and a second lens is provided to form a pair of lenses.

(D108) The lens of one or more of the above D examples, wherein a pair of lenses are provided for use by an individual to substantially correct the individual's vision.

(D109) A method for making or using one or more of the lenses of one or more of the above D examples.

(D110) The lens of one or more of the above D examples, wherein the lens does not substantially reduce the amount of light passing through the lens.

(D111) The lens of one or more of the above D examples, wherein the amount of light passing through the lens is at least 80%, 85%, 90%, 95% or 99%.

Example Set E (E1) A lens for an eye, the lens comprising: an optical axis; an aberration profile about the optical axis and having a focal distance; and at least two optical surfaces; and wherein the lens's optical properties can be characterised upon testing by at least the following properties: two or more higher order aberrations having one or more of the following components: a primary spherical aberration C(4,0), a secondary spherical aberration C(6,0), a tertiary spherical aberration C(8,0), a quaternary spherical aberration C(10,0), a pentanary spherical aberration C(12,0), a hexanary spherical aberration C(14,0), a heptanary spherical aberration C(16,0), an octanary spherical aberration C(18,0) and a nanonary spherical aberration C(20,0); the aberration profile when tested on a model eye with no, or substantially no, aberrations and having an on-axis length equal, or substantially equal, to the focal distance, results in a retinal image quality (RIQ) with a through focus slope so that the RIQ decreases in a direction of eye growth, where the RIQ is determined by a visual Strehl Ratio that is measured substantially along the optical axis; and the RIQ is measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive.

(E2) A lens for an eye, the lens comprising: an optical axis; an aberration profile about the optical axis and having a focal distance; and at least two optical surfaces; and wherein the lens's optical properties can be characterised upon testing by at least the following properties: two or more higher order aberrations having one or more of the following components: a primary spherical aberration $C(4,0)$, a secondary spherical aberration $C(6,0)$, a tertiary spherical aberration $C(8,0)$, a quaternary spherical aberration $C(10,0)$, a pentanary spherical aberration $C(12,0)$, a hexanary spherical aberration $C(14,0)$, a heptanary spherical aberration $C(16,0)$, an octanary spherical aberration $C(18,0)$ and a nanonary spherical aberration $C(20,0)$; the aberration profile when tested on a model eye with no aberrations and having an on-axis length equal to the focal distance, results in a retinal image quality (RIQ) with a through focus slope so that the RIQ decreases in a direction of eye growth, where the RIQ is determined by a visual Strehl Ratio that is measured along the optical axis; and the RIQ is measured for a model eye with no aberrations and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive.

(E3) A lens for an eye, the lens comprising: an optical axis; an aberration profile about the optical axis and having a focal distance; and at least two optical surfaces; and wherein the lens's optical properties can be characterised upon testing by at least the following properties: two or more higher order aberrations having one or more of the following components: a primary spherical aberration $C(4,0)$, a secondary spherical aberration $C(6,0)$, a tertiary spherical aberration $C(8,0)$, a quaternary spherical aberration $C(10,0)$, a pentanary spherical aberration $C(12,0)$, a hexanary spherical aberration $C(14,0)$, a heptanary spherical aberration $C(16,0)$, an octanary spherical aberration $C(18,0)$ and a nanonary spherical aberration $C(20,0)$; the aberration profile when tested on a model eye with no aberrations and having an on-axis length equal to the focal distance, results in a retinal image quality (RIQ) with a through focus slope so that the RIQ increases in a direction of eye growth, where the RIQ is determined by a visual Strehl Ratio that is measured along the optical axis; and the RIQ is measured for a model eye with no aberrations and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive.

(E4) A lens for an eye, the lens comprising: an optical axis; an aberration profile about the optical axis and having a focal distance; and at least two optical surfaces; and wherein the lens's optical properties can be characterised upon testing by at least the following properties: two or more higher order aberrations having one or more of the following components: a primary spherical aberration $C(4,0)$, a secondary spherical aberration $C(6,0)$, a tertiary spherical aberration $C(8,0)$, a quaternary spherical aberration $C(10,0)$, a pentanary spherical aberration $C(12,0)$, a hexanary spherical aberration $C(14,0)$, a heptanary spherical aberration $C(16,0)$, an octanary spherical aberration $C(18,0)$ and a nanonary spherical aberration $C(20,0)$; the aberration profile when tested on a model eye with no, or substantially no, aberrations and having an on-axis length equal, or substantially equal, to the focal distance, results in a retinal image quality (RIQ) with a through focus slope so that the RIQ increases in a direction of eye growth, where the RIQ is determined by a visual Strehl Ratio that is measured substantially along the optical axis; and the RIQ is measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive.

(E5) A lens for an eye, the lens comprising: an optical axis; an aberration profile about the optical axis and having a focal distance; and at least two optical surfaces; and wherein the lens's optical properties can be characterised upon testing by at least the following properties: two or more higher order aberrations having one or more of the following components: a primary spherical aberration $C(4,0)$, a secondary spherical aberration $C(6,0)$, a tertiary spherical aberration $C(8,0)$, a quaternary spherical aberration $C(10,0)$, a pentanary spherical aberration $C(12,0)$, a hexanary spherical aberration $C(14,0)$, a heptanary spherical aberration $C(16,0)$, an octanary spherical aberration $C(18,0)$ and a nanonary spherical aberration $C(20,0)$; the aberration profile when tested on a model eye with no, or substantially no, aberrations and having an on-axis length equal, or substantially equal, to the focal distance, results in a through focus RIQ, within the through focus range, a first RIQ which is a peak RIQ and that remains at or above a second RIQ over the through focus range that includes the focal distance; and the first and second RIQs are measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive.

(E6) A lens for an eye, the lens comprising: an optical axis; an aberration profile about the optical axis and having a focal distance; and at least two optical surfaces; and wherein the lens's optical properties can be characterised upon testing by at least the following properties: two or more higher order aberrations having one or more of the following components: a primary spherical aberration $C(4,0)$, a secondary spherical aberration $C(6,0)$, a tertiary spherical aberration $C(8,0)$, a quaternary spherical aberration $C(10,0)$, a pentanary spherical aberration $C(12,0)$, a hexanary spherical aberration $C(14,0)$, a heptanary spherical aberration $C(16,0)$, an octanary spherical aberration $C(18,0)$ and a nanonary spherical aberration $C(20,0)$; the aberration profile when tested on a model eye with no aberrations and having an on-axis length equal to the focal distance, results in a through focus RIQ, within the through focus range, a first RIQ which is a peak RIQ and that remains at or above a second RIQ over the through focus range that includes the focal distance; and the first and second RIQs are measured for a model eye with no aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive.

(E7) The lens of one or more of the above E examples, wherein the single-vision lens is one or more of the following: prescribed, appropriately prescribed, correctly prescribed and effectively prescribed.

(E8) The lens of one or more of the above E examples, wherein the lens does not substantially reduce the amount of light passing through the lens.

(E9) The lens of one or more of the above E examples, wherein the amount of light passing through the lens is at least 80%, 85%, 90%, 95% or 99%.

(E10) The lens of one or more of the above E examples, wherein the single-vision lens is a lens with a substantially constant power across a substantial portion of an optic zone of the single-vision lens.

(E11) The lens of one or more of the above E examples, wherein the single-vision lens is a lens with a constant power across a portion of an optic zone of the single-vision lens.

(E12) The lens of one or more of the above E examples, wherein the single-vision lens is a lens with a substantially constant power across a portion of one or more optic zones of the single-vision lens.

(E13) The lens of one or more of the above E examples, wherein the lens is further characterised by minimal, substantially no or no, ghosting at near, intermediate and far distances.

(E14) The lens of one or more of the above E examples, wherein the lens is further characterised by minimal, substantially no or no, ghosting at near distances, intermediate distances and far distances.

(E15) The lens of one or more of the above E examples, wherein the lens is further configured to provide minimal, substantially no or no, ghosting at near, intermediate and far distances.

(E16) The lens of one or more of the above E examples, wherein the minimal ghosting is a lack of an undesired secondary image appearing at the image plane of the optical system.

(E17) The lens of one or more of the above E examples, wherein the minimal ghosting is a lack of an undesired secondary image appearing on the retina of the eye.

(E18) The lens of one or more of the above E examples, wherein the minimal ghosting is a lack of an undesired double image appearing on the retina of the eye.

(E19) The lens of one or more of the above E examples, wherein the minimal ghosting is a lack of false out-of-focus image appearing along side of the primary image in an optical system.

(E20) The lens of one or more of the above E examples, wherein the lens is further configured to provide a sufficient lack of ghosting in a portion of near, intermediate and far distances.

(E21) The lens of one or more of the above E examples, wherein the lens is further configured to provide a sufficient lack of ghosting at near distances, intermediate distances and far distances.

(E22) The lens of one or more of the above E examples, wherein the lens is further configured to provide a sufficient lack of ghosting in a portion of two or more of the following: near, intermediate and far distances.

(E23) The lens of one or more of the above E examples, wherein lack of ghosting is lack of undesired image appearing at the image plane of the optical system.

(E24) The lens of one or more of the above E examples, wherein lack of ghosting is a lack of false out of focus images appearing along side of the primary image in an optical system.

(E25) The lens of one or more of the above E examples, wherein the lens is further configured to provide a sufficient lack of ghosting in a portion of two or more of the following: near distances, intermediate distances and far distances.

(E26) The lens of one or more of the above E examples, wherein the lens is further configured to provide the RIQ of at least 0.1, 0.13, 0.17, 0.2, 0.225, or 0.25 in the near distance range, the RIQ of at least 0.27, 0.3, 0.33, 0.35, 0.37 or 0.4 in the intermediate distance range and the RIQ of at least 0.35, 0.37, 0.4, 0.42, 0.45, 0.47, or 0.5 in the far distance range.

(E27) The lens of one or more of the above E examples, wherein the lens is further configured to provide two or more of the following; the RIQ of at least 0.1, 0.13, 0.17, 0.2, 0.225, or 0.25 in the near distance range, the RIQ of at least 0.27, 0.3, 0.33, 0.35, 0.37 or 0.4 in the intermediate distance range and the RIQ of at least 0.35, 0.37, 0.4, 0.42, 0.45, 0.47, or 0.5 in the far distance range.

(E28) The lens of one or more of the above E examples, wherein the RIQs are selected in the near, intermediate and far distance ranges such that the lens is configured to provide minimal, or no, ghosting in near, intermediate and far distances.

(E29) The lens of one or more of the above E examples, wherein the lens is configured to substantially eliminate, or substantially reduce, ghosting at near, intermediate and far distances.

(E30) The lens of one or more of the above E examples, wherein the lens is configured to substantially eliminate, or substantially reduce, ghosting at near distances, intermediate distances and far distances.

(E31) The lens of one or more of the above E examples, wherein near distance is the range of 33 cm to 50 cm or 40 cm to 50 cm; intermediate distance is the range of 50 cm to 100 cm, 50 cm to 80 cm or 50 cm to 70 cm; and far distance is the range of 100 cm or greater, 80 cm or greater or 70 cm or greater.

(E32) The lens of one or more of the above E examples, wherein near distance is the range of 33 cm to 50 cm or 40 cm to 50 cm; intermediate distance is the range of 50 cm to 100 cm, 50 cm to 80 cm or 50 cm to 70 cm; and far distance is the range of 100 cm or greater, 80 cm or greater or 70 cm or greater and the near, intermediate and far distances are determined by the distance from the object being focused on.

(E33) The lens of one or more of the above E examples, wherein near distance is the range of 40 cm to 50 cm; intermediate distance is the range of 50 cm to 100 cm; and far distance is the range of 100 cm or greater.

(E34) The lens of one or more of the above E examples, wherein near distance is the range of 40 cm to 50 cm; intermediate distance is the range of 50 cm to 100 cm; and far distance is the range of 100 cm or greater and the near, intermediate and far distances are determined by the distance from the object being focused on.

(E35) The lens of one or more of the above E examples, wherein near distance is the range of 40 cm to 50 cm; intermediate distance is the range of 50 cm to 100 cm; and far distance is the range of 100 cm to optical infinity.

(E36) The lens of one or more of the above E examples, wherein near distance is the range of 40 cm to 50 cm; intermediate distance is the range of 50 cm to 100 cm; and far distance is the range of 100 cm to optical infinity and the near, intermediate and far distances are determined by the distance from the object being focused on.

(E37) The lens of one or more of the above E examples, wherein the lens is configured to minimize, or reduce, ghosting at near, intermediate and far distances when used on an eye.

(E38) The lens of one or more of the above E examples, wherein the lens is configured to minimize, or reduce, ghosting at near distances, intermediate distances and far distances when used on an eye.

(E39) The lens of one or more of the above E examples, wherein the range of substantially continuous distances is continuous.

(E40) The lens of one or more of the above E examples, wherein the range of substantially continuous distances is continuous and goes from 40 cm to optical infinity.

(E41) The lens of one or more of the above E examples, wherein the range of substantially continuous distances is from 33 cm to optical infinity.

(E42) The lens of one or more of the above E examples, wherein the lens is configured such that at least 40%, 50%, 60% or 70% of a randomly selected group of 15 affected individuals in the near distances, intermediate distances and far distances perceive minimal, or no, ghosting at near distances, intermediate distances and far distances.

(E43) The lens of one or more of the above E examples, wherein the lens is configured such that at least 60%, 70%, 80% or 90% of a randomly selected group of 15 affected individuals in the intermediate distances and far distances perceive minimal, or no, ghosting at intermediate distances and far distances.

(E44) The lens of one or more of the above E examples, wherein the single vision lens provides a visual acuity for the user of one or more of the following: at least 20/20, at least 20/30, at least 20/40, at least about 20/20, at least about 20/30 and at least about 20/40, at far visual distances.

(E45) The lens of one or more of the above E examples, wherein the aberration profile is comprised of a defocus term and at least two, two or more, three, three or more, four, four or more, five, five or more, six, six or more, seven, seven or more, eight, eight or more, nine, nine or more, ten, or ten or more spherical aberration terms.

(E46) The lens of one or more of the above E examples, wherein the aberration profile is comprised of a defocus term and at least two, three, four, five, six, seven, eight, nine, or at least ten spherical aberration terms.

(E47) The lens of one or more of the above E examples, wherein the aberration profile is comprised of a defocus term and spherical aberration terms between $C(4,0)$ and $C(6,0)$, $C(4,0)$ and $C(8,0)$, $C(4,0)$ and $C(10,0)$, $C(4,0)$ and $C(12,0)$, $C(4,0)$ and $C(14,0)$, $C(4,0)$ and $C(16,0)$, $C(4,0)$ and $C(18,0)$ or $C(4,0)$ and $C(20,0)$.

(E48) The lens of one or more of the above E examples, wherein the single vision lens provides a visual acuity that is the best-corrected visual acuity.

(E49) The lens of one or more of the above E examples, wherein the best-corrected visual acuity is a visual acuity that cannot be substantially improved by further manipulating the power of the single vision lens.

(E50) The lens of one or more of the above E examples, wherein the lens has two optical surfaces.

(E51) The lens of one or more of the above E examples, wherein the least one aberration profile is along the optical axis of the lens.

(E52) The lens of one or more of the above E examples, wherein the lens has a focal distance.

(E53) The lens of one or more of the above E examples, wherein the aberration profile includes higher order aberrations having at least one of a primary spherical aberration component $C(4,0)$ and a secondary spherical aberration component $C(6,0)$.

(E54) The lens of one or more of the above E examples, wherein the focal distance is a prescription focal distance for a myopic, hyperopic, astigmatic, and/or presbyopic eye and wherein the focal distance differs from the focal distance for a $C(2,0)$ Zernike coefficient of the aberration profile.

(E55) The lens of one or more of the above E examples, wherein the higher order aberrations include at least two spherical aberration terms selected from the group $C(4,0)$ to $C(20,0)$.

(E56) The lens of one or more of the above E examples, wherein the higher order aberrations include at least three spherical aberration terms selected from the group $C(4,0)$ to $C(20,0)$.

(E57) The lens of one or more of the above E examples, wherein the higher order aberrations include at least five spherical aberration terms selected from the group $C(4,0)$ to $C(20,0)$.

(E58) The lens of one or more of the above E examples, wherein the average slope over a horizontal field of at least $-20°$ to $+20°$ degrades in a direction of eye growth.

(E59) The lens of one or more of the above E examples, wherein the average slope over a horizontal field of at least $-20°$ to $+20°$ improves in a direction of eye growth.

(E60) The lens of one or more of the above E examples, wherein the average slope over a vertical field of at least $-20°$ to $+20°$ degrades in a direction of eye growth.

(E61) The lens of one or more of the above E examples, wherein the average slope over a vertical field of at least $-20°$ to $+20°$ improves in a direction of eye growth.

(E62) The lens of one or more of the above E examples, wherein the slope for a substantial portion of the field angles over a horizontal field of at least $-20°$ to $+20°$ degrades in a direction of eye growth.

(E63) The lens of one or more of the above E examples, wherein the substantial portion of the field angles over a horizontal field is at least 75%, 85%, 95% or 99% of the field angles.

(E64) The lens of one or more of the above E examples, wherein the substantial portion of the field angles over a horizontal field is every field angle.

(E65) The lens of one or more of the above E examples, wherein the slope for a substantial portion of the field angles over a vertical field of at least $-20°$ to $+20°$ degrades in a direction of eye growth.

(E66) The lens of one or more of the above E examples, wherein the substantial portion of the field angles over a vertical field is every angle.

(E67) The lens of one or more of the above E examples, wherein the substantial portion of the field angles over a vertical field is at least 75%, 85%, 95% or 99% of the field angles.

(E68) The lens of one or more of the above E examples, wherein the aberration profile provides the RIQ of at least 0.3 at the focal length for a substantial portion of pupil diameters in the range 3 mm to 6 mm.

(E69) The lens of one or more of the above E examples, wherein the aberration profile provides the RIQ of at least 0.3 at the focal length for a substantial portion of pupil diameters in the range 4 mm to 5 mm.

(E70) The lens of one or more of the above E examples, wherein the aberration profile provides the RIQ with a through focus slope that degrades in a direction of eye growth when primary or secondary astigmatism is added to the aberration profile.

(E71) The lens of one or more of the above E examples, wherein the aberration profile provides the RIQ with a through focus slope that improves in a direction of eye growth when primary or secondary astigmatism is added to the aberration profile.

(E72) The lens of one or more of the above E examples, wherein the primary or secondary astigmatism is added to the desired aberration profile by altering one or more of the following terms: C(2,-2), C(2,2), C(4,-2), C(4,2), C(6,-2) and/or C(6,2).

(E73) The lens of one or more of the above E examples, wherein the aberration profile provides the RIQ with a through focus slope that degrades in a direction of eye growth when secondary astigmatism is added to the aberration profile.

(E74) The lens of one or more of the above E examples, wherein the secondary astigmatism is added to the desired aberration profile by altering one or more of the following terms: C(2,-2), C(2,2), C(4,-2), C(4,2), C(6,-2) and/or C(6,2).

(E75) The lens of one or more of the above E examples, wherein the RIQ is characterised by $$RIQ = \frac{\int\int_{-Fmin}^{+Fmax} CSF(x, y) * \left(real\left(\left(\left[FT\left(\left|FT\left\{A(\rho, \theta) * \exp\left[\frac{2\pi i}{\lambda} * W(\rho, \theta)\right]\right\}\right|^2\right)\right]\right)\right)\right)}{\int\int_{-Fmin}^{+Fmax} CSF(x, y) * \left(\left(\left[FT\left(\left|FT\left\{A(\rho, \theta) * \exp\left[\frac{2\pi i}{\lambda} * Wdiff(\rho, \theta)\right]\right\}\right|^2\right)\right]\right)\right)}$$

wherein:
Fmin is 0 cycles/degree and Fmax is 30 cycles/degree;
CSF(x, y) denotes the contrast sensitivity function $CSF(F) = 2.6(0.0192 + 0.114f)e^{-(0.114*f)^{1.1}}$, where f specifies the tested spatial frequency, in the range of $F_{min}$ to $F_{max}$;
FT denotes a 2 D fast Fourier transform;
A($\rho$, $\theta$) denotes the pupil amplitude function across the pupil diameter;
($\rho$, $\theta$) denotes wavefront of the test case measured for i=1 to 20

$$W(\rho, \theta) = \sum_{i=1}^{k} a_i Z_i(\rho, \theta);$$

Wdiff($\rho$, $\theta$) denotes wavefront of the diffraction limited case;
$\rho$ and $\theta$ are normalised polar coordinates, where $\rho$ represents the radial coordinate and $\theta$ represents the angular coordinate or azimuth; and
$\lambda$ denotes wavelength.

(E76) The lens of one or more of the above E examples, wherein the RIQ is characterised by $$RIQ = \frac{\int\int_{-Fmin}^{+Fmax} CSF(x, y) * \left(real\left(\left(\left[FT\left(\left|FT\left\{A(\rho, \theta) * \exp\left[\frac{2\pi i}{\lambda} * W(\rho, \theta)\right]\right\}\right|^2\right)\right]\right)\right)\right)}{\int\int_{-Fmin}^{+Fmax} CSF(x, y) * \left(\left(\left[FT\left(\left|FT\left\{A(\rho, \theta) * \exp\left[\frac{2\pi i}{\lambda} * Wdiff(\rho, \theta)\right]\right\}\right|^2\right)\right]\right)\right)}$$

wherein:
Fmin is 0 cycles/degree and Fmax is 30 cycles/degree;
CSF(x, y) denotes the contrast sensitivity function $CSF(F) = 2.6(0.0192 + 0.114f)e^{-(0.114*f)^{1.1}}$, where f specifies the tested spatial frequency, in the range of $F_{min}$ to $F_{max}$;
FT denotes a 2 D Fourier transform, for example a 2 D fast Fourier transform;
A($\rho$, $\theta$) denotes the pupil amplitude function across the pupil diameter;
W($\rho$, $\theta$) denotes wavefront of the test case measured for i=1 to k;
wherein k is a positive integer;

$$W(\rho, \theta) = \sum_{i=1}^{k} a_i Z_i(\rho, \theta);$$

Wdiff($\rho$, $\theta$) denotes wavefront of the diffraction limited case;
$\rho$ and $\theta$ are normalised polar coordinates, where $\rho$ represents the radial coordinate and $\theta$ represents the angular coordinate or azimuth; and
$\lambda$ denotes wavelength.

(E77) The lens of one or more of the above E examples, wherein the first visual Strehl Ratio is at least 0.3, 0.35, 0.4, 0.5, 0.6, 0.7 or 0.8.

(E78) The lens of one or more of the above E examples, wherein the second visual Strehl Ratio is at least 0.1, 0.12, 0.15, 0.18 or 0.2.

(E79) The lens of one or more of the above E examples, wherein the through focus range is at least 1.7, 1.8, 1.9, 2, 2.1, 2.25 or 2.5 Dioptres.

(E80) The lens of one or more of the above E examples, wherein the lens has a prescription focal distance located within 0.75, 0.5, 0.3, or 0.25 Dioptres, inclusive, of an end of the through focus range.

(E81) The lens of one or more of the above E examples, wherein the end of the through focus range is the negative power end.

(E82) The lens of one or more of the above E examples, wherein the end of the through focus range is the positive power end.

(E83) The lens of one or more of the above E examples, wherein the visual Strehl Ratio remains at or above the second visual Strehl Ratio over the through focus range and over a range of pupil diameters of at least 1 mm, 1.5 mm, 2 mm, 2.5 mm or 3 mm.

(E84) The lens of one or more of the above E examples, wherein the combination of higher order aberrations includes at least one of primary spherical aberration and secondary spherical aberration.

(E85) The lens of one or more of the above E examples, wherein the higher order aberrations include at least two, three, or five spherical aberration terms selected from the group C(4,0) to C(20,0).

(E86) The lens of one or more of the above E examples, wherein the higher order aberrations include at least six, seven or eight spherical aberration terms selected from the group C(4,0) to C(20,0).

(E87) The lens of one or more of the above E examples, wherein the aberration profile is capable of being characterised using only spherical aberration Zernike coefficients C(4, 0) to C(20, 0).

(E88) The lens of one or more of the above E examples, wherein the RIQ for a substantial portion of the angles over a horizontal field of at least −10° to +10°, −20° to +20° or −30° to +30° is at least 0.3, 0.35 or 0.4.

(E89) The lens of one or more of the above E examples, wherein the RIQ for a substantial portion of the angles over a vertical field of at least −10° to +10°, −20° to +20° or −30° to +30° is at least 0.3, 0.35 or 0.4.

(E90) The lens of one or more of the above E examples, wherein the RIQ for a substantial portion of the angles over a horizontal field of at least −10° to +10°, −20° to +20° or −30° to +30° is at least 0.3.

(E91) The lens of one or more of the above E examples, wherein the lens is one or more of the following: contact lens, corneal onlays, corneal inlays, anterior chamber intraocular lens or posterior chamber intraocular lens.

(E92) The lens of one or more of the above E examples, wherein the RIQ for a substantial portion of the angles over a vertical field of at least −10° to +10°, −20° to +20° or −30° to +30° is at least 0.3.

(E93) The lens of one or more of the above E examples, wherein the lens is one of the following: contact lens, corneal onlays, corneal inlays, anterior chamber intraocular lens or posterior chamber intraocular lens.

(E94) The lens of one or more of the above E examples, wherein a first lens is provided based on one or more of the E examples and a second lens is provided based on one or more of the E examples to form a pair of lenses.

(E95) The lens of one or more of the above E examples, wherein the first lens is provided based on one or more of the E examples and a second lens is provided to form a pair of lenses.

(E96) The lens of one or more of the above E examples, wherein a pair of lenses are provided for use by an individual to substantially correct the individual's vision.

(E97) The lens of one or more of the above E examples, wherein the slope averaged over a horizontal field of at least −20° to +20° degrades in a direction of eye growth.

(E98) The lens of one or more of the above E examples, wherein the slope averaged over a horizontal field of at least −20° to +20° improves in a direction of eye growth.

(E99) The lens of one or more of the above E examples, wherein the slope averaged over a vertical field of at least −20° to +20° degrades in a direction of eye growth.

(E100) The lens of one or more of the above E examples, wherein the slope averaged over a vertical field of at least −20° to +20° improves in a direction of eye growth.

(E101) A method for making or using one or more of the lenses of one or more of the above E examples.

(E102) A lens of one or more of the above E examples, wherein a power profile is associated with the optical axis and the power profile has a transition between a maxima and a minima, and the maxima is within 0.2 mm of the centre of the optic zone and the minima is less than or equal to 0.3, 0.6, 0.9 or 1 mm distance from the maxima; wherein the amplitude of the transition between the maxima and the minima is at least 2.5 D, 4 D, 5 D, or 6 D.

(E103) The lens of one of the claims E, wherein the transition between the maxima and the minima is one or more of the following: continuous, discontinuous, monotonic and non-monotonic.

Examples Set F (F1) A lens comprising: an optical axis; an aberration profile about the optical axis and having a focal distance; at least two optical surfaces; an aperture size greater than 2 mm; wherein the lens is configured such that the lens is characterised by one or more power profiles and the one or more power profiles provide a lens that has the following properties: the visual performance of the multifocal lens at near, intermediate and far visual distances is substantially equivalent to or better than an appropriately prescribed single-vision lens for far visual distance and produces minimal ghosting at distances from far distance to near.

(F2) A lens comprising: an optical axis; an aberration profile having a focal distance; and at least two optical surfaces; wherein the lens is configured at least in part by one or more power profiles and the lens has the following properties: the visual performance of the lens at near, intermediate and far visual distances is substantially equivalent to, or better than, an appropriately prescribed single-vision lens for far visual distance and produces minimal ghosting at distances from far distance to near.

(F3) A lens comprising: an optical axis; an aberration profile having a focal distance; at least two optical surfaces; wherein the lens is configured at least in part by one or more power profiles and the lens has the following properties: the visual performance of the lens at intermediate and far visual distances is substantially equivalent to, or better than, a properly prescribed single-vision lens for far visual distance and produces minimal ghosting at distances from far distance to near.

(F4) A lens comprising: an optical axis; an aberration profile having a focal distance; at least two optical surfaces; the lens is configured by one or more power profiles and has the following lens properties: the lens is capable of decreasing the rate of progression of myopia; the lens is capable of decreasing the rate of growth of the eye as measured by axial length; and provides visual performance at intermediate and far visual distances that is at least substantially equivalent to a properly prescribed single-vision lens for far visual distance and produces minimal ghosting at distances from far distance to near.

(F5) A lens comprising: an optical axis; at least two optical surfaces; an aberration profile having a focal distance and/or at least one power profile, wherein the aberration profile and/or at least one power profile configure the lens to provide an image profile and the image profile in use with an eye is capable of stabilising and/or altering the growth of the eye; and wherein the lens is configured to provide visual performance at intermediate and far visual distances that is substantially equivalent to or better than a correctly prescribed single-vision lens for far visual distance and produces minimal ghosting at distances from far distance to near; wherein the image profile generates one or more of the following: myopic and/or hyperopic defocus at centre and/or periphery of the retina; a RIQ of at least 0.3, 0.35 or 0.4 at the retina and a slope of through-focus RIQ that degrades in the direction of eye growth; and a RIQ of at least 0.3, 0.35 or 0.4 at the retina and a slope of through-focus RIQ that improves in the direction of eye growth.

(F6) The lens of one or more of the above F examples, wherein the image profile created by the lens has the effect of slowing the growth of the myopic eye by one or more stop signals.

(F7) The lens of one or more of the above F examples, wherein the slope of through-focus RIQ that degrades in the direction of eye growth is one or more of the following: substantial, partial, sufficient or combinations thereof, (F8) The lens of one or more of the above F examples, myopia control lens.

(F9) The lens of one or more of the above F examples, wherein the improvement in the direction of growth is one or more of the following: substantial, partial, sufficient or combinations thereof.

(F10) The lens of one or more of the above F examples, wherein the lens has an aperture size of 2 mm or greater; 2.5 mm or greater, 3 mm or greater, 3.5 mm or greater or 4 mm or greater.

(F11) The lens of one or more of the above F examples, wherein the lens is a multifocal lens with at least 1 Dioptre, at least 1.25 Dioptre, or at least 1.5 Dioptre of power variation across a central and/or a mid-peripheral portion of the optical zone of the lens.

(F12) The lens of one or more of the above F examples, wherein the lens is a presbyopic multifocal lens with at least 1 Dioptre, at least 1.25 Dioptre or at least 1 Dioptre of power variation across a central and/or a mid-peripheral portion of the optical zone of the lens.

(F13) The lens of one or more of the above F examples, wherein the lens is non-monotonic and non-periodic.

(F14) The lens of one or more of the above F examples, wherein the lens is a non-pinhole lens.

(F15) The lens of one or more of the above F examples, wherein the lens is a non-pinhole lens and the lens is a multifocal lens with at least 1, 1.25 or 1.5 Dioptre of power variation across a central and/or a mid-peripheral portion of the optical zone of the lens.

(F16) The lens of one or more of the above F examples, wherein in the lens produces a retinal image quality (RIQ) with a through focus slope that degrades in a direction of eye growth, where the RIQ is determined by a visual Strehl Ratio that is measured substantially along the optical axis when the aberration profile is tested on a model eye with no or substantially no aberrations and having an on-axis length equal or substantially equal to the focal distance.

(F17) The lens of one or more of the above F examples, wherein in the lens produces a retinal image quality (RIQ) with a through focus slope that degrades in a direction of eye growth, where the RIQ is determined by a visual Strehl Ratio that is measured along the optical axis when the aberration profile is tested on a model eye with no aberrations and having an on-axis length equal to the focal distance.

(F18) The lens of one or more of the above F examples, wherein the lens has at least one wavefront aberration profile associated with the optical axis, and the aberration profile is comprised of: at least two spherical aberration selected at least in part from a group comprising Zernike coefficients $C(4,0)$ to $C(20,0)$.

(F19) The lens of one or more of the above F examples, wherein the lens can be characterised upon testing by at least the following properties: two or more higher order aberrations having one or more of the following components: a primary spherical aberration $C(4,0)$, a secondary spherical aberration ($C(6,0)$, a tertiary spherical aberration $C(8,0)$, a quaternary spherical aberration $C(10,0)$, a pentanary spherical aberration $C(12,0)$, a hexanary spherical aberration $C(14,0)$, a heptanary spherical aberration $C(16,0)$, an octanary spherical aberration $C(18,0)$ and a nanonary spherical aberration $C(20,0)$.

(F20) The lens of one or more of the above F examples, wherein the lens does not substantially reduce the amount of light passing through the lens.

(F21) The lens of one or more of the above F examples, wherein the amount of light passing through the lens is at least 80%, 85%, 90%, 95% or 99%.

Examples Set G (G1) A multifocal lens comprising: an optical axis; the multifocal lens is configured based on an aberration profile associated with the optical axis; the aberration profile is comprised of at least two spherical aberration terms and a defocus term; the multifocal lens is configured such that the visual performance of the multifocal lens at intermediate and far visual distances is substantially equivalent to, or better than, an appropriately or properly prescribed single-vision lens for far visual distance; and when tested with a defined visual rating scale of 1 to 10 units, the visual performance at the near visual distance is within two units of the visual performance of the appropriately prescribed single-vision lens at far distance.

(G2) A multifocal lens comprising: an optical axis; the multifocal lens is configured in part on an aberration profile associated with the optical axis; the aberration profile is comprised of at least two spherical aberration terms and a defocus term; wherein the multifocal lens is configured such that the visual performance of the multifocal lens at intermediate and far visual distances is equivalent to or better than, an appropriately or correctly prescribed single-vision lens for far visual distance; and wherein upon testing with a defined visual rating scale of 1 to 10 units, the visual performance at the near visual distance is within two units of the visual performance of the correctly prescribed single-vision lens at far distance.

(G3) A multifocal lens comprising: an optical axis; the multifocal lens is configured based on an aberration profile associated with the optical axis; the aberration profile is comprised of at least two spherical aberration terms and a defocus term; and wherein upon testing with a defined overall visual rating scale of 1 to 10 units, the multifocal lens is configured such that the overall visual performance of the multifocal lens is substantially equivalent to or better than an appropriately prescribed single-vision lens for far visual distance.

(G4) A multifocal lens comprising: an optical axis; the multifocal lens is configured based in part on an aberration profile associated with the optical axis; the aberration profile is comprised of at least two spherical aberration terms and a defocus term; and wherein the multifocal lens is configured such that the visual performance on a visual analogue scale, with the multifocal lens, at far visual distance, has a score of 9 or above in 55%, 60%, 65%, 70%, 75% or 80% of a representative sample of presbyopes; wherein the multifocal lens is configured such that the visual performance on a visual analogue scale, with the multifocal lens, at intermediate visual distance, has a score of 9 or above in 45%, 50%, 55%, 60%, 65%, 70% or 75% of a representative sample of presbyopes; and wherein the multifocal lens is configured such that the visual performance on a visual analogue scale, with the multifocal lens, at near visual distance has a score of 9 or above in 25%, 30%, 35%, 40%, 45%, 50% or 55% of a representative sample of presbyopes.

(G5) A multifocal lens comprising: an optical axis; the multifocal lens being characterised or configured in part on an aberration profile associated with the optical axis; the aberration profile is comprised of at least two spherical aberration terms and a defocus term; and wherein the multifocal lens is configured such that the overall visual performance on a visual analogue scale results in a score of 9 or above in 18%, 25%, 30%, 35%, 40% or 45% of a representative sample of presbyopes.

(G6) The multifocal lens of one or more of the above G examples, wherein the multifocal lens in use provides substantially minimal ghosting to the vision of the user at near and far visual distances.

(G7) The multifocal lens of one or more of the above G examples, wherein the substantially equivalent to or better visual performance is determined at least in part by a visual rating scale of 1 to 10 units.

(G8) The multifocal lens of one or more of the above G examples, wherein the average visual performance of the lens in use for a representative sample of the affected population has a distance vision score of at least 8.5, has an intermediate vision score of at least 8.5 and has a near vision score of at least 7.5.

(G9) The multifocal lens of one or more of the above G examples, wherein the average visual performance of the lens in use for a representative sample of the affected population has a distance vision score of at least 8.0, at least 8.2 or at least 8.4; has an intermediate vision score of at least 8.0, at least 8.2 or at least 8.4; has a near vision score of at least 7.0, at least 7.2 or at least 7.4; or combinations thereof.

(G10) The multifocal lens of one or more of the above G examples, wherein the multifocal lens provides substantially minimal ghosting for a representative sample of the affected population at near and/or intermediate visual distances.

(G11) The multifocal lens of one or more of the above G examples, wherein substantial minimal ghosting is an average visual performance score of less than or equal to 2.4, 2.2, 2, 1.8, 1.6 or 1.4 on the vision analogue ghosting scale of 1 to 10 units for a representative sample of the affected population using the multifocal lens.

(G12) The multifocal lens of one or more of the above G example, wherein substantial minimal ghosting is a score of less than or equal to 2.4, 2.2, 2, 1.8, 1.6 or 1.4 on the vision rating ghosting scale 1 to 10 units utilising the average visual performance of the lens in use on a sample of people needing vision correction and/or therapy, for one or more of the following: myopia, hyperopia, astigmatism, emmetropia and presbyopia.

(G13) The multifocal lens of one or more of the above G examples, wherein the lens provides myopia control therapy with minimal ghosting with or without vision correction.

(G14) The multifocal lens of one or more of the above G examples, wherein the lens provides presbyopia correction with minimal ghosting with or without far vision correction.

(G15) The multifocal lens of one or more of the above G examples, wherein the lens corrects astigmatism up to 1 Dioptre without substantial use of rotationally stable toric lens design features.

(G16) The multifocal lens of one or more of the above G examples, wherein the lens corrects astigmatism up to 1 Dioptre without substantial use of rotationally stable toric lens design features with minimal ghosting.

(G17) The multifocal lens of one or more of the above G examples, further comprising a first lens and a second lens wherein the first lens is biased to substantially optimise distance vision and the second lens is biased to substantially optimise near vision, and when used together provide monocular and binocular vision substantially equivalent to, or better than, an appropriately prescribed single-vision lens for far visual distance, wherein the pair of lenses provide stereopsis with minimal ghosting.

(G18) The multifocal lens of one or more of the above G examples, wherein the average overall visual performance of the lens in use for a representative sample of the affected population has an overall vision score of at least 7.8, 8, 8.2, 8.4, 8.6, 8.8 or 9.

(G19) The multifocal lens of one or more of the above G examples, wherein the average overall visual performance of the lens in use for a representative sample of the affected population has an overall vision score of at least 7.8, 8, 8.2, 8.4, 8.6, 8.8 or 9.

(G20) The multifocal lens of one or more of the above G examples, wherein the multifocal lens in use provides substantially minimal ghosting to the vision of the user at near and far visual distances.

(G21) The multifocal lens of one or more of the above G examples, wherein the substantially equivalent to or better visual performance is determined at least in part by a visual rating scale of 1 to 10 units.

(G22) The multifocal lens of one or more of the above G examples, wherein the substantially equivalent to or better visual performance is substantially determined by a visual rating scale of 1 to 10 units.

(G23) The multifocal lens of one or more of the above G examples, wherein the average visual performance of the lens in use for a representative sample of the affected population has a distance vision score of at least 8.5, has an intermediate vision score of at least 8.5 and has a near vision score of at least 7.5.

(G24) The multifocal lens of one or more of the above G examples, wherein the average visual performance of the lens in use for a representative sample of the affected population has a distance vision score of at least 8.0, at least 8.2 or at least 8.4; has an intermediate vision score of at least 8.0, at least 8.2 or at least 8.4; has a near vision score of at least 7.0, at least 7.2 or at least 7.4, or combinations thereof.

(G25) The multifocal lens of one or more of the above G examples, wherein the multifocal lens in use provides the average visual performance of the lens in use for a representative sample of the affected population provide substantially minimal ghosting to the vision of the user at near and/or intermediate visual distances.

(G26) The multifocal lens of one or more of the above G examples, wherein substantial minimal ghosting is defined as a score of less than or equal to 2.5, 2.2, 2, 1.8, 1.6 or 1.4 on the vision rating ghosting scale 1 to 10 units utilising the average visual performance of the lens in use for a representative sample of the affected population.

(G27) The multifocal lens of one or more of the above G examples, wherein the average overall visual performance of the lens in use for a representative sample of the affected population has an overall vision score of at least 7.8, 8, 8.2, 8.4, 8.6, 8.8 or 9.

(G28) The multifocal lens of one or more of the above G examples, wherein the single-vision lens is a lens with a substantially constant power across a substantial portion of an optic zone of the single-vision lens.

(G29) The multifocal lens of one or more of the above G examples, wherein the lens is used for a presbyopic eye.

(G30) The multifocal lens of one or more of the above G examples, wherein the lens is further characterised by minimal, or no, ghosting at near, intermediate and far distances.

(G31) The multifocal lens of one or more of the above G examples, where in the substantially continuous distances is continuous.

(G32) The multifocal lens of one or more of the above G examples, wherein the single-vision lens is one or more of the following: prescribed, appropriately prescribed, correctly prescribed and effectively prescribed.

(G33) The multifocal lens of one or more of the above G examples, wherein the single-vision lens is a lens with a substantially constant power across a substantial portion of an optic zone of the single-vision lens.

(G34) The multifocal lens of one or more of the above G examples, wherein the single-vision lens is a lens with a constant power across a portion of an optic zone of the single-vision lens.

(G35) The multifocal lens of one or more of the above G examples, wherein the single-vision lens is a lens with a substantially constant power across a portion of one or more optic zones of the single-vision lens.

(G36) The multifocal lens of one or more of the above G examples, wherein the multifocal lens is used for a presbyopic eye.

(G37) The multifocal lens of one or more of the above G examples, wherein the lens is configured for a presbyopic eye.

(G38) The multifocal lens of one or more of the above G examples, wherein the lens is configured to optically correct or substantially correct presbyopia.

(G39) The multifocal lens of one or more of the above G examples, wherein the lens is configured to mitigate or substantially mitigate the optical consequences of presbyopia.

(G40) The multifocal lens of one or more of the above G examples, wherein the lens is configured to alter or substantially alter a presbyopic condition to a non-presbyopic condition.

(G41) The multifocal lens of one or more of the above G examples, wherein the multifocal lens is used for at least correcting a presbyopic eye condition and when used provides an appropriate correction to adjust the vision of the user towards substantially normal non-presbyopic vision.

(G42) The multifocal lens of one or more of the above G examples, wherein normal vision is 6/6 or better.

(G43) The multifocal lens of one or more of the above G examples, wherein the multifocal lens is further characterised by minimal, substantially no or no, ghosting at near, intermediate and far distances.

(G44) The multifocal lens of one or more of the above G examples, wherein the multifocal lens is further characterised by minimal, substantially no or no, ghosting at near distances, intermediate distances and far distances.

(G45) The multifocal lens of one or more of the above G examples, wherein the multifocal lens is further configured to provide minimal, substantially no or no, ghosting at near, intermediate and far distances.

(G46) The multifocal lens of one or more of the above G examples, wherein the minimal ghosting is a lack of an undesired secondary image appearing at the image plane of the optical system.

(G47) The multifocal lens of one or more of the above G examples, wherein the minimal ghosting is a lack of an undesired secondary image appearing on the retina of the eye.

(G48) The multifocal lens of one or more of the above G examples, wherein the minimal ghosting is a lack of an undesired double image appearing on the retina of the eye.

(G49) The multifocal lens of one or more of the above G examples, wherein the minimal ghosting is a lack of false out-of-focus image appearing along side of the primary image in an optical system.

(G50) The multifocal lens of one or more of the above G examples, wherein the multifocal lens is further configured to provide a sufficient lack of ghosting in a portion of near, intermediate and far distances.

(G51) The multifocal lens of one or more of the above G examples, wherein the multifocal lens is further configured to provide a sufficient lack of ghosting at near distances, intermediate distances and far distances.

(G52) The multifocal lens of one or more of the above G examples, wherein the multifocal lens is further configured to provide a sufficient lack of ghosting in a portion of two or more of the following: near, intermediate and far distances.

(G53) The multifocal lens of one or more of the above G examples, wherein lack of ghosting is lack of undesired image appearing at the image plane of the optical system.

(G54) The multifocal lens of one or more of the above G examples, wherein lack of ghosting is a lack of false out of focus images appearing along side of the primary image in an optical system.

(G55) The multifocal lens of one or more of the above G examples, wherein the multifocal lens is further configured to provide a sufficient lack of ghosting in a portion of two or more of the following: near distances, intermediate distances and far distances.

(G56) The multifocal lens of one or more of the above G examples, wherein the multifocal lens is further configured to provide the RIQ of at least 0.1, 0.13, 0.17, 0.2, 0.225, or 0.25 in the near distance range, the RIQ of at least 0.27, 0.3, 0.33, 0.35, 0.37 or 0.4 in the intermediate distance range and the RIQ of at least 0.35, 0.37, 0.4, 0.42, 0.45, 0.47, or 0.5 in the far distance range.

(G57) The multifocal lens of one or more of the above G examples, wherein the multifocal lens is further configured to provide two or more of the following: the RIQ of at least 0.1, 0.13, 0.17, 0.2, 0.225, or 0.25 in the near distance range, the RIQ of at least 0.27, 0.3, 0.33, 0.35, 0.37 or 0.4 in the intermediate distance range and the RIQ of at least 0.35, 0.37, 0.4, 0.42, 0.45, 0.47, or 0.5 in the far distance range.

(G58) The multifocal lens of one or more of the above G examples, wherein the RIQs are selected in the near, intermediate and far distance ranges such that the multifocal lens is configured to provide minimal, or no, ghosting in near, intermediate and far distances.

(G59) The multifocal lens of one or more of the above G examples, wherein the multifocal lens is configured to substantially eliminate, or substantially reduce, ghosting at near, intermediate and far distances.

(G60) The multifocal lens of one or more of the above G examples, wherein the multifocal lens is configured to substantially eliminate, or substantially reduce, ghosting at near distances, intermediate distances and far distances.

(G61) The multifocal lens of one or more of the above G examples, wherein near distance is the range of 33 cm to 50 cm or 40 cm to 50 cm; intermediate distance is the range of 50 cm to 100 cm, 50 cm to 80 cm or 50 cm to 70 cm; and far distance is the range of 100 cm or greater, 80 cm or greater or 70 cm or greater.

(G62) The multifocal lens of one or more of the above G examples, wherein near distance is the range of 33 cm to 50 cm or 40 cm to 50 cm; intermediate distance is the range of 50 cm to 100 cm, 50 cm to 80 cm or 50 cm to 70 cm; and far distance is the range of 100 cm or greater, 80 cm or greater or 70 cm or greater and the near, intermediate and far distances are determined by the distance from the object being focused on.

(G63) The multifocal lens of one or more of the above G examples, wherein near distance is the range of 40 cm to 50 cm; intermediate distance is the range of 50 cm to 100 cm; and far distance is the range of 100 cm or greater.

(G64) The multifocal lens of one or more of the above G examples, wherein near distance is the range of 40 cm to 50 cm; intermediate distance is the range of 50 cm to 100 cm; and far distance is the range of 100 cm or greater and the near, intermediate and far distances are determined by the distance from the object being focused on.

(G65) The multifocal lens of one or more of the above G examples, wherein near distance is the range of 40 cm to 50 cm; intermediate distance is the range of 50 cm to 100 cm; and far distance is the range of 100 cm to optical infinity.

(G66) The multifocal lens of one or more of the above G examples, wherein near distance is the range of 40 cm to 50 cm; intermediate distance is the range of 50 cm to 100 cm;

and far distance is the range of 100 cm to optical infinity and the near, intermediate and far distances are determined by the distance from the object being focused on.

(G67) The multifocal lens of one or more of the above G examples, wherein the multifocal lens is configured to minimize, or reduce, ghosting at near, intermediate and far distances when used on an eye.

(G68) The multifocal lens of one or more of the above G examples, wherein the multifocal lens is configured to minimize, or reduce, ghosting at near distances, intermediate distances and far distances when used on an eye.

(G69) The multifocal lens of one or more of the above G examples, wherein the range of substantially continuous distances is continuous.

(G70) The multifocal lens of one or more of the above G examples, wherein the range of substantially continuous distances is continuous and goes from 40 cm to optical infinity.

(G71) The multifocal lens of one or more of the above G examples, wherein the range of substantially continuous distances is from 33 cm to optical infinity.

(G72) The multifocal lens of one or more of the above G examples, wherein the lens is configured such that at least 40/%, 50%, 60% or 70% of a randomly selected group of 15 affected individuals in the near distances, intermediate distances and far distances perceive minimal, or no, ghosting at near distances, intermediate distances and far distances.

(G73) The multifocal lens of one or more of the above G examples, wherein the lens is configured such that at least 60%, 70%, 80% or 90% of a randomly selected group of 15 affected individuals in the intermediate distances and far distances perceive minimal, or no, ghosting at intermediate distances and far distances.

(G74) The multifocal lens of one or more of the above G examples, wherein the single vision lens provides a visual acuity for the user of one or more of the following: at least 20/20, at least 20/30, at least 20/40, at least about 20/20, at least about 20/30 and at least about 20/40, at far visual distances.

(G75) The multifocal lens of one or more of the above G examples, wherein the aberration profile is comprised of a defocus term and at least two, two or more, three, three or more, four, four or more, five, five or more, six, six or more, seven, seven or more, eight, eight or more, nine, nine or more, ten, or ten or more spherical aberration terms.

(G76) The multifocal lens of one or more of the above G examples, wherein the aberration profile is comprised of a defocus term and at least two, three, four, five, six, seven, eight, nine, or at least ten spherical aberration terms.

(G77) The multifocal lens of one or more of the above G examples, wherein the aberration profile is comprised of a defocus term and spherical aberration terms between $C(4,0)$ and $C(6,0)$, $C(4,0)$ and $C(8,0)$, $C(4,0)$ and $C(10,0)$, $C(4,0)$ and $C(12,0)$, $C(4,0)$ and $C(14,0)$, $C(4,0)$ and $C(16,0)$, $C(4,0)$ and $C(18,0)$, or $C(4,0)$ and $C(20,0)$.

(G78) The multifocal lens of one or more of the above G examples, wherein the single vision lens provides a visual acuity that is the best-corrected visual acuity.

(G79) The multifocal lens of one or more of the above G examples, wherein the best-corrected visual acuity is a visual acuity that cannot be substantially improved by further manipulating the power of the single vision lens.

(G80) The multifocal lens of one or more of the above G examples, wherein the lens has two optical surfaces.

(G81) The multifocal lens of one or more of the above G examples, wherein the least one aberration profile is along the optical axis of the lens.

(G82) The multifocal lens of one or more of the above G examples, wherein the lens has a focal distance.

(G83) The multifocal lens of one or more of the above G examples, wherein the aberration profile includes higher order aberrations having at least one of a primary spherical aberration component $C(4,0)$ and a secondary spherical aberration component $C(6,0)$.

(G84) The multifocal lens of one or more of the above G examples, wherein the aberration profile provides, for a model eye with no, or substantially no, aberrations and an on-axis length equal to the focal distance: the retinal image quality (RIQ) with a through focus slope that degrades in a direction of eye growth; and the RIQ of at least 0.3; wherein the RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(G85) The multifocal lens of one or more of the above G examples, wherein the aberration profile provides, for a model eye with no, or substantially no, aberrations and an on-axis length equal to the focal distance: the retinal image quality (RIQ) with a through focus slope that improves in a direction of eye growth; and the RIQ of at least 0.3; wherein the RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(G86) The multifocal lens of one or more of the above G examples, wherein the lens has an optical axis and an aberration profile about its optical axis, the aberration profile: having a focal distance; and including higher order aberrations having at least one of a primary spherical aberration component $C(4,0)$ and a secondary spherical aberration component $C(6,0)$, wherein the aberration profile provides, for a model eye with no, or substantially no, aberrations and an on-axis length equal, or substantially equal, to the focal distance: the RIQ with a through focus slope that degrades in a direction of eye growth; and the RIQ of at least 0.3; wherein the RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(G87) The multifocal lens of one or more of the above G examples, wherein the lens has an optical axis and an aberration profile about its optical axis, the aberration profile: having a focal distance; and including higher order aberrations having at least one of a primary spherical aberration component $C(4,0)$ and a secondary spherical aberration component $C(6,0)$, wherein the aberration profile provides, for a model eye with no, or substantially no, aberrations and an on-axis length equal, or substantially equal, to the focal distance: the RIQ with a through focus slope that improves in a direction of eye growth; and the RIQ of at least 0.3; wherein the RIQ is visual Strehl Ratio measured along the optical axis for at least one pupil diameter in the range 3 mm to 6 mm, over a spatial frequency range of 0 to 30 cycles/degree inclusive and at a wavelength selected from within the range 540 nm to 590 nm inclusive.

(G88) The multifocal lens of one or more of the above G examples, wherein the focal distance is a prescription focal distance for a myopic, hyperopic, astigmatic, and/or presbyopic eye and wherein the focal distance differs from the focal distance for a C(2,0) Zernike coefficient of the aberration profile.

(G89) The multifocal lens of one or more of the above G examples, wherein the higher order aberrations include at least two spherical aberration terms selected from the group C(4,0) to C(20,0).

(G90) The multifocal lens of one or more of the above G examples, wherein the higher order aberrations include at least three spherical aberration terms selected from the group C(4,0) to C(20,0).

(G91) The multifocal lens of one or more of the above G examples, wherein the higher order aberrations include at least five spherical aberration terms selected from the group C(4,0) to C(20,0).

(G92) The multifocal lens of one or more of the above G examples, wherein the average slope over a horizontal field of at least −20° to +20° degrades in a direction of eye growth.

(G93) The multifocal lens of one or more of the above G examples, wherein the average slope over a horizontal field of at least −20° to +20° improves in a direction of eye growth.

(G94) The multifocal lens of one or more of the above G examples, wherein the average slope over a vertical field of at least −20° to +20° degrades in a direction of eye growth.

(G95) The multifocal lens of one or more of the above G examples, wherein the average slope over a vertical field of at least −20° to +20° improves in a direction of eye growth.

(G96) The multifocal lens of one or more of the above G examples, wherein the slope for a substantial portion of the field angles over a horizontal field of at least −20° to +20° degrades in a direction of eye growth.

(G97) The multifocal lens of one or more of the above G examples, wherein the substantial portion of the field angles over a horizontal field is at least 75%, 85%, 95% or 99% of the field angles.

(G98) The multifocal lens of one or more of the above G examples, wherein the substantial portion of the field angles over a horizontal field is every field angle.

(G99) The multifocal lens of one or more of the above G examples, wherein the slope for a substantial portion of the field angles over a vertical field of at least −20° to +20° degrades in a direction of eye growth.

(G100) The multifocal lens of one or more of the above G examples, wherein the substantial portion of the field angles over a vertical field is every angle.

(G101) The multifocal lens of one or more of the above G examples, wherein the substantial portion of the field angles over a vertical field is at least 75%, 85%, 95% or 99% of the field angles.

(G102) The multifocal lens of one or more of the above G examples, wherein the aberration profile provides the RIQ of at least 0.3 at the focal length for a substantial portion of pupil diameters in the range 3 mm to 6 mm.

(G103) The multifocal lens of one or more of the above G examples, wherein the aberration profile provides the RIQ of at least 0.3 at the focal length for a substantial portion of pupil diameters in the range 4 mm to 5 mm.

(G104) The multifocal lens of one or more of the above G examples, wherein the aberration profile provides the RIQ with a through focus slope that degrades in a direction of eye growth when primary or secondary astigmatism is added to the aberration profile.

(G105) The multifocal lens of one or more of the above G examples, wherein the aberration profile provides the RIQ with a through focus slope that improves in a direction of eye growth when primary or secondary astigmatism is added to the aberration profile.

(G106) The multifocal lens of one or more of the above G examples, wherein the primary or secondary astigmatism is added to the desired aberration profile by altering one or more of the following terms: C(2,−2), C(2,2), C(4,−2), C(4,2), C(6,−2), and/or C(6,2).

(G107) The multifocal lens of one or more of the above G examples, wherein the aberration profile provides the RIQ with a through focus slope that degrades in a direction of eye growth when secondary astigmatism is added to the aberration profile.

(G108) The multifocal lens of one or more of the above G examples, wherein the secondary astigmatism is added to the desired aberration profile by altering one or more of the following terms: C(2,−2), C(2,2), C(4,−2), C(4,2), C(6,−2), and/or C(6,2).

(G109) The multifocal lens of one or more of the above G examples, wherein the RIQ is characterised by $$RIQ = \frac{\int\int_{-Fmin}^{+Fmax} CSF(x,y) * \left(\text{real}\left(\left(\left[FT\left(\left[FT\left\{A(\rho,\theta)*\exp\left[\frac{2\pi i}{\lambda}*W(\rho,\theta)\right]\right\}\right]\right)\right]\right|^2\right)\right))}{\int\int_{-Fmin}^{+Fmax} CSF(x,y) * \left(\left(\left(\left[FT\left(\left[FT\left\{A(\rho,\theta)*\exp\left[\frac{2\pi i}{\lambda}*Wdiff(\rho,\theta)\right]\right\}\right]\right)\right]\right|^2\right)\right)}$$

wherein:
Fmin is 0 cycles/degree and Fiax is 30 cycles/degree;
CSF(x, y) denotes the contrast sensitivity function
$CSF(F)=2.6(0.0192+0.114f)e^{-(0.114*f)^{1.1}}$,
where f specifies the tested spatial frequency, in the range of $F_{min}$ to $F_{max}$;
FT denotes a 2 D fast Fourier transform;
A(ρ, θ) denotes the pupil amplitude function across pupil diameter,
W(ρ, θ) denotes wavefront of the test case measured for i=1 to 20

$$W(\rho,\theta) = \sum_{i=1}^{k} a_i Z_i(\rho,\theta)$$

Wdiff(ρ, θ) denotes wavefront of the diffraction limited case;
ρ and θ are normalised polar coordinates, where ρ represents the radial coordinate and θ represents the angular coordinate or azimuth; and
λ denotes wavelength.

(G110) The multifocal lens of one or more of the above G examples, wherein the RIQ is characterised by $$RIQ = \frac{\int\int_{-Fmin}^{+Fmax}\left(\text{real}\left(\left(\left[FT\left(\left[FT\left\{A(\rho,\theta)*\exp\left[\frac{2\pi i}{\lambda}*W(\rho,\theta)\right]\right\}\right]\right)\right]\right|^2\right)\right)}{\int\int_{-Fmin}^{+Fmax}\left(\left(\left(\left[FT\left(\left[FT\left\{A(\rho,\theta)*\exp\left[\frac{2\pi i}{\lambda}*Wdiff(\rho,\theta)\right]\right\}\right]\right)\right]\right|^2\right)\right)}$$

wherein:
Fmin is 0 cycles/degree and Fmax is 30 cycles/degree;
CSF(x, y) denotes the contrast sensitivity function
$CSF(F)=2.6(0.0192+0.114f)e^{-(0.114*f)^{1.1}}$, where f specifies the tested spatial frequency, in the range of $F_{min}$ to $F_{max}$;
FT denotes a 2 D Fourier transform, for example a 2 D fast Fourier transform;
$A(\rho, \theta)$ denotes the pupil amplitude function across pupil diameter;
$W(\rho, \theta)$ denotes wavefront of the test case measured for i=1 to k;
wherein k is a positive integer, $$W(\rho, \theta) = \sum_{i=1}^{k} a_i Z_i(\rho, \theta)$$

Wdiff($\rho, \theta$) denotes wavefront of the diffraction limited case;
$\rho$ and $\theta$ are normalised polar coordinates, where $\rho$ represents the radial coordinate and $\theta$ represents the angular coordinate or azimuth; and
$\lambda$ denotes wavelength.

(G111) The multifocal lens of one or more of the above G examples, wherein the multifocal lens includes an optical axis and an aberration profile along the optical axis that provides: a focal distance for a C(2,0) Zernike coefficient term; a peak visual Strehl Ratio ('first visual Strehl Ratio') within a through focus range, and a visual Strehl Ratio that remains at or above a second visual Strehl Ratio over the through focus range that includes said focal distance, wherein the visual Strehl Ratio is measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive, and wherein the first visual Strehl Ratio is at least 0.35, the second visual Strehl Ratio is at least 0.1 and the through focus range is at least 1.8 Dioptres.

(G112) The multifocal lens of one or more of the above G examples, wherein the multifocal lens includes an optical axis and an aberration profile along the optical axis that provides: a focal distance for a C(2,0) Zernike coefficient term; a peak visual Strehl Ratio ('first visual Strehl Ratio') within a through focus range, and a visual Strehl Ratio that remains at or above a second visual Strehl Ratio over the through focus range that includes said focal distance, wherein the visual Strehl Ratio is measured for a model eye with no aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive, and wherein the first visual Strehl Ratio is at least 0.35, the second visual Strehl Ratio is at least 0.1 and the through focus range is at least 1.8 Dioptres.

(G113) The multifocal lens of one or more of the above G examples, wherein the first visual Strehl Ratio is at least 0.3, 0.35, 0.4, 0.5, 0.6, 0.7 or 0.8.

(G114) The multifocal lens of one or more of the above G examples, wherein the second visual Strehl Ratio is at least 0.1, 0.12, 0.15, 0.18 or 0.2.

(G115) The multifocal lens of one or more of the above G examples, wherein the through focus range is at least 1.7, 1.8, 1.9, 2, 2.1, 2.25 or 2.5 Dioptres.

(G116) The multifocal lens of one or more of the above G examples, wherein the lens has a prescription focal distance located within 0.75, 0.5, 0.3, or 0.25 Dioptres, inclusive, of an end of the through focus range.

(G117) The multifocal lens of one or more of the above G examples, wherein the end of the through focus range is the negative power end.

(G118) The multifocal lens of one or more of the above G examples, wherein the end of the through focus range is the positive power end.

(G119) The multifocal lens of one or more of the above G examples, wherein the visual Strehl Ratio remains at or above the second visual Strehl Ratio over the through focus range and over a range of pupil diameters of at least 1 mm, 1.5 mm, 2 mm, 2.5 mm, or 3 mm.

(G120) The multifocal lens of one or more of the above G examples, wherein the combination of higher order aberrations includes at least one of primary spherical aberration and secondary spherical aberration.

(G121) The multifocal lens of one or more of the above G examples, wherein the higher order aberrations include at least two, three, or five spherical aberration terms selected from the group C(4,0) to C(20,0).

(G122) The multifocal lens of one or more of the above G examples, wherein the aberration profile can be substantially characterised using spherical aberration Zernike coefficients C(4, 0) to C(20, 0).

(G123) The multifocal lens of one or more of the above G examples, wherein the RIQ for a substantial portion of the angles over a horizontal field of at least −10° to +10°, −20° to +20° or −30° to +30° is at least 0.4.

(G124) The multifocal lens of one or more of the above G examples, wherein the RIQ for a substantial portion of the angles over a horizontal field of at least −10° to +10°, −20° to +20° or −30° to +30° is at least 0.35.

(G125) The multifocal lens of one or more of the above G examples, wherein the RIQ for a substantial portion of the angles over a horizontal field of at least −10° to +10°, −20° to +20° or −30° to +30° is at least 0.3.

(G126) The multifocal lens of one or more of the above G examples, wherein the lens is one or more of the following: contact lens, corneal onlays, corneal inlays, anterior chamber intraocular lens or posterior chamber intraocular lens.

(G127) The multifocal lens of one or more of the above G examples, wherein the lens is one of the following: contact lens, corneal onlays, corneal inlays, anterior chamber intraocular lens or posterior chamber intraocular lens.

(G128) The multifocal lens of one or more of the above G examples, wherein a first multifocal lens is provided based on one or more of the above of the G examples and a second multifocal lens is provided based on one or more of the above of the G examples to form a pair of lenses.

(G129) The multifocal lens of one or more of the above G examples, wherein the first multifocal lens is provided based on one or more of the above of the G examples and a second lens is provided to form a pair of lenses.

(G130) The multifocal lens of one or more of the above G examples, wherein a pair of multifocal lenses are provided for use by an individual to substantially correct the individual's vision.

(G131) The lens of one or more of the above G examples, wherein the lens does not substantially reduce the amount of light passing through the lens.

(G132) The lens of one or more of the above G examples, wherein the amount of light passing through the lens is at least 80%, 85%, 90%, 95% or 99%.

(G133) A method for making or using one or more of the multifocal lenses of one or more of the above G examples.

Example Set H (H1) A system of lenses comprising: a series of lenses, wherein the lenses in the series of lenses have the following properties: at least two spherical aberration terms selected at least in part from a group comprising spherical aberration coefficients from C(4,0) to C(20,0), that provides correction of astigmatism up to 1 Dioptre without substantial use of rotationally stable toric lens design features; and wherein the lenses in the series of lenses eliminate the need for maintaining additional inventory for astigmatic corrections relating to cylinder powers of 0.5, 0.75 and 1 D, resulting in a reduction of stock keeping units by at least six, eight, twelve, sixteen, eighteen, thirty six, fifty-four or 108 times for each sphere power.

Example Set J (J1) A multifocal lens for an eye comprising: at least one optical axis; at least one wavefront aberration profile associated with the optical axis and the prescription focal power of the lens; wherein, the multifocal lens is configured to expand the depth-of-focus of the eye by altering the retinal image quality over a range of distances via manipulation of the at least one wavefront aberration profile for the eye.

(J2) A multifocal lens for an eye comprising: at least one optical axis; at least one wavefront aberration profile associated with the optical axis and the aberration profile is comprised of at least two spherical aberration terms and the prescription focal power of the lens; wherein the lens is configured such that the lens expands the depth-of-focus of the eye by altering the retinal image quality over a range of distances via manipulation of at least one wavefront aberration profile for the eye.

(J3) A multifocal lens for an eye comprising: at least one optical axis; at least one wavefront aberration profile associated with the optical axis, and the aberration profile is comprised of: at least two spherical aberration selected at least in part from a group comprising Zernike coefficients C(4,0) to C(20,0), and a prescription focal power of the lens that may be provided at least in part by C(2,0) Zernike coefficient term either with, or without, one or more prescription offset terms; wherein, the multifocal lens is configured to expand the depth-of-focus of the eye by improving the retinal image quality over a range of distances via manipulation of the at least one wavefront aberration profile.

(J4) The lens of one or more of the above J examples, wherein the lens does not substantially reduce the amount of light passing through the lens.

(J5) The lens of one or more of the above J examples, wherein the amount of light passing through the lens is at least 80%, 85%, 90%, 95% or 99%.

Example Set K (K1) A lens comprising: an optical axis; at least two surfaces; wherein the lens has at least one power profile, the power profile is characterised upon testing by a function that is non-monotonic over a substantial portion of the half-chord optical zone of the lens.

(K2) A lens comprising: an optical axis; at least two surfaces; wherein the lens has at least one power profile, the power profile is characterised by a function that is non-monotonic over a substantial portion of the half-chord optical zone of the lens.

(K3) A lens comprising: an optical axis; at least two surfaces; wherein the lens has at least one power profile, the power profile is characterised by a function that is aperiodic over a substantial portion of the half-chord optical zone of the lens.

(K4) A lens comprising: an optical axis; at least two surfaces; wherein the lens has at least one power profile, the power profile is characterised upon testing by a function that is aperiodic over a substantial portion of the half-chord optical zone of the lens.

(K5) A lens comprising: an optical axis; at least two surfaces; wherein the lens has at least one power profile, the power profile is characterised by a function that is aperiodic and non-monotonic over a substantial portion of the half-chord optical zone of the lens.

(K6) A lens comprising: an optical axis; at least two surfaces; wherein the lens has at least one power profile, the power profile is characterised upon testing by a function that is aperiodic and non-monotonic over a substantial portion of the half-chord optical zone of the lens.

(K7) A lens comprising: an optical axis; at least two surfaces; wherein the lens has at least one power profile, the power profile is configured such that the power profile is non-monotonic over a substantial portion of the half-chord optical zone of the lens.

(K8) A lens comprising: an optical axis; at least two surfaces; wherein the lens has at least one power profile, the power profile is configured such that the power profile is aperiodic over a substantial portion of the half-chord optical zone of the lens.

(K9) A lens comprising: an optical axis; at least two surfaces; wherein the lens has at least one power profile, the power profile is configured such that the power profile is aperiodic and non-monotonic over a substantial portion of the half-chord optical zone of the lens.

(K10) A lens comprising: an optical axis; at least two surfaces; and wherein the lens has at least one power profile, the power profile is configured such that the absolute of a first derivative of the power profile has at least 5 peaks whose absolute amplitude is greater than 0.025 with units of 1 D per 0.01 mm along its half-chord.

(K11) A lens comprising: an optical axis; at least two surfaces; and wherein the lens has at least one power profile, the power profile is characterised such that the absolute of a first derivative of the power profile has at least 5 peaks whose absolute amplitude is greater than 0.025 with units of 1 D per 0.01 mm along its half-chord.

(K12) The multifocal lens comprising: an optical axis; at least two surfaces; and wherein the multifocal lens has a power profile such that an absolute of a first derivative of the power profile, as a function of half-chord diameter, has at least 5 peaks whose absolute amplitude is greater than 0.025 with units of 1 D per 0.01 mm along its half-chord diameter.

(K13) The lens of one or more of the above of K examples, wherein the lens is configured at least in part on an aberration profile associated with the optical axis.

(K14) The lens of one or more of the above of K examples, wherein the lens has an aberration profile comprised of a defocus term and at least two spherical aberration terms.

(K15) The lens of one or more of the above of K examples, wherein the lens is a multifocal or bifocal. K15 The lens of one or more of the above of K examples, wherein the substantial portion of the half-chord is 50%, 60%, 70%, 80%, 90% or 95% of the half-chord.

(K16) A method of characterising lens power profile comprising the steps of: measuring the spatially resolved power profile; computing a first derivative of the power profile; and analysing or describing the power profile as a first derivative of the power profile.

(K17) The method of one or more of the above of K examples, wherein the first of derivative of the power profile is an absolute of the first derivative of the power profile.

(K18) A method of characterising lens power profile comprising the steps of: measuring the power profile; computing a Fourier transform of the power profile; and describing the power profile as a Fourier spectrum, wherein a normalised absolute amplitude of the Fourier transform of the power profile is greater than 0.2 at one or more spatial frequencies at or above 1.25 cycles per millimeter.

(K19) The method of one more K examples, wherein the Fourier spectrum of the power profile is the amplitude of the Fourier spectrum.

(K20) The method of one more K examples, wherein the Fourier spectrum of the power profile is the phase of the Fourier spectrum.

(K21) The method of one more K examples, wherein the Fourier spectrum is an absolute of the Fourier spectrum.

(K22) The method of one more K examples, wherein the Fourier spectrum is a real of the Fourier spectrum.

(K23) The method of one more K examples, wherein the Fourier spectrum is a normalised absolute of the Fourier spectrum.

(K24) A lens comprising: an optical axis; at least two surfaces; wherein the lens has at least one power profile that is characterised by a normalised absolute amplitude of the Fourier transform of the power profile that is greater than 0.2 at one or more spatial frequencies at or above 1.25 cycles per millimeter.

(K25) The lens of one or more of the above K examples, wherein the lens does not substantially reduce the amount of light passing through the lens.

(K26) The lens of one or more of the above K examples, wherein the amount of light passing through the lens is at least 80%, 85%, 90%, 95% or 99%.

Example Set L (L1) A multifocal lens comprising: an optical axis; an effective near addition power of at least 1 D; an optic zone associated with the optical axis with an aberration profile; wherein the aberration profile is comprised of at least two spherical aberration terms; and the multifocal lens is configured to provide minimal ghosting along a range of visual distances, including near, intermediate and far distances.

(L2) The multifocal lens of one or more of the above L examples, wherein minimal ghosting is an average rating of two or less for a group of at least 15 subjects on a 1 to 10 visual analogue scale.

(L3) The multifocal lens of one or more of the above L examples, wherein minimal ghosting is an average rating of two or less for a group of at least 15 subjects on a 1 to 10 visual analogue scale, wherein the at least 15 subjects are selected from a representative population of individuals with one or more of the following conditions: myopia, hyperopia, astigmatism and presbyopia.

(L4) The multifocal lens of one or more of the above L examples, wherein minimal ghosting is an average rating of two or less for a group of at least 15 subjects on a 1 to 10 visual analogue scale, wherein the at least 15 subjects are selected from a representative population of emmetropic non-presbyopes.

(L5) The multifocal lens of one or more of the above L examples, wherein minimal ghosting is a score of less than or equal to 2.4, 2.2, 2, 1.8, 1.6 or 1.4 on the vision analogue rating scale 1 to 10 units utilising the average visual performance of the lens in use on a sample of people needing vision correction and/or therapy, for one or more of the following: myopia, hyperopia, astigmatism, emmetropia and presbyopia.

(L6) The multifocal lens of one or more of the above L examples, wherein at least 30% of the individuals tested report no ghosting at near visual distances and far visual distances.

(L7) The multifocal lens of one or more of the above L examples, wherein at least 30% of the individuals tested report no ghosting for visual distances along a range of substantially continuous visual distances, including near, intermediate and far distances.

(L8) The multifocal lens of one or more of the above L examples, wherein at least 40% of the individuals tested report no ghosting at near visual distances and far visual distances.

(L9) The multifocal lens of one or more of the above L examples, wherein at least 40% of the individuals tested report no ghosting at near, intermediate and far distances.

(L10) The multifocal lens of one or more of the above L examples, wherein at least 40% of the individuals tested report a rating of less than two for ghosting at both near and far visual distances reported.

(L11) A multifocal lens comprising: an optical axis; the optical properties of the multifocal lens include an aberration profile associated with the optical axis; the aberration profile is comprised of a defocus term and at least two spherical aberration terms; and an effective additional power of at least 1 D; the multifocal lens is configured to provide: an average rating of at least 9 for distance vision on a visual analogue scale of 1 to 10; an average rating of at least 8.5 for intermediate vision on the visual analogue scale; an average rating of at least 7.5 for near vision on the visual analogue scale; an average rating of less than 2 for ghosting for far vision on the visual analogue scale; an average rating of less than 2 for ghosting for near vision on the visual analogue scale; and when tested on a sample of at least 15 participants who are correctable to at least 6/6 or better in both eyes and have an astigmatism of less than 1.5 D and who are selected from an affected population.

(L12) A multifocal lens comprising: an optical axis; the optical properties of the multifocal lens include an aberration profile associated with the optical axis; the aberration profile is comprised of a defocus term and at least two spherical aberration terms; and an effective additional power of at least 1 D; the multifocal lens is configured to provide: at least 60% of the individuals tested for far visual distances report a score of greater than 9 on a visual analogue scale ranging between 1 and 10; at least 50% of the individuals tested for intermediate visual distances report a score of greater than 9 on the visual analogue scale; at least 30% of the individuals tested for near visual distances report a score of greater than 9 on the visual analogue scale; below 15% of the individuals tested for ghosting at distance report a score of less than 3 on the visual analogue scale; at least 40% of the individuals tested for ghosting at either distance or near report a score of less than 2 on the visual analogue scale; and at least 25% of the individuals tested report a score of greater than 9 on the visual analogue scale for cumulative vision encompassing distance, intermediate, near, lack of ghosting at distance, and lack of ghosting at near.

(L13) The multifocal lens of one or more of the above L examples, wherein at least 30% of the individuals tested report a score of greater than 9 on the visual analogue scale for cumulative vision encompassing distance, intermediate, near, lack of ghosting at distance, and lack of ghosting at near.

(L14) The multifocal lens of one or more of the above L examples, wherein at least 35% of the individuals tested report a score of greater than 9 on the visual analogue scale for cumulative vision encompassing distance, intermediate, near, lack of ghosting at distance, and lack of ghosting at near.

(L15) The multifocal lens of one or more of the above L examples, wherein at least 40% of the individuals tested report a score of greater than 9 on the visual analogue scale for cumulative vision encompassing distance, intermediate, near, lack of ghosting at distance, and lack of ghosting at near.

(L16) The multifocal lens of one or more of the above L examples, wherein at least 55% of the individuals tested for intermediate visual distances report a score of greater than 9 on a visual analogue scale ranging between 1 and 10.

(L17) The multifocal lens of one or more of the above L examples, wherein at least 35% of the individuals tested for near visual distances report a score of greater than 9 on the visual analogue scale ranging between 1 and 10.

(L18) The multifocal lens of one or more of the above L examples, wherein at least 40% of the individuals tested for near visual distances report a score of greater than 9 on the visual analogue scale ranging between 1 and 10.

(L19) The multifocal lens of one or more of the above L examples, wherein at least 45% of the individuals tested for near visual distances report a score of greater than 9 on the visual analogue scale ranging between 1 and 10.

(L20) The multifocal lens of one or more of the above L examples, wherein at least 30% of the individuals tested report a score of greater than 9 on the visual analogue scale for cumulative vision encompassing distance, intermediate, near, lack of ghosting at distance, and lack of ghosting at near.

(L21) The multifocal lens of one or more of the above L examples, wherein at least 30% of the individuals tested report a score of greater than 9 on the visual analogue scale for cumulative vision encompassing distance, intermediate, near, lack of ghosting at distance, and lack of ghosting at near.

(L22) The multifocal lens of one or more of the above L examples, wherein at least 35% of the individuals tested report a score of greater than 9 on the visual analogue scale for cumulative vision encompassing distance, intermediate, near, lack of ghosting at distance, and lack of ghosting at near.

(L23) The multifocal lens of one or more of the above L examples, wherein at least 40% of the individuals tested report a score of greater than 9 on the visual analogue scale for cumulative vision encompassing distance, intermediate, near, lack of ghosting at distance, and lack of ghosting at near.

(L24) The multifocal lens of one or more of the above L examples, wherein at least 45% of the individuals tested report a score of greater than 9 on the visual analogue scale for cumulative vision encompassing distance, intermediate, near, lack of ghosting at distance, and lack of ghosting at near.

(L25) The multifocal lens of one or more of the above L examples, wherein at least 45% of the individuals tested for ghosting at either distance or near report a score of less than 2 on the visual analogue scale.

(L26) The multifocal lens of one or more of the above L examples, wherein at least 50% of the individuals tested for ghosting at either distance or near report a score of less than 2 on the visual analogue scale.

(L27) The multifocal lens of one or more of the above L examples, wherein at least 55% of the individuals tested for ghosting at either distance or near report a score of less than 2 on the visual analogue scale.

(L28) The multifocal lens of one or more of the above L examples, wherein at least 60% of the individuals tested for ghosting at either distance or near report a score of less than 2 on the visual analogue scale.

(L29) A multifocal lens comprising: an optical axis; the optical properties of the multifocal lens include an aberration profile associated with the optical axis; the aberration profile is comprised of a defocus term and at least two spherical aberration terms; and an effective additional power of at least 1 D; the multifocal lens is configured to provide: an average visual acuity for far visual distances of at least 0.00 on a LogMAR visual acuity chart; an average visual acuity for intermediate visual distances at least 0.00 on a LogMAR visual acuity chart; an average visual acuity for near visual distances at least 0.02 on a LogMAR visual acuity chart; an average rating of less than 2 for ghosting for far vision on the visual analogue scale; an average rating of less than 2 for ghosting for near vision on the visual analogue scale; and when tested on a sample of at least 15 participants who are correctable to at least 6/6 visual acuity or better in both eyes and have an astigmatism of less than 1.5 D.

(L30) The multifocal lens of one or more of the above L examples, wherein the multifocal lens has an effective additional power of at least 1.25 D.

(L31) The multifocal lens of one or more of the above L examples, wherein the multifocal lens has an effective additional power of at least 1.5 D.

(L32) The lens of one or more of the above L examples, wherein the lens does not substantially reduce the amount of light passing through the lens.

(L33) The lens of one or more of the above L examples, wherein the amount of light passing through the lens is at least 80%, 85%, 90%, 95% or 99%.

(L34) The multifocal lens of one or more of the above L examples, wherein the participants are selected from an affected population.

(L35) A multifocal lens comprising: an optical axis; the optical properties of the multifocal lens are configured or described based on an aberration profile associated with the optical axis; the aberration profile is comprised of a defocus term and at least two spherical aberration terms; and the multifocal lens is configured to provide: an average subjective visual rating of at least 9 for distance vision on a visual analogue scale; an average subjective visual rating of at least 9 for intermediate vision on a visual analogue scale; an average subjective visual rating of at least 7.5 for near vision on a visual analogue scale; an average subjective visual rating of less than 2 for far vision on a ghosting analogue scale; and/or an average subjective visual rating of less than 2 for near vision on a ghosting analogue scale; when tested on a sample of at least 15 participants randomly selected from an affected population.

(L36) It will be understood that the inventions disclosed and defined in this specification extends to alternative combinations of two or more of the individual features mentioned or evident from the text or drawings. These different combinations constitute various alternative aspects of the embodiments disclosed.

Example Set M (M1) A lens comprising: an optical axis; at least two surfaces; wherein the lens has a power profile, the power profile has a best fit with a $R^2>0.975$ and/or a RMSE<0.15 D when characterised upon testing by a function that uses between 40 and 80 non-zero, symmetric, Zernike power polynomial coefficients.

(M2) A lens comprising: an optical axis; at least two surfaces; wherein the lens has a power profile, the power profile has a best fit with a $R^2>0.975$ and/or a RMSE<0.15 D when characterised upon testing by a function that uses at least 14 non-zero coefficients of a Fourier series expansion.

(M3) A lens comprising: an optical axis; at least two surfaces; wherein the lens has a power profile, the power profile has a best fit with a $R^2>0.975$ and/or a RMSE<0.15 D when characterised upon testing by a function that uses at least 14 non-zero, coefficients of a Fourier series and between 40 and 80 non-zero, symmetric, Zernike power polynomial coefficients.

(M4) The lens of one or more of the M examples, wherein the lens further comprises a focal distance and an aberration profile with three or more higher order aberrations; wherein the aberration profile provides for a model eye with no aberrations, or substantially no aberrations, and an on-axis length equal to, or substantial equal to, the focal distance: a retinal image quality (RIQ) with a through focus slope that degrades in a direction of eye growth; and a RIQ of at least 0.3; wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(M5) The lens of one or more of the above M examples, wherein the lens further comprises a focal distance and an aberration profile with three or more higher order aberrations; wherein the aberration profile provides for a model eye with substantially no aberrations an on-axis length equal to, or substantially equal to, the desired focal distance; a retinal image quality (RIQ) with a through focus slope that improves in a direction of eye growth; and a RIQ of at least 0.3; wherein the RIQ is measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(M6) The lens of one or more of the above M examples, wherein the lens further comprises an aberration profile with three or more higher order aberrations; wherein the aberration profile provides: a focal distance for a C(2,0) Zernike coefficient term; a first visual Strehl Ratio within a through focus range, and the first visual Strehl Ratio that remains at or above a second visual Strehl Ratio over the through focus range that includes said focal distance, wherein the first and second visual Strehl Ratio is measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive, and wherein the first visual Strehl Ratio is at least 0.35, the second visual Strehl Ratio is at least 0.1 and the through focus range is at least 1.8 Dioptres (M7) The lens of one or more of the above M examples, wherein the aberration profile comprises at least four spherical aberration terms selected from the group C(4,0) to C(20,0).

(M8) The lens of one or more of the above M examples, wherein the aberration profile comprises at least five spherical aberration terms selected from the group C(4,0) to C(20,0).

(M9) The lens of one or more of the above M examples, wherein the aberration profile comprises at least six spherical aberration terms selected from the group C(4,0) to C(20,0).

(M10) The lens of one or more of the above M examples, wherein the aberration profile comprises at least seven spherical aberration terms selected from the group C(4,0) to C(20,0).

(M11) The lens of one or more of the above M examples, wherein the aberration profile provides an effective near additional power of at least 1 D; and wherein the lens is configured to provide a visual performance over near, intermediate and far distances that is at least substantially equivalent to the visual performance of a correctly prescribed single-vision lens at the far visual distance; and wherein the lens is configured to provide minimal ghosting at far, intermediate and near distances.

(M12) The lens of one or more of the above M examples, wherein the fitted coefficients are substantially non-zero.

Example Set P (P1) An intra-ocular lens system for an eye comprising: a first lens comprising: a first optical axis; the optical properties of the first lens are at least in part configured with a first aberration profile; the first aberration profile is comprised of a first defocus term; a second lens comprising: a second optical axis; the optical properties of the second lens are at least in part configured with a second aberration profile; the second aberration profile is comprised of a second defocus term; wherein at least one of the first lens or the second lens further comprise at least three higher order aberration terms.

(P2) The intra-ocular lens system of one or more of the above P examples, wherein the first lens and the second lens are adjacent to each other.

(P3) The intra-ocular lens system of one or more of the above P examples, wherein the first lens comprises at least three higher order aberration terms and the second lens comprises at least three higher order aberration terms.

(P4) The intra-ocular lens system of one or more of the above P examples, wherein the intra-ocular lens provides a visual performance over one or more of the following: near, intermediate and far distances, and the visual performance is at least substantially equivalent to the visual performance of a correctly prescribed single-vision intra-ocular lens at the far visual distance; and is configured to provide minimal ghosting at far, intermediate and near distances.

(P5) The intra-ocular lens system of one or more of the above P examples, wherein at least one of the first lens or the second lens comprises at least four higher order aberration terms.

(P6) The intra-ocular lens system of one or more of the above P examples, wherein at least one of the first lens or the second lens comprises at least five higher order aberration terms.

(P7) The intra-ocular lens system of one or more of the above P examples, wherein at least one of the first lens or the second lens comprises at least six higher order aberration terms.
(P8) The intra-ocular lens system of one or more of the above P examples, wherein at least one of the first lens or the second lens comprises at least seven higher order aberration terms.
(P9) The intra-ocular lens system of one or more of the above P examples, wherein the first lens comprise at least four higher order aberration terms and the second lens comprise at least four higher order aberration terms.
(P10) The intra-ocular lens system of one or more of the above P examples, wherein the first lens comprise at least five higher order aberration terms and the second lens comprise at least five higher order aberration terms.
(P11) The intra-ocular lens system of one or more of the above P examples, wherein the first lens comprise at least six higher order aberration terms and the second lens comprise at least six higher order aberration terms.
(P12) The intra-ocular lens system of one or more of the above P examples, wherein the first lens comprise at least seven higher order aberration terms and the second lens comprise at least seven higher order aberration terms.
(P13) The intra-ocular lens system of one or more of the above P examples, wherein the one or more of the higher order aberration terms are spherical aberration terms.
(P14) The intra-ocular lens system of one or more of the above P examples, wherein the higher order aberration terms are spherical aberration terms.
(P15) The intra-ocular lens system of one or more of the above P examples, wherein the at least three spherical aberration terms are selected from the group C(4, 0) to C(20, 0).
(P16) The intra-ocular lens system of one or more of the above P examples, wherein the at least four spherical aberration terms are selected from the group C(4, 0) to C(20, 0).
(P17) The intra-ocular lens system of one or more of the above P examples, wherein the at least five spherical aberration terms are selected from the group C(4, 0) to C(20, 0).
(P18) The intra-ocular lens system of one or more of the above P examples, wherein the at least six spherical aberration terms are selected from the group C(4, 0) to C(20, 0).
(P19) The intra-ocular lens system of one or more of the above P examples, wherein the at least seven spherical aberration terms selected from the group C(4, 0) to C(20, 0).
(P20) The intra-ocular lens system of one or more of the above P examples, wherein the intra-ocular system with the at least three higher aberration profile provides: a focal distance; a first visual Strehl Ratio within a through focus range, and the first visual Strehl Ratio that remains at or above a second visual Strehl Ratio over the through focus range that includes said focal distance, wherein the visual Strehl Ratio is measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive, and wherein the first visual Strehl Ratio is at least 0.3, the second visual Strehl Ratio is at least 0.1 and the through focus range is at least 1.8 Dioptres.
(P21) The intra-ocular lens system of one or more of the above P examples, wherein the intra-ocular system with the at least three higher aberrations provide: a focal distance; a first Strehl Ratio within a through focus range, and the first Strehl Ratio that remains at or above a second Strehl Ratio over the through focus range that includes said focal distance, wherein the Strehl Ratio is measured along the optical axis for at least one portion of the optic zone diameter in the range 3 mm to 5 mm, over a spatial frequency range of 0 to 30 cycles/degree inclusive, at a wavelength selected from within the range 540 nm to 590 nm inclusive, and wherein the first Strehl Ratio is at least 0.2, the second Strehl Ratio is at least 0.1 and the through focus range is at least 1.8 Dioptres.
(P22) The intra-ocular lens system of one or more of the above P examples, wherein the first visual Strehl Ratio is at least 0.28, 0.25, 0.22 or 0.20.
(P23) The intra-ocular lens system of one or more of the above P examples, wherein the second visual Strehl Ratio is at least 0.08, 0.1, 0.12, 0.14, 0.16, 0.18 or 0.2.
(P24) The intra-ocular lens system of one or more of the above P examples, wherein the through focus range is at least 2 Dioptres, 2.2 Dioptres or 2.5 Dioptres.
(P25) The intra-ocular lens system of one or more of the above P examples, wherein the end of the through focus range is the negative power end.
(P26) The intra-ocular lens system of one or more of the above P examples, wherein the end of the through focus range is the positive power end.
(P27) The intra-ocular lens system of one or more of the above P examples, wherein the first visual Strehl Ratio remains at or above the second visual Strehl Ratio over the through focus range and over a range of pupil diameters of at least 1 mm, 1.5 mm or 2 mm.
(P28) The intra-ocular lens system of one or more of the above P examples, wherein the first Strehl Ratio remains at or above the second Strehl Ratio over the through focus range and over a portion of optic zone diameters of at least 1 mm, 1.5 mm or 2 mm.
(P29) The intra-ocular lens system of one or more of the above P examples; wherein the intra-ocular lens system is configured to provide a visual performance on a presbyopic eye substantially equivalent to the visual performance of a single-vision lens on the pre-presbyopic eye; and wherein the first and the second lens have an aperture size greater than 1.5 mm.
(P30) The intra-ocular lens system of one or more of the above P examples; wherein the intra-ocular lens system is configured to provide a visual performance, along a range of substantially continuous visual distances, including near, intermediate and far distances.
(P31) The intra-ocular lens system of one or more of the above P examples; wherein the intra-ocular lens system is configured to provide minimal ghosting at far, intermediate and near distances.
(P32) The intra-ocular lens system of one or more of the above P examples; wherein the intra-ocular lens system is configured to provide near visual acuity of at least 6/6 in individuals that can achieve 6/6 visual acuity.
(P33) The intra-ocular lens system of one or more of the above P examples; wherein the intra-ocular lens system is configured to provide at least acceptable visual performance at near distances.
(P34) The intra-ocular lens system of one or more of the above P examples; wherein the intra-ocular lens system is configured to provide a visual performance, along a range of substantially continuous near visual distances, wherein the visual performance of the intra-ocular lens system is at least substantially equivalent to the visual performance of a correctly prescribed single-vision lens at the far visual distance.

(P35) The intra-ocular lens system of one or more of the above P examples; wherein the intra-ocular lens system is configured to provide a visual performance, along a range of substantially continuous visual distances, including near, intermediate and far distances, wherein the visual performance of the intra-ocular lens system is at least substantially equivalent to the visual performance of a correctly prescribed single-vision lens at the far visual distance.

Example Set Q (Q1) A multifocal lens comprising: an optical axis; at least two surfaces; wherein the lens has at least one power profile and the power profile has at least three peaks and/or three troughs along the half-chord diameter of the optic zone of the multifocal lens.

(Q2) The multifocal lens of the example Q1, wherein the at least three peaks and/or three troughs are further characterised by having an amplitude between one of the peaks and an adjacent trough that is at least 0.5 D, 1 D, 2 D or 3 D.

(Q3) The multifocal lens of the example Q1, wherein the at least three peaks and/or three troughs are further characterised by having an amplitude between one of the peaks and an adjacent trough that is at least 0.25 D, 0.5 D, 0.75 D, 1 D, 1.25 D, 1.5 D, 1.75 D, 2 D, 2.25 D, 2.5 D, 2.75 D, 3 D, 3.25 D, 3.5 D, 3.75 D or 4 D.

(Q4) The multifocal lens of the example Q1, wherein the at least three peaks and/or three troughs are further characterised by having an amplitude between one of the peaks and an adjacent trough that is between 0.5 D and 1 D, 1.25 D and 2 D, 2.25, and 3 D or 3.25 D and 4 D.

(Q5) The multifocal lens of one or more of the above Q examples, wherein the power profile starts substantially in the vicinity of a trough or a peak.

(Q6) The multifocal lens of one or more of the above Q examples, wherein the spatial separation between each peak and its and adjacent troughs of the power profile of the multifocal lens is at least 0.125 mm, 0.25 mm, 0.5 mm, 0.75 mm or 1 mm.

(Q7) The multifocal lens of one or more of the above Q examples, wherein the difference between the amplitudes of two adjacent peaks or two adjacent troughs of the power profile of the multifocal lens is between 0.5 D and 1 D, 1.25 D and 2 D, 2.25, and 3 D or 3.25 D and 4 D.

(Q5) The multifocal lens of one or more of the above Q examples, wherein the difference between the amplitudes of two adjacent peaks or two adjacent troughs of the power profile of the multifocal lens is at least 0.5 D, 1 D, 2 D or 3 D.

(Q9) The multifocal lens of one or more of the above Q examples, wherein the difference between the amplitudes of two adjacent peaks or two adjacent troughs of the power profile of the multifocal lens is at least 0.25 D, 0.5 D, 0.75 D, 1 D, 1.25 D, 1.5 D, 1.75 D, 2 D, 2.25 D, 2.5 D, 2.75 D, 3 D, 3.25 D, 3.5 D, 3.75 D or 4 D.

(Q10) The multifocal lens of one or more of the above Q examples, wherein the peaks and troughs of the power profile of the multifocal lens are generated by surface modulations of the front surface of the multifocal lens.

(Q11) The multifocal lens of one or more of the above Q examples, wherein the peaks and troughs of the power profile of the multifocal lens are generated by surface modulations of the back surface of the multifocal lens.

(Q12) The multifocal lens of one or more of the above Q examples, wherein the peaks and troughs of the power profile of the multifocal lens are generated by surface modulations of the front and the back surface of the multifocal lens.

(Q13) The multifocal lens of one or more of the above Q examples, wherein the spatial separation between each peak and its and adjacent troughs of the power profile of the multifocal lens is at least 0.125 mm, 0.25 mm, 0.5 mm, 0.75 mm or 1 mm.

Example Set R (R1) An ophthalmic lens, the lens having an optic zone, an optical axis and an aberration profile associated with the optical axis, the aberration profile having a focal power and three or more higher order aberrations, wherein the aberration profile produces a Strehl ratio with a through focus slope that degrades in the negative power end and the Strehl ratio is at least 0.2 at the focal distance; and wherein the Strehl Ratio is measured substantially along the optical axis, for at least a portion of the optic zone diameter ranging from 3 mm to 6 mm, over a spatial frequency range of 0 to 30 cycles/degree inclusive and at a wavelength selected from within the range 540 nm to 590 nm inclusive.

(R2) An ophthalmic lens, the lens having an optic zone, an optical axis and an aberration profile associated with the optical axis, the aberration profile having a focal power and three or more higher order aberrations, wherein the aberration profile produces a Strehl ratio with a through focus slope that improves in the negative power end and the Strehl ratio is at least 0.2 at the focal distance; and wherein the Strehl Ratio is measured substantially along the optical axis, for at least a portion of the optic zone diameter ranging from 3 mm to 6 mm, over a spatial frequency range of 0 to 30 cycles/degree inclusive and at a wavelength selected from within the range 540 nm to 590 nm inclusive.

(R3) An ophthalmic lens, the lens having an optic zone, an optical axis and an aberration profile associated with the optical axis, the aberration profile having a focal distance and three or more higher order aberrations; wherein the aberration profile provides: a first Strehl Ratio within a through focus range, and the first Strehl Ratio remains at or above a second Strehl Ratio over the through focus range that includes said focal distance, wherein the first and the second Strehl Ratio are calculated for at least a portion of the optic zone diameter in the range 3 mm to 5 mm, over a spatial frequency range of 0 to 30 cycles/degree inclusive, at a wavelength selected from within the range 540 nm to 590 nm inclusive, and wherein the first Strehl Ratio is at least 0.20, the second Strehl Ratio is at least 0.1 and the through focus range is at least 1.8 D.

(R4) The ophthalmic lens of the example R1, wherein the lens is configured to be used with a myopic eye.

(R5) The ophthalmic lens of the example R2, wherein the lens is configured to be used with a hyperopic eye.

(R6) The ophthalmic lens of one or more R examples, wherein the Strehl ratio at the focal distance is at least 0.22, 0.24, 0.26 or 0.28.

(R7) The ophthalmic lens of one or more R examples, wherein the first Strehl ratio is at least 0.22, 0.24, 0.26 or 0.28.

(R8) The ophthalmic lens of one or more R examples, wherein the second Strehl ratio is at least 0.08, 0.1, 0.12 or 0.14.

(R9) The ophthalmic lens of one or more R examples, wherein the through-focus range is at least 2 D, 2.2 D or 2.4 D.

(R10) The ophthalmic lens of one or more R examples, wherein the higher order aberrations comprises at least four spherical aberration terms selected from the group C(4,0) to C(20,0).

(R11) The ophthalmic lens of one or more R examples, wherein the higher order aberrations comprises at least five spherical aberration terms selected from the group C(4,0) to C(20,0).

(R12) The ophthalmic lens of one or more R examples, wherein the higher order aberrations comprises at least six spherical aberration terms selected from the group C(4,0) to C(20,0).

(R13) The ophthalmic lens of one or more R examples, wherein the higher order aberrations comprises at least seven spherical aberration terms selected from the group C(4,0) to C(20,0).

(R14) The lens of one or more of the above R examples, wherein the aberration profile provides an effective near additional power of at least 1 D; wherein the lens is configured to provide a visual performance over near, intermediate and far distances that is at least substantially equivalent to the visual performance of a correctly prescribed single-vision lens at the far visual distance; and wherein the lens is configured to provide minimal ghosting at far, intermediate and near distances.

(R15) The lens of one or more of the above R examples, wherein the Strehl ratio is characterised by $$RIQ = \frac{\int\int_{-Fmin}^{+Fmax} CSF(x, y) * \left(\text{real}\left(\left(FT\left(\left|FT\left\{A(\rho, \theta) * \exp\left[\frac{2\pi i}{\lambda} * W(\rho, \theta)\right]\right\}\right|^2\right)\right)\right)\right)}{\int\int_{-Fmin}^{+Fmax} CSF(x, y) * \left(\left(\left(FT\left(\left|FT\left\{A(\rho, \theta) * \exp\left[\frac{2\pi i}{\lambda} * Wdiff(\rho, \theta)\right]\right\}\right|^2\right)\right)\right)\right)}$$

wherein:

f specifies the tested spatial frequency, in the range of $F_{min}$ to $F_{max}$;

Fmin is 0 cycles/degree and Fmax is in the range of 5 to 30 cycles/degree;

FT denotes a 2 D Fourier transform, for example a 2 D fast Fourier transform;

$A(\rho, \theta)$ denotes the pupil amplitude function across pupil diameter, $W(\rho, \theta)$ denotes wavefront of the test case measured for i=1 to k;

wherein k is a positive integer;

$$W(\rho, \theta) = \sum_{i=1}^{k} a_i Z_i(\rho, \theta)$$

Wdiff($\rho$, $\theta$) denotes wavefront of the diffraction limited case;

$\rho$ and $\theta$ are normalised polar coordinates, where $\rho$ represents the radial coordinate and $\theta$ represents the angular coordinate or azimuth; and $\lambda$ denotes wavelength.

Example Set S (S1) A lens for an eye, the lens having a first optical axis and an aberration profile associated with the first optical axis, the aberration profile comprising: a focal distance; and higher order aberrations having at least one primary spherical aberration component C(4,0) and a secondary spherical aberration component C(6,0), wherein the aberration profile provides, for a model eye having a second optical axis, with no aberrations, or substantially no aberrations, and a length along the second optical axis equal to, or substantial equal to, the focal distance; and a retinal image quality (RIQ) of at least 0.25 wherein the RIQ is a visual Strehl Ratio measured substantially along the second optical axis for at least one pupil diameter in the range 3 mm to 6 mm.

(S2) The lens of the example S1, wherein the visual Strehl ratio is measured within a spatial frequency range from one of the following: 5 to 20 cycles/degree, 10 to 20 cycles/degree, 15 to 30 cycles/degree, 20 to 35 cycles/degree or 25 to 40 cycles/degree for a range of wavelengths selected from within the range 380 nm to 800 nm inclusive.

(S3) The lens of the example S2, wherein the range of wavelengths is selected from within the range 540 nm to 590 nm inclusive.

(S4) The lens of example S2, wherein the visual Strehl ratio is also measured over a field angle of from on-axis to the second optical axis to 5° from the second optical axis, or from on-axis to the second optical axis to 10° from the second optical axis.

(S5) The lens of example S2, wherein the visual Strehl ratio is also measured over a field angle of from on-axis to the second optical axis to 5° from the second optical axis, or from on-axis to the second optical axis to 15° from the second optical axis.

(S6) The lens of example S3, wherein the visual Strehl ratio is also measured over a field angle of from on-axis to the second optical axis to 5° from the second optical axis, or from on-axis to the second optical axis to 10° from the second optical axis.

(S7) The lens of example S3, wherein the visual Strehl ratio is also measured over a field angle of from on-axis to the second optical axis to 5° from the second optical axis, or from on-axis to the second optical axis to 15° from the second optical axis.

(S8) The lens of example S2, wherein the visual Strehl ratio is also measured over a field angle of from on-axis to the second optical axis to 10° from the second optical axis, or from on-axis to the second optical axis to 20° from the second optical axis.

(S9) The lens of example S3, wherein the visual Strehl ratio is also measured over a field angle of from on-axis to the second optical axis to 10° from the second optical axis, or from on-axis to the second optical axis to 20° from the second optical axis.

(S10) The lens of examples S1 to S9, wherein the lens is configured to provide a visual performance for the eye with a second optical axis, at at least one visual distance that is at least equivalent to the visual performance for the eye of a correctly prescribed single-vision lens at the visual distance, wherein the visual performance is visual acuity and the lens has an aperture size greater than 1.5 mm.

(S11) The lens of example S2, wherein the lens is configured to provide a visual performance for the eye with a second optical axis, at at least one visual distance that is at least equivalent to the visual performance for the eye of a correctly prescribed single-vision lens at the visual distance, wherein the visual performance is contrast sensitivity and the lens has an aperture size greater than 1.5 mm.

(S12) The lens of examples S1 to S11, wherein the visual Strehl ratio is at least 0.2, 0.22 or 0.24.

(S13) The lens of examples S1 to S12, wherein the aberration profile comprises at least four, five or six spherical aberration terms selected from the group C(4,0) to C(20,0).

Example Set T (T1) A lens for an eye, the lens comprising: a first optical axis; an aberration profile associated with the first optical axis and having a focal distance; and at least two optical surfaces, wherein the optical properties of the lens is characterised upon testing by at least the following properties: three or more higher order aberrations having one or more of the following components: a primary spherical aberration C(4,0), a secondary spherical aberration C(6,0), a tertiary spherical aberration C(8,0), a quaternary spherical aberration C(10,0), a pentanary spherical aberration C(12,0), a hexanary spherical aberration C(14,0), a heptanary spherical aberration C(16,0), an octanary spherical aberration C(18,0) and a nanonary spherical aberration C(20,0);
the aberration profile when tested on a model eye having a second optical axis, with no, or substantially no, aberrations and having a length along the second optical axis equal to, or substantial equal to, the focal distance, results in a retinal image quality (RIQ) of at least 0.25, wherein the RIQ is a visual Strehl Ratio that is measured for the model eye, and is measured substantially along the second optical axis for at least one pupil diameter in the range 3 mm to 6 mm.
(T2) The lens of the example T1, wherein the visual Strehl ratio is measured within a spatial frequency range from one of the following: 10 to 20 cycles/degree, 15 to 20 cycles/degree, 15 to 25 cycles/degree, 20 to 25 cycles/degree, 20 to 30 cycles/degree, 25 to 30 cycles/degree, 25 to 35 cycles/degree, 30 to 35 cycles/degree or 30 to 40 cycles/degree for a range of wavelengths selected from within the range 380 nm to 800 nm inclusive.
(T3) The lens of the example T2, wherein the range of wavelengths is selected from within the range 540 nm to 590 nm inclusive.
(T4) The lens of example T2, wherein the visual Strehl ratio is also measured over a field angle of from on-axis to the second optical axis to 5° from the second optical axis, or from on-axis to the second optical axis to 10° from the second optical axis.
(T5) The lens of example T2, wherein the visual Strehl ratio is also measured over a field angle of from on-axis to the second optical axis to 5° from the second optical axis, or from on-axis to the second optical axis to 15° from the second optical axis.
(T6) The lens of example T3, wherein the visual Strehl ratio is also measured over a field angle of from on-axis to the second optical axis to 5° from the second optical axis, or from on-axis to the second optical axis to 10° from the second optical axis.
(T7) The lens of example T3, wherein the visual Strehl ratio is also measured over a field angle of from on-axis to the second optical axis to 5° from the second optical axis, or from on-axis to the second optical axis to 15° from the second optical axis.
(T8) The lens of example T2, wherein the visual Strehl ratio is also measured over a field angle of from on-axis to the second optical axis to 10° from the second optical axis, or from on-axis to the second optical axis to 20° from the second optical axis.
(T9) The lens of example T3, wherein the visual Strehl ratio is also measured over a field angle of from on-axis to the second optical axis to 10° from the second optical axis, or from on-axis to the second optical axis to 20° from the second optical axis.
(T10) The lens of examples T1 to T9, wherein the lens is configured to provide a visual performance for the eye with a second optical axis, at least one visual distance that is at least equivalent to the visual performance for the eye of a correctly prescribed single-vision lens at the visual distance, wherein the visual performance is visual acuity and the lens has an aperture size greater than 1.5 mm.
(T11) The lens of example T2, wherein the lens is configured to provide a visual performance for the eye with a second optical axis, at at least one visual distance that is at least equivalent to the visual performance for the eye of a correctly prescribed single-vision lens at the visual distance, wherein the visual performance is contrast sensitivity and the lens has an aperture size greater than 1.5 mm.
(T12) The lens of examples T1 to T11, wherein the visual Strehl ratio is at least 0.2, 0.22 or 0.24.

Example Set V (V1) A contact lens comprising: at least one carrier portion and at least one optic zone portion; the optic zone comprises a first optical axis and an aberration profile associated with the first optical axis; the aberration profile comprises: a focal distance and at least three higher order aberrations with at least one of a primary spherical aberration component C(4,0) and a secondary spherical aberration component C(6,0), wherein the aberration profile provides, for a model eye, a retinal image quality (RIQ) with a through focus slope that degrades in a direction of eye growth and an RIQ of at least 0.3; wherein the model eye has a second optical axis, no aberrations, or substantially no aberrations and has an on-axis length equal to, or substantially equal to, the focal distance; wherein the RIQ is a visual Strehl Ratio and is measured substantially along the second optical axis for at least one pupil diameter in the range 3 mm to 6 mm, over a spatial frequency range of 0 to 30 cycles/degree inclusive and for a range of wavelengths from 380 nm to 800 nm inclusive; wherein the lens has a centroid of the at least one carrier portion and a centroid of the at least one optic zone portion; and wherein the centroid of the optic zone is spaced apart from the centroid of the carrier location by at least 0.1 mm, 0.3 mm, 0.5 mm or 0.7 mm; and/or the first optical axis is spaced apart from the optic zone centroid by at least 0.1 mm, 0.3 mm, 0.5 mm or 0.7 mm; and/or the first optical axis is spaced apart from the carrier centroid location by at least 0.1 mm, 0.3 mm, 0.5 mm or 0.7 mm.
(V2) The lens of example V1, wherein the lens is a multi-focal lens and has an effective near additional power of at least +1 D.
(V3) The lens of example V1 to V2, wherein the lens is configured to provide a visual performance over near, intermediate and far distances that is at least substantially equivalent to the visual performance of a correctly prescribed single-vision lens at the far visual distance.
(V4) The lens of example V1 to V3, wherein the lens is configured to provide minimal ghosting at far, intermediate and near distances.
(V5) The lens of examples V1 to V4, wherein the aberration profile comprises at least four, five or six spherical aberration terms selected from the group C(4,0) to C(20,0).

Example Set X (X1) A lens comprising: an optical axis; an optic zone; and a power profile associated with the optical axis; wherein the power profile has a transition between a maxima and a minima, and the maxima is within 0.2 mm of the centre of the optic zone and the minima is less than or equal to 0.3, 0.6, 0.9 or 1 mm distance from the maxima; wherein the amplitude of the transition between the maxima and the minima is at least 2.5 D, 4 D, 5 D, or 6 D.

(X2) The lens of one of the claims X, wherein the transition between the maxima and the minima is one or more of the following: continuous, discontinuous, monotonic and non-monotonic.

(X3) The lens of one or more of the above X examples, wherein the lens further comprises a focal distance; an aberration profile with three or more higher order aberrations; wherein the aberration profile provides, for a model eye with no aberrations, or substantially no aberrations, and an on-axis length equal to, or substantial equal to, the focal distance: a retinal image quality (RIQ) with a through focus slope that degrades in a direction of eye growth; and a RIQ of at least 0.3 wherein the RIQ is visual Strehl Ratio measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(X4) The lens of one or more of the above X examples, wherein the lens further comprises a focal distance; an aberration profile with three or more higher order aberrations; wherein the aberration profile provides, for a model eye with substantially no aberrations an on-axis length equal to, or substantially equal to, the desired focal distance; a retinal image quality (RIQ) with a through focus slope that improves in a direction of eye growth; and a RIQ of at least 0.3; wherein the RIQ is measured substantially along the optical axis for at least one pupil diameter in the range 3 mm to 6 mm, over a spatial frequency range of 0 to 30 cycles/degree inclusive and at a wavelength selected from within the range 540 nm to 590 nm inclusive.

(X5) The lens of one or more of the above X examples, wherein the lens further comprises an aberration profile with three or more higher order aberrations; wherein the aberration profile provides: a focal distance for a C(2,0) Zernike coefficient term; a peak visual Strehl Ratio ('first visual Strehl Ratio') within a through focus range, and a visual Strehl Ratio that remains at or above a second visual Strehl Ratio over the through focus range that includes said focal distance, wherein the visual Strehl Ratio is measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive, and wherein the first visual Strehl Ratio is at least 0.35, the second visual Strehl Ratio is at least 0.1 and the through focus range is at least 1.8 Dioptres (X6) The lens of one or more of the above X examples, wherein the aberration profile comprises at least four spherical aberration terms selected from the group C(4,0) to C(20,0).

(X7) The lens of one or more of the above X examples, wherein the aberration profile comprises at least five spherical aberration terms selected from the group C(4,0) to C(20,0).

(X8) The lens of one or more of the above X examples, wherein the aberration profile comprises at least six spherical aberration terms selected from the group C(4,0) to C(20,0).

(X9) The lens of one or more of the above X examples, wherein the aberration profile comprises at least seven spherical aberration terms selected from the group C(4,0) to C(20,0).

(X10) The lens of one or more of the above X examples, wherein the aberration profile provides an effective near additional power of at least 1 D; and wherein the lens is configured to provide a visual performance over intermediate and far distances that is at least substantially equivalent to the visual performance of a correctly prescribed single-vision lens at the far visual distance; and wherein the lens is configured to provide minimal ghosting at far, intermediate and near distances.

APPENDIX A

Example combinations of spherical aberration

| Combination | C (2,0) | C(4,0) | C(6,0) | C(8,0) | C(10,0) | C(12,0) | C(14,0) | C(16,0) | C(18,0) | C(20,0) |
|---|---|---|---|---|---|---|---|---|---|---|
| No Aberr | 0 | 0 | 0 | 0 | 0 | 0 | 0 | 0 | 0 | 0 |
| 1 | 0 | −0.125 | −0.075 | 0.000 | 0.000 | 0.000 | 0.000 | 0.000 | 0.000 | 0.000 |
| 2 | 0 | −0.100 | −0.075 | 0.000 | 0.000 | 0.000 | 0.000 | 0.000 | 0.000 | 0.000 |
| 3 | 0 | −0.100 | −0.025 | 0.025 | 0.000 | 0.000 | 0.000 | 0.000 | 0.000 | 0.000 |
| 4 | 0 | −0.100 | 0.025 | 0.075 | 0.025 | 0.025 | 0.025 | 0.025 | 0.025 | 0.000 |
| 5 | 0 | −0.075 | −0.075 | 0.000 | 0.000 | 0.000 | 0.000 | 0.000 | 0.000 | 0.000 |
| 6 | 0 | −0.075 | −0.025 | 0.050 | 0.000 | −0.025 | −0.025 | 0.000 | 0.025 | 0.000 |
| 7 | 0 | −0.050 | −0.075 | 0.000 | 0.000 | 0.000 | 0.000 | 0.000 | 0.000 | 0.000 |
| 8 | 0 | −0.050 | −0.050 | 0.050 | 0.025 | 0.000 | 0.000 | 0.000 | 0.000 | 0.000 |
| 9 | 0 | −0.050 | −0.025 | 0.050 | 0.000 | −0.025 | −0.025 | 0.000 | 0.025 | 0.025 |
| 10 | 0 | −0.025 | −0.075 | 0.000 | 0.000 | 0.000 | 0.000 | 0.000 | 0.000 | 0.000 |
| 11 | 0 | −0.025 | −0.025 | 0.050 | 0.025 | −0.025 | −0.025 | 0.000 | 0.025 | 0.025 |
| 12 | 0 | 0.000 | −0.075 | 0.000 | 0.000 | 0.000 | 0.000 | 0.000 | 0.000 | 0.000 |
| 13 | 0 | 0.000 | −0.075 | 0.050 | 0.025 | 0.000 | 0.025 | 0.000 | −0.025 | 0.000 |
| 14 | 0 | 0.000 | −0.050 | 0.000 | −0.025 | −0.025 | 0.025 | 0.025 | −0.025 | −0.025 |
| 15 | 0 | 0.000 | −0.050 | 0.050 | 0.025 | −0.025 | −0.025 | −0.025 | 0.000 | 0.025 |
| 16 | 0 | 0.000 | −0.025 | 0.075 | 0.000 | −0.025 | 0.025 | 0.025 | 0.025 | 0.025 |
| 17 | 0 | 0.025 | −0.075 | 0.000 | −0.025 | −0.025 | 0.025 | 0.025 | 0.000 | 0.000 |
| 18 | 0 | 0.025 | −0.075 | 0.000 | 0.000 | 0.000 | 0.000 | 0.000 | 0.000 | 0.000 |
| 19 | 0 | 0.025 | −0.075 | 0.025 | 0.025 | −0.025 | −0.025 | −0.025 | 0.000 | 0.025 |
| 20 | 0 | 0.025 | −0.075 | 0.050 | 0.025 | −0.025 | −0.025 | −0.025 | 0.000 | 0.000 |
| 21 | 0 | 0.025 | −0.050 | 0.000 | 0.000 | 0.000 | 0.000 | 0.000 | 0.000 | 0.000 |
| 22 | 0 | 0.025 | −0.050 | 0.050 | 0.000 | −0.025 | −0.025 | 0.000 | 0.025 | 0.025 |
| 23 | 0 | 0.025 | −0.050 | 0.050 | 0.025 | 0.000 | 0.000 | −0.025 | −0.025 | 0.000 |
| 24 | 0 | 0.025 | −0.025 | 0.075 | 0.000 | −0.025 | 0.025 | 0.025 | 0.025 | 0.025 |
| 25 | 0 | 0.050 | −0.075 | 0.000 | 0.000 | −0.025 | 0.000 | 0.000 | 0.025 | 0.025 |

APPENDIX A-continued

Example combinations of spherical aberration

| Combination | C(2,0) | C(4,0) | C(6,0) | C(8,0) | C(10,0) | C(12,0) | C(14,0) | C(16,0) | C(18,0) | C(20,0) |
|---|---|---|---|---|---|---|---|---|---|---|
| 26 | 0 | 0.050 | −0.075 | 0.000 | 0.000 | 0.000 | 0.000 | 0.000 | 0.000 | 0.000 |
| 27 | 0 | 0.050 | −0.075 | 0.025 | 0.025 | −0.025 | 0.000 | 0.000 | −0.025 | 0.000 |
| 28 | 0 | 0.050 | −0.075 | 0.025 | 0.025 | −0.025 | 0.000 | 0.000 | 0.025 | 0.025 |
| 29 | 0 | 0.050 | −0.075 | 0.025 | 0.025 | 0.000 | 0.000 | −0.025 | −0.025 | 0.000 |
| 30 | 0 | 0.050 | −0.075 | 0.025 | 0.025 | 0.000 | 0.025 | 0.025 | 0.025 | 0.025 |
| 31 | 0 | 0.050 | −0.050 | 0.000 | 0.000 | 0.000 | 0.000 | 0.000 | 0.000 | 0.000 |
| 32 | 0 | 0.050 | −0.025 | −0.025 | −0.025 | −0.025 | 0.025 | 0.025 | 0.000 | −0.025 |
| 33 | 0 | 0.050 | −0.025 | 0.075 | 0.025 | −0.025 | 0.025 | 0.025 | 0.025 | 0.025 |
| 34 | 0 | 0.075 | 0.050 | −0.025 | −0.025 | 0.000 | 0.000 | 0.000 | 0.000 | 0.000 |
| 35 | 0 | 0.075 | −0.075 | −0.025 | −0.025 | 0.000 | 0.025 | 0.000 | 0.000 | 0.000 |
| 36 | 0 | 0.075 | −0.075 | −0.025 | 0.000 | 0.000 | 0.025 | 0.025 | 0.000 | 0.000 |
| 37 | 0 | 0.075 | −0.075 | 0.000 | 0.000 | −0.025 | −0.025 | 0.000 | 0.000 | 0.000 |
| 38 | 0 | 0.075 | −0.075 | 0.000 | 0.000 | −0.025 | 0.000 | 0.000 | 0.000 | 0.000 |
| 39 | 0 | 0.075 | −0.075 | 0.000 | 0.000 | 0.000 | 0.000 | 0.000 | 0.000 | 0.000 |
| 40 | 0 | 0.075 | −0.075 | 0.000 | 0.025 | −0.025 | −0.025 | 0.000 | 0.000 | 0.000 |
| 41 | 0 | 0.075 | −0.075 | 0.000 | 0.025 | −0.025 | 0.000 | 0.000 | 0.000 | 0.000 |
| 42 | 0 | 0.075 | −0.050 | −0.050 | −0.025 | 0.000 | 0.000 | 0.025 | 0.000 | −0.025 |
| 43 | 0 | 0.075 | −0.050 | 0.000 | 0.000 | 0.000 | 0.000 | 0.000 | 0.000 | 0.000 |
| 44 | 0 | 0.075 | −0.025 | 0.000 | 0.000 | 0.000 | 0.000 | 0.000 | 0.000 | 0.000 |
| 45 | 0 | 0.075 | −0.025 | 0.050 | 0.000 | −0.025 | 0.025 | 0.025 | 0.000 | 0.000 |
| 46 | 0 | 0.100 | −0.075 | −0.050 | −0.025 | 0.000 | 0.025 | 0.025 | −0.025 | −0.025 |
| 47 | 0 | 0.100 | −0.075 | −0.050 | 0.000 | 0.000 | 0.025 | 0.025 | −0.025 | −0.025 |
| 48 | 0 | 0.100 | −0.075 | −0.025 | 0.000 | 0.000 | 0.000 | 0.000 | 0.000 | 0.000 |
| 49 | 0 | 0.100 | −0.075 | −0.025 | 0.000 | 0.000 | 0.025 | 0.000 | 0.000 | 0.000 |
| 50 | 0 | 0.100 | −0.075 | 0.000 | 0.000 | 0.000 | 0.000 | 0.000 | 0.000 | 0.000 |
| 51 | 0 | 0.100 | −0.075 | 0.000 | 0.025 | −0.025 | −0.025 | 0.025 | 0.025 | 0.000 |
| 52 | 0 | 0.100 | −0.050 | −0.050 | −0.025 | 0.000 | −0.025 | −0.025 | −0.025 | −0.025 |
| 53 | 0 | 0.100 | −0.050 | −0.025 | −0.025 | −0.025 | 0.025 | 0.000 | −0.025 | 0.000 |
| 54 | 0 | 0.100 | −0.050 | 0.000 | 0.000 | 0.000 | 0.000 | 0.000 | 0.000 | 0.000 |
| 55 | 0 | 0.100 | −0.050 | 0.000 | 0.000 | 0.000 | 0.025 | 0.025 | 0.000 | 0.000 |
| 56 | 0 | 0.100 | −0.050 | 0.000 | 0.000 | 0.000 | 0.025 | 0.025 | 0.025 | 0.025 |
| 57 | 0 | 0.100 | −0.050 | 0.000 | 0.025 | 0.025 | 0.000 | −0.025 | −0.025 | −0.025 |
| 58 | 0 | 0.100 | −0.025 | 0.000 | 0.000 | 0.000 | 0.000 | 0.000 | 0.000 | 0.000 |
| 59 | 0 | 0.100 | −0.025 | 0.000 | 0.025 | 0.025 | 0.000 | −0.025 | −0.025 | −0.025 |
| 60 | 0 | 0.100 | −0.025 | 0.025 | −0.025 | −0.025 | 0.025 | 0.025 | 0.000 | 0.000 |
| 61 | 0 | 0.100 | 0.000 | 0.000 | −0.025 | 0.000 | 0.025 | 0.000 | 0.000 | 0.025 |
| 62 | 0 | 0.100 | 0.000 | 0.000 | 0.000 | 0.000 | 0.000 | 0.000 | 0.000 | 0.000 |
| 63 | 0 | 0.100 | 0.000 | 0.050 | 0.000 | −0.025 | 0.025 | 0.000 | −0.025 | 0.000 |
| 64 | 0 | 0.125 | −0.075 | −0.075 | −0.025 | 0.000 | 0.025 | 0.025 | −0.025 | −0.025 |
| 65 | 0 | 0.125 | −0.075 | −0.075 | 0.000 | 0.000 | 0.000 | 0.000 | 0.000 | 0.000 |
| 66 | 0 | 0.125 | −0.075 | 0.000 | 0.000 | 0.000 | 0.000 | 0.000 | 0.000 | 0.000 |
| 67 | 0 | 0.125 | −0.050 | −0.025 | −0.025 | −0.025 | 0.000 | 0.000 | 0.000 | 0.000 |
| 68 | 0 | 0.125 | −0.050 | −0.025 | −0.025 | −0.025 | 0.025 | 0.000 | 0.000 | 0.000 |
| 69 | 0 | 0.125 | −0.050 | −0.025 | 0.000 | 0.000 | 0.025 | 0.025 | 0.000 | 0.000 |
| 70 | 0 | 0.125 | −0.050 | 0.000 | 0.000 | 0.000 | 0.000 | 0.000 | 0.000 | 0.000 |
| 71 | 0 | 0.125 | −0.050 | 0.000 | 0.025 | 0.025 | 0.025 | 0.000 | 0.000 | 0.000 |
| 72 | 0 | 0.125 | −0.025 | 0.000 | −0.025 | −0.025 | 0.000 | 0.000 | −0.025 | −0.025 |
| 73 | 0 | 0.125 | −0.025 | 0.000 | 0.000 | 0.000 | 0.000 | 0.000 | 0.000 | 0.000 |
| 74 | 0 | 0.125 | −0.025 | 0.025 | 0.000 | −0.025 | 0.000 | 0.000 | 0.000 | 0.000 |
| 75 | 0 | 0.125 | −0.025 | 0.025 | 0.000 | 0.000 | 0.025 | 0.025 | 0.000 | 0.000 |
| 76 | 0 | 0.125 | −0.025 | 0.025 | 0.025 | 0.025 | −0.025 | 0.025 | 0.025 | 0.025 |
| 77 | 0 | 0.125 | 0.000 | 0.000 | 0.000 | 0.000 | 0.000 | 0.000 | 0.000 | 0.000 |
| 78 | 0 | 0.125 | 0.000 | 0.025 | −0.025 | −0.025 | 0.025 | 0.000 | −0.025 | −0.025 |

APPENDIX B

Through focus RIQ for combinations of spherical aberration in Appendix A

| Combination | −1.50 | −1.25 | −1.00 | −0.75 | −0.50 | −0.25 | 0.00 | 0.25 | 0.50 | 0.75 | 1.00 | 1.25 | 1.50 |
|---|---|---|---|---|---|---|---|---|---|---|---|---|---|
| No Aberr | 0.024 | 0.040 | 0.073 | 0.148 | 0.307 | 0.709 | 1.000 | 0.709 | 0.307 | 0.148 | 0.073 | 0.040 | 0.024 |
| 1 | 0.089 | 0.135 | 0.192 | 0.243 | 0.304 | 0.434 | 0.606 | 0.667 | 0.542 | 0.329 | 0.152 | 0.056 | 0.021 |
| 2 | 0.084 | 0.131 | 0.196 | 0.265 | 0.346 | 0.482 | 0.643 | 0.676 | 0.514 | 0.281 | 0.113 | 0.036 | 0.012 |
| 3 | 0.028 | 0.053 | 0.115 | 0.258 | 0.473 | 0.628 | 0.648 | 0.595 | 0.479 | 0.310 | 0.161 | 0.071 | 0.028 |
| 4 | 0.039 | 0.067 | 0.153 | 0.313 | 0.458 | 0.493 | 0.477 | 0.492 | 0.470 | 0.361 | 0.220 | 0.112 | 0.052 |
| 5 | 0.082 | 0.128 | 0.198 | 0.281 | 0.384 | 0.532 | 0.675 | 0.675 | 0.481 | 0.236 | 0.080 | 0.021 | 0.006 |
| 6 | 0.100 | 0.129 | 0.157 | 0.246 | 0.402 | 0.514 | 0.542 | 0.559 | 0.515 | 0.338 | 0.146 | 0.051 | 0.024 |
| 7 | 0.083 | 0.129 | 0.199 | 0.289 | 0.412 | 0.576 | 0.704 | 0.666 | 0.445 | 0.196 | 0.054 | 0.010 | 0.002 |
| 8 | 0.069 | 0.105 | 0.176 | 0.305 | 0.479 | 0.603 | 0.614 | 0.565 | 0.454 | 0.262 | 0.099 | 0.030 | 0.010 |
| 9 | 0.124 | 0.168 | 0.181 | 0.212 | 0.338 | 0.502 | 0.579 | 0.579 | 0.508 | 0.319 | 0.117 | 0.027 | 0.016 |
| 10 | 0.089 | 0.133 | 0.201 | 0.293 | 0.425 | 0.607 | 0.730 | 0.656 | 0.409 | 0.161 | 0.034 | 0.003 | 0.001 |
| 11 | 0.104 | 0.159 | 0.199 | 0.247 | 0.359 | 0.508 | 0.581 | 0.570 | 0.502 | 0.326 | 0.125 | 0.035 | 0.023 |
| 12 | 0.098 | 0.141 | 0.206 | 0.293 | 0.423 | 0.618 | 0.749 | 0.649 | 0.377 | 0.134 | 0.021 | 0.001 | 0.002 |

APPENDIX B-continued

Through focus RIQ for combinations of spherical aberration in Appendix A

| Combination | −1.50 | −1.25 | −1.00 | −0.75 | −0.50 | −0.25 | 0.00 | 0.25 | 0.50 | 0.75 | 1.00 | 1.25 | 1.50 |
| --- | --- | --- | --- | --- | --- | --- | --- | --- | --- | --- | --- | --- | --- |
| 13 | 0.157 | 0.206 | 0.250 | 0.282 | 0.354 | 0.482 | 0.542 | 0.480 | 0.364 | 0.232 | 0.120 | 0.060 | 0.032 |
| 14 | 0.092 | 0.184 | 0.314 | 0.371 | 0.390 | 0.505 | 0.592 | 0.481 | 0.297 | 0.204 | 0.161 | 0.097 | 0.041 |
| 15 | 0.153 | 0.215 | 0.247 | 0.261 | 0.324 | 0.453 | 0.533 | 0.514 | 0.447 | 0.307 | 0.129 | 0.038 | 0.025 |
| 16 | 0.152 | 0.207 | 0.237 | 0.260 | 0.363 | 0.509 | 0.531 | 0.442 | 0.363 | 0.265 | 0.137 | 0.056 | 0.029 |
| 17 | 0.158 | 0.218 | 0.286 | 0.308 | 0.324 | 0.457 | 0.611 | 0.564 | 0.352 | 0.181 | 0.101 | 0.048 | 0.011 |
| 18 | 0.111 | 0.152 | 0.213 | 0.293 | 0.410 | 0.604 | 0.754 | 0.650 | 0.356 | 0.113 | 0.013 | 0.004 | 0.004 |
| 19 | 0.168 | 0.205 | 0.235 | 0.285 | 0.367 | 0.476 | 0.539 | 0.482 | 0.365 | 0.253 | 0.138 | 0.052 | 0.023 |
| 20 | 0.161 | 0.202 | 0.237 | 0.282 | 0.361 | 0.468 | 0.518 | 0.465 | 0.378 | 0.267 | 0.124 | 0.038 | 0.019 |
| 21 | 0.081 | 0.116 | 0.174 | 0.255 | 0.405 | 0.680 | 0.878 | 0.715 | 0.342 | 0.093 | 0.015 | 0.002 | 0.001 |
| 22 | 0.151 | 0.212 | 0.253 | 0.256 | 0.304 | 0.463 | 0.584 | 0.514 | 0.360 | 0.223 | 0.095 | 0.016 | 0.003 |
| 23 | 0.153 | 0.205 | 0.242 | 0.255 | 0.316 | 0.493 | 0.638 | 0.563 | 0.363 | 0.201 | 0.096 | 0.041 | 0.023 |
| 24 | 0.159 | 0.214 | 0.250 | 0.256 | 0.322 | 0.476 | 0.548 | 0.465 | 0.357 | 0.251 | 0.127 | 0.046 | 0.021 |
| 25 | 0.158 | 0.201 | 0.231 | 0.253 | 0.312 | 0.472 | 0.648 | 0.612 | 0.359 | 0.141 | 0.075 | 0.067 | 0.043 |
| 26 | 0.126 | 0.166 | 0.222 | 0.293 | 0.388 | 0.567 | 0.739 | 0.657 | 0.350 | 0.099 | 0.008 | 0.005 | 0.006 |
| 27 | 0.161 | 0.203 | 0.236 | 0.253 | 0.304 | 0.475 | 0.648 | 0.593 | 0.370 | 0.190 | 0.091 | 0.039 | 0.015 |
| 28 | 0.164 | 0.201 | 0.226 | 0.253 | 0.323 | 0.472 | 0.604 | 0.547 | 0.352 | 0.197 | 0.112 | 0.058 | 0.031 |
| 29 | 0.171 | 0.206 | 0.240 | 0.274 | 0.328 | 0.463 | 0.608 | 0.564 | 0.362 | 0.193 | 0.094 | 0.036 | 0.012 |
| 30 | 0.171 | 0.206 | 0.231 | 0.259 | 0.326 | 0.475 | 0.626 | 0.589 | 0.363 | 0.150 | 0.057 | 0.031 | 0.015 |
| 31 | 0.097 | 0.135 | 0.192 | 0.268 | 0.389 | 0.628 | 0.848 | 0.728 | 0.347 | 0.078 | 0.006 | 0.001 | 0.003 |
| 32 | 0.074 | 0.134 | 0.238 | 0.370 | 0.462 | 0.553 | 0.624 | 0.516 | 0.286 | 0.156 | 0.129 | 0.096 | 0.052 |
| 33 | 0.159 | 0.212 | 0.245 | 0.251 | 0.305 | 0.461 | 0.564 | 0.496 | 0.375 | 0.264 | 0.138 | 0.048 | 0.019 |
| 34 | 0.022 | 0.044 | 0.114 | 0.279 | 0.496 | 0.623 | 0.634 | 0.591 | 0.479 | 0.310 | 0.160 | 0.069 | 0.030 |
| 35 | 0.161 | 0.200 | 0.244 | 0.318 | 0.404 | 0.493 | 0.584 | 0.550 | 0.352 | 0.162 | 0.072 | 0.032 | 0.009 |
| 36 | 0.151 | 0.217 | 0.289 | 0.353 | 0.390 | 0.455 | 0.568 | 0.563 | 0.373 | 0.173 | 0.080 | 0.042 | 0.013 |
| 37 | 0.151 | 0.206 | 0.264 | 0.304 | 0.336 | 0.450 | 0.630 | 0.628 | 0.372 | 0.127 | 0.038 | 0.014 | 0.004 |
| 38 | 0.164 | 0.211 | 0.254 | 0.279 | 0.309 | 0.455 | 0.681 | 0.686 | 0.400 | 0.126 | 0.027 | 0.011 | 0.005 |
| 39 | 0.142 | 0.181 | 0.232 | 0.292 | 0.364 | 0.512 | 0.699 | 0.664 | 0.364 | 0.097 | 0.005 | 0.006 | 0.008 |
| 40 | 0.155 | 0.222 | 0.286 | 0.331 | 0.369 | 0.465 | 0.601 | 0.579 | 0.365 | 0.172 | 0.085 | 0.037 | 0.008 |
| 41 | 0.151 | 0.204 | 0.251 | 0.282 | 0.320 | 0.459 | 0.661 | 0.659 | 0.405 | 0.163 | 0.062 | 0.031 | 0.018 |
| 42 | 0.118 | 0.171 | 0.252 | 0.367 | 0.460 | 0.506 | 0.539 | 0.496 | 0.329 | 0.166 | 0.098 | 0.069 | 0.035 |
| 43 | 0.115 | 0.156 | 0.212 | 0.283 | 0.376 | 0.563 | 0.784 | 0.729 | 0.371 | 0.080 | 0.001 | 0.003 | 0.005 |
| 44 | 0.086 | 0.126 | 0.186 | 0.272 | 0.392 | 0.602 | 0.826 | 0.761 | 0.391 | 0.094 | 0.012 | 0.005 | 0.001 |
| 45 | 0.153 | 0.203 | 0.257 | 0.284 | 0.316 | 0.452 | 0.609 | 0.566 | 0.367 | 0.207 | 0.104 | 0.035 | 0.011 |
| 46 | 0.180 | 0.256 | 0.316 | 0.408 | 0.497 | 0.493 | 0.427 | 0.336 | 0.212 | 0.122 | 0.109 | 0.104 | 0.064 |
| 47 | 0.171 | 0.253 | 0.325 | 0.407 | 0.458 | 0.443 | 0.429 | 0.400 | 0.289 | 0.173 | 0.131 | 0.112 | 0.066 |
| 48 | 0.151 | 0.211 | 0.281 | 0.358 | 0.417 | 0.470 | 0.566 | 0.585 | 0.397 | 0.155 | 0.035 | 0.004 | 0.004 |
| 49 | 0.155 | 0.203 | 0.255 | 0.330 | 0.407 | 0.472 | 0.560 | 0.561 | 0.375 | 0.168 | 0.075 | 0.042 | 0.018 |
| 50 | 0.159 | 0.197 | 0.240 | 0.289 | 0.339 | 0.449 | 0.636 | 0.663 | 0.396 | 0.110 | 0.005 | 0.007 | 0.009 |
| 51 | 0.185 | 0.272 | 0.360 | 0.392 | 0.353 | 0.357 | 0.461 | 0.486 | 0.330 | 0.168 | 0.108 | 0.077 | 0.037 |
| 52 | 0.096 | 0.141 | 0.222 | 0.351 | 0.472 | 0.508 | 0.515 | 0.524 | 0.412 | 0.196 | 0.057 | 0.024 | 0.021 |
| 53 | 0.158 | 0.206 | 0.242 | 0.306 | 0.392 | 0.462 | 0.534 | 0.533 | 0.381 | 0.208 | 0.116 | 0.063 | 0.025 |
| 54 | 0.134 | 0.177 | 0.231 | 0.296 | 0.365 | 0.494 | 0.694 | 0.710 | 0.409 | 0.101 | 0.001 | 0.004 | 0.007 |
| 55 | 0.152 | 0.204 | 0.259 | 0.316 | 0.366 | 0.464 | 0.626 | 0.630 | 0.369 | 0.110 | 0.031 | 0.028 | 0.016 |
| 56 | 0.161 | 0.207 | 0.253 | 0.290 | 0.338 | 0.458 | 0.619 | 0.607 | 0.360 | 0.117 | 0.033 | 0.027 | 0.022 |
| 57 | 0.143 | 0.197 | 0.268 | 0.357 | 0.426 | 0.471 | 0.522 | 0.486 | 0.298 | 0.128 | 0.086 | 0.078 | 0.044 |
| 58 | 0.105 | 0.151 | 0.214 | 0.299 | 0.398 | 0.542 | 0.721 | 0.717 | 0.423 | 0.123 | 0.017 | 0.003 | 0.003 |
| 59 | 0.110 | 0.169 | 0.259 | 0.371 | 0.457 | 0.518 | 0.571 | 0.515 | 0.302 | 0.113 | 0.068 | 0.073 | 0.053 |
| 60 | 0.158 | 0.202 | 0.246 | 0.308 | 0.374 | 0.455 | 0.553 | 0.536 | 0.366 | 0.196 | 0.093 | 0.030 | 0.008 |
| 61 | 0.118 | 0.160 | 0.205 | 0.284 | 0.407 | 0.520 | 0.588 | 0.569 | 0.421 | 0.224 | 0.088 | 0.026 | 0.007 |
| 62 | 0.076 | 0.119 | 0.189 | 0.297 | 0.437 | 0.593 | 0.722 | 0.683 | 0.425 | 0.165 | 0.053 | 0.021 | 0.006 |
| 63 | 0.156 | 0.207 | 0.243 | 0.258 | 0.318 | 0.460 | 0.563 | 0.511 | 0.364 | 0.236 | 0.140 | 0.075 | 0.044 |
| 64 | 0.194 | 0.280 | 0.335 | 0.402 | 0.502 | 0.516 | 0.402 | 0.272 | 0.179 | 0.124 | 0.113 | 0.113 | 0.086 |
| 65 | 0.155 | 0.251 | 0.353 | 0.432 | 0.463 | 0.418 | 0.355 | 0.368 | 0.387 | 0.303 | 0.163 | 0.062 | 0.021 |
| 66 | 0.175 | 0.210 | 0.246 | 0.284 | 0.316 | 0.385 | 0.554 | 0.643 | 0.439 | 0.141 | 0.009 | 0.008 | 0.010 |
| 67 | 0.163 | 0.214 | 0.265 | 0.328 | 0.402 | 0.466 | 0.529 | 0.536 | 0.389 | 0.186 | 0.072 | 0.031 | 0.009 |
| 68 | 0.163 | 0.201 | 0.232 | 0.294 | 0.397 | 0.476 | 0.522 | 0.506 | 0.365 | 0.192 | 0.103 | 0.062 | 0.031 |
| 69 | 0.157 | 0.220 | 0.281 | 0.355 | 0.428 | 0.468 | 0.519 | 0.533 | 0.375 | 0.160 | 0.065 | 0.050 | 0.032 |
| 70 | 0.153 | 0.198 | 0.248 | 0.304 | 0.354 | 0.431 | 0.590 | 0.664 | 0.449 | 0.143 | 0.010 | 0.005 | 0.008 |
| 71 | 0.153 | 0.201 | 0.261 | 0.343 | 0.412 | 0.458 | 0.535 | 0.552 | 0.372 | 0.143 | 0.051 | 0.040 | 0.024 |
| 72 | 0.151 | 0.207 | 0.259 | 0.316 | 0.391 | 0.466 | 0.517 | 0.487 | 0.353 | 0.210 | 0.114 | 0.042 | 0.006 |
| 73 | 0.126 | 0.176 | 0.241 | 0.320 | 0.401 | 0.489 | 0.609 | 0.645 | 0.446 | 0.168 | 0.033 | 0.005 | 0.004 |
| 74 | 0.161 | 0.203 | 0.237 | 0.270 | 0.333 | 0.456 | 0.608 | 0.618 | 0.406 | 0.179 | 0.081 | 0.038 | 0.010 |
| 75 | 0.159 | 0.202 | 0.243 | 0.289 | 0.349 | 0.456 | 0.592 | 0.584 | 0.367 | 0.145 | 0.046 | 0.010 | 0.003 |
| 76 | 0.076 | 0.148 | 0.260 | 0.351 | 0.375 | 0.411 | 0.515 | 0.518 | 0.321 | 0.134 | 0.082 | 0.053 | 0.008 |
| 77 | 0.096 | 0.147 | 0.224 | 0.329 | 0.451 | 0.554 | 0.619 | 0.595 | 0.422 | 0.202 | 0.074 | 0.027 | 0.007 |
| 78 | 0.160 | 0.216 | 0.272 | 0.318 | 0.372 | 0.434 | 0.455 | 0.411 | 0.344 | 0.276 | 0.169 | 0.060 | 0.018 |

APPENDIX C

| Combination | C (2,0) | C(4,0) | C(6,0) | C(8,0) | C(10,0) | C(12,0) | C(14,0) | C(16,0) | C(18,0) | C(20,0) |
|---|---|---|---|---|---|---|---|---|---|---|
| No Aberr | 0 | 0 | 0 | 0 | 0 | 0 | 0 | 0 | 0 | 0 |
| 101 | 0 | −0.125 | −0.075 | 0.000 | 0.025 | −0.025 | −0.025 | 0.025 | 0.000 | −0.025 |
| 102 | 0 | −0.125 | −0.050 | 0.000 | 0.025 | 0.000 | −0.025 | 0.025 | 0.000 | −0.025 |
| 103 | 0 | −0.125 | −0.050 | 0.000 | 0.025 | 0.000 | −0.025 | 0.025 | 0.025 | −0.025 |
| 104 | 0 | −0.125 | −0.050 | 0.025 | 0.025 | −0.025 | −0.025 | 0.025 | 0.000 | −0.025 |
| 105 | 0 | −0.125 | −0.050 | 0.050 | 0.025 | −0.025 | 0.000 | 0.025 | −0.025 | −0.025 |
| 106 | 0 | −0.125 | −0.050 | 0.050 | 0.025 | −0.025 | 0.025 | 0.000 | 0.000 | 0.025 |
| 107 | 0 | −0.125 | −0.025 | −0.025 | 0.025 | 0.025 | −0.025 | 0.000 | 0.025 | 0.000 |
| 108 | 0 | −0.125 | −0.025 | 0.000 | 0.000 | 0.025 | −0.025 | −0.025 | 0.025 | 0.025 |
| 109 | 0 | −0.125 | −0.025 | 0.000 | 0.000 | 0.025 | 0.000 | −0.025 | 0.025 | 0.025 |
| 110 | 0 | −0.125 | −0.025 | 0.000 | 0.025 | 0.025 | −0.025 | −0.025 | 0.025 | 0.000 |
| 111 | 0 | −0.125 | −0.025 | 0.000 | 0.025 | 0.025 | −0.025 | 0.000 | 0.025 | 0.000 |
| 112 | 0 | −0.125 | −0.025 | 0.000 | 0.025 | 0.025 | −0.025 | 0.025 | 0.025 | 0.000 |
| 113 | 0 | −0.125 | −0.025 | 0.025 | 0.025 | 0.000 | −0.025 | 0.025 | 0.025 | −0.025 |
| 114 | 0 | −0.125 | −0.025 | 0.075 | 0.025 | −0.025 | 0.025 | 0.000 | 0.000 | 0.025 |
| 115 | 0 | −0.125 | 0.000 | 0.050 | 0.025 | 0.000 | −0.025 | 0.025 | 0.025 | −0.025 |
| 116 | 0 | −0.125 | 0.000 | 0.075 | 0.025 | −0.025 | −0.025 | 0.025 | 0.000 | −0.025 |
| 117 | 0 | −0.125 | 0.050 | 0.075 | 0.025 | 0.025 | 0.000 | 0.000 | 0.000 | −0.025 |
| 118 | 0 | −0.125 | 0.075 | 0.075 | −0.025 | 0.000 | −0.025 | −0.025 | 0.000 | 0.000 |
| 119 | 0 | −0.100 | −0.075 | −0.050 | 0.025 | 0.025 | −0.025 | −0.025 | 0.025 | 0.025 |
| 120 | 0 | −0.100 | −0.050 | −0.050 | 0.025 | 0.025 | −0.025 | −0.025 | 0.025 | 0.025 |
| 121 | 0 | −0.100 | −0.050 | −0.025 | 0.025 | 0.025 | −0.025 | −0.025 | 0.025 | 0.025 |
| 122 | 0 | −0.100 | −0.025 | −0.050 | 0.025 | 0.025 | −0.025 | −0.025 | 0.025 | 0.000 |
| 123 | 0 | −0.100 | −0.025 | −0.025 | 0.000 | 0.025 | −0.025 | −0.025 | 0.025 | 0.025 |
| 124 | 0 | −0.100 | −0.025 | −0.025 | 0.025 | 0.025 | −0.025 | −0.025 | 0.025 | 0.000 |
| 125 | 0 | −0.100 | 0.050 | 0.075 | −0.025 | −0.025 | −0.025 | −0.025 | −0.025 | 0.000 |
| 126 | 0 | −0.100 | 0.075 | 0.075 | −0.025 | 0.000 | −0.025 | −0.025 | 0.000 | 0.000 |
| 127 | 0 | −0.100 | 0.075 | 0.075 | 0.000 | 0.000 | −0.025 | −0.025 | −0.025 | −0.025 |
| 128 | 0 | −0.100 | 0.075 | 0.075 | 0.000 | 0.000 | −0.025 | −0.025 | 0.000 | −0.025 |
| 129 | 0 | −0.075 | 0.025 | 0.075 | 0.025 | −0.025 | −0.025 | 0.025 | −0.025 | −0.025 |
| 130 | 0 | −0.075 | 0.050 | 0.075 | −0.025 | −0.025 | 0.000 | −0.025 | 0.000 | 0.025 |
| 131 | 0 | −0.075 | 0.050 | 0.075 | −0.025 | −0.025 | 0.025 | 0.000 | 0.025 | 0.025 |
| 132 | 0 | −0.075 | 0.050 | 0.075 | 0.025 | −0.025 | −0.025 | 0.000 | −0.025 | −0.025 |
| 133 | 0 | −0.075 | 0.050 | 0.075 | 0.025 | 0.000 | −0.025 | 0.025 | 0.000 | −0.025 |
| 134 | 0 | −0.075 | 0.075 | 0.075 | −0.025 | −0.025 | −0.025 | −0.025 | 0.000 | 0.000 |
| 135 | 0 | −0.075 | 0.075 | 0.075 | −0.025 | −0.025 | −0.025 | −0.025 | 0.000 | 0.025 |
| 136 | 0 | −0.075 | 0.075 | 0.075 | −0.025 | −0.025 | 0.000 | −0.025 | 0.025 | 0.025 |
| 137 | 0 | −0.075 | 0.075 | 0.075 | −0.025 | −0.025 | 0.000 | 0.000 | 0.000 | 0.025 |
| 138 | 0 | −0.075 | 0.075 | 0.075 | −0.025 | −0.025 | 0.025 | 0.000 | 0.000 | 0.025 |
| 139 | 0 | −0.075 | 0.075 | 0.075 | −0.025 | −0.025 | 0.025 | 0.000 | 0.025 | 0.025 |
| 140 | 0 | −0.050 | −0.050 | −0.075 | 0.025 | 0.025 | −0.025 | 0.000 | 0.000 | 0.000 |
| 141 | 0 | −0.050 | 0.050 | 0.075 | −0.025 | −0.025 | 0.000 | −0.025 | 0.000 | 0.025 |
| 142 | 0 | −0.050 | 0.050 | 0.075 | −0.025 | −0.025 | 0.000 | −0.025 | 0.025 | 0.025 |
| 143 | 0 | −0.050 | 0.050 | 0.075 | 0.025 | −0.025 | −0.025 | 0.025 | −0.025 | −0.025 |
| 144 | 0 | −0.050 | 0.075 | 0.075 | −0.025 | −0.025 | −0.025 | −0.025 | 0.025 | 0.025 |
| 145 | 0 | −0.050 | 0.075 | 0.075 | −0.025 | −0.025 | 0.025 | 0.000 | 0.000 | 0.025 |
| 146 | 0 | −0.050 | 0.075 | 0.075 | −0.025 | −0.025 | 0.025 | 0.000 | 0.025 | 0.025 |
| 147 | 0 | −0.025 | 0.075 | 0.075 | −0.025 | −0.025 | 0.025 | 0.000 | 0.000 | 0.025 |
| 148 | 0 | −0.025 | 0.075 | 0.075 | −0.025 | −0.025 | 0.025 | 0.000 | 0.025 | 0.025 |
| 149 | 0 | 0.000 | 0.075 | 0.075 | −0.025 | −0.025 | 0.025 | 0.000 | 0.000 | 0.025 |
| 150 | 0 | 0.000 | 0.075 | 0.075 | −0.025 | −0.025 | 0.025 | 0.000 | 0.025 | 0.025 |
| 151 | 0 | 0.025 | −0.050 | −0.075 | 0.025 | 0.025 | 0.025 | 0.025 | −0.025 | −0.025 |
| 152 | 0 | 0.050 | 0.075 | −0.050 | −0.025 | 0.025 | −0.025 | −0.025 | −0.025 | −0.025 |
| 153 | 0 | 0.075 | 0.075 | −0.050 | 0.000 | 0.025 | −0.025 | −0.025 | −0.025 | −0.025 |
| 154 | 0 | 0.100 | 0.050 | −0.075 | −0.025 | 0.000 | −0.025 | 0.025 | 0.000 | 0.000 |
| 155 | 0 | 0.100 | 0.050 | −0.075 | −0.025 | 0.025 | 0.000 | 0.025 | 0.000 | −0.025 |
| 156 | 0 | 0.100 | 0.050 | −0.075 | −0.025 | 0.025 | 0.025 | 0.025 | 0.025 | 0.000 |
| 157 | 0 | 0.100 | 0.050 | −0.075 | 0.000 | 0.025 | 0.000 | 0.000 | −0.025 | −0.025 |
| 158 | 0 | 0.100 | 0.075 | −0.075 | −0.025 | 0.000 | −0.025 | 0.000 | 0.000 | 0.000 |
| 159 | 0 | 0.100 | 0.075 | −0.075 | −0.025 | 0.025 | 0.000 | 0.025 | 0.025 | 0.000 |
| 160 | 0 | 0.100 | 0.075 | −0.075 | −0.025 | 0.025 | 0.025 | 0.025 | 0.025 | 0.025 |
| 161 | 0 | 0.125 | 0.050 | −0.075 | 0.000 | −0.025 | −0.025 | 0.000 | 0.000 | 0.000 |
| 162 | 0 | 0.125 | 0.075 | −0.075 | −0.025 | 0.000 | −0.025 | −0.025 | 0.000 | 0.000 |
| 163 | 0 | 0.125 | 0.075 | −0.075 | −0.025 | 0.000 | −0.025 | 0.000 | 0.000 | 0.000 |
| 164 | 0 | 0.125 | 0.075 | −0.050 | 0.000 | 0.000 | −0.025 | 0.000 | −0.025 | −0.025 |
| 165 | 0 | 0.125 | 0.075 | −0.050 | 0.000 | 0.000 | −0.025 | 0.000 | −0.025 | 0.000 |
| 166 | 0 | 0.125 | 0.075 | −0.050 | 0.000 | 0.000 | −0.025 | 0.000 | 0.000 | 0.000 |
| 167 | 0 | 0.125 | 0.075 | −0.050 | 0.000 | 0.000 | −0.025 | 0.000 | 0.025 | 0.025 |

APPENDIX D

Through focus RIQ for combinations of spherical aberration in Appendix C

| Combination | -1.50 | -1.25 | -1.00 | -0.75 | -0.50 | -0.25 | 0.00 | 0.25 | 0.50 | 0.75 | 1.00 | 1.25 | 1.50 |
|---|---|---|---|---|---|---|---|---|---|---|---|---|---|
| No Aberr | 0.024 | 0.040 | 0.073 | 0.148 | 0.307 | 0.709 | 1.000 | 0.709 | 0.307 | 0.148 | 0.073 | 0.040 | 0.024 |
| 101 | 0.071 | 0.102 | 0.206 | 0.371 | 0.466 | 0.446 | 0.409 | 0.397 | 0.365 | 0.305 | 0.236 | 0.171 | 0.114 |
| 102 | 0.075 | 0.113 | 0.213 | 0.357 | 0.421 | 0.407 | 0.430 | 0.459 | 0.402 | 0.301 | 0.220 | 0.160 | 0.110 |
| 103 | 0.071 | 0.106 | 0.224 | 0.382 | 0.431 | 0.388 | 0.385 | 0.405 | 0.374 | 0.309 | 0.238 | 0.173 | 0.120 |
| 104 | 0.045 | 0.079 | 0.216 | 0.430 | 0.524 | 0.446 | 0.376 | 0.385 | 0.383 | 0.326 | 0.240 | 0.161 | 0.106 |
| 105 | 0.043 | 0.075 | 0.203 | 0.427 | 0.551 | 0.478 | 0.377 | 0.355 | 0.350 | 0.314 | 0.242 | 0.160 | 0.101 |
| 106 | 0.045 | 0.108 | 0.230 | 0.382 | 0.459 | 0.413 | 0.366 | 0.386 | 0.382 | 0.312 | 0.221 | 0.151 | 0.109 |
| 107 | 0.032 | 0.091 | 0.212 | 0.323 | 0.360 | 0.391 | 0.463 | 0.483 | 0.407 | 0.317 | 0.255 | 0.198 | 0.141 |
| 108 | 0.044 | 0.109 | 0.239 | 0.330 | 0.354 | 0.389 | 0.444 | 0.462 | 0.422 | 0.347 | 0.264 | 0.183 | 0.111 |
| 109 | 0.029 | 0.106 | 0.231 | 0.314 | 0.358 | 0.427 | 0.489 | 0.478 | 0.403 | 0.321 | 0.251 | 0.176 | 0.107 |
| 110 | 0.028 | 0.098 | 0.234 | 0.343 | 0.359 | 0.364 | 0.439 | 0.503 | 0.447 | 0.324 | 0.232 | 0.168 | 0.109 |
| 111 | 0.033 | 0.093 | 0.221 | 0.343 | 0.385 | 0.402 | 0.469 | 0.514 | 0.446 | 0.326 | 0.234 | 0.168 | 0.113 |
| 112 | 0.049 | 0.091 | 0.202 | 0.327 | 0.384 | 0.405 | 0.450 | 0.467 | 0.400 | 0.303 | 0.223 | 0.163 | 0.116 |
| 113 | 0.048 | 0.082 | 0.211 | 0.400 | 0.476 | 0.408 | 0.365 | 0.391 | 0.387 | 0.325 | 0.239 | 0.167 | 0.118 |
| 114 | 0.044 | 0.095 | 0.211 | 0.386 | 0.486 | 0.426 | 0.358 | 0.375 | 0.370 | 0.305 | 0.231 | 0.167 | 0.119 |
| 115 | 0.053 | 0.096 | 0.212 | 0.360 | 0.420 | 0.374 | 0.361 | 0.416 | 0.420 | 0.340 | 0.239 | 0.164 | 0.119 |
| 116 | 0.067 | 0.121 | 0.220 | 0.342 | 0.392 | 0.355 | 0.361 | 0.434 | 0.455 | 0.389 | 0.277 | 0.169 | 0.101 |
| 117 | 0.039 | 0.095 | 0.206 | 0.321 | 0.369 | 0.365 | 0.383 | 0.422 | 0.418 | 0.358 | 0.268 | 0.180 | 0.120 |
| 118 | 0.061 | 0.120 | 0.212 | 0.315 | 0.388 | 0.387 | 0.350 | 0.353 | 0.365 | 0.344 | 0.304 | 0.244 | 0.168 |
| 119 | 0.065 | 0.127 | 0.213 | 0.309 | 0.364 | 0.393 | 0.432 | 0.436 | 0.395 | 0.342 | 0.269 | 0.183 | 0.111 |
| 120 | 0.040 | 0.098 | 0.211 | 0.322 | 0.354 | 0.366 | 0.412 | 0.425 | 0.391 | 0.355 | 0.296 | 0.204 | 0.125 |
| 121 | 0.039 | 0.104 | 0.236 | 0.352 | 0.374 | 0.383 | 0.441 | 0.469 | 0.426 | 0.351 | 0.264 | 0.173 | 0.102 |
| 122 | 0.028 | 0.085 | 0.205 | 0.324 | 0.362 | 0.371 | 0.405 | 0.413 | 0.372 | 0.322 | 0.267 | 0.194 | 0.125 |
| 123 | 0.039 | 0.083 | 0.201 | 0.313 | 0.367 | 0.431 | 0.486 | 0.458 | 0.392 | 0.348 | 0.288 | 0.192 | 0.105 |
| 124 | 0.020 | 0.075 | 0.204 | 0.339 | 0.396 | 0.417 | 0.452 | 0.459 | 0.403 | 0.317 | 0.242 | 0.172 | 0.107 |
| 125 | 0.044 | 0.096 | 0.203 | 0.327 | 0.395 | 0.383 | 0.359 | 0.389 | 0.423 | 0.393 | 0.304 | 0.194 | 0.101 |
| 126 | 0.057 | 0.106 | 0.205 | 0.327 | 0.410 | 0.411 | 0.368 | 0.358 | 0.369 | 0.346 | 0.293 | 0.224 | 0.147 |
| 127 | 0.038 | 0.087 | 0.200 | 0.338 | 0.402 | 0.383 | 0.367 | 0.388 | 0.397 | 0.359 | 0.282 | 0.194 | 0.123 |
| 128 | 0.037 | 0.097 | 0.206 | 0.319 | 0.378 | 0.380 | 0.379 | 0.396 | 0.381 | 0.319 | 0.250 | 0.188 | 0.134 |
| 129 | 0.053 | 0.097 | 0.219 | 0.353 | 0.404 | 0.378 | 0.365 | 0.397 | 0.395 | 0.323 | 0.235 | 0.163 | 0.112 |
| 130 | 0.050 | 0.106 | 0.211 | 0.342 | 0.446 | 0.474 | 0.421 | 0.381 | 0.381 | 0.347 | 0.267 | 0.179 | 0.109 |
| 131 | 0.058 | 0.121 | 0.201 | 0.302 | 0.420 | 0.465 | 0.419 | 0.397 | 0.393 | 0.330 | 0.238 | 0.161 | 0.104 |
| 132 | 0.025 | 0.082 | 0.215 | 0.346 | 0.385 | 0.372 | 0.406 | 0.470 | 0.463 | 0.365 | 0.248 | 0.158 | 0.104 |
| 133 | 0.059 | 0.103 | 0.205 | 0.318 | 0.370 | 0.369 | 0.394 | 0.451 | 0.437 | 0.328 | 0.219 | 0.151 | 0.109 |
| 134 | 0.045 | 0.095 | 0.210 | 0.336 | 0.389 | 0.380 | 0.383 | 0.424 | 0.441 | 0.388 | 0.295 | 0.199 | 0.116 |
| 135 | 0.046 | 0.094 | 0.209 | 0.331 | 0.379 | 0.374 | 0.371 | 0.392 | 0.413 | 0.383 | 0.303 | 0.207 | 0.121 |
| 136 | 0.048 | 0.102 | 0.208 | 0.326 | 0.393 | 0.391 | 0.358 | 0.355 | 0.377 | 0.356 | 0.289 | 0.213 | 0.142 |
| 137 | 0.028 | 0.082 | 0.201 | 0.325 | 0.378 | 0.368 | 0.367 | 0.418 | 0.461 | 0.422 | 0.319 | 0.200 | 0.103 |
| 138 | 0.024 | 0.083 | 0.205 | 0.344 | 0.424 | 0.411 | 0.371 | 0.380 | 0.404 | 0.376 | 0.299 | 0.206 | 0.126 |
| 139 | 0.036 | 0.107 | 0.214 | 0.316 | 0.387 | 0.398 | 0.373 | 0.388 | 0.408 | 0.363 | 0.278 | 0.191 | 0.120 |
| 140 | 0.067 | 0.117 | 0.201 | 0.311 | 0.384 | 0.416 | 0.461 | 0.485 | 0.422 | 0.312 | 0.219 | 0.151 | 0.102 |
| 141 | 0.055 | 0.105 | 0.215 | 0.361 | 0.464 | 0.483 | 0.431 | 0.379 | 0.364 | 0.333 | 0.256 | 0.169 | 0.101 |
| 142 | 0.075 | 0.131 | 0.218 | 0.317 | 0.399 | 0.438 | 0.415 | 0.382 | 0.374 | 0.331 | 0.245 | 0.168 | 0.110 |
| 143 | 0.052 | 0.090 | 0.204 | 0.350 | 0.411 | 0.382 | 0.371 | 0.406 | 0.398 | 0.313 | 0.222 | 0.161 | 0.118 |
| 144 | 0.078 | 0.118 | 0.208 | 0.319 | 0.381 | 0.398 | 0.405 | 0.407 | 0.399 | 0.353 | 0.273 | 0.194 | 0.124 |
| 145 | 0.028 | 0.086 | 0.212 | 0.359 | 0.437 | 0.421 | 0.381 | 0.386 | 0.403 | 0.368 | 0.286 | 0.192 | 0.116 |
| 146 | 0.036 | 0.105 | 0.226 | 0.341 | 0.402 | 0.405 | 0.382 | 0.390 | 0.405 | 0.360 | 0.269 | 0.179 | 0.109 |
| 147 | 0.035 | 0.092 | 0.218 | 0.372 | 0.454 | 0.434 | 0.387 | 0.383 | 0.391 | 0.352 | 0.272 | 0.183 | 0.111 |
| 148 | 0.042 | 0.104 | 0.231 | 0.363 | 0.423 | 0.415 | 0.388 | 0.386 | 0.392 | 0.348 | 0.260 | 0.171 | 0.104 |
| 149 | 0.046 | 0.102 | 0.223 | 0.381 | 0.471 | 0.449 | 0.391 | 0.374 | 0.371 | 0.329 | 0.255 | 0.177 | 0.110 |
| 150 | 0.053 | 0.107 | 0.230 | 0.378 | 0.449 | 0.430 | 0.391 | 0.375 | 0.370 | 0.328 | 0.249 | 0.168 | 0.104 |
| 151 | 0.087 | 0.139 | 0.218 | 0.318 | 0.389 | 0.428 | 0.447 | 0.425 | 0.379 | 0.315 | 0.228 | 0.150 | 0.103 |
| 152 | 0.048 | 0.099 | 0.206 | 0.320 | 0.374 | 0.384 | 0.417 | 0.463 | 0.443 | 0.336 | 0.220 | 0.154 | 0.125 |
| 153 | 0.042 | 0.095 | 0.205 | 0.324 | 0.375 | 0.387 | 0.427 | 0.466 | 0.430 | 0.318 | 0.209 | 0.153 | 0.130 |
| 154 | 0.075 | 0.124 | 0.201 | 0.316 | 0.436 | 0.454 | 0.387 | 0.368 | 0.367 | 0.303 | 0.217 | 0.152 | 0.104 |
| 155 | 0.072 | 0.118 | 0.205 | 0.348 | 0.488 | 0.481 | 0.376 | 0.359 | 0.381 | 0.320 | 0.222 | 0.157 | 0.118 |
| 156 | 0.040 | 0.096 | 0.200 | 0.357 | 0.504 | 0.508 | 0.407 | 0.366 | 0.363 | 0.301 | 0.213 | 0.155 | 0.119 |
| 157 | 0.047 | 0.097 | 0.202 | 0.355 | 0.455 | 0.420 | 0.357 | 0.393 | 0.426 | 0.345 | 0.223 | 0.156 | 0.132 |
| 158 | 0.053 | 0.110 | 0.206 | 0.316 | 0.403 | 0.413 | 0.369 | 0.385 | 0.428 | 0.385 | 0.276 | 0.183 | 0.122 |
| 159 | 0.071 | 0.127 | 0.209 | 0.315 | 0.415 | 0.418 | 0.355 | 0.370 | 0.417 | 0.368 | 0.260 | 0.175 | 0.126 |
| 160 | 0.050 | 0.107 | 0.206 | 0.329 | 0.429 | 0.429 | 0.363 | 0.363 | 0.389 | 0.335 | 0.236 | 0.164 | 0.125 |
| 161 | 0.056 | 0.121 | 0.211 | 0.304 | 0.386 | 0.420 | 0.400 | 0.393 | 0.387 | 0.319 | 0.226 | 0.161 | 0.121 |
| 162 | 0.055 | 0.122 | 0.222 | 0.313 | 0.355 | 0.361 | 0.363 | 0.401 | 0.449 | 0.410 | 0.285 | 0.170 | 0.107 |
| 163 | 0.063 | 0.129 | 0.233 | 0.335 | 0.403 | 0.411 | 0.363 | 0.354 | 0.400 | 0.387 | 0.291 | 0.189 | 0.118 |
| 164 | 0.062 | 0.106 | 0.202 | 0.330 | 0.412 | 0.421 | 0.394 | 0.375 | 0.371 | 0.348 | 0.275 | 0.177 | 0.105 |
| 165 | 0.050 | 0.107 | 0.217 | 0.345 | 0.423 | 0.426 | 0.379 | 0.351 | 0.361 | 0.332 | 0.240 | 0.151 | 0.101 |
| 166 | 0.047 | 0.105 | 0.201 | 0.312 | 0.411 | 0.459 | 0.438 | 0.418 | 0.420 | 0.366 | 0.262 | 0.173 | 0.112 |
| 167 | 0.053 | 0.119 | 0.210 | 0.307 | 0.405 | 0.466 | 0.447 | 0.416 | 0.394 | 0.311 | 0.212 | 0.161 | 0.122 |

The invention claimed is:

1. A lens for an eye, the lens comprising:
an optical axis;
an aberration profile about the optical axis and having a focal distance; and
at least two optical surfaces;
wherein the lens's optical properties can be characterised upon testing by at least the following properties: two or more higher order aberrations having one or more of the following components: a primary spherical aberration C(4,0), a secondary spherical aberration C(6,0), a tertiary spherical aberration C(8,0), a quaternary spherical aberration C(10,0), a pentanary spherical aberration C(12,0), a hexanary spherical aberration C(14,0), a heptanary spherical aberration C(16, 0), an octanary spherical aberration C(18,0) and a nanonary spherical aberration C(20,0); and wherein the aberration profile when tested on a model eye with no, or substantially no, aberrations and having an on-axis length equal, or substantially equal, to the focal distance, results in a retinal image quality (RIQ) with a through focus slope so that the RIQ decreases in a direction of eye growth, where the RIQ is determined by a visual Strehl Ratio that is measured substantially along the optical axis; and the RIQ is measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive; and wherein the aberration profile provides a RIQ with a through focus slope that degrades in the direction of eye growth when primary astigmatism is added to the aberration profile.

2. The lens of claim 1, wherein the lens is further characterised by minimal ghosting at near, intermediate and far distances.

3. The lens of claim 1, wherein the lens is further configured to provide the RIQ of at least 0.1 in the near distance range, the RIQ of at least 0.27 in the intermediate distance range and the RIQ of at least 0.35 in the far distance range.

4. The lens of claim 1, wherein the lens is further configured to provide two or more of the following: the RIQ of at least 0.1 in the near distance range, the RIQ of at least 0.27 in the intermediate distance range and the RIQ of at least 0.35 in the far distance range.

5. The lens of claim 1, wherein the slope averaged over a horizontal field of at least −20° to +20° degrades in a direction of eye growth.

6. The lens of claim 1, wherein the slope averaged over a horizontal field of at least −20° to +20° improves in a direction of eye growth.

7. The lens of claim 1, wherein the slope averaged over a vertical field of at least −20° to +20° degrades in a direction of eye growth.

8. The lens of claim 1, wherein the slope averaged over a vertical field of at least −20° to +20° improves in a direction of eye growth.

9. The lens of claim 1, wherein the aberration profile provides the RIQ with a through focus slope that degrades in a direction of eye growth when secondary astigmatism is added to the aberration profile.

10. The lens of claim 9, wherein the primary or secondary astigmatism is added to the desired aberration profile by altering one or more of the following terms: C(2,−2), C(2,2), C(4,−2), C(4,2), C(6,−2) and/or C(6,2).

11. The lens of claim 1, wherein the RIQ is characterised by $$RIQ = \frac{\iint_{-Fmin}^{+Fmax} CSF(x, y) * \left( real\left(\left[FT\left(\left|FT\{A(p, \theta) * \exp\left[\frac{2\pi i}{\lambda} * W(p, \theta)\right]\}\right|^2\right)\right]\right)\right)}{\iint_{-Fmin}^{+Fmax} CSF(x, y) * \left(\left(\left[FT\left(\left|FT\{A(p, \theta) * \exp\left[\frac{2\pi i}{\lambda} * Wdiff(p, \theta)\right]\}\right|^2\right)\right]\right)\right)}$$

wherein:

Fmin is 0 cycles/degree and Fmax is 30 cycles/degree;

CSF(x, y) denotes the contrast sensitivity function CSF (F)=2.6(0.0192+0.114f)$e^{-(0.114*f)^{1.1}}$, where f specifies the tested spatial frequency, in the range of $F_{min}$ to $F_{max}$;

FT denotes a 2 D fast Fourier transform;

A(ρ, θ) denotes the pupil amplitude function across the pupil diameter;

W(ρ, θ) denotes wavefront of the test case measured for i=1 to 20

$$W(\rho, \theta) = \sum_{i=1}^{k} a_i Z_i(\rho, \theta);$$

Wdiff(ρ, θ) denotes wavefront of the diffraction limited case;

ρ and θ are normalised polar coordinates, where ρ represents the radial coordinate and θ represents the angular coordinate or azimuth; and λ denotes wavelength.

12. The lens of claim 1, wherein a power profile is associated with the optical axis and the power profile has a transition between a maxima and a minima, and the maxima is within 0.2 mm of the centre of the optic zone and the minima is less than or equal to 0.3 mm distance from the maxima; wherein the amplitude of the transition between the maxima and the minima is at least 2.5 D.

13. The lens of claim 12, wherein the transition between the maxima and the minima is one or more of the following: continuous, discontinuous, monotonic and non-monotonic.

14. A lens for an eye, the lens comprising:

an optical axis;

an aberration profile about the optical axis and having a focal distance;

at least two optical surfaces;

wherein the lens's optical properties can be characterised upon testing by at least the following properties: two or more higher order aberrations having one or more of the following components: a primary spherical aberration C(4,0), a secondary spherical aberration C(6,0), a tertiary spherical aberration C(8,0), a quaternary spherical aberration C(10,0), a pentanary spherical aberration C(12,0), a hexanary spherical aberration C(14,0), a heptanary spherical aberration C(16, 0), an octanary spherical aberration C(18,0) and a nanonary spherical aberration C(20,0); the aberration profile when tested on a model eye with no, or substantially no, aberrations and having an on-axis length equal, or substantially equal, to the focal distance, results in a through focus RIQ, within the through focus range, a first RIQ which is a peak RIQ and that remains at or above a second RIQ over the through focus range that includes the focal distance; and the first and second RIQs are measured for a model eye with no, or substantially no, aberration and is measured along the optical axis for at least one pupil diameter in the range 3 mm to 5 mm, over a spatial frequency range of 0 to 30 cycles/degree inclusive, at a wavelength selected from within the range 540 nm to 590 nm inclusive; and wherein the aberration profile provides a RIQ with a through focus slope that degrades in the direction of eye growth when primary astigmatism is added to the aberration profile.

15. The lens of claim 14, wherein the first visual Strehl Ratio is at least 0.3.

16. The lens of claim 14, wherein the second visual Strehl Ratio is at least 0.1.

17. The lens of claim 14, wherein the through focus range is at least 1.7 D.

* * * * *